(12) United States Patent
Vechorkin et al.

(10) Patent No.: US 10,934,288 B2
(45) Date of Patent: *Mar. 2, 2021

(54) PYRAZOLOPYRIDINE COMPOUNDS AND USES THEREOF

(71) Applicant: Incyte Corporation, Wilmington, DE (US)

(72) Inventors: Oleg Vechorkin, Wilmington, DE (US); Kai Liu, Bel Air, MD (US); Alexander Sokolsky, Philadelphia, PA (US); Anlai Wang, Wilmington, DE (US); Hai Fen Ye, Newark, DE (US); Qinda Ye, Claymont, DE (US); Wenqing Yao, Chadds Ford, PA (US)

(73) Assignee: Incyte Corporation, Wilmington, DE (US)

(*) Notice: Subject to any disclaimer, the term of this patent is extended or adjusted under 35 U.S.C. 154(b) by 0 days.

This patent is subject to a terminal disclaimer.

(21) Appl. No.: 16/545,778

(22) Filed: Aug. 20, 2019

(65) Prior Publication Data

US 2020/0087301 A1 Mar. 19, 2020

Related U.S. Application Data

(63) Continuation of application No. 16/209,856, filed on Dec. 4, 2018, now Pat. No. 10,435,405, which is a continuation of application No. 15/698,788, filed on Sep. 8, 2017, now Pat. No. 10,266,530.

(60) Provisional application No. 62/385,584, filed on Sep. 9, 2016.

(51) Int. Cl.
| | |
|---|---|
| *A61K 31/4162* | (2006.01) |
| *A61K 31/437* | (2006.01) |
| *C07D 471/04* | (2006.01) |
| *C07D 519/00* | (2006.01) |

(52) U.S. Cl.
CPC ......... *C07D 471/04* (2013.01); *C07D 519/00* (2013.01)

(58) Field of Classification Search
CPC .............. A61K 31/4162; A61K 31/437; C07D 471/04; C07D 519/00
See application file for complete search history.

(56) References Cited

U.S. PATENT DOCUMENTS

| | | | |
|---|---|---|---|
| 5,250,534 A | 10/1993 | Bell et al. | |
| 6,200,980 B1 | 3/2001 | Piazza et al. | |
| 6,333,330 B1 | 12/2001 | Bunnage et al. | |
| 6,458,951 B1 | 10/2002 | Bunnage et al. | |
| 6,512,002 B2 | 1/2003 | Lee et al. | |
| 6,670,366 B1 | 12/2003 | Bunnage et al. | |
| 6,743,799 B2 | 6/2004 | Westbrook et al. | |
| 6,756,373 B1 | 6/2004 | Allerton et al. | |
| 6,770,645 B2 | 8/2004 | Denton et al. | |
| 6,784,185 B2 | 8/2004 | Allerton et al. |
| 6,916,927 B2 | 7/2005 | Bunnage et al. |
| 7,105,532 B2 | 9/2006 | Rawlings |
| 7,166,293 B2 | 1/2007 | Teng et al. |
| 7,259,165 B2 | 8/2007 | Bernotas et al. |
| 7,345,178 B2 | 3/2008 | Nunes et al. |
| 7,576,087 B2 | 8/2009 | Bernotas et al. |
| 7,919,487 B2 | 4/2011 | Sun et al. |
| 7,968,719 B2 | 6/2011 | Zoller et al. |
| 8,106,190 B2 | 1/2012 | Kuramochi et al. |
| 8,450,335 B2 | 5/2013 | Singh et al. |
| 8,546,403 B2 | 10/2013 | Whitten et al. |
| 8,637,507 B2 | 1/2014 | Zhou et al. |
| 8,722,691 B2 | 3/2014 | He et al. |
| 8,987,273 B2 | 3/2015 | Rehwinkel et al. |
| 9,090,593 B2 | 7/2015 | Wang et al. |
| 9,260,425 B2 | 2/2016 | Do et al. |
| 9,284,319 B2 | 3/2016 | Eis et al. |
| 9,320,737 B2 | 4/2016 | Eis et al. |
| 9,718,818 B2 | 8/2017 | DeMong et al. |
| 9,730,929 B2 | 8/2017 | Eis et al. |
| 10,266,530 B2 | 4/2019 | Vechorkin et al. |
| 10,280,164 B2 | 5/2019 | Ye et al. |
| 10,435,405 B2 | 10/2019 | Vechorkin et al. |
| 10,722,495 B2 | 7/2020 | Vechorkin et al. |
| 10,745,388 B2 | 8/2020 | Vechorkin et al. |
| 10,752,635 B2 | 8/2020 | Sokolsky et al. |
| 2002/0013327 A1 | 1/2002 | Lee et al. |
| 2003/0162782 A1 | 8/2003 | Grossman et al. |
| 2003/0186996 A1 | 10/2003 | Teng et al. |
| 2004/0063730 A1 | 4/2004 | Eggenweiler et al. |
| 2004/0077681 A1 | 4/2004 | Rawlings et al. |
| 2004/0147546 A1 | 7/2004 | Tanaka et al. |
| 2004/0157866 A1 | 8/2004 | Takasugi et al. |
| 2004/0167030 A1 | 8/2004 | Bernotas et al. |

(Continued)

FOREIGN PATENT DOCUMENTS

| | | |
|---|---|---|
| CN | 102206172 | 10/2011 |
| CN | 102503959 | 6/2012 |

(Continued)

OTHER PUBLICATIONS

Waddell et al., "Benzothiazolylthio Carbapenems: Potent Anti-MRSA Agents," Biorg & Med Chem Lett., 1995, 5(13):1427-1432.

Alzabin et al., "Hematopoietic progenitor kinase 1 is a critical component of prostaglandin E2-mediated suppression of the antitumor immune response," Cancer Immunol Immunother, 2010, 59(3):419-429.

(Continued)

*Primary Examiner* — Brenda L Coleman

(74) *Attorney, Agent, or Firm* — Fish & Richardson P.C.

(57) ABSTRACT

Disclosed are compounds of Formula (I), methods of using the compounds for inhibiting HPK1 activity and pharmaceutical compositions comprising such compounds. The compounds are useful in treating, preventing or ameliorating diseases or disorders associated with HPK1 activity such as cancer.

8 Claims, No Drawings

(56) References Cited

U.S. PATENT DOCUMENTS

| | | |
|---|---|---|
| 2004/0204417 A1 | 10/2004 | Perez et al. |
| 2005/0070557 A1 | 3/2005 | Fryburg et al. |
| 2005/0075795 A1 | 4/2005 | Pandit |
| 2005/0119278 A1 | 6/2005 | Teng et al. |
| 2005/0137226 A1 | 6/2005 | Ji et al. |
| 2005/0208582 A1 | 9/2005 | Ohi et al. |
| 2005/0261339 A1 | 11/2005 | Ohi et al. |
| 2006/0106032 A1 | 5/2006 | Kuo et al. |
| 2007/0087988 A1 | 4/2007 | Sawasdikosol et al. |
| 2007/0161673 A1 | 7/2007 | Barker et al. |
| 2007/0185152 A1 | 8/2007 | Yamashita et al. |
| 2007/0270412 A1 | 11/2007 | Bell et al. |
| 2008/0280891 A1 | 11/2008 | Kelly et al. |
| 2010/0035891 A1 | 2/2010 | Bunnage et al. |
| 2010/0087464 A1 | 4/2010 | Mi et al. |
| 2010/0216798 A1 | 8/2010 | Nakai et al. |
| 2012/0129852 A1 | 5/2012 | Duan et al. |
| 2012/0225869 A1 | 9/2012 | Liu et al. |
| 2012/0295884 A1 | 11/2012 | Altmann et al. |
| 2013/0039906 A1 | 2/2013 | Do et al. |
| 2013/0040949 A1 | 2/2013 | Gray et al. |
| 2013/0281433 A1 | 10/2013 | Babaoglu et al. |
| 2014/0225073 A1 | 8/2014 | Lee et al. |
| 2014/0249135 A1 | 9/2014 | Burger et al. |
| 2014/0288045 A1 | 9/2014 | Ren et al. |
| 2014/0288069 A1 | 9/2014 | Eis et al. |
| 2014/0350017 A1 | 11/2014 | Williams et al. |
| 2014/0364605 A1 | 12/2014 | Li et al. |
| 2015/0038485 A1 | 2/2015 | Eis et al. |
| 2015/0191462 A1 | 7/2015 | Hommel et al. |
| 2015/0239868 A1 | 8/2015 | Pais et al. |
| 2015/0239889 A1 | 8/2015 | Nakajima et al. |
| 2015/0243908 A1 | 8/2015 | Lee et al. |
| 2015/0274639 A1 | 10/2015 | Williams et al. |
| 2015/0328188 A1 | 11/2015 | Orlemans et al. |
| 2016/0013427 A1 | 1/2016 | Kim et al. |
| 2016/0046648 A1 | 2/2016 | Petrukhin et al. |
| 2016/0068529 A1 | 3/2016 | KC et al. |
| 2016/0068547 A1 | 3/2016 | KC et al. |
| 2016/0068548 A1 | 3/2016 | KC et al. |
| 2016/0068551 A1 | 3/2016 | KC et al. |
| 2016/0200722 A1 | 7/2016 | DeMong et al. |
| 2018/0072718 A1 | 3/2018 | Liu et al. |
| 2018/0072719 A1 | 3/2018 | Ye et al. |
| 2018/0072720 A1 | 3/2018 | Vechorkin et al. |
| 2018/0072741 A1 | 3/2018 | Vechorkin et al. |
| 2018/0228786 A1 | 8/2018 | Sokolsky |
| 2019/0076401 A1 | 3/2019 | Vechorkin et al. |
| 2019/0106419 A1 | 4/2019 | Vechorkin et al. |
| 2019/0256500 A1 | 8/2019 | Vechorkin et al. |
| 2019/0256520 A1 | 8/2019 | Sokolsky |
| 2019/0315717 A1 | 10/2019 | Hummel et al. |
| 2019/0315743 A1 | 10/2019 | Liu et al. |
| 2019/0343814 A1 | 11/2019 | Sokolsky |
| 2019/0382380 A1 | 12/2019 | Vechorkin et al. |
| 2020/0048241 A1 | 2/2020 | Hummel et al. |
| 2020/0172545 A1 | 6/2020 | Vechorkin et al. |

FOREIGN PATENT DOCUMENTS

| | | |
|---|---|---|
| CN | 102516263 | 6/2012 |
| CN | 103570709 | 2/2014 |
| DE | 10 2004 054 666 | 5/2006 |
| EP | 2543372 | 1/2013 |
| EP | 2824099 | 1/2015 |
| IN | 187433 | 4/2002 |
| JP | H03287584 | 12/1991 |
| JP | 2000-038350 | 2/2000 |
| JP | 2007-055940 | 3/2007 |
| JP | 2010-111624 | 5/2010 |
| JP | 2011-246389 | 12/2011 |
| KR | 963644 | 2/1996 |
| KR | 10 2014 0019055 | 2/2014 |
| MX | 9910322 | 7/2003 |
| MY | 146643 | 9/2012 |
| WO | WO 1989/008263 | 9/1989 |
| WO | WO 2000/043394 | 7/2000 |
| WO | WO 2001/019827 | 3/2001 |
| WO | WO 2001/019828 | 3/2001 |
| WO | WO 2001/021576 | 3/2001 |
| WO | WO 2001/046124 | 6/2001 |
| WO | WO 2002/000196 | 1/2002 |
| WO | WO 2002/016348 | 2/2002 |
| WO | WO 2002/019975 | 3/2002 |
| WO | WO 2002/050073 | 6/2002 |
| WO | WO 2002/090347 | 11/2002 |
| WO | WO 2003/037432 | 5/2003 |
| WO | WO 2003/049681 | 6/2003 |
| WO | WO 2004/072069 | 8/2004 |
| WO | WO 2004/096810 | 11/2004 |
| WO | WO 2004/108133 | 12/2004 |
| WO | WO 2005/004799 | 1/2005 |
| WO | WO 2005/011681 | 2/2005 |
| WO | WO 2005/028475 | 3/2005 |
| WO | WO 2005/051906 | 6/2005 |
| WO | WO 2005/066167 | 7/2005 |
| WO | WO 2005/073199 | 8/2005 |
| WO | WO 2005/073232 | 8/2005 |
| WO | WO 2003/101968 | 9/2005 |
| WO | WO 2005/085227 | 9/2005 |
| WO | WO 2005/085248 | 9/2005 |
| WO | WO 2005/085249 | 9/2005 |
| WO | WO 2006/013095 | 2/2006 |
| WO | WO 2006/028958 | 3/2006 |
| WO | WO 2006/038001 | 4/2006 |
| WO | WO 2006/045010 | 4/2006 |
| WO | WO 2006/050097 | 5/2006 |
| WO | WO 2006/053109 | 5/2006 |
| WO | WO 2006/053121 | 5/2006 |
| WO | WO 2006/053227 | 5/2006 |
| WO | WO 2006/074428 | 7/2006 |
| WO | WO 2006/105289 | 10/2006 |
| WO | WO 2006/128172 | 11/2006 |
| WO | WO 2007/019344 | 2/2007 |
| WO | WO 2007/019345 | 2/2007 |
| WO | WO 2007/019346 | 2/2007 |
| WO | WO 2007/019417 | 2/2007 |
| WO | WO 2007/020050 | 2/2007 |
| WO | WO 2007/023110 | 3/2007 |
| WO | WO 2007/023111 | 3/2007 |
| WO | WO 2007/023114 | 3/2007 |
| WO | WO 2007/030582 | 3/2007 |
| WO | WO 2007/056280 | 5/2007 |
| WO | WO 2007/063925 | 6/2007 |
| WO | WO 2007/065924 | 6/2007 |
| WO | WO 2007/080382 | 7/2007 |
| WO | WO 2007/093402 | 8/2007 |
| WO | WO 2007/112093 | 10/2007 |
| WO | WO 2007/114848 | 10/2007 |
| WO | WO 2007/137030 | 11/2007 |
| WO | WO 2008/008059 | 1/2008 |
| WO | WO 2008/008539 | 1/2008 |
| WO | WO 2008/012027 | 1/2008 |
| WO | WO 2008/045627 | 4/2008 |
| WO | WO 2008/070313 | 6/2008 |
| WO | WO 2008/089307 | 7/2008 |
| WO | WO 2008/089310 | 7/2008 |
| WO | WO 2008/113856 | 9/2008 |
| WO | WO 2009/019167 | 2/2009 |
| WO | WO 2009/024341 | 2/2009 |
| WO | WO 2009/032651 | 3/2009 |
| WO | WO 2009/038784 | 3/2009 |
| WO | WO 2009/100130 | 8/2009 |
| WO | WO 2009/139834 | 11/2009 |
| WO | WO 2009/152356 | 12/2009 |
| WO | WO 2010/029300 | 3/2010 |
| WO | WO 2010/035217 | 4/2010 |
| WO | WO 2010/035219 | 4/2010 |
| WO | WO 2010/035221 | 4/2010 |
| WO | WO 2010/046780 | 4/2010 |
| WO | WO 2010/080503 | 7/2010 |
| WO | WO 2010/104306 | 9/2010 |
| WO | WO 2010/107765 | 9/2010 |
| WO | WO 2010/107768 | 9/2010 |

(56) References Cited

FOREIGN PATENT DOCUMENTS

| | | |
|---|---|---|
| WO | WO 2010/111624 | 9/2010 |
| WO | WO 2010/118367 | 10/2010 |
| WO | WO 2011/019780 | 2/2011 |
| WO | WO 2011/031628 | 3/2011 |
| WO | WO 2011/050245 | 4/2011 |
| WO | WO 2011/051535 | 5/2011 |
| WO | WO 2011/062253 | 5/2011 |
| WO | WO 2011/078143 | 6/2011 |
| WO | WO 2011/082400 | 7/2011 |
| WO | WO 2011/082488 | 7/2011 |
| WO | WO 2011/107186 | 9/2011 |
| WO | WO 2011/133920 | 10/2011 |
| WO | WO 2011/139489 | 11/2011 |
| WO | WO 2011/141756 | 11/2011 |
| WO | WO 2011/147765 | 12/2011 |
| WO | WO 2011/153553 | 12/2011 |
| WO | WO 2011/157653 | 12/2011 |
| WO | WO 2011/158108 | 12/2011 |
| WO | WO 2012/048058 | 4/2012 |
| WO | WO 2012/049277 | 4/2012 |
| WO | WO 2012/078777 | 6/2012 |
| WO | WO 2012/080376 | 6/2012 |
| WO | WO 2012/109263 | 8/2012 |
| WO | WO 2012/130780 | 10/2012 |
| WO | WO 2012/141487 | 10/2012 |
| WO | WO 2012/143144 | 10/2012 |
| WO | WO 2012/158810 | 11/2012 |
| WO | WO 2012/163959 | 12/2012 |
| WO | WO 2013/007708 | 1/2013 |
| WO | WO 2013/021276 | 2/2013 |
| WO | WO 2013/024002 | 2/2013 |
| WO | WO 2013/024011 | 2/2013 |
| WO | WO 2013/042137 | 3/2013 |
| WO | WO 2013/064445 | 5/2013 |
| WO | WO 2013/123215 | 8/2013 |
| WO | WO 2013/130890 | 9/2013 |
| WO | WO 2013/146942 | 10/2013 |
| WO | WO 2014/003405 | 1/2014 |
| WO | WO 2014/024125 | 2/2014 |
| WO | WO 2014/047616 | 3/2014 |
| WO | WO 2014/055955 | 4/2014 |
| WO | WO 2014/151616 | 9/2014 |
| WO | WO 2015/026683 | 2/2015 |
| WO | WO 2015/037965 | 3/2015 |
| WO | WO 2015/038503 | 3/2015 |
| WO | WO 2015/058163 | 4/2015 |
| WO | WO 2015/061247 | 4/2015 |
| WO | WO 2015/089327 | 6/2015 |
| WO | WO 2015/089479 | 6/2015 |
| WO | WO 2015/090235 | 6/2015 |
| WO | WO 2015/091426 | 6/2015 |
| WO | WO 2015/104662 | 7/2015 |
| WO | WO 2015/117718 | 8/2015 |
| WO | WO 2015/164956 | 11/2015 |
| WO | WO 2015/192939 | 12/2015 |
| WO | WO 2015/193506 | 12/2015 |
| WO | WO 2015/193846 | 12/2015 |
| WO | WO 2015/200682 | 12/2015 |
| WO | WO 2016/040180 | 3/2016 |
| WO | WO 2016/040181 | 3/2016 |
| WO | WO 2016/041618 | 3/2016 |
| WO | WO 2016/057500 | 4/2016 |
| WO | WO 2016/083433 | 6/2016 |
| WO | WO 2016/090300 | 6/2016 |
| WO | WO 2016/124304 | 8/2016 |
| WO | WO 2016/144351 | 9/2016 |
| WO | WO 2016/144702 | 9/2016 |
| WO | WO 2016/164285 | 10/2016 |
| WO | WO 2016/174183 | 11/2016 |
| WO | WO 2016/205942 | 12/2016 |
| WO | WO 2017/009798 | 1/2017 |
| WO | WO 2017/009806 | 1/2017 |
| WO | WO 2017/023894 | 2/2017 |
| WO | WO 2017/023972 | 2/2017 |
| WO | WO 2017/027400 | 2/2017 |
| WO | WO 2017/045955 | 3/2017 |
| WO | WO 2017/058915 | 4/2017 |
| WO | WO 2017/108744 | 6/2017 |
| ZA | 2003005330 | 7/2003 |

OTHER PUBLICATIONS

Alzabin et al., "Hematopoietic progenitor kinase 1 is a negative regulator of dendritic cell activation," J Immunol, 2009, 182(10):6187-6194

Anonymous, "Crystalline ethyl 1-(4-methoxyphenyl)-6-(4-nitrophenyl)-7-oxo-,5,6,7-tetrahydro-1H-pyrazolo[3,4-c]pyridine-3-carboxylate," ip.com #IPCOM000233229D, Dec. 3, 2019, 4 pages.

Anonymous, "Crystalline APX," ip.com #IPCOM000233879, Dec. 25, 2013, 3 pages.

Antoine et al., "Efficient synthesis of novel disubstituted pyrido[3,4-b]pyrazines for the design of protein kinase inhibitors," Med Chem Common., 2016, 6:224-229.

Antunes et al., "In silico prediction of novel phosphodiesterase type-5 inhibitors derived from Sildenafil, Vardenafil and Tadalafil," Bioorg Med Chem., Aug. 15, 2008, 16(16):7599-7606.

Atzrodt et al., "The Renaissance of H/D Exchange," Angew. Chem. Int. Ed., 2007, 7744-7765.

Ballell et al., "Fueling Open-Source Drug Discovery: 177 Small-Molecule Leads against Tuberculosis," ChemMedChem., 2013, 8(2):313-321.

Balog et al., "The synthesis and evaluation of [2.2.1]—bicycloazahydantoins as androgen receptor antagonists," Bioorg. Med. Chem. Lett., Dec. 20, 2004, 14(24):6107-6111.

Batliwalla et al., "Microarray analyses of peripheral blood cells identifies unique gene expression signature in psoriatic arthritis," Mol Med, 2005, 11(1-12):21-29.

Berge et al., "Pharmaceutical Salts," J. Pharm. Sci., 1977, 66(1):1-19.

Blom et al., "Optimizing Preparative LC-MS Configurations and Methods for Parallel Synthesis Purification," J. Combi. Chem., 2003, 5:670.

Blom et al., "Preparative LC-MS Purification: Improved Compound Specific Method Optimization," J. Combi. Chem., 2004, 6:874-883.

Blom et al., "Two-Pump at Column Dilution Configuration for Preparative LC-MS," J. Combi. Chem., 2002, 4: 295.

Brioche et al., "Chiral Phosphoric Acid—Catalyzed Enantioselective Three-Component Aza-Diels—Alder Reactions of Aminopyrroles and Aminopyrazoles," Advanced Synthesis & Catalysis, 2014, 356(8):1719-1724.

Chessari et al., "Fragment-Based Drug Discovery Targeting Inhibitor of Apoptosis Proteins: Discovery of a Non-Alanine Lead Series with Dual Activity Against cIAP1 and XIAP," J. Med. Chem., Jul. 18, 2018, 58(16):6574-6588.

Chinchilla and Najera, "Recent advances in Sonogashira reactions," Chem. Soc. Rev., 2011, 40: 5084-5121.

Cheung et al., "A Parallel Synthesis Approach to the Identification of Novel Diheteroarylamide-Based Compounds Blocking HIV Replication: Potential Inhibitors of HIV-1 Pre-mRNA Alternative Splicing," J Med Chem., Mar. 10, 2016, 59(5):1869-1879.

Choi et al., "In Vitro metabolism of a novel phosphodiesterase-5 inhibitor DA-8159 in rat liver preparations using liquid chromatography/electrospray mass spectrometry," Biomed Chromatogr, Sep. 2002, 16(6):395-399.

Cordovilla et al., "The Stille Reaction, 38 Years Later," ACS Catalysis, 2015, 5: 3040-3053.

Devegowda et al., "Novel 6-N-arylcarboxamidopyrazolo[4,3-d]pyrimidin-7-one derivatives as potential anti-cancer agents," Bioorg Med Chem Lett., Mar. 1, 2010, 20(5):1630-1633.

Di Bartolo et al., "A novel pathway down-modulating T cell activation involves HPK-1-dependent recruitment of 14-3-3 proteins on SLP-76," J. Exp. Med., Mar. 2007, 204(3): 681-691.

Dong et al., "Pharmacophore identification, virtual screening and biological evaluation of prenylated flavonoids derivatives as PKB/Akt1 inhibitors," Eur J Med Chem., Dec. 2011, 46(12):5949-5958.

(56) References Cited

OTHER PUBLICATIONS

Dong et al., "QSAR study of Akt/protein kinase B (PKB) inhibitors using support vector machine," Eur J Med Chem, Oct. 2009, 44(10):4090-4097.
Dornow et al., "Syntheses of nitrogen-containing heterocycles. XXXVIII. Preparation and reaction of several substituted 3-nitropyridines," Chemische Berichte, 1966, 99(1):244-253 (Machine Translation).
Dumestre-Toulet et al., "Last performance with VIAGRA: postmortem identification of sildenafil and its metabolites in biological specimens including hair sample," Forensic Sci Int., Mar. 28, 2002, 126(1):71-76.
El-Aziz et al., "Synthesis and in vitro anti-breast cancer activity of some novel 1,4-dihydropyridine derivatives," Int J of Pharm Pharma. Sci., 2013, 5(Suppl. 3):183-189.
El Sayed et al., "New route for the preparation of pyrazolo[4,3-c]pyridines," Bulletin of the Chemical Society of Japan (1973), 46(6), 1801-1803.
Edmondson et al., "Aminopiperidine-fused imidazoles as dipeptidyl peptidase—IV inhibidors," Bioorg Med Chm Lett., Aug. 2009, 19(15):4097-4101.
Elgemeie et al., "A new general method for substituted 4-alkylthio-N-arylsulfonylamino-2-pyridones: Reaction of ketene-S,S-acetals with arylsulfonylhydrazides," Phosphorus, Sulfur and Silicon and the Related Elements, 2001, 170:171-179.
Elgemeie et al., "Novel N-Substituted Amino-4-methylsulfanyl-2-pyridones and Deazapurine Analogues from Ketene Dithioacetals," J Chem Res., 1998, 3:164-165.
Elgemeie et al., "Novel synthesis of N-aroylaminated pyridones via reaction of ketene dithioacetals with cyanoaceto-N-aroylhydrazides," Synth Comm., 2003, 33(2):253-258.
Elgemeie et al., "Novel Nucleoside Analogues: First Synthesis of Pyridine-4-Thioglycosides and Their Cytotoxic Evaluation," Nucleosides, Nucleotides and Nucleic Acids, Jun. 27, 2015, 34:659-673.
Elgemeie et al., "Synthesis of Novel Derivatives of 4-Methylthio-N-Aryl-2-Pyridone and Deazapurine Analogues: The Reaction of Ketene Dithioacetals with Substituted Acetanilides," Phosphorus, Sulfur and Silicon, 2000, 164:189-197.
Erian, "2-Aryl-1,1-dicyano-3-phenylsulfonylpropenes in heterocyclic synthesis. A synthetic strategy towards heterocyclic sulfone," Monatshefte fuer Chemie, Oct. 1998, 129(10):1049-1056.
Figueiredo et al., "A chemometric study of phosphodiesterase 5 inhibitors," J Mol Graph Model., Jan. 2006, 24(4):227-232.
Gao, "Slidenafil" Handbook of Metabolic Pathways of Xenobiotics, 2014, 5:2151-2154.
Goodarzi et al., "Feature Selection and Linear/Nonlinear Regression Methods for the Accurate Prediction of Glycogen Synthase Kinase—3β Inhibitory Activities," J. Chem. Inf. Model, 2009, 49(4):824-832.
Haas et al., "Recent Developments in Negishi Cross-Coupling Reactions," ACS Catalysis, 2016, 6: 1540-1552.
Haning et al., "Comparison of different heterocyclic scaffolds as substrate analog PDE5 inhibitors," Sep. 1, 2005, 15(17):3900-3907.
Hanson, "Diterpenoids of Terrestrial Origin", National Product Reports, 2016, 33:1227-1238.
He et al., "Predicting the Genotoxicity of Polycyclic Aromatic Compounds from Molecular Structure with Different Classifiers," Chemical Research in Toxicology (2003), 16(12):1567-1580.
Hu et al., "Discovery of 3,5-substituted 6-azaindazoles as potent pan-Pim inhibitors," Bioorg Med Chem Lett., 2015, 25(22):5258-5264.
Hu et al., "Human HPK1, a novel human hematopoietic progenitor kinase that activates the JNK/SAPK kinase cascade," Genes Dev, 1996, 10(18): p. 2251-2264.
Ho et al., "Discovery of 4-phenyl-2-phenylaminopyridine based TNIK inhibitors," Boorg Med Chem Lett, 2013, 23(2):569-573.
Howard et al., "Identification of potent phosphodiesterase inhibitors that demonstrate cyclic nucleotide-dependent functions in apicomplexan parasites," ACS Chem Biol., Apr. 17, 2015, 10(4):1145-1154.

Ikegami et al., "The expression of prostaglandin E receptors EP2 and EP4 and their different regulation by lipopolysaccharide in C3H/HeN peritoneal macrophages," J. Immunol., Apr. 2001, 166(7): 4689-4696.
International Search Report and Written Opinion in International Application No. PCT/US2017/048880, dated Nov. 2, 2017, 15 pages.
International Search Report and Written Opinion in International Application No. PCT/US2017/050669, dated Nov. 6, 2017, 16 pages.
International Search Report and Written Opinion in International Application No. PCT/US2017/050727, dated Nov. 2, 2017, 16 pages.
International Search Report and Written Opinion in International Application No. PCT/US2017/050737, dated Nov. 2, 2017, 16 pages.
International Search Report and Written Opinion in International Application No. PCT/US2017/050757, dated Nov. 10, 2017, 20 pages.
International Search Report and Written Opinion in International Application No. PCT/US2018/018205, dated Apr. 30, 2018, 16 pages.
International Search Report and Written Opinion in International Application No. PCT/US2018/049908, dated Nov. 7, 2018.
International Search Report and Written Opinion in International Application No. PCT/US2019/018609, dated May 13, 2019, 12 pages.
International Search Report and Written Opinion in International Application No. PCT/US2019/018608, dated Apr. 16, 2019, 14 pages.
International Preliminary Report on Patentability in International Application No. PCT/US2017/050669, dated Mar. 12, 2019, 8 pages.
International Preliminary Report on Patentability in International Application No. PCT/US2017/050737, dated Mar. 12, 2019, 8 pages.
International Preliminary Report on Patentability in International Application No. PCT/US2017/050727, dated Mar. 12, 2019, 8 pages.
International Preliminary Report on Patentability in International Application No. PCT/US2017/050757, dated Mar. 12, 2019, 10 pages.
International Preliminary Report on Patentability in International Application No. PCT/US2018/018205, dated Aug. 20, 2019, 10 pages.
Ivon et al., "Synthesis of a 2,5-Diazabicyclo[2.2.1]heptane-Derived α,β-Diamino Acid," Synthesis, 2015, 47(8):1123-1130.
Karaman "Analyzing the efficiency in intramolecular amide hydrolysis of Kirby's N-alkylmaleamic acids—A computational approach," Computational and Theoretical Chemistry, 2011, 974(1-3):133-142.
Katritzky et al., "QSAR modeling of the inhibition of Glycogen Synthase Kinase-3," Bioorganic & Medicinal Chemistry, 2006, 14(14):4987-5002.
Kerekes et al., "Aurora kinase inhibitors based on the imidazo[1,2-a]pyrazine core: fluorine and deuterium incorporation improve oral absorption and exposure," J. Med. Chem., Jan. 2011, 54(1): 201-210.
Kiefer et al., "HPK1, a hematopoietic protein kinase activating the SAPK/JNK pathway," EMBO. J., Dec. 1996, 15(24): 7013-7025.
Kim et al., "Reliable screening and confirmation of 156 multi-class illegal adulterants in dietary supplements based on extracted common ion chromatograms by ultra-high-performance liquid chromatography-quadrupole/time of flight-mass spectrometry," J Chromatogr A., Mar. 31, 2017, 1491:43-56.
Kotha et al., "Recent applications of the Suzuki—Miyaura cross-coupling reaction in organic synthesis," Tetrahedron, 2002, 58: 9633-9695.
Kumar et al., "3-(1H-Indol-2-yl)-1H-pyrazolo[4,3-b]pyridines as Wnt pathway modulators and their preparation," retrieved from STN Database Accession No. 2017: 232331, Feb. 9, 2017, Chemical Abstracts Service, Columbus, Ohio, US, XP002775032.
Kumar et al., "3-(1H-Indol-2-yl)-1H-pyrazolo[4,3-b]pyridines as Wnt pathway modulators and their preparation," retrieved from

(56) References Cited

OTHER PUBLICATIONS

STN Database Accession No. 2017: 232415, Feb. 9, 2017, Chemical Abstracts Service, Columbus, Ohio, US, XP002775031.
Kumar et al., "3-(1H-Indol-2-yl)-1H-pyrazolo[4,3-b]pyridines as Wnt pathway modulators and their preparation," retrieved from STN Database Accession No. 2017: 232564, Feb. 9, 2017, Chemical Abstracts Service, Columbus, Ohio, US, XP002775030.
Kumar et al., "3-(1H-Indol-2-yl)-1H-pyrazolo[4,3-b]pyridines as Wnt pathway modulators and their preparation," retrieved from STN Database Accession No. 2017: 233013, Feb. 9, 2017, Chemical Abstracts Service, Columbus, Ohio, US, XP002775029.
Kumar et al., "3-(1H-Indo;-2-yl)-1H-pyrazolo[4,3-b]pyridines as Wnt pathway modulators and their preparation," retrieved from STN Database Accession No. 2017: 233418, Feb. 9, 2017, Chemical Abstracts Service, Columbus, Ohio, US, XP002775028.
Kumar et al., "3-(1H-Indol-2-yl)-1H-pyrazolo[4,3-b]pyridines as Wnt pathway modulators and their preparation," retrieved from STN Database Accession No. 2017: 233427, Feb. 9, 2017, Chemical Abstracts Service, Columbus, Ohio, US, XP002775027.
Kumar et al., "3-(1H-Indol-2-yl)-1H-pyrazolo[4,3-b]pyridines as Wnt pathway modulators and their preparation," retrieved from STN Database Accession No. 2017: 233436, Feb. 9, 2017, Chemical Abstracts Service, Columbus, Ohio, US, XP002775026.
Lebel et al., "A rapid, quantitative liquid chromatography—mass spectrometry screening method for 71 active and 11 natural erectile dysfunction ingredients present in potentially adulterated or counterfeit products," J Chromatogr A., May 23, 2014, 1343:143-151.
Lee et al., "Comparative metabolism of sildenafil in liver microsomes of different species by using LC/MS-based multivariate analysis," J of Chromato., Oct. 15, 2011, 879(28):3005-3011.
Li et al., "Metabolism of aildenafil in vivo in rats and in vitro in mouse, rat, dog, and human liver microsomes," Drug Test Anal., Jun. 2014., 6(6):552-562.
Li et al., "A highly effective one-pot synthesis of quinolines from o-nitroarylcarbaldehydes," Organic & Biomolecular Chemistry, 2007, 5(1):61-64.
Li et al., "One-pot Friedlander quinoline synthesis: scope and limitations," Synthesis, 2010, 10:1678-1686.
Lim et al., "Discovery of 1-(1 H-Pyrazolo [4,3-c]pyridin-6-yl)urea Inhibitors of Extracellular Signal-Regulated Kinase (ERK) for the Treatment of Cancers," Journal of Medicinal Chemistry, Jul. 2016, 59(13): 6501-6511.
Lin et al., "2,3,5-Trisbustituted pyridines as selective AKT inhibitors. Part II: Improved drug-like properties and kinase selectivity from azaindazoles," Bioorganic & Medicinal Chemistry Letters, 2010, 20: 679-683.
Lin et al., "2,3-5—Tetrasubstituted pyridines as potent and selective AKT inhibitors: Reduced CYP450 and hERG inhibition of aminopyridines," Bioorg Med Chem Lett. Jan. 15, 2010;20(2):684-688.
Liou et al., "HPK1 is activated by lymphocyte antigen receptors and negatively regulates AP-1," Immunity, Apr. 2000, 12(4): 399-408.
Liu et al., "Synthesis and SAR of 1,9-dihydro-9-hydroxypyrazolo[3,4-b]quinolin-4-ones as novel, selective c-Jun N-terminal kinase inhibitors," Bioorg Med Chem Lett., May 15, 2006, 16(10):2590-2594.
Michelotti et al., "Two Classes of p38a MAP kinase inhibitors having a common core but exhibiting divergent binding modes," 2005, 15:5274-5279.
Miyazaki et al., "Design and effective synthesis of novel templates, 3,7-diphenyl-4-amino-thieno and furo-[3,2-c]pyridines as protein kinase inhibitors and in vitro evaluation targeting angiogenetic kinases," Bioorg Med Chem Lett., Jan. 1, 2007, 17(1):250-254.
Muddassar et al., "Elucidation of binding mode and three dimensional quantitative structure—activity relationship studies of a novel series of protein kinase B/Akt inhibitors," J Mol Model., Feb. 2009, 15(2):183-192.
Mulvihill et al., "Novel 2-phenylquinolin-7-yl-derived imidazo[1,5-a]pyrazines as potent insulin-like growth factor-I receptor (IGF-IR) inhibitors," Bioorg Med Chem Lett, Feb. 2008, 16(3):1359-1375.

Patel et al., "Selectivity criterion for pyrazolo[3,4-b]pyrid[az]ine derivatives as GSK-3 inhibitors: CoMFA and molecular docking studies," European Journal of Medicinal Chemistry, 2008, 43: 949-957.
Petursson et al., "Protecting Groups in Carbohydrate Chemistry," J. Chem. Educ., 1997, 74(11), 1297.
Piersanti et al., "Synthesis of Benzo[1,2-d;3,4-d']diimidazole and 1H-Pyrazolo[4,3-b]pyridine as Putative A2A Receptor Antagonists," Organic a& Biomolecular Chemistry, Jul. 13, 2007, 5:2567-2571.
Pitt et al., "Heteroaromatic rings of the future," J Med Chem., May 14, 2009, 52(9):2952-2963.
Pozharskii et al., Heterocycles in Life and Society Wiley, 1997, pp. 1-6.
Remington's Pharmaceutical Sciences, 17th Ed., (Mack Publishing Company, Easton, 1985), p. 1418.
Sawasdikosol et al., "HPK1 as a novel target for cancer immunotherapy," Immunologic Research, Apr. 4, 2012, 54(1-3): 262-265.
Sawasdikosol, S. et al., The journal of immunology, 2012. 188(supplement 1): p. 163.
Shaughnessy et al., "Copper-Catalyzed Amination of Aryl and Alkenyl Electrophiles," Organic Reactions, Chapter 1, 2014, 85: 1-668.
Shou et al., "Simple means to alleviate sensitivity loss by trifluoroacetic acid (TFA) mobile phases in the hydrophilic interaction chromatography—electrospray tandem mass spectrometric (HILIC-ESI/MS/MS) bioanalysis of basic compounds," J Chromatogr B Analyt Technol Biomed Life Sci., Oct. 25, 2005, 825:186-192.
Shui et al., "Hematopoietic progenitor kinase 1 negatively regulates T cell receptor signaling and T cell-mediated immune responses," Nat. Immunol., Jan. 2007, 8(1): 84-91.
Smyth et al., "Synthesis and reactivity of 3-amino-1H-pyrazolo[4,3-c]pyridin-4(5H)-ones: development of a novel kinase-focussed library," Tetrahedron, Apr. 2010, 66(15): 2843-2854.
Subramanyam et al., "6-(4-Pyridinyl)-1H-1,2,3-triazolo[4,5-d]-pyrimidin-4(5H)-one: A Structurally Novel Competitive AMPA Receptor Antagonist," J Med Chem., 1995, 38(4):587-589.
Surry and Buchwald, "Dialkylbiaryl Phosphines in Pd-Catalyzed Amination: A User's Guide," Chem. Sci., 2011, 2(1): 27-50.
Taha et al., "Pharmacophore Modeling, Quantitative Structure—Activity Relationship Analysis, and in Silico Screening Reveal Potent Glycogen Synthase Kinase-3β Inhibitory Activities for Cimetidine, Hydroxychloroquine, and Gemifloxacin," J. Med. Chem., 2008, 51(7):2062-2077.
Terrett et al., "Sildenafil (VIAGRATM), a potent and selective inhibitor of type 5 cGMP phosphodiesterase with utility for the treatment of male erectile dysfunction," Bioorg & Med Chem Lett., Aug. 6, 1996, 6(15):1819-1824.
Vaclavik et al., "Single-Laboratory Validation Study of a Method for Screening and Identification of Phosphodiesterase Type 5 Inhibitors in Dietary Ingredients and Supplements Using Liquid Chromatography/Quadrupole—Orbital Ion Trap Mass Spectrometry: First Action 2015.12," J AOAC Int., Jan.-Feb. 2016, 99(1):55-72.
Vymetalova et al., "5-Substituted 3-isopropyl-7-[4-(2-pyridyl)benzyl]amino-1(2)H-pyrazolo[4,3-d]pyrimidines with antiproliferative activity as potent and selective inhibitors of cyclin-dependent kinases," Eur J Med Chem., Mar. 3, 2016, 110:391-301.
Wang et al., "Activation of the hematopoietic progenitor kinase-1 (HPK1)-dependent, stress-activated c-Jun N-terminal kinase (JNK) pathway by transforming growth factor beta (TGF-beta)—activated kinase (TAK1), a kinase mediator of TGF beta signal transduction," J. Biol. Chem., Sep. 1997, 272(36): 22771-22775.
Wang et al., "Down-regulation of B cell receptor signaling by hematopoietic progenitor kinase 1 (HPK-1)—mediated phosphorylation and ubiquitination of activated B cell linker protein (BLNK)," J. Biol. Chem., Mar. 2012, 297(14): 11037-11048.
Wang et al., "Fragment-based identification and optimization of a class of potent pyrrolo [2,1-f][1,2,4]triazine MAP4K4 inhibitors," Boorg Med Chem Lett., 24(18):4546-4552, 2014.
Wang et al., "Synthesis and evaluation of human phosphodiesterases (PDE) 5 inhibitor analogs as trypanosomal PDE inhibitors. Part 1. Sildenafil analogs," Bioorg Med Chem Lett., Apr. 1, 2012, 22(7):2579-2581.

(56) References Cited

OTHER PUBLICATIONS

Weinmann et al., "Identification of lorazepam and sildenafil as examples for the application of LC/ionspray—MS and MS-MS with mass spectra library searching in forensic toxicology," Forensic Sci Int., Sep. 11, 2000, 113(1-3):339-344.

Witherington et al., "5-Aryl-pyrazolo[3,4-b]pyridazines: Potent Inhibitors of Glycogen Synthase Kinase-3 (GSK-3)," Bioorganic & Medicinal Letters, 2003, 13: 1577-1580.

Witherington et al., "5-Aryl-pyrazolo[3,4-b]pyridazines: Potent Inhibitors of Glycogen Synthase Kinase-3 (GSK-3)," Bioorganic & Medicinal Letters, 2003, 13: 1581-1584.

Wislicenus "Adolph Strecker's Short Textbook of Organic Chemistry," 1881, Spottiswood, London, pp. 38-39.

Xu et al., "Design, synthesis and biological evaluation of euterated nintedanib for improving pharmacokinetic properties," J. Labelled Comp. Radiopharm., Jun. 2015, 58(7): 308-312.

Yang et al., "Highly efficient synthesis of fused bicyclic 2,3-diarylpyrimidin-4(3H)-ones via Lewis acid assisted cyclization reaction," Tetrahedron Letters, Mar. 10, 2008, 49(11):1725-1728.

Yeo et al., "New metabolites of hongdenafil, homosildenafil and hydroxyhomosildenafil," J Pharm Biomed Anal., Feb. 5, 2018, 149:586-590.

Zhang et al., "Anti-angiogenic effects of novel cyclin-dependent kinase inhibitors with a pyrazolo[4,3-d]pyrimidine scaffold," Br J Pharmacol., Sep. 2016, 173(17):2645-2656.

Zhou et al., "Hematopoietic progenitor kinase 1 is a component of transforming growth factor beta-induced c-Jun N-terminal kinase signaling cascade," J. Biol. Chem., May 1999, 274(19): 13133-13138.

Zhu et al., "Design and Synthesis of Pyridine-pyrazolopyridine based inhibitors of protein kinase B/Akt," Bioorganic and Medicinal Chemistry, Jan. 17, 2007, 15: 2441-2452.

Zhu et al., "Characterization of TPN729 metabolites in humans using ultra-performance liquid chromatography/quadrupole time-of-flight mass spectrometry," J Pharm Biomed Anal., Jan. 5, 2016, 117:217-226.

Zhu et al., "Syntheses of potent, selective, and orally bioavailable indazole-pyridine series of protein kinase B/Akt inhibitors with reduced hypotension," J Med Chem., Jun. 28, 2007, 50(13):2990-3003.

Literature and Patent Chemical Structure Search, Science IP, The CAS Search Service, Jul. 1, 2016, 441 pages.

Literature and Patent Chemical Structure Search, Science IP, The CAS Search Service, Jun. 30, 2016, 200 pages.

Structure 4: Substance Search Patent and Non-Patent Databases, Science IP, The CAS Search Service, Jun. 8, 2016, 820 pages.

Structure 3: Substance Search Patent and Non-Patent Databases, Science IP, The CAS Search Service, Jun. 7, 2016, 512 pages.

Structure 2: Substance Search Patent and Non-Patent Databases, Science IP, The CAS Search Service, Jun. 7, 2016, 833 pages.

Structure 1: Substance Search Patent and Non-Patent Databases, Science IP, The CAS Search Service, Jun. 6, 2016, 583 pages.

STN Search Report dated Aug. 17, 2016, 157 pages.

STN Search Report dated Aug. 25, 2016, 25 pages.

STN Search Report dated Aug. 30, 2016, 31 pages.

STN Search Report dated Aug. 31, 2016, 32 pages.

STN Search Report dated Jan. 27, 2017, 94 pages.

STN Search Report dated Sep. 5, 2017, 26 pages.

STN Search Report dated Sep. 5, 2017, 5 pages.

STN Search Report dated Jan. 23, 2018, 26 pages.

STN Search Report dated Apr. 25, 2018, 19 pages.

STN Search Report dated Apr. 9, 2018, 7 pages.

STN Search Report dated May 9, 2018, 16 pages.

Eurasian Office Action in Eurasian Application No. 201990665, dated Feb. 17, 2020, 5 pages.

International Preliminary Report on Patentability in International Application No. PCT/US2018/049908, dated Mar. 10, 2020, 8 pages.

McMahon "VEGF Receptor Signaling in Tumor Angiogenesis," The Oncologist, 2000, 5(suppl 1):3-10.

Pinedo et al., "Translational Research: The Role of VEGF in Tumor Angiogenesis," The Oncologist, 2000, 5(suppl 1):1-2.

STN Search Report dated Jan. 22, 2018, 9 pages.

PYRAZOLOPYRIDINE COMPOUNDS AND USES THEREOF

FIELD OF THE INVENTION

The disclosure provides compounds as well as their compositions and methods of use. The compounds modulate hematopoietic progenitor kinase 1 (HPK1) activity and are useful in the treatment of various diseases including cancer.

BACKGROUND OF THE INVENTION

Hematopoietic progenitor kinase 1 (HPK1) originally cloned from hematopoietic progenitor cells is a member of MAP kinase kinase kinase kinases (MAP4Ks) family, which includes MAP4K1/HPK1, MAP4K2/GCK, MAP4K3/GLK, MAP4K4/HGK, MAP4K5/KHS, and MAP4K6/MINK (Hu, M. C., et al., Genes Dev, 1996. 10(18): p. 2251-64). HPK1 is of particular interest because it is predominantly expressed in hematopoietic cells such as T cells, B cells, macrophages, dendritic cells, neutrophils, and mast cells (Hu, M. C., et al., Genes Dev, 1996. 10(18): p. 2251-64; Kiefer, F., et al., EMBO J, 1996. 15(24): p. 7013-25). HPK1 kinase activity has been shown to be induced upon activation of T cell receptors (TCR) (Liou, J., et al., Immunity, 2000. 12(4): p. 399-408), B cell receptors (BCR) (Liou, J., et al., Immunity, 2000. 12(4): p. 399-408), transforming growth factor receptor (TGF-βR) (Wang, W., et al., J Biol Chem, 1997. 272(36): p. 22771-5; Zhou, G., et al., J Biol Chem, 1999. 274(19): p. 13133-8), or $G_s$-coupled PGE2 receptors (EP2 and EP4) (Ikegami, R., et al., J Immunol, 2001. 166(7): p. 4689-96). As such, HPK1 regulates diverse functions of various immune cells.

HPK1 is important in regulating the functions of various immune cells and it has been implicated in autoimmune diseases and anti-tumor immunity (Shui, J. W., et al., Nat Immunol, 2007. 8(1): p. 84-91; Wang, X., et al., J Biol Chem, 2012. 287(14): p. 11037-48). HPK1 knockout mice were more susceptible to the induction of experimental autoimmune encephalomyelitis (EAE) (Shui, J. W., et al., Nat Immunol, 2007. 8(1): p. 84-91). In human, HPK1 was downregulated in peripheral blood mononuclear cells of psoriatic arthritis patients or T cells of systemic lupus erythematosus (SLE) patients (Batliwalla, F. M., et al., Mol Med, 2005. 11(1-12): p. 21-9). Those observations suggested that attenuation of HPK1 activity may contribute to autoimmunity in patients. Furthermore, HPK1 may also control anti-tumor immunity via T cell-dependent mechanisms. In the PGE2-producing Lewis lung carcinoma tumor model, the tumors developed more slowly in HPK1 knockout mice as compared to wild-type mice (see US 2007/0087988). In addition, it was shown that adoptive transfer of HPK1 deficient T cells was more effective in controlling tumor growth and metastasis than wild-type T cells (Alzabin, S., et al., Cancer Immunol Immunother, 2010. 59(3): p. 419-29). Similarly, BMDCs from HPK1 knockout mice were more efficient to mount a T cell response to eradicate Lewis lung carcinoma as compared to wild-type BMDCs (Alzabin, S., et al., J Immunol, 2009. 182(10): p. 6187-94). These data, in conjunction with the restricted expression of HPK1 in hematopoietic cells and lack of effect on the normal development of immune cells, suggest that HPK1 may be an excellent drug target for enhancing antitumor immunity. Accordingly, there is a need for new compounds that modulate HPK1 activity.

SUMMARY

The present disclosure provides, inter alia, a compound of Formula (I):

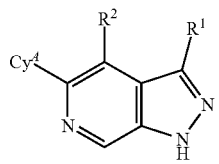

or a pharmaceutically acceptable salt thereof, wherein constituent variables are defined herein.

The present disclosure further provides a pharmaceutical composition comprising a compound of the disclosure, or a pharmaceutically acceptable salt thereof, and at least one pharmaceutically acceptable carrier or excipient.

The present disclosure further provides methods of inhibiting HPK1 activity, which comprises administering to an individual a compound of the disclosure, or a pharmaceutically acceptable salt thereof.

The present disclosure further provides methods of treating a disease or disorder in a patient comprising administering to the patient a therapeutically effective amount of a compound of the disclosure, or a pharmaceutically acceptable salt thereof.

DETAILED DESCRIPTION

Compounds

The present disclosure provides, a compound of Formula (I):

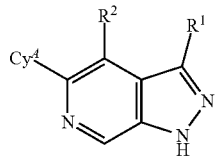

or a pharmaceutically acceptable salt thereof, wherein:

$R^1$ is selected from $Cy^1$, $C_{1-6}$ alkyl, $C_{2-6}$ alkenyl, $C_{2-6}$ alkynyl, $C_{1-6}$ haloalkyl, halo, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NOR^a)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, and $S(O)_2NR^cR^d$; wherein said $C_{1-6}$ alkyl, $C_{2-6}$ alkenyl and $C_{2-6}$ alkynyl are each optionally substituted with 1, 2, 3, or 4 substituents independently selected from $R^{10}$;

$Cy^1$ is selected from $C_{3-10}$ cycloalkyl, 4-10 membered heterocycloalkyl, $C_{6-10}$ aryl and 5-10 membered heteroaryl, wherein each 4-10 membered heterocycloalkyl and 5-10 membered heteroaryl has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl and 4-10 membered heterocycloalkyl is optionally substituted by oxo to form a carbonyl group; and wherein the $C_{3-10}$ cycloalkyl, 4-10 membered heterocycloalkyl, $C_{6-10}$ aryl and 5-10 membered heteroaryl are each optionally substituted with 1, 2, 3 or 4 substituents independently selected from $R^{10}$;

$Cy^4$ is $C_{6-10}$ aryl optionally substituted with 1, 2, 3 or 4 substituents independently selected from $R^{20}$;

$R^2$ is selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, CN, $SR^{a7}$, $C(O)R^{b7}$, $C(O)NR^{c7}R^{d7}$, $C(O)OR^{a7}$, $NR^{c7}R^{d7}$, $NR^{c7}C(O)R^{b7}$, $NR^{c7}C(O)OR^{d7}$, $NR^{c7}S(O)R^{b7}$, $NR^{c7}S(O)_2R^{b7}$, $NR^{c7}S(O)_2NR^{c7}R^{d7}$, $S(O)R^{b7}$, $S(O)NR^{c7}R^{d7}$, $S(O)_2R^{b7}$, and $S(O)_2NR^{c7}R^{d7}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{30}$;

each $R^{10}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$ $C(=NR^{e1})R^{b1}$, $C(=NOR^{a1})R^{b1}$, $C(=NR^{e1})NR^{c1}R^{d1}$, $NR^{c1}C(=NR^{c1})NR^{c1}R^{d1}$, $NR^{c1}S(O)R^{b1}$, $NR^{c1}S(O)_2R^{b1}$, $NR^{c1}R^{d1}$, $S(O)R^{b1}$, $S(O)NR^{c1}R^{d1}$, $S(O)_2R^{b1}$, and $S(O)_2NR^{c1}R^{d1}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{11}$;

or two $R^{10}$ substituents taken together with the carbon atom to which they are attached form a spiro 3-7-membered heterocycloalkyl ring, or a spiro $C_{3-6}$ cycloalkyl ring; wherein each spiro 3-7-membered heterocycloalkyl ring has at least one ring-forming carbon atom and 1, 2 or 3, ring-forming heteroatoms independently selected from N, O, and S; wherein a ring-forming carbon atom of each spiro 3-7-membered heterocycloalkyl ring is optionally substituted by oxo to form a carbonyl group; and wherein the spiro 3-7-membered heterocycloalkyl ring and spiro $C_{3-6}$ cycloalkyl ring are each optionally substituted with 1, 2, 3 or 4 substituents independently selected from $R^{11}$;

each $R^{11}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ alkylene, 5-10 membered heteroaryl-$C_{1-3}$ alkylene, halo, CN, $OR^{a3}$, $SR^{a3}$, $C(O)R^{b3}$, $C(O)NR^{c3}R^{d3}$, $C(O)OR^{a3}$, $NR^{c3}R^{d3}$, $NR^{c3}C(O)R^{b3}$, $NR^{c3}C(O)OR^{a3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{12}$;

each $R^{12}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, $C_{6-10}$ aryl, 5-10 membered heteroaryl, 4-7 membered heterocycloalkyl, halo, CN, $OR^{a5}$, $SR^{a5}$, $C(O)R^{b5}$, $C(O)NR^{c5}R^{d5}$, $C(O)OR^{a5}$, $NR^{c5}R^{d5}$, $NR^{c5}C(O)R^{b5}$, $NR^{c5}C(O)OR^{a5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, and $S(O)_2NR^{c3}R^{d5}$; wherein said $C_{1-6}$ alkyl, $C_{2-6}$ alkenyl, $C_{2-6}$ alkynyl, $C_{3-6}$ cycloalkyl, $C_{6-10}$ aryl, 5-10 membered heteroaryl and 4-7 membered heterocycloalkyl are each optionally substituted with 1, 2, 3, or 4 substituents independently selected from $R^g$;

each $R^{20}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NOR^{a2})R^{b2}$, $C(=NR^{e2})NR^{c2}R^{d2}$, $NR^{c2}C(=NR^{e2})NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{21}$;

or two adjacent $R^{20}$ substituents on the $Cy^4$ ring, taken together with the atoms to which they are attached, form a fused $C_{3-7}$ cycloalkyl ring; wherein a ring-forming carbon atom of the fused $C_{3-7}$ cycloalkyl ring is optionally substituted by oxo to form a carbonyl group; and wherein the fused $C_{3-7}$ cycloalkyl ring is optionally substituted with 1, 2, 3 or 4 substituents independently selected from $R^{21}$;

each $R^{21}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, CN, $OR^{a4}$; $SR^{a4}$, $C(O)R^{b4}$, $C(O)NR^{c4}R^{d4}$, $C(O)OR^{a4}$, $NR^{c4}R^{d4}$, $NR^{c4}C(O)R^{b4}$, $NR^{c4}C(O)OR^{a4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{22}$;

or two $R^{21}$ substituents taken together with the carbon atom to which they are attached form a spiro $C_{3-7}$ cycloalkyl ring; wherein a ring-forming carbon atom of the spiro $C_{3-7}$ cycloalkyl ring is optionally substituted by oxo to form a carbonyl group; and wherein the spiro $C_{3-7}$ cycloalkyl ring is optionally substituted with 1, 2, 3 or 4 substituents independently selected from $R^{22}$;

each $R^{22}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, CN, $OR^{a6}$, $SR^{a6}$, $C(O)R^{b6}$, $C(O)NR^{c6}R^{d6}$, $C(O)OR^{a6}$, $NR^{c6}R^{d6}$, $NR^{c6}C(O)R^{b6}$, $NR^{c6}C(O)OR^{a6}$, $NR^{c6}S(O)R^{b6}$, $NR^{c6}S(O)_2R^{b6}$, $NR^{c6}S(O)_2NR^{c6}R^{d6}$, $S(O)R^{b6}$, $S(O)NR^{c6}R^{d6}$, $S(O)_2R^{b6}$, and $S(O)_2NR^{c6}R^{d6}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^g$;

each $R^{30}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, CN, $OR^{a8}$, $SR^{a8}$, $C(O)R^{b8}$, $C(O)NR^{c8}R^{d8}$, $C(O)OR^{a8}$, $NR^{c8}R^{d8}$, $NR^{c8}C(O)R^{b8}$, $NR^{c8}C(O)OR^{a8}$, $NR^{c8}S(O)R^{b8}$, $NR^{c8}S(O)_2R^{b8}$, $NR^{c8}S(O)_2NR^{c8}R^{d8}$, $S(O)R^{b8}$, $S(O)NR^{c8}R^{d8}$, $S(O)_2R^{b8}$, and $S(O)_2NR^{c8}R^{d8}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^g$;

each $R^a$ and $R^c$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{10}$;

each $R^d$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{10}$;

or any $R^c$ and $R^d$ attached to the same N atom, together with the N atom to which they are attached, form a 4-10 membered heterocycloalkyl group optionally substituted with 1, 2, 3 or 4 substituents independently selected from $R^{10}$;

each $R^b$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{10}$;

each $R^e$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, alkyl)carbamyl, aminosulfonyl, alkylaminosulfonyl and di($C_{1-6}$ alkyl)aminosulfonyl;

each $R^{a1}$, $R^{c1}$ and $R^{d1}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{11}$;

or any $R^{c1}$ and $R^{d1}$ attached to the same N atom, together with the N atom to which they are attached, form a 4-, 5-, 6- or 7-membered heterocycloalkyl group optionally substituted with 1, 2, 3 or 4 substituents independently selected from $R^{11}$;

each $R^{b1}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{11}$;

each $R^{e1}$ is independently selected from H, CN, $C_{1-6}$ alkyl, $C_{1-6}$ haloalkyl, $C_{1-6}$ alkylthio, alkylsulfonyl, $C_{1-6}$ alkylcarbonyl, $C_{1-6}$ alkylaminosulfonyl, carbamyl, $C_{1-6}$ alkylcarbamyl, alkyl)carbamyl, aminosulfonyl, $C_{1-6}$ alkylaminosulfonyl and di($C_{1-6}$ alkyl)aminosulfonyl;

each $R^{a2}$, $R^{c2}$ and $R^{d2}$, is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{21}$;

or any $R^{c2}$ and $R^{d2}$ attached to the same N atom, together with the N atom to which they are attached, form a 4-, 5-, 6- or 7-membered heterocycloalkyl group optionally substituted with 1, 2, 3 or 4 substituents independently selected from $R^{21}$;

each $R^{b2}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{21}$;

each $R^{e2}$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{a3}$, $R^{c3}$ and $R^{d3}$, is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl, $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{12}$;

or any $R^{c3}$ and $R^{d3}$ attached to the same N atom, together with the N atom to which they are attached, form a 4-, 5-, 6- or 7-membered heterocycloalkyl group optionally substituted with 1, 2 or 3 substituents independently selected from $R^{12}$;

each $R^{b3}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl, $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{12}$;

each $R^{a4}$, $R^{c4}$ and $R^{d4}$, is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl, $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{22}$;

or any $R^{c4}$ and $R^{d4}$ attached to the same N atom, together with the N atom to which they are attached, form a 4-, 5-, 6- or 7-membered heterocycloalkyl group optionally substituted with 1, 2 or 3 substituents independently selected from $R^{22}$;

each $R^{b4}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl, $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{22}$;

each $R^{a5}$, $R^{c5}$ and $R^{d5}$, is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{b5}$ is independently selected from $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{a6}$, $R^{c6}$ and $R^{d6}$ is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{b6}$ is independently selected from $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{a7}$, $R^{c7}$, and $R^{d7}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{30}$;

or any $R^{c7}$ and $R^{d7}$ attached to the same N atom, together with the N atom to which they are attached, form a 4-, 5-, 6- or 7-membered heterocycloalkyl group optionally substituted with 1, 2 or 3 substituents independently selected from $R^{30}$;

each $R^{b7}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{30}$;

each $R^{a8}$, $R^{c8}$ and $R^{d8}$, is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl, $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^g$;

or any $R^{c8}$ and $R^{d8}$ attached to the same N atom, together with the N atom to which they are attached, form a 4-, 5-, 6- or 7-membered heterocycloalkyl group optionally substituted with 1, 2 or 3 substituents independently selected from $R^g$;

each $R^{b8}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl, $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-6}$ haloalkyl, $C_{3-6}$ cycloalkyl, $C_{3-6}$ cycloalkyl-$C_{1-2}$ alkylene, $C_{1-6}$ alkoxy, $C_{1-6}$ haloalkoxy, $C_{1-3}$ alkoxy-$C_{1-3}$ alkyl, $C_{1-3}$ alkoxy-$C_{1-3}$ alkoxy, HO—$C_{1-3}$ alkoxy, HO—$C_{1-3}$ alkyl, cyano-$C_{1-3}$ alkyl, $H_2N$—$C_{1-3}$ alkyl, amino, $C_{1-6}$ alkylamino, di($C_{1-6}$alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl) carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$alkyl)aminocarbonylamino;

provided that
1) $R^1$ is other than $CH_3$;
2) $R^b$ is other than unsubstituted or substituted piperidine;
3) $R^b$ is other than unsubstituted or substituted propyl;
4) when $R^b$ is phenyl, then $R^{10}$ is other than pyrrolidin-1-ylmethyl; and
5) when $Cy^4$ is phenyl or halo-phenyl, then $R^b$ is other than cyclopropyl and cyclopentyl.

In some embodiments, $Cy^4$ is $C_{6-10}$ aryl optionally substituted with 1, 2, or 3 substituents independently selected from $R^{20}$.

In some embodiments, $Cy^4$ is phenyl optionally substituted with 1, 2, 3, or 4 substituents independently selected from $R^{20}$. In some embodiments, $Cy^4$ is phenyl optionally substituted with 1, 2, or 3 substituents independently selected from $R^{20}$.

In some embodiments, $Cy^4$ is phenyl optionally substituted with 1, 2, 3, or 4 substituents independently selected from $R^{20}$; wherein optionally two adjacent $R^{20}$ substituents on the $Cy^4$ ring, taken together with the atoms to which they are attached, form a fused $C_{3-7}$ cycloalkyl ring; wherein a ring-forming carbon atom of each fused $C_{3-7}$ cycloalkyl ring is optionally substituted by oxo to form a carbonyl group; and wherein the fused $C_{3-7}$ cycloalkyl ring are each optionally substituted with 1, 2, 3 or 4 substituents independently selected from $R^{21}$.

In some embodiments, each $R^{20}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, 4-10 membered heterocycloalkyl-$C_{1-3}$ alkylene, $C_{6-10}$ aryl, 5-10 membered heteroaryl, halo, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$; wherein said $C_{1-6}$ alkyl, $C_{2-6}$ alkenyl, $C_{2-6}$ alkynyl, $C_{3-10}$ cycloalkyl, 4-10 membered heterocycloalkyl, 4-10 membered heterocycloalkyl-$C_{1-3}$ alkylene, $C_{6-10}$ aryl, and 5-10 membered heteroaryl are each optionally substituted with 1, 2, or 3 substituents independently selected from $R^{21}$; or two adjacent $R^{20}$ substituents on the $Cy^4$ ring, taken together with the atoms to which they are attached, form a fused $C_{3-7}$ cycloalkyl ring; wherein a ring-forming carbon atom of each fused $C_{3-7}$ cycloalkyl ring is optionally substituted by oxo to form a carbonyl group; and wherein the fused $C_{3-7}$ cycloalkyl ring are each optionally substituted with 1, 2, 3 or 4 substituents independently selected from $R^{21}$.

In some embodiments, each $R^{20}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}S(O)R^{b2}$, $NR^{c2}S(O)_2R^{b2}$, $NR^{c2}S(O)_2NR^{c2}R^{d2}$, $S(O)_2R^{b2}$, and $S(O)_2NR^{c2}R^{d2}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, and 5-10 membered heteroaryl are each optionally substituted with 1, 2, or 3 substituents independently selected from $R^{21}$; or two adjacent $R^{20}$ substituents on the $Cy^A$ ring, taken together with the atoms to which they are attached, form a fused $C_{3-7}$ cycloalkyl ring; wherein a ring-forming carbon atom of each fused $C_{3-7}$ cycloalkyl ring is optionally substituted by oxo to form a carbonyl group; and wherein the fused $C_{3-7}$ cycloalkyl ring are each optionally substituted with 1, 2, 3 or 4 substituents independently selected from $R^{21}$.

In some embodiments, each $R^{20}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, 4-10 membered heterocycloalkyl-$C_{1-3}$ alkylene, $C_{6-10}$ aryl, 5-10 membered heteroaryl, halo, $OR^{a2}$, $C(O)R^{b2}$, $C(O)NR^{c2}R^{d2}$, $C(O)OR^{a2}$, $OC(O)NR^{c2}R^{d2}$, $NR^{c2}C(O)R^{b2}$, $NR^{c2}C(O)OR^{a2}$, and $NR^{c2}C(O)NR^{c2}R^{d2}$; wherein said $C_{1-6}$ alkyl, $C_{2-6}$ alkenyl, $C_{2-6}$ alkynyl, $C_{3-10}$ cycloalkyl, 4-10 membered heterocycloalkyl, 4-10 membered heterocycloalkyl-$C_{1-3}$ alkylene, $C_{6-10}$ aryl, and 5-10 membered heteroaryl are each optionally substituted with 1, 2, or 3 substituents independently selected from $R^{21}$; or two adjacent $R^{20}$ substituents on the $Cy^A$ ring, taken together with the atoms to which they are attached, form a fused $C_{3-7}$ cycloalkyl ring; wherein a ring-forming carbon atom of each fused $C_{3-7}$ cycloalkyl ring is optionally substituted by oxo to form a carbonyl group; and wherein the fused $C_{3-7}$ cycloalkyl ring are each optionally substituted with 1, 2, 3 or 4 substituents independently selected from $R^{21}$.

In some embodiments, each $R^{20}$ is independently selected from $C_{1-6}$ alkyl, $C_{2-6}$ alkenyl, $C_{2-6}$ alkynyl, C, haloalkyl, $C_{3-10}$ cycloalkyl, 4-10 membered heterocycloalkyl, $C_{6-10}$ aryl, 5-10 membered heteroaryl, halo, $OR^{a2}$, $C(O)R^{b2}$, $C(O)NR^{c2}R^{d2}$, $C(O)OR^{a2}$, $NR^{c2}R^{d2}$, $NR^{c2}C(O)R^{b2}$, and $NR^{c2}C(O)OR^{a2}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, and 5-10 membered heteroaryl are each optionally substituted with 1, 2, or 3 substituents independently selected from $R^{21}$; or two adjacent $R^{20}$ substituents on the $Cy^A$ ring, taken together with the atoms to which they are attached, form a fused $C_{3-7}$ cycloalkyl ring; wherein a ring-forming carbon atom of each fused $C_{3-7}$ cycloalkyl ring is optionally substituted by oxo to form a carbonyl group; and wherein the fused $C_{3-7}$ cycloalkyl ring are each optionally substituted with 1, 2, 3 or 4 substituents independently selected from $R^{21}$.

In some embodiments, each $R^{20}$ is independently selected from $C_{1-6}$ alkyl, $C_{1-6}$ haloalkyl, $C_{3-10}$ cycloalkyl, halo, 4-10 membered heterocycloalkyl, 4-10 membered heterocycloalkyl-$C_{1-3}$ alkylene, $OR^{a2}$, $C(O)R^{b2}$, $C(O)NR^{c2}R^{d2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, and $NR^{c2}C(O)NR^{c2}R^{d2}$; wherein said $C_{1-6}$ alkyl, $C_{3-10}$ cycloalkyl, 4-10 membered heterocycloalkyl, and 4-10 membered heterocycloalkyl-$C_{1-3}$ alkylene are each optionally substituted with 1 or 2 substituents independently selected from $R^{21}$; or two adjacent $R^{20}$ substituents on the $Cy^A$ ring, taken together with the atoms to which they are attached, form a fused $C_{3-7}$ cycloalkyl ring; and wherein the fused $C_{3-7}$ cycloalkyl ring is optionally substituted with 1, 2, 3 or 4 substituents independently selected from $R^{21}$.

In some embodiments, each $R^{20}$ is independently selected from $C_{1-6}$ alkyl, $C_{1-6}$ haloalkyl, $C_{3-10}$ cycloalkyl, halo, and $OR^{a2}$; wherein said $C_{1-6}$ alkyl and $C_{3-10}$ cycloalkyl are each optionally substituted with 1 or 2 substituents independently selected from $R^{21}$; or two adjacent $R^{20}$ substituents on the $Cy^A$ ring, taken together with the atoms to which they are attached, form a fused $C_{3-7}$ cycloalkyl ring; and wherein the fused $C_{3-7}$ cycloalkyl ring is optionally substituted with 1, 2, 3 or 4 substituents independently selected from $R^{21}$.

In some embodiments, each $R^{20}$ is independently selected from $C_{1-6}$ alkyl, $C_{1-6}$ haloalkyl, 4-10 membered heterocycloalkyl, 4-10 membered heterocycloalkyl-$C_{1-3}$ alkylene, and halo; wherein said $C_{1-6}$ alkyl, 4-10 membered heterocycloalkyl, and 4-10 membered heterocycloalkyl-$C_{1-3}$ alkylene are each optionally substituted with 1 or 2 substituents independently selected from $R^{21}$; or two adjacent $R^{20}$ substituents on the $Cy^A$ ring, taken together with the atoms to which they are attached, form a fused $C_{3-7}$ cycloalkyl ring; and wherein the fused $C_{3-7}$ cycloalkyl ring is optionally substituted with 1, 2, 3 or 4 substituents independently selected from $R^{21}$.

In some embodiments, each $R^{20}$ is independently selected from $C_{1-6}$ alkyl optionally substituted with 1 or 2 substituents independently selected from $R^{21}$. In some embodiments, each $R^{21}$ is independently selected from 4-10 membered heterocycloalkyl or $NR^{c4}R^{d4}$. In some embodiments, each $R^{c4}$ and $R^{d4}$, is independently selected from H or $C_{1-6}$ alkyl. In some embodiments, $R^{20}$ is $CH_2$—$NH(C_{1-6}$ alkyl), 4-6 membered heterocycloalkyl, $CH_2$—(4-6 membered heterocycloalkyl). In some embodiments, $R^{20}$ is $CH_2NHCH_3$, $CH_2NH(i$-propyl), $CH_2$-azetidinyl, $CH_2NH(CH_2)CH_3$, or $CH(CH_3)(NHCH_3)$.

In some embodiments, $R^{20}$ is halo, $C_{1-6}$ alkyl, $C_{1-6}$ haloalkyl, $CH_2$—$NH(C_{1-6}$ alkyl), 4-6 membered heterocycloalkyl, or $CH_2$-(4-6 membered heterocycloalkyl). In some embodiments, $R^{20}$ is fluoro, methyl, trifluoromethyl, $CH_2NHCH_3$, $CH_2NH(i$-propyl), $CH_2$-azetidinyl, $CH_2NH(CH_2)CH_3$, or $CH(CH_3)(NHCH_3)$.

In some embodiments, each $R^{20}$ is independently selected from methyl, trifluoromethyl, cyclopropyl substituted with methanamine, fluoro, chloro, hydroxy, methoxy, ethoxy, $C(O)NH(CH_2)_2OCH_3$, CO-(3-methoxyazetidin-1-yl), NHC(O)-cyclobutyl, NHC(O)-benzyl, methylamino, dimethylamino, NHC(O)CH$_2$-(pyrrolidin-1-yl), NHC(O)-(1-methyl-1H-pyrazol-4-yl), NH(CO)CH$_2$-(cyclopentyl), NHC(O)CH$_2$-(pyridin-3-yl), NHC(O)CH$_2$-(7-azabicyclo[2.2.1]heptan-7-yl), NHC(O)-(7-oxa-2-azaspiro[3.5]nonan-2-yl), NHC(O)CH(CH$_3$)-(pyrrolidin-1-yl), NHC(O)NH(CH$_2$)$_2$OCH$_3$, NHC(O)CH$_2$-(azetidin-1-yl), NHC(O)CH$_2$-(3,3-dimethylazetidin-1-yl), NHC(O)O-(1-methylpiperidin-4-yl), NHC(O)CH$_2$-(dimethylamino), NHC(O)CH$_2$-((1R,4S)-2-azabicyclo[2.2.1]heptan-2-yl), NHC(O)(CH$_2$)$_2$-(dimethylamino), NHC(O)CH$_2$CN, (methylamino)methyl, azetidin-1-ylmethyl, CH$_2$NH-(tetrahydro-2H-pyran-4-yl), (isopropylamino)methyl, cyclobutyl-NHCH(CH$_3$)$_2$, (methylamino)ethyl, (CH$_2$)$_2$NH-(tetrahydro-2H-pyran-4-yl), (CH$_2$)$_2$NH-(1-isopropylazetidin-3-yl), OCH$_2$-(azetidin-2-yl), tetrahydro-2H-pyran-4-yloxy, OCH$_2$-(pyridin-4-yl), OC(O)N(CH$_3$)$_2$, OC(O)-(morpholin-4-yl), CH$_2$NH-(pyridin-5-yl), CH$_2$NH-(1-methyl-1H-pyrazol-3-yl), CH$_2$NH(CH$_2$)$_2$OH, CH$_2$NH-cyclopropyl, (3-methoxypiperidin-1-yl)methyl, (ethylamino)methyl, pyrrolidin-1-ylmethyl, 3-methoxyazetidin-1-yl)methyl, pyrrolidin-2-yl, 1-methylpyrrolidin-2-yl, piperidin-2-yl, CH$_2$NHCH$_2$CF$_3$, CH$_2$NH-(3-cyclobutan-1-ol), (1-pyrrolidin-3-ol)methyl, CH$_2$NHCH$_2$C(CH$_3$)$_2$OH, CH$_2$NHCH$_2$-(1-methyl-1H-imidazol-4-yl), CH$_2$NHCH$_2$-(oxazol-4-yl), CH$_2$NHCH$_2$CN, CH(CH$_3$)NH(CH$_3$), CH$_2$NHC(O)CH$_3$, CH$_2$NHC(O)O (CH$_3$), difluoromethoxy, cyanomethyl, aminomethyl, (hydroxyl)methyl, amino, CH$_2$(3,3-dimethylazetidin-1-yl), CH$_2$NH-(3-methoxycyclobutyl), CH$_2$NHCH$_2$-(1-methylcyclopropyl), and morpholinyl.

In some embodiments, each $R^{20}$ is independently selected from methyl, trifluoromethyl, cyclopropyl substituted with methanamine, fluoro, chloro, hydroxy, methoxy, and ethoxy. For example, each $R^{20}$ is independently methoxy or fluoro.

In some embodiments, Cy$^A$ is selected from 2-fluoro-6-methoxyphenyl, 1-[1-(3-fluoro-5-phenyl)cyclopropyl]methanamine, 2,6-difluorophenyl, 2,6-dimethylphenyl, 2,4,6-trifluorophenyl, 2-chloro-6-fluorophenyl, 1-hydroxy-3,5-difluoro-phen-4-yl, 2-fluoro-6-methylphenyl, 2-ethoxy-6-fluorophenyl, 2-chloro-6-methoxyphenyl, and 2-fluoro-6-(trifluoromethyl)phenyl.

In some embodiments, $R^1$ is selected from Cy$^1$, C$_{1-6}$ alkyl, C$_{2-6}$ alkenyl, C$_{2-6}$ alkynyl, C$_{1-6}$ haloalkyl, halo, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)OR$^a$, NR$^c$S(O)R$^b$, NR$^c$S(O)$_2$R$^b$, S(O)R$^b$, S(O)NR$^c$R$^d$, and S(O)$_2$NR$^c$R$^d$; wherein said C$_{1-6}$ alkyl, C$_{2-6}$ alkenyl and C$_{2-6}$ alkynyl are each optionally substituted with 1, 2, 3, or 4 substituents independently selected from R$^{10}$.

In some embodiments, $R^1$ is selected from Cy$^1$, C$_{1-6}$ alkyl, C$_{2-6}$ alkenyl, C$_{2-6}$ alkynyl, C$_{1-6}$ haloalkyl, halo, OR$^a$, C(O)R$^b$, C(O)NR$^c$R$^d$, C(O)OR$^a$, NR$^c$R$^d$, NR$^c$C(O)R$^b$, and NR$^c$C(O)OR$^d$; wherein said C$_{1-6}$ alkyl, C$_{2-6}$ alkenyl and C$_{2-6}$ alkynyl are each optionally substituted with 1, 2, 3, or 4 substituents independently selected from R$^{10}$.

In some embodiments, $R^1$ is selected from Cy$^1$, C$_{2-6}$ alkenyl, C(O)NR$^c$R$^d$, NR$^c$R$^d$, and NR$^c$C(O)R$^b$; wherein said C$_{2-6}$ alkenyl is optionally substituted with 1, 2, 3, or 4 substituents independently selected from R$^{10}$.

In some embodiments, $R^1$ is selected from Cy$^1$, C(O)NR$^c$R$^d$, NR$^c$R$^d$, and NR$^c$C(O)R$^b$. In some embodiments, $R^1$ is selected from phenyl, pyridinyl, pyrazolyl, thiazolyl, C(O)NR$^c$R$^d$ and NR$^c$C(O)R$^b$; wherein the phenyl, pyridinyl, pyrazolyl, and thiazolyl are each optionally substituted with 1, 2 or 3 substituents independently selected from R$^{10}$.

In some embodiments:
each R$^c$ is independently selected from H, C$_{1-6}$ alkyl, C$_{2-6}$ alkenyl, C$_{2-6}$ alkynyl, and C$_{1-6}$ haloalkyl;
each R$^d$ is independently selected from C$_{1-6}$ alkyl, C$_{2-6}$ alkenyl, C$_{2-6}$ alkynyl, C$_{1-6}$ haloalkyl, and C$_{6-10}$ aryl; wherein said C$_{1-6}$ alkyl, C$_{2-6}$ alkenyl, C$_{2-6}$ alkynyl, and C$_{6-10}$ aryl are each optionally substituted with 1, 2, 3, or 4 substituents independently selected from R$^{10}$; and
each R$^b$ is independently selected from 7-10 membered heterocycloalkyl, C$_{6-10}$ aryl, and 5-10 membered heteroaryl; wherein said 7-10 membered heterocycloalkyl, C$_{6-10}$ aryl and 5-10 membered heteroaryl are each optionally substituted with 1, 2, 3, or 4 substituents independently selected from R$^{10}$.

In some embodiments:
each R$^c$ is H;
each R$^d$ is independently selected from C$_{1-6}$ alkyl and C$_{6-10}$ aryl; wherein said C$_{1-6}$ alkyl and C$_{6-10}$ aryl are each optionally substituted with 1 or 2 substituents independently selected from R$^{10}$; and
each R$^b$ is independently selected from 7-10 membered heterocycloalkyl, C$_{6-10}$ aryl, and 5-10 membered heteroaryl; wherein said 7-10 membered heterocycloalkyl, C$_{6-10}$ aryl and 5-10 membered heteroaryl are each optionally substituted with 1 or 2 substituents independently selected from R$^{10}$.

In some embodiments, $R^1$ is NR$^c$C(O)R$^b$. For example, R$^c$ can be H, C$_{1-6}$ alkyl, C$_{2-6}$ alkenyl, C$_{2-6}$ alkynyl, or C$_{1-6}$ haloalkyl; wherein said C$_{1-6}$ alkyl, C$_{2-6}$ alkenyl, and C$_{2-6}$ alkynyl of R$^c$ are each optionally substituted with 1, 2, 3, or 4 substituents independently selected from R$^{10}$ and R$^b$ can be selected from C$_{1-6}$ alkyl, C$_{2-6}$ alkenyl, C$_{2-6}$ alkynyl, C$_{1-6}$ haloalkyl, C$_{3-10}$ cycloalkyl, 4-10 membered heterocycloalkyl, C$_{6-10}$ aryl, and 5-10 membered heteroaryl; wherein said C$_{1-6}$ alkyl, C$_{2-6}$ alkenyl, C$_{2-6}$ alkynyl, C$_{3-10}$ cycloalkyl, 4-10 membered heterocycloalkyl, C$_{6-10}$ aryl and 5-10 membered heteroaryl of R$^b$ are each optionally substituted with 1, 2, 3, or 4 substituents independently selected from R$^{10}$. In certain embodiments, R$^c$ is H or C$_{1-6}$ alkyl; and R$^b$ is selected from C$_{3-10}$ cycloalkyl, 4-10 membered heterocycloalkyl, C$_{6-10}$ aryl, and 5-10 membered heteroaryl; wherein said C$_{3-10}$ cycloalkyl, 4-10 membered heterocycloalkyl, C$_{6-10}$ aryl and 5-10 membered heteroaryl are each optionally substituted with 1, 2, 3, or 4 substituents independently selected from R$^{10}$. In certain embodiments, R$^c$ is H; and R$^b$ is selected from 4-10 membered heterocycloalkyl, C$_{6-10}$ aryl, and 5-10 membered heteroaryl; wherein said 4-10 membered heterocycloalkyl, C$_{6-10}$ aryl and 5-10 membered heteroaryl are each optionally substituted with 1, 2, or 3 substituents independently selected from R$^{10}$.

In certain embodiments, R$^1$ is Cy$^1$. In certain embodiments, Cy$^1$ is selected from 4-10 membered heterocycloalkyl, C$_{6-10}$ aryl and 5-10 membered heteroaryl, wherein each 4-10 membered heterocycloalkyl and 5-10 membered heteroaryl has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl and 4-10 membered heterocycloalkyl is optionally substituted by oxo to form a carbonyl group; and wherein the 4-10 membered heterocycloalkyl, C$_{6-10}$ aryl and 5-10 membered heteroaryl are each optionally substituted with 1, 2, 3 or 4 substituents independently selected from R$^{10}$.

In some embodiments, Cy$^1$ is thiazolyl, isoxazolyl, piperazinonyl, 1,2,3,4-tetrahydroisoquinolinyl, piperazinyl, phenyl, pyrazolyl, pyridinyl, imidazolyl, or pyrimidinyl; each is optionally with 1, 2, 3 or 4 substituents independently selected from R$^{10}$.

In some embodiments, Cy$^1$ is pyrazolyl optionally with 1, 2, or 3 substituents independently selected from R$^{10}$. In some embodiments, Cy$^1$ is pyrazolyl optionally with 1 substituents independently selected from R$^{10}$. In some embodiments, R$^{10}$ is C$_{1-6}$ alkyl. In some embodiments, Cy$^1$ is pyrazolyl optionally substituted with C$_{1-6}$ alkyl (e.g., methyl or ethyl). In some embodiments, Cy$^1$ is 1-methyl-1H-pyrazol-4-yl. In some embodiments, Cy$^1$ is 1-ethyl-1H-pyrazol-4-yl.

In certain embodiments, Cy$^1$ is thiazolyl, isoxazolyl, piperazinonyl, 1,2,3,4-tetrahydroisoquinolinyl, piperazinyl, or phenyl; each is optionally with 1, 2, 3 or 4 substituents independently selected from R$^{10}$.

In certain embodiments, R$^1$ is C(O)NR$^c$R$^d$. In certain embodiments, R$^c$ is selected from H, C$_{1-6}$ alkyl, C$_{2-6}$ alkenyl, C$_{2-6}$ alkynyl, and C$_{1-6}$ haloalkyl; wherein said C$_{1-6}$ alkyl, C$_{2-6}$ alkenyl, and C$_{2-6}$ alkynyl of R$^c$ are each optionally substituted with 1, 2, 3, or 4 substituents independently selected from R$^{10}$; and R$^d$ is selected from C$_{3-10}$ cycloalkyl, 4-10 membered heterocycloalkyl, C$_{6-10}$ aryl and 5-10 membered heteroaryl; wherein said C$_{3-10}$ cycloalkyl, 4-10 membered heterocycloalkyl, $C_{6-10}$ aryl and 5-10 membered heteroaryl of $R^d$ are each optionally substituted with 1, 2, 3, or 4 substituents independently selected from $R^{10}$. In certain embodiments, $R^c$ is H; and $R^d$ is $C_{6-10}$ aryl optionally substituted with 1, 2, or 3 substituents independently selected from $R^{10}$.

In certain embodiments, $R^1$ is $NR^cR^d$. In certain embodiments, $R^c$ is selected from H, $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl, and $C_{2-6}$ alkynyl of $R^c$ are each optionally substituted with 1, 2, 3, or 4 substituents independently selected from $R^{10}$; and $R^d$ is selected from $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl, and $C_{2-6}$ alkynyl of $R^d$ are each optionally substituted with 1, 2, 3, or 4 substituents independently selected from $R^{10}$. In certain embodiments, $R^c$ is H; and $R^d$ is $C_{1-6}$ alkyl optionally substituted with 1, 2, or 3 substituents independently selected from $R^{10}$.

In certain embodiments, each $R^{10}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, CN, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, and 5-10 membered heteroaryl are each optionally substituted with 1, 2, 3, or 4 substituents independently selected from $R^{11}$.

In certain embodiments, each $R^{10}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, CN, $OR^{a1}$, $SR^{a1}$, $C(O)R^{b1}$, $C(O)NR^{c1}R^{d1}$, $C(O)OR^{a1}$, $NR^{c1}R^{d1}$, and $NR^{c1}C(O)R^{b1}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, and 5-10 membered heteroaryl are each optionally substituted with 1, 2, 3, or 4 substituents independently selected from $R^{11}$.

In some embodiments, each $R^{10}$ is independently selected from $C_{1-6}$ alkyl, $C_{3-10}$ cycloalkyl, 4-10 membered heterocycloalkyl, $C_{6-10}$ aryl, 5-10 membered heteroaryl, halo, CN, $OR^{a1}$, $C(O)NR^{c1}R^{d1}$, and $NR^{c1}R^{d1}$; wherein said $C_{1-6}$ alkyl, $C_{3-10}$ cycloalkyl, 4-10 membered heterocycloalkyl, $C_{6-10}$ aryl, and 5-10 membered heteroaryl are each optionally substituted with 1, 2, or 3 substituents independently selected from $R^{11}$.

In certain embodiments, each $R^{10}$ is independently selected from $C_{1-6}$ alkyl, $C_{3-10}$ cycloalkyl, 4-10 membered heterocycloalkyl, $C_{6-10}$ aryl, 5-10 membered heteroaryl, halo, CN, and $OR^{a1}$; wherein said $C_{1-6}$ alkyl, $C_{3-10}$ cycloalkyl, 4-10 membered heterocycloalkyl, $C_{6-10}$ aryl, and 5-10 membered heteroaryl are each optionally substituted with 1, 2, or 3 substituents independently selected from $R^{11}$.

In some embodiments, each is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, CN, $OR^{a3}$, $SR^{a3}$, $C(O)R^{b3}$, $C(O)NR^{c3}R^{d3}$, $C(O)OR^{a3}$, $NR^{c3}R^{d3}$, $NR^{c3}C(O)R^{b3}$, and $NR^{c3}C(O)OR^{a3}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{12}$.

In some embodiments, each $R^{11}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, CN, $OR^{a3}$, $C(O)R^{b3}$, $C(O)NR^{c3}R^{d3}$, $C(O)OR^{a3}$, $NR^{c3}R^{d3}$, and $NR^{c3}C(O)R^{b3}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, and 5-10 membered heteroaryl are each optionally substituted with 1, 2, 3, or 4 substituents independently selected from $R^{12}$.

In some embodiments, each $R^{11}$ is independently selected from $C_{1-6}$ alkyl, $C_{6-10}$ aryl, 5-10 membered heteroaryl, halo, CN, $OR^{a3}$, $C(O)OR^{a3}$; wherein said $C_{1-6}$ alkyl, $C_{6-10}$ aryl, and 5-10 membered heteroaryl are each optionally substituted with 1, 2, or 3 substituents independently selected from $R^{12}$.

In some embodiments, each $R^{10}$ is independently selected from methyl, bromo, fluoro, CN, ethyl, methoxy, 4-morpholinyl, 3-oxopiperazin-1-yl, 4-methylpiperazin-1-yl, 4-methyl-3-oxopiperazin-1-yl, 4-ethylpiperazin-1-yl, 3-oxo-4-(2,2,2-trifluoroethyl)piperazin-1-yl, 4-(methylsulfonyl)piperazin-1-yl, piperazin-1-yl, 4-isopropylpiperazin-1-yl, 4-cyclopropyl-3-oxopiperazin-1-yl, 4-(methylsulfonyl)piperazin-1-yl, 4-bromo-phenyl, 4-cyanophenyl, 4-pyridyl, methylaminocarbonyl, isopropylaminocarbonyl, 3-hydroxypyrrolidin-1-yl, 3-methoxypiperidin-1-yl, 1-methylpiperidin-4-yl, ethylmethylamino, cyclopropyl, ethyl, 2-cyanophenyl, tetrahydro-2H-pyran-4-yl, azetidin-3-yl, hydroxyethyl, 4-methoxypiperidin-1-yl, 3-fluoropyrrolidin-1-yl, 4-methylcarbonylpiperazin-1-yl, and 4-hydroxypiperidin-1-yl, 4-methoxycarbonylpiperazin-1-yl, amino, 2-hydroxypropylamino, (1-methyl-1H-pyrazol-5-yl)methylamino, and 3-cyanocyclopentylamino.

In certain embodiments, each $R^{10}$ is independently selected from methyl, bromo, fluoro, CN, ethyl, methoxy, 4-morpholinyl, 3-oxopiperazin-1-yl, 4-methylpiperazin-1-yl, 4-methyl-3-oxopiperazin-1-yl, 4-ethylpiperazin-1-yl, 3-oxo-4-(2,2,2-trifluoroethyl)piperazin-1-yl, 4-(methylsulfonyl)piperazin-1-yl, piperazin-1-yl, 4-isopropylpiperazin-1-yl, 4-cyclopropyl-3-oxopiperazin-1-yl, 4-(methylsulfonyl)piperazin-1-yl, 4-bromo-phenyl, 4-cyanophenyl, and 4-pyridyl.

In certain embodiments, $R^2$ is selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, halo, $OR^{a7}$, $C(O)R^{b7}$, $C(O)NR^{c7}R^{d7}$, $C(O)OR^{a7}$, $NR^{c7}R^{d7}$, $NR^{c7}C(O)R^{b7}$, and $NR^{c7}C(O)OR^{a7}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, and 5-10 membered heteroaryl are each optionally substituted with 1, 2, 3, or 4 substituents independently selected from $R^{30}$.

In certain embodiments, $R^2$ is selected from H, $C_{1-6}$ alkyl, $C_{2-6}$ alkenyl, $C_{2-6}$ alkynyl, $C_{1-6}$ haloalkyl, halo, $OR^{a7}$, $C(O)R^{b7}$, $C(O)NR^{c7}R^{d7}$, $C(O)OR^{a7}$, $NR^{c7}R^{d7}$, $NR^{c7}C(O)R^{b7}$, and $NR^{c7}C(O)OR^{a7}$; wherein said $C_{1-6}$ alkyl, $C_{2-6}$ alkenyl, and $C_{2-6}$ alkynyl are each optionally substituted with 1, 2, 3, or 4 substituents independently selected from $R^{30}$.

In certain embodiments, $R^2$ is selected from H, $C_{1-6}$ alkyl, $C_{2-6}$ alkenyl, $C_{2-6}$ alkynyl, $C_{1-6}$ haloalkyl, and halo.

In certain embodiments, $R^2$ is selected from H, $C_{1-6}$ alkyl, $C_{2-6}$ alkenyl, $C_{2-6}$ alkynyl, $C_{1-6}$ haloalkyl, halo, and $OR^{a7}$.

In certain embodiments, $R^2$ is H.

In some embodiments, provided herein is a compound having Formula II:

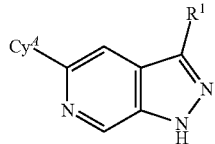
(II)

wherein Cy$^A$ and R$^1$ are as described herein, or a pharmaceutically acceptable salt thereof.

In some embodiments, provided herein is a compound having Formula III:

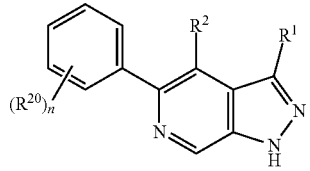
(III)

wherein n is 1, 2, 3, or 4; and R$^1$, R$^2$, and R$^{20}$ are as described herein; or a pharmaceutically acceptable salt thereof.

In some embodiments, provided herein is a compound having Formula IV:

(IV)

wherein n is 1, 2, 3, or 4; and R$^1$ and R$^{20}$ are as described herein; or a pharmaceutically acceptable salt thereof.

In some embodiments, provided herein is a compound having Formula Va, Formula Vb, Formula Vc, or Formula Vd:

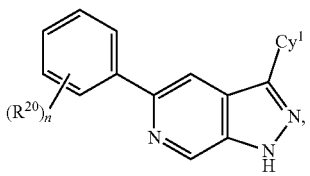
(Va)

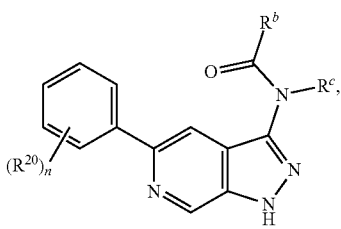
(Vb)

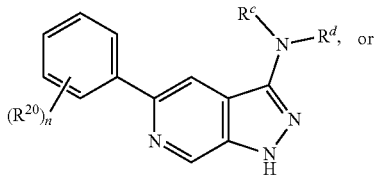
(Vc)

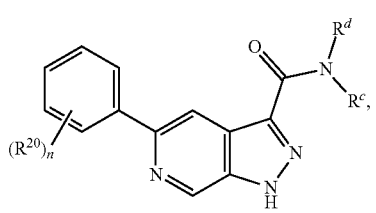
(Vd)

wherein n is 1, 2, 3, or 4; and R$^{20}$, Cy$^1$, R$^b$, R$^c$ and R$^d$ are as described herein; or a pharmaceutically acceptable salt thereof.

In some embodiments, provided herein is a compound having Formula Va:

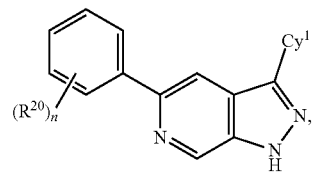
(Va)

wherein n is 1, 2, 3, or 4; and R$^{20}$ and Cy$^1$ are as described herein; or a pharmaceutically acceptable salt thereof.

In some embodiments, provided herein is a compound having Formula Vb:

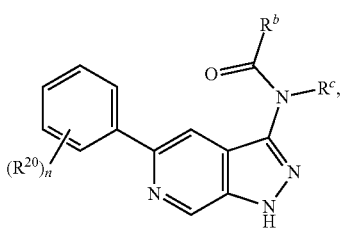
(Vb)

wherein n is 1, 2, 3, or 4; and R$^{20}$, R$^b$ and R$^c$ are as described herein; or a pharmaceutically acceptable salt thereof.

In some embodiments, provided herein is a compound having Formula Vc:

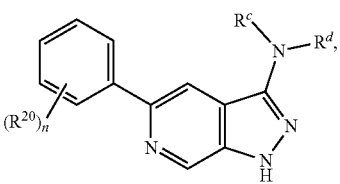
(Vc)

wherein n is 1, 2, 3, or 4; and R$^{20}$, R$^c$ and R$^d$ are as described herein; or a pharmaceutically acceptable salt thereof.

In some embodiments, provided herein is a compound having Formula Vd:

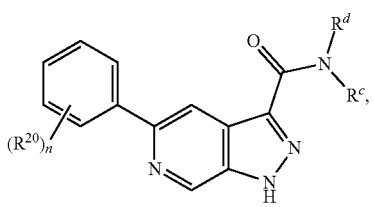

(Vd)

wherein n is 1, 2, 3, or 4; and $R^{20}$, $R^c$, and $R^d$ are as described herein; or a pharmaceutically acceptable salt thereof.

In some embodiments, provided herein is a compound having Formula Va1:

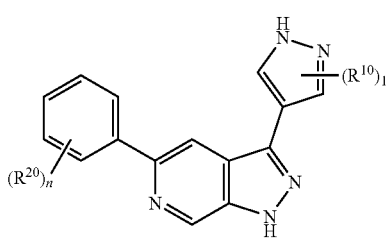

(Va1)

wherein n is 1, 2, 3, or 4; and $R^{20}$ and $R^{10}$ are as described herein; or a pharmaceutically acceptable salt thereof.

In some embodiments, n of Formula III, Formula IV, Formula Va, Formula Vb, Formula Vc, Formula Vd and Formula Va1 is 2. In some embodiments, n of Formula III, Formula IV, Formula Va, Formula Vb, Formula Vc and Formula Vd is 2.

In some embodiments, n of Formula III, Formula IV, Formula Va, Formula Vb, Formula Vc, Formula Vd and Formula Va1 is 1. In some embodiments, n of Formula III, Formula IV, Formula Va, Formula Vb, Formula Vc and Formula Vd is 1.

In some embodiments, n of Formula III, Formula IV, Formula Va, Formula Vb, Formula Vc, Formula Vd, and Formula Va1 is 3. In some embodiments, n of Formula III, Formula IV, Formula Va, Formula Vb, Formula Vc and Formula Vd is 3.

In some embodiments, n of Formula III, Formula IV, Formula Va, Formula Vb, Formula Vc, Formula Vd and Formula Va1 is 4.

In some embodiments, each $R^{20}$ of Formula III, Formula IV, Formula Va, Formula Vb, Formula Vc and Formula Vd is independently methoxy or fluoro. In some embodiments, each $R^{20}$ of Formula III, Formula IV, Formula Va, Formula Vb, Formula Vc, Formula Vd and Formula Va1 is independently methoxy or fluoro.

In some embodiments, one or more of the hydrogens of any of the formulae described herein is replaced or substituted with deuterium.

In some embodiments:

$R^1$ is selected from $Cy^1$, $C_{2-6}$ alkenyl, $C_{2-6}$ alkynyl, $C_{1-6}$ haloalkyl, halo, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NOR^a)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, and $S(O)_2NR^cR^d$; wherein said $C_{2-6}$ alkenyl and $C_{2-6}$ alkynyl are each optionally substituted with 1, 2, 3, or 4 substituents independently selected from $R^{10}$;

$Cy^1$ is selected from $C_{3-10}$ cycloalkyl, 4-10 membered heterocycloalkyl, $C_{6-10}$ aryl and 5-10 membered heteroaryl, wherein each 4-10 membered heterocycloalkyl and 5-10 membered heteroaryl has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl and 4-10 membered heterocycloalkyl is optionally substituted by oxo to form a carbonyl group; and wherein the $C_{3-10}$ cycloalkyl, 4-10 membered heterocycloalkyl, $C_{6-10}$ aryl and 5-10 membered heteroaryl are each optionally substituted with 1, 2, 3 or 4 substituents independently selected from $R^{10}$;

$Cy^A$ is $C_{6-10}$ aryl optionally substituted with 1, 2, 3 or 4 substituents independently selected from $R^{20}$;

$R^2$ is selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, CN, $SR^{a7}$, $C(O)R^{b7}$, $C(O)NR^{c7}R^{d7}$, $C(O)OR^{a7}$, $NR^{c7}R^{d7}$, $NR^{c7}C(O)R^{b7}$, $NR^{c7}C(O)OR^{a7}$, $NR^{c7}S(O)R^{b7}$, $NR^{c7}S(O)_2R^{b7}$, $NR^{c7}S(O)_2NR^{c7}R^{d7}$, $S(O)R^{b7}$, $S(O)NR^{c7}R^{d7}$, $S(O)_2R^{b7}$, and $S(O)_2NR^{c7}R^{d7}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{30}$;

each $R^{10}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 6-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NOR^{a1})R^{b1}$, $C(=NR^{e1})NR^{c1}R^{d1}$, $NR^{c1}C(=NR^{e1})NR^{c1}R^{d1}$, $NR^{c1}S(o)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$; wherein said $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 6-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{11}$;

or two $R^{10}$ substituents taken together with the carbon atom to which they are attached form a spiro 3-7-membered heterocycloalkyl ring, or a spiro $C_{3-6}$ cycloalkyl ring; wherein each spiro 3-7-membered heterocycloalkyl ring has at least one ring-forming carbon atom and 1, 2 or 3, ring-forming heteroatoms independently selected from N, O, and S; wherein a ring-forming carbon atom of each spiro 3-7-membered heterocycloalkyl ring is optionally substituted by oxo to form a carbonyl group; and wherein the spiro 3-7-membered heterocycloalkyl ring and spiro $C_{3-6}$ cycloalkyl ring are each optionally substituted with 1, 2, 3 or 4 substituents independently selected from $R^{11}$;

each $R^{11}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, CN, $OR^{a3}$, $SR^{a3}$, $C(O)R^{b3}$, $C(O)NR^{c3}R^{d3}$, $C(O)OR^{a3}$, $NR^{c3}R^{d3}$, $NR^{c3}C(O)R^{b3}$, $NR^{c3}C(O)OR^{a3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{12}$;

each $R^{12}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, $C_{6-10}$ aryl, 5-10 membered heteroaryl, 4-7 membered heterocycloalkyl, halo, CN, $OR^{a5}$, $SR^{a5}$, $C(O)R^{b5}$, $C(O)NR^{c5}R^{d5}$, $C(O)OR^{a5}$, $NR^{c5}R^{d5}$, $NR^{c5}C(O)R^{b5}$, $NR^{c5}C(O)OR^{a5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$; wherein said $C_{1-6}$ alkyl, $C_{2-6}$ alkenyl, $C_{2-6}$ alkynyl, $C_{3-6}$ cycloalkyl, $C_{6-10}$ aryl, 5-10 membered heteroaryl and 4-7 membered heterocycloalkyl are each optionally substituted with 1, 2, 3, or 4 substituents independently selected from $R^g$;

each $R^{20}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, CN, $NO_2$, $OR^{a2}$, $SR^{a2}$, $C(O)R^{b2}$; $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NOR^{a2})R^{b2}$, $C(=NR^{e2})NR^{c2}R^{d2}$, $NR^{c2}C(=NR^{e2})NR^{c2}R^{d2}$, $NR^{c2}S(O)R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{21}$;

or two adjacent $R^{20}$ substituents on the $Cy^A$ ring, taken together with the atoms to which they are attached, form a fused $C_{3-7}$ cycloalkyl ring; wherein a ring-forming carbon atom of the fused $C_{3-7}$ cycloalkyl ring is optionally substituted by oxo to form a carbonyl group; and wherein the fused $C_{3-7}$ cycloalkyl ring is optionally substituted with 1, 2, 3 or 4 substituents independently selected from $R^{21}$;

each $R^{21}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, CN, $OR^{a4}$; $SR^{a4}$, $C(O)R^{b4}$, $C(O)NR^{c4}R^{d4}$, $C(O)OR^{a4}$, $NR^{c4}R^{d4}$, $NR^{c4}C(O)R^{b4}$, $NR^{c4}C(O)OR^{a4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{22}$;

or two $R^{21}$ substituents taken together with the carbon atom to which they are attached form a spiro $C_{3-7}$ cycloalkyl ring; wherein a ring-forming carbon atom of the spiro $C_{3-7}$ cycloalkyl ring is optionally substituted by oxo to form a carbonyl group; and wherein the spiro $C_{3-7}$ cycloalkyl ring is optionally substituted with 1, 2, 3 or 4 substituents independently selected from $R^{22}$;

each $R^{22}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, CN, $OR^{a6}$, $SR^{a6}$, $C(O)R^{b6}$, $C(O)NR^{c6}R^{d6}$, $C(O)OR^{a6}$, $NR^{c6}R^{d6}$, $NR^{c6}C(O)R^{b6}$, $NR^{c6}C(O)OR^{a6}$, $NR^{c6}S(O)R^{b6}$, $NR^{c6}S(O)_2R^{b6}$, $NR^{c6}S(O)_2NR^{c6}R^{d6}$, $S(O)R^{b6}$, $S(O)NR^{c6}R^{d6}$, $S(O)_2R^{b6}$, and $S(O)_2NR^{c6}R^{d6}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^g$;

each $R^{30}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, CN, $OR^{a8}$, $SR^{a8}$, $C(O)R^{b8}$, $C(O)NR^{c8}R^{d8}$, $C(O)OR^{a8}$, $NR^{c8}R^{d8}$, $NR^{c8}C(O)R^{b8}$, $NR^{c8}C(O)OR^{a8}$, $NR^{c8}S(O)R^{b8}$, $NR^{c8}S(O)_2R^{b8}$, $NR^{c8}S(O)_2NR^{c8}R^{d8}$, $S(O)R^{b8}$, $S(O)NR^{c8}R^{d8}$, $S(O)_2R^{b8}$, and $S(O)_2NR^{c8}R^{d8}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^g$;

each $R^a$ and $R^c$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{10}$;

each $R^d$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{10}$;

or any $R^c$ and $R^d$ attached to the same N atom, together with the N atom to which they are attached, form a 4-10 membered heterocycloalkyl group optionally substituted with 1, 2, 3 or 4 substituents independently selected from $R^{10}$;

each $R^b$ is independently selected from $C_{2-6}$ alkenyl, $C_{2-6}$ alkynyl, $C_{1-6}$ haloalkyl, 7-10 membered heterocycloalkyl, $C_{6-10}$ aryl, and 5-10 membered heteroaryl; wherein said $C_{2-6}$ alkenyl, $C_{2-6}$ alkynyl, 7-10 membered heterocycloalkyl, $C_{6-10}$ aryl and 5-10 membered heteroaryl are each optionally substituted with 1, 2, 3, or 4 substituents independently selected from $R^{10}$;

each $R^e$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$alkyl)carbamyl, aminosulfonyl, alkylaminosulfonyl and di($C_{1-6}$ alkyl)aminosulfonyl;

each $R^{a1}$, $R^{c1}$ and $R^{d1}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{11}$;

or any $R^{c1}$ and $R^{d1}$ attached to the same N atom, together with the N atom to which they are attached, form a 4-, 5-, 6- or 7-membered heterocycloalkyl group optionally substituted with 1, 2, 3 or 4 substituents independently selected from $R^{11}$;

each $R^{b1}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{11}$;

each $R^{e1}$ is independently selected from H, CN, $C_{1-6}$ alkyl, $C_{1-6}$ haloalkyl, $C_{1-6}$ alkylthio, alkylsulfonyl, $C_{1-6}$ alkylcarbonyl, $C_{1-6}$ alkylaminosulfonyl, carbamyl, $C_{1-6}$ alkylcarbamyl, alkyl)carbamyl, aminosulfonyl, $C_{1-6}$ alkylaminosulfonyl and di($C_{1-6}$ alkyl)aminosulfonyl;

each $R^{a2}$, $R^{c2}$ and $R^{d2}$, is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{21}$;

or any $R^{c2}$ and $R^{d2}$ attached to the same N atom, together with the N atom to which they are attached, form a 4-, 5-, 6- or 7-membered heterocycloalkyl group optionally substituted with 1, 2, 3 or 4 substituents independently selected from $R^{21}$;

each $R^{b2}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{21}$;

each $R^{e2}$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{a3}$, $R^{c3}$ and $R^{d3}$, is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl, $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{12}$;

or any $R^{c3}$ and $R^{d3}$ attached to the same N atom, together with the N atom to which they are attached, form a 4-, 5-, 6- or 7-membered heterocycloalkyl group optionally substituted with 1, 2 or 3 substituents independently selected from $R^{12}$;

each $R^{b3}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl, $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{12}$;

each $R^{a4}$, $R^{c4}$ and $R^{d4}$, is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl, $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{22}$;

or any $R^{c4}$ and $R^{d4}$ attached to the same N atom, together with the N atom to which they are attached, form a 4-, 5-, 6- or 7-membered heterocycloalkyl group optionally substituted with 1, 2 or 3 substituents independently selected from $R^{22}$;

each $R^{b4}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl, $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{22}$;

each $R^{a5}$, $R^{c5}$ and $R^{d5}$, is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{b5}$ is independently selected from $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{a6}$, $R^{c6}$ and $R^{d6}$ is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{b6}$ is independently selected from $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{a7}$, $R^{c7}$, and $R^{d7}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{30}$;

or any $R^{c7}$ and $R^{d7}$ attached to the same N atom, together with the N atom to which they are attached, form a 4-, 5-, 6- or 7-membered heterocycloalkyl group optionally substituted with 1, 2 or 3 substituents independently selected from $R^{30}$;

each $R^{b7}$ is independently selected from $C_{1-6}$ alkyl, $C_{2-6}$ alkenyl, $C_{2-6}$ alkynyl, and $C_{1-6}$ haloalkyl;

each $R^{a8}$, $R^{c8}$ and $R^{d8}$, is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl, $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^g$;

or any $R^{c8}$ and $R^{d8}$ attached to the same N atom, together with the N atom to which they are attached, form a 4-, 5-, 6- or 7-membered heterocycloalkyl group optionally substituted with 1, 2 or 3 substituents independently selected from $R^g$;

each $R^{b8}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl, $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-6}$ haloalkyl, $C_{3-6}$ cycloalkyl, $C_{3-6}$ cycloalkyl-$C_{1-2}$ alkylene, $C_{1-6}$ alkoxy, $C_{1-6}$ haloalkoxy, $C_{1-3}$ alkoxy-$C_{1-3}$ alkyl, $C_{1-3}$ alkoxy-$C_{1-3}$ alkoxy, HO—$C_{1-3}$ alkoxy, HO—$C_{1-3}$ alkyl, cyano-$C_{1-3}$ alkyl, $H_2N$—$C_{1-3}$ alkyl, amino, $C_{1-6}$ alkylamino, di($C_{1-6}$alkyl)amino, thio, $C_{1-6}$ alkylthio, Cis alkylsulfinyl, $C_{1-6}$ alkylsulfonyl, carbamyl, $C_{1-6}$ alkylcarbamyl, di($C_{1-6}$ alkyl) carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments:

$R^1$ is selected from $Cy^1$, $C_{2-6}$ alkenyl, $C_{2-6}$ alkynyl, $C_{1-6}$ haloalkyl, halo, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, and $NR^cC(O)OR^a$; wherein said $C_{2-6}$ alkenyl and $C_{2-6}$ alkynyl are each optionally substituted with 1, 2, 3, or 4 substituents independently selected from $R^{10}$;

$Cy^1$ is selected from $C_{3-10}$ cycloalkyl, 4-10 membered heterocycloalkyl, $C_{6-10}$ aryl and 5-10 membered heteroaryl, wherein each 4-10 membered heterocycloalkyl and 5-10 membered heteroaryl has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl and 4-10 membered heterocycloalkyl is optionally substituted by oxo to form a carbonyl group; and wherein the $C_{3-10}$ cycloalkyl, 4-10 membered heterocycloalkyl, $C_{6-10}$ aryl and 5-10 membered heteroaryl are each optionally substituted with 1, 2, 3 or 4 substituents independently selected from $R^{10}$;

$Cy^4$ is $C_{6-10}$ aryl optionally substituted with 1, 2, 3 or 4 substituents independently selected from $R^{20}$;

$R^2$ is selected from H, $C_{1-6}$ alkyl, $C_{2-6}$ alkenyl, $C_{2-6}$ alkynyl, $C_{1-6}$ haloalkyl, halo, CN, $OR^{a7}$, $SR^{a7}$, $C(O)R^{b7}$, $C(O)NR^{c7}R^{d7}$, $C(O)OR^{a7}$, $NR^{c7}R^{d7}$, $NR^{c7}C(O)R^{b7}$, $NR^{c7}C(O)OR^{a7}$, $NR^{c7}S(O)R^{b7}$, $NR^{c7}S(O)_2R^{b7}$, $NR^{c7}S(O)_2NR^{c7}R^{d7}$, $S(O)R^{b7}$, $S(O)NR^{c7}R^{d7}$, $S(O)_2R^{b7}$, and $S(O)_2NR^{c7}R^{d7}$; wherein said $C_{1-6}$ alkyl, $C_{2-6}$ alkenyl, and $C_{2-6}$ alkynyl are each optionally substituted with 1, 2, 3, or 4 substituents independently selected from $R^{30}$;

each $R^{10}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$ and $NR^{c1}C(O)OR^{a1}$; wherein said $C_{2-6}$ alkenyl, $C_{2-6}$ alkynyl, $C_{3-10}$ cycloalkyl, 4-10 membered heterocycloalkyl, $C_{6-10}$ aryl, and 5-10 membered heteroaryl are each optionally substituted with 1, 2, 3, or 4 substituents independently selected from $R^{11}$;

each $R^{11}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, CN, $OR^{a3}$, $SR^{a3}$, $C(O)R^{b3}$, $C(O)NR^{c3}R^{d3}$, $C(O)OR^{a3}$, $NR^{c3}R^{d3}$, $NR^{c3}C(O)R^{b3}$, $NR^{c3}C(O)OR^{a3}$, $S(O)R^{b3}$, $S(O)NR^{c3}R^{d3}$, $S(O)_2R^{b3}$, and $S(O)_2NR^{c3}R^{d3}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, and 5-10 membered heteroaryl are each optionally substituted with 1, 2, 3, or 4 substituents independently selected from $R^{12}$;

each $R^{12}$ is independently selected from $C_{1-6}$ alkyl, $C_{2-6}$ alkenyl, $C_{2-6}$ alkynyl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $NR^{c5}R^{d5}$, $NR^{c5}C(O)R^{b5}$, $NR^{c5}C(O)OR^{a5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$; wherein said $C_{1-6}$ alkyl, $C_{2-6}$ alkenyl, and $C_{2-6}$ alkynyl are each optionally substituted with 1, 2, 3, or 4 substituents independently selected from $R^g$;

each $R^{20}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, and $NR^{c2}C(O)OR^{a2}$, wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, and 5-10 membered heteroaryl are each optionally substituted with 1, 2, 3, or 4 substituents independently selected from $R^{21}$;

each $R^{21}$ is independently selected from $C_{1-6}$ alkyl, $C_{2-6}$ alkenyl, $C_{2-6}$ alkynyl, $C_{1-6}$ haloalkyl, halo, CN, $OR^{a4}$, $SR^{a4}$, $C(O)R^{b4}$, $C(O)NR^{c4}R^{d4}$, $C(O)OR^{a4}$, $NR^{c4}R^{d4}$, $NR^{c4}C(O)R^{b4}$, and $NR^{c4}C(O)OR^{a4}$; wherein said $C_{1-6}$ alkyl, $C_{2-6}$ alkenyl, and $C_{2-6}$ alkynyl are each optionally substituted with 1, 2, 3, or 4 substituents independently selected from $R^{22}$;

each $R^{22}$ is independently selected from $C_{1-6}$ alkyl, $C_{2-6}$ alkenyl, $C_{2-6}$ alkynyl, $C_{1-6}$ haloalkyl, phenyl, halo, CN, $OR^{a6}$, $SR^{a6}$, $C(O)R^{b6}$, $C(O)NR^{c6}R^{d6}$, $C(O)OR^{a6}$, $NR^{c6}R^{d6}$, $NR^{c6}C(O)R^{b6}$, and $NR^{c6}C(O)OR^{a6}$;

each $R^{30}$ is independently selected from $C_{1-6}$ alkyl, $C_{2-6}$ alkenyl, $C_{2-6}$ alkynyl, and $C_{1-6}$ haloalkyl;

each $R^a$ and $R^c$ is independently selected from H, $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl, and $C_{2-6}$ alkynyl are each optionally substituted with 1, 2, 3, or 4 substituents independently selected from $R^{10}$;

each $R^d$ is independently selected from $C_{1-6}$ alkyl, $C_{2-6}$ alkenyl, $C_{2-6}$ alkynyl, $C_{1-6}$ haloalkyl, and $C_{6-10}$ aryl; wherein said $C_{1-6}$ alkyl, $C_{2-6}$ alkenyl, $C_{2-6}$ alkynyl, and $C_{6-10}$ aryl are each optionally substituted with 1, 2, 3, or 4 substituents independently selected from $R^{10}$;

each $R^b$ is independently selected from $C_{2-6}$ alkenyl, $C_{2-6}$ alkynyl, $C_{1-6}$ haloalkyl, 7-10 membered heterocycloalkyl, $C_{6-10}$ aryl, and 5-10 membered heteroaryl; wherein said $C_{2-6}$ alkenyl, $C_{2-6}$ alkynyl, 7-10 membered heterocycloalkyl, $C_{6-10}$ aryl and 5-10 membered heteroaryl are each optionally substituted with 1, 2, 3, or 4 substituents independently selected from $R^{10}$;

each $R^{a1}$, $R^{c1}$ and $R^{d1}$ is independently selected from H, $C_{1-6}$ alkyl, $C_{2-6}$ alkenyl, $C_{2-6}$ alkynyl, and $C_{1-6}$ haloalkyl;

each $R^{b1}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{11}$;

each $R^{a2}$, $R^{c2}$ and $R^{d2}$, is independently selected from H, $C_{1-6}$ alkyl, $C_{2-6}$ alkenyl, $C_{2-6}$ alkynyl, and $C_{1-6}$ haloalkyl;

each $R^{b2}$ is independently selected from $C_{1-6}$ alkyl, $C_{2-6}$ alkenyl, $C_{2-6}$ alkynyl, and $C_{1-6}$ haloalkyl;

each $R^{a3}$, $R^{c3}$ and $R^{d3}$, is independently selected from H, $C_{1-6}$ alkyl, $C_{2-6}$ alkenyl, $C_{2-6}$ alkynyl, and $C_{1-6}$ haloalkyl;

each $R^{b3}$ is independently selected from $C_{1-6}$ alkyl, $C_{2-6}$ alkenyl, $C_{2-6}$ alkynyl, $C_{1-6}$ haloalkyl, and phenyl;

each $R^{a4}$, $R^{c4}$ and $R^{d4}$, is independently selected from H, $C_{1-6}$ alkyl, $C_{2-6}$ alkenyl, $C_{2-6}$ alkynyl, $C_{1-6}$ haloalkyl, and phenyl;

each $R^{b4}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, and phenyl;

each $R^{a5}$, $R^{c5}$ and $R^{d5}$, is independently selected from H, $C_{1-6}$ alkyl, $C_{2-6}$ alkenyl, $C_{2-6}$ alkynyl and $C_{1-6}$ haloalkyl;

each $R^{b5}$ is independently selected from $C_{1-6}$ alkyl, $C_{2-6}$ alkenyl, $C_{2-6}$ alkynyl and $C_{1-6}$ haloalkyl;

each $R^{a6}$, $R^{c6}$ and $R^{d6}$ is independently selected from H, $C_{1-6}$ alkyl, $C_{2-6}$ alkenyl, $C_{2-6}$ alkynyl and $C_{1-6}$ haloalkyl;

each $R^{b6}$ is independently selected from $C_{1-6}$ alkyl, $C_{2-6}$ alkenyl, $C_{2-6}$ alkynyl, and $C_{1-6}$ haloalkyl;

each $R^{a7}$, $R^{c7}$, and $R^{d7}$ is independently selected from H, $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl, and $C_{2-6}$ alkynyl are each optionally substituted with 1, 2, 3, or 4 substituents independently selected from $R^{30}$;

each $R^{b7}$ is independently selected from $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl, and $C_{2-6}$ alkynyl are each optionally substituted with 1, 2, 3, or 4 substituents independently selected from $R^{30}$;

each $R^g$ is independently selected from OH, $NO_2$, CN, halo, $C_{1-6}$ alkyl, $C_{2-6}$ alkenyl, $C_{2-6}$ alkynyl, $C_{1-6}$ haloalkyl, $C_{3-6}$ cycloalkyl, $C_{3-6}$ cycloalkyl-$C_{1-2}$ alkylene, $C_{1-6}$ alkoxy, $C_{1-6}$ haloalkoxy, $C_{1-3}$ alkoxy-$C_{1-3}$ alkyl, $C_{1-3}$ alkoxy-$C_{1-3}$ alkoxy, HO—$C_{1-3}$ alkoxy, HO—$C_{1-3}$ alkyl, cyano-$C_{1-3}$ alkyl, $H_2N$—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments:

$R^1$ is selected from $Cy^1$, $C_{2-6}$ alkenyl, $C_{2-6}$ alkynyl, $C_{1-6}$ haloalkyl, halo, CN, $OR^a$, $C(O)R^b$, $C(O)NR^cR^d$, $C(O)OR^a$, $NR^cR^d$, $NR^cC(O)R^b$, and $NR^cC(O)OR^a$; wherein said $C_{2-6}$ alkenyl and $C_{2-6}$ alkynyl are each optionally substituted with 1, 2, 3, or 4 substituents independently selected from $R^{10}$;

$Cy^1$ is selected from 4-10 membered heterocycloalkyl, $C_{6-10}$ aryl and 5-10 membered heteroaryl, wherein each 4-10 membered heterocycloalkyl and 5-10 membered heteroaryl has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl and 4-10 membered heterocycloalkyl is optionally substituted by oxo to form a carbonyl group; and wherein the 4-10 membered heterocycloalkyl, $C_{6-10}$ aryl and 5-10 membered heteroaryl are each optionally substituted with 1, 2, 3 or 4 substituents independently selected from $R^{10}$;

$Cy^A$ is $C_{6-10}$ aryl optionally substituted with 1, 2, 3 or 4 substituents independently selected from $R^{20}$;

$R^2$ is selected from H, $C_{1-6}$ alkyl, $C_{2-6}$ alkenyl, $C_{2-6}$ alkynyl, $C_{1-6}$ haloalkyl, and halo;

each $R^{10}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, CN, and $OR^{a1}$; wherein said $C_{2-6}$ alkenyl, $C_{2-6}$ alkynyl, $C_{3-10}$ cycloalkyl, 4-10 membered heterocycloalkyl, $C_{6-10}$ aryl, and 5-10 membered heteroaryl are each optionally substituted with 1, 2, 3, or 4 substituents independently selected from $R^{11}$;

each $R^{11}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, CN, $OR^{a3}$, $C(O)NR^{c3}R^{d3}$, $NR^{c3}R^{d3}$, $NR^{c3}C(O)R^{b3}$, $S(O)_2R^{b3}$, and $S(O)_2NR^{c3}R^{d3}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, and 5-10 membered heteroaryl are each optionally substituted with 1, 2, 3, or 4 substituents independently selected from $R^{12}$;

each $R^{12}$ is independently selected from $C_{1-6}$ alkyl, $C_{2-6}$ alkenyl, $C_{2-6}$ alkynyl, $C_{1-6}$ haloalkyl, and halo;

each $R^{20}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, and $OR^{a2}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, and 5-10 membered heteroaryl are each optionally substituted with 1, 2, 3, or 4 substituents independently selected from $R^{21}$;

each $R^{21}$ is independently selected from $C_{1-6}$ alkyl, $C_{2-6}$ alkenyl, $C_{2-6}$ alkynyl, $C_{1-6}$ haloalkyl, and halo; wherein said $C_{1-6}$ alkyl, $C_{2-6}$ alkenyl, and $C_{2-6}$ alkynyl are each optionally substituted with 1, 2, 3, or 4 substituents independently selected from $R^{22}$;

each $R^{22}$ is independently selected from $C_{1-6}$ alkyl, $C_{2-6}$ alkenyl, $C_{2-6}$ alkynyl, $C_{1-6}$ haloalkyl, phenyl, halo, $NR^{c6}R^{d6}$, and $NR^{c6}C(O)R^{b6}$, each $R^a$ and $R^c$ is independently selected from H and $C_{1-6}$ alkyl;

each $R^d$ is independently selected from $C_{1-6}$ alkyl, $C_{2-6}$ alkenyl, $C_{2-6}$ alkynyl, $C_{1-6}$ haloalkyl, and $C_{6-10}$ aryl; wherein said $C_{1-6}$ alkyl, $C_{2-6}$ alkenyl, $C_{2-6}$ alkynyl, and $C_{6-10}$ aryl are each optionally substituted with 1, 2, 3, or 4 substituents independently selected from $R^{10}$;

each $R^b$ is independently selected from $C_{2-6}$ alkenyl, $C_{2-6}$ alkynyl, $C_{1-6}$ haloalkyl, 7-10 membered heterocycloalkyl, $C_{6-10}$ aryl, and 5-10 membered heteroaryl; wherein said $C_{2-6}$ alkenyl, $C_{2-6}$ alkynyl, 7-10 membered heterocycloalkyl, $C_{6-10}$ aryl and 5-10 membered heteroaryl are each optionally substituted with 1, 2, 3, or 4 substituents independently selected from $R^{10}$;

each $R^{a1}$ is independently selected from H and $C_{1-6}$ alkyl;

each $R^{a\ a2}$ is independently selected from H, $C_{1-6}$ alkyl, $C_{2-6}$ alkenyl, $C_{2-6}$ alkynyl, and $C_{1-6}$ haloalkyl;

each $R^{a3}$, $R^{c3}$ and $R^{d3}$, is independently selected from H, $C_{1-6}$ alkyl, $C_{2-6}$ alkenyl, $C_{2-6}$ alkynyl, and $C_{1-6}$ haloalkyl;

each $R^{b3}$ is independently selected from $C_{1-6}$ alkyl, $C_{2-6}$ alkenyl, $C_{2-6}$ alkynyl, $C_{1-6}$ haloalkyl, and phenyl;

each $R^{c6}$ and $R^{d6}$ is independently selected from H, $C_{1-6}$ alkyl, $C_{2-6}$ alkenyl, $C_{2-6}$ alkynyl and $C_{1-6}$ haloalkyl; and each $R^{b6}$ is independently selected from $C_{1-6}$ alkyl, $C_{2-6}$ alkenyl, $C_{2-6}$ alkynyl, and $C_{1-6}$ haloalkyl.

In some embodiments:

$R^1$ is selected from $Cy^1$, $C(O)NR^cR^d$, and $NR^cR^d$, $NR^cC(O)R^b$;

$Cy^1$ is selected from 4-10 membered heterocycloalkyl, $C_{6-10}$ aryl and 5-10 membered heteroaryl, wherein each 4-10 membered heterocycloalkyl and 5-10 membered heteroaryl has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl and 4-10 membered heterocycloalkyl is optionally substituted by oxo to form a carbonyl group; and wherein the 4-10 membered heterocycloalkyl, $C_{6-10}$ aryl and 5-10 membered heteroaryl are each optionally substituted with 1 or 2 substituents independently selected from $R^{10}$;

$Cy^A$ is $C_{6-10}$ aryl optionally substituted with 1 or 2 substituents independently selected from $R^{20}$;

$R^2$ is H;

each $R^{10}$ is independently selected from $C_{1-6}$ alkyl, $C_{3-10}$ cycloalkyl, 4-10 membered heterocycloalkyl, $C_{6-10}$ aryl, 5-10 membered heteroaryl, halo, CN, and $OR^{a1}$; wherein said $C_{3-10}$ cycloalkyl, 4-10 membered heterocycloalkyl, $C_{6-10}$ aryl, and 5-10 membered heteroaryl are each optionally substituted with 1 or 2 substituents independently selected from $R^{11}$;

each $R^{11}$ is independently selected from $C_{1-6}$ alkyl, $C_{1-6}$ haloalkyl, 4-10 membered heterocycloalkyl, halo, CN, and $S(O)_2R^{b3}$; wherein said $C_{1-6}$ alkyl and 4-10 membered heterocycloalkyl are each optionally substituted with 1 or 2 substituents independently selected from $R^{12}$;

each $R^{12}$ is $C_{1-6}$ alkyl;

each $R^{20}$ is independently selected from $C_{1-6}$ alkyl, $C_{1-6}$ haloalkyl, $C_{3-10}$ cycloalkyl, halo, and $OR^{a2}$; wherein said $C_{1-6}$ alkyl and $C_{3-10}$ cycloalkyl are each optionally substituted with 1 or 2 substituents independently selected from $R^{21}$;

each $R^{21}$ is $C_{1-6}$ alkyl optionally substituted with 1 or 2 substituents independently selected from $R^{22}$;

each $R^{22}$ is independently $NR^{c6}R^{d6}$;

each $R^a$ and $R^c$ is H;

each $R^d$ is independently selected from $C_{1-6}$ alkyl and $C_{6-10}$ aryl; wherein said $C_{1-6}$ alkyl and $C_{6-10}$ aryl are each optionally substituted with 1 or 2 substituents independently selected from $R^{10}$;

each $R^b$ is independently selected from 7-10 membered heterocycloalkyl, $C_{6-10}$ aryl, and 5-10 membered heteroaryl; wherein said 7-10 membered heterocycloalkyl, $C_{6-10}$ aryl and 5-10 membered heteroaryl are each optionally substituted with 1 or 2 substituents independently selected from $R^{10}$;

each $R^{a1}$ is $C_{1-6}$ alkyl;

each $R^{a2}$ is independently selected from H and $C_{1-6}$ alkyl;

each $R^{b3}$ is $C_{1-6}$ alkyl; and each $R^{c6}$ and $R^{d6}$ is H.

In some embodiments:

$R^1$ is selected from $Cy^1$, $C_{2-6}$ alkenyl, $C_{2-6}$ alkynyl, $C_{1-6}$ haloalkyl, halo, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, and $NR^cC(O)OR^a$; wherein said $C_{2-6}$ alkenyl and $C_{2-6}$ alkynyl are each optionally substituted with 1, 2, 3, or 4 substituents independently selected from $R^{10}$;

$Cy^1$ is selected from $C_{3-10}$ cycloalkyl, 4-10 membered heterocycloalkyl, $C_{6-10}$ aryl and 5-10 membered heteroaryl, wherein each 4-10 membered heterocycloalkyl and 5-10 membered heteroaryl has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl and 4-10 membered heterocycloalkyl is optionally substituted by oxo to form a carbonyl group; and wherein the $C_{3-10}$ cycloalkyl, 4-10 membered heterocycloalkyl, $C_{6-10}$ aryl and 5-10 membered heteroaryl are each optionally substituted with 1, 2, 3 or 4 substituents independently selected from $R^{10}$;

$Cy^A$ is $C_{6-10}$ aryl optionally substituted with 1, 2, 3 or 4 substituents independently selected from $R^{20}$;

$R^2$ is selected from H, $C_{1-6}$ alkyl, $C_{2-6}$ alkenyl, $C_{2-6}$ alkynyl, $C_{1-6}$ haloalkyl, halo, CN, $OR^{a7}$, $SR^{a7}$, $C(O)R^{b7}$, $C(O)NR^{c7}R^{d7}$, $C(O)OR^{a7}$, $NR^{c7}R^{d7}$, $NR^{c7}C(O)R^{b7}$, $NR^{c7}C(O)OR^{a7}$, $NR^{c7}S(O)R^{b7}$, $NR^{c7}S(O)_2R^{b7}$, $NR^{c7}S(O)_2NR^{c7}R^{d7}$, $S(O)NR^{c7}R^{d7}$, $S(O)_2R^{b7}$, and $S(O)_2NR^{c7}R^{d7}$; wherein said $C_{1-6}$ alkyl, $C_{2-6}$ alkenyl, and $C_{2-6}$ alkynyl are each optionally substituted with 1, 2, 3, or 4 substituents independently selected from $R^{30}$;

each $R^{10}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, and $NR^{c1}C(O)OR^{a1}$; wherein said $C_{2-6}$ alkenyl, $C_{2-6}$ alkynyl, $C_{3-10}$ cycloalkyl, 4-10 membered heterocycloalkyl, $C_{6-10}$ aryl, and 5-10 membered heteroaryl are each optionally substituted with 1, 2, 3, or 4 substituents independently selected from $R^{11}$;

each $R^{11}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, CN, $OR^{a3}$, $SR^{a3}$, $C(O)R^{b3}$, $C(O)NR^{c3}R^{d3}$, $C(O)OR^{a3}$, $NR^{c3}R^{d3}$, $NR^{c3}C(O)R^{b3}$, $NR^{c3}C(O)OR^{a3}$, $S(O)R^{b3}$, $S(O)NR^{c3}R^{d3}$, $S(O)_2R^{b3}$, and $S(O)_2NR^{c3}R^{d3}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, and 5-10 membered heteroaryl are each optionally substituted with 1, 2, 3, or 4 substituents independently selected from $R^{12}$;

each $R^{12}$ is independently selected from $C_{1-6}$ alkyl, $C_{2-6}$ alkenyl, $C_{2-6}$ alkynyl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $NR^{c5}R^{d5}$, $NR^{c5}C(O)R^{b5}$, $NR^{c5}C(O)OR^{a5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$; wherein said $C_{1-6}$ alkyl, $C_{2-6}$ alkenyl, and $C_{2-6}$ alkynyl are each optionally substituted with 1, 2, 3, or 4 substituents independently selected from $R^g$;

each $R^{20}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, 4-10 membered heterocycloalkyl-$C_{1-3}$ alkylene, halo, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, and $NR^{c2}C(O)OR^{a2}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, and 4-10 membered heterocycloalkyl-$C_{1-3}$ alkylene are each optionally substituted with 1, 2, 3, or 4 substituents independently selected from $R^{21}$;

or two adjacent $R^{20}$ substituents on the $Cy^A$ ring, taken together with the atoms to which they are attached, form a fused $C_{3-7}$ cycloalkyl ring; wherein a ring-forming carbon atom of the fused $C_{3-7}$ cycloalkyl ring is optionally substituted by oxo to form a carbonyl group; and wherein the fused $C_{3-7}$ cycloalkyl ring is optionally substituted with 1, 2, 3 or 4 substituents independently selected from $R^{21}$;

each $R^{21}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, CN, $OR^{a4}$, $SR^{a4}$, $C(O)R^{b4}$, $C(O)NR^{c4}R^{d4}$, $C(O)OR^{a4}$, $NR^{c4}R^{d4}$, $NR^{c4}C(O)R^{b4}$, and $NR^{c4}C(O)OR^{a4}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, and 5-10 membered heteroaryl are each optionally substituted with 1, 2, 3, or 4 substituents independently selected from $R^{22}$;

each $R^{22}$ is independently selected from $C_{1-6}$ alkyl, $C_{2-6}$ alkenyl, $C_{2-6}$ alkynyl, $C_{1-6}$ haloalkyl, phenyl, 5-6 membered heteroaryl, 4-7 membered heterocycloalkyl, halo, CN, $OR^{a6}$, $SR^{a6}$, $C(O)R^{b6}$, $C(O)NR^{c6}R^{d6}$, $C(O)OR^{a6}$, $NR^{c6}R^{d6}$, $NR^{c6}C(O)R^{b6}$, and $NR^{c6}C(O)OR^{a6}$; wherein said $C_{1-6}$ alkyl, $C_{2-6}$ alkenyl, $C_{2-6}$ alkynyl, and 5-6 membered heteroaryl are each optionally substituted with 1 substituents independently selected from $R^g$;

each $R^{30}$ is independently selected from $C_{1-6}$ alkyl, $C_{2-6}$ alkenyl, $C_{2-6}$ alkynyl, and $C_{1-6}$ haloalkyl;

each $R^a$ and $R^c$ is independently selected from H, $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl, and $C_{2-6}$ alkynyl are each optionally substituted with 1, 2, 3, or 4 substituents independently selected from $R^{10}$;

each $R^d$ is independently selected from $C_{1-6}$ alkyl, $C_{2-6}$ alkenyl, $C_{2-6}$ alkynyl, $C_{1-6}$ haloalkyl, and $C_{6-10}$ aryl; wherein said $C_{1-6}$ alkyl, $C_{2-6}$ alkenyl, $C_{2-6}$ alkynyl, and $C_{6-10}$ aryl are each optionally substituted with 1, 2, 3, or 4 substituents independently selected from $R^{10}$;

each $R^b$ is independently selected from $C_{2-6}$ alkenyl, $C_{2-6}$ alkynyl, $C_{1-6}$ haloalkyl, 7-10 membered heterocycloalkyl, $C_{6-10}$ aryl, and 5-10 membered heteroaryl; wherein said $C_{2-6}$ alkenyl, $C_{2-6}$ alkynyl, 7-10 membered heterocycloalkyl, $C_{6-10}$ aryl and 5-10 membered heteroaryl are each optionally substituted with 1, 2, 3, or 4 substituents independently selected from $R^{10}$;

each $R^{aa}$, $R^{c1}$ and $R^{d1}$ is independently selected from H, $C_{1-6}$ alkyl, $C_{2-6}$ alkenyl, $C_{2-6}$ alkynyl, $C_{1-6}$ haloalkyl, and $C_{3-10}$ cycloalkyl; wherein said $C_{1-6}$ alkyl, $C_{2-6}$ alkenyl, $C_{2-6}$ alkynyl, and $C_{3-10}$ cycloalkyl are each optionally substituted with 1, 2, or 3 substituents independently selected from $R^{11}$;

each $R^{b1}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{11}$;

each $R^{a2}$, $R^{c2}$ and $R^{d2}$, is independently selected from H, $C_{1-6}$ alkyl, $C_{2-6}$ alkenyl, $C_{2-6}$ alkynyl, $C_{1-6}$ haloalkyl, and 4-10 membered heterocycloalkyl; said $C_{1-6}$ alkyl and 4-10 membered heterocycloalkyl are each optionally substituted with 1, 2, or 3 substituents independently selected from $R^{21}$;

or any $R^{c2}$ and $R^{d2}$ attached to the same N atom, together with the N atom to which they are attached, form a 4-, 5-, 6- or 7-membered heterocycloalkyl group optionally substituted with 1, 2, 3 or 4 substituents independently selected from $R^{21}$;

each $R^{b2}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, and 5-10 membered heteroaryl; wherein said $C_{1-6}$ alkyl, $C_{3-10}$ cycloalkyl, 4-10 membered heterocycloalkyl, and 5-10 membered heteroaryl are each optionally substituted with 1, 2, or 3 substituents independently selected from $R^{21}$;

each $R^{a3}$, $R^{c3}$ and $R^{d3}$, is independently selected from H, $C_{1-6}$ alkyl, $C_{2-6}$ alkenyl, $C_{2-6}$ alkynyl, and $C_{1-6}$ haloalkyl;

each $R^{b3}$ is independently selected from $C_{1-6}$ alkyl, $C_{2-6}$ alkenyl, $C_{2-6}$ alkynyl, $C_{1-6}$ haloalkyl, and phenyl;

each $R^{a4}$, $R^{c4}$ and $R^{d4}$, is independently selected from H, $C_{1-6}$ alkyl, $C_{2-6}$ alkenyl, $C_{2-6}$ alkynyl, $C_{1-6}$ haloalkyl, phenyl, $C_{3-6}$ cycloalkyl, 5-6 membered heteroaryl and 4-7 membered heterocycloalkyl; wherein said $C_{1-6}$ alkyl, $C_{2-6}$ alkenyl, $C_{2-6}$ alkynyl, phenyl, $C_{3-6}$ cycloalkyl, 5-6 membered heteroaryl and 4-7 membered heterocycloalkyl are each optionally substituted with 1, 2, or 3 substituents independently selected from $R^{22}$;

or any $R^{c4}$ and $R^{d4}$ attached to the same N atom, together with the N atom to which they are attached, form a 4-, 5-, 6- or 7-membered heterocycloalkyl group;

each $R^{b4}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, and phenyl;

each $R^{a5}$, $R^{c5}$ and $R^{d5}$, is independently selected from H, $C_{1-6}$ alkyl, $C_{2-6}$ alkenyl, $C_{2-6}$ alkynyl and $C_{1-6}$ haloalkyl;

each $R^{b5}$ is independently selected from $C_{1-6}$ alkyl, $C_{2-6}$ alkenyl, $C_{2-6}$ alkynyl and $C_{1-6}$ haloalkyl;

each $R^{a6}$, $R^{c6}$ and $R^{d6}$ is independently selected from H, $C_{1-6}$ alkyl, $C_{2-6}$ alkenyl, $C_{2-6}$ alkynyl and $C_{1-6}$ haloalkyl;

each $R^{b6}$ is independently selected from $C_{1-6}$ alkyl, $C_{2-6}$ alkenyl, $C_{2-6}$ alkynyl, and $C_{1-6}$ haloalkyl;

each $R^{a7}$, $R^{c7}$, and $R^{d7}$ is independently selected from H, $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl, and $C_{2-6}$ alkynyl are each optionally substituted with 1, 2, 3, or 4 substituents independently selected from $R^{30}$;

each $R^{b7}$ is independently selected from $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl, and $C_{2-6}$ alkynyl are each optionally substituted with 1, 2, 3, or 4 substituents independently selected from $R^{30}$;

each $R^g$ is independently selected from OH, $NO_2$, CN, halo, $C_{1-6}$ alkyl, $C_{2-6}$ alkenyl, $C_{2-6}$ alkynyl, $C_{1-6}$ haloalkyl, $C_{3-6}$ cycloalkyl, $C_{3-6}$ cycloalkyl-$C_{1-2}$ alkylene, $C_{1-6}$ alkoxy, $C_{1-6}$ haloalkoxy, $C_{1-3}$ alkoxy-$C_{1-3}$ alkyl, $C_{1-3}$ alkoxy-$C_{1-3}$ alkoxy, HO—$C_{1-3}$ alkoxy, HO—$C_{1-3}$ alkyl, cyano-$C_{1-3}$ alkyl, $H_2N$—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl) carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments:

$R^1$ is selected from $Cy^1$, $C_{2-6}$ alkenyl, $C_{2-6}$ alkynyl, $C_{1-6}$ haloalkyl, halo, CN, $OR^a$, $C(O)R^b$, $C(O)NR^cR^d$, $C(O)OR^a$, $NR^cR^d$, $NR^cC(O)R^b$, and $NR^cC(O)OR^a$; wherein said $C_{2-6}$ alkenyl and $C_{2-6}$ alkynyl are each optionally substituted with 1, 2, 3, or 4 substituents independently selected from $R^{10}$;

$Cy^1$ is selected from 4-10 membered heterocycloalkyl, $C_{6-10}$ aryl and 5-10 membered heteroaryl, wherein each 4-10 membered heterocycloalkyl and 5-10 membered heteroaryl has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl and 4-10 membered heterocycloalkyl is optionally substituted by oxo to form a carbonyl group; and wherein the 4-10 membered heterocycloalkyl, $C_{6-10}$ aryl and 5-10 membered heteroaryl are each optionally substituted with 1, 2, 3 or 4 substituents independently selected from $R^{10}$;

$Cy^A$ is $C_{6-10}$ aryl optionally substituted with 1, 2, 3 or 4 substituents independently selected from $R^{20}$;

$R^2$ is selected from H, $C_{1-6}$ alkyl, $C_{2-6}$ alkenyl, $C_{2-6}$ alkynyl, $C_{1-6}$ haloalkyl, halo, and $OR^{a7}$;

each $R^{10}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, CN, $OR^{a1}$, $C(O)NR^{c1}R^{d1}$, and $NR^{c1}R^{d1}$; wherein said $C_{2-6}$ alkenyl, $C_{2-6}$ alkynyl, $C_{3-10}$ cycloalkyl, 4-10 membered heterocycloalkyl, $C_{6-10}$ aryl, and 5-10 membered heteroaryl are each optionally substituted with 1, 2, 3, or 4 substituents independently selected from $R^{11}$;

each $R^{11}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, CN, $OR^{a3}$, $C(O)OR^{a3}$, $C(O)NR^{c3}R^{d3}$, $NR^{c3}R^{d3}$, $NR^{c3}C(O)R^{b3}$, $S(O)_2R^{b3}$, and $S(O)_2NR^{c3}R^{d3}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, and 5-10 membered heteroaryl are each optionally substituted with 1, 2, 3, or 4 substituents independently selected from $R^{12}$;

each $R^{12}$ is independently selected from $C_{1-6}$ alkyl, $C_{2-6}$ alkenyl, $C_{2-6}$ alkynyl, $C_{1-6}$ haloalkyl, halo, and CN;

each $R^{20}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, 4-10 membered heterocycloalkyl-$C_{1-3}$ alkylene, halo, $OR^{a2}$, $C(O)R^{b2}$, $C(O)NR^{c2}R^{d2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, and $NR^{c2}C(O)NR^{c2}R^{d2}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, and 4-10 membered heterocycloalkyl-$C_{1-3}$ alkylene are each optionally substituted with 1, 2, 3, or 4 substituents independently selected from $R^{21}$;

or two adjacent $R^{20}$ substituents on the $Cy^A$ ring, taken together with the atoms to which they are attached, form a fused $C_{3-7}$ cycloalkyl ring; wherein a ring-forming carbon atom of the fused $C_{3-7}$ cycloalkyl ring is optionally substituted by oxo to form a carbonyl group; and wherein the fused $C_{3-7}$ cycloalkyl ring is optionally substituted with 1, 2, 3 or 4 substituents independently selected from $R^{21}$;

each $R^{21}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, CN, $OR^{a4}$, $NR^{c4}R^{d4}$, $NR^{c4}C(O)R^{b4}$, and $NR^{c4}C(O)OR^{a4}$; wherein said $C_{1-6}$ alkyl, $C_{2-6}$ alkenyl, $C_{2-6}$ alkynyl, and $C_{3-10}$ cycloalkyl, 4-10 membered heterocycloalkyl, $C_{6-10}$ aryl, and 5-10 membered heteroaryl are each optionally substituted with 1, 2, 3, or 4 substituents independently selected from $R^{22}$;

each $R^{22}$ is independently selected from $C_{1-6}$ alkyl, $C_{2-6}$ alkenyl, $C_{2-6}$ alkynyl, $C_{1-6}$ haloalkyl, phenyl, 5-6 membered heteroaryl, 4-7 membered heterocycloalkyl, halo, CN, $OR^{6a}$, $NR^{c6}R^{d6}$, and $NR^{c6}C(O)R^{b6}$; wherein said $C_{1-6}$ alkyl, $C_{2-6}$ alkenyl, $C_{2-6}$ alkynyl, and 5-6 membered heteroaryl are each optionally substituted with 1 or 2 substituents independently selected from $R^g$;

each $R^a$ and $R^c$ is independently selected from H and $C_{1-6}$ alkyl;

each $R^d$ is independently selected from $C_{1-6}$ alkyl, $C_{2-6}$ alkenyl, $C_{2-6}$ alkynyl, $C_{1-6}$ haloalkyl, and $C_{6-10}$ aryl; wherein said $C_{1-6}$ alkyl, $C_{2-6}$ alkenyl, $C_{2-6}$ alkynyl, and $C_{6-10}$ aryl are each optionally substituted with 1, 2, 3, or 4 substituents independently selected from $R^{10}$;

each $R^b$ is independently selected from $C_{2-6}$ alkenyl, $C_{2-6}$ alkynyl, $C_{1-6}$ haloalkyl, 7-10 membered heterocycloalkyl, $C_{6-10}$ aryl, and 5-10 membered heteroaryl; wherein said $C_{2-6}$ alkenyl, $C_{2-6}$ alkynyl, 7-10 membered heterocycloalkyl, $C_{6-10}$ aryl and 5-10 membered heteroaryl are each optionally substituted with 1, 2, 3, or 4 substituents independently selected from $R^{10}$;

each $R^{a1}$, $R^{c1}$, and $R^{d1}$ is independently selected from H, $C_{1-6}$ alkyl, and $C_{3-10}$ cycloalkyl; wherein said $C_{1-6}$ alkyl and $C_{3-10}$ cycloalkyl, are each optionally substituted with 1 or 2 substituents independently selected from $R^{11}$;

each $R^{a2}$, $R^{c2}$ and $R^{d2}$ is independently selected from H, $C_{1-6}$ alkyl, $C_{2-6}$ alkenyl, $C_{2-6}$ alkynyl, $C_{1-6}$ haloalkyl, and 4-10 membered heterocycloalkyl; wherein said $C_{1-6}$ alkyl, $C_{2-6}$ alkenyl, $C_{2-6}$ alkynyl, and 4-10 membered heterocycloalkyl are each optionally substituted with 1 or 2 substituents independently selected from $R^{21}$;

or any $R^{c2}$ and $R^{d2}$ attached to the same N atom, together with the N atom to which they are attached, form a 4-, 5-, 6- or 7-membered heterocycloalkyl group optionally substituted with 1, 2, 3 or 4 substituents independently selected from $R^{21}$;

each $R^{b2}$ is independently selected from $C_{1-6}$ alkyl, $C_{3-10}$ cycloalkyl, 4-10 membered heterocycloalkyl, and 5-10 membered heteroaryl; wherein said $C_{1-6}$ alkyl, $C_{3-10}$ cycloalkyl, 4-10 membered heterocycloalkyl, and 5-10 membered heteroaryl are each optionally substituted with 1 or 2 substituents independently selected from $R^{21}$;

each $R^{a3}$, $R^{c3}$ and $R^{d3}$, is independently selected from H, $C_{1-6}$ alkyl, $C_{2-6}$ alkenyl, $C_{2-6}$ alkynyl, and $C_{1-6}$ haloalkyl;

each $R^{b3}$ is independently selected from $C_{1-6}$ alkyl, $C_{2-6}$ alkenyl, $C_{2-6}$ alkynyl, $C_{1-6}$ haloalkyl, and phenyl;

each $R^{a4}$, $R^{c4}$ and $R^{d4}$ is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, 5-6 membered heteroaryl and 4-7 membered heterocycloalkyl; wherein said $C_{1-6}$ alkyl, $C_{2-6}$ alkenyl, $C_{2-6}$ alkynyl, $C_{1-6}$ haloalkyl, $C_{3-6}$ cycloalkyl, 5-6 membered heteroaryl and 4-7 membered heterocycloalkyl are each optionally substituted with 1 or 2 substituents independently selected from $R^{22}$;

or any $R^{c4}$ and $R^{d4}$ attached to the same N atom, together with the N atom to which they are attached, form a 4-, 5-, 6- or 7-membered heterocycloalkyl group;

each $R^{b4}$ is independently selected from $C_{1-6}$ alkyl;

each $R^{a6}$ is independently selected from H and $C_{1-6}$ alkyl;

each $R^{c6}$ and $R^{d6}$ is independently selected from H, $C_{1-6}$ alkyl, $C_{2-6}$ alkenyl, $C_{2-6}$ alkynyl and $C_{1-6}$ haloalkyl;

each $R^{b6}$ is independently selected from $C_{1-6}$ alkyl, $C_{2-6}$ alkenyl, $C_{2-6}$ alkynyl, and $C_{1-6}$ haloalkyl;

each $R^{a7}$ is independently selected from H and $C_{1-6}$ alkyl; and each $R^g$ is independently selected from $C_{1-6}$ alkyl.

In some embodiments:

$R^1$ is selected from $Cy^1$, $C_{2-6}$ alkenyl, $C(O)NR^cR^d$, and $NR^cR^d$, $NR^cC(O)R^b$; wherein said $C_{2-6}$ alkenyl is optionally substituted with 1 independently selected from $R^{10}$;

$Cy^1$ is selected from 4-10 membered heterocycloalkyl, $C_{6-10}$ aryl and 5-10 membered heteroaryl, wherein each 4-10 membered heterocycloalkyl and 5-10 membered heteroaryl has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl and 4-10 membered heterocycloalkyl is optionally substituted by oxo to form a carbonyl group; and wherein the 4-10 membered heterocycloalkyl, $C_{6-10}$ aryl and 5-10 membered heteroaryl are each optionally substituted with 1 or 2 substituents independently selected from $R^{10}$;

$Cy^A$ is $C_{6-10}$ aryl optionally substituted with 1, 2, 3, or 4 substituents independently selected from $R^{20}$;

$R^2$ is H, halo, or $OR^{a7}$;

each $R^{10}$ is independently selected from $C_{1-6}$ alkyl, $C_{3-10}$ cycloalkyl, 4-10 membered heterocycloalkyl, $C_{6-10}$ aryl, 5-10 membered heteroaryl, halo, CN, $OR^{a1}$, $C(O)NR^{c1}R^{d1}$, and $NR^{c1}R^{d1}$; wherein said $C_{3-10}$ cycloalkyl, 4-10 membered heterocycloalkyl, $C_{6-10}$ aryl, and 5-10 membered heteroaryl are each optionally substituted with 1 or 2 substituents independently selected from $R^{11}$;

each $R^{11}$ is independently selected from $C_{1-6}$ alkyl, $C_{1-6}$ haloalkyl, $C_{6-10}$ aryl, 5-10 membered heteroaryl, 4-10 membered heterocycloalkyl, halo, CN, $OR^{a3}$, $C(O)OR^{a3}$, and $S(O)_2R^{b3}$; wherein said $C_{1-6}$ alkyl, $C_{6-10}$ aryl, 5-10 membered heteroaryl, and 4-10 membered heterocycloalkyl are each optionally substituted with 1 or 2 substituents independently selected from $R^{12}$;

each $R^{12}$ is $C_{1-6}$ alkyl, halo, or CN;

each $R^{20}$ is independently selected from $C_{1-6}$ alkyl, $C_{1-6}$ haloalkyl, $C_{3-10}$ cycloalkyl, 4-10 membered heterocycloalkyl, 4-10 membered heterocycloalkyl-$C_{1-3}$ alkylene, halo, $OR^{a2}$, $C(O)R^{b2}$, $C(O)NR^{c2}R^{d2}$, $OC(O)R^{b2}$, $OC(O)NR^{c2}R^{d2}$, $NR^{c2}C(O)R^{b2}$, $NR^{c2}C(O)OR^{a2}$, and $NR^{c2}C(O)NR^{c2}R^{d2}$; wherein said $C_{1-6}$ alkyl, $C_{3-10}$ cycloalkyl, 4-10 membered heterocycloalkyl, and 4-10 membered heterocycloalkyl-$C_{1-3}$ alkylene are each optionally substituted with 1 or 2 substituents independently selected from $R^{21}$;

or two adjacent $R^{20}$ substituents on the $Cy^A$ ring, taken together with the atoms to which they are attached, form a fused $C_{3-7}$ cycloalkyl ring; and wherein the fused $C_{3-7}$ cycloalkyl ring is optionally substituted with 1 or 2 substituents independently selected from $R^{21}$;

each $R^{21}$ is $C_{1-6}$ alkyl, $C_{3-10}$ cycloalkyl, 4-10 membered heterocycloalkyl, $C_{6-10}$ aryl, 5-10 membered heteroaryl, halo, CN, $OR^{a4}$, $NR^{c4}R^{d4}$, $NR^{c4}C(O)R^{b4}$, and $NR^{c4}C(O)OR^{a4}$; wherein said $C_{1-6}$ alkyl, $C_{3-10}$ cycloalkyl, 4-10 membered heterocycloalkyl, $C_{6-10}$ aryl, and 5-10 membered heteroaryl are each optionally substituted with 1 or 2 substituents independently selected from $R^{22}$;

each $R^{22}$ is independently selected from $C_{1-6}$ alkyl, 5-6 membered heteroaryl, 4-7 membered heterocycloalkyl, CN, $OR^{a6}$ and $NR^{c6}R^{d6}$; wherein said $C_{1-6}$ alkyl and 5-6 membered heteroaryl are each optionally substituted with 1 or 2 substituents independently selected from $R^g$;

each $R^a$ and $R^c$ is H;

each $R^d$ is independently selected from $C_{1-6}$ alkyl, $C_{6-10}$ aryl, and 5-10 membered heteroaryl; wherein said $C_{1-6}$ alkyl, $C_{6-10}$ aryl, and 5-10 membered heteroaryl are each optionally substituted with 1 or 2 substituents independently selected from $R^{10}$;

each $R^b$ is independently selected from 7-10 membered heterocycloalkyl, $C_{6-10}$ aryl, and 5-10 membered heteroaryl; wherein said 7-10 membered heterocycloalkyl, $C_{6-10}$ aryl and 5-10 membered heteroaryl are each optionally substituted with 1 or 2 substituents independently selected from $R^{10}$;

each $R^{a1}$, $R^{c1}$ and $R^{d1}$ is independently selected from H, $C_{1-6}$ alkyl, and $C_{3-10}$ cycloalkyl; wherein said $C_{1-6}$ alkyl and $C_{3-10}$ cycloalkyl, are each optionally substituted with 1 or 2 substituents independently selected from $R^{11}$;

each $R^{a2}$, $R^{c2}$ and $R^{d2}$ is independently selected from H, $C_{1-6}$ alkyl, $C_{1-6}$ haloalkyl, and 4-10 membered heterocycloalkyl; wherein said $C_{1-6}$ alkyl and 4-10 membered heterocycloalkyl are each optionally substituted with 1 or 2 substituents independently selected from $R^{21}$;

or any $R^{c2}$ and $R^{d2}$ attached to the same N atom, together with the N atom to which they are attached, form a 4-, 5-, 6- or 7-membered heterocycloalkyl group optionally substituted with 1 or 2 substituents independently selected from $R^{21}$;

each $R^{b2}$ is independently selected from $C_{1-6}$ alkyl, $C_{3-10}$ cycloalkyl, 4-10 membered heterocycloalkyl, and 5-10 membered heteroaryl; wherein said $C_{1-6}$ alkyl, $C_{3-10}$ cycloalkyl, 4-10 membered heterocycloalkyl, and 5-10 membered heteroaryl are each optionally substituted with 1 or 2 substituents independently selected from $R^{21}$;

each $R^{a3}$ is independently selected from H and $C_{1-6}$ alkyl;

each $R^{b3}$ is $C_{1-6}$ alkyl;

each $R^{a4}$, $R^{c4}$ and $R^{d4}$ is independently selected from H, $C_{1-6}$ alkyl, $C_{1-6}$ haloalkyl, $C_{3-6}$ cycloalkyl, 5-6 membered heteroaryl and 4-7 membered heterocycloalkyl; wherein said $C_{1-6}$ alkyl, $C_{3-6}$ cycloalkyl, 5-6 membered heteroaryl and 4-7 membered heterocycloalkyl are each optionally substituted with 1 or 2 substituents independently selected from $R^{22}$;

or any $R^{c4}$ and $R^{d4}$ attached to the same N atom, together with the N atom to which they are attached, form a 4-, 5-, 6- or 7-membered heterocycloalkyl group;

each $R^{b4}$ is independently selected from $C_{1-6}$ alkyl;

each $R^{a6}$ is independently selected from H and $C_{1-6}$ alkyl;

each $R^{c6}$ and $R^{d6}$ is H;

each $R^{a7}$ is independently selected from H and $C_{1-6}$ alkyl; and each $R^g$ is independently selected from $C_{1-6}$ alkyl.

It is further appreciated that certain features of the invention, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable subcombination. Thus, it is contemplated as features described as embodiments of the compounds of Formula (I) can be combined in any suitable combination.

At various places in the present specification, certain features of the compounds are disclosed in groups or in ranges. It is specifically intended that such a disclosure include each and every individual subcombination of the members of such groups and ranges. For example, the term "$C_{1-6}$ alkyl" is specifically intended to individually disclose (without limitation) methyl, ethyl, $C_3$ alkyl, $C_4$ alkyl, $C_5$ alkyl and $C_6$ alkyl.

The term "n-membered," where n is an integer, typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring and 1,2,3,4-tetrahydro-naphthalene is an example of a 10-membered cycloalkyl group.

At various places in the present specification, variables defining divalent linking groups may be described. It is specifically intended that each linking substituent include both the forward and backward forms of the linking substituent. For example, —NR(CR'R")$_n$— includes both —NR(CR'R")$_n$— and —(CR'R")$_n$NR— and is intended to disclose each of the forms individually. Where the structure requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The term "substituted" means that an atom or group of atoms formally replaces hydrogen as a "substituent" attached to another group. The term "substituted", unless otherwise indicated, refers to any level of substitution, e.g., mono-, di-, tri-, tetra- or penta-substitution, where such substitution is permitted. The substituents are independently selected, and substitution may be at any chemically accessible position. It is to be understood that substitution at a given atom is limited by valency. It is to be understood that substitution at a given atom results in a chemically stable molecule. The phrase "optionally substituted" means unsubstituted or substituted. The term "substituted" means that a hydrogen atom is removed and replaced by a substituent. A single divalent substituent, e.g., oxo, can replace two hydrogen atoms.

The term "$C_{n-m}$" indicates a range which includes the endpoints, wherein n and m are integers and indicate the number of carbons. Examples include $C_{1-4}$, $C_{1-6}$ and the like.

The term "alkyl," employed alone or in combination with other terms, refers to a saturated hydrocarbon group that may be straight-chained or branched. The term "$C_{n-m}$ alkyl", refers to an alkyl group having n to m carbon atoms. An alkyl group formally corresponds to an alkane with one C—H bond replaced by the point of attachment of the alkyl group to the remainder of the compound. In some embodiments, the alkyl group contains from 1 to 6 carbon atoms, from 1 to 4 carbon atoms, from 1 to 3 carbon atoms, or 1 to 2 carbon atoms. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl and the like.

The term "alkenyl," employed alone or in combination with other terms, refers to a straight-chain or branched hydrocarbon group corresponding to an alkyl group having one or more double carbon-carbon bonds. An alkenyl group formally corresponds to an alkene with one C—H bond replaced by the point of attachment of the alkenyl group to the remainder of the compound. The term "$C_{n-m}$ alkenyl" refers to an alkenyl group having n to m carbons. In some embodiments, the alkenyl moiety contains 2 to 6, 2 to 4, or 2 to 3 carbon atoms. Example alkenyl groups include, but are not limited to, ethenyl, n-propenyl, isopropenyl, n-butenyl, sec-butenyl and the like.

The term "alkynyl," employed alone or in combination with other terms, refers to a straight-chain or branched hydrocarbon group corresponding to an alkyl group having one or more triple carbon-carbon bonds. An alkynyl group formally corresponds to an alkyne with one C—H bond replaced by the point of attachment of the alkyl group to the remainder of the compound. The term "$C_{n-m}$ alkynyl" refers to an alkynyl group having n to m carbons. Example alkynyl groups include, but are not limited to, ethynyl, propyn-1-yl, propyn-2-yl and the like. In some embodiments, the alkynyl moiety contains 2 to 6, 2 to 4, or 2 to 3 carbon atoms.

The term "alkylene," employed alone or in combination with other terms, refers to a divalent alkyl linking group. An alkylene group formally corresponds to an alkane with two C—H bond replaced by points of attachment of the alkylene group to the remainder of the compound. The term "$C_{n-m}$ alkylene" refers to an alkylene group having n to m carbon atoms. Examples of alkylene groups include, but are not limited to, ethan-1,2-diyl, ethan-1,1-diyl, propan-1,3-diyl, propan-1,2-diyl, propan-1,1-diyl, butan-1,4-diyl, butan-1,3-diyl, butan-1,2-diyl, 2-methyl-propan-1,3-diyl and the like.

The term "alkoxy," employed alone or in combination with other terms, refers to a group of formula —O-alkyl, wherein the alkyl group is as defined above. The term "$C_{n-m}$ alkoxy" refers to an alkoxy group, the alkyl group of which has n to m carbons. Example alkoxy groups include methoxy, ethoxy, propoxy (e.g., n-propoxy and isopropoxy), t-butoxy and the like. In some embodiments, the alkyl group has 1 to 6, 1 to 4, or 1 to 3 carbon atoms.

The term "amino" refers to a group of formula —$NH_2$.

The term "carbonyl," employed alone or in combination with other terms, refers to a —C(=O)— group, which also may be written as C(O).

The term "cyano" or "nitrile" refers to a group of formula which also may be written as —CN.

The terms "halo" or "halogen", used alone or in combination with other terms, refers to fluoro, chloro, bromo and iodo. In some embodiments, "halo" refers to a halogen atom selected from F, Cl, or Br. In some embodiments, halo groups are F.

The term "haloalkyl" as used herein refers to an alkyl group in which one or more of the hydrogen atoms has been replaced by a halogen atom. The term "$C_{n-m}$ haloalkyl" refers to a $C_{n-m}$ alkyl group having n to m carbon atoms and from at least one up to {2(n to m)+1} halogen atoms, which may either be the same or different. In some embodiments, the halogen atoms are fluoro atoms. In some embodiments, the haloalkyl group has 1 to 6 or 1 to 4 carbon atoms. Example haloalkyl groups include $CF_3$, $C_2F_5$, $CHF_2$, $CH_2F$, $CCl_3$, $CHCl_2$, $C_2Cl_5$ and the like. In some embodiments, the haloalkyl group is a fluoroalkyl group.

The term "haloalkoxy," employed alone or in combination with other terms, refers to a group of formula —O-haloalkyl, wherein the haloalkyl group is as defined above. The term "$C_{n-m}$ haloalkoxy" refers to a haloalkoxy group, the haloalkyl group of which has n to m carbons. Example haloalkoxy groups include trifluoromethoxy and the like. In some embodiments, the haloalkoxy group has 1 to 6, 1 to 4, or 1 to 3 carbon atoms.

The term "oxo" refers to an oxygen atom as a divalent substituent, forming a carbonyl group when attached to carbon, or attached to a heteroatom forming a sulfoxide or sulfone group, or an N-oxide group. In some embodiments, heterocyclic groups may be optionally substituted by 1 or 2 oxo (=O) substituents.

The term "sulfido" refers to a sulfur atom as a divalent substituent, forming a thiocarbonyl group (C=S) when attached to carbon.

The term "aromatic" refers to a carbocycle or heterocycle having one or more polyunsaturated rings having aromatic character (i.e., having (4n+2) delocalized π (pi) electrons where n is an integer).

The term "aryl," employed alone or in combination with other terms, refers to an aromatic hydrocarbon group, which may be monocyclic or polycyclic (e.g., having 2 fused rings). The term "$C_{n-m}$ aryl" refers to an aryl group having from n to m ring carbon atoms. Aryl groups include, e.g., phenyl, naphthyl, and the like. In some embodiments, aryl groups have from 6 to about 10 carbon atoms. In some embodiments aryl groups have 6 carbon atoms. In some embodiments aryl groups have 10 carbon atoms. In some embodiments, the aryl group is phenyl. In some embodiments, the aryl group is naphthyl.

The term "heteroaryl" or "heteroaromatic," employed alone or in combination with other terms, refers to a monocyclic or polycyclic aromatic heterocycle having at least one heteroatom ring member selected from sulfur, oxygen and nitrogen. In some embodiments, the heteroaryl ring has 1, 2, 3 or 4 heteroatom ring members independently selected from nitrogen, sulfur and oxygen. In some embodiments, any ring-forming N in a heteroaryl moiety can be an N-oxide. In some embodiments, the heteroaryl has 5-14 ring atoms including carbon atoms and 1, 2, 3 or 4 heteroatom ring members independently selected from nitrogen, sulfur and oxygen. In some embodiments, the heteroaryl has 5-10 ring atoms including carbon atoms and 1, 2, 3 or 4 heteroatom ring members independently selected from nitrogen, sulfur and oxygen. In some embodiments, the heteroaryl has 5-6 ring atoms and 1 or 2 heteroatom ring members independently selected from nitrogen, sulfur and oxygen. In some embodiments, the heteroaryl is a five-membered or six-membered heteroaryl ring. In other embodiments, the heteroaryl is an eight-membered, nine-membered or ten-membered fused bicyclic heteroaryl ring. Example heteroaryl groups include, but are not limited to, pyridinyl (pyridyl), pyrimidinyl, pyrazinyl, pyridazinyl, pyrrolyl, pyrazolyl, azolyl, oxazolyl, isoxazolyl, thiazolyl, imidazolyl, furanyl, thiophenyl, quinolinyl, isoquinolinyl, naphthyridinyl (including 1,2-, 1,3-, 1,4-, 1,5-, 1,6-, 1,7-, 1,8-, 2,3- and 2,6-naphthyridine), indolyl, benzothiophenyl, benzofuranyl, benzisoxazolyl, imidazo[1,2-b]-thiazolyl, purinyl, and the like. In some embodiments, the heteroaryl group is pyridone (e.g., 2-pyridone).

A five-membered heteroaryl ring is a heteroaryl group having five ring atoms wherein one or more (e.g., 1, 2 or 3) ring atoms are independently selected from N, O and S. Exemplary five-membered ring heteroaryls include thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl and 1,3,4-oxadiazolyl.

A six-membered heteroaryl ring is a heteroaryl group having six ring atoms wherein one or more (e.g., 1, 2 or 3) ring atoms are independently selected from N, O and S. Exemplary six-membered ring heteroaryls are pyridyl, pyrazinyl, pyrimidinyl, triazinyl and pyridazinyl.

The term "cycloalkyl," employed alone or in combination with other terms, refers to a non-aromatic hydrocarbon ring system (monocyclic, bicyclic or polycyclic), including cyclized alkyl and alkenyl groups. The term "$C_{n-m}$ cycloalkyl" refers to a cycloalkyl that has n to m ring member carbon atoms. Cycloalkyl groups can include mono- or polycyclic (e.g., having 2, 3 or 4 fused rings) groups and spirocycles. Cycloalkyl groups can have 3, 4, 5, 6 or 7 ring-forming carbons ($C_{3-7}$). In some embodiments, the cycloalkyl group has 3 to 6 ring members, 3 to 5 ring members, or 3 to 4 ring members. In some embodiments, the cycloalkyl group is monocyclic. In some embodiments, the cycloalkyl group is monocyclic or bicyclic. In some embodiments, the cycloalkyl group is a $C_{3-6}$ monocyclic cycloalkyl group. Ring-forming carbon atoms of a cycloalkyl group can be optionally oxidized to form an oxo or sulfido group. Cycloalkyl groups also include cycloalkylidenes. In some embodiments, cycloalkyl is cyclopropyl, cyclobutyl, cyclopentyl or cyclohexyl. Also included in the definition of cycloalkyl are moieties that have one or more aromatic rings fused (i.e., having a bond in common with) to the cycloalkyl ring, e.g., benzo or thienyl derivatives of cyclopentane, cyclohexane and the like. A cycloalkyl group containing a fused aromatic ring can be attached through any ring-forming atom including a ring-forming atom of the fused aromatic ring. Examples of cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, bicyclo[1.1.1]pentanyl, bicyclo[2.1.1]hexanyl, and the like. In some embodiments, the cycloalkyl group is cyclopropyl, cyclobutyl, cyclopentyl, or cyclohexyl.

The term "heterocycloalkyl," employed alone or in combination with other terms, refers to a non-aromatic ring or ring system, which may optionally contain one or more alkenylene groups as part of the ring structure, which has at least one heteroatom ring member independently selected from nitrogen, sulfur oxygen and phosphorus, and which has 4-10 ring members, 4-7 ring members, or 4-6 ring members. Included within the term "heterocycloalkyl" are monocyclic 4-, 5-, 6- and 7-membered heterocycloalkyl groups. Heterocycloalkyl groups can include mono- or bicyclic (e.g., having two fused or bridged rings) or spirocyclic ring systems. In some embodiments, the heterocycloalkyl group is a monocyclic group having 1, 2 or 3 heteroatoms independently selected from nitrogen, sulfur and oxygen. Ring-forming carbon atoms and heteroatoms of a heterocycloalkyl group can be optionally oxidized to form an oxo or sulfido group or other oxidized linkage (e.g., C(O), S(O), C(S) or $S(O)_2$, N-oxide etc.) or a nitrogen atom can be quaternized. The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the heterocycloalkyl ring, e.g., benzo or thienyl derivatives of piperidine, morpholine, azepine, etc. A heterocycloalkyl group containing a fused aromatic ring can be attached through any ring-forming atom including a ring-forming atom of the fused aromatic ring. Examples of heterocycloalkyl groups include azetidinyl, azepanyl, dihydrobenzofuranyl, dihydrofuranyl, dihydropyranyl, morpholino, 3-oxopiperazin-1-yl, 3-oxa-9-azaspiro[5.5]undecanyl, 1-oxa-8-azaspiro[4.5]decanyl, piperidinyl, piperazinyl, piperazinonyl, oxopiperazinyl, pyranyl, pyrrolidinyl, quinuclidinyl, tetrahydrofuranyl, tetrahydropyranyl, 1,2,3,4-tetrahydroquinolinyl, 1,2,3,4-tetrahydroisoquinolinyl, tropanyl, benzodioxole, and thiomorpholino.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas an azetidin-3-yl ring is attached at the 3-position.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. One method includes fractional recrystallization using a chiral resolving acid which is an optically active, salt-forming organic acid. Suitable resolving agents for fractional recrystallization methods are, e.g., optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane and the like.

Resolution of racemic mixtures can also be carried out by elution on a column packed with an optically active resolving agent (e.g., dinitrobenzoylphenylglycine). Suitable elution solvent composition can be determined by one skilled in the art.

In some embodiments, the compounds of the invention have the (R)-configuration. In other embodiments, the compounds have the (S)-configuration. In compounds with more than one chiral centers, each of the chiral centers in the compound may be independently (R) or (S), unless otherwise indicated.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone enol pairs, amide-imidic acid pairs, lactam lactim pairs, enamine imine pairs, and annular forms where a proton can occupy two or more positions of a heterocyclic system, e.g., 1H- and 3H-imidazole, 1H-, 2H- and 4H-1,2,4-triazole, 1H- and 2H-isoindole and 1H- and 2H-pyrazole. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers. For example, isotopes of hydrogen include tritium and deuterium. One or more constituent atoms of the compounds of the invention can be replaced or substituted with isotopes of the atoms in natural or non-natural abundance. In some embodiments, the compound includes at least one deuterium atom. For example, one or more hydrogen atoms in a compound of the present disclosure can be replaced or substituted by deuterium. In some embodiments, the compound includes two or more deuterium atoms. In some embodiments, the compound includes 1, 2, 3, 4, 5, 6, 7, 8, 9, 10, 11 or 12 deuterium atoms. Synthetic methods for including isotopes into organic compounds are known in the art (Deuterium Labeling in Organic Chemistry by Alan F. Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765). Isotopically labeled compounds can used in various studies such as NMR spectroscopy, metabolism experiments, and/or assays.

Substitution with heavier isotopes such as deuterium, may afford certain therapeutic advantages resulting from greater metabolic stability, for example, increased in vivo half-life or reduced dosage requirements, and hence may be preferred in some circumstances. (A. Kerekes et. al. *J. Med. Chem.* 2011, 54, 201-210; R. Xu et. al. *J. Label Compd. Radiopharm.* 2015, 58, 308-312). The term, "compound," as used herein is meant to include all stereoisomers, geometric isomers, tautomers and isotopes of the structures depicted. The term is also meant to refer to compounds of the inventions, regardless of how they are prepared, e.g., synthetically, through biological process (e.g., metabolism or enzyme conversion), or a combination thereof.

All compounds, and pharmaceutically acceptable salts thereof, can be found together with other substances such as water and solvents (e.g., hydrates and solvates) or can be isolated. When in the solid state, the compounds described herein and salts thereof may occur in various forms and may, e.g., take the form of solvates, including hydrates. The compounds may be in any solid state form, such as a polymorph or solvate, so unless clearly indicated otherwise, reference in the specification to compounds and salts thereof should be understood as encompassing any solid state form of the compound.

In some embodiments, the compounds of the invention, or salts thereof, are substantially isolated. By "substantially isolated" is meant that the compound is at least partially or substantially separated from the environment in which it was formed or detected. Partial separation can include, e.g., a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof.

The phrase "pharmaceutically acceptable" is employed herein to refer to those compounds, materials, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature," as used herein, are understood in the art, and refer generally to a temperature, e.g., a reaction temperature, that is about the temperature of the room in which the reaction is carried out, e.g., a temperature from about 20° C. to about 30° C.

The present invention also includes pharmaceutically acceptable salts of the compounds described herein. The term "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the non-toxic salts of the parent compound formed, e.g., from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol or butanol) or acetonitrile (MeCN) are preferred. Lists of suitable salts are found in *Remington's Pharmaceutical Sciences*, 17th Ed., (Mack Publishing Company, Easton, 1985), p. 1418, Berge et al., *J. Pharm. Sci.*, 1977, 66(1), 1-19 and in Stahl et al., *Handbook of Pharmaceutical Salts: Properties, Selection, and Use*, (Wiley, 2002). In some embodiments, the compounds described herein include the N-oxide forms.

Synthesis

Compounds of the invention, including salts thereof, can be prepared using known organic synthesis techniques and can be synthesized according to any of numerous possible synthetic routes, such as those in the Schemes below.

The reactions for preparing compounds of the invention can be carried out in suitable solvents which can be readily selected by one of skill in the art of organic synthesis. Suitable solvents can be substantially non-reactive with the starting materials (reactants), the intermediates or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups is described, e.g., in Kocienski, *Protecting Groups*, (Thieme, 2007); Robertson, *Protecting Group Chemistry*, (Oxford University Press, 2000); Smith et al., *March's Advanced Organic Chemistry: Reactions, Mechanisms, and Structure*, 6th Ed. (Wiley, 2007); Peturssion et al., "Protecting Groups in Carbohydrate Chemistry," *J. Chem. Educ.*, 1997, 74(11), 1297; and Wuts et al., *Protective Groups in Organic Synthesis*, 4th Ed., (Wiley, 2006).

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry or by chromatographic methods such as high performance liquid chromatography (HPLC) or thin layer chromatography (TLC).

The Schemes below provide general guidance in connection with preparing the compounds of the invention. One skilled in the art would understand that the preparations shown in the Schemes can be modified or optimized using general knowledge of organic chemistry to prepare various compounds of the invention.

Compounds of Formula (I) can be prepared, e.g., using a process as illustrated in the schemes below.

Compounds of Formula (I) with various substitutions at position $R^1$ such as those described herein can be prepared using a process as illustrated in Scheme 1. In the process depicted in Scheme 1, compounds of Formula 1-2 are formed after protection of the NH group of the compounds of Formula 1-1 with a suitable protecting group (e.g. SEM or Boc). The chloro substituent in the compounds of Formula 1-2 can be converted into $Cy^A$ via a number of different cross-coupling reactions, including Suzuki (e.g., in the presence of a palladium catalyst, such as Xphos Pd G2, and a base, such as potassium phosphate) or Stille (e.g., in the presence of a palladium(O) catalyst, such as tetrakis(triphenylphosphine)palladium(O)), and others, to give the compounds of Formula 1-3. Deprotection of the protecting group (e.g., under acidic conditions, such as treatment with HCl or TFA) results in the formation of compounds of Formula 1-4. These compounds can be further halogenated with one of the halogenation agents (e.g., NIS or iodine) to form compounds of Formula 1-5. The NH group of the pyrazole ring of the compounds of Formula 1-5 is protected with a suitable protecting group, such as Boc or SEM, to form compounds of Formula 1-6. The halogen substituent in the compounds of Formula 1-6 can be converted into $R^1$ via a number of different cross-coupling reactions, including Stille (ACS Catalysis 2015, 5, 3040-3053), Suzuki (Tetrahedron 2002, 58, 9633-9695), Sonogashira (Chem. Soc. Rev. 2011, 40, 5084-5121), Negishi (ACS Catalysis 2016, 6, 1540-1552), Buchwald-Hartwig amination (Chem. Sci. 2011, 2, 27-50), Cu-catalyzed amination (Org. React. 2014, 85, 1-688) and others, to give the compounds of Formula 1-7. Finally, deprotection of the protecting group under acidic conditions (e.g., treatment with HCl or TFA) results in the formation of the desired compounds of Formula (I).

Scheme 1

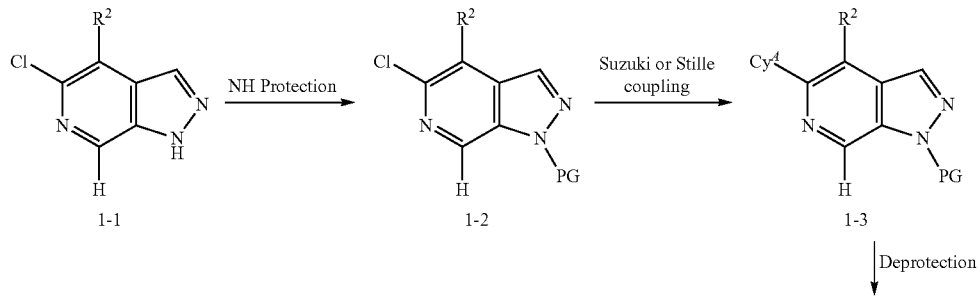

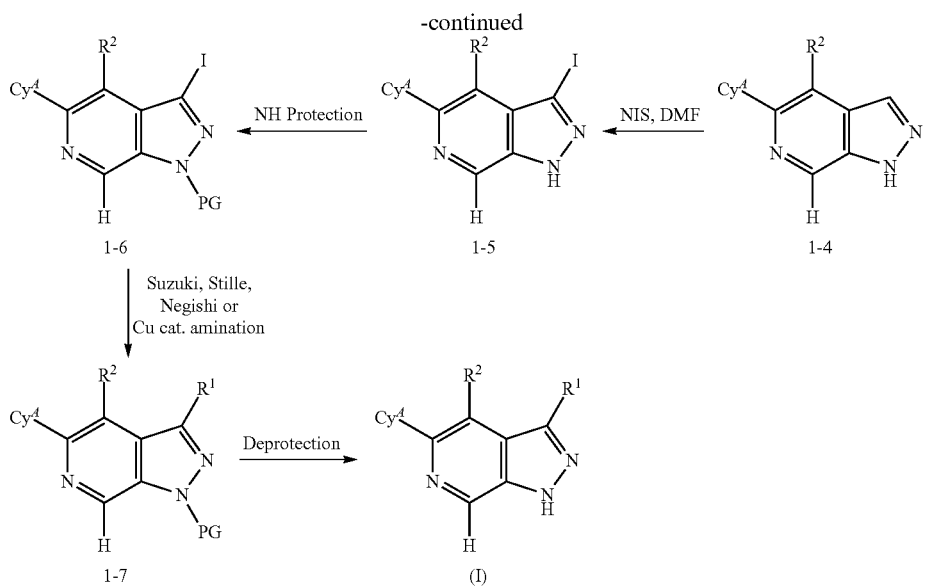

Alternatively, for the exploration of the substitution at position $Cy^4$, compounds of Formula (I) can be prepared, using a process as illustrated in Scheme 2. Iodination of the compounds of Formula 1-1 with one of the iodination agents, such as iodine or NIS, forms compounds of Formula 2-2. The NH group of the pyrazole ring of the compounds of Formula 2-2 is protected with a suitable protecting group (e.g., Boc or SEM) to form compounds of Formula 2-3. The iodo substituent in the compounds of Formula 2-3 can be converted into $R^1$ via a number of different cross-coupling reactions, including Suzuki, Sonogashira, Negishi, Buchwald-Hartwig amination, Cu-catalyzed amination and others, to give the compounds of Formula 2-4. The chloro substituent in the compounds of Formula 2-4 can be further converted into $Cy^4$ via a number of different cross-coupling reactions, including Suzuki, Stille, and others, to give the compounds of Formula 2-5. Finally, deprotection of the protecting group, e.g. under acidic conditions, such as treatment with HCl or TFA, results in the formation of the desired compounds of Formula (I).

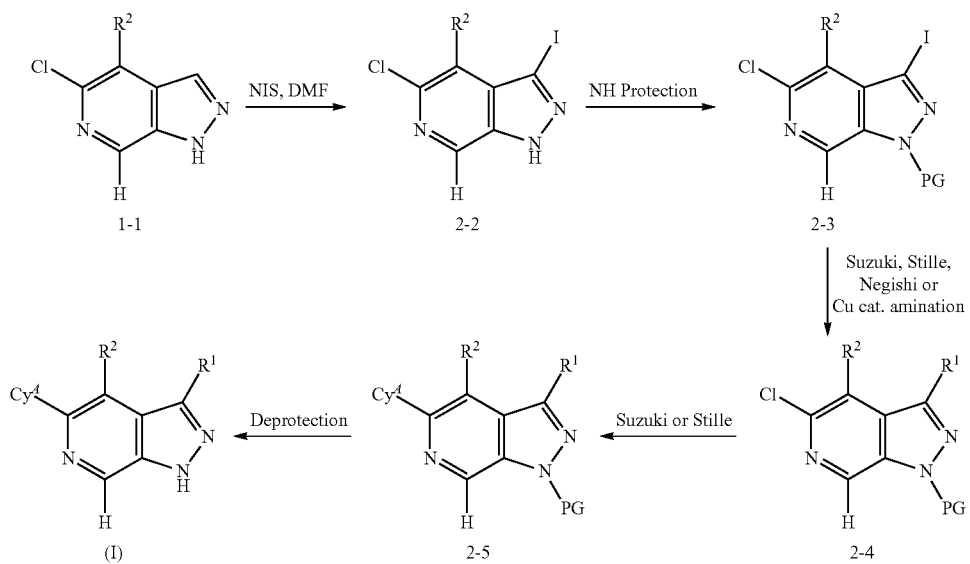

Compounds of Formula (Ia) (compounds of Formula I wherein $R^1$ is $NR^cC(O)R^b$) can be prepared, using a process as illustrated in Scheme 3. In the process depicted in Scheme 3, compounds of Formula 3-1 react which hydroxylamine hydrochloride to form oxime intermediates, which are further converted to compounds of Formula 3-2 under the standard conditions (e.g. under treatment with cyanuric chloride). Cyclization upon treatment of the compounds of Formula 3-2 with hydrazine hydrate results in compounds of Formula 3-3. The NH group of the pyrazole ring of the compounds of Formula 3-3 is protected with a suitable protecting group (e.g., Boc) to form compounds of Formula 3-4. The halo substituent in the compounds of Formula 3-4 can be further converted into Cy$^A$ via a number of different cross-coupling reactions, including Suzuki, Stille, and others, to give the compounds of Formula 3-5. Compounds of Formula 3-5 react with different acid chlorides in a presence of base, such as triethylamine or DIPEA, to form compounds of Formula 3-6. Finally, deprotection of the protecting group, e.g. under acidic conditions, such as treatment with HCl or TFA, results in the formation of the desired compounds of Formula (Ia). Alternatively compounds of Formula 3-6 can be alkylated or arylated and then deprotected to prepare amides wherein R$^c$ is other than hydrogen.

as illustrated in Scheme 4. In the process depicted in Scheme 4, compounds of Formula 1-6 are converted into compounds of Formula 4-2 under Pd-catalyzed carbonylation conditions, such as in a presence of Pd catalyst (e.g., Pd(dppf)Cl$_2$*DCM) and base (e.g., triethylamine) under carbon monoxide atmosphere. Hydrolysis of the ester group under basic conditions, such as LiOH or NaOH, forms the compounds of Formula 4-3. Compounds of Formula 4-3 can be coupled to an amine, HNR$^c$R$^d$, using standard amide coupling agents (e.g., HBTU, HATU or EDC) to give compounds of Formula 4-4. Finally, deprotection of the protecting group, e.g. under

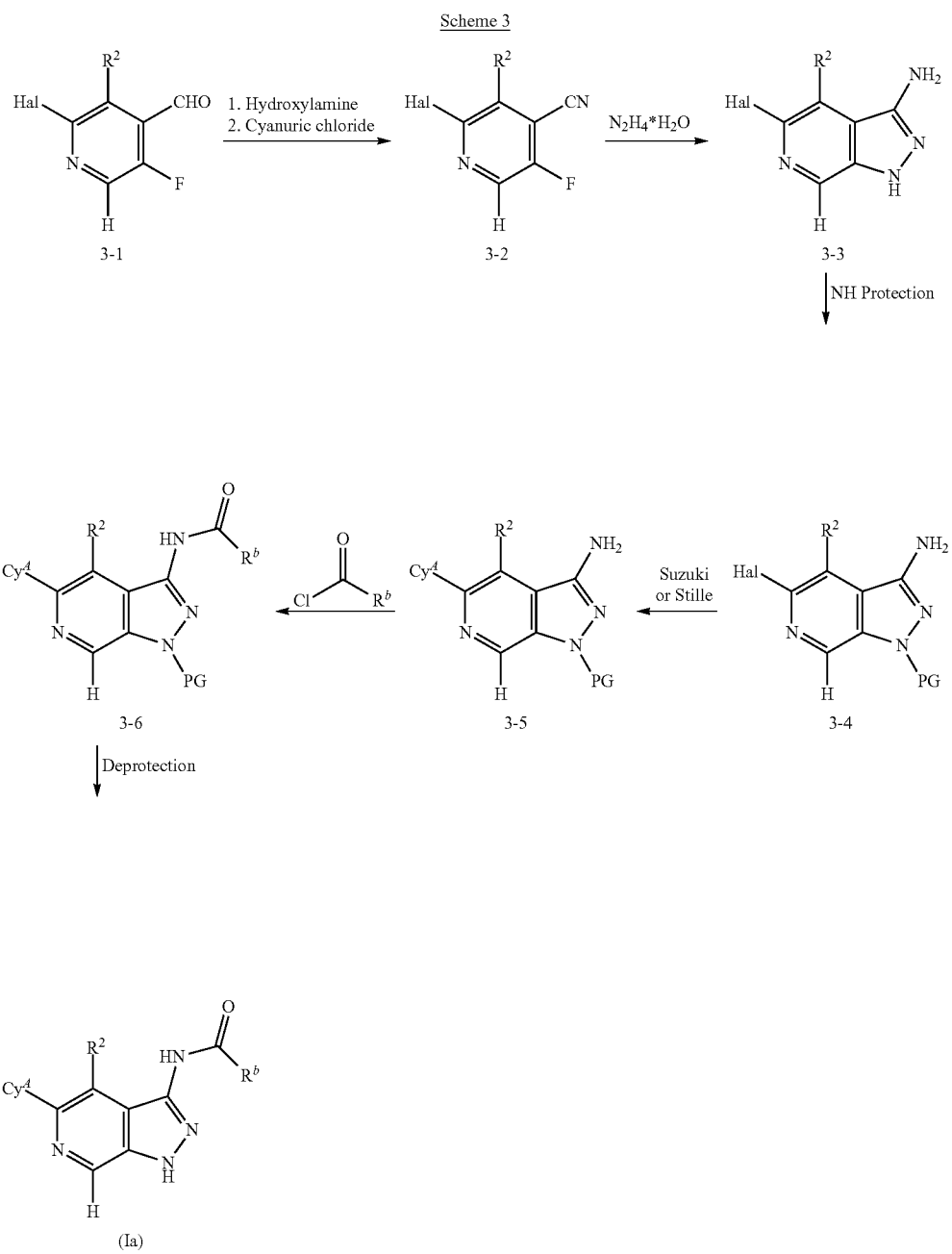

Compounds of Formula (Ib) (compounds of Formula I wherein R$^1$ is C(O)NR$^c$R$^d$) can be prepared, using a process acidic conditions, such as treatment with HCl or TFA, results in the formation of the desired compounds of Formula (Ib).

Scheme 4

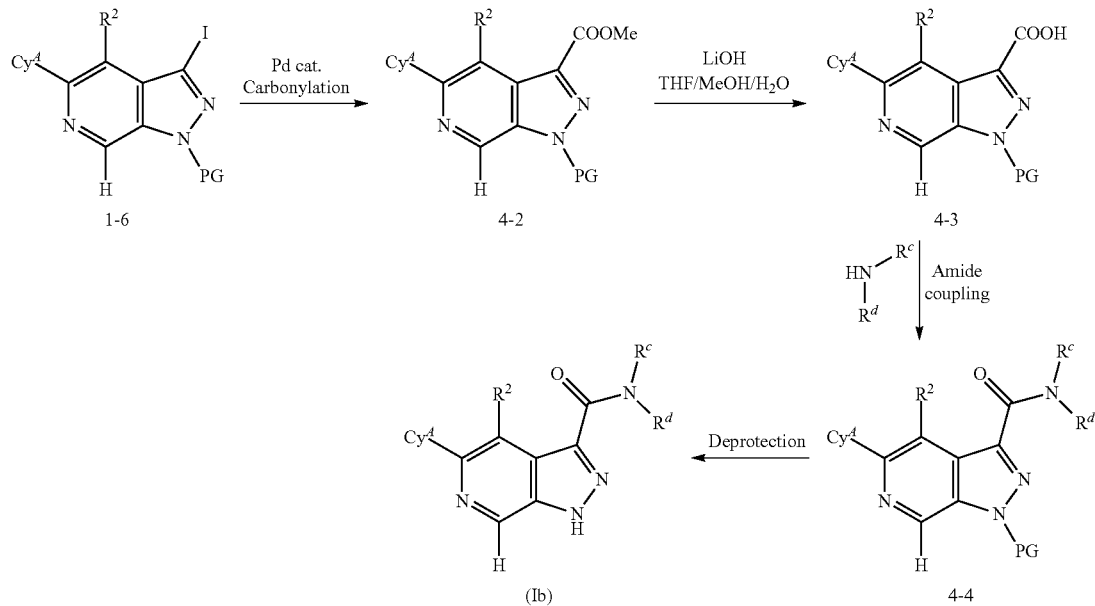

Compounds of Formula (Ic) (compounds of Formula I wherein $R^2$ is F) can be prepared, using a process as illustrated in Scheme 5. As depicted in Scheme 5, the cross-coupling reactions (e.g., Suzuki and Stille) with 2-bromo-3,5-difluoropyridine afford the compounds of Formula 5-2. Treating 5-2 with LDA at −78° C. followed by quenching with methyl Formate gives 5-3 which is subsequently converted into 5-4 by treating with hydrazine. Upon treating with NIS, 5-4 is converted into 5-5. The NH group of the pyrazole ring of 5-5 is protected with a suitable protecting group (e.g., Boc) to form compounds of Formula 5-6. The iodo substituent in 5-6 can be further converted into $R^1$ via a number of cross-coupling reactions (e.g., Suzuki, Stille, Buchwald-Hartwig and others) to give compounds of Formula 5-7. Finally, deprotection of the protecting group affords the desired compounds of Formula (Ic).

Scheme 5

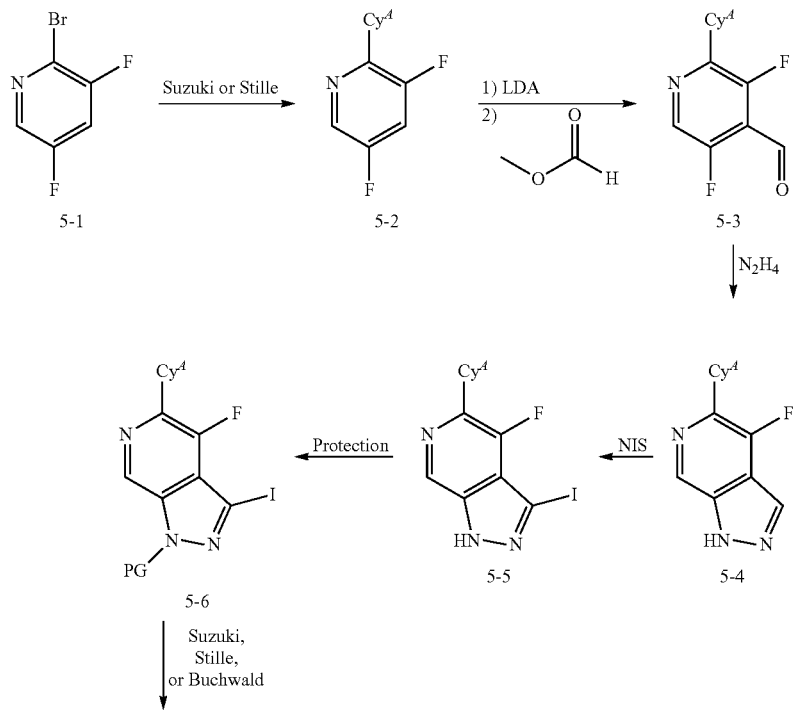

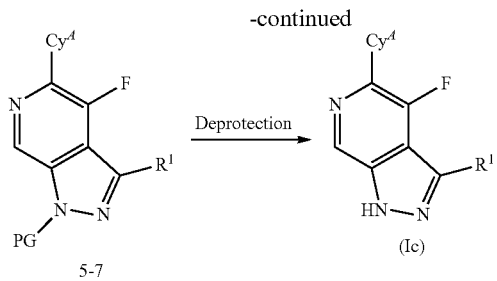

Alternatively, compounds of Formula (Ic) (compounds of Formula I wherein $R^2$ is F) can be prepared, using a process as illustrated in Scheme 6. As depicted in Scheme 6, treating 2-bromo-3,5-difluoropyridine with LDA at −78° C. followed by quenching with methyl formate gives 2-bromo-3,5-difluoroisonicotinaldehyde which is subsequently reduced into (2-bromo-3,5-difluoropyridin-4-yl)methanol by treating with $NaBH_4$. (2-Bromo-3,5-difluoropyridin-4-yl)methanol is then converted into the compounds of Formula 6-3 via the cross-coupling reactions (e.g., Suzuki or Stille). Upon oxidation (e.g., with Dess-Martin periodinane), 6-3 is converted into 5-3 which is subsequently converted into 5-4 by treating with hydrazine. Treating 5-4 with NIS gives 5-5. The NH group of the pyrazole ring of 5-5 is protected with a suitable protecting group (e.g., Boc) to form compounds of Formula 5-6. The iodo substituent in 5-6 can be further converted into $R^1$ via a number of cross-coupling reactions (e.g., Suzuki, Stille, Buchwald-Hartwig, and others) to give the compounds of Formula 5-7. Finally, deprotection of the protecting group affords the desired compounds of Formula (Ic).

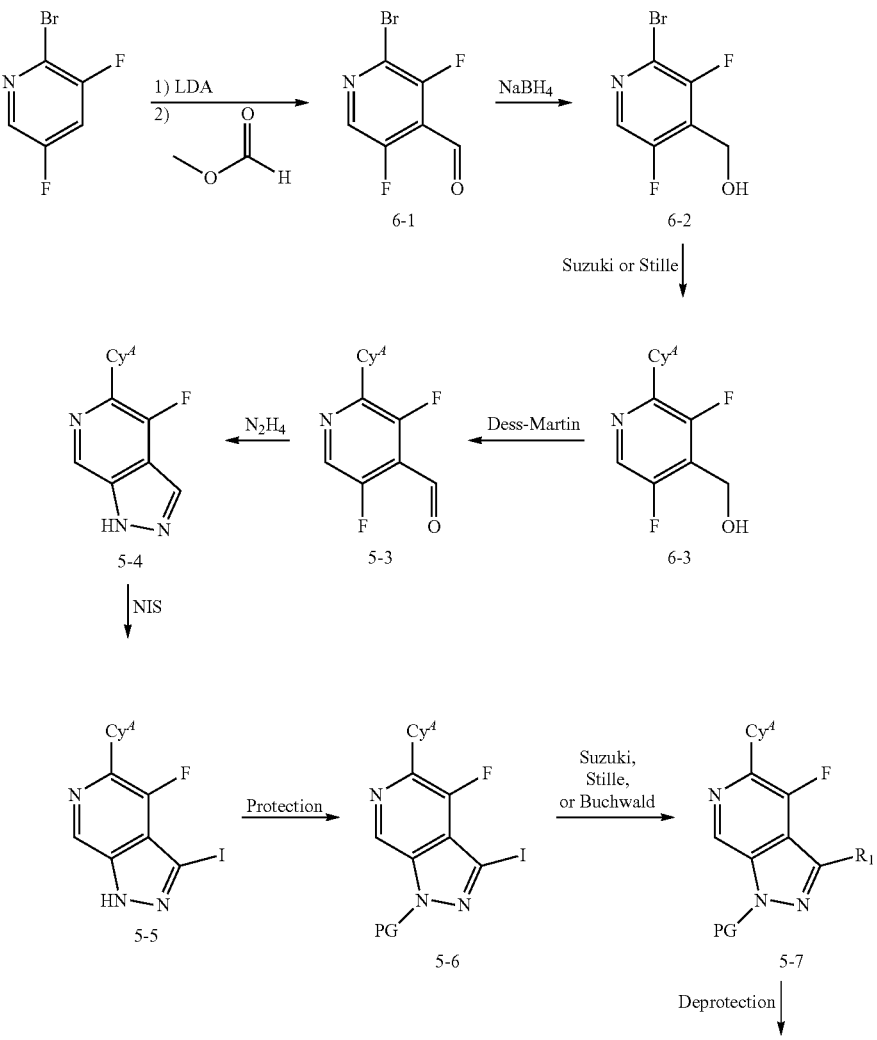

Scheme 6

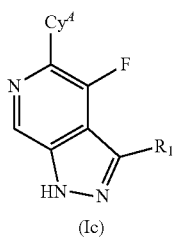

(Ic)

Compounds of Formula (I) with a variety of substitution at position R² (rings, alkyl and alkenyl chains and various functional groups) can be prepared, using a process as illustrated in Scheme 7. In the process depicted in Scheme 7, bromination 5-chloro-4-methylpyridin-3-amine 7-1 with brominating agents (e.g., bromine or NBS) forms compounds of Formula 7-2. Acylation of the NH₂ group in the compounds of Formula 7-2 with acylating agents (e.g., Ac₂O or AcCl) followed by the treatment with amyl nitrite forms compounds of Formula 7-3. These compounds can be further iodinated with one of the iodinating agents (e.g., NIS or iodine) to form compounds of Formula 7-4. The NH group of the pyrazole ring in the compounds of Formula 7-4 is protected with a suitable protecting group, such as Boc or SEM, to form compounds of Formula 7-5. The iodo substituent in the compounds of Formula 7-5 can be converted into R¹ via a number of different cross-coupling reactions, including Suzuki, Stille, Negishi, Cu-catalyzed amination, and others, to give the compounds of Formula 7-6. The bromo substituent in the compounds of Formula 7-6 can be further converted into Cy⁴ via a number of different cross-coupling reactions, including Suzuki, Stille, Negishi, and others, to give the compounds of Formula 7-7. The chloro substituent in the compounds of Formula 7-7 can be further converted into R² via a number of different cross-coupling reactions, including Suzuki, Stille, Negishi, and others, to give the compounds of Formula 7-8. Finally, deprotection of the protecting group, e.g. under acidic conditions, such as treatment with HCl or TFA, results in the formation of the desired compounds of Formula (I).

Scheme 7

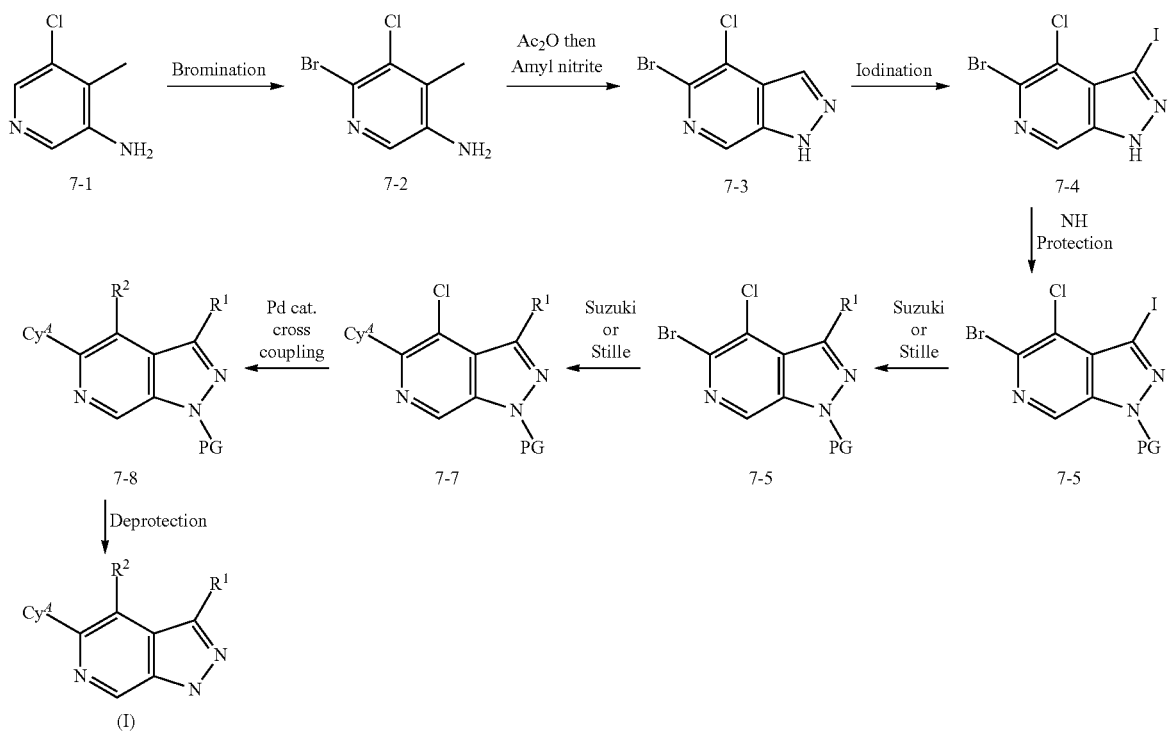

HPK1 Kinase

Extensive studies have established that HPK1 is a negative regulator of T cell and B cell activation (Hu, M. C., et al., Genes Dev, 1996. 10(18): p. 2251-64; Kiefer, F., et al., EMBO J, 1996. 15(24): p. 7013-25). HPK1-deficient mouse T cells showed dramatically increased activation of TCR proximal signaling, enhanced IL-2 production, and hyper-proliferation in vitro upon anti-CD3 stimulation (Shui, J. W., et al., Nat Immunol, 2007. 8(1): p. 84-91). Similar to T cells, HPK1 knockout B cells produced much higher levels of IgM and IgG isoforms after KLH immunization and displayed hyper-proliferation potentially as a result of enhanced BCR signaling. Wang, X., et al., J Biol Chem, 2012. 287(14): p. 11037-48. Mechanistically, during TCR or BCR signaling, HPK1 is activated by LCK/ZAP70 (T cells) or SYK/LYN (B cells) mediated-Tyr379 phosphorylation and its subsequent binding to adaptor protein SLP-76 (T cells) or BLNK (B cells) (Wang, X., et al., J Biol Chem, 2012. 287(14): p. 11037-48). Activated HPK1 phosphorylates SLP-76 on Ser376 or BLNK on Thr152, leading to the recruitment of signaling molecule 14-3-3 and ultimate ubiquitination-mediated degradation of SLP-76 or BLNK (Liou, J., et al., Immunity, 2000. 12(4): p. 399-408; Di Bartolo, V., et al., J Exp Med, 2007. 204(3): p. 681-91). As SLP-76 and BLNK are essential for TCR/BCR-mediated signaling activation (e.g. ERK, phospholipase Cγ1, calcium flux, and NFAT activation), HPK1-mediated downregulation of these adaptor proteins provide a negative feedback mechanism to attenuate signaling intensity during T cell or B cell activation (Wang, X., et al., J Biol Chem, 2012. 287(14): p. 11037-48).

The bone marrow-derived dendritic cells (BDMCs) from HPK1 knockout mice showed higher expression of co-stimulatory molecules (e.g. CD80/CD86) and enhanced production of proinflammatory cytokines (IL-12, TNF-α etc.), and demonstrated superior ability to stimulate T cell proliferation in vitro and in vivo as compared to wild-type DCs (Alzabin, S., et al., J Immunol, 2009. 182(10): p. 6187-94). These data suggest that HPK1 is also an important negative regulator of dendritic cell activation (Alzabin, S., et al., J Immunol, 2009. 182(10): p. 6187-94). However, the signaling mechanisms underlying HPK-1 mediated negative regulation of DC activation remains to be elucidated.

In contrast, HPK1 appears to be a positive regulator of suppressive functions of regulatory T cells (Treg) (Sawasdikosol, S. et al., The journal of immunology, 2012. 188 (supplement 1): p. 163). HPK1 deficient mouse Foxp3+ Tregs were defective in suppressing TCR-induced effector T cell proliferation, and paradoxically gained the ability to produce IL-2 following TCR engagement (Sawasdikosol, S. et al., The Journal of Immunology, 2012. 188 (supplement 1): p. 163). These data suggest that HPK1 is an important regulator of Treg functions and peripheral self-tolerance.

HPK1 was also involved in PGE2-mediated inhibition of CD4+ T cell activation (Ikegami, R., et al., J Immunol, 2001. 166(7): p. 4689-96). Studies published in US 2007/0087988 indicated that HPK1 kinase activity was increased by exposure to physiological concentrations of PGE2 in CD4+ T cells and this effect was mediated by PEG2-induced PKA activation. The proliferation of HPK1 deficient T cells was resistant to the suppressive effects of PGE2 (see US 2007/0087988). Therefore, PGE2-mediated activation of HPK1 may represent a novel regulatory pathway of modulating immune response.

Uses of the Compounds

The present disclosure provides methods of modulating (e.g., inhibiting) HPK1 activity, said method comprising administering to a patient a compound provided herein, or a pharmaceutically acceptable salt thereof. In certain embodiments, the compounds of the present disclosure, or pharmaceutically acceptable salts thereof, are useful for therapeutic administration to enhance, stimulate and/or increase immunity in cancer. For example, a method of treating a disease or disorder associated with inhibition of HPK1 interaction can include administering to a patient in need thereof a therapeutically effective amount of a compound provided herein, or a pharmaceutically acceptable salt thereof. The compounds of the present disclosure can be used alone, in combination with other agents or therapies or as an adjuvant or neoadjuvant for the treatment of diseases or disorders, including cancers. For the uses described herein, any of the compounds of the disclosure, including any of the embodiments thereof, may be used.

Examples of cancers that are treatable using the compounds of the present disclosure include, but are not limited to, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, endometrial cancer, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or urethra, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. In some embodiments, cancers treatable with compounds of the present disclosure include melanoma (e.g., metastatic malignant melanoma), renal cancer (e.g. clear cell carcinoma), prostate cancer (e.g. hormone refractory prostate adenocarcinoma), breast cancer, triple-negative breast cancer, colon cancer and lung cancer (e.g. non-small cell lung cancer and small cell lung cancer). Additionally, the disclosure includes refractory or recurrent malignancies whose growth may be inhibited using the compounds of the disclosure.

In some embodiments, cancers that are treatable using the compounds of the present disclosure include, but are not limited to, solid tumors (e.g., prostate cancer, colon cancer, esophageal cancer, endometrial cancer, ovarian cancer, uterine cancer, renal cancer, hepatic cancer, pancreatic cancer, gastric cancer, breast cancer, lung cancer, cancers of the head and neck, thyroid cancer, glioblastoma, sarcoma, bladder cancer, etc.), hematological cancers (e.g., lymphoma, leukemia such as acute lymphoblastic leukemia (ALL), acute myelogenous leukemia (AML), chronic lymphocytic leukemia (CLL), chronic myelogenous leukemia (CML), DLBCL, mantle cell lymphoma, Non-Hodgkin lymphoma (including relapsed or refractory NHL and recurrent follicular), Hodgkin lymphoma or multiple myeloma) and combinations of said cancers.

In some embodiments, diseases and indications that are treatable using the compounds of the present disclosure include, but are not limited to hematological cancers, sarcomas, lung cancers, gastrointestinal cancers, genitourinary tract cancers, liver cancers, bone cancers, nervous system cancers, gynecological cancers, and skin cancers.

Exemplary hematological cancers include lymphomas and leukemias such as acute lymphoblastic leukemia (ALL), acute myelogenous leukemia (AML), acute promyelocytic leukemia (APL), chronic lymphocytic leukemia (CLL), chronic myelogenous leukemia (CML), diffuse large B-cell lymphoma (DLBCL), mantle cell lymphoma, Non-Hodgkin lymphoma (including relapsed or refractory NHL and recurrent follicular), Hodgkin lymphoma, myeloproliferative diseases (e.g., primary myelofibrosis (PMF), polycythemia vera (PV), essential thrombocytosis (ET)), myelodysplasia syndrome (MDS), T-cell acute lymphoblastic lymphoma (T-ALL), multiple myeloma, cutaneous T-cell lymphoma, Waldenstrom's Macroglubulinemia, hairy cell lymphoma, chronic myelogenic lymphoma and Burkitt's lymphoma.

Exemplary sarcomas include chondrosarcoma, Ewing's sarcoma, osteosarcoma, rhabdomyosarcoma, angiosarcoma, fibrosarcoma, liposarcoma, myxoma, rhabdomyoma, rhabdosarcoma, fibroma, lipoma, harmatoma, and teratoma.

Exemplary lung cancers include non-small cell lung cancer (NSCLC), small cell lung cancer, bronchogenic carcinoma (squamous cell, undifferentiated small cell, undifferentiated large cell, adenocarcinoma), alveolar (bronchiolar) carcinoma, bronchial adenoma, chondromatous hamartoma, and mesothelioma.

Exemplary gastrointestinal cancers include cancers of the esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma), and colorectal cancer.

Exemplary genitourinary tract cancers include cancers of the kidney (adenocarcinoma, Wilm's tumor [nephroblastoma]), bladder and urethra (squamous cell carcinoma, transitional cell carcinoma, adenocarcinoma), prostate (adenocarcinoma, sarcoma), and testis (seminoma, teratoma, embryonal carcinoma, teratocarcinoma, choriocarcinoma, sarcoma, interstitial cell carcinoma, fibroma, fibroadenoma, adenomatoid tumors, lipoma).

Exemplary liver cancers include hepatoma (hepatocellular carcinoma), cholangiocarcinoma, hepatoblastoma, angiosarcoma, hepatocellular adenoma, and hemangioma.

Exemplary bone cancers include, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma, and giant cell tumors Exemplary nervous system cancers include cancers of the skull (osteoma, hemangioma, granuloma, xanthoma, osteitis deformans), meninges (meningioma, meningiosarcoma, gliomatosis), brain (astrocytoma, meduoblastoma, glioma, ependymoma, germinoma (pinealoma), glioblastoma, glioblastoma multiform, oligodendroglioma, schwannoma, retinoblastoma, congenital tumors), and spinal cord (neurofibroma, meningioma, glioma, sarcoma), as well as neuroblastoma and Lhermitte-Duclos disease.

Exemplary gynecological cancers include cancers of the uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), and fallopian tubes (carcinoma).

Exemplary skin cancers include melanoma, basal cell carcinoma, squamous cell carcinoma, Kaposi's sarcoma, Merkel cell skin cancer, moles dysplastic nevi, lipoma, angioma, dermatofibroma, and keloids. In some embodiments, diseases and indications that are treatable using the compounds of the present disclosure include, but are not limited to, sickle cell disease (e.g., sickle cell anemia), triple-negative breast cancer (TNBC), myelodysplastic syndromes, testicular cancer, bile duct cancer, esophageal cancer, and urothelial carcinoma.

Exemplary head and neck cancers include glioblastoma, melanoma, rhabdosarcoma, lymphosarcoma, osteosarcoma, squamous cell carcinomas, adenocarcinomas, oral cancer, laryngeal cancer, nasopharyngeal cancer, nasal and paranasal cancers, thyroid and parathyroid cancers.

In some embodiments, HPK1 inhibitors may be used to treat tumors producing PGE2 (e.g. Cox-2 overexpressing tumors) and/or adenosine (CD73 and CD39 over-expressing tumors). Overexpression of Cox-2 has been detected in a number of tumors, such as colorectal, breast, pancreatic and lung cancers, where it correlates with a poor prognosis. Overexpression of COX-2 has been reported in hematological cancer models such as RAJI (Burkitt's lymphoma) and U937 (acute promonocytic leukemia) as well as in patient's blast cells. CD73 is up-regulated in various human carcinomas including those of colon, lung, pancreas and ovary. Importantly, higher expression levels of CD73 are associated with tumor neovascularization, invasiveness, and metastasis and with shorter patient survival time in breast cancer.

The terms "individual" or "patient," used interchangeably, refer to any animal, including mammals, preferably mice, rats, other rodents, rabbits, dogs, cats, swine, cattle, sheep, horses, or primates, and most preferably humans.

The phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein, the term "treating" or "treatment" refers to one or more of (1) inhibiting the disease; e.g., inhibiting a disease, condition or disorder in an individual who is experiencing or displaying the pathology or symptomatology of the disease, condition or disorder (i.e., arresting further development of the pathology and/or symptomatology); and (2) ameliorating the disease; e.g., ameliorating a disease, condition or disorder in an individual who is experiencing or displaying the pathology or symptomatology of the disease, condition or disorder (i.e., reversing the pathology and/or symptomatology) such as decreasing the severity of disease.

In some embodiments, the compounds of the invention are useful in preventing or reducing the risk of developing any of the diseases referred to herein; e.g., preventing or reducing the risk of developing a disease, condition or disorder in an individual who may be predisposed to the disease, condition or disorder but does not yet experience or display the pathology or symptomatology of the disease.

Combination Therapies

Cancer cell growth and survival can be impacted by multiple signaling pathways. Thus, it is useful to combine different enzyme/protein/receptor inhibitors, exhibiting different preferences in the targets which they modulate the activities of, to treat such conditions. Examples of agents that may be combined with compounds of the present disclosure include inhibitors of the PI3K-AKT-mTOR pathway, inhibitors of the Raf-MAPK pathway, inhibitors of JAK-STAT pathway, inhibitors of beta catenin pathway, inhibitors of notch pathway, inhibitors of hedgehog pathway, inhibitors of Pim kinases, and inhibitors of protein chaperones and cell cycle progression. Targeting more than one signaling pathway (or more than one biological molecule involved in a given signaling pathway) may reduce the likelihood of drug-resistance arising in a cell population, and/or reduce the toxicity of treatment.

The compounds of the present disclosure can be used in combination with one or more other enzyme/protein/receptor inhibitors for the treatment of diseases, such as cancer. Examples of cancers include solid tumors and liquid tumors, such as blood cancers. For example, the compounds of the present disclosure can be combined with one or more inhibitors of the following kinases for the treatment of cancer: Akt1, Akt2, Akt3, TGF-βR, PKA, PKG, PKC, CaM-kinase, phosphorylase kinase, MEKK, ERK, MAPK, mTOR, EGFR, HER2, HER3, HER4, INS-R, IGF-1R, IR-R, PDGFαR, PDGFPR, CSFIR, KIT, FLK-II, KDR/FLK-1, FLK-4, flt-1, FGFR1, FGFR2, FGFR3, FGFR4, c-Met, Ron, Sea, TRKA, TRKB, TRKC, FLT3, VEGFR/F1t2, Flt4, EphA1, EphA2, EphA3, EphB2, EphB4, Tie2, Src, Fyn, Lck, Fgr, Btk, Fak, SYK, FRK, JAK, ABL, ALK and B-Raf. In some embodiments, the compounds of the present disclosure can be combined with one or more of the following inhibitors for the treatment of cancer. Non-limiting examples of inhibitors that can be combined with the compounds of the present disclosure for treatment of cancers include an FGFR inhibitor (FGFR1, FGFR2, FGFR3 or FGFR4, e.g., AZD4547, BAY1187982, ARQ087, BGJ398, BIBF1120, TKI258, lucitanib, dovitinib, TAS-120, JNJ-42756493, Debio1347, INCB54828, INCB62079 and INCB63904), a JAK inhibitor (JAK1 and/or JAK2, e.g., ruxolitinib, baricitinib or INCB39110), an IDO inhibitor (e.g., epacadostat and NLG919), an LSD1 inhibitor (e.g., GSK2979552, INCB59872 and INCB60003), a TDO inhibitor, a PI3K-delta inhibitor (e.g., INCB50797 and INCB50465), a PI3K-gamma inhibitor such as a PI3K-gamma selective inhibitor, a CSF1R inhibitor (e.g., PLX3397 and LY3022855), a TAM receptor tyrosine kinases (Tyro-3, Ax1, and Mer), an angiogenesis inhibitor, an interleukin receptor inhibitor, bromo and extra terminal family members inhibitors (for example, bromodomain inhibitors or BET inhibitors such as OTX015, CPI-0610, INCB54329 and INCB57643) and an adenosine receptor antagonist or combinations thereof. Inhibitors of HDAC such as panobinostat and vorinostat. Inhibitors of c-Met such as onartumzumab, tivantnib, and INC-280. Inhibitors of BTK such as ibrutinib. Inhibitors of mTOR such as rapamycin, sirolimus, temsirolimus, and everolimus. Inhibitors of Raf, such as vemurafenib and dabrafenib. Inhibitors of MEK such as trametinib, selumetinib and GDC-0973. Inhibitors of Hsp90 (e.g., tanespimycin), cyclin dependent kinases (e.g., palbociclib), PARP (e.g., olaparib) and Pim kinases (LGH447, INCB053914 and SGI-1776) can also be combined with compounds of the present disclosure.

Compounds of the present disclosure can be used in combination with one or more immune checkpoint inhibitors. Exemplary immune checkpoint inhibitors include inhibitors against immune checkpoint molecules such as CD20, CD27, CD28, CD39, CD40, CD122, CD96, CD73, CD47, OX40, GITR, CSF1R, JAK, PI3K delta, PI3K gamma, TAM, arginase, CD137 (also known as 4-1BB), ICOS, A2AR, B7-H3, B7-H4, BTLA, CTLA-4, LAG3, TIM3, VISTA, PD-1, PD-L1 and PD-L2. In some embodiments, the immune checkpoint molecule is a stimulatory checkpoint molecule selected from CD27, CD28, CD40, ICOS, OX40, GITR and CD137. In some embodiments, the immune checkpoint molecule is an inhibitory checkpoint molecule selected from A2AR, B7-H3, B7-H4, BTLA, CTLA-4, IDO, KIR, LAG3, PD-1, TIM3, and VISTA. In some embodiments, the compounds provided herein can be used in combination with one or more agents selected from MR inhibitors, TIGIT inhibitors, LAIR1 inhibitors, CD160 inhibitors, 2B4 inhibitors and TGFR beta inhibitors.

In some embodiments, the inhibitor of an immune checkpoint molecule is anti-PD1 antibody, anti-PD-L1 antibody, or anti-CTLA-4 antibody.

In some embodiments, the inhibitor of an immune checkpoint molecule is an inhibitor of PD-1, e.g., an anti-PD-1 monoclonal antibody. In some embodiments, the anti-PD-1 monoclonal antibody is nivolumab, pembrolizumab (also known as MK-3475), pidilizumab, SHR-1210, PDR001, or AMP-224. In some embodiments, the anti-PD-1 monoclonal antibody is nivolumab or pembrolizumab. In some embodiments, the anti-PD1 antibody is pembrolizumab. In some embodiments, the anti PD-1 antibody is SHR-1210.

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, MEDI4736, MPDL3280A (also known as RG7446), or MSB0010718C. In some embodiments, the anti-PD-L1 monoclonal antibody is MPDL3280A or MEDI4736.

In some embodiments, the inhibitor of an immune checkpoint molecule is an inhibitor of CTLA-4, e.g., an anti-CTLA-4 antibody. In some embodiments, the anti-CTLA-4 antibody is ipilimumab.

In some embodiments, the inhibitor of an immune checkpoint molecule is an inhibitor of CSF1R, e.g., an anti-CSF1R antibody. In some embodiments, the anti-CSF1R antibody is IMC-CS4 or RG7155.

In some embodiments, the inhibitor of an immune checkpoint molecule is an inhibitor of LAG3, e.g., an anti-LAG3 antibody. In some embodiments, the anti-LAG3 antibody is BMS-986016, LAG525, IMP321 or GSK2831781.

In some embodiments, the inhibitor of an immune checkpoint molecule is an inhibitor of GITR, e.g., an anti-GITR antibody. In some embodiments, the anti-GITR antibody is TRX518, MK-4166, MK1248, BMS-986156, MEDI1873 or GWN323.

In some embodiments, the inhibitor of an immune checkpoint molecule is an inhibitor of OX40, e.g., an anti-OX40 antibody or OX40L fusion protein. In some embodiments, the anti-OX40 antibody is MEDI0562, MEDI6469, MOXR0916, PF-04518600 or GSK3174998. In some embodiments, the OX40L fusion protein is MEDI6383.

In some embodiments, the inhibitor of an immune checkpoint molecule is an inhibitor of TIM3, e.g., an anti-TIM3 antibody. In some embodiments, the anti-TIM3 antibody is MBG-453.

In some embodiments, the inhibitor of an immune checkpoint molecule is an inhibitor of CD20, e.g., an anti-CD20 antibody. In some embodiments, the anti-CD20 antibody is obinutuzumab or rituximab.

In some embodiments, the compounds of the invention can be used in combination with one or more metabolic enzyme inhibitors. In some embodiments, the metabolic enzyme inhibitor is an inhibitor of IDO1, TDO, or arginase. Examples of IDO1 inhibitors include epacadostat and NLG919. An example of an arginase inhibitor is CB-1158.

The compounds of the present disclosure can be used in combination with bispecific antibodies. In some embodiments, one of the domains of the bispecific antibody targets PD-1, PD-L1, CTLA-4, GITR, OX40, TIM3, LAG3, CD137, ICOS, CD3 or TGFβ receptor.

Compounds of the present disclosure can be used in combination with one or more agents for the treatment of diseases such as cancer. In some embodiments, the agent is an alkylating agent, a proteasome inhibitor, a corticosteroid, or an immunomodulatory agent. Examples of an alkylating agent include bendamustine, nitrogen mustards, ethylenimine derivatives, alkyl sulfonates, nitrosoureas and triazenes, uracil mustard, chlormethine, cyclophosphamide (Cytoxan™), ifosfamide, melphalan, chlorambucil, pipobroman, triethylene-melamine, triethylenethiophosphoramine, busulfan, carmustine, lomustine, streptozocin, dacarbazine, and temozolomide. In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM).

The compounds of the present disclosure can further be used in combination with other methods of treating cancers, for example by chemotherapy, irradiation therapy, tumor-targeted therapy, adjuvant therapy, immunotherapy or surgery. Examples of immunotherapy include cytokine treatment (e.g., interferons, GM-CSF, G-CSF, IL-2), CRS-207 immunotherapy, cancer vaccine, monoclonal antibody, adoptive T cell transfer, oncolytic virotherapy and immunomodulating small molecules, including thalidomide or JAK1/2 inhibitor and the like. The compounds can be administered in combination with one or more anti-cancer drugs, such as a chemotherapeutics. Example chemotherapeutics include any of: abarelix, abiraterone, afatinib, aflibercept, aldesleukin, alemtuzumab, alitretinoin, allopurinol, altretamine, anastrozole, arsenic trioxide, asparaginase, axitinib, azacitidine, bevacizumab, bexarotene, baricitinib, bicalutamide, bleomycin, bortezombi, bortezomib, brivanib, buparlisib, busulfan intravenous, busulfan oral, calusterone, capecitabine, carboplatin, carmustine, cediranib, cetuximab, chlorambucil, cisplatin, cladribine, clofarabine, crizotinib, cyclophosphamide, cytarabine, dacarbazine, dacomitinib, dactinomycin, dalteparin sodium, dasatinib, dactinomycin, daunorubicin, decitabine, degarelix, denileukin, denileukin diftitox, deoxycoformycin, dexrazoxane, docetaxel, doxorubicin, droloxafine, dromostanolone propionate, eculizumab, enzalutamide, epidophyllotoxin, epirubicin, erlotinib, estramustine, etoposide phosphate, etoposide, exemestane, fentanyl citrate, filgrastim, floxuridine, fludarabine, fluorouracil, flutamide, fulvestrant, gefitinib, gemcitabine, gemtuzumab ozogamicin, goserelin acetate, histrelin acetate, ibritumomab tiuxetan, idarubicin, idelalisib, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mithramycin, mitomycin C, mitotane, mitoxantrone, nandrolone phenpropionate, navelbene, necitumumab, nelarabine, neratinib, nilotinib, nilutamide, nofetumomab, oserelin, oxaliplatin, paclitaxel, pamidronate, panitumumab, pazopanib, pegaspargase, pegfilgrastim, pemetrexed disodium, pentostatin, pilaralisib, pipobroman, plicamycin, ponatinib, prednisone, procarbazine, quinacrine, rasburicase, regorafenib, reloxafine, rituximab, ruxolitinib, sorafenib, streptozocin, sunitinib, sunitinib maleate, tamoxifen, tegafur, temozolomide, teniposide, testolactone, thalidomide, thioguanine, thiotepa, topotecan, toremifene, tositumomab, trastuzumab, tretinoin, triptorelin, uracil mustard, valrubicin, vandetanib, vinblastine, vincristine, vinorelbine, vorinostat and zoledronate.

Other anti-cancer agent(s) include antibody therapeutics such as trastuzumab (Herceptin), antibodies to costimulatory molecules such as CTLA-4 (e.g., ipilimumab or tremelimumab), 4-1BB, antibodies to PD-1 and PD-L1, or antibodies to cytokines (IL-10, TGF-β, etc.). Examples of antibodies to PD-1 and/or PD-L1 that can be combined with compounds of the present disclosure for the treatment of cancer or infections such as viral, bacteria, fungus and parasite infections include, but are not limited to, nivolumab, pembrolizumab, MPDL3280A, MEDI-4736 and SHR-1210.

Other anti-cancer agents include inhibitors of kinases associated cell proliferative disorder. These kinases include but not limited to Aurora-A, CDK1, CDK2, CDK3, CDK5, CDK7, CDK8, CDK9, ephrin receptor kinases, CHK1, CHK2, SRC, Yes, Fyn, Lck, Fer, Fes, Syk, Itk, Bmx, GSK3, JNK, PAK1, PAK2, PAK3, PAK4, PDK1, PKA, PKC, Rsk and SGK.

Other anti-cancer agents also include those that block immune cell migration such as antagonists to chemokine receptors, including CCR2 and CCR4.

The compounds of the present disclosure can further be used in combination with one or more anti-inflammatory agents, steroids, immunosuppressants or therapeutic antibodies.

The compounds of Formula (I) or any of the formulas as described herein, a compound as recited in any of the claims and described herein, or salts thereof can be combined with another immunogenic agent, such as cancerous cells, purified tumor antigens (including recombinant proteins, peptides, and carbohydrate molecules), cells, and cells transfected with genes encoding immune stimulating cytokines. Non-limiting examples of tumor vaccines that can be used include peptides of melanoma antigens, such as peptides of gp100, MAGE antigens, Trp-2, MARTI and/or tyrosinase, or tumor cells transfected to express the cytokine GM-CSF.

The compounds of Formula (I) or any of the formulas as described herein, a compound as recited in any of the claims and described herein, or salts thereof can be used in combination with a vaccination protocol for the treatment of cancer. In some embodiments, the tumor cells are transduced to express GM-CSF. In some embodiments, tumor vaccines include the proteins from viruses implicated in human cancers such as Human Papilloma Viruses (HPV), Hepatitis Viruses (HBV and HCV) and Kaposi's Herpes Sarcoma Virus (KHSV). In some embodiments, the compounds of the present disclosure can be used in combination with tumor specific antigen such as heat shock proteins isolated from tumor tissue itself. In some embodiments, the compounds of Formula (I) or any of the formulas as described herein, a compound as recited in any of the claims and described herein, or salts thereof can be combined with dendritic cells immunization to activate potent anti-tumor responses.

The compounds of the present disclosure can be used in combination with bispecific macrocyclic peptides that target Fc alpha or Fc gamma receptor-expressing effectors cells to tumor cells. The compounds of the present disclosure can also be combined with macrocyclic peptides that activate host immune responsiveness.

The compounds of the present disclosure can be used in combination with bone marrow transplant for the treatment of a variety of tumors of hematopoietic origin.

Suitable antiviral agents contemplated for use in combination with the compounds of the present disclosure can comprise nucleoside and nucleotide reverse transcriptase inhibitors (NRTIs), non-nucleoside reverse transcriptase inhibitors (NNRTIs), protease inhibitors and other antiviral drugs.

Example suitable NRTIs include zidovudine (AZT); didanosine (ddI); zalcitabine (ddC); stavudine (d4T);

lamivudine (3TC); abacavir (1592U89); adefovir dipivoxil [bis(POM)-PMEA]; lobucavir (BMS-180194); BCH-10652; emitricitabine [(−)-FTC]; beta-L-FD4 (also called beta-L-D4C and named beta-L-2',3'-dicleoxy-5-fluoro-cytidene); DAPD, ((−)-beta-D-2,6,-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4 (1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfnavir (AG-1343); amprenavir (141W94); lasinavir (BMS-234475); DMP-450; BMS-2322623; ABT-378; and AG-1 549. Other antiviral agents include hydroxyurea, ribavirin, IL-2, IL-12, pentafuside and Yissum Project No. 11607.

When more than one pharmaceutical agent is administered to a patient, they can be administered simultaneously, separately, sequentially, or in combination (e.g., for more than two agents).

Formulation, Dosage Forms and Administration

When employed as pharmaceuticals, the compounds of the present disclosure can be administered in the form of pharmaceutical compositions. Thus the present disclosure provides a composition comprising a compound of Formula (I) or any of the formulas as described herein, a compound as recited in any of the claims and described herein, or a pharmaceutically acceptable salt thereof, or any of the embodiments thereof, and at least one pharmaceutically acceptable carrier or excipient. These compositions can be prepared in a manner well known in the pharmaceutical art, and can be administered by a variety of routes, depending upon whether local or systemic treatment is indicated and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, e.g., by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, the compound of the present disclosure or a pharmaceutically acceptable salt thereof, in combination with one or more pharmaceutically acceptable carriers or excipients. In some embodiments, the composition is suitable for topical administration. In making the compositions of the invention, the active ingredient is typically mixed with an excipient, diluted by an excipient or enclosed within such a carrier in the form of, e.g., a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, e.g., up to 10% by weight of the active compound, soft and hard gelatin capsules, suppositories, sterile injectable solutions and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g., about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art see, e.g., WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup and methyl cellulose. The formulations can additionally include: lubricating agents such as talc, magnesium stearate and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

In some embodiments, the pharmaceutical composition comprises silicified microcrystalline cellulose (SMCC) and at least one compound described herein, or a pharmaceutically acceptable salt thereof. In some embodiments, the silicified microcrystalline cellulose comprises about 98% microcrystalline cellulose and about 2% silicon dioxide w/w.

In some embodiments, the composition is a sustained release composition comprising at least one compound described herein, or a pharmaceutically acceptable salt thereof, and at least one pharmaceutically acceptable carrier or excipient. In some embodiments, the composition comprises at least one compound described herein, or a pharmaceutically acceptable salt thereof, and at least one component selected from microcrystalline cellulose, lactose monohydrate, hydroxypropyl methylcellulose and polyethylene oxide. In some embodiments, the composition comprises at least one compound described herein, or a pharmaceutically acceptable salt thereof, and microcrystalline cellulose, lactose monohydrate and hydroxypropyl methylcellulose. In some embodiments, the composition comprises at least one compound described herein, or a pharmaceutically acceptable salt thereof, and microcrystalline cellulose, lactose monohydrate and polyethylene oxide. In some embodiments, the composition further comprises magnesium stearate or silicon dioxide. In some embodiments, the microcrystalline cellulose is Avicel PH102™. In some embodiments, the lactose monohydrate is Fast-flo 316™. In some embodiments, the hydroxypropyl methylcellulose is hydroxypropyl methylcellulose 2208 K4M (e.g., Methocel K4 M Premier™) and/or hydroxypropyl methylcellulose 2208 K100LV (e.g., Methocel KOOLV™) In some embodiments, the polyethylene oxide is polyethylene oxide WSR 1105 (e.g., Polyox WSR 1105™).

In some embodiments, a wet granulation process is used to produce the composition. In some embodiments, a dry granulation process is used to produce the composition.

The compositions can be formulated in a unit dosage form, each dosage containing from about 5 to about 1,000 mg (1 g), more usually about 100 mg to about 500 mg, of the active ingredient. In some embodiments, each dosage contains about 10 mg of the active ingredient. In some embodiments, each dosage contains about 50 mg of the active ingredient. In some embodiments, each dosage contains about 25 mg of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The components used to formulate the pharmaceutical compositions are of high purity and are substantially free of potentially harmful contaminants (e.g., at least National Food grade, generally at least analytical grade, and more typically at least pharmaceutical grade). Particularly for human consumption, the composition is preferably manufactured or formulated under Good Manufacturing Practice standards as defined in the applicable regulations of the U.S. Food and Drug Administration. For example, suitable formulations may be sterile and/or substantially isotonic and/or in full compliance with all Good Manufacturing Practice regulations of the U.S. Food and Drug Administration.

The active compound may be effective over a wide dosage range and is generally administered in a therapeutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms and the like.

The therapeutic dosage of a compound of the present invention can vary according to, e.g., the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, e.g., about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, e.g., liquid paraffin, polyoxyethylene alkyl ether, propylene glycol, white Vaseline, and the like. Carrier compositions of creams can be based on water in combination with glycerol and one or more other components, e.g., glycerinemonostearate, PEG-glycerinemonostearate and cetylstearyl alcohol. Gels can be formulated using isopropyl alcohol and water, suitably in combination with other components such as, e.g., glycerol, hydroxyethyl cellulose, and the like. In some embodiments, topical formulations contain at least about 0.1, at least about 0.25, at least about 0.5, at least about 1, at least about 2 or at least about 5 wt % of the compound of the invention. The topical formulations can be suitably packaged in tubes of, e.g., 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers or stabilizers will result in the formation of pharmaceutical salts.

The therapeutic dosage of a compound of the present invention can vary according to, e.g., the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

Labeled Compounds and Assay Methods

The compounds of the present disclosure can further be useful in investigations of biological processes in normal and abnormal tissues. Thus, another aspect of the present invention relates to fluorescent dye, spin label, heavy metal or radio-labeled compounds provided herein that would be useful not only in imaging techniques but also in assays, both in vitro and in vivo, for localizing and quantitating HPK1 protein in tissue samples, including human, and for identifying HPK1 ligands by inhibition binding of a labeled compound. Accordingly, the present invention includes HPK1 binding assays that contain such labeled compounds.

The present invention further includes isotopically-substituted compounds of the disclosure. An "isotopically-substituted" compound is a compound of the invention where one or more atoms are replaced or substituted by an atom having the same atomic number but a different atomic mass or mass number. Compounds of the invention may contain isotopes in a natural abundance as found in nature. Compounds of the invention may also have isotopes in amounts greater to that found in nature, e.g., synthetically incorporating low natural abundance isotopes into the compounds of the invention so they are enriched in a particularly useful isotope (e.g., $^2$H and $^{13}$C). It is to be understood that a "radio-labeled" compound is a compound that has incorporated at least one isotope that is radioactive (e.g., radionuclide), e.g., $^3$H and $^{14}$C. Suitable radionuclides that may be incorporated in compounds of the present invention include but are not limited to $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. The radionuclide that is incorporated in the instant radio-labeled compounds will depend on the specific application of that radio-labeled compound. In some embodiments the radionuclide is selected from the group consisting of $^3$H, $^{14}$C, $^{125}$I, $^{35}$S and $^{82}$Br. For in vitro HPK1 labeling and competition assays, compounds that incorporate $^3$H, $^{14}$C, $^{82}$Br, $^{125}$I, $^{131}$I or $^{35}$S will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful. Synthetic methods for incorporating radio-isotopes into organic compounds are known in the art.

Specifically, a labeled compound of the invention can be used in a screening assay to identify and/or evaluate compounds. For example, a newly synthesized or identified compound (i.e., test compound) which is labeled can be evaluated for its ability to bind a HPK1 protein by monitoring its concentration variation when contacting with the HPK1, through tracking of the labeling. For example, a test compound (labeled) can be evaluated for its ability to reduce binding of another compound which is known to bind to a HPK1 protein (i.e., standard compound). Accordingly, the ability of a test compound to compete with the standard compound for binding to the HPK1 protein directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present disclosure also includes pharmaceutical kits useful, e.g., in the treatment or prevention of diseases or disorders associated with the activity of HPK1, such as cancer or infections, which include one or more containers containing a pharmaceutical composition comprising a therapeutically effective amount of a compound of Formula (I), or any of the embodiments thereof. Such kits can further include one or more of various conventional pharmaceutical kit components, such as, e.g., containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples have been found to inhibit the activity of HPK1 according to at least one assay described herein.

EXAMPLES

Experimental procedures for compounds of the invention are provided below. Preparatory LC-MS purifications of some of the compounds prepared were performed on Waters mass directed fractionation systems. The basic equipment setup, protocols, and control software for the operation of these systems have been described in detail in the literature. See e.g. "Two-Pump At Column Dilution Configuration for Preparative LC-MS", K. Blom, *J. Combi. Chem.*, 4, 295 (2002); "Optimizing Preparative LC-MS Configurations and Methods for Parallel Synthesis Purification", K. Blom, R. Sparks, J. Doughty, G. Everlof, T. Hague, A. Combs, *J. Combi. Chem.*, 5, 670 (2003); and "Preparative LC-MS Purification: Improved Compound Specific Method Optimization", K. Blom, B. Glass, R. Sparks, A. Combs, *J. Combi. Chem.*, 6, 874-883 (2004). The separated compounds were typically subjected to analytical liquid chromatography mass spectrometry (LCMS) for purity check under the following conditions: Instrument; Agilent 1100 series, LC/MSD, Column: Waters Sunfire™ $C_{18}$ 5 µm particle size, 2.1×5.0 mm, Buffers: mobile phase A: 0.025% TFA in water and mobile phase B: acetonitrile; gradient 2% to 80% of B in 3 minutes with flow rate 2.0 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

pH=2 purifications: Waters Sunfire™ $C_{18}$ 5 µm particle size, 19×100 mm column, eluting with mobile phase A: 0.1% TFA (trifluoroacetic acid) in water and mobile phase B: acetonitrile; the flow rate was 30 mL/minute, the separating gradient was optimized for each compound using the Compound Specific Method Optimization protocol as described in the literature (see "Preparative LCMS Purification: Improved Compound Specific Method Optimization", K. Blom, B. Glass, R. Sparks, A. Combs, *J. Comb. Chem.*, 6, 874-883 (2004)). Typically, the flow rate used with the 30×100 mm column was 60 mL/minute.

pH=10 purifications: Waters XBridge $C_{18}$ 5 µm particle size, 19×100 mm column, eluting with mobile phase A: 0.15% $NH_4OH$ in water and mobile phase B: acetonitrile; the flow rate was 30 mL/minute, the separating gradient was optimized for each compound using the Compound Specific Method Optimization protocol as described in the literature (See "Preparative LCMS Purification: Improved Compound Specific Method Optimization", K. Blom, B. Glass, R. Sparks, A. Combs, *J. Comb. Chem.*, 6, 874-883 (2004)). Typically, the flow rate used with 30×100 mm column was 60 mL/minute.

Degassed water refers to water where the dissolved oxygen has been displaced by nitrogen through a procedure of bubbling nitrogen through the water for 15 minutes.

Example 1. N-(5-(2-Fluoro-6-methoxyphenyl)-1H-pyrazolo[3,4-c]pyridin-3-yl)benzamide

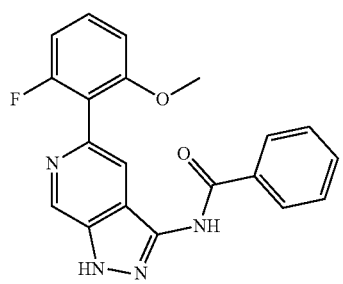 [SMILES: COc1cccc(F)c1-c1cc2c(NC(=O)c3ccccc3)n[nH]c2cn1]

Step 1. 2-Bromo-5-fluoroisoniconnonitrile

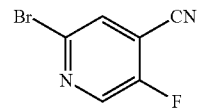

Hydroxylamine hydrochloride (2.73 g, 39.2 mmol) was added to a solution of 2-bromo-5-fluoroisonicotinaldehyde (Combi-Blocks, 2.0 g, 9.80 mmol) in 2-propanol (19.61 mL). The reaction mixture was refluxed for 2 h, and then the solvent was removed in vacuo. The residue was redissolved in EtOAc. The organic phase was washed with the saturated $NaHCO_3$ solution and brine, and was dried over sodium sulfate. The solvent was evaporated in vacuo to give the oxime.

Cyanuric chloride (2.41 g, 13.04 mmol) was slowly add to DMF (19.61 mL) at 0° C. After it was completely dissolved, obtained oxime was slowly added at 0° C. to this solution, and the reaction was stirred at r.t. for 1 h. Then the reaction was quenched with water. The product was extracted with ethyl acetate and the organic phase was washed with brine. The organic phase was dried over sodium sulfate and the solvents were evaporated under reduced pressure. Obtained crude product was used in the next step without further purification (1 g, 51%).

Step 2. 5-Bromo-1H-pyrazolo[3,4-c]pyridin-3-amine

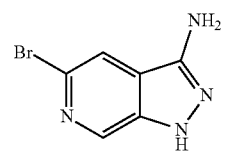 [SMILES: Nc1n[nH]c2cnc(Br)cc12]

Water solution of hydrazine (0.6 mL, 10 mmol) was added to a solution of 2-bromo-5-fluoroisonicotinonitrile (1.0 g, 4.98 mmol) in ethanol (15 mL). After stirring at reflux for 2 h, the solvent was evaporated and the obtained crude product was used in the next step without further purification. LCMS calculated for $C_6H_6BrN_4$ $(M+H)^+$ m/z=213.0; found 213.1.

Step 3. tert-Butyl 3-amino-5-bromo-1H-pyrazolo[3,4-c]pyridine-1-carboxylate

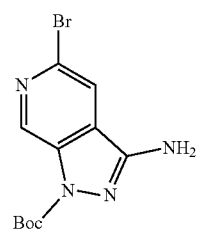 [SMILES: CC(C)(C)OC(=O)n1nc(N)c2cc(Br)ncc21]

Di-tert-butyl dicarbonate (1.127 g, 5.16 mmol) was added to a solution of 5-bromo-1H-pyrazolo[3,4-c]pyridin-3-amine (1.0 g, 4.69 mmol) and triethylamine (0.785 mL, 5.63 mmol) in $CH_2Cl_2$ (15 mL). After stirring at r.t. for 1 h., water was added, and the mixture was extracted with DCM. The organic phase was washed with brine and dried over sodium sulfate. The solvent was evaporated under reduced pressure and obtained crude product was purified by Biotage Isolera™ (1.4 g, 87%). LCMS calculated for $C_{11}H_{14}BrN_4O_2$ (M+H)$^+$ m/z=313.0; found 313.0.

Step 4. tert-Butyl 3-amino-5-(2-fluoro-6-methoxyphenyl)-1H-pyrazolo[3,4-c]pyridine-1-carboxylate

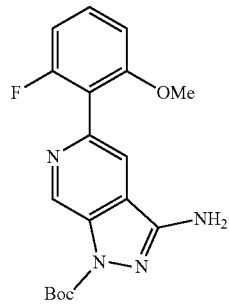 [SMILES: COc1cccc(F)c1-c1cc2c(N)nn(C(=O)OC(C)(C)C)c2cn1]

tert-Butyl 3-amino-5-bromo-1H-pyrazolo[3,4-c]pyridine-1-carboxylate (1.0 g, 3.19 mmol), (2-fluoro-6-methoxyphenyl)boronic acid (0.814 g, 4.79 mmol), chloro(2-dicyclohexylphosphino-2',4',6'-triisopropyl-1,1'-biphenyl)[2-(2'-amino-1,1'-biphenyl)]palladium(II) (Pd XPhos G2) (0.251 g, 0.319 mmol) and potassium phosphate (1.356 g, 6.39 mmol) were placed in a flask, and the flask was evacuated and backfilled with nitrogen three times. Then dioxane (20 mL) and degassed water (2 mL) were added, and reaction was stirred at 90° C. for 2 h. After cooling to r.t., the reaction mixture was diluted with ethyl acetate, and the resulting mixture was washed with brine. The separated organic phase was dried over sodium sulfate. The solvents were evaporated under reduced pressure and obtained crude product was purified by Biotage Isolera™ (1.05 g, 92%). LCMS calculated for $C_{18}H_{20}FN_4O_3$ (M+H)$^+$ m/z=359.2; found 359.2.

Step 5. N-(5-(2-Fluoro-6-methoxyphenyl)-1H-pyrazolo[3,4-c]pyridin-3-yl)benzamide Benzoyl chloride (6.47 mg, 0.046 mmol) was added to a solution of tert-butyl 3-amino-5-(2-fluoro-6-methoxyphenyl)-1H-pyrazolo[3,4-c]pyridine-1-carboxylate (15 mg, 0.042 mmol) and DIPEA (10.97 0.063 mmol) in THF (1 mL). After stirring at 60° C. for 2 h, reaction was quenched with methanol and solvents were evaporated in vacuo. DCM (1 mL) and trifluoroacetic acid (1 mL) were added to the obtained residue and the reaction was stirred at r.t. for 1 h. The reaction mixture was then diluted with acetonitrile and was purified with prep-LCMS (XBridge C18 column, eluting with a gradient of acetonitrile/water containing 0.1% TFA, at flow rate of 60 mL/min). LCMS calculated for $C_{20}H_{16}FN_4O_2$ (M+H)$^+$: m/z=363.1; Found: 363.2.

Example 2. N-(5-(2-Fluoro-6-methoxyphenyl)-1H-pyrazolo[3,4-c]pyridin-3-yl)-4-methylbenzamide

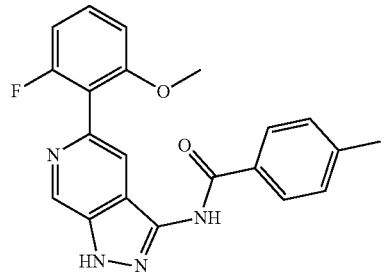 [SMILES: COc1cccc(F)c1-c1cc2c(NC(=O)c3ccc(C)cc3)n[nH]c2cn1]

This compound was prepared according to the procedures described in Example 1, using 4-methylbenzoyl chloride instead of benzoyl chloride as starting material. LCMS calculated for $C_{21}H_{18}FN_4O_2$ (M+H)$^+$: m/z=377.1; Found: 377.2.

Example 3. 4-Bromo-N-(5-(2-fluoro-6-methoxyphenyl)-1H-pyrazolo[3,4-c]pyridin-3-yl)benzamide

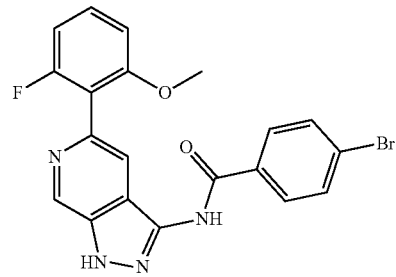 [SMILES: COc1cccc(F)c1-c1cc2c(NC(=O)c3ccc(Br)cc3)n[nH]c2cn1]

This compound was prepared according to the procedures described in Example 1, using 4-bromobenzoyl chloride instead of benzoyl chloride as starting material. LCMS calculated for $C_{20}H_{15}BrFN_4O_2$ (M+H)$^+$: m/z=441.0; Found: 441.1.

Example 4. 3-Bromo-N-(5-(2-fluoro-6-methoxyphenyl)-1H-pyrazolo[3,4-c]pyridin-3-yl)benzamide

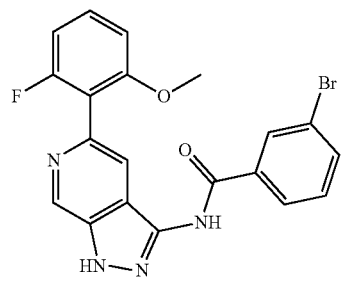 [SMILES: COc1cccc(F)c1-c1cc2c(NC(=O)c3cccc(Br)c3)n[nH]c2cn1]

This compound was prepared according to the procedures described in Example 1, using 3-bromobenzoyl chloride instead of benzoyl chloride as starting material. LCMS calculated for $C_{20}H_{15}BrFN_4O_2$ (M+H)$^+$: m/z=441.0; Found: 441.1.

Example 5. 4-Fluoro-N-(5-(2-fluoro-6-methoxyphenyl)-1H-pyrazolo[3,4-c]pyridin-3-yl)benzamide

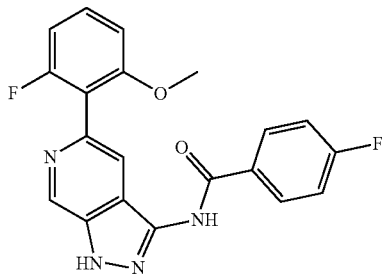 [SMILES: COc1cccc(F)c1-c1cc2c(NC(=O)c3ccc(F)cc3)n[nH]c2cn1]

This compound was prepared according to the procedures described in Example 1, using 4-fluorobenzoyl chloride instead of benzoyl chloride as starting material. LCMS calculated for $C_{20}H_{15}F_2N_4O_2$ (M+H)$^+$: m/z=381.1; Found: 381.2.

Example 6. 3-Fluoro-N-(5-(2-fluoro-6-methoxyphenyl)-1H-pyrazolo[3,4-c]pyridin-3-yl)benzamide

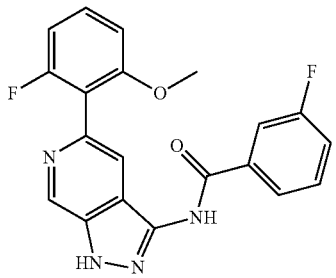 [SMILES: COc1cccc(F)c1-c1cc2c(NC(=O)c3cccc(F)c3)n[nH]c2cn1]

This compound was prepared according to the procedures described in Example 1, using 3-fluorobenzoyl chloride instead of benzoyl chloride as starting material. LCMS calculated for $C_{20}H_{15}F_2N_4O_2$ (M+H)$^+$: m/z=381.1; Found: 381.2.

Example 7. 3-Cyano-N-(5-(2-fluoro-6-methoxyphenyl)-1H-pyrazolo[3,4-c]pyridin-3-yl)benzamide

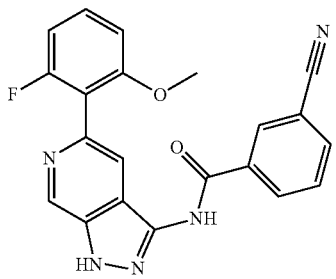 [SMILES: COc1cccc(F)c1-c1cc2c(NC(=O)c3cccc(C#N)c3)n[nH]c2cn1]

This compound was prepared according to the procedures described in Example 1, using 3-cyanobenzoyl chloride instead of benzoyl chloride as starting material. LCMS calculated for $C_{21}H_{15}FN_5O_2$ (M+H)$^+$: m/z=388.1; Found: 388.2.

Example 8. 4-Ethyl-N-(5-(2-fluoro-6-methoxyphenyl)-1H-pyrazolo[3,4-c]pyridin-3-yl)benzamide

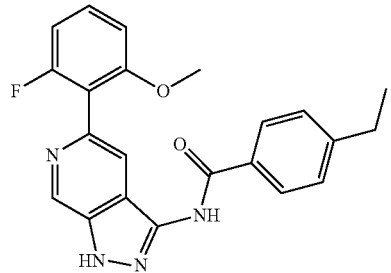 [SMILES: CCc1ccc(C(=O)Nc2n[nH]c3cnc(-c4c(F)cccc4OC)cc23)cc1]

This compound was prepared according to the procedures described in Example 1, using 4-ethylbenzoyl chloride instead of benzoyl chloride as starting material. LCMS calculated for $C_{22}H_{20}FN_4O_2$ (M+H)$^+$: m/z=391.2; Found: 391.3.

Example 9. N-(5-(2-Fluoro-6-methoxyphenyl)-1H-pyrazolo[3,4-c]pyridin-3-yl)-3-methoxybenzamide

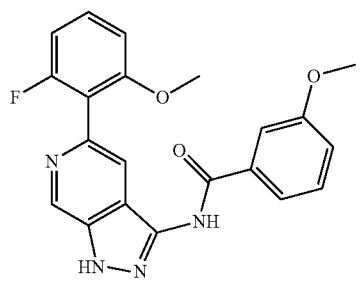

This compound was prepared according to the procedures described in Example 1, using 3-methoxybenzoyl chloride instead of benzoyl chloride as starting material. LCMS calculated for $C_{21}H_{18}FN_4O_3$ (M+H)$^+$: m/z=393.1; Found: 393.2.

Example 10. 4-Fluoro-N-(5-(2-fluoro-6-methoxyphenyl)-1H-pyrazolo[3,4-c]pyridin-3-yl)-3-methylbenzamide

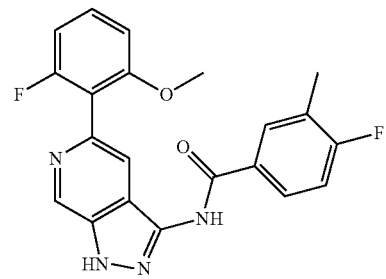 [SMILES: COc1cccc(F)c1-c1cc2c(NC(=O)c3ccc(F)c(C)c3)n[nH]c2cn1]

This compound was prepared according to the procedures described in Example 1, using 4-fluoro-3-methylbenzoyl chloride instead of benzoyl chloride as starting material. LCMS calculated for $C_{21}H_{17}F_2N_4O_2$ (M+H)$^+$: m/z=395.1; Found: 395.2.

Example 11. 3,5-Difluoro-N-(5-(2-fluoro-6-methoxyphenyl)-1H-pyrazolo[3,4-c]pyridin-3-yl)benzamide

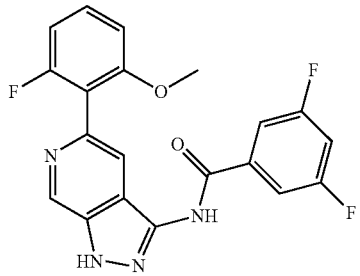 [SMILES: COc1cccc(F)c1-c1cc2c(NC(=O)c3cc(F)cc(F)c3)n[nH]c2cn1]

This compound was prepared according to the procedures described in Example 1, using 3,5-difluorobenzoyl chloride instead of benzoyl chloride as starting material. LCMS calculated for $C_{20}H_{14}F_3N_4O_2$ (M+H)$^+$: m/z=399.1; Found: 399.2.

Example 12. 3,4-Difluoro-N-(5-(2-fluoro-6-methoxyphenyl)-1H-pyrazolo[3,4-c]pyridin-3-yl)benzamide

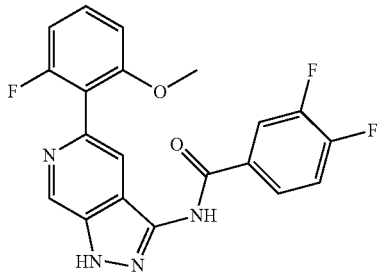

This compound was prepared according to the procedures described in Example 1, using 3,4-difluorobenzoyl chloride instead of benzoyl chloride as starting material. LCMS calculated for $C_{20}H_{14}F_3N_4O_2$ (M+H)$^+$: m/z=399.1; Found: 399.2.

Example 13. N-(5-(2-Fluoro-6-methoxyphenyl)-1H-pyrazolo[3,4-c]pyridin-3-yl)benzo[d][1,3]dioxole-5-carboxamide

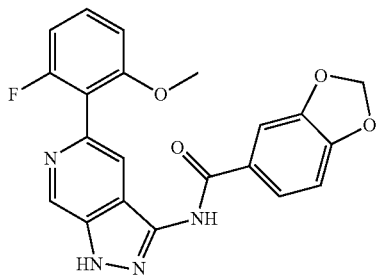 [SMILES: COc1cccc(F)c1-c1cc2c(NC(=O)c3ccc4c(c3)OCO4)n[nH]c2cn1]

This compound was prepared according to the procedures described in Example 1, using benzo[d][1,3]dioxole-5-carbonyl chloride instead of benzoyl chloride as starting material. LCMS calculated for $C_{21}H_{16}FN_4O_4$ (M+H)$^+$: m/z=407.1; Found: 407.2.

Example 14. N-(5-(2-Fluoro-6-methoxyphenyl)-1H-pyrazolo[3,4-c]pyridin-3-yl)-1-methyl-1H-pyrazole-4-carboxamide

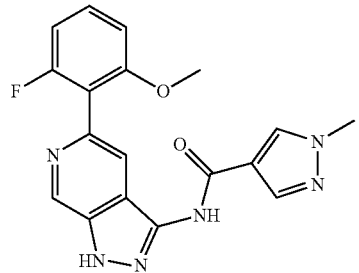 [SMILES: COc1cccc(F)c1-c1cc2c(NC(=O)c3cnn(C)c3)n[nH]c2cn1]

This compound was prepared according to the procedures described in Example 1, using 1-methyl-1H-pyrazole-4-carbonyl chloride instead of benzoyl chloride as starting material. LCMS calculated for $C_{18}H_{16}FN_6O_2$ (M+H)$^+$: m/z=367.1; Found: 367.2.

Example 15. N-(5-(2-Fluoro-6-methoxyphenyl)-1H-pyrazolo[3,4-c]pyridin-3-yl)-1-methyl-1H-pyrazole-3-carboxamide

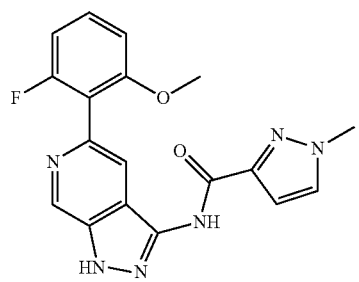 [SMILES: COc1cccc(F)c1-c1cc2c(NC(=O)c3ccn(C)n3)n[nH]c2cn1]

This compound was prepared according to the procedures described in Example 1, using 1-methyl-1H-pyrazole-3-carbonyl chloride instead of benzoyl chloride as starting material. LCMS calculated for $C_{18}H_{16}FN_6O_2$ (M+H)$^+$: m/z=367.1; Found: 367.2.

Example 16. N-(5-(2-Fluoro-6-methoxyphenyl)-1H-pyrazolo[3,4-c]pyridin-3-yl)-3-orpholinobenzamide

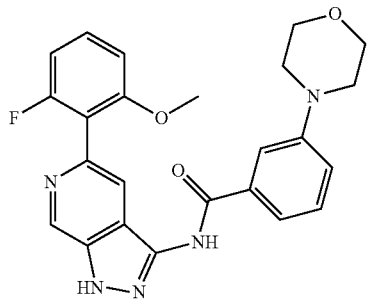 [SMILES: COc1cccc(F)c1-c1cc2c(NC(=O)c3cccc(N4CCOCC4)c3)n[nH]c2cn1]

Step 1. tert-Butyl 3-(3-bromobenzamido)-5-(2-fluoro-6-methoxyphenyl)-1H-pyrazolo[3,4-c]pyridine-1-carboxylate

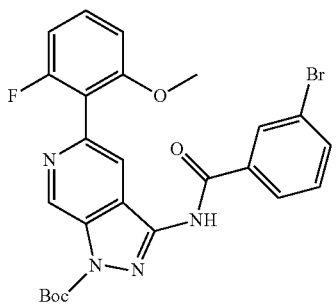 [SMILES: COc1cccc(F)c1-c1cc2c(NC(=O)c3cccc(Br)c3)nn(C(=O)OC(C)(C)C)c2cn1]

3-Bromobenzoyl chloride (206 mg, 0.939 mmol) was added to a solution of tert-butyl 3-amino-5-(2-fluoro-6-methoxyphenyl)-1H-pyrazolo[3,4-c]pyridine-1-carboxylate (Example 1, Step 4, 306 mg, 0.854 mmol) and DIPEA (224 μL, 1.281 mmol) in THF (6 mL). The reaction mixture was stirred at 60° C. for 2 h. Then methanol (1 mL) was added, and the solvents were evaporated in vacuo. Obtained crude product was purified by Biotage Isolera™ (360 mg, 87%). LCMS calculated for $C_{25}H_{23}BrFN_4O_4$ (M+H)$^+$: m/z=541.1; Found: 541.2.

Step 2. N-(5-(2-Fluoro-6-methoxyphenyl)-1H-pyrazolo[3,4-c]pyridin-3-yl)-3-morpholinobenzamide tert-Butyl 3-(3-bromobenzamido)-5-(2-fluoro-6-methoxyphenyl)-1H-pyrazolo[3,4-c]pyridine-1-carboxylate (15 mg, 0.028 mmol), morpholine (3.62 mg, 0.042 mmol), cesium carbonate (18.1 mg, 0.055 mmol) and chloro(2-dicyclohexylphosphino-2',6'-di-i-propoxy-1,1'-biphenyl)(2'-amino-1,1'-biphenyl-2-yl)palladium(II) (RuPhos Pd G2, 2.2 mg, 2.77 μmol) were placed in a vial, and the vial was evacuated and backfilled with nitrogen three times. Then dioxane (2 mL) was added, and the reaction mixture was stirred at 100° C. for 2 h. The mixture was cooled to r.t. and solids were filtered off. The filtrate concentrated in vacuo.

DCM (1 mL) and trifluoroacetic acid (1 mL) were added to the obtained residue, and the reaction was stirred at r.t. for 1 h. The reaction mixture was then diluted with acetonitrile and was purified with prep-LCMS (XBridge C18 column, eluting with a gradient of acetonitrile/water containing 0.1% TFA, at flow rate of 60 mL/min). LCMS calculated for $C_{24}H_{23}FN_5O_3$ (M+H)$^+$: m/z=448.2; Found: 448.3.

Example 17. N-(5-(2-Fluoro-6-methoxyphenyl)-1H-pyrazolo[3,4-c]pyridin-3-yl)-3-(3-oxopiperazin-1-yl)benzamide

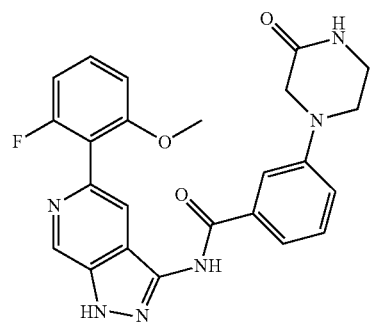 [SMILES: COc1cccc(F)c1-c1cc2c(NC(=O)c3cccc(N4CCNC(=O)C4)c3)n[nH]c2cn1]

This compound was prepared according to the procedures described in Example 16, using piperazin-2-one instead of morpholine as starting material. LCMS calculated for $C_{24}H_{22}FN_6O_3$ (M+H)$^+$: m/z=461.2; Found: 461.2.

Example 18. N-(5-(2-Fluoro-6-methoxyphenyl)-1H-pyrazolo[3,4-c]pyridin-3-yl)-3-(4-methylpiperazin-1-yl)benzamide

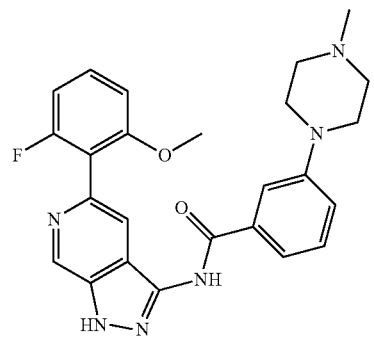 [SMILES: COc1cccc(F)c1-c1cc2c(NC(=O)c3cccc(N4CCN(C)CC4)c3)n[nH]c2cn1]

This compound was prepared according to the procedures described in Example 16, using 1-methylpiperazine instead of morpholine as starting material. LCMS calculated for $C_{25}H_{26}FN_6O_2$ (M+H)$^+$: m/z=461.2; Found: 461.2.

Example 19. N-(5-(2-Fluoro-6-methoxyphenyl)-1H-pyrazolo[3,4-c]pyridin-3-yl)-3-(4-methyl-3-oxopiperazin-1-yl)benzamide

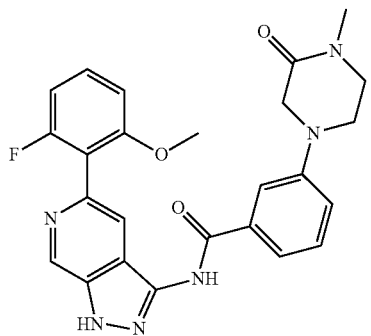 [SMILES: COc1cccc(F)c1-c1cc2c(NC(=O)c3cccc(N4CCN(C)C(=O)C4)c3)n[nH]c2cn1]

This compound was prepared according to the procedures described in Example 16, using 1-methylpiperazin-2-one instead of morpholine as starting material. LCMS calculated for $C_{25}H_{24}FN_6O_3$ (M+H)$^+$: m/z=475.2; Found: 475.3.

Example 20. 3-(4-Ethylpiperazin-1-yl)-N-(5-(2-fluoro-6-methoxyphenyl)-1H-pyrazolo[3,4-c]pyridin-3-yl)benzamide

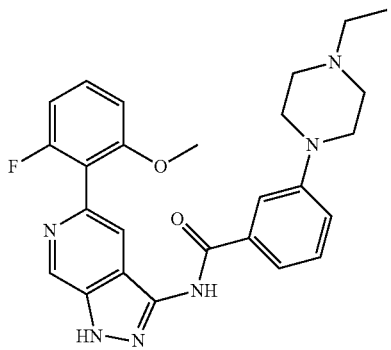 [SMILES: CCN1CCN(c2cccc(C(=O)Nc3n[nH]c4cnc(-c5c(F)cccc5OC)cc34)c2)CC1]

This compound was prepared according to the procedures described in Example 16, using 1-ethylpiperazine instead of morpholine as starting material. LCMS calculated for $C_{26}H_{28}FN_6O_2$ (M+H)$^+$: m/z=475.2; Found: 475.2.

Example 21. N-(5-(2-Fluoro-6-methoxyphenyl)-1H-pyrazolo[3,4-c]pyridin-3-yl)-3-(3-oxo-4-(2,2,2-trifluoroethyl)ninerazin-1-yl)benzamide

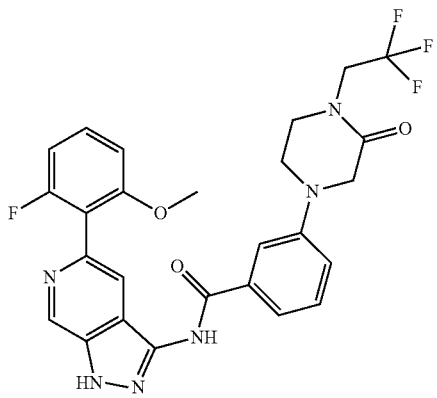 [SMILES: COc1cccc(F)c1-c1cc2c(NC(=O)c3cccc(N4CCN(CC(F)(F)F)C(=O)C4)c3)n[nH]c2cn1]

This compound was prepared according to the procedures described in Example 16, using 1-(2,2,2-trifluoroethyl)piperazin-2-one instead of morpholine as starting material. LCMS calculated for $C_{26}H_{23}F_4N_6O_3$ (M+H)$^+$: m/z=543.2; Found: 543.3.

Example 22. N-(5-(2-Fluoro-6-methoxyphenyl)-1H-pyrazolo[3,4-c]pyridin-3-yl)-3-(4-(methylsulfonyl)piperazin-1-yl)benzamide

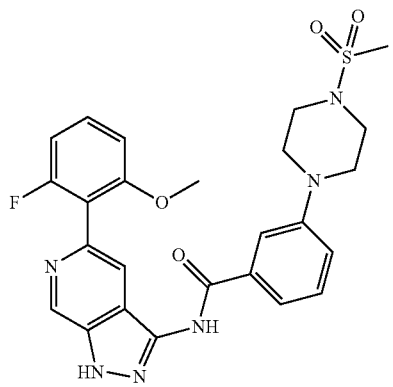 [SMILES: COc1cccc(F)c1-c1cc2c(NC(=O)c3cccc(N4CCN(S(C)(=O)=O)CC4)c3)n[nH]c2cn1]

This compound was prepared according to the procedures described in Example 16, using 1-(methylsulfonyl)piperazine instead of morpholine as starting material. LCMS calculated for $C_{25}H_{26}FN_6O_4S$ (M+H)$^+$: m/z=525.2; Found: 525.1.

Example 23. N-(5-(2-fluoro-6-methoxyphenyl)-1H-pyrazolo[3,4-c]pyridin-3-yl)-3-(piperazin-1-yl)benzamide

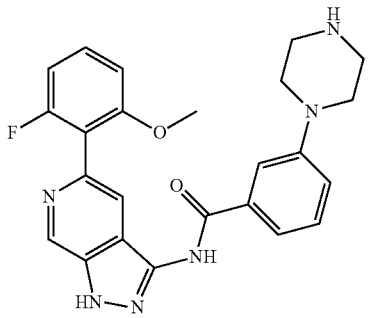 [SMILES: COc1cccc(F)c1-c1cc2c(NC(=O)c3cccc(N4CCNCC4)c3)n[nH]c2cn1]

This compound was prepared according to the procedures described in Example 16, using tert-butyl piperazine-1-carboxylate instead of morpholine as starting material. LCMS calculated for $C_{24}H_{24}FN_6O_2$ (M+H)$^+$: m/z=447.2; Found: 447.2.

Example 24. N-(5-(2-Fluoro-6-methoxyphenyl)-1H-pyrazolo[3,4-c]pyridin-3-yl)-4-morpholinobenzamide

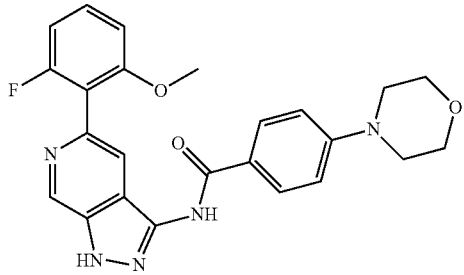 [SMILES: COc1cccc(F)c1-c1cc2c(NC(=O)c3ccc(N4CCOCC4)cc3)n[nH]c2cn1]

Step 1. tert-Butyl 3-(4-bromobenzamido)-5-(2-fluoro-6-methoxyphenyl)-1H-pyrazolo[3,4-c]pyridine-1-carboxylate

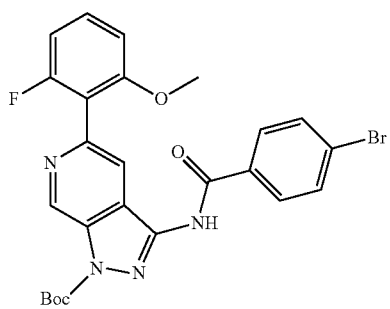 [SMILES: COc1cccc(F)c1-c1cc2c(NC(=O)c3ccc(Br)cc3)nn(C(=O)OC(C)(C)C)c2cn1]

This compound was prepared according to the procedures described in Example 16, Step 1, using 4-bromobenzoyl chloride instead of 3-bromobenzoyl chloride as starting material. LCMS calculated for $C_{25}H_{23}BrFN_4O_4$ (M+H)$^+$: m/z=541.1; Found: 541.2.

Step 2. N-(5-(2-Fluoro-6-methoxyphenyl)-1H-pyrazolo[3,4-c]pyridin-3-yl)-4-morpholinobenzamide tert-Butyl 3-(4-bromobenzamido)-5-(2-fluoro-6-methoxyphenyl)-1H-pyrazolo[3,4-c]pyridine-1-carboxylate (15 mg, 0.028 mmol), morpholine (3.62 mg, 0.042 mmol), cesium carbonate (18.1 mg, 0.055 mmol) and chloro(2-dicyclohexylphosphino-2',6'-di-i-propoxy-1,1'-biphenyl)(2'-amino-1,1'-biphenyl-2-yl)palladium(II) (RuPhos Pd G2, 2.2 mg, 2.77 μmol) were placed in a vial, and the vial was evacuated and backfilled with nitrogen three times. Then dioxane (2 mL) was added, and the reaction mixture was stirred at 100° C. for 2 h. The mixture was cooled to r.t. and the solids were filtered off. The filtrate was concentrated in vacuo.

DCM (1 mL) and trifluoroacetic acid (1 mL) were added to the obtained residue, and the reaction was stirred at r.t. for 1 h. The reaction mixture was then diluted with acetonitrile and was purified with prep-LCMS (XBridge C18 column, eluting with a gradient of acetonitrile/water containing 0.1% TFA, at flow rate of 60 mL/min). LCMS calculated for $C_{24}H_{23}FN_5O_3$ (M+H)$^+$: m/z=448.2; Found: 448.2.

Example 25. N-(5-(2-Fluoro-6-methoxyphenyl)-1H-pyrazolo[3,4-c]pyridin-3-yl)-4-(3-oxopiperazin-1-yl)benzamide

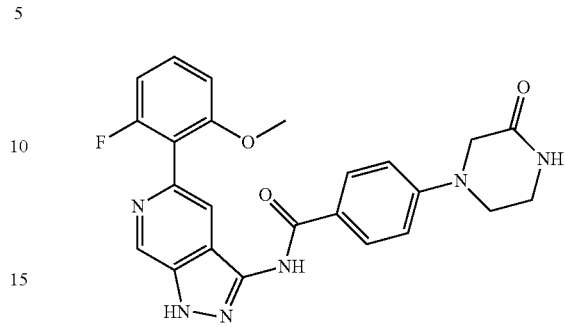

This compound was prepared according to the procedures described in Example 24, using piperazin-2-one instead of morpholine as starting material. LCMS calculated for $C_{24}H_{22}FN_6O_3$ (M+H)$^+$: m/z=461.2; Found: 461.3.

Example 26. N-(5-(2-Fluoro-6-methoxyphenyl)-1H-pyrazolo[3,4-c]pyridin-3-yl)-4-(4-methylpiperazin-1-yl)benzamide

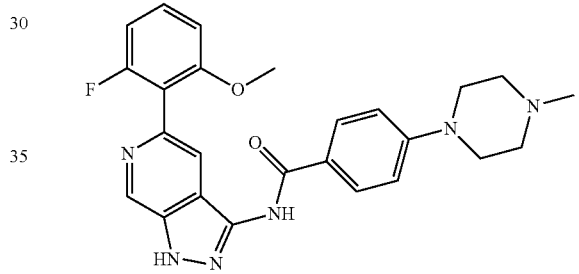

This compound was prepared according to the procedures described in Example 24, using 1-methylpiperazine instead of morpholine as starting material. LCMS calculated for $C_{25}H_{26}FN_6O_2$ (M+H)$^+$: m/z=461.2; Found: 461.3.

Example 27. N-(5-(2-fluoro-6-methoxyphenyl)-1H-pyrazolo[3,4-c]pyridin-3-yl)-4-(4-methyl-3-oxopiperazin-1-yl)benzamide

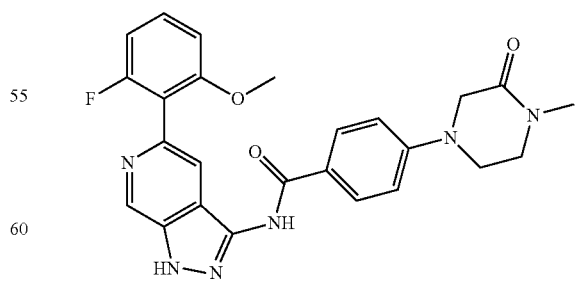

This compound was prepared according to the procedures described in Example 24, using 1-methylpiperazin-2-one instead of morpholine as starting material. LCMS calculated for $C_{25}H_{24}FN_6O_3$ (M+H)$^+$: m/z=475.2; Found: 475.3.

Example 28. 4-(4-Ethylpiperazin-1-yl)-N-(5-(2-fluoro-6-methoxyphenyl)-1H-pyrazolo[3,4-c]pyridin-3-yl)benzamide

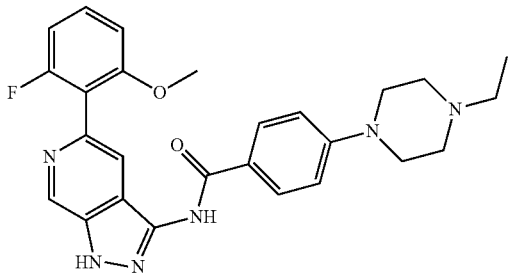 [SMILES: CCN1CCN(c2ccc(C(=O)Nc3n[nH]c4cnc(-c5c(F)cccc5OC)cc34)cc2)CC1]

This compound was prepared according to the procedures described in Example 24, using 1-ethylpiperazine instead of morpholine as starting material. LCMS calculated for $C_{26}H_{28}FN_6O_2$ (M+H)$^+$: m/z=475.2; Found: 475.3.

Example 29. N-(5-(2-Fluoro-6-methoxyphenyl)-1H-pyrazolo[3,4-c]pyridin-3-yl)-4-(3-oxo-4-(2,2,2-trifluoroethyl)piperazin-1-yl)benzamide

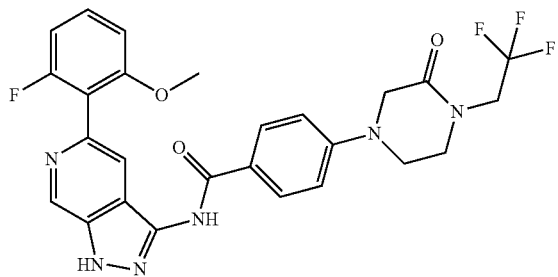 [SMILES: COc1cccc(F)c1-c1cc2c(NC(=O)c3ccc(N4CCN(CC(F)(F)F)C(=O)C4)cc3)n[nH]c2cn1]

This compound was prepared according to the procedures described in Example 24, using 1-(2,2,2-trifluoroethyl)piperazin-2-one instead of morpholine as starting material. LCMS calculated for $C_{26}H_{23}F_4N_6O_3$ (M+H)$^+$: m/z=543.2; Found: 543.2.

Example 30. N-(5-(2-Fluoro-6-methoxyphenyl)-1H-pyrazolo[3,4-c]pyridin-3-yl)-4-(4-isopropylpiperazin-1-yl)benzamide

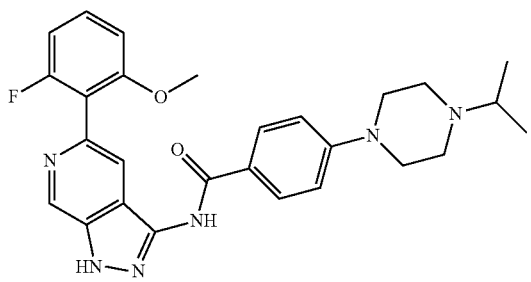 [SMILES: COc1cccc(F)c1-c1cc2c(NC(=O)c3ccc(N4CCN(C(C)C)CC4)cc3)n[nH]c2cn1]

This compound was prepared according to the procedures described in Example 24, using 1-isopropylpiperazine instead of morpholine as starting material. LCMS calculated for $C_{27}H_{30}FN_6O_2$ (M+H)$^+$: m/z=489.2; Found: 489.3.

Example 31. 4-(4-Cyclopropyl-3-oxopiperazin-1-yl)-N-(5-(2-fluoro-6-methoxyphenyl)-1H-pyrazolo[3,4-c]pyridin-3-yl)benzamide

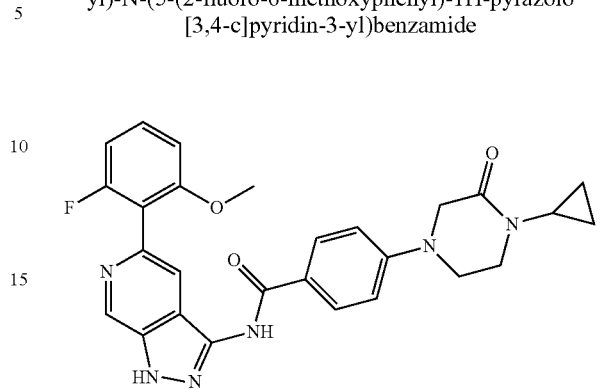

This compound was prepared according to the procedures described in Example 24, using 1-cyclopropylpiperazin-2-one instead of morpholine as starting material. LCMS calculated for $C_{27}H_{26}FN_6O_3$ (M+H)$^+$: m/z=501.2; Found: 501.3.

Example 32. N-(5-(2-Fluoro-6-methoxyphenyl)-1H-pyrazolo[3,4-c]pyridin-3-yl)-4-(4-(methylsulfonyl)piperazin-1-yl)benzamide

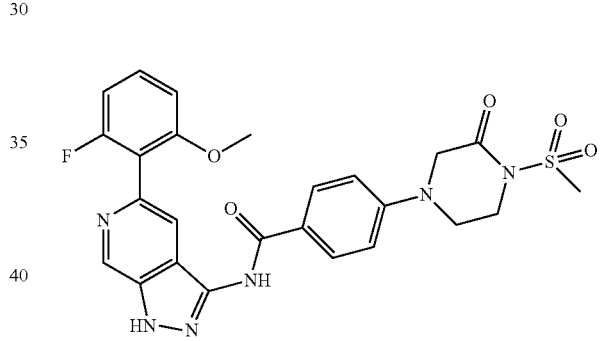

This compound was prepared according to the procedures described in Example 24, using 1-(methylsulfonyl)piperazine instead of morpholine as starting material. LCMS calculated for $C_{25}H_{26}FN_6O_4S$ (M+H)$^+$: m/z=525.2; Found: 525.2.

Example 33. N-(5-(2-Fluoro-6-methoxyphenyl)-1H-pyrazolo[3,4-c]pyridin-3-yl)-4-(piperazin-1-yl)benzamide

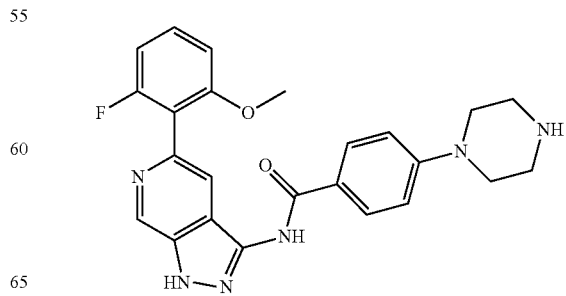

83

This compound was prepared according to the procedures described in Example 24, using tert-butyl piperazine-1-carboxylate instead of morpholine as starting material. LCMS calculated for $C_{24}H_{24}FN_6O_2$ (M+H)$^+$: m/z=447.2; Found: 447.1.

Example 34. 4-(5-(5-(2-Fluoro-6-methoxyphenyl)-1H-pyrazolo[3,4-c]pyridin-3-yl)thiazol-2-yl)morpholine

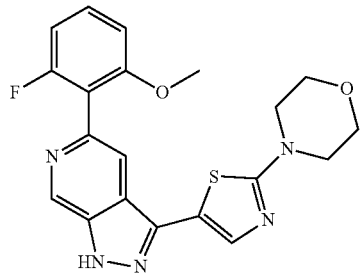 [SMILES: COc1cccc(F)c1-c1cc2c(-c3cnc(N4CCOCC4)s3)n[nH]c2cn1]

Step 1. 5-Bromo-1-((2-(trimethylsilyl)ethoxy)methyl)-1H-pyrazolo[3,4-c]pyridine

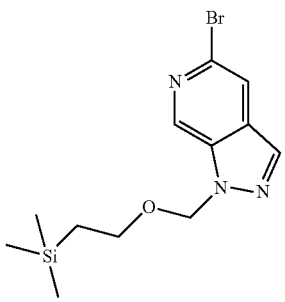 [SMILES: C[Si](C)(C)CCOCn1ncc2cc(Br)ncc21]

NaH in mineral oil (510 mg, 13 mmol) was slowly added at 0° C. to a solution of 5-bromo-1H-pyrazolo[3,4-c]pyridine (Astatech, 2.1 g, 11 mmol) and [β-(trimethylsilypethoxy]methyl chloride (2.30 mL, 13 mmol) in tetrahydrofuran (25 mL). After stirring at r.t. for 1 h, the reaction mixture was quenched with water and extracted with ethyl acetate. The organic phase was washed with brine and dried over sodium sulfate. The solvents were evaporated under reduced pressure, and the obtained crude product was purified by Biotage Isolera™ (2.5 g, 70%). LCMS calculated for $C_{12}H_{19}BrN_3OSi$ (M+H)$^+$ m/z=328.1; found 328.1.

84

Step 2. 5-(2-Fluoro-6-methoxyphenyl)-1-((2-(trimethylsilyl)ethoxy)methyl)-1H-pyrazolo[3,4-c]pyridine

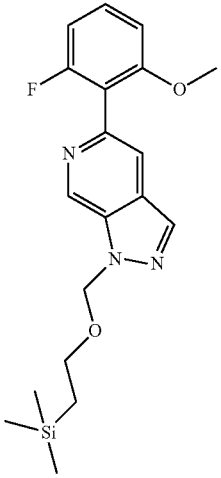

5-Bromo-1-{[2-(trimethylsilyl)ethoxy]methyl}-1H-pyrazolo[3,4-c]pyridine (1.36 g, 4.16 mmol), (2-fluoro-6-methoxyphenyl)boronic acid (0.85 g, 5.0 mmol), chloro(2-dicyclohexylphosphino-2',4',6'-triisopropyl-1,1'-biphenyl)[2-(2'-amino-1,1'-biphenyl)]palladium(II) (Pd XPhos G2) (400 mg, 0.5 mmol), potassium phosphate (3.6 g, 17 mmol) and a magnet bar were placed in a flask. The flask was sealed with a rubber cap, evacuated and backfilled with nitrogen (this process was repeated a total of three times). After dioxane (20 mL) and degassed water (2 mL) were added, the mixture was heated at 90° C. for 1 h. The reaction mixture was then diluted with ethyl acetate, washed with brine and the separated organic phase was dried over sodium sulfate. The solvents were removed in vacuo and obtained crude product was purified by Biotage Isolera™ (0.7 g, 45%). LCMS calculated for $C_{19}H_{25}FN_3O_2Si$ (M+H)$^+$ m/z=374.2; found 374.1.

Step 3. 5-(2-Fluoro-6-methoxyphenyl)-1H-pyrazolo[3,4-c]pyridine

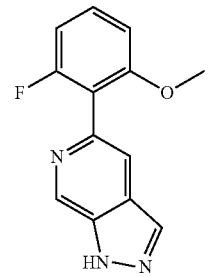 [SMILES: COc1cccc(F)c1-c1cc2cn[nH]c2cn1]

A solution of 5-(2-fluoro-6-methoxyphenyl)-1-{[2-(trimethylsilyl)ethoxy]methyl}-1H-pyrazolo[3,4-c]pyridine (0.70 g, 1.9 mmol) in a mixture of 1.0 M solution of hydrogen chloride in water (8 mL, 8 mmol) and 4.0 M solution of hydrogen chloride in dioxane (8 mL, 33.6 mmol) was stirred at 80° C. for 1 h. Then methanol (8 mL) was added, and the reaction mixture was further stirred at 80° C.

for 30 min. After cooling to r.t., the reaction was neutralized to pH 7. The mixture was then extracted with ethyl acetate, and the organic phase was washed with brine. The organic phase was dried over sodium sulfate and the solvents were evaporated in vacuo. The obtained crude product was used in the next step without further purification. LCMS calculated for $C_{13}H_{11}FN_3O$ (M+H)$^+$ m/z=244.1; found 244.0.

Step 4. 5-(2-Fluoro-6-methoxyphenyl)-3-iodo-1H-pyrazolo[3,4-c]pyridine

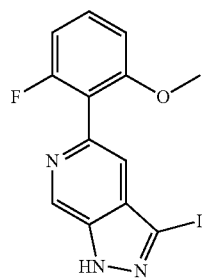 [SMILES: COc1cccc(F)c1-c1cc2c(I)n[nH]c2cn1]

Potassium hydroxide (0.39 g, 6.9 mmol) and iodine (0.88 g, 3.4 mmol) were added to a solution of 5-(2-fluoro-6-methoxyphenyl)-1H-pyrazolo[3,4-c]pyridine (from previous step) in 1,4-dioxane (10 mL). The reaction mixture was stirred at 50° C. for 2 hours. After cooling to r.t., water was added, and reaction was neutralized to pH 7. The mixture was then extracted with ethyl acetate, and the organic phase was washed saturated solution of sodium thiosulfate and brine. The organic phase was dried over sodium sulfate, and the solvents were evaporated in vacuo. The obtained crude product was used in the next step without further purification. LCMS calculated for $C_{13}H_{10}FIN_3O$ (M+H)$^+$ m/z=370.0; found 370.0.

Step 5. 5-(2-Fluoro-6-methoxyphenyl)-3-iodo-1-((2-(trimethylsilyl)ethoxy)methyl)-1H-pyrazolo[3,4-c]pyridine

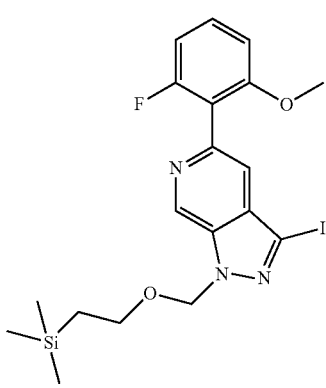

NaH in mineral oil (95 mg, 2.4 mmol) was slowly added at 0° C. to a solution of 5-(2-fluoro-6-methoxyphenyl)-3-iodo-1H-pyrazolo[3,4-c]pyridine (0.80 g, 2.2 mmol) and [β-(trimethylsilyl)ethoxy]methyl chloride (0.42 mL, 2.4 mmol) in tetrahydrofuran (10 mL). After stirring at r.t. for 1 h, the reaction mixture was quenched with water, and the mixture was extracted with ethyl acetate. The organic phase was washed with brine and dried over sodium sulfate. The solvents were evaporated in vacuo and obtained crude product was purified by Biotage Isolera™ (650 mg, 59%). LCMS calculated for $C_{19}H_{24}FIN_3O_2Si$ (M+H)$^+$ m/z=500.1; found 500.0.

Step 6. 4-(5-(5-(2-Fluoro-6-methoxyphenyl)-1H-pyrazolo[3,4-c]pyridin-3-yl)thiazol-2-yl)morpholine 5-(2-Fluoro-6-methoxyphenyl)-3-iodo-1-((2-(trimethylsilyl)ethoxy)methyl)-1H-pyrazolo[3,4-c]pyridine (15 mg, 0.030 mmol), 4-(5-(4,4,5,5-tetramethyl-1,3,2-dioxaborolan-2-yl)thiazol-2-yl)morpholine (13.3 mg, 0.045 mmol), chloro(2-dicyclohexylphosphino-2',4',6'-triisopropyl-1,1'-biphenyl)[2-(2'-amino-1,1'-biphenyl)]palladium(II) (Pd XPhos G2) (2.4 mg, 0.0030 mmol), potassium phosphate (13 mg, 0.062 mmol) and a magnet bar were placed in a vial with septum, which was then evacuated and backfilled with nitrogen three times. 1,4-Dioxane (1.5 mL) and degassed water (0.2 mL) were added and the reaction mixture was stirred at 80° C. for 1 h. Then 1M solution of HCl in water (1 mL) and 4M solution of HCl in dioxane (1 mL) were added, and reaction mixture was stirred at 80° C. for 1 h. After this, methanol (1 mL) was added and reaction was further stirred at 80° C. for 30 min. The reaction mixture was then diluted with acetonitrile and was purified with prep-LCMS (XBridge C18 column, eluting with a gradient of acetonitrile/water containing 0.1% TFA, at flow rate of 60 mL/min). LCMS calculated for $C_{20}H_{19}FN_5O_2S$ (M+H)$^+$: m/z=412.1; Found: 412.1.

Example 35. 5-(5-(2-Fluoro-6-methoxyphenyl)-1H-pyrazolo[3,4-c]pyridin-3-yl)-3-methylisoxazole

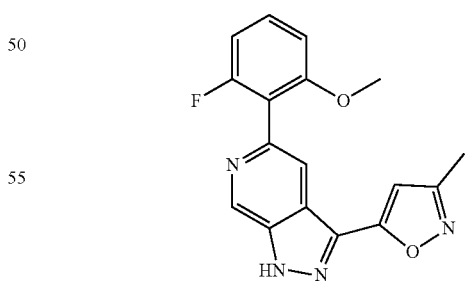

This compound was prepared according to the procedures described in Example 34, using 3-methyl-5-(4,4,5,5-tetramethyl-1,3,2-dioxaborolan-2-yl)isoxazole instead of 4-(5-(4,4,5,5-tetramethyl-1,3,2-dioxaborolan-2-yl)thiazol-2-yl)morpholine as starting material. LCMS calculated for $C_{17}H_{14}FN_4O_2$ (M+H)$^+$: m/z=325.1; Found: 325.1.

Example 36. 5-(5-(2-Fluoro-6-methoxyphenyl)-1H-pyrazolo[3,4-c]pyridin-3-yl)-2-methylthiazole

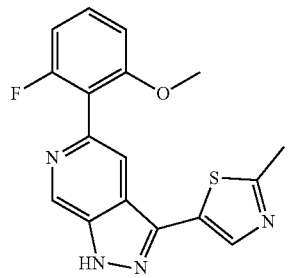 [SMILES: COc1cccc(F)c1-c1cc2c(-c3cnc(C)s3)n[nH]c2cn1]

This compound was prepared according to the procedures described in Example 34, using 2-methyl-5-(4,4,5,5-tetramethyl-1,3,2-dioxaborolan-2-yl)thiazole instead of 4-(5-(4,4,5,5-tetramethyl-1,3,2-dioxaborolan-2-yl)thiazol-2-yl)morpholine as starting material. LCMS calculated for $C_{14}H_{14}FN_4OS$ (M+H)$^+$: m/z=341.1; Found: 341.2.

Example 37. 1-(4-Bromophenyl)-4-(5-(2-fluoro-6-methoxyphenyl)-1H-pyrazolo[3,4-c]pyridin-3-yl)piperazin-2-one

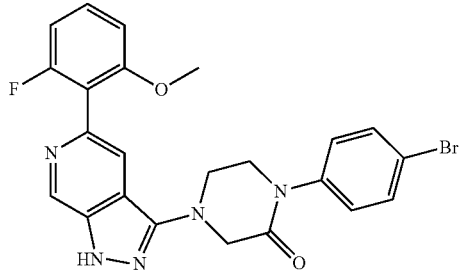 [SMILES: COc1cccc(F)c1-c1cc2c(N3CCN(c4ccc(Br)cc4)C(=O)C3)n[nH]c2cn1]

5-(2-Fluoro-6-methoxyphenyl)-3-iodo-1-((2-(trimethylsilyl)ethoxy)methyl)-1H-pyrazolo[3,4-c]pyridine (Example 34, Step 5, 15 mg, 0.030 mmol), 1-(4-bromophenyl)piperazin-2-one (11 mg, 0.042 mmol), cesium carbonate (18.1 mg, 0.055 mmol) and chloro(2-dicyclohexylphosphino-2',6'-di-i-propoxy-1,1'-biphenyl)(2'-amino-1,1'-biphenyl-2-yl) palladium(II) (RuPhos Pd G2, 2.2 mg, 2.77 µmol) were placed in a vial and the vial was evacuated and backfilled with nitrogen three times. Then dioxane (2 mL) was added, and the reaction mixture was stirred at 100° C. for 2 h. The mixture was cooled to r.t., solids were filtered off, and the solvent of the filtrate was evaporated in vacuo.

Then 1M solution of HCl in water (1 mL) and 4M solution of HCl in dioxane (1 mL) were added to the crude residue, and reaction mixture was stirred at 80° C. for 1 h. Methanol (1 mL) was added, and the resulting reaction mixture was further stirred at 80° C. for 30 min. The reaction mixture was then diluted with acetonitrile and was purified with prep-LCMS (XBridge C18 column, eluting with a gradient of acetonitrile/water containing 0.1% TFA, at flow rate of 60 mL/min). LCMS calculated for $C_{23}H_{20}BrFN_5O_2$ (M+H)$^+$: m/z=496.1; Found: 496.2.

Example 38. 2-(5-(2-Fluoro-6-methoxyphenyl)-1H-pyrazolo[3,4-c]pyridin-3-yl)-1,2,3,4-tetrahydroisoquinoline-7-carbonitrile

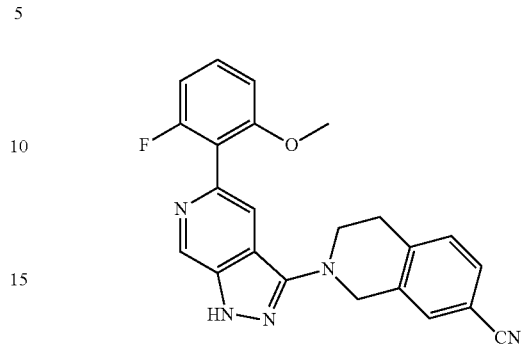

This compound was prepared according to the procedures described in Example 37, using 1,2,3,4-tetrahydroisoquinoline-7-carbonitrile instead of 1-(4-bromophenyl)piperazin-2-one as starting material. LCMS calculated for $C_{23}FINFN_5O$ (M+H)$^+$: m/z=400.2; Found: 400.1.

Example 39. 4-(4-(5-(2-Fluoro-6-methoxyphenyl)-1H-pyrazolo[3,4-c]pyridin-3-yl)piperazin-1-yl)benzonitrile

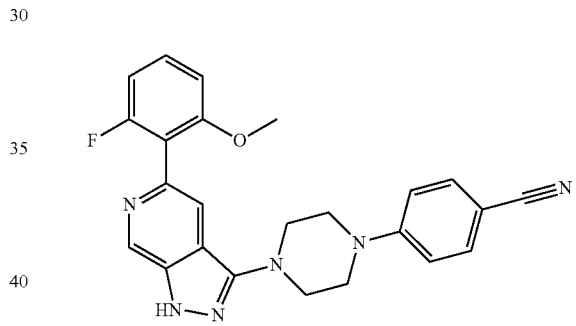

This compound was prepared according to the procedures described in Example 37, using 4-piperazin-1-ylbenzonitrile instead of 1-(4-bromophenyl)piperazin-2-one as starting material. LCMS calculated for $C_{24}H_{22}FN_6O$ (M+H)$^+$: m/z=429.2; Found: 429.2.

Example 40. 5-(2-Fluoro-6-methoxyphenyl)-3-(4-(pyridin-4-yl)piperazin-1-yl)-1H-pyrazolo[3,4-c]pyridine

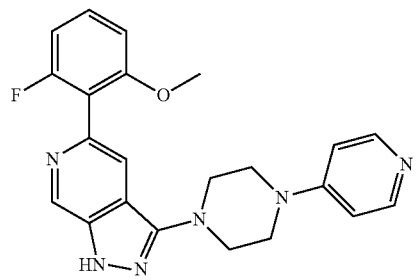 [SMILES: COc1cccc(F)c1-c1cc2c(N3CCN(c4ccncc4)CC3)n[nH]c2cn1]

This compound was prepared according to the procedures described in Example 37, using 1-(pyridin-4-yl)piperazine instead of 1-(4-bromophenyl)piperazin-2-one as starting material. LCMS calculated for $C_{22}H_{22}FN_6O$ (M+H)$^+$: m/z=405.2; Found: 405.2.

Example 41. 5-(2-Fluoro-6-methoxyphenyl)-N-(4-(4-methylpiperazin-1-yl)benzyl)-1H-pyrazolo[3,4-c]pyridin-3-amine

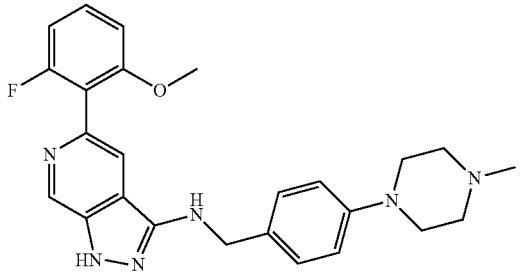 [SMILES: COc1cccc(F)c1-c1cc2c(NCc3ccc(N4CCN(C)CC4)cc3)n[nH]c2cn1]

This compound was prepared according to the procedures described in Example 37, using (4-(4-methylpiperazin-1-yl)phenyl)methanamine instead of 1-(4-bromophenyl)piperazin-2-one as starting material. LCMS calculated for $C_{25}H_{28}FN_6O$ (M+H)$^+$: m/z=447.2; Found: 447.2.

Example 42. 1-[1-(3-Fluoro-5-{3-[4-(4-methylpiperazin-1-yl)phenyl]-1H-pyrazolo[3,4-c]pyridin-5-yl}phenyl)cyclopropyl]methanamine

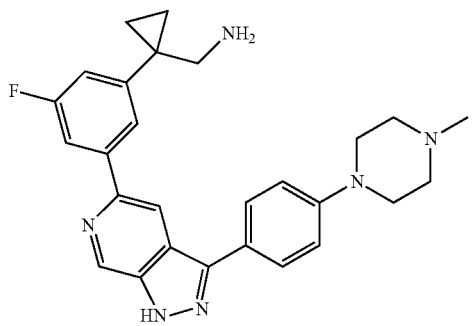 [SMILES: CN1CCN(c2ccc(-c3n[nH]c4cnc(-c5cc(F)cc(C6(CN)CC6)c5)cc34)cc2)CC1]

Step 1. 5-Chloro-3-iodo-1H-pyrazolo[3,4-c]pyridine

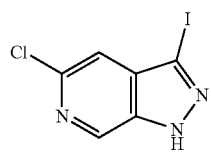 [SMILES: Clc1cc2c(I)n[nH]c2cn1]

To a solution of 5-chloro-1H-pyrazolo[3,4-c]pyridine (2.012 g, 13.10 mmol) in DMF (40.0 mL) was added N-iodosuccinimide (4.47 g, 19.9 mmol). The mixture was then heated to 80° C. for 1 h. After cooling to room temperature, the mixture was concentrated in vacuo. The resulting residue was purified on silica gel (120 g, 0-100% EtOAc in hexanes) to give the desired product as a white solid (3.16 g, 86%). LCMS calculated for $C_6H_4ClIN_3$ (M+H)$^+$: m/z=279.9; found 279.9.

Step 2. 5-Chloro-3-iodo-1-{[2-(trimethylsilyl)ethoxy]methyl}-1H-pyrazolo[3,4-c]pyridine

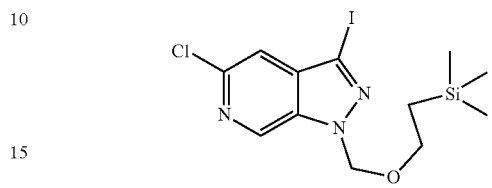

To a suspension of NaH (60% in mineral oil, 348.2 mg, 8.706 mmol) in DMF (10.0 mL) at 0° C. was added a solution of 5-chloro-3-iodo-1H-pyrazolo[3,4-c]pyridine (1.488 g, 5.324 mmol) in DMF (10.0 mL) dropwise over a period of 10 min. The mixture was then allowed to warm to room temperature and stirred for 20 min. After the reaction was cooled to 0° C., a solution of [(3-(trimethylsilyl)ethoxy]methyl chloride (1184 mg, 7.102 mmol) in DMF (5.0 mL) was added dropwise over a period of 10 min. The reaction was allowed to warm to room temperature and stirred for 16 h. The reaction was quenched with sat. NH$_4$Cl (aq), and extracted with EtOAc. The separated organic layer was washed with brine, dried over Na$_2$SO$_4$, filtered and concentrated. The residue was purified on silica gel (120 g, 0-50% EtOAc in hexanes) to give the desired product as a pale yellow solid (1.429 g, 66%). LCMS calculated for $C_{12}H_{18}ClIN_3OSi$ (M+H)$^+$: m/z=410.0; found 410.0.

Step 3. 5-Chloro-3-[4-(4-methylpiperazin-1-yl)phenyl]-1-{[2-(trimethylsilyl)ethoxy]methyl}-1H-pyrazolo[3,4-c]pyridine

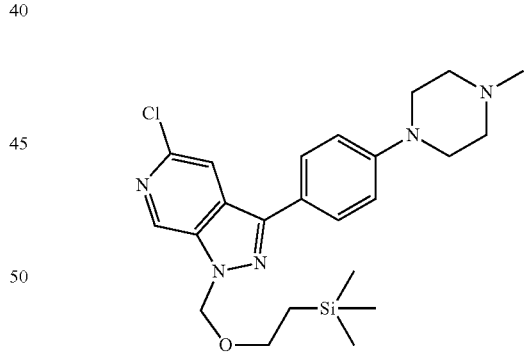

To a screw-cap vial equipped with a magnetic stir bar was added 5-chloro-3-iodo-1-{[2-(trimethylsilyl)ethoxy]methyl}-1H-pyrazolo[3,4-c]pyridine (1.429 g, 3.488 mmol), [4-(4-methylpiperazin-1-yl)phenyl]boronic acid (1.147 g, 5.212 mmol), [1,1'-bis(diphenylphosphino)ferrocene]dichloropalladium(II) complexed with dichloromethane (1:1) (310.2 mg, 0.3798 mmol) and K$_3$PO$_4$ (2.424 g, 11.42 mmol). The vial was sealed with a teflon-lined septum, evacuated and backfilled with nitrogen (this process was repeated a total of three times). 1,4-Dioxane (15.0 mL) was added followed by degassed water (5.00 mL). The reaction was stirred at 100° C. for 3 h. After cooling to room temperature, the reaction was diluted with EtOAc. The organic phase was washed with brine, dried over Na$_2$SO$_4$, filtered, and concentrated. The resulting residue was purified on silica gel (40 g, 0-100% EtOAc in hexanes, then 10% MeOH in CH$_2$Cl$_2$) to give the desired product as a dark solid (1.379 g, 86%). LCMS calculated for C$_{23}$H$_{33}$ClN$_5$OSi (M+H)$^+$: m/z=458.2; found 458.3.

Step 4. 1-[1-(3-Bromo-5-fluorophenyl)cyclopropyl] methanamine

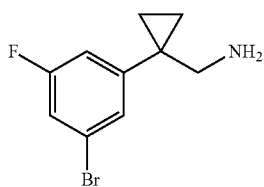 [SMILES: NCC1(c2cc(F)cc(Br)c2)CC1]

To 1-(3-bromo-5-fluorophenyl)cyclopropanecarbonitrile (1.005 g, 4.186 mmol) was added a solution of 1.0 M borane in THF (13.0 mL, 13.0 mmol). The mixture was heated to 70° C. for 2 h. After cooling to room temperature, the mixture was treated with 6.0 M HCl (aq) (14.0 mL, 84.0 mmol). The mixture was stirred at 60° C. for 5 h. The mixture was diluted with EtOAc, and adjusted to pH 12 with 4 N NaOH(aq). The separated aqueous layer was extracted with EtOAc (3×). The combined organic layer was dried over Na$_2$SO$_4$, filtered and concentrated to give the crude product as a yellow oil, which was used directly in the next step without further purification (2.11 g). LCMS calculated for C$_{10}$H$_{12}$BrFN (M+H)$^+$: m/z=244.0; found 244.0.

Step 5. tert-Butyl {[1-(3-bromo-5-fluorophenyl) cyclopropyl]methyl}carbamate

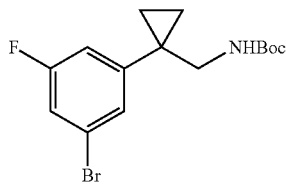 [SMILES: CC(C)(C)OC(=O)NCC1(c2cc(F)cc(Br)c2)CC1]

To a solution of 1-[1-(3-bromo-5-fluorophenyl)cyclopropyl]methanamine (1.022 g, 4.187 mmol) in CH$_2$Cl$_2$ (10.0 mL) was added di-tert-butyldicarbonate (1.531 g, 7.015 mmol). The mixture was stirred at room temperature for 10 min, and then concentrated. The mixture was purified on silica gel (120 g, 0-100% EtOAc in hexanes) to give the desired product as a white solid (1.252 g, 87%). LCMS calculated for C$_{15}$H$_{20}$BrFNO$_2$ (M+H)$^+$: m/z=344.1; found 344.0.

Step 6. tert-Butyl ({1-[3-fluoro-5-(4,4,5,5-tetramethyl-1,3,2-dioxaborolan-2-yl)phenyl] cyclopropyl}methyl)carbamate

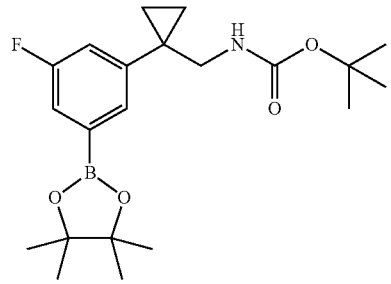 [SMILES: CC(C)(C)OC(=O)NCC1(c2cc(F)cc(B3OC(C)(C)C(C)(C)O3)c2)CC1]

To a screw-cap vial equipped with a magnetic stir bar was added tert-butyl {[1-(3-bromo-5-fluorophenyl)cyclopropyl] methyl}carbamate (589.7 mg, 1.713 mmol), 4,4,5,5,4',4',5', 5'-octamethyl-[2,2']bi[[1,3,2]dioxaborolanyl] (672.2 mg, 2.647 mmol), [1,1'-bis(diphenylphosphino)ferrocene]dichloropalladium(II) complexed with dichloromethane (1:1) (389.8 mg, 0.4773 mmol), and KOAc (509.0 mg, 5.186 mmol). The vial was sealed with a teflon-lined septum, evacuated and backfilled with nitrogen (this process was repeated a total of three times). 1,4-Dioxane (10.0 mL) was added. The reaction was stirred at 100° C. for 3 h. After cooling to room temperature, the reaction was diluted with CH$_2$Cl$_2$ and filtered. The filtrate was concentrated. The resulting residue was purified on silica gel (40 g, 0-100% EtOAc in hexanes) to give the desired product as a light yellow oil (571.4 mg, 85%). LCMS calculated for C$_{21}$H$_{31}$BFNNaO$_4$ (M+Na)$^+$: m/z=414.2; found 414.3.

Step 7. 1-[1-(3-Fluoro-5-{3-[4-(4-methylpiperazin-1-yl)phenyl]-1H-pyrazolo[3,4-c]pyridin-5-yl}phenyl)cyclopropyl]methanamine To a screw-cap vial equipped with a magnetic stir bar was added 5-chloro-3-[4-(4-methylpiperazin-1-yl)phenyl]-1-{[2-(trimethylsilyl)ethoxy]methyl}-1H-pyrazolo[3,4-c]pyridine (30.0 mg, 0.0655 mmol), tert-butyl ({1-[3-fluoro-5-(4, 4,5,5-tetramethyl-1,3,2-dioxaborolan-2-yl)phenyl] cyclopropyl}methyl)carbamate (49.5 mg, 0.126 mmol), dicyclohexyl(2',4',6'-triisopropylbiphenyl-2-yl)phosphine-(2'-aminobiphenyl-2-yl)(chloro)palladium (1:1) (XPhos Pd G2, 5.0 mg, 0.0063 mmol), and K$_3$PO$_4$ (54.2 mg, 0.255 mmol). The vial was sealed with a teflon-lined septum, evacuated and backfilled with nitrogen (this process was repeated a total of three times). 1,4-Dioxane (1.50 mL) was added, followed by water (150.0 µL). The reaction was stirred at 80° C. for 1 h. After cooling to room temperature, the reaction mixture was diluted with CH$_2$Cl$_2$, filtered and concentrated. The residue was dissolved in MeOH (3.00 mL) and treated with 4.0 M HCl in dioxane (2.00 mL, 8.00 mmol). The mixture was stirred at 65° C. for 2 h. After cooling to room temperature, the mixture was purified using prep-LCMS (XBridge C18 column, eluting with a gradient of acetonitrile/water containing 0.1% TFA, at flow rate of 60 mL/min) to afford the desired product as a yellow solid (17.9 mg). LCMS calculated for C$_{27}$H$_{30}$FN$_6$ (M+H)$^+$: m/z=457.3; Found: 457.3.

Example 43. 5-(2-Fluoro-6-methoxyphenyl)-3-(4-(4-methylpiperazin-1-yl)phenyl)-1H-pyrazolo[3,4-c]pyridine

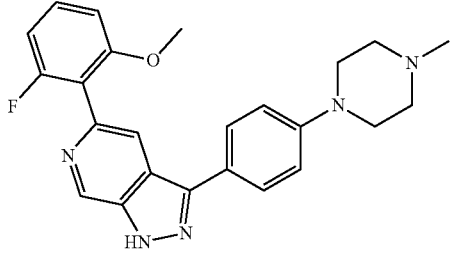 [SMILES: COc1cccc(F)c1-c1cc2c(-c3ccc(N4CCN(C)CC4)cc3)n[nH]c2cn1]

To a screw-cap vial equipped with a magnetic stir bar was added 5-chloro-3-(4-(4-methylpiperazin-1-yl)phenyl)-1-((2-(trimethylsilyl)ethoxy)methyl)-1H-pyrazolo[3,4-c]pyridine (Example 42, Step 3, 30.1 mg, 0.066 mmol), (2-fluoro-6-methoxyphenyl)boronic acid (22.9 mg, 0.135 mmol), chloro(2-dicyclohexylphosphino-2',4',6'-triisopropyl-1,1'-biphenyl)[2-(2'-amino-1,1'-biphenyl)]palladium(II) (XPhos Pd G2, 5.0 mg, 0.0063 mmol) and $K_3PO_4$ (51.4 mg, 0.242 mmol). The vial was sealed with a teflon-lined septum, evacuated and backfilled with nitrogen (this process was repeated a total of three times). 1,4-Dioxane (1.50 mL) was added, followed by water (150.0 µL). The reaction was stirred at 65° C. for 2 h. After cooling to room temperature, the reaction mixture was diluted with $CH_2Cl_2$, filtered and concentrated. The residue was dissolved in MeOH (3.00 mL) and treated with 4.0 M HCl in dioxane (2.00 mL, 8.00 mmol). The mixture was stirred at 65° C. for 2 h. After cooling to room temperature, the mixture was purified using prep-LCMS (XBridge C18 column, eluting with a gradient of acetonitrile/water containing 0.1% TFA, at flow rate of 60 mL/min) to afford the desired product as a yellow solid (19.4 mg). LCMS calculated for $C_{24}H_{25}FN_5O$ $(M+H)^+$: m/z=418.2; Found: 418.3.

Example 44. 5-(2,6-Difluorophenyl)-3-(4-(4-methylpiperazin-1-yl)phenyl)-1H-pyrazolo[3,4-c]pyridine

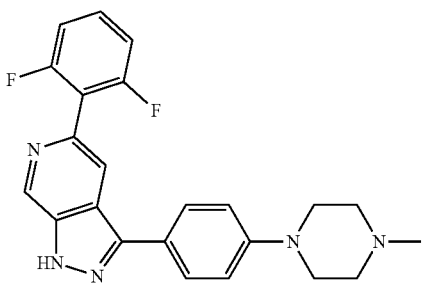

This compound was prepared according to the procedures described in Example 43, using (2,6-difluorophenyl)boronic acid instead of 2-fluoro-6-methoxyphenylboronic acid as starting material. LCMS calculated for $C_{23}H_{22}F_2N_5$ $(M+H)^+$: m/z=406.2; Found: 406.2.

Example 45. 5-(2,6-Dimethylphenyl)-3-(4-(4-methylpiperazin-1-yl)phenyl)-1H-pyrazolo[3,4-c]pyridine

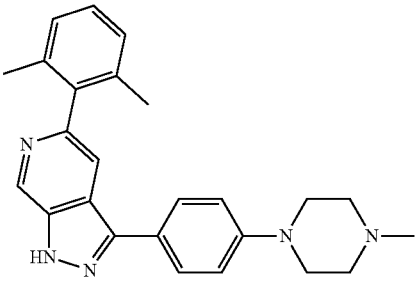

This compound was prepared according to the procedures described in Example 43, using (2,6-dimethylphenyl)boronic acid instead of 2-fluoro-6-methoxyphenylboronic acid as starting material. LCMS calculated for $C_{25}H_{28}N_5$ $(M+H)^+$: m/z=398.2; Found: 398.1.

Example 46. 3-(4-(4-Methylpiperazin-1-yl)phenyl)-5-(2,4,6-trifluorophenyl)-1H-pyrazolo[3,4-c]pyridine

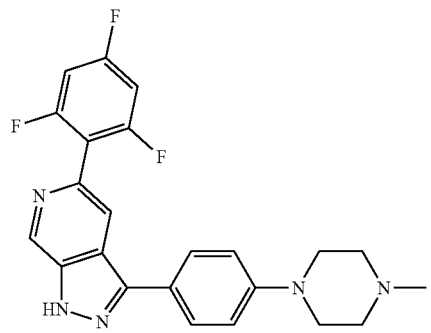 [SMILES: CN1CCN(c2ccc(-c3n[nH]c4cnc(-c5c(F)cc(F)cc5F)cc34)cc2)CC1]

This compound was prepared according to the procedures described in Example 43, using (2,4,6-trifluorophenyl)boronic acid instead of 2-fluoro-6-methoxyphenylboronic acid as starting material. LCMS calculated for $C_{23}H_{21}F_3N_5$ $(M+H)^+$: m/z=424.2; Found: 424.2.

Example 47. 5-(2-Chloro-6-fluorophenyl)-3-(4-(4-methylpiperazin-1-yl)phenyl)-1H-pyrazolo[3,4-c]pyridine

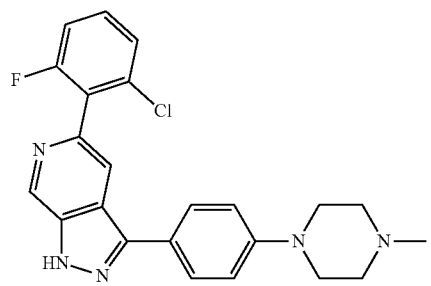

This compound was prepared according to the procedures described in Example 43, using (2-chloro-6-fluorophenyl)

boronic acid instead of 2-fluoro-6-methoxyphenylboronic acid as starting material. LCMS calculated for $C_{23}H_{22}ClFN_5$ (M+H)$^+$: m/z=422.2; Found: 422.2.

Example 48. 3,5-Difluoro-4-(3-(4-(4-methylpiperazin-1-yl)phenyl)-1H-pyrazolo[3,4-c]pyridin-5-yl)phenol

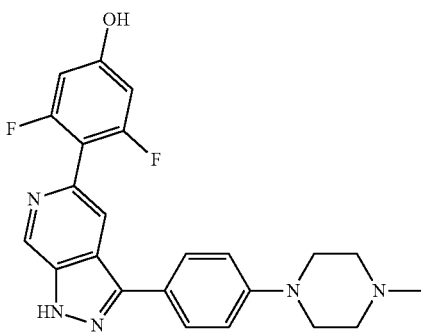

This compound was prepared according to the procedures described in Example 43, using (2,6-difluoro-4-hydroxyphenyl)boronic acid instead of 2-fluoro-6-methoxyphenylboronic acid as starting material. LCMS calculated for $C_{23}H_{22}F_2N_5O$ (M+H)$^+$: m/z=422.2; Found: 422.2.

Example 49. 5-(2-Fluoro-6-methylphenyl)-3-(4-(4-methylpiperazin-1-yl)phenyl)-1H-pyrazolo[3,4-c]pyridine

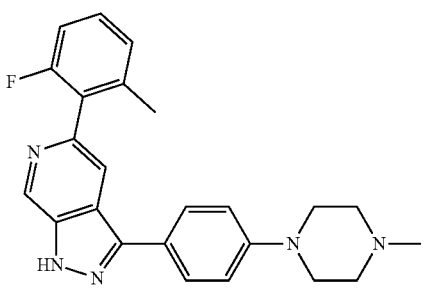

This compound was prepared according to the procedures described in Example 43, using (2-fluoro-6-methylphenyl)boronic acid instead of 2-fluoro-6-methoxyphenylboronic acid as starting material. LCMS calculated for $C_{24}H_{25}FN_5$ (M+H)$^+$: m/z=402.2; Found: 402.2.

Example 50. 5-(2-Chloro-6-(trifluoromethyl)phenyl)-3-(4-(4-methylpiperazin-1-yl)phenyl)-1H-pyrazolo[3,4-c]pyridine

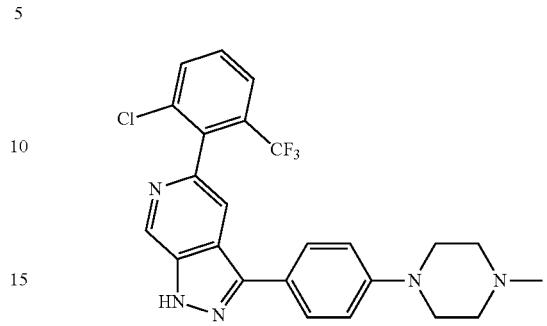

This compound was prepared according to the procedures described in Example 43, using (2-chloro-6-(trifluoromethyl)phenyl)boronic acid instead of 2-fluoro-6-methoxyphenylboronic acid as starting material. LCMS calculated for $C_{24}H_{22}ClF_3N_5$ (M+H)$^+$: m/z=472.2; Found: 472.2.

Example 51. 5-(2-Ethoxy-6-fluorophenyl)-3-(4-(4-methylpiperazin-1-yl)phenyl)-1H-pyrazolo[3,4-c]pyridine

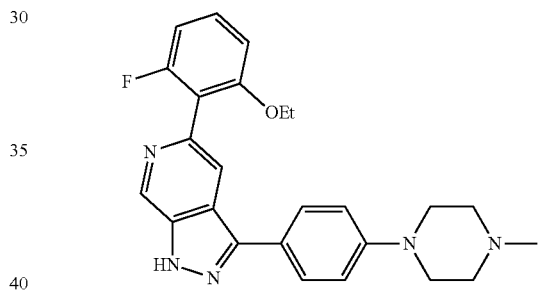

This compound was prepared according to the procedures described in Example 43, using (2-ethoxy-6-fluorophenyl)boronic acid instead of 2-fluoro-6-methoxyphenylboronic acid as starting material. LCMS calculated for $C_{25}H_{27}FN_5O$ (M+H)$^+$: m/z=432.2; Found: 432.2.

Example 52. 5-(2-Chloro-6-methoxyphenyl)-3-(4-(4-methylpiperazin-1-yl)phenyl)-1H-pyrazolo[3,4-c]pyridine

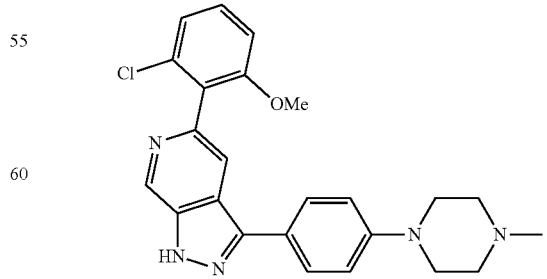

This compound was prepared according to the procedures described in Example 43, using (2-chloro-6-methoxyphe-

97 nyl)boronic acid instead of 2-fluoro-6-methoxyphenylboronic acid as starting material. LCMS calculated for $C_{24}H_{25}ClN_5O$ (M+H)$^+$: m/z=434.2; Found: 434.2.

Example 53. 5-(2-Fluoro-6-(trifluoromethyl)phenyl)-3-(4-(4-methylpiperazin-1-yl)phenyl)-1H-pyrazolo[3,4-c]pyridine

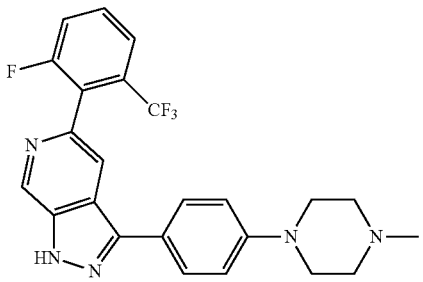 [SMILES: CN1CCN(c2ccc(-c3n[nH]c4cnc(-c5c(F)cccc5C(F)(F)F)cc34)cc2)CC1]

This compound was prepared according to the procedures described in Example 43, using (2-fluoro-6-(trifluoromethyl)phenyl)boronic acid instead of 2-fluoro-6-methoxyphenylboronic acid as starting material. LCMS calculated for $C_{24}H_{22}F_4N_5$ (M+H)$^+$: m/z=456.2; Found: 456.2.

Example 54. 5-(2-Fluoro-6-methoxyphenyl)-N-(4-(4-methylpiperazin-1-yl)phenyl)-1H-pyrazolo[3,4-c]pyridine-3-carboxamide

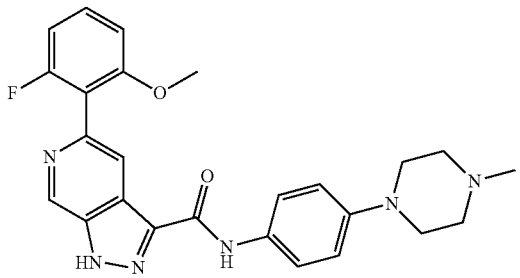 [SMILES: COc1cccc(F)c1-c1cc2c(C(=O)Nc3ccc(N4CCN(C)CC4)cc3)n[nH]c2cn1]

Step 1. Methyl 5-(2-fluoro-6-methoxyphenyl)-1-((2-(trimethylsilyl)ethoxy)methyl)-1H-pyrazolo[3,4-c]pyridine-3-carboxylate

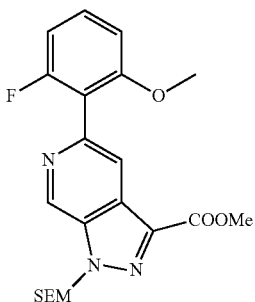 [SMILES: COC(=O)c1nn(COCC[Si](C)(C)C)c2cnc(-c3c(F)cccc3OC)cc12]

A mixture of 5-(2-fluoro-6-methoxyphenyl)-3-iodo-1-((2-(trimethylsilyethoxy)methyl)-1H-pyrazolo[3,4-c]pyridine (Example 34, Step 5, 1.0 g, 2 mmol) and [1,1'-bis(diphenylphosphino)ferrocene]dichloropallalium(II) complexed with dichloromethane (1:1) (170 mg, 0.2 mmol, Combi-Blocks) was placed in a flask with a septum. The flask was then evacuated and backfilled with nitrogen three times. After addition of methanol (20 mL) and triethylamine (0.57 mL, 4 mmol), the flask was evacuated and backfilled with carbon monoxide gas three times. Then balloon with carbon monoxide gas was connected to the reaction flask and reaction mixture was heated at 85° C. overnight. After cooling to r.t., the reaction mixture was filtered through Celite, and the filtrate was concentrated in vacuo. The crude material was purified by Biotage Isolera to give the desired product (440 mg, 51%). LCMS calculated for $C_{21}H_{27}FN_3O_4Si$ (M+H)$^+$ m/z=432.2; found: 432.2.

Step 2. 5-(2-Fluoro-6-methoxyphenyl)-1-((2-(trimethylsilyl)ethoxy)methyl)-1H-pyrazolo[3,4-c]pyridine-3-carboxylic acid

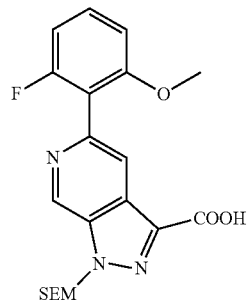 [SMILES: COc1cccc(F)c1-c1cc2c(C(=O)O)nn(COCC[Si](C)(C)C)c2cn1]

1M Solution of sodium hydroxide in water (5 mL, 5 mmol) was added to a solution of methyl 5-(2-fluoro-6-methoxyphenyl)-1-((2-(trimethylsilyl)ethoxy)methyl)-1H-pyrazolo[3,4-c]pyridine-3-carboxylate (450 mg, 1 mmol) in tetrahydrofuran (5 mL) and methanol (3 mL). After stirring at r.t. for 2 h, pH was adjusted to 5 by the addition of the 1M solution of HCl. The mixture was then extracted with ethyl acetate, and the separated organic phase was washed with brine. The organic phase was dried over sodium sulfate, and the solvents were evaporated under reduced pressure. The obtained solid product was used in the next step without further purification (396 mg, 95%). LCMS calculated for $C_{20}H_{25}FN_3O_4Si$ (M+H)$^+$ m/z=418.2; found 418.3.

Step 3. 5-(2-Fluoro-6-methoxyphenyl)-N-(4-(4-methylpiperazin-1-yl)phenyl)-1H-pyrazolo[3,4-c]pyridine-3-carboxamide To a solution of 5-(2-fluoro-6-methoxyphenyl)-1-((2-(trimethylsilypethoxy)methyl)-1H-pyrazolo[3,4-c]pyridine-3-carboxylic acid (15 mg, 0.035 mmol) and 4-(4-methylpiperazin-1-yl)aniline (10 mg, 0.05 mmol) in N,N-dimethylformamide (1.5 mL) were added N,N-diisopropylethylamine (13 µL, 0.07 mmol) and N,N,N',N'-tetramethyl-O-(7-azabenzotriazol-1-yl)uronium hexafluorophosphate (15 mg, 0.04 mmol). After the reaction mixture was stirred at r.t. for 2 hours, it was quenched with water. The mixture was extracted with ethyl acetate. The organic phases were washed with brine and dried over sodium sulfate, and the solvents were evaporated in vacuo. Then 1M solution of HCl in water (1 mL) and 4M solution of HCl in dioxane (1 mL) were added to the crude residue, and reaction mixture was stirred at 80° C. for 1 h. Methanol (1 mL) was added, and reaction mixture was further stirred at 80° C. for 30 min. The reaction mixture was then diluted with acetonitrile and was purified with prep-LCMS (XBridge C18 column, eluting with a gradient of acetonitrile/water containing 0.1% TFA, at flow rate of 60 mL/min). LCMS calculated for $C_{25}H_{26}FN_6O_2$ (M+H)$^+$: m/z=461.2; Found: 461.3.

Example 55. 5-(2-Fluoro-6-methoxyphenyl)-N-(4-morpholinophenyl)-1H-pyrazolo[3,4-c]pyridine-3-carboxamide

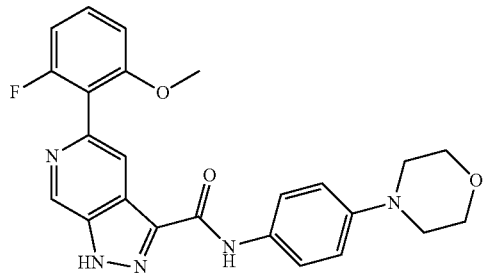 [SMILES: COc1cccc(F)c1-c1cc2c(C(=O)Nc3ccc(N4CCOCC4)cc3)n[nH]c2cn1]

This compound was prepared according to the procedures described in Example 54, using 4-morpholinoaniline instead of 4-(4-methylpiperazin-1-yl)aniline as starting material. LCMS calculated for $C_{24}H_{23}FN_5O_3$ (M+H)$^+$: m/z=448.2; Found: 448.3.

Example 56. N-(4-(4-Ethylpiperazin-1-yl)phenyl)-5-(2-fluoro-6-methoxyphenyl)-1H-pyrazolo[3,4-c]pyridine-3-carboxamide

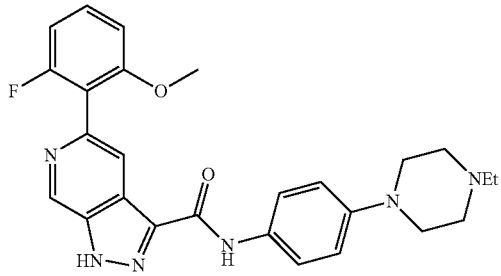

This compound was prepared according to the procedures described in Example 54, using 4-(4-ethylpiperazin-1-yl) aniline instead of 4-(4-methylpiperazin-1-yl)aniline as starting material. LCMS calculated for $C_{26}H_{28}FN_6O_2$ (M+H)$^+$: m/z=475.2; Found: 475.2.

Intermediate 1. tert-Butyl 5-chloro-3-(1-methyl-1H-pyrazol-4-yl)-1H-pyrazolo[3,4-c]pyridine-1-carboxylate

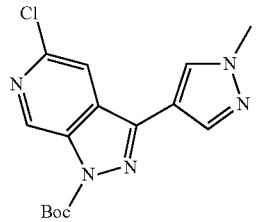 [SMILES: Cn1cc(-c2nn(C(=O)OC(C)(C)C)c3cnc(Cl)cc23)cn1]

Step 1. tert-Butyl 5-chloro-3-iodo-1H-pyrazolo[3,4-c]pyridine-1-carboxylate

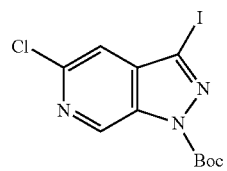 [SMILES: CC(C)(C)OC(=O)n1nc(I)c2cc(Cl)ncc21]

NIS (10.57 g, 47.0 mmol) was added to a solution of 5-chloro-1H-pyrazolo[3,4-c]pyridine (7.07 g, 46.0 mmol) in DMF (115 ml). After stirring at 70° C. for 2 h, reaction mixture was cooled to r.t. and triethylamine (9.63 ml, 69.1 mmol) was added followed by boc-anhydride (15.07 g, 69.1 mmol). After stirring for an additional 2 h at r.t., water was added and precipitated product was collected by filtration, dried and was used in the next step without further purification (17 g, 97%). LCMS calculated for $C_{11}H_{12}ClIN_3O_2$ (M+H)$^+$: m/z=380.0; found 380.0.

Step 2. tert-Butyl 5-chloro-3-(1-methyl-1H-pyrazol-4-yl)-1H-pyrazolo[3,4-c]pyridine-1-carboxylate

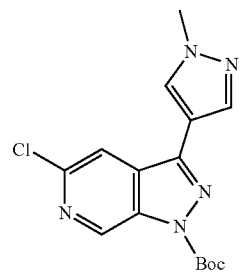 [SMILES: Cn1cc(-c2nn(C(=O)OC(C)(C)C)c3cnc(Cl)cc23)cn1]

tert-Butyl 5-chloro-3-iodo-1H-pyrazolo[3,4-c]pyridine-1-carboxylate (6.64 g, 17.49 mmol), PdCl$_2$(dppf)-CH$_2$Cl$_2$ adduct (1.429 g, 1.749 mmol), 1-methyl-4-(4,4,5,5-tetramethyl-1,3,2-dioxaborolan-2-yl)-1H-pyrazole (3.64 g, 17.49 mmol) and potassium phosphate (7.43 g, 35.0 mmol) were placed in a flask and the flask was evacuated and backfilled with nitrogen three times. Then dioxane (100 ml) and degassed water (10.0 ml) were added, and the reaction mixture was stirred at 80° C. for 1 h. After cooling to r.t., water was added, and the mixture was extracted with EtOAc. The combined organic phases were washed with brine, dried over sodium sulfate and solvent evaporated. The crude product was purified by Biotage Isolera™ (4.7 g, 81%). LCMS calculated for $C_{15}H_{17}ClN_5O_2$ (M+H)$^+$ m/z=334.1; found 334.2.

Intermediate 2. 5-Chloro-3-(1-methyl-1H-pyrazol-4-yl)-1-((2-(trimethylsilyl)ethoxy)methyl)-1H-pyrazolo[3,4-c]pyridine

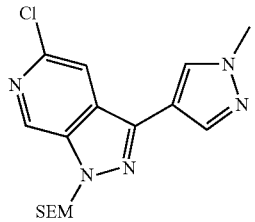 [SMILES: Cn1cc(-c2nn(COCC[Si](C)(C)C)c3cnc(Cl)cc23)cn1]

This compound was prepared according to the procedures described in Example 42 (Steps 1-3), using 1-methyl-4-(4,4,5,5-tetramethyl-1,3,2-dioxaborolan-2-yl)-1H-pyrazole instead of [4-(4-methylpiperazin-1-yl)phenyl]boronic acid as starting material. LCMS calculated for $C_{16}H_{23}ClN_5OSi$ (M+H)$^+$: m/z=364.1; Found: 364.1.

Example 57. 3,5-Difluoro-N-(2-methoxyethyl)-4-(3-(1-methyl-1H-pyrazol-4-yl)-1H-pyrazolo[3,4-c]pyridin-5-yl)benzamide

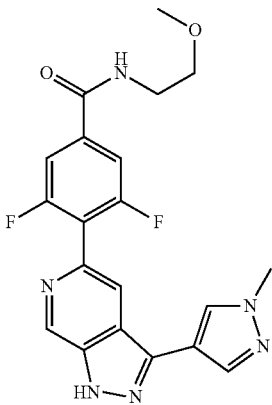 [SMILES: COCCNC(=O)c1cc(F)c(-c2cc3c(-c4cnn(C)c4)n[nH]c3cn2)c(F)c1]

Step 1. Methyl 3,5-difluoro-4-(3-(1-methyl-1H-pyrazol-4-yl)-1-((2-(trimethylsilyl)ethoxy)methyl)-1H-pyrazolo[3,4-c]pyridin-5-yl-benzoate

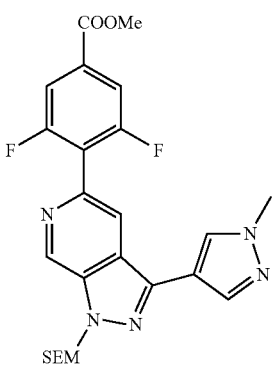 [SMILES: COC(=O)c1cc(F)c(-c2cc3c(-c4cnn(C)c4)nn(COCC[Si](C)(C)C)c3cn2)c(F)c1]

5-Chloro-3-(1-methyl-1H-pyrazol-4-yl)-1-((2-(trimethylsilyl)ethoxy)methyl)-1H-pyrazolo[3,4-c]pyridine (348 mg, 0.956 mmol, Intermediate 2), methyl 3,5-difluoro-4-(4,4,5,5-tetramethyl-1,3,2-dioxaborolan-2-yl)benzoate (342 mg, 1.148 mmol), chloro(2-dicyclohexylphosphino-2',4',6'-triisopropyl-1,1'-biphenyl)[2-(2'-amino-1,1'-biphenyl)]palladium(II) (Pd XPhos G2) (75 mg, 0.096 mmol) and potassium phosphate (406 mg, 1.91 mmol) were placed in a flask and the flask was evacuated and backfilled with nitrogen three times. Then dioxane (20 mL) and degassed water (2 mL) were added, and reaction mixture was stirred at 90° C. for 2 h. After cooling to r.t., the reaction mixture was diluted with ethyl acetate, and the resulting mixture was washed with brine. The separated organic phase was dried over sodium sulfate and concentrated under reduced pressure. The obtained crude product was purified by Biotage Isolera™ (440 mg, 92%). LCMS calculated for $C_{24}H_{28}F_2N_5O_3Si$ (M+H)$^+$ m/z=500.2; found 500.2.

Step 2. 3,5-Difluoro-4-(3-(1-methyl-1H-pyrazol-4-yl)-1-((2-(trimethylsilyl)ethoxy)methyl)-1H-pyrazolo[3,4-c]pyridin-5-yl)benzoic acid

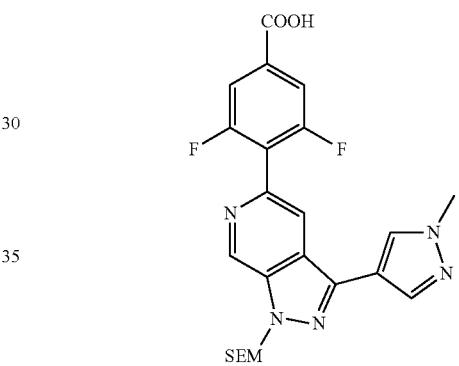

1M Solution of sodium hydroxide in water (5 mL, 5 mmol) was added to a solution of methyl 3,5-difluoro-4-(3-(1-methyl-1H-pyrazol-4-yl)-1-((2-(trimethylsilyethoxy)methyl)-1H-pyrazolo[3,4-c]pyridin-5-yl)benzoate (440 mg, 0.881 mmol) in tetrahydrofuran (5 mL) and methanol (3 mL). After stirring at r.t. for 2 h, the pH was adjusted to 5 by the addition of an 1M solution of HCl. The resulting mixture was then extracted with ethyl acetate and organic phase was washed with brine. The organic phase was dried over sodium sulfate and the solvents were evaporated in vacuo. The obtained solid product was used in the next step without further purification (403 mg, 94%). LCMS calculated for $C_{23}H_{26}F_2N_5O_3Si$ (M+H)$^+$ m/z=486.2; found 486.3.

Step 3. 3,5-Difluoro-N-(2-methoxyethyl)-4-(3-(1-methyl-1H-pyrazol-4-yl)-1H-pyrazolo[3,4-c]pyridin-5-yl)benzamide To a solution of 3,5-difluoro-4-(3-(1-methyl-1H-pyrazol-4-yl)-1-((2-(trimethylsilyl)ethoxy)methyl)-1H-pyrazolo[3,4-c]pyridin-5-yl)benzoic acid (15 mg, 0.031 mmol) and 2-methoxyethan-1-amine (4.64 mg, 0.062 mmol) in N,N-dimethylformamide (1.5 mL) were added N,N-diisopropylethylamine (13 μL, 0.07 mmol) and N,N,N',N'-tetramethyl-O-(7-azabenzotriazol-1-yl)uronium hexafluorophosphate (15 mg, 0.04 mmol). After the reaction mixture was stirred at r.t. for 2 hours, it was quenched with water. The mixture was extracted with ethyl acetate, and the separated organic phases were washed with brine, dried over sodium sulfate. The solvents were evaporated in vacuo. Then 1M solution of HCl in water (1 mL) and 4M solution of HCl in dioxane (1 mL) were added to the crude residue and the reaction was stirred at 80° C. for 1 h. Then methanol (1 mL) was added, and reaction mixture was further stirred at 80° C. for 30 min. The reaction mixture was then diluted with acetonitrile and was purified with prep-LCMS (XBridge C18 column, eluting with a gradient of acetonitrile/water containing 0.1% TFA, at flow rate of 60 mL/min). LCMS calculated for $C_{20}H_{19}F_2N_6O_2$ (M+H)$^+$: m/z=413.2; Found: 413.3.

Example 58. (3,5-Difluoro-4-(3-(1-methyl-1H-pyrazol-4-yl)-1H-pyrazolo[3,4-c]pyridin-5-yl)phenyl)(3-methoxyazetidin-1-yl)methanone

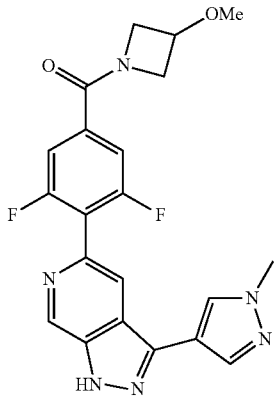 [SMILES: COC1CN(C(=O)c2cc(F)c(-c3cc4c(-c5cnn(C)c5)n[nH]c4cn3)c(F)c2)C1]

This compound was prepared according to the procedures described in Example 57, using 3-methoxyazetidine instead of 2-methoxyethan-1-amine as starting material. LCMS calculated for $C_{21}H_{19}F_2N_6O_2$ (M+H)$^+$: m/z=425.2; Found: 425.2.

Example 59. N-(2,4-Difluoro-3-(3-(1-methyl-1H-pyrazol-4-yl)-1H-pyrazolo[3,4-c]pyridin-5-yl)phenyl)cyclobutanecarboxamide

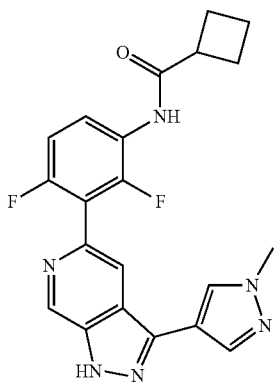 [SMILES: Cn1cc(-c2n[nH]c3cnc(-c4c(F)ccc(NC(=O)C5CCC5)c4F)cc23)cn1]

Step 1. 2,4-Difluoro-3-(4,4,5,5-tetramethyl-1,3,2-dioxaborolan-2-yl)aniline

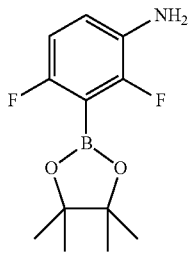 [SMILES: CC1(C)OB(c2c(F)ccc(N)c2F)OC1(C)C]

To a mixture of 4,4,5,5,4',4',5',5'-octamethyl-[2,2]bi[[1,3,2]dioxaborolanyl] (1.831 g, 7.21 mmol), potassium acetate (1.415 g, 14.42 mmol) and [1,1'-bis(diphenylphosphino)ferrocene]dichloropalladium(II) complexed with dichloromethane (1:1) (0.785 g, 0.962 mmol) under nitrogen was added a solution of 3-bromo-2,4-difluoroaniline (1.0 g, 4.81 mmol) in 1,4-dioxane (20 mL). The mixture was stirred at 100° C. overnight. After cooling to room temperature, the mixture was diluted with DCM and filtered through Celite. The filtrated was concentrated in vacuo. The residue was purified by Biotage Isolera™ (740 mg, 60%). LCMS calculated for $C_{12}H_{17}BF_2NO_2$ (M+H)$^+$ m/z=256.1; found 256.1.

Step 2. 2,4-Difluoro-3-(3-(1-methyl-1H-pyrazol-4-yl)-1-((2-(trimethylsilyl)ethoxy)methyl)-1H-pyrazolo[3,4-c]pyridin-5-yl)aniline

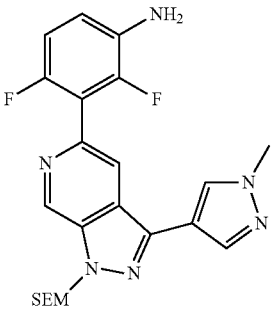 [SMILES: Cn1cc(-c2nn(COCC[Si](C)(C)C)c3cnc(-c4c(F)ccc(N)c4F)cc23)cn1]

5-Chloro-3-(1-methyl-1H-pyrazol-4-yl)-1-((2-(trimethylsilyl)ethoxy)methyl)-1H-pyrazolo[3,4-c]pyridine (348 mg, 0.956 mmol, Intermediate 2), 2,4-difluoro-3-(4,4,5,5-tetramethyl-1,3,2-dioxaborolan-2-yl)aniline (293 mg, 1.148 mmol), chloro(2-dicyclohexylphosphino-2',4',6'-triisopropyl-1,1'-biphenyl)[2-(2'-amino-1,1'-biphenyl)]palladium(II) (Pd XPhos G2) (75 mg, 0.096 mmol) and potassium phosphate (406 mg, 1.91 mmol) were placed in a flask and the flask was evacuated and backfilled with nitrogen three times. Then dioxane (20 mL) and degassed water (2 mL) were added, and reaction mixture was stirred at 90° C. for 2 h. After cooling to r.t., the reaction mixture was diluted with ethyl acetate, the resulting mixture was washed with brine, The separated organic phase was dried over sodium sulfate. The solvents were evaporated in vacuo and obtained crude product was purified by Biotage Isolera™ (380 mg, 87%). LCMS calculated for $C_{22}H_{27}F_2N_6OSi$ (M+H)$^+$ m/z=457.2; found 457.2.

Step 3. N-(2,4-Difluoro-3-(3-(1-methyl-1H-pyrazol-4-yl)-1H-pyrazolo[3,4-c]pyridin-5-yl)phenyl)cyclobutanecarboxamide To a solution of 2,4-difluoro-3-(3-(1-methyl-1H-pyrazol-4-yl)-1-((2-(trimethylsilyl)ethoxy)methyl)-1H-pyrazolo[3,4-c]pyridin-5-yl)aniline (15 mg, 0.033 mmol) and cyclobutanecarboxylic acid (3.29 mg, 0.033 mmol) in N,N-dimethylformamide (1.5 mL) were added N,N-diisopropylethylamine (13 μL, 0.07 mmol) and N,N,N',N'-tetramethyl-O-(7-azabenzotriazol-1-yl)uronium hexafluorophosphate (15 mg, 0.04 mmol). After the reaction mixture was stirred at r.t. for 2 hours, it was quenched with water. The mixture was extracted with ethyl acetate, and the organic phases were washed with brine, dried over sodium sulfate and solvents evaporated in vacuo. Then 1M solution of HCl in water (1 mL) and 4M solution of HCl in dioxane (1 mL) were added to the crude residue, and reaction was stirred at 80° C. for 1 h. After this methanol (1 mL) was added and reaction was further stirred at 80° C. for 30 min. The reaction mixture was then diluted with acetonitrile and was purified with prep-LCMS (XBridge C18 column, eluting with a gradient of acetonitrile/water containing 0.1% TFA, at flow rate of 60 mL/min). LCMS calculated for $C_{21}H_{19}F_2N_6O$ (M+H)$^+$: m/z=409.2; Found: 409.1.

Example 60. N-(2,4-Difluoro-3-(3-(1-methyl-1H-pyrazol-4-yl)-1H-pyrazolo[3,4-c]pyridin-5-yl)phenyl)-2-phenylacetamide

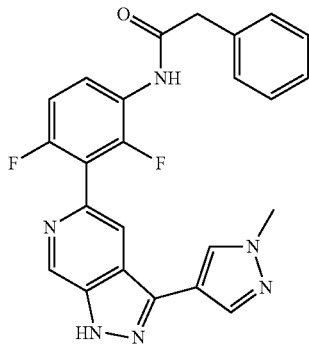 [SMILES: Cn1cc(-c2n[nH]c3cnc(-c4c(F)ccc(NC(=O)Cc5ccccc5)c4F)cc23)cn1]

This compound was prepared according to the procedures described in Example 59, using 2-phenylacetic acid instead of cyclobutanecarboxylic acid as starting material. LCMS calculated for $C_{24}H_{19}F_2N_6O$ (M+H)$^+$: m/z=445.2; Found: 445.3.

Example 61. 2,4-Difluoro-N-methyl-3-(3-(1-methyl-1H-pyrazol-4-yl)-1H-pyrazolo[3,4-c]pyridin-5-yl)aniline

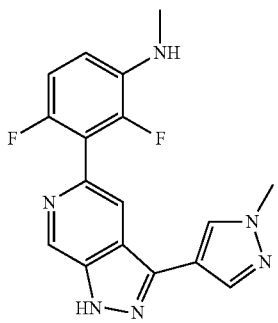

Example 62. 2,4-Difluoro-N,N-dimethyl-3-(3-(1-methyl-1H-pyrazol-4-yl)-1H-pyrazolo[3,4-c]pyridin-5-yl)aniline

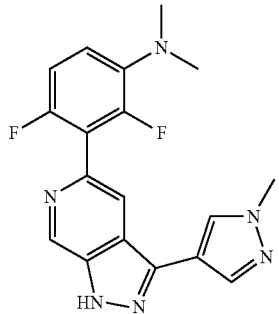 [SMILES: CN(C)c1ccc(F)c(-c2cc3c(-c4cnn(C)c4)n[nH]c3cn2)c1F]

Sodium hydride (2 mg, 0.049 mmol, 60% in mineral oil) was added to a solution of 2,4-difluoro-3-(3-(1-methyl-1H-pyrazol-4-yl)-1-((2-(trimethylsilyl)ethoxy)methyl)-1H-pyrazolo[3,4-c]pyridin-5-yl)aniline (15 mg, 0.033 mmol, Example 59, Step 2) and iodomethane (13.99 mg, 0.099 mmol) in THF (2.0 mL). After the reaction mixture was stirred at r.t. for 2 hours, it was quenched with water. The mixture was extracted with ethyl acetate. The organic phases were washed with brine, dried over sodium sulfate and solvents evaporated in vacuo. Then 1M solution of HCl in water (1 mL) and 4M solution of HCl in dioxane (1 mL) were added to the crude residue, and reaction was stirred at 80° C. for 1 h. Then methanol (1 mL) was added, and reaction mixture was further stirred at 80° C. for 30 min. The reaction mixture was then diluted with acetonitrile and was purified with prep-LCMS (XBridge C18 column, eluting with a gradient of acetonitrile/water containing 0.1% TFA, at flow rate of 60 mL/min) to give both products Example 61 and Example 62. Example 61. LCMS calculated for $C_{17}H_{15}F_2N_6$ (M+H)$^+$: m/z=341.1; Found: 341.2. Example 62. LCMS calculated for $C_{18}H_{17}F_2N_6$ (M+H)$^+$: m/z=355.2; Found: 355.2.

Example 63. 3,5-Difluoro-N,N-dimethyl-4-(3-(1-methyl-1H-pyrazol-4-yl)-1H-pyrazolo[3,4-c]pyridin-5-yl)aniline

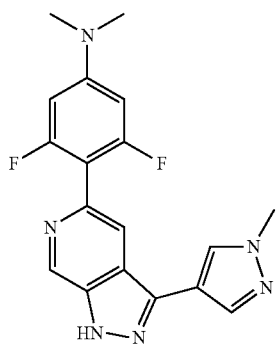 [SMILES: CN(C)c1cc(F)c(-c2cc3c(-c4cnn(C)c4)n[nH]c3cn2)c(F)c1]

Step 1. 3,5-Difluoro-4-(4,4,5,5-tetramethyl-1,3,2-dioxaborolan-2-yl)aniline

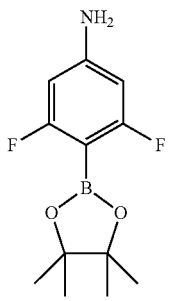

To a mixture of 4,4,5,5,4',4',5',5'-octamethyl-[2,2]bi[[1,3,2]dioxaborolanyl] (2.75 g, 10.8 mmol), potassium acetate (2.1 g, 21.6 mmol) and [1,1'-bis(diphenylphosphino)ferrocene]dichloropalladium(II) complexed with dichloromethane (1:1) (0.785 g, 0.962 mmol) under nitrogen was added a solution of 4-bromo-3,5-difluoroaniline (1.5 g, 7.21 mmol) in 1,4-dioxane (20 mL). The mixture was stirred at 100° C. overnight. After cooling to room temperature, the mixture was diluted with DCM and filtered through Celite. The filtrated was concentrated in vacuo. The residue was purified by Biotage Isolera™ (1.4 g, 76%). LCMS calculated for $C_{12}H_{17}BF_2NO_2$ (M+H) m/z=256.1; found 256.2.

Step 2. 3,5-Difluoro-4-(3-(1-methyl-1H-pyrazol-4-yl)-1-((2-(trimethylsilyl)ethoxy)methyl)-1H-pyrazolo[3,4-c]pyridin-5-yl)aniline

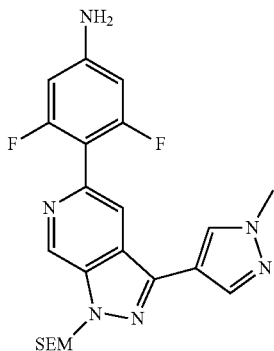 [SMILES: Cn1cc(-c2nn(COCC[Si](C)(C)C)c3cnc(-c4c(F)cc(N)cc4F)cc23)cn1]

5-Chloro-3-(1-methyl-1H-pyrazol-4-yl)-1-((2-(trimethylsilyl)ethoxy)methyl)-1H-pyrazolo[3,4-c]pyridine (348 mg, 0.956 mmol, Intermediate 2), 3,5-difluoro-4-(4,4,5,5-tetramethyl-1,3,2-dioxaborolan-2-yl)aniline (293 mg, 1.148 mmol), chloro(2-dicyclohexylphosphino-2',4',6'-triisopropyl-1,1'-biphenyl)[2-(2'-amino-1,1'-biphenyl)]palladium(II) (Pd XPhos G2) (75 mg, 0.096 mmol) and potassium phosphate (406 mg, 1.91 mmol) were placed in a flask and the flask was evacuated and backfilled with nitrogen three times. Then dioxane (20 mL) and degassed water (2 mL) were added and the reaction was stirred at 90° C. for 2 h. After cooling to r.t., the reaction mixture was extracted with ethyl acetate. The separate organic layer was washed with brine and dried over sodium sulfate. The solvents were evaporated under reduced pressure and obtained crude product was purified by Biotage Isolera™ (354 mg, 81%). LCMS calculated for $C_{22}H_{27}F_2N_6OSi$ (M+H)$^+$ m/z=457.2; found 457.2.

Step 3. 3,5-Difluoro-N,N-dimethyl-4-(3-(1-methyl-1H-pyrazol-4-yl)-1H-pyrazolo[3,4-c]pyridin-5-yl)aniline Sodium hydride (2 mg, 0.049 mmol, 60% in mineral oil) was added to a solution of 3,5-difluoro-4-(3-(1-methyl-1H-pyrazol-4-yl)-1-((2-(trimethylsilyl)ethoxy)methyl)-1H-pyrazolo[3,4-c]pyridin-5-yl)aniline (15 mg, 0.033 mmol) and iodomethane (13.99 mg, 0.099 mmol) in THF (2.0 mL). After the reaction mixture was stirred at r.t. for 2 hours, it was quenched with water. The mixture was extracted with ethyl acetate. The separated organic phases were washed with brine, dried over sodium sulfate and solvents evaporated in vacuo. Then 1M solution of HCl in water (1 mL) and 4M solution of HCl in dioxane (1 mL) were added to the crude residue, and the resulting mixture was stirred at 80° C. for 1 h. After this methanol (1 mL) was added and reaction was further stirred at 80° C. for 30 min. The reaction mixture was then diluted with acetonitrile and was purified with prep-LCMS (XBridge C18 column, eluting with a gradient of acetonitrile/water containing 0.1% TFA, at flow rate of 60 mL/min). LCMS calculated for $C_{18}H_{17}F_2N_6$ (M+H)$^+$: m/z=355.2; Found: 355.3.

Example 64. N-(3,5-Difluoro-4-(3-(1-methyl-1H-pyrazol-4-yl)-1H-pyrazolo[3,4-c]pyridin-5-yl)phenyl)-2-(pyrrolidin-1-yl)acetamide

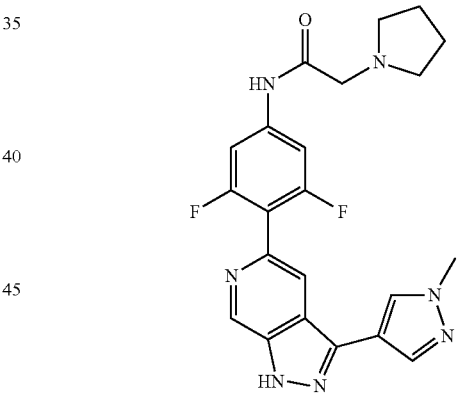

To a solution of 3,5-difluoro-4-(3-(1-methyl-1H-pyrazol-4-yl)-1-((2-(trimethylsilyl)ethoxy)methyl)-1H-pyrazolo[3,4-c]pyridin-5-yl)aniline (15 mg, 0.033 mmol, Example 63, Step 2) and 2-(pyrrolidin-1-yl)acetic acid (4.24 mg, 0.033 mmol) in N,N-dimethylformamide (1.5 mL) were added N,N-diisopropylethylamine (13 µL, 0.07 mmol) and N,N,N',N'-tetramethyl-O-(7-azabenzotriazol-1-yl)uronium hexafluorophosphate (15 mg, 0.04 mmol). After the reaction mixture was stirred at r.t. for 2 hours, it was quenched with water. The mixture was extracted with ethyl acetate. The separated organic phases were washed with brine, dried over sodium sulfate and solvents evaporated in vacuo. Then 1M solution of HCl in water (1 mL) and 4M solution of HCl in dioxane (1 mL) were added to the crude residue, and resulting mixture was stirred at 80° C. for 1 h. Methanol (1 mL) was then added and reaction was further stirred at 80° C. for 30 min. The reaction mixture was then diluted with acetonitrile and was purified with prep-LCMS (XBridge C18 column, eluting with a gradient of acetonitrile/water containing 0.1% TFA, at flow rate of 60 mL/min). LCMS calculated for $C_{22}H_{22}F_2N_7O$ (M+H)$^+$: m/z=438.2; Found: 438.2. $^1$H NMR (500 MHz, DMSO-d$_6$) δ 11.12 (s, 1H), 9.15 (s, 1H), 8.48 (s, 1H), 8.22 (s, 1H), 8.06 (s, 1H), 7.47 (d, J=9.2 Hz, 2H), 4.34 (s, 2H), 3.93 (s, 3H), 3.66 (s, 2H), 3.17 (s, 2H), 1.99 (d, J=50.3 Hz, 4H) ppm.

Example 65. N-(3,5-Difluoro-4-(3-(1-methyl-1H-pyrazol-4-yl)-1H-pyrazolo[3,4-c]pyridin-5-yl)phenyl)-1-methyl-1H-pyrazole-4-carboxamide

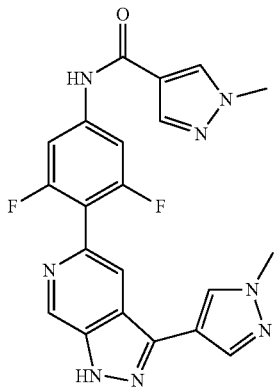

This compound was prepared according to the procedures described in Example 64, using 1-methyl-1H-pyrazole-4-carboxylic acid instead of 2-(pyrrolidin-1-yl)acetic acid as starting material. LCMS calculated for $C_{21}H_{17}F_2N_8O$ (M+H)$^+$: m/z=435.2; Found: 435.1.

Example 66. 2-Cyclopentyl-N-(3,5-difluoro-4-(3-(1-methyl-1H-pyrazol-4-yl)-1H-pyrazolo[3,4-c]pyridin-5-yl)phenyl)acetamide

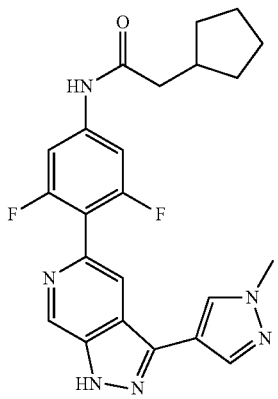 [SMILES: Cn1cc(-c2n[nH]c3cnc(-c4c(F)cc(NC(=O)CN5CCCC5)cc4F)cc23)cn1]

This compound was prepared according to the procedures described in Example 64, using 2-cyclopentylacetic acid instead of 2-(pyrrolidin-1-yl)acetic acid as starting material. LCMS calculated for $C_{23}H_{23}F_2N_6O$ (M+H)$^+$: m/z=437.2; Found: 437.2.

Example 67. N-(3,5-Difluoro-4-(3-(1-methyl-1H-pyrazol-4-yl)-1H-pyrazolo[3,4-c]pyridin-5-yl)phenyl)-2-(pyridin-3-yl)acetamide

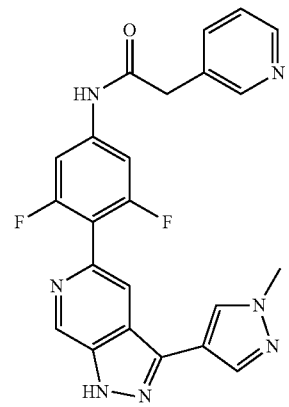 [SMILES: Cn1cc(-c2n[nH]c3cnc(-c4c(F)cc(NC(=O)Cc5cccnc5)cc4F)cc23)cn1]

This compound was prepared according to the procedures described in Example 64, using 2-(pyridin-3-yl)acetic acid instead of 2-(pyrrolidin-1-yl)acetic acid as starting material. LCMS calculated for $C_{23}H_{18}F_2N_7O$ (M+H)$^+$: m/z=446.2; Found: 446.2.

Example 68. 2-(7-Azabicyclo[2.2.1]heptan-7-yl)-N-(3,5-difluoro-4-(3-(1-methyl-1H-pyrazol-4-yl)-1H-pyrazolo[3,4-c]pyridin-5-yl)phenyl)acetamide

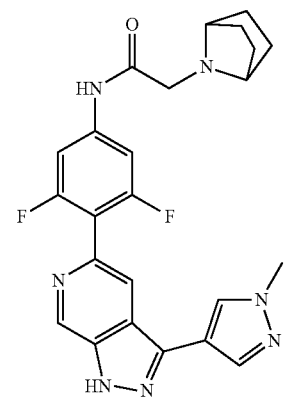 [SMILES: Cn1cc(-c2n[nH]c3cnc(-c4c(F)cc(NC(=O)CN5C6CCC5CC6)cc4F)cc23)cn1]

111

Step 1. tert-Butyl 5-(4-amino-2,6-difluorophenyl)-3-(1-methyl-1H-pyrazol-4-yl)-1H-pyrazolo[3,4-c]pyridine-1-carboxylate

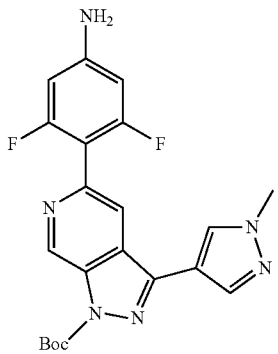

This compound was prepared according to the procedures described in Example 63 (Steps 1-2), using Intermediate 1 instead of Intermediate 2 as starting material. LCMS calculated for $C_{21}H_{21}F_2N_6O_2$ (M+H)$^+$: m/z=427.2; Found: 427.2.

Step 2. tert-Butyl 5-(4-(2-chloroacetamido)-2,6-difluorophenyl)-3-(1-methyl-1H-pyrazol-4-yl)-1H-pyrazolo[3,4-c]pyridine-1-carboxylate

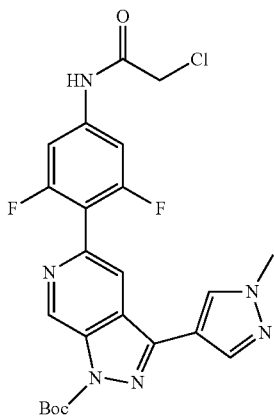 [SMILES: Cn1cc(-c2nn(C(=O)OC(C)(C)C)c3cnc(-c4c(F)cc(NC(=O)CCl)cc4F)cc23)cn1]

To a solution of tert-butyl 5-(4-amino-2,6-difluorophenyl)-3-(1-methyl-1H-pyrazol-4-yl)-1H-pyrazolo[3,4-c]pyridine-1-carboxylate (385 mg, 0.903 mmol) and 2-chloroacetic acid (85 mg, 0.903 mmol) in N,N-dimethylformamide (4 mL) were added N,N-diisopropylethylamine (315 μL, 1.8 mmol) and N,N,N',N'-tetramethyl-O-(7-azabenzotriazol-1-yl)uronium hexafluorophosphate (515 mg, 1.35 mmol). After stirring at r.t. for 2 h, water was added and the precipitated product was collected by filtration, dried and was used in the next step without further purification (427 mg, 94%). LCMS calculated for $C_{23}H_{22}ClF_2N_6O_3$ (M+H)$^+$: m/z=503.1; found 503.1.

Step 3. 2-(7-Azabicyclo[2.2.1]heptan-7-yl)-N-(3,5-difluoro-4-(3-(1-methyl-1H-pyrazol-4-yl)-1H-pyrazolo[3,4-c]pyridin-5-yl)phenyl)acetamide 7-Azabicyclo[2.2.1]heptane (4.4 mg, 0.045 mmol) was added to a solution of tert-butyl 5-(4-(2-chloroacetamido)-

112

2,6-difluorophenyl)-3-(1-methyl-1H-pyrazol-4-yl)-1H-indazole-1-carboxylate (15 mg, 0.030 mmol) and DIPEA (0.01 mL, 0.06 mmol) in DMF (1 mL). After stirring at 80° C. overnight, the reaction mixture was diluted with acetonitrile and was purified with prep-LCMS (XBridge C18 column, eluting with a gradient of acetonitrile/water containing 0.1% TFA, at flow rate of 60 mL/min). LCMS calculated for $C_{24}H_{24}F_2N_7O$ (M+H)$^+$: m/z=464.2; Found: 464.3. $^1$H NMR (500 MHz, DMSO-d$_6$) δ 11.12 (s, 1H), 9.14 (s, 1H), 8.48 (s, 1H), 8.22 (s, 1H), 8.12-8.00 (m, 1H), 7.48 (d, J=9.3 Hz, 2H), 4.26 (s, 2H), 4.15 (d, J=4.9 Hz, 2H), 3.93 (s, 3H), 2.05 (d, J=7.5 Hz, 4H), 1.76 (dd, J=19.6, 8.2 Hz, 4H) ppm.

Example 69. N-(3,5-Difluoro-4-(3-(1-methyl-1H-pyrazol-4-yl)-1H-pyrazolo[3,4-c]pyridin-5-yl)phenyl)-2-(7-oxa-2-azaspiro[3.5]nonan-2-yl)acetamide

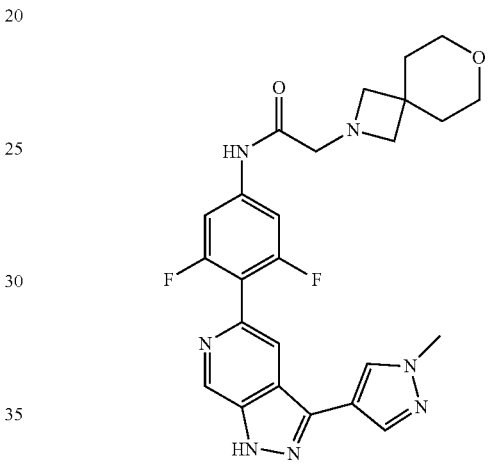

This compound was prepared according to the procedures described in Example 68, using 7-oxa-2-azaspiro[3.5]nonane instead of 7-azabicyclo[2.2.1]heptane as starting material. LCMS calculated for $C_{25}H_{26}F_2N_7O_2$ (M+H)$^+$: m/z=494.2; Found: 494.3.

Example 70. N-(3,5-Difluoro-4-(3-(1-methyl-1H-pyrazol-4-yl)-1H-pyrazolo[3,4-c]pyridin-5-yl)phenyl)-2-(pyrrolidin-1-yl)propanamide

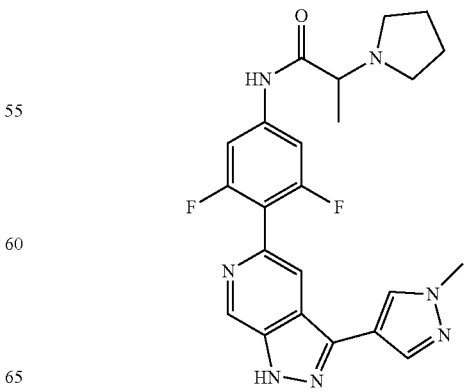

113

Step 1. tert-Butyl 5-(4-(2-chloropropanamido)-2,6-difluorophenyl)-3-(1-methyl-1H-pyrazol-4-yl)-1H-pyrazolo[3,4-c]pyridine-1-carboxylate

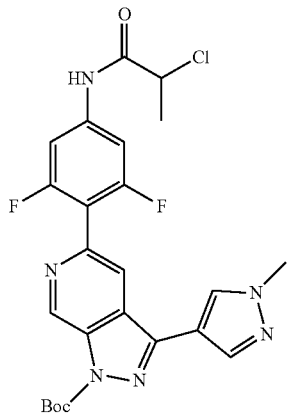

To a solution of tert-butyl 5-(4-amino-2,6-difluorophenyl)-3-(1-methyl-1H-pyrazol-4-yl)-1H-pyrazolo[3,4-c]pyridine-1-carboxylate (385 mg, 0.903 mmol, Example 68, Step 1) and 2-chloropropanoic acid (98 mg, 0.903 mmol) in N,N-dimethylformamide (4 mL) were added N,N-diisopropylethylamine (315 μL, 1.8 mmol) and N,N,N',N'-tetramethyl-O-(7-azabenzotriazol-1-yl)uronium hexafluorophosphate (515 mg, 1.35 mmol). After stirring at r.t. for 2 h, water was added and the precipitated product was collected by filtration, dried and was used in the next step without further purification (427 mg, 88%). LCMS calculated for $C_{24}H_{24}ClF_2N_6O_3$ (M+H)$^+$: m/z=517.2; found 517.2.

Step 3. N-(3,5-Difluoro-4-(3-(1-methyl-1H-pyrazol-4-yl)-1H-pyrazolo[3,4-c]pyridin-5-yl)phenyl)-2-(pyrrolidin-1-yl)propanamide Pyrrolidine (4 mg, 0.06 mmol) was added to a solution of tert-butyl 5-(4-(2-chloropropanamido)-2,6-difluorophenyl)-3-(1-methyl-1H-pyrazol-4-yl)-1H-pyrazolo[3,4-c]pyridine-1-carboxylate (15 mg, 0.029 mmol) and DIPEA (0.01 mL, 0.06 mmol) in DMF (1 mL). After stirring at 80° C. overnight, the reaction mixture was diluted with acetonitrile and was purified with prep-LCMS (XBridge C18 column, eluting with a gradient of acetonitrile/water containing 0.1% TFA, at flow rate of 60 mL/min). LCMS calculated for $C_{23}H_{24}F_2N_7O$ (M+H)$^+$: m/z=452.2; Found: 452.3.

Example 71. 1-(3,5-Difluoro-4-(3-(1-methyl-1H-pyrazol-4-yl)-1H-pyrazolo[3,4-c]pyridin-5-yl)phenyl)-3-(2-methoxyethyl)urea

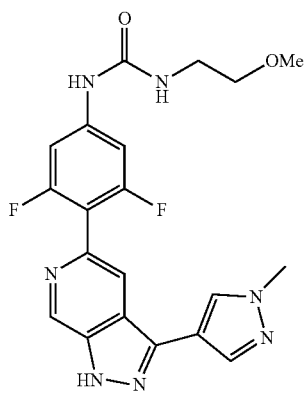 [SMILES: COCCNC(=O)Nc1cc(F)c(-c2cc3c(-c4cnn(C)c4)n[nH]c3cn2)c(F)c1]

114

Bis(trichloromethyl) carbonate (14.62 mg, 0.049 mmol) was added to a solution of 3,5-difluoro-4-(3-(1-methyl-1H-pyrazol-4-yl)-1-((2-(trimethylsilyl)ethoxy)methyl)-1H-pyrazolo[3,4-c]pyridin-5-yl)aniline (15 mg, 0.033 mmol, Example 63, Step 2) and triethylamine (0.018 mL, 0.131 mmol) in tetrahydrofuran (1.5 mL). After stirring at r.t. for 1 h, 2-methoxyethan-1-amine (5 mg, 0.06 mmol) was added and the resulting mixture was stirred for an additional 1 h. The reaction mixture was quenched with water and was extracted with ethyl acetate. The separated organic phases were washed with brine, dried over sodium sulfate and solvents evaporated in vacuo. Then 1M solution of HCl in water (1 mL) and 4M solution of HCl in dioxane (1 mL) were added to the crude residue, and the resulting mixture was stirred at 80° C. for 1 h. Methanol (1 mL) was then added and reaction was further stirred at 80° C. for 30 min. The reaction mixture was then diluted with acetonitrile and was purified with prep-LCMS (XBridge C18 column, eluting with a gradient of acetonitrile/water containing 0.1% TFA, at flow rate of 60 mL/min). LCMS calculated for $C_{20}H_{20}F_2N_7O_2$ (M+H)$^+$: m/z=428.2; Found: 428.1.

Example 72. 2-(Azetidin-1-yl)-N-(3-(difluoromethoxy)-5-fluoro-4-(3-(1-methyl-1H-pyrazol-4-yl)-1H-pyrazolo[3,4-c]pyridin-5-yl)phenyl)acetamide

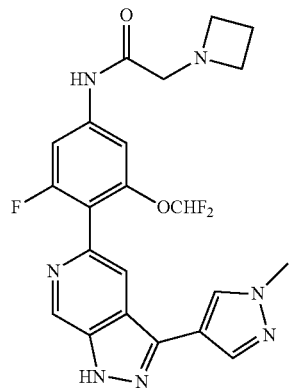 [SMILES: Cn1cc(-c2n[nH]c3cnc(-c4c(F)cc(NC(=O)CN5CCC5)cc4OC(F)F)cc23)cn1]

Step 1.
1-(Difluoromethoxy)-3-fluoro-5-nitrobenzene

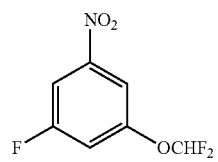 [SMILES: Nc1cc(F)cc(OC(F)F)c1]

To a mixture of sodium chlorodifluoroacetate (5.82 g, 38.2 mmol) and potassium carbonate (2.64 g, 19.10 mmol) in DMF (17 ml) and water (2 ml) was added 3-fluoro-5-nitrophenol (1.5 g, 9.55 mmol), and the mixture was stirred at 100° C. for 6 h (caution! a lot of $CO_2$ is produced). After cooling down, the mixture was quenched with water and extracted with EtOAc. The separated organic layer was then washed with water, brine and dried over sodium sulfate, filtered and concentrated. The crude material was purified by Biotage Isolera™ (1.3 g, 66%).

Step 2. 3-(Difluoromethoxy)-5-fluoroaniline

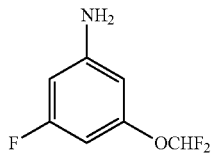

A mixture of 1-(difluoromethoxy)-3-fluoro-5-nitrobenzene (1.3 g, 6.28 mmol), iron (2.454 g, 43.9 mmol) and ammonium chloride (2.02 g, 37.7 mmol) in tetrahydrofuran (5 ml), water (7 ml) and methanol (5 ml) was refluxed for 3 h. After cooling to r.t., the solids were filtered off and the solvents were evaporated in vacuo. The crude product concentrate was purified by Biotage Isolera™ (1.27 g, 99%). LCMS calculated for $C_7H_7F_3NO$ (M+H)$^+$: m/z=178.1; Found: 178.1.

Step 3.
4-Bromo-3-(difluoromethoxy)-5-fluoroaniline

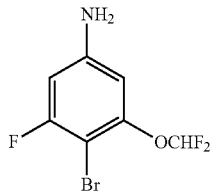 [SMILES: Nc1cc(F)c(Br)c(OC(F)F)c1]

NBS (1.3 g, 7.3 mmol) was added to a solution of 3-(difluoromethoxy)-5-fluoroaniline (1.27 g, 7.17 mmol) in DMF (15 mL) at 0° C. After stirring at r.t. for 1 h, water was added and the reaction mixture was extracted with EtOAc. The separate organic layer was washed with brine and purified by Biotage Isolera™ (0.91 g, 50%). LCMS calculated for $C_7H_6BrF_3NO$ (M+H)$^+$: m/z=256.0; Found: 256.0.

Step 4. 3-(Difluoromethoxy)-5-fluoro-4-(4,4,5,5-tetramethyl-1,3,2-dioxaborolan-2-yl)aniline

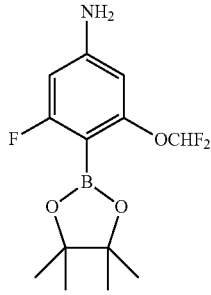 [SMILES: CC1(C)OB(c2c(F)cc(N)cc2OC(F)F)OC1(C)C]

To a mixture of 4,4,5,5,4',4',5',5'-octamethyl-[2,2']bi[[1,3,2]dioxaborolanyl] (1.35 g, 5.33 mmol), potassium acetate (1.05 g, 10.6 mmol) and [1,1'-bis(diphenylphosphino)ferrocene]dichloropalladium(II) complexed with dichloromethane (1:1) (0.29 g, 0.36 mmol) under nitrogen was added a solution of 4-bromo-3-(difluoromethoxy)-5-fluoroaniline (0.909 g, 3.55 mmol) in 1,4-dioxane (20 mL). The mixture was stirred at 100° C. overnight. After cooling to room temperature, the mixture was diluted with DCM and filtered through Celite. The filtrate was concentrated in vacuo. The residue was purified by Biotage Isolera™ (540 mg, 50%). LCMS calculated for $C_{13}H_{18}BF_3NO_3$ (M+H)$^+$ m/z=304.1; found 304.2.

Step 5. tert-Butyl 5-(4-amino-2-(difluoromethoxy)-6-fluorophenyl)-3-(1-methyl-1H-pyrazol-4-yl)-1H-pyrazolo[3,4-c]pyridine-1-carboxylate

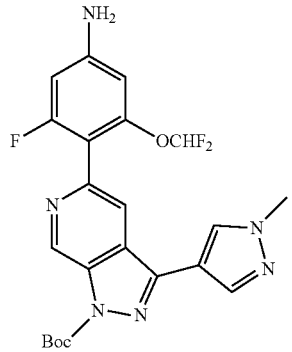 [SMILES: Cn1cc(-c2nn(C(=O)OC(C)(C)C)c3cnc(-c4c(F)cc(N)cc4OC(F)F)cc23)cn1]

tert-Butyl 5-chloro-3-(1-methyl-1H-pyrazol-4-yl)-1H-pyrazolo[3,4-c]pyridine-1-carboxylate (330 mg, 0.989 mmol, Intermediate 1), 3-(difluoromethoxy)-5-fluoro-4-(4,4,5,5-tetramethyl-1,3,2-dioxaborolan-2-yl)aniline (360 mg, 1.186 mmol), chloro(2-dicyclohexylphosphino-2',4',6'-triisopropyl-1,1'-biphenyl)[2-(2'-amino-1,1'-biphenyl)]palladium(II) (Pd XPhos G2) (75 mg, 0.096 mmol) and potassium phosphate (406 mg, 1.91 mmol) were placed in a flask and the flask was evacuated and backfilled with nitrogen three times. Then dioxane (20 mL) and degassed water (2 mL) were added, and the reaction mixture was stirred at 90° C. for 2 h. After cooling to r.t., the reaction mixture was diluted with ethyl acetate, and the resulting mixture was washed with brine. The separated organic phase was dried over sodium sulfate. The solvents were evaporated in vacuo and the obtained crude product was purified by Biotage Isolera™ (291 mg, 62%). LCMS calculated for $C_{22}H_{22}F_3N_6O_3$ (M+H)$^+$ m/z=475.2; found 475.2.

Step 6. tert-Butyl 5-(4-(2-chloroacetamido)-2-(difluoromethoxy)-6-fluorophenyl)-3-(1-methyl-1H-pyrazol-4-yl)-1H-pyrazolo[3,4-c]pyridine-1-carboxylate

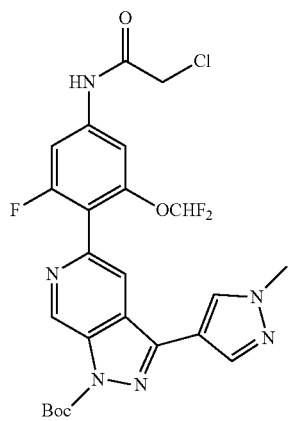 [SMILES: Cn1cc(-c2nn(C(=O)OC(C)(C)C)c3cnc(-c4c(F)cc(NC(=O)CCl)cc4OC(F)F)cc23)cn1]

To a solution of tert-butyl 5-(4-amino-2-(difluoromethoxy)-6-fluorophenyl)-3-(1-methyl-1H-pyrazol-4-yl)-1H-pyrazolo[3,4-c]pyridine-1-carboxylate (188 mg, 0.396 mmol) and 2-chloroacetic acid (37 mg, 0.39 mmol) in N,N-dimethylformamide (3 mL) were added N,N-diisopropylethylamine (138 μL, 0.79 mmol) and N,N,N',N'-tetramethyl-O-(7-azabenzotriazol-1-yl)uronium hexafluorophosphate (226 mg, 0.59 mmol). After stirring at r.t. for 2 h, water was added and the precipitated product was collected by filtration, dried and was used in the next step without further purification (209 mg, 96%). LCMS calculated for $C_{24}H_{23}ClF_3N_6O_4$ (M+H)$^+$: m/z=551.1; found 551.2.

Step 7. 2-(Azetidin-1-yl)-N-(3-(difluoromethoxy)-5-fluoro-4-(3-(1-methyl-1H-pyrazol-4-yl)-1H-pyrazolo[3,4-c]pyridin-5-yl)phenyl)acetamide Azetidine (3 mg, 0.05 mmol) was added to a solution of tert-butyl 5-(4-(2-chloroacetamido)-2-(difluoromethoxy)-6-fluorophenyl)-3-(1-methyl-1H-pyrazol-4-yl)-1H-pyrazolo[3,4-c]pyridine-1-carboxylate (15 mg, 0.027 mmol) and DIPEA (0.01 mL, 0.06 mmol) in DMF (1 mL). After stirring at 80° C. overnight, the reaction mixture was diluted with acetonitrile and was purified with prep-LCMS (XBridge C18 column, eluting with a gradient of acetonitrile/water containing 0.1% TFA, at flow rate of 60 mL/min). LCMS calculated for $C_{22}H_{21}F_3N_7O_2$ (M+H)$^+$: m/z=472.2; Found: 472.2.

Example 73. N-(3-Chloro-5-fluoro-4-(3-(1-methyl-1H-pyrazol-4-yl)-1H-pyrazolo[3,4-c]pyridin-5-yl)phenyl)-2-(pyrrolidin-1-yl)acetamide

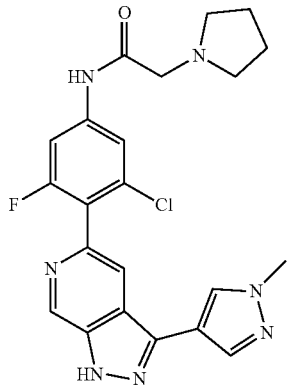 [SMILES: Cn1cc(-c2n[nH]c3cnc(-c4c(F)cc(NC(=O)CN5CCCC5)cc4Cl)cc23)cn1]

Step 1. tert-Butyl 5-(2-chloro-4-(2-chloroacetamido)-6-fluorophenyl)-3-(1-methyl-1H-pyrazol-4-yl)-1H-pyrazolo[3,4-c]pyridine-1-carboxylate

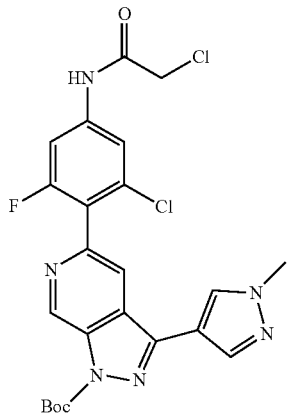 [SMILES: Cn1cc(-c2nn(C(=O)OC(C)(C)C)c3cnc(-c4c(F)cc(NC(=O)CCl)cc4Cl)cc23)cn1]

This compound was prepared according to the procedures described in Example 72 (Steps 3-6), using 3-chloro-5-fluoroaniline instead of 3-(difluoromethoxy)-5-fluoroaniline as starting material. LCMS calculated for $C_{23}H_{22}Cl_2FN_6O_3$ (M+H)$^+$: m/z=519.1; Found: 519.1.

Step 2. N-(3-Chloro-5-fluoro-4-(3-(1-methyl-1H-pyrazol-4-yl)-1H-pyrazolo[3,4-c]pyridin-5-yl)phenyl)-2-(pyrrolidin-1-yl)acetamide Pyrrolidine (4 mg, 0.06 mmol) was added to a solution of tert-butyl 5-(2-chloro-4-(2-chloroacetamido)-6-fluorophenyl)-3-(1-methyl-1H-pyrazol-4-yl)-1H-pyrazolo[3,4-c]pyridine-1-carboxylate (15 mg, 0.029 mmol) and DIPEA (0.01 mL, 0.06 mmol) in DMF (1 mL). After stirring at 80° C. overnight, the reaction mixture was diluted with acetonitrile and was purified with prep-LCMS (XBridge C18 column, eluting with a gradient of acetonitrile/water containing 0.1% TFA, at flow rate of 60 mL/min). LCMS calculated for $C_{22}H_{22}ClFN_7O$ (M+H)$^+$: m/z=454.2; Found: 454.2.

Example 74. N-(3-Fluoro-5-methoxy-4-(3-(1-methyl-1H-pyrazol-4-yl)-1H-pyrazolo[3,4-c]pyridin-5-yl)phenyl)-2-(pyrrolidin-1-yl)acetamide

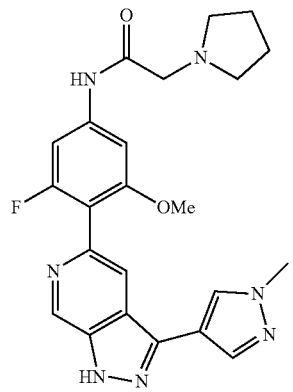

Step 1. tert-Butyl 5-(4-(2-chloroacetamido)-2-fluoro-6-methoxyphenyl)-3-(1-methyl-1H-pyrazol-4-yl)-1H-pyrazolo[3,4-c]pyridine-1-carboxylate

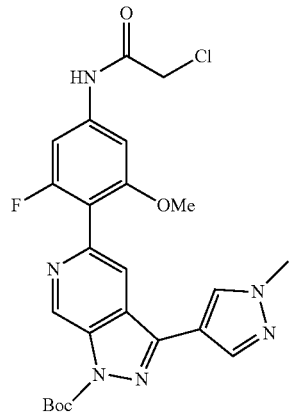

This compound was prepared according to the procedures described in Example 72 (Steps 3-6), using 3-fluoro-5-methoxyaniline instead of 3-(difluoromethoxy)-5-fluoroaniline as starting material. LCMS calculated for $C_{24}H_{25}ClFN_6O_4$ (M+H)$^+$: m/z=515.2; Found: 515.2.

Step 2. N-(3-Fluoro-5-methoxy-4-(3-(1-methyl-1H-pyrazol-4-yl)-1H-pyrazolo[3,4-c]pyridin-5-yl)phenyl)-2-(pyrrolidin-1-yl)acetamide Pyrrolidine (4 mg, 0.06 mmol) was added to a solution of tert-butyl 5-(4-(2-chloroacetamido)-2-fluoro-6-methoxyphenyl)-3-(1-methyl-1H-pyrazol-4-yl)-1H-pyrazolo[3,4-c]pyridine-1-carboxylate (15 mg, 0.029 mmol) and DIPEA (0.01 mL, 0.06 mmol) in DMF (1 mL). After stirring at 80° C. overnight, the reaction mixture was diluted with acetonitrile and was purified with prep-LCMS (XBridge C18 column, eluting with a gradient of acetonitrile/water containing 0.1% TFA, at flow rate of 60 mL/min). LCMS calculated for $C_{23}H_{25}FN_7O_2$ (M+H)$^+$: m/z=450.2; Found: 450.3.

Example 75. 2-(3,3-Dimethylazetidin-1-yl)-N-(3-fluoro-5-methoxy-4-(3-(1-methyl-1H-pyrazol-4-yl)-1H-pyrazolo[3,4-c]pyridin-5-yl)phenyl)acetamide

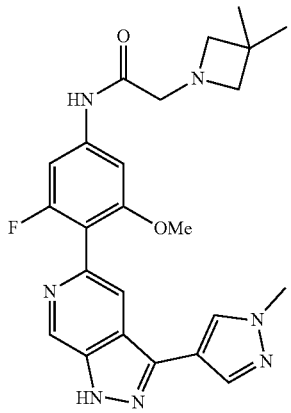 [SMILES: COc1cc(NC(=O)CN2CC(C)(C)C2)cc(F)c1-c1cc2c(-c3cnn(C)c3)n[nH]c2cn1]

This compound was prepared according to the procedures described in Example 74, using 3,3-dimethylazetidine instead of pyrrolidine as starting material. LCMS calculated for $C_{24}H_{27}FN_7O_2$ (M+H)$^+$: m/z=464.2; Found: 464.3.

Example 76. 1-Methylpiperidin-4-yl 3-fluoro-5-methoxy-4-(3-(1-methyl-1H-pyrazol-4-yl)-1H-pyrazolo[3,4-c]pyridin-5-yl)phenylcarbamate

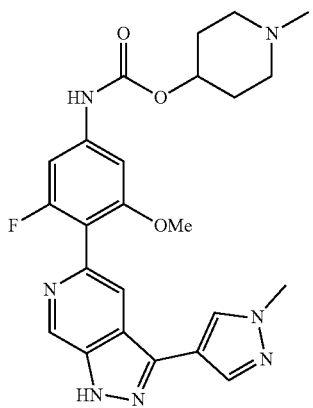 [SMILES: COc1cc(NC(=O)OC2CCN(C)CC2)cc(F)c1-c1cc2c(-c3cnn(C)c3)n[nH]c2cn1]

Step 1. tert-Butyl 5-(4-amino-2-fluoro-6-methoxyphenyl)-3-(1-methyl-1H-pyrazol-4-yl)-1H-pyrazolo[3,4-c]pyridine-1-carboxylate

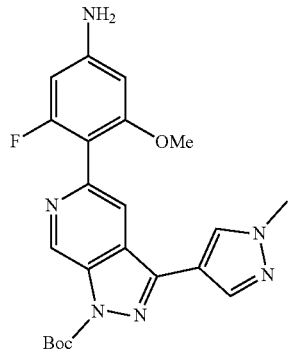

This compound was prepared according to the procedures described in Example 72 (Steps 3-5), using 3-fluoro-5-methoxyaniline instead of 3-(difluoromethoxy)-5-fluoroaniline as starting material. LCMS calculated for $C_{22}H_{24}FN_6O_3$ (M+H)$^+$: m/z=439.2; Found: 439.2.

Step 2. 1-Methylpiperidin-4-yl 3-fluoro-5-methoxy-4-(3-(1-methyl-1H-pyrazol-4-yl)-1H-pyrazolo[3,4-c]pyridin-5-yl)phenylcarbamate Bis(trichloromethyl) carbonate (15.23 mg, 0.051 mmol) was added to a solution of tert-butyl 5-(4-amino-2-fluoro-6-methoxyphenyl)-3-(1-methyl-1H-pyrazol-4-yl)-1H-pyrazolo[3,4-c]pyridine-1-carboxylate (15 mg, 0.034 mmol) and triethylamine (0.019 mL, 0.137 mmol) in tetrahydrofuran (1.0 mL). After stirring at r.t. for 30 min, 1-methylpiperidin-4-ol (3.94 mg, 0.034 mmol) was added and the reaction mixture was stirred for 1 h more. After quenching with methanol, the solvents were evaporated and TFA (1 mL) added. After stirring at r.t. for 30 min, the reaction mixture was diluted with acetonitrile and was purified with prep-LCMS (XBridge C18 column, eluting with a gradient of acetonitrile/water containing 0.1% TFA, at flow rate of 60 mL/min). LCMS calculated for $C_{24}H_{27}FN_7O_3$ (M+H)$^+$: m/z=480.2; Found: 480.1.

Example 77. 2-(Azetidin-1-yl)-N-(2,3,5-trifluoro-4-(3-(1-methyl-1H-pyrazol-4-yl)-1H-pyrazolo[3,4-c]pyridin-5-yl)phenyl)acetamide

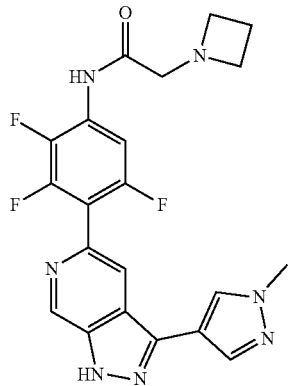 [SMILES: Cn1cc(-c2n[nH]c3cnc(-c4c(F)cc(NC(=O)CN5CCC5)c(F)c4F)cc23)cn1]

121

Step 1. tert-Butyl 5-(4-(2-chloroacetamido)-2,3,6-trifluorophenyl)-3-(1-methyl-1H-pyrazol-4-yl)-1H-pyrazolo[3,4-c]pyridine-1-carboxylate

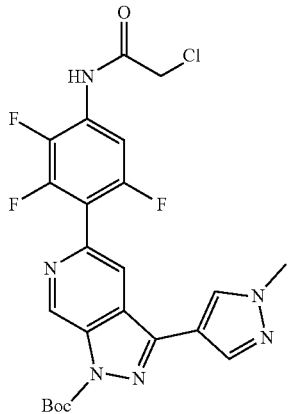 [SMILES: Cn1cc(-c2nn(C(=O)OC(C)(C)C)c3cnc(-c4c(F)cc(NC(=O)CCl)c(F)c4F)cc23)cn1]

This compound was prepared according to the procedures described in Example 72 (Steps 3-6), using 2,3,5-trifluoroaniline instead of 3-(difluoromethoxy)-5-fluoroaniline as starting material. LCMS calculated for $C_{23}H_{21}ClF_3N_6O_3$ (M+H)+: m/z=521.2; Found: 521.2.

Step 2. 2-(Azetidin-1-yl)-N-(2,3,5-trifluoro-4-(3-(1-methyl-1H-pyrazol-4-yl)-1H-pyrazolo[3,4-c]pyridin-5-yl)phenyl)acetamide Azetidine (2.2 mg, 0.04 mmol) was added to a solution of tert-butyl 5-(4-(2-chloroacetamido)-2,3,6-trifluorophenyl)-3-(1-methyl-1H-pyrazol-4-yl)-1H-pyrazolo[3,4-c]pyridine-1-carboxylate (10 mg, 0.019 mmol) and DIPEA (0.01 mL, 0.06 mmol) in DMF (1 mL). After stirring at 80° C. overnight, the reaction mixture was diluted with acetonitrile and was purified with prep-LCMS (XBridge C18 column, eluting with a gradient of acetonitrile/water containing 0.1% TFA, at flow rate of 60 mL/min). LCMS calculated for $C_{21}H_{19}F_3N_7O$ (M+H)+: m/z=442.2; Found: 442.1.

Example 78. N-(3-Chloro-5-methyl-4-(3-(1-methyl-1H-pyrazol-4-yl)-1H-pyrazolo[3,4-c]pyridin-5-yl)phenyl)-2-(dimethylamino)acetamide

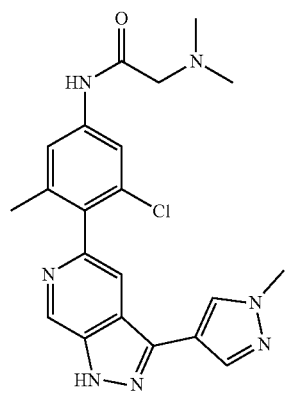

122

Step 1. tert-Butyl 5-(2-chloro-4-(2-chloroacetamido)-6-methylphenyl)-3-(1-methyl-1H-pyrazol-4-yl)-1H-pyrazolo[3,4-c]pyridine-1-carboxylate

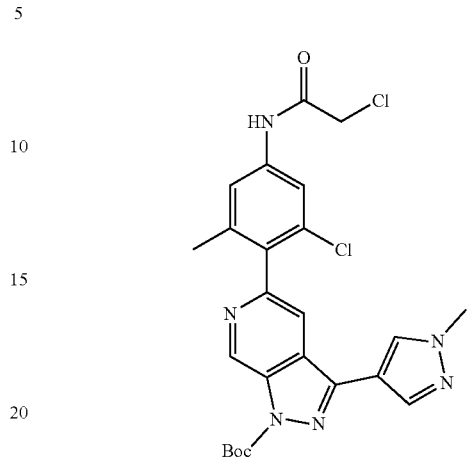

This compound was prepared according to the procedures described in Example 72 (Steps 3-6), using 3-chloro-5-methylaniline instead of 3-(difluoromethoxy)-5-fluoroaniline as starting material. LCMS calculated for $C_{24}H_{25}Cl_2N_6O_3$ (M+H)+: m/z=515.1; Found: 515.2.

Step 2. N-(3-Chloro-5-methyl-4-(3-(1-methyl-1H-pyrazol-4-yl)-1H-pyrazolo[3,4-c]pyridin-5-yl)phenyl)-2-(dimethylamino)acetamide Dimethylamine HCl salt (2 mg, 0.04 mmol) was added to a solution of tert-butyl 5-(2-chloro-4-(2-chloroacetamido)-6-methylphenyl)-3-(1-methyl-1H-pyrazol-4-yl)-1H-pyrazolo[3,4-c]pyridine-1-carboxylate (10 mg, 0.019 mmol) and DIPEA (0.01 mL, 0.06 mmol) in DMF (1 mL). After stirring at 80° C. overnight, the reaction mixture was diluted with acetonitrile and was purified with prep-LCMS (XBridge C18 column, eluting with a gradient of acetonitrile/water containing 0.1% TFA, at flow rate of 60 mL/min). LCMS calculated for $C_{21}H_{23}ClN_7O$ (M+H)+: m/z=424.2; Found: 424.2.

Example 79. 2-((1R,4S)-2-Azabicyclo[2.2.1]heptan-2-yl)-N-(3-methyl-4-(3-(1-methyl-1H-pyrazol-4-yl)-1H-pyrazolo[3,4-c]pyridin-5-yl)phenyl)acetamide

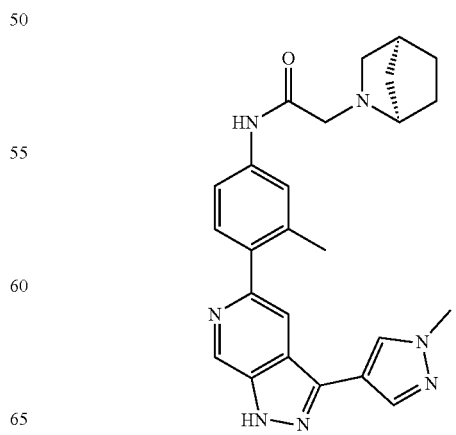

Step 1. tert-Butyl 5-(4-(2-chloroacetamido)-2-methylphenyl)-3-(1-methyl-1H-pyrazol-4-yl)-1H-pyrazolo[3,4-c]pyridine-1-carboxylate

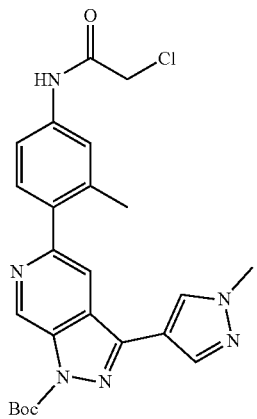 [SMILES: Cc1cc(NC(=O)CCl)ccc1-c1cc2c(-c3cnn(C)c3)nn(C(=O)OC(C)(C)C)c2cn1]

This compound was prepared according to the procedures described in Example 72 (Steps 4-6), using 4-bromo-3-methylaniline instead of 4-bromo-3-(difluoromethoxy)-5-fluoroaniline as starting material. LCMS calculated for $C_{24}H_{26}ClN_6O_3$ (M+H)$^+$: m/z=481.2; Found: 481.2.

Step 2. (1R,4S)-2-Azabicyclo[2.2.1]heptan-3-one

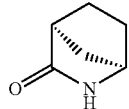

Pd/C (0.583 g, 5 wt %) was added to a solution of (1S,4R)-2-azabicyclo[2.2.1]hept-5-en-3-one (2.39 g, 21.90 mmol) in MeOH (15.0 mL). After stirring under hydrogen for 2 h at r.t., the catalyst was filtered-off and the solvent was evaporated in vacuo. Obtained crude product was used in the next step without further purification. LCMS calculated for $C_6H_{10}NO$ (M+H)$^+$: m/z=112.1; Found: 112.1.

Step 3. (1R,4S)-2-azabicyclo[2.2.1]heptane, HCl salt

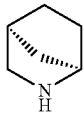

LAH (25.4 mL, 25.4 mmol) solution (1.0M in THF) was added to a solution of (1R,4S)-2-azabicyclo[2.2.1]heptan-3-one (2.35 g, 21.14 mmol) in THF (15.0 mL). Reaction was refluxed for 3 h. Then reaction was carefully quenched with water and NaOH solution. Solids were filtered off, and 4M HCl solution in dioxane was added to the obtained solution. After solvent evaporation in vacuo, obtained crude HCl salt of the desired product was used in the next step without further purification. LCMS calculated for $C_6H_{12}N$ (M+H)$^+$: m/z=98.1; Found: 98.1.

Step 4. 2-((1R,4S)-2-Azabicyclo[2.2.1]heptan-2-yl)-N-(3-methyl-4-(3-(1-methyl-1H-pyrazol-4-yl)-1H-pyrazolo[3,4-c]pyridin-5-yl)phenyl)acetamide (1R,4S)-2-Azabicyclo[2.2.1]heptane (4 mg, 0.04 mmol) was added to a solution of tert-butyl 5-(4-(2-chloroacetamido)-2-methylphenyl)-3-(1-methyl-1H-pyrazol-4-yl)-1H-pyrazolo[3,4-c]pyridine-1-carboxylate (10 mg, 0.021 mmol) and DIPEA (0.01 mL, 0.06 mmol) in DMF (1 mL). After stirring at 80° C. overnight, the reaction mixture was diluted with acetonitrile and was purified with prep-LCMS (XBridge C18 column, eluting with a gradient of acetonitrile/water containing 0.1% TFA, at flow rate of 60 mL/min). LCMS calculated for $C_{25}H_{28}N_7O$ (M+H)$^+$: m/z=442.2; Found: 442.2. $^1$H NMR (500 MHz, DMSO-d$_6$) δ 10.69-10.58 (m, 1H), 9.55 (s, 1H), 9.22 (s, 1H), 8.53 (s, 1H), 8.18 (s, 1H), 8.09 (s, 1H), 7.63-7.53 (m, 2H), 7.54-7.45 (m, 1H), 4.36-4.04 (m, 3H), 3.93 (s, 3H), 3.63-2.58 (m, 3H), 2.35 (s, 3H), 2.09-1.36 (m, 6H) ppm.

Example 80. N-(3-Fluoro-5-methyl-4-(3-(1-methyl-1H-pyrazol-4-yl)-1H-pyrazolo[3,4-c]pyridin-5-yl)phenyl)-2-(pyrrolidin-1-yl)acetamide

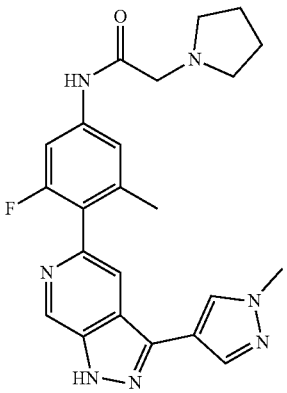 [SMILES: Cc1cc(NC(=O)CN2CCCC2)cc(F)c1-c1cc2c(-c3cnn(C)c3)n[nH]c2cn1]

Step 1. tert-Butyl 5-(4-(2-chloroacetamido)-2-fluoro-6-methylphenyl)-3-(1-methyl-1H-pyrazol-4-yl)-1H-pyrazolo[3,4-c]pyridine-1-carboxylate

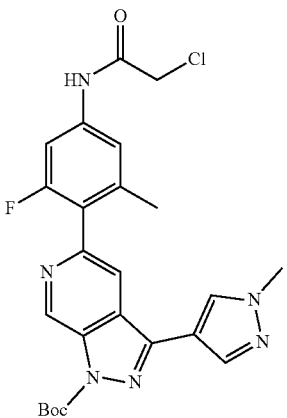

This compound was prepared according to the procedures described in Example 72 (Steps 3-6), using 3-fluoro-5-methylaniline instead of 3-(difluoromethoxy)-5-fluoroaniline as starting material. LCMS calculated for $C_{24}H_{25}ClFN_6O_3$ (M+H)$^+$: m/z=499.2; Found: 499.2.

Step 2. N-(3-Fluoro-5-methyl-4-(3-(1-methyl-1H-pyrazol-4-yl)-1H-pyrazolo[3,4-c]pyridin-5-yl)phenyl)-2-(pyrrolidin-1-yl)acetamide Pyrrolidine (5 μl, 0.06 mmol) was added to a solution of tert-butyl 5-(4-(2-chloroacetamido)-2-fluoro-6-methylphenyl)-3-(1-methyl-1H-pyrazol-4-yl)-1H-pyrazolo[3,4-c]pyridine-1-carboxylate (15 mg, 0.03 mmol) and DIPEA (0.01 mL, 0.06 mmol) in DMF (1 mL). After stirring at 80° C. overnight, the reaction mixture was diluted with acetonitrile and was purified with prep-LCMS (XBridge C18 column, eluting with a gradient of acetonitrile/water containing 0.1% TFA, at flow rate of 60 mL/min). LCMS calculated for $C_{23}H_{25}FN_7O$ (M+H)$^+$: m/z=434.2; Found: 434.2. $^1$H NMR (600 MHz, DMSO-d$_6$) δ 10.78 (s, 1H), 9.15 (s, 1H), 8.49 (s, 1H), 8.08 (s, 1H), 8.07-8.01 (m, 1H), 7.54 (dd, J=11.4, 1.6 Hz, 1H), 7.27 (s, 1H), 4.30 (d, J=3.8 Hz, 2H), 3.92 (s, 3H), 3.66 (br, 2H), 3.17 (br, 2H), 2.17 (s, 3H), 2.04 (br, 2H), 1.94 (br, 2H) ppm.

Example 81. 2-(Dimethylamino)-N-(3-fluoro-5-methyl-4-(3-(1-methyl-1H-pyrazol-4-yl)-1H-pyrazolo[3,4-c]pyridin-5-yl)phenyl)acetamide

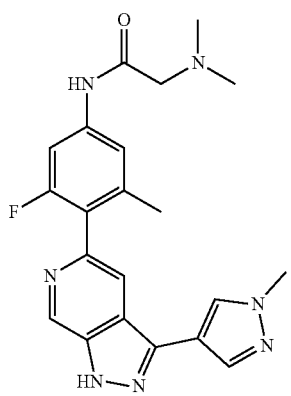 [SMILES: Cc1cc(NC(=O)CN(C)C)cc(F)c1-c1cc2c(-c3cnn(C)c3)n[nH]c2cn1]

This compound was prepared according to the procedures described in Example 80, using dimethylamine instead of pyrrolidine as starting material. LCMS calculated for $C_{21}H_{23}FN_7O$ (M+H)$^+$: m/z=408.2; Found: 408.2. $^1$H NMR (500 MHz, DMSO-d$_6$) δ 10.84 (s, 1H), 9.20 (s, 1H), 8.51 (s, 1H), 8.14 (s, 1H), 8.06 (s, 1H), 7.61-7.49 (m, 1H), 7.28 (s, 1H), 4.20 (s, 2H), 3.92 (s, 3H), 2.92 (s, 6H), 2.18 (s, 3H) ppm.

Example 82. 2-(7-Azabicyclo[2.2.1]heptan-7-yl)-N-(3-fluoro-5-methyl-4-(3-(1-methyl-1H-pyrazol-4-yl)-1H-pyrazolo[3,4-c]pyridin-5-yl)phenyl)acetamide

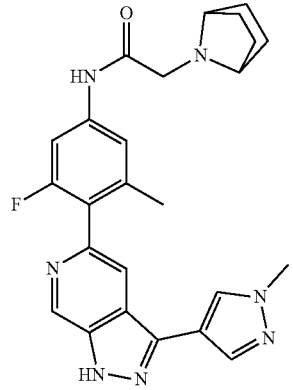 [SMILES: Cc1cc(NC(=O)CN2C3CCC2CC3)cc(F)c1-c1cc2c(-c3cnn(C)c3)n[nH]c2cn1]

This compound was prepared according to the procedures described in Example 80, using 7-azabicyclo[2.2.1]heptane instead of pyrrolidine as starting material. LCMS calculated for $C_{25}H_{27}FN_7O$ (M+H)$^+$: m/z=460.2; Found: 460.2. $^1$H NMR (500 MHz, DMSO-d$_6$) δ 10.90 (s, 1H), 9.23 (s, 1H), 8.52 (s, 1H), 8.18 (s, 1H), 8.07 (s, 1H), 7.57 (d, J=11.3 Hz, 1H), 7.31 (s, 1H), 4.25 (s, 2H), 4.13 (d, J=4.3 Hz, 2H), 3.92 (s, 3H), 2.18 (s, 3H), 2.05 (s, 4H), 1.76 (dd, J=20.9, 8.2 Hz, 4H) ppm.

Example 83. 2-((1R,4S)-2-Azabicyclo[2.2.1]heptan-2-yl)-N-(3-fluoro-5-methyl-4-(3-(1-methyl-1H-pyrazol-4-yl)-1H-pyrazolo[3,4-c]pyridin-5-yl)phenyl)acetamide

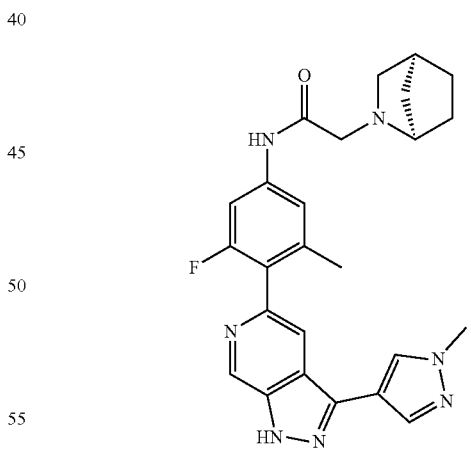

This compound was prepared according to the procedures described in Example 80, using 7-(1R,4S)-2-azabicyclo[2.2.1]heptane (Example 79, Step 3) instead of pyrrolidine as starting material. LCMS calculated for $C_{25}H_{27}FN_7O$ (M+H)$^+$: m/z=460.2; Found: 460.2. $^1$H NMR (500 MHz, DMSO-d$_6$) δ 10.84-10.71 (m, 1H), 9.15 (s, 1H), 8.49 (s, 1H), 8.09 (s, 1H), 8.05 (s, 1H), 7.53 (d, J=11.5 Hz, 1H), 7.28 (s, 1H), 4.40-4.04 (m, 3H), 3.92 (s, 3H), 3.65-2.84 (m, 2H), 2.70-2.59 (m, 1H), 2.17 (s, 3H), 2.06-1.37 (m, 6H) ppm.

Example 84. 3-(Dimethylamino)-N-(3-fluoro-5-methyl-4-(3-(1-methyl-1H-pyrazol-4-yl)-1H-pyrazolo[3,4-c]pyridin-5-yl)phenyl)propanamide

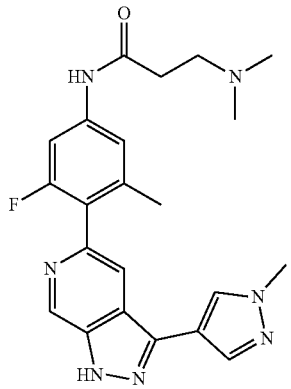 [SMILES: Cc1cc(NC(=O)CCN(C)C)cc(F)c1-c1cc2c(-c3cnn(C)c3)n[nH]c2cn1]

Step 1. tert-Butyl 5-(4-amino-2-fluoro-6-methylphenyl)-3-(1-methyl-1H-pyrazol-4-yl)-1H-pyrazolo[3,4-c]pyridine-1-carboxylate

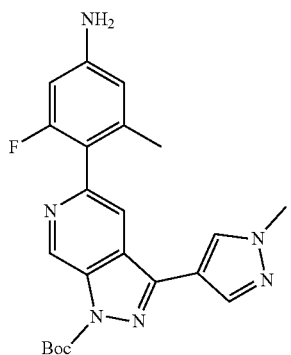

This compound was prepared according to the procedures described in Example 72 (Steps 3-5), using 3-fluoro-5-methylaniline instead of 3-(difluoromethoxy)-5-fluoroaniline as starting material. LCMS calculated for $C_{22}H_{24}FN_6O_2$ (M+H)$^+$: m/z=423.2; Found: 423.2.

Step 2. 3-(Dimethylamino)-N-(3-fluoro-5-methyl-4-(3-(1-methyl-1H-pyrazol-4-yl)-1H-pyrazolo[3,4-c]pyridin-5-yl)phenyl)propanamide To a solution of tert-butyl 5-(4-amino-2-fluoro-6-methylphenyl)-3-(1-methyl-1H-pyrazol-4-yl)-1H-pyrazolo[3,4-c]pyridine-1-carboxylate (10 mg, 0.024 mmol) and 3-(dimethylamino)propanoic acid (2.77 mg, 0.024 mmol) in N,N-dimethylformamide (1.5 mL) were added N,N-diisopropylethylamine (13 µL, 0.07 mmol) and N,N,N',N'-tetramethyl-O-(7-azabenzotriazol-1-yl)uronium hexafluorophosphate (15 mg, 0.04 mmol). After the reaction mixture was stirred at r.t. for 2 hours, it was quenched with water. The resulting mixture was extracted with ethyl acetate. The separated organic phases were washed with brine, dried over sodium sulfate and solvents evaporated in vacuo. Then TFA (1 mL) was added and the mixture was stirred at r.t. for 30 min. The reaction mixture was then diluted with acetonitrile and was purified with prep-LCMS (XBridge C18 column, eluting with a gradient of acetonitrile/water containing 0.1% TFA, at flow rate of 60 mL/min). LCMS calculated for $C_{22}H_{25}FN_7O$ (M+H)$^+$: m/z=422.2; Found: 422.3.

Example 85. 2-Cyano-N-(3-fluoro-5-methyl-4-(3-(1-methyl-1H-pyrazol-4-yl)-1H-pyrazolo[3,4-c]pyridin-5-yl)phenyl)acetamide

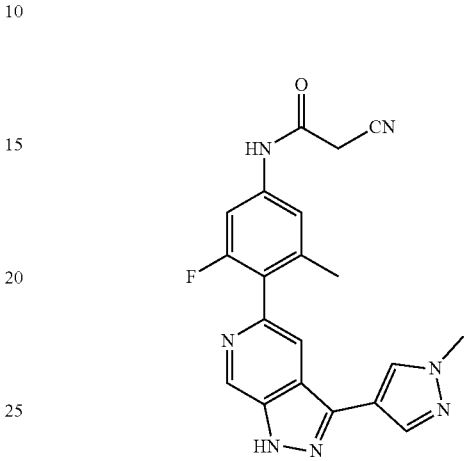

This compound was prepared according to the procedures described in Example 84, using 2-cyanoacetic acid instead of 3-(dimethylamino)propanoic acid as starting material. LCMS calculated for $C_{20}H_{17}FN_7O$ (M+H)$^+$: m/z=390.2; Found: 390.3.

Example 86. N-Methyl-1-(2-methyl-3-(3-(1-methyl-1H-pyrazol-4-yl)-1H-pyrazolo[3,4-c]pyridin-5-yl)phenyl)methanamine

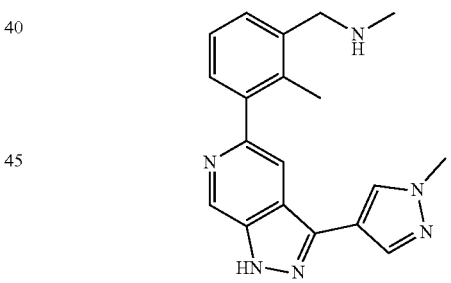

Step 1. (2-Methyl-3-(4,4,5,5-tetramethyl-1,3,2-dioxaborolan-2-yl)phenyl)methanol

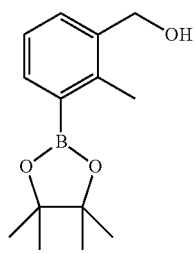 [SMILES: Cc1c(CO)cccc1B1OC(C)(C)C(C)(C)O1]

To a mixture of 4,4,5,5,4',4',5',5'-octamethyl-[2,2']bi[[1,3,2]dioxaborolanyl] (2.05 g, 8.1 mmol), potassium acetate (1.05 g, 10.7 mmol) and [1,1'-bis(diphenylphosphino)ferrocene]dichloropalladium(II) complexed with dichloromethane (1:1) (0.44 g, 0.54 mmol) under nitrogen was added a solution of (3-bromo-2-methylphenyl)methanol (1.08 g, 5.37 mmol) in 1,4-dioxane (20 mL). The mixture was stirred at 100° C. overnight. After cooling to room temperature, the mixture was diluted with DCM and filtered through Celite. The filtrate was concentrated in vacuo. The residue was purified by Biotage Isolera™ (446 mg, 36%). LCMS calculated for $C_{14}H_{20}BO_2$ (M+H—H$_2$O)$^+$ m/z=231.2; found 231.2.

Step 2. tert-Butyl 5-(3-(hydroxymethyl)-2-methylphenyl)-3-(1-methyl-1H-pyrazol-4-yl)-1H-pyrazolo[3,4-c]pyridine-1-carboxylate

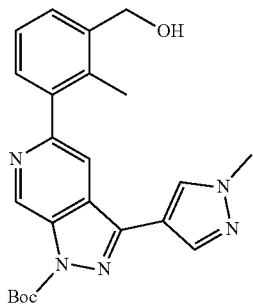 [SMILES: Cc1c(CO)cccc1-c1cc2c(-c3cnn(C)c3)nn(C(=O)OC(C)(C)C)c2cn1]

tert-Butyl 5-chloro-3-(1-methyl-1H-pyrazol-4-yl)-1H-pyrazolo[3,4-c]pyridine-1-carboxylate (500 mg, 1.498 mmol, Intermediate 1), (2-methyl-3-(4,4,5,5-tetramethyl-1,3,2-dioxaborolan-2-yl)phenyl)methanol (446 mg, 1.798 mmol), chloro(2-dicyclohexylphosphino-2',4',6'-triisopropyl-1,1'-biphenyl)[2-(2'-amino-1,1'-biphenyl)]palladium(II) (Pd XPhos G2) (118 mg, 0.15 mmol) and potassium phosphate (636 mg, 3 mmol) were placed in a flask and the flask was evacuated and backfilled with nitrogen three times. Then dioxane (15 mL) and degassed water (1.5 mL) were added. The mixture was stirred at 90° C. for 2 h. After cooling to r.t., the reaction mixture was diluted with ethyl acetate, and the resulting mixture was washed with brine. The separated organic phase was dried over sodium sulfate. The solvents were evaporated in vacuo and the obtained crude product was purified by Biotage Isolera™ (190 mg, 30%). LCMS calculated for $C_{23}H_{26}N_5O_3$ (M+H)$^+$ m/z=420.2; found 420.3.

Step 3. tert-Butyl 5-(3-formyl-2-methylphenyl)-3-(1-methyl-1H-pyrazol-4-yl)-1H-pyrazolo[3,4-c]pyridine-1-carboxylate

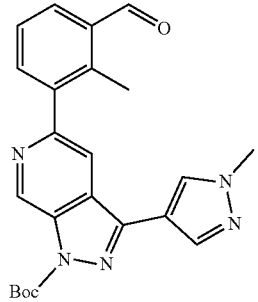 [SMILES: Cc1c(C=O)cccc1-c1cc2c(-c3cnn(C)c3)nn(C(=O)OC(C)(C)C)c2cn1]

Dess-Martin periodinane (231 mg, 0.544 mmol) was added to a solution of tert-butyl 5-(3-(hydroxymethyl)-2-methylphenyl)-3-(1-methyl-1H-pyrazol-4-yl)-1H-pyrazolo[3,4-c]pyridine-1-carboxylate (190 mg, 0.453 mmol) and pyridine (44.0 μl, 0.544 mmol) in DCM (5 ml). After stirring at r.t. for 1 h, solvent was evaporated in vacuo and the obtained crude product was purified by Biotage Isolera™ (170 mg, 90%). LCMS calculated for $C_{23}H_{24}N_5O_3$ (M+H)$^+$ m/z=418.2; found 418.2.

Step 4. N-Methyl-1-(2-methyl-3-(3-(1-methyl-1H-pyrazol-4-yl)-1H-pyrazolo[3,4-c]pyridin-5-yl)phenyl)methanamine Sodium triacetoxyborohydride (10.15 mg, 0.048 mmol) was added to a solution of methanamine (2M in THF, 12 μl, 0.024 mmol), acetic acid (2.74 μl, 0.048 mmol) and tert-butyl 5-(3-formyl-2-methylphenyl)-3-(1-methyl-1H-pyrazol-4-yl)-1H-pyrazolo[3,4-c]pyridine-1-carboxylate (10 mg, 0.024 mmol) in DCE (1 ml). After the reaction mixture was stirred at r.t. for 2 hours, it was quenched with water. The mixture was extracted with ethyl acetate. The separated organic phases washed with brine, dried over sodium sulfate and solvents evaporated in vacuo. Then TFA (1 mL) was added and the reaction was stirred at r.t. for 30 min. The reaction mixture was then diluted with acetonitrile and was purified with prep-LCMS (XBridge C18 column, eluting with a gradient of acetonitrile/water containing 0.1% TFA, at flow rate of 60 mL/min). LCMS calculated for $C_{19}H_{21}N_6$ (M+H)$^+$: m/z=333.2; Found: 333.2.

Example 87. N-Methyl-1-(4-methyl-3-(3-(1-methyl-1H-pyrazol-4-yl)-1H-pyrazolo[3,4-c]pyridin-5-yl)phenyl)methanamine

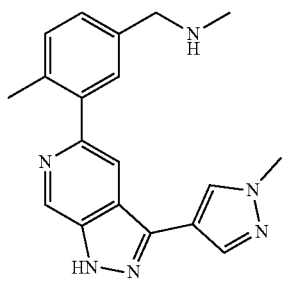

This compound was prepared according to the procedures described in Example 86, using (3-bromo-4-methylphenyl)methanol instead of (3-bromo-2-methylphenyl)methanol as starting material. LCMS calculated for $C_{19}H_{21}N_6$ (M+H)$^+$: m/z=333.2; Found: 333.2.

Intermediate 3.
(3-Bromo-2-(trifluoromethyl)phenyl)methanol

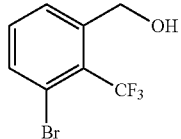 [SMILES: OCc1cccc(Br)c1C(F)(F)F]

To a mixture of 3-bromo-2-(trifluoromethyl)benzoic acid (0.97 g, 3.61 mmol) and triethylamine (0.528 mL, 3.79 mmol) in tetrahydrofuran (20 mL) was added isobutyl carbonochloridate (0.491 mL, 3.79 mmol). After stirring for 30 min at r.t., the solids were filtered-off, and a solution of sodium tetrahydroborate (0.273 g, 7.21 mmol) in water (1.300 mL) was slowly added to the filtrate. After stirring at r.t. for 30 min, the reaction mixture was diluted with ethyl acetate, and the resulting mixture was washed with brine. The separated organic phase was dried over sodium sulfate. The solvents were evaporated in vacuo and the obtained crude product was purified by Biotage Isolera™ (550 mg, 64%).

Example 88. N-Methyl-1-(3-(3-(1-methyl-1H-pyrazol-4-yl)-1H-pyrazolo[3,4-c]pyridin-5-yl)-2-(trifluoromethyl)phenyl)methanamine

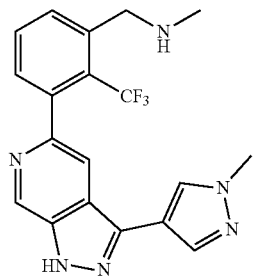 [SMILES: CNCc1cccc(-c2cc3c(-c4cnn(C)c4)n[nH]c3cn2)c1C(F)(F)F]

This compound was prepared according to the procedures described in Example 86, using (3-bromo-2-(trifluoromethyl)phenyl)methanol (Intermediate 3) instead of (3-bromo-2-methylphenyl)methanol as starting material. LCMS calculated for $C_{19}H_{18}F_3N_6$ (M+H)$^+$: m/z=387.2; Found: 387.1.

$^1$H NMR (600 MHz, DMSO-d$_6$) δ 9.10-9.00 (m, 2H), 8.48 (s, 1H), 8.10 (d, J=1.2 Hz, 1H), 8.06 (d, J=0.6 Hz, 1H), 7.86 (t, J=7.7 Hz, 1H), 7.81 (d, J=7.7 Hz, 1H), 7.67 (d, J=7.5 Hz, 1H), 4.41 (s, 2H), 3.92 (s, 3H), 2.75 (t, J=5.2 Hz, 3H) ppm.

Example 89. 5-(3-(Azetidin-1-ylmethyl)-2-(trifluoromethyl)phenyl)-3-(1-methyl-1H-pyrazol-4-yl)-1H-pyrazolo[3,4-c]pyridine

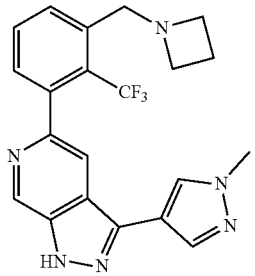 [SMILES: Cn1cc(-c2n[nH]c3cnc(-c4cccc(CN5CCC5)c4C(F)(F)F)cc23)cn1]

This compound was prepared according to the procedures described in Example 86 and 88, using azetidine instead of methanamine as starting material. LCMS calculated for $C_{21}H_{20}F_3N_6$ (M+H)$^+$: m/z=413.2; Found: 413.2.

Example 90. N-(3-(3-(1-Methyl-1H-pyrazol-4-yl)-1H-pyrazolo[3,4-c]pyridin-5-yl)-2-(trifluoromethyl)benzyl)tetrahydro-2H-pyran-4-amine

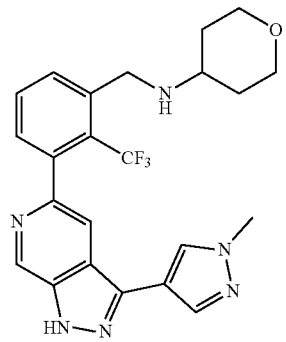 [SMILES: Cn1cc(-c2n[nH]c3cnc(-c4cccc(CNC5CCOCC5)c4C(F)(F)F)cc23)cn1]

This compound was prepared according to the procedures described in Example 86 and 88, using tetrahydro-2H-pyran-4-amine instead of methanamine as starting material. LCMS calculated for $C_{23}H_{24}F_3N_6O$ (M+H)$^+$: m/z=457.2; Found: 457.1.

Example 91. N-(3-(3-(1-Methyl-1H-pyrazol-4-yl)-1H-pyrazolo[3,4-c]pyridin-5-yl)-2-(trifluoromethyl)benzyl)propan-2-amine

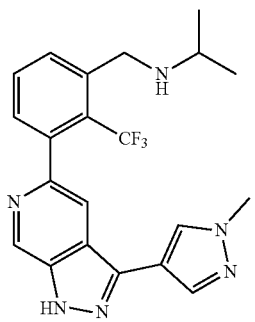 [SMILES: CC(C)NCc1cccc(-c2cc3c(-c4cnn(C)c4)n[nH]c3cn2)c1C(F)(F)F]

This compound was prepared according to the procedures described in Example 86 and 88, using propan-2-amine instead of methanamine as starting material. LCMS calculated for $C_{21}H_{22}F_3N_6$ (M+H)$^+$: m/z=415.2; Found: 415.3.
$^1$H NMR (500 MHz, DMSO-d$_6$) δ 9.06 (d, J=1.0 Hz, 1H), 8.91 (br, 1H), 8.46 (s, 1H), 8.14-8.04 (m, 2H), 7.92-7.81 (m, 2H), 7.68 (t, J=4.4 Hz, 1H), 4.39 (br, 2H), 3.93 (s, 3H), 3.52 (dq, J=11.9, 5.9 Hz, 1H), 1.35 (d, J=6.5 Hz, 6H) ppm.

Intermediate 4.
(3-Bromo-4-fluoro-2-methylphenyl)methanol

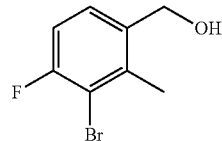

LAH solution (5.75 mL, 5.75 mmol, 1.0M in THF) was added to a solution of ethyl 3-bromo-4-fluoro-2-methylbenzoate (Enamine, 1.25 g, 4.79 mmol) in THF (15.0 mL). The reaction mixture was stirred at r.t. for 2 h. Then reaction was carefully quenched with water and NaOH solution. After solids were filtered off, the solvent of the filtrate was evaporated in vacuo. Obtained crude product was used in the next step without further purification. LCMS calculated for $C_8H_7BrF$ (M+H—H$_2$O)$^+$: m/z=201.0; Found: 201.0.

Example 92. 1-(4-Fluoro-2-methyl-3-(3-(1-methyl-1H-pyrazol-4-yl)-1H-pyrazolo[3,4-c]pyridin-5-yl)phenyl)-N-methylmethanamine

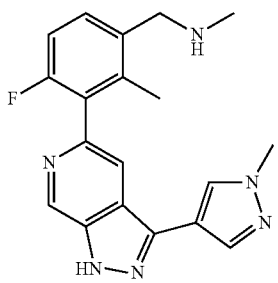 [SMILES: CNCc1ccc(F)c(-c2cc3c(-c4cnn(C)c4)n[nH]c3cn2)c1C]

This compound was prepared according to the procedures described in Example 86, using (3-bromo-4-fluoro-2-methylphenyl)methanol (Intermediate 4) instead of (3-bromo-2-methylphenyl)methanol as starting material. LCMS calculated for $C_{19}H_{20}FN_6$ (M+H)$^+$: m/z=351.2; Found: 351.2.

Example 93. N-(4-Fluoro-2-methyl-3-(3-(1-methyl-1H-pyrazol-4-yl)-1H-pyrazolo[3,4-c]pyridin-5-yl)benzyl)propan-2-amine

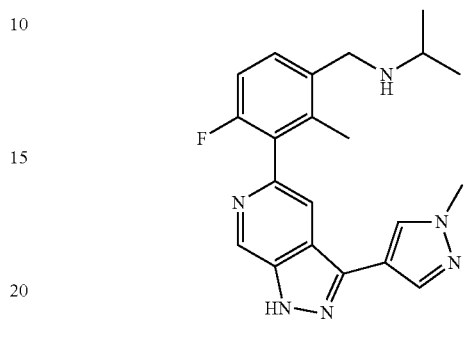

This compound was prepared according to the procedures described in Example 86 and 92, using propan-2-amine instead of methanamine as starting material. LCMS calculated for $C_{21}H_{24}FN_6$ (M+H)$^+$: m/z=379.2; Found: 379.3.

$^1$H NMR (600 MHz, DMSO-d$_6$) δ 9.16 (s, 1H), 8.67 (br, 1H), 8.48 (s, 1H), 8.04 (s, 2H), 7.58 (dd, J=8.5, 5.7 Hz, 1H), 7.30 (t, J=8.7 Hz, 1H), 4.30-4.16 (m, 2H), 3.92 (s, 3H), 3.48 (dp, J=12.4, 6.3 Hz, 1H), 2.15 (s, 3H), 1.34 (d, J=6.5 Hz, 6H) ppm.

Example 94. 5-(3-(Azetidin-1-ylmethyl)-6-fluoro-2-methylphenyl)-3-(1-methyl-1H-pyrazol-4-yl)-1H-pyrazolo[3,4-c]pyridine

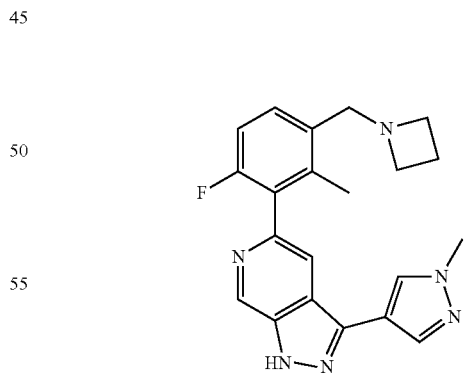

This compound was prepared according to the procedures described in Example 86 and 92, using azetidine instead of methanamine as starting material. LCMS calculated for $C_{21}H_{22}FN_6$ (M+H)$^+$: m/z=377.2; Found: 377.3.

Example 95. 3-(3,5-Difluoro-4-(3-(1-methyl-1H-pyrazol-4-yl)-1H-pyrazolo[3,4-c]pyridin-5-yl)phenyl)-N-isopropylcyclobutanamine

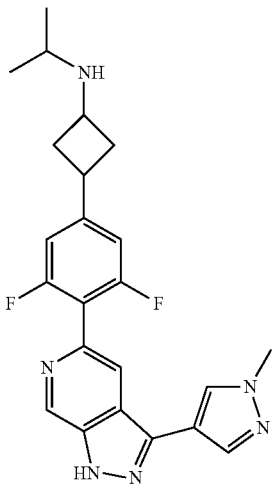 [SMILES: CC(C)NC1CC(c2cc(F)c(-c3cc4c(-c5cnn(C)c5)n[nH]c4cn3)c(F)c2)C1]

Step 1. tert-Butyl 3-(3,5-difluorophenyl)cyclobutylcarbamate

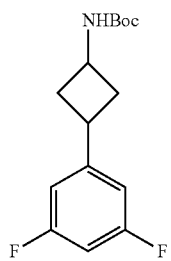 [SMILES: CC(C)(C)OC(=O)NC1CC(c2cc(F)cc(F)c2)C1]

Di-tert-butyl dicarbonate (4.77 g, 21.83 mmol) was added to a solution of 3-(3,5-difluorophenyl)cyclobutan-1-amine (2.5 g, 13.65 mmol) and triethylamine (4.14 g, 40.9 mmol) in THF (25 ml). After stirring at r.t. for 1 h, solvent was evaporated in vacuo and the obtained crude product was purified by Biotage Isolera™ (3.2 g, 90%). LCMS calculated for $C_{11}H_{12}F_2NO_2$ (M+H—$C_4H_8$)+ m/z=228.1; found 228.1.

Step 2. tert-Butyl 3-(3,5-difluoro-4-(4,4,5,5-tetramethyl-1,3,2-dioxaborolan-2-yl)phenyl)cyclobutylcarbamate

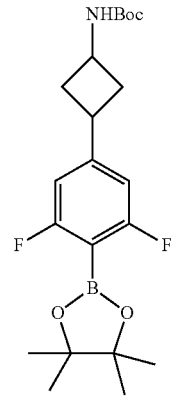 [SMILES: CC(C)(C)OC(=O)NC1CC(c2cc(F)c(B3OC(C)(C)C(C)(C)O3)c(F)c2)C1]

To a solution of tert-butyl 3-(3,5-difluorophenyl)cyclobutylcarbamate (3.2 g, 11.29 mmol) in THF (35 mL) at −78° C. was added n-butyllithium, 2.5 M in hexane (13.55 mL, 33.9 mmol). The reaction mixture was stirred at −78° C. for 1 hour before 2-isopropoxy-4,4,5,5-tetramethyl-1,3,2-dioxaborolane (6.3 g, 33.9 mmol) was added dropwise. The resulting solution was stirred at −78° C. for another 1 hour, then warmed up to r.t. and quenched with saturated NH$_4$Cl solution in water (50 mL). The reaction mixture was diluted with ethyl acetate, and the resulting mixture was washed with brine. The separated organic phase was dried over sodium sulfate. The solvents were evaporated in vacuo and obtained crude product was purified by Biotage Isolera™ (2.7 g, 65%). LCMS calculated for $C_{17}H_{23}BF_2NO_4$ (M+H—$C_4H_8$)+ m/z=354.2; found 354.2.

Step 3. tert-Butyl 5-(4-(3-(tert-butoxycarbonylamino)cyclobutyl)-2,6-difluorophenyl)-3-(1-methyl-1H-pyrazol-4-yl)-1H-pyrazolo[3,4-c]pyridine-1-carboxylate

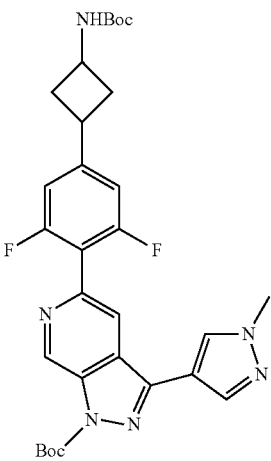 [SMILES: Cn1cc(-c2nn(C(=O)OC(C)(C)C)c3cnc(-c4c(F)cc(C5CC(NC(=O)OC(C)(C)C)C5)cc4F)cc23)cn1]

5-Chloro-3-(1-methyl-1H-pyrazol-4-yl)-1-((2-(trimethylsilyl)ethoxy)methyl)-1H-pyrazolo[3,4-c]pyridine (600 mg, 1.8 mmol, Intermediate 1), tert-butyl (3-(3,5-difluoro-4-(4, 4,5,5-tetramethyl-1,3,2-dioxaborolan-2-yl)phenyl)cyclobutyl)carbamate (1.177 g, 2.88 mmol), chloro(2-dicyclohexylphosphino-2',4',6'-triisopropyl-1,1'-biphenyl)[2-(2'-amino-1,1'-biphenyl)]palladium(II) (Pd XPhos G2) (280 mg, 0.36 mmol) and potassium phosphate (626 mg, 2.9 mmol) were placed in a flask and the flask was evacuated and backfilled with nitrogen three times. Then dioxane (20 mL) and degassed water (2 mL) were added. The reaction mixture was stirred at 90° C. for 2 h. After cooling to r.t., the reaction mixture was diluted with ethyl acetate, and the resulting mixture was washed with brine. The separated organic phase was dried over sodium sulfate. The solvents were evaporated under reduced pressure and obtained crude product was purified by Biotage Isolera™ (753 mg, 72%). LCMS calculated for $C_{30}H_{35}F_2N_6O_4$ $(M+H)^+$ m/z=581.3; found 581.3.

Step 4. 3-(3,5-Difluoro-4-(3-(1-methyl-1H-pyrazol-4-yl)-1H-pyrazolo[3,4-c]pyridin-5-yl)phenyl)cyclobutanamine

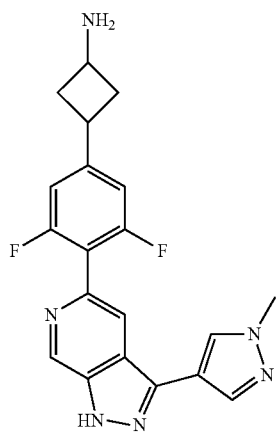 [SMILES: Cn1cc(-c2n[nH]c3cnc(-c4c(F)cc(C5CC(N)C5)cc4F)cc23)cn1]

4M HCl solution in dioxane (2 mL, 8 mmol) was added to tert-butyl 5-(4-(3-((tert-butoxycarbonyl)amino)cyclobutyl)-2,6-difluorophenyl)-3-(1-methyl-1H-pyrazol-4-yl)-1H-pyrazolo[3,4-c]pyridine-1-carboxylate (550 mg, 0.9 mmol), and the reaction mixture was stirred at r.t. for 1 h. Then solvent was evaporated in vacuo, the obtained crude product was dried and was used in the next step without further purification. LCMS calculated for $C_{20}H_{19}F_2N_6$ $(M+H)^+$ m/z=381.2; found 381.1.

Step 5. 3-(3,5-Difluoro-4-(3-(1-methyl-1H-pyrazol-4-yl)-1H-pyrazolo[3,4-c]pyridin-5-yl)phenyl)-N-isopropylcyclobutanamine Sodium triacetoxyborohydride (16.7 mg, 0.08 mmol) was added to a solution of propan-2-one (2.290 mg, 0.039 mmol), acetic acid (2.74 µl, 0.048 mmol) and 3-(3,5-difluoro-4-(3-(1-methyl-1H-pyrazol-4-yl)-1H-pyrazolo[3,4-c]pyridin-5-yl)phenyl)cyclobutan-1-amine (15.0 mg, 0.039 mmol) in DCE (1 ml). After the reaction mixture was stirred at r.t. for 2 hours, it was diluted with acetonitrile and was purified with prep-LCMS (XBridge C18 column, eluting with a gradient of acetonitrile/water containing 0.1% TFA, at flow rate of 60 mL/min). LCMS calculated for $C_{23}H_{25}F_2N_6$ $(M+H)^+$: m/z=423.2; Found: 423.3.

Example 96. 2-(3,5-Difluoro-4-(3-(1-methyl-1H-pyrazol-4-yl)-1H-pyrazolo[3,4-c]pyridin-5-yl)phenyl)-N-methylethanamine

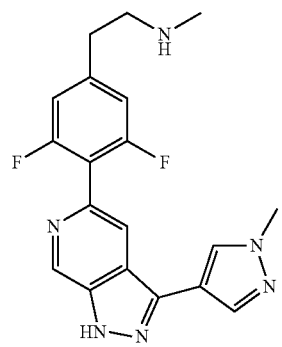 [SMILES: CNCCc1cc(F)c(-c2cc3c(-c4cnn(C)c4)n[nH]c3cn2)c(F)c1]

Step 1. tert-Butyl 5-(2,6-difluoro-4-(2-hydroxyethyl)phenyl)-3-(1-methyl-1H-pyrazol-4-yl)-1H-pyrazolo[3,4-c]pyridine-1-carboxylate

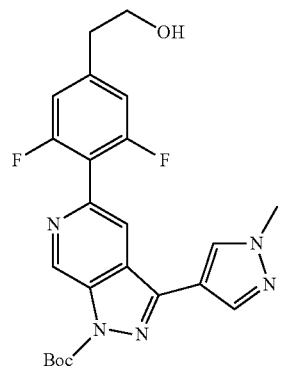 [SMILES: Cn1cc(-c2nn(C(=O)OC(C)(C)C)c3cnc(-c4c(F)cc(CCO)cc4F)cc23)cn1]

This compound was prepared according to the procedures described in Example 95 (Steps 2-3), using 2-(3,5-difluorophenyl)ethanol instead of tert-butyl 3-(3,5-difluorophenyl)cyclobutylcarbamate as starting material. LCMS calculated for $C_{23}H_{24}F_2N_5O_3$ $(M+H)^+$: m/z=456.2; Found: 456.2.

Step 2. tert-Butyl 5-(2,6-difluoro-4-(2-oxoethyl)phenyl)-3-(1-methyl-1H-pyrazol-4-yl)-1H-pyrazolo[3,4-c]pyridine-1-carboxylate

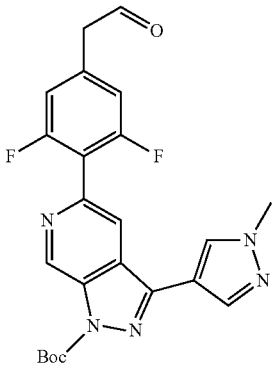 [SMILES: Cn1cc(-c2nn(C(=O)OC(C)(C)C)c3cnc(-c4c(F)cc(CC=O)cc4F)cc23)cn1]

Dess-Martin periodinane (870 mg, 2.05 mmol) was added to a solution of tert-butyl 5-(2,6-difluoro-3-(2-hydroxyethyl)phenyl)-3-(1-methyl-1H-pyrazol-4-yl)-1H-pyrazolo[3,4-c]pyridine-1-carboxylate (0.78 g, 1.713 mmol) and pyridine (166.0 µl, 2.05 mmol) in DCM (15 ml). After stirring at r.t. for 1 h, solvent was evaporated in vacuo and the obtained crude product was purified by Biotage Isolera™ (653 mg, 84%). LCMS calculated for $C_{23}H_{22}F_2N_5O_3$ $(M+H)^+$ m/z=454.2; found 454.2.

Step 3. 2-(3,5-Difluoro-4-(3-(1-methyl-1H-pyrazol-4-yl)-1H-pyrazolo[3,4-c]pyridin-5-yl)phenyl)-N-methylethanamine Sodium triacetoxyborohydride (10.15 mg, 0.048 mmol) was added to a solution of methanamine (2M in THF, 12 µl, 0.024 mmol), acetic acid (2.74 µl, 0.048 mmol) and tert-butyl 5-(2,6-difluoro-4-(2-oxoethyl)phenyl)-3-(1-methyl-1H-pyrazol-4-yl)-1H-pyrazolo[3,4-c]pyridine-1-carboxylate (11.0 mg, 0.024 mmol) in DCE (1 ml). After the reaction mixture was stirred at r.t. for 2 hours, it was quenched with water. The reaction mixture was extracted with ethyl acetate. The separated organic phases were washed with brine, dried over sodium sulfate and solvents evaporated in vacuo. Then TFA (1 mL) was added, and the mixture was stirred at r.t. for 30 min. The reaction mixture was then diluted with acetonitrile and was purified with prep-LCMS (XBridge C18 column, eluting with a gradient of acetonitrile/water containing 0.1% TFA, at flow rate of 60 mL/min). LCMS calculated for $C_{19}H_{19}F_2N_6$ $(M+H)^+$: m/z=369.2; Found: 369.2.

Example 97. 2-(2,4-Difluoro-3-(3-(1-methyl-1H-pyrazol-4-yl)-1H-pyrazolo[3,4-c]pyridin-5-yl)phenyl)-N-methylethanamine

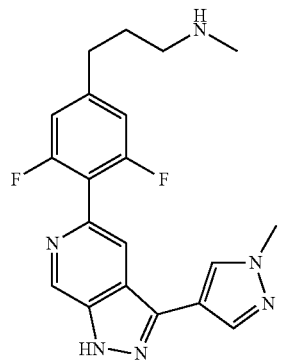 [SMILES: CNCCCc1cc(F)c(-c2cc3c(-c4cnn(C)c4)n[nH]c3cn2)c(F)c1]

This compound was prepared according to the procedures described in Example 96, using 2-(2,4-difluorophenyl)ethanol instead of 2-(3,5-difluorophenyl)ethanol as starting material. LCMS calculated for $C_{19}H_{19}F_2N_6$ $(M+H)^+$: m/z=369.2; Found: 369.1.

Example 98. N-(2,4-Difluoro-3-(3-(1-methyl-1H-pyrazol-4-yl)-1H-pyrazolo[3,4-c]pyridin-5-yl)phenethyl)tetrahydro-2H-pyran-4-amine

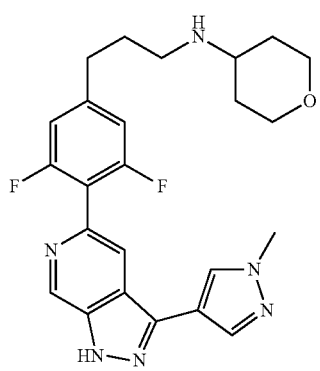 [SMILES: Cn1cc(-c2n[nH]c3cnc(-c4c(F)cc(CCCNC5CCOCC5)cc4F)cc23)cn1]

This compound was prepared according to the procedures described in Example 97, using tetrahydro-2H-pyran-4-amine instead of methanamine as starting material. LCMS calculated for $C_{23}H_{25}F_2N_6O$ $(M+H)^+$: m/z=439.2; Found: 439.2.

141

Example 99. N-(3,5-Difluoro-4-(3-(1-methyl-1H-pyrazol-4-yl)-1H-pyrazolo[3,4-c]pyridin-5-yl)phenethyl)-1-isopropylazetidin-3-amine

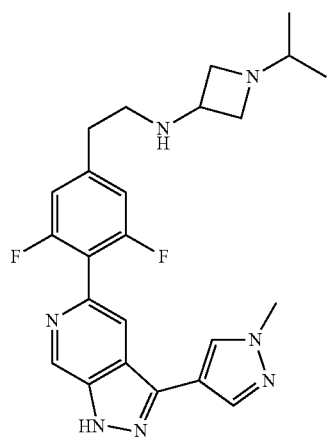 [SMILES: CC(C)N1CC(NCCc2cc(F)c(-c3cc4c(-c5cnn(C)c5)n[nH]c4cn3)c(F)c2)C1]

This compound was prepared according to the procedures described in Example 96, using 1-isopropylazetidin-3-amine instead of methanamine as starting material. LCMS calculated for $C_{24}H_{28}F_2N_7$ (M+H)$^+$: m/z=452.2; Found: 452.2.

Intermediate 5. tert-Butyl 5-(2-fluoro-6-methoxyphenyl)-3-iodo-1H-pyrazolo[3,4-c]pyridine-1-carboxylate

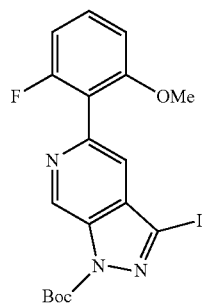 [SMILES: COc1cccc(F)c1-c1cc2c(I)nn(C(=O)OC(C)(C)C)c2cn1]

This compound was prepared according to the procedures described in Example 34 (Steps 1-5), using Boc$_2$O instead of SEM-Cl as reagent. LCMS calculated for $C_{18}H_{18}FIN_3O_3$ (M+H)$^+$: m/z=470.0; Found: 470.0.

142

Example 100. 2-Fluoro-4-(5-(2-fluoro-6-methoxyphenyl)-1H-pyrazolo[3,4-c]pyridin-3-yl)-N-methylbenzamide

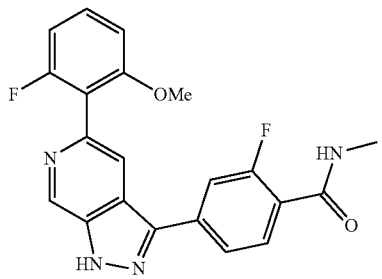 [SMILES: CNC(=O)c1ccc(-c2n[nH]c3cnc(-c4c(F)cccc4OC)cc23)cc1F]

Step 1. tert-Butyl 3-(3-fluoro-4-(methoxycarbonyl)phenyl)-5-(2-fluoro-6-methoxyphenyl)-1H-pyrazolo[3,4-c]pyridine-1-carboxylate

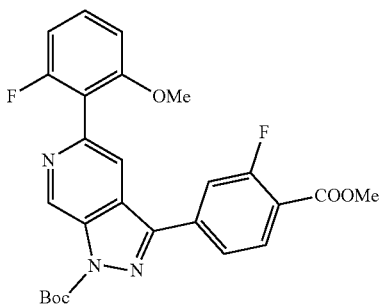 [SMILES: COC(=O)c1ccc(-c2nn(C(=O)OC(C)(C)C)c3cnc(-c4c(F)cccc4OC)cc23)cc1F]

tert-Butyl 5-(2-fluoro-6-methoxyphenyl)-3-iodo-1H-pyrazolo[3,4-c]pyridine-1-carboxylate (1.00 g, 2.131 mmol, Intermediate 5), (3-fluoro-4-(methoxycarbonyl)phenyl)boronic acid (0.506 g, 2.56 mmol), chloro(2-dicyclohexylphosphino-2',4',6'-triisopropyl-1,1'-biphenyl)[2-(2'-amino-1,1'-biphenyl)]palladium(II) (Pd XPhos G2) (280 mg, 0.36 mmol) and potassium phosphate (626 mg, 2.9 mmol) were placed in a flask and the flask was evacuated and backfilled with nitrogen three times. Then dioxane (20 mL) and degassed water (2 mL) were added and reaction was stirred at 90° C. for 2 h. After cooling to r.t., the reaction mixture was diluted with ethyl acetate, and the resulting mixture was washed with brine. The separated organic phase was dried over sodium sulfate. The solvents were evaporated in vacuo and the obtained crude product was purified by Biotage Isolera™ (835 mg, 79%). LCMS calculated for $C_{26}H_{24}F_2N_3O_5$ (M+H)$^+$ m/z=496.2; found 496.1.

Step 2. 2-Fluoro-4-(5-(2-fluoro-6-methoxyphenyl)-1H-pyrazolo[3,4-c]pyridin-3-yl)benzoic acid

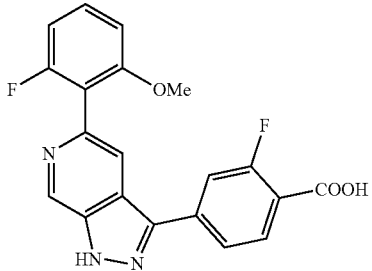 [SMILES: COc1cccc(F)c1-c1cc2c(-c3ccc(C(=O)O)c(F)c3)n[nH]c2cn1]

Lithium hydroxide (0.149 g, 6.23 mmol) was added to a solution of tert-butyl 3-(3-fluoro-4-(methoxycarbonyl)phenyl)-5-(2-fluoro-6-methoxyphenyl)-1H-pyrazolo[3,4-c]pyridine-1-carboxylate (618 mg, 1.246 mmol) in methanol (4 ml), THF (6.00 ml) and water (2.0 ml). After stirring at 45° C. for 3 h, the reaction mixture was neutralized with an HCl solution and the solvents were evaporated in vacuo. Obtained crude product was dried and used in the next step without further purification. LCMS calculated for $C_{20}H_{14}F_2N_3O_3$ (M+H)$^+$ m/z=382.1; found 382.1.

Step 3. 2-Fluoro-4-(5-(2-fluoro-6-methoxyphenyl)-1H-pyrazolo[3,4-c]pyridin-3-yl)-N-methylbenzamide To a solution of 2-fluoro-4-(5-(2-fluoro-6-methoxyphenyl)-1H-pyrazolo[3,4-c]pyridin-3-yl)benzoic acid (10 mg, 0.026 mmol) and methanamine (2M in THF, 24 µl, 0.048 mmol) in N,N-dimethylformamide (1.5 mL) were added N,N-diisopropylethylamine (13 µL, 0.07 mmol) and N,N,N',N'-tetramethyl-O-(7-azabenzotriazol-1-yl)uronium hexafluorophosphate (15 mg, 0.04 mmol). After the reaction mixture was stirred at r.t. for 2 hours, it was then diluted with acetonitrile and was purified with prep-LCMS (XBridge C18 column, eluting with a gradient of acetonitrile/water containing 0.1% TFA, at flow rate of 60 mL/min). LCMS calculated for $C_{21}H_{17}F_2N_4O_2$ (M+H)$^+$: m/z=395.1; Found: 395.2.

Example 101. 5-(5-(2-Fluoro-6-methoxyphenyl)-1H-pyrazolo[3,4-c]pyridin-3-yl)-N-methylpicolinamide

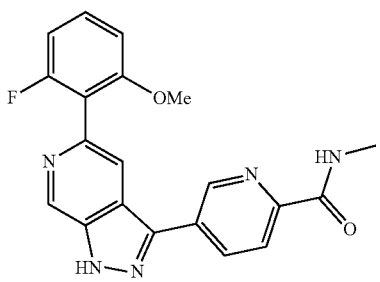 [SMILES: CNC(=O)c1ccc(-c2n[nH]c3cnc(-c4c(F)cccc4OC)cc23)cn1]

This compound was prepared according to the procedures described in Example 100, using methyl 5-(4,4,5,5-tetramethyl-1,3,2-dioxaborolan-2-yl)picolinate instead of (3-fluoro-4-(methoxycarbonyl)phenyl)boronic acid as starting material. LCMS calculated for $C_{20}H_{17}FN_5O_2$ (M+H)$^+$: m/z=378.1; Found: 378.1.

Example 102. 4-(5-(2-Fluoro-6-methoxyphenyl)-1H-pyrazolo[3,4-c]pyridin-3-yl)-2-methoxy-N-methylbenzamide

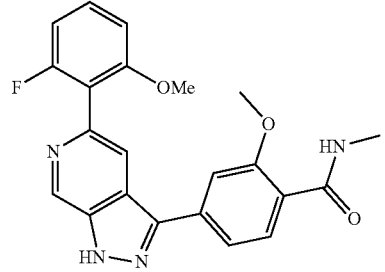 [SMILES: CNC(=O)c1ccc(-c2n[nH]c3cnc(-c4c(F)cccc4OC)cc23)cc1OC]

This compound was prepared according to the procedures described in Example 100, using 3-methoxy-4-(methoxycarbonyl)phenylboronic acid instead of (3-fluoro-4-(methoxycarbonyl)phenyl)boronic acid as starting material. LCMS calculated for $C_{22}H_{20}FN_4O_3$ (M+H)$^+$: m/z=407.2; Found: 407.2.

Example 103. 4-(5-(2-Fluoro-6-methoxyphenyl)-1H-pyrazolo[3,4-c]pyridin-3-yl)-N,2-dimethylbenzamide

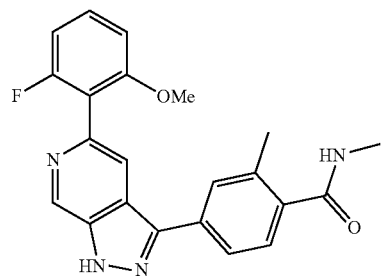 [SMILES: CNC(=O)c1ccc(-c2n[nH]c3cnc(-c4c(F)cccc4OC)cc23)cc1C]

This compound was prepared according to the procedures described in Example 100, using 4-(methoxycarbonyl)-3-methylphenylboronic acid instead of (3-fluoro-4-(methoxycarbonyl)phenyl)boronic acid as starting material. LCMS calculated for $C_{22}H_{20}FN_4O_2$ (M+H)$^+$: m/z=391.2; Found: 391.2.

Example 104. 1-(5-(2-Fluoro-6-methoxyphenyl)-1H-pyrazolo[3,4-c]pyridin-3-yl)-N-isopropyl-1H-imidazole-4-carboxamide

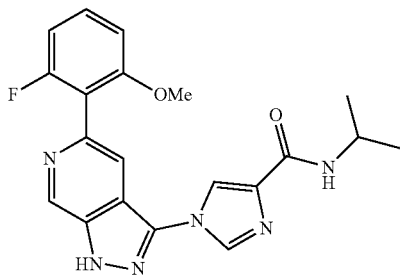 [SMILES: COc1cccc(F)c1-c1cc2c(-n3cnc(C(=O)NC(C)C)c3)n[nH]c2cn1]

Step 1. Methyl 1-(5-(2-fluoro-6-methoxyphenyl)-1-((2-(trimethylsilyl)ethoxy)methyl)-1H-pyrazolo[3,4-c]pyridin-3-yl)-1H-imidazole-4-carboxylate

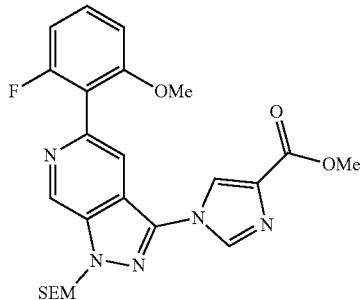 [SMILES: COC(=O)c1cn(-c2nn(COCC[Si](C)(C)C)c3cnc(-c4c(F)cccc4OC)cc23)cn1]

5-(2-Fluoro-6-methoxyphenyl)-3-iodo-1-((2-(trimethylsilyl)ethoxy)methyl)-1H-pyrazolo[3,4-c]pyridine (200 mg, 0.400 mmol, Example 34, Step 5), 8-hydroxyquinoline (11.63 mg, 0.080 mmol), potassium carbonate (111 mg, 0.801 mmol) and copper(I) iodide (15.2 mg, 0.080 mmol) were placed in a vial with septum. The vial was evacuated and backfilled with nitrogen 3 times. After a solution of methyl 1H-imidazole-4-carboxylate (76 mg, 0.601 mmol) in DMSO (2 ml) was added, the reaction mixture was stirred at 100° C. overnight. After cooling to r.t. water was added, the mixture was extracted with EtOAc. The separated organic layer was washed with brine, dried over sodium sulfate and the solvent was evaporated. The crude product was purified by Biotage Isolera™. LCMS calculated for $C_{24}H_{29}FN_5O_4Si$ (M+H)$^+$ m/z=498.2; found 498.3.

Step 2. 1-(5-(2-Fluoro-6-methoxyphenyl)-1-((2-(trimethylsilyl)ethoxy)methyl)-1H-pyrazolo[3,4-c]pyridin-3-yl)-1H-imidazole-4-carboxylic acid

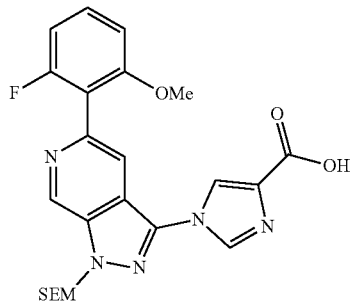 [SMILES: COc1cccc(F)c1-c1cc2c(-n3cnc(C(=O)O)c3)nn(COCC[Si](C)(C)C)c2cn1]

1M Solution of sodium hydroxide in water (1 mL, 1 mmol) was added to a solution of methyl 1-(5-(2-fluoro-6-methoxyphenyl)-1-((2-(trimethylsilyl)ethoxy)methyl)-1H-pyrazolo[3,4-c]pyridin-3-yl)-1H-imidazole-4-carboxylate (25 mg, 0.049 mmol) in tetrahydrofuran (2 mL) and methanol (1 mL). After stirring at r.t. for 2 h, the pH was adjusted to 5 by the addition of a 1M HCl solution. The mixture was then extracted with ethyl acetate and organic phase was washed with brine. The organic phase was dried over sodium sulfate and the solvents were evaporated under reduced pressure. The obtained solid product was used in the next step without further purification. LCMS calculated for $C_{23}H_{27}FN_5O_4Si$ (M+H)$^+$ m/z=484.2; found 484.1.

Step 3. 1-(5-(2-Fluoro-6-methoxyphenyl)-1H-pyrazolo[3,4-c]pyridin-3-yl)-N-isopropyl-1H-imidazole-4-carboxamide To a solution of 1-(5-(2-fluoro-6-methoxyphenyl)-1-((2-(trimethylsilyl)ethoxy)methyl)-1H-pyrazolo[3,4-c]pyridin-3-yl)-1H-imidazole-4-carboxylic acid (0.01 g, 0.02 mmol) and isopropylamine (4.43 µl, 0.052 mmol) in N,N-dimethylformamide (1.5 mL) were added N,N-diisopropylethylamine (13 µl, 0.07 mmol) and N,N,N',N',N'-tetramethyl-O-(7-azabenzotriazol-1-yl)uronium hexafluorophosphate (15 mg, 0.04 mmol). After the reaction mixture was stirred at r.t. for 2 hours, it was quenched with water. The mixture was extracted with ethyl acetate. The separated organic phases were washed with brine and dried over sodium sulfate, and solvents were evaporated in vacuo. Then 1M solution of HCl in water (1 mL) and 4M solution of HCl in dioxane (1 mL) were added to the crude residue, and reaction mixture was stirred at 80° C. for 1 h. Then methanol (1 mL) was added, and the reaction mixture was further stirred at 80° C. for 30 min. The reaction mixture was then diluted with acetonitrile and was purified with prep-LCMS (XBridge C18 column, eluting with a gradient of acetonitrile/water containing 0.1% TFA, at flow rate of 60 mL/min). LCMS calculated for $C_{20}H_{20}FN_6O_2$ (M+H)$^+$: m/z=395.2; Found: 395.2.

Example 105. 1-(5-(2-Fluoro-6-methoxyphenyl)-1H-pyrazolo[3,4-c]pyridin-3-yl)-N-methyl-1H-imidazole-4-carboxamide

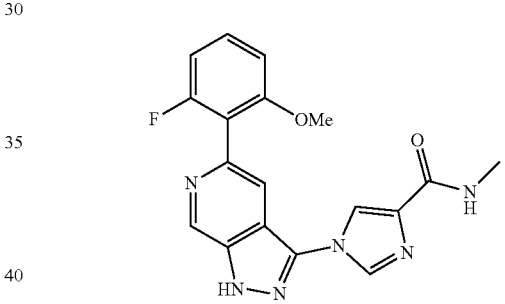

This compound was prepared according to the procedures described in Example 104, using methanamine instead of isopropylamine as starting material. LCMS calculated for $C_{18}H_{16}FN_6O_2$ (M+H)$^+$: m/z=367.1; Found: 367.1.

Example 106. 5-(4-(Azetidin-2-ylmethoxy)-2,6-difluorophenyl)-3-(1-methyl-1H-pyrazol-4-yl)-1H-pyrazolo[3,4-c]pyridine

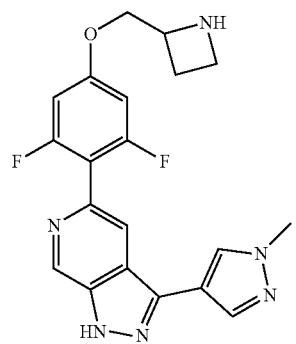 [SMILES: Cn1cc(-c2n[nH]c3cnc(-c4c(F)cc(OCC5CCN5)cc4F)cc23)cn1]

147

Step 1. 3,5-Difluoro-4-(3-(1-methyl-1H-pyrazol-4-yl)-1-((2-(trimethylsilyl)ethoxy)methyl)-1H-pyrazolo[3,4-c]pyridin-5-yl)phenol

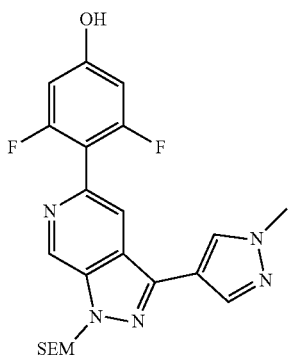 [SMILES: Cn1cc(-c2nn(COCC[Si](C)(C)C)c3cnc(-c4c(F)cc(O)cc4F)cc23)cn1]

This compound was prepared according to the procedures described in Example 57 (Step 1), using (2,6-difluoro-4-hydroxyphenyl)boronic acid instead of methyl 3,5-difluoro-4-(4,4,5,5-tetramethyl-1,3,2-dioxaborolan-2-yl)benzoate as starting material. LCMS calculated for $C_{22}H_{26}F_2N_5O_2Si$ $(M+H)^+$: m/z=458.2; Found: 458.2.

Step 2. 5-(4-(Azetidin-2-ylmethoxy)-2,6-difluorophenyl)-3-(1-methyl-1H-pyrazol-4-yl)-1H-pyrazolo[3,4-c]pyridine To a solution of 3,5-difluoro-4-(3-(1-methyl-1H-pyrazol-4-yl)-1-((2-(trimethylsilyl)ethoxy)methyl)-1H-pyrazolo[3,4-c]pyridin-5-yl)phenol (30 mg, 0.066 mmol) in DMF (1 ml) was added tert-butyl 2-(bromomethyl)azetidine-1-carboxylate (24.60 mg, 0.098 mmol) and cesium carbonate (32.0 mg, 0.098 mmol). After the reaction mixture was stirred at 90° C. overnight, it was quenched with water. The mixture was extracted with ethyl acetate. The separated organic phases were washed with brine and dried over sodium sulfate. The solvents were evaporated in vacuo. Then 1M solution of HCl in water (1 mL) and 4M solution of HCl in dioxane (1 mL) were added to the crude residue, and reaction mixture was stirred at 80° C. for 1 h. Methanol (1 mL) was added, and the reaction mixture was further stirred at 80° C. for 30 min. The reaction mixture was then diluted with acetonitrile and was purified with prep-LCMS (XBridge C18 column, eluting with a gradient of acetonitrile/water containing 0.1% TFA, at flow rate of 60 mL/min). LCMS calculated for $C_{20}H_{19}F_2N_6O$ $(M+H)^+$: m/z=397.2; Found: 397.2.

148

Example 107. 5-(2,6-Difluoro-4-(tetrahydro-2H-pyran-4-yloxy)phenyl)-3-(1-methyl-1H-pyrazol-4-yl)-1H-pyrazolo[3,4-c]pyridine

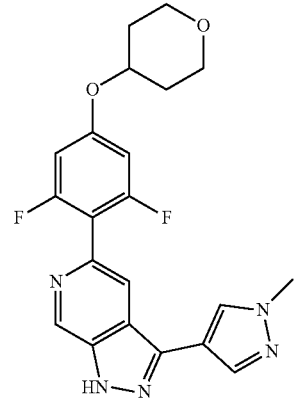 [SMILES: Cn1cc(-c2n[nH]c3cnc(-c4c(F)cc(OC5CCOCC5)cc4F)cc23)cn1]

This compound was prepared according to the procedures described in Example 106, using 4-chlorotetrahydro-2H-pyran instead of tert-butyl 2-(bromomethyl)azetidine-1-carboxylate as starting material. LCMS calculated for $C_{21}H_{20}F_2N_5O_2$ $(M+H)^+$: m/z=412.2; Found: 412.2.

Example 108. 5-(2,6-Difluoro-4-(pyridin-4-ylmethoxy)phenyl)-3-(1-methyl-1H-pyrazol-4-yl)-1H-pyrazolo[3,4-c]pyridine

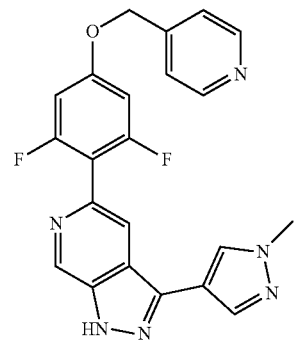 [SMILES: Cn1cc(-c2n[nH]c3cnc(-c4c(F)cc(OCc5ccncc5)cc4F)cc23)cn1]

This compound was prepared according to the procedures described in Example 106, using 4-(bromomethyl)pyridine instead of tert-butyl 2-(bromomethyl)azetidine-1-carboxylate as starting material. LCMS calculated for $C_{22}H_{17}F_2N_6O$ $(M+H)^+$: m/z=419.1; Found: 419.1.

Example 109. 3,5-Difluoro-4-(3-(1-methyl-1H-pyrazol-4-yl)-1H-pyrazolo[3,4-c]pyridin-5-yl)phenyl dimethylcarbamate

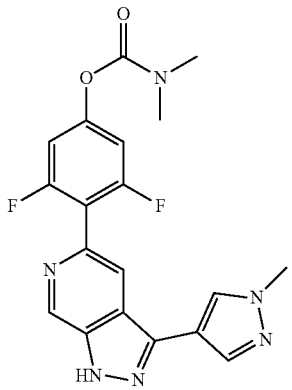 [SMILES: CN(C)C(=O)Oc1cc(F)c(-c2cc3c(-c4cnn(C)c4)n[nH]c3cn2)c(F)c1]

To a solution of 3,5-difluoro-4-(3-(1-methyl-1H-pyrazol-4-yl)-1-((2-(trimethylsilyl)ethoxy)methyl)-1H-pyrazolo[3,4-c]pyridin-5-yl)phenol (30 mg, 0.066 mmol, Example 106, Step 1) in THF (1 ml) was added dimethylcarbamic chloride (10.58 mg, 0.098 mmol) and triethylamine (0.018 ml, 0.131 mmol). After stirring at r.t. for 30 min, 1-methylpiperidin-4-ol (3.94 mg, 0.034 mmol) was added, and the reaction mixture was stirred for 1 h. After the reaction mixture was stirred at r.t. for 1 h, it was quenched with water. The mixture was extracted with ethyl acetate. The separated organic phases were washed with brine and dried over sodium sulfate. The solvents were evaporated in vacuo. Then 1M solution of HCl in water (1 mL) and 4M solution of HCl in dioxane (1 mL) were added to the crude residue, and reaction mixture was stirred at 80° C. for 1 h. Methanol (1 mL) was added, and reaction mixture was further stirred at 80° C. for 30 min. The reaction mixture was then diluted with acetonitrile and was purified with prep-LCMS (XBridge C18 column, eluting with a gradient of acetonitrile/water containing 0.1% TFA, at flow rate of 60 mL/min). LCMS calculated for $C_{19}H_{17}F_2N_6O_2$ (M+H)$^+$: m/z=399.1; Found: 399.1.

Example 110. 3,5-Difluoro-4-(3-(1-methyl-1H-pyrazol-4-yl)-1H-pyrazolo[3,4-c]pyridin-5-yl)phenyl morpholine-4-carboxylate

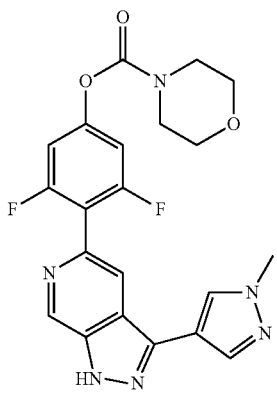 [SMILES: Cn1cc(-c2n[nH]c3cnc(-c4c(F)cc(OC(=O)N5CCOCC5)cc4F)cc23)cn1]

This compound was prepared according to the procedures described in Example 109, using morpholine-4-carbonyl chloride instead of dimethylcarbamic chloride as starting material. LCMS calculated for $C_{21}H_{19}F_2N_6O_3$ (M+H)$^+$: m/z=441.2; Found: 441.1.

Example 111. N-Methyl-1-(3-methyl-4-(3-(1-methyl-1H-pyrazol-4-yl)-1H-pyrazolo[3,4-c]pyridin-5-yl)phenyl)methanamine

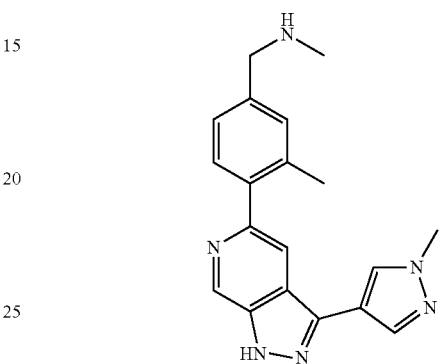

This compound was prepared according to the procedures described in Example 86, using (4-bromo-3-methylphenyl)methanol instead of (3-bromo-2-methylphenyl)methanol as starting material. LCMS calculated for $C_{19}H_{21}N_6$ (M+H)$^+$: m/z=333.2; Found: 333.1.

Example 112. N-Methyl-1-(4-(3-(1-methyl-1H-pyrazol-4-yl)-1H-pyrazolo[3,4-c]pyridin-5-yl)-3-(trifluoromethyl)phenyl)methanamine

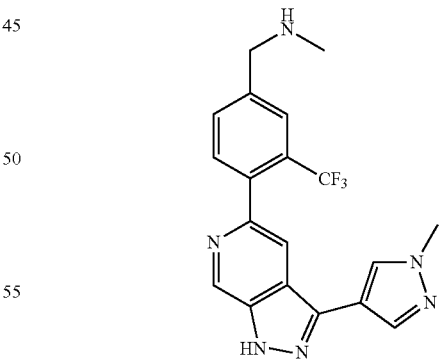

This compound was prepared according to the procedures described in Example 86, using (4-bromo-3-(trifluoromethyl)phenyl)methanol instead of (3-bromo-2-methylphenyl)methanol as starting material. LCMS calculated for $C_{19}H_{18}F_3N_6$ (M+H)$^+$: m/z=387.2; Found: 387.1.

Example 113. 1-(5-(5-(2-Fluoro-6-methyl-4-((methylamino)methyl)phenyl)-1H-pyrazolo[3,4-c]pyridin-3-yl)pyridin-2-yl)pyrrolidin-3-ol

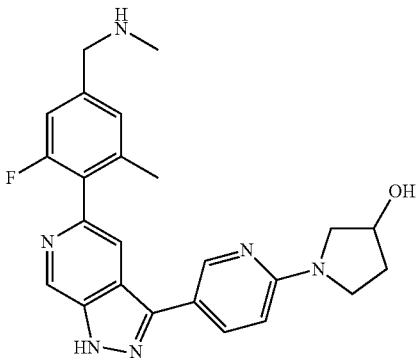 [SMILES: CNCc1cc(C)c(-c2cc3c(-c4ccc(N5CCC(O)C5)nc4)n[nH]c3cn2)c(F)c1]

Step 1. 4-Bromo-3-fluoro-5-methylaniline

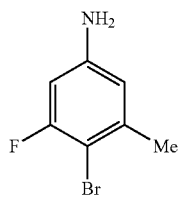

N-Bromosuccinimide (15.8 g, 89 mmol) was added to a solution of 3-fluoro-5-methylaniline (Combi-Blocks, 11 g, 88 mmol) in DMF (80 mL) cooled to 0° C. in an ice bath. The reaction mixture was stirred at 0° C. for 30 minutes. After warming to r.t., the reaction was stirred for an additional 1 hour. Water and EtOAc were then added, and the organic phase was washed with saturated aqueous NaHCO$_3$ and brine. The organic phase was then dried over magnesium sulfate and the solvents were evaporated under reduced pressure. The crude product was purified by Biotage Isolera™ (17.2 g, 96%). LCMS calculated for C$_7$H$_8$BrFN (M+H)$^+$ m/z=203.9; found 204.0.

Step 2. 2-Bromo-1-fluoro-5-iodo-3-methylbenzene

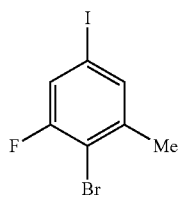

To a solution of 4-bromo-3-fluoro-5-methylaniline (7.28 g, 36 mmol) in acetonitrile (190 mL) cooled to 0° C. in an ice bath was added sulfuric acid (4.75 mL, 89 mmol) dissolved in H$_2$O (10 mL). After stirring for 5 minutes, a solution of sodium nitrite (4.92 g, 71.4 mmol) in water (10 mL) was added dropwise and the reaction mixture was stirred for an additional 15 minutes at 0° C. Potassium iodide (23.7 g, 143 mmol) in water (20 mL) was then added, and the ice-bath was removed. After warming to r.t. the reaction mixture was stirred for an additional 20 minutes before the reaction was quenched via the addition of aqueous Na$_2$S$_2$O$_3$. The mixture was then extracted with ethyl acetate and the combined organic phases were washed with brine, dried over magnesium sulfate, and concentrated under reduced pressure. The crude product was purified by Biotage Isolera™ (10.3 g, 94%). $^1$H NMR (400 MHz, CDCl$_3$) δ 7.39 (br s, 1H), 7.29 (m, 1H), 2.38 (s, 3H) ppm.

Step 3. 2-Bromo-1-fluoro-3-methyl-5-vinylbenzene

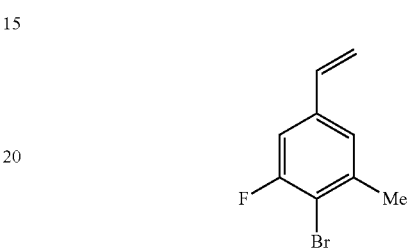

To a solution of 2-bromo-1-fluoro-5-iodo-3-methylbenzene (10.3 g, 32.8 mmol) in 1,4-dioxane (80 mL) and water (13.3 mL) was added 4,4,5,5-tetramethyl-2-vinyl-1,3,2-dioxaborolane (Aldrich, 6.16 mL, 34.5 mmol), [1,1'-bis(diphenylphosphino)ferrocene]dichloropalladium(II) (Pd(dppf)Cl$_2$) (2.40 g, 3.3 mmol), and potassium phosphate tribasic (13.9 g, 65.7 mmol). The reaction mixture was degassed, backfilled with nitrogen, and heated to 70° C. for 1 h. After cooling to r.t. the reaction mixture was filtered over a pad of Celite. The filtrate was diluted with water and extracted with ethyl acetate. The combined organic phases were washed with brine, dried over magnesium sulfate, and concentrated under reduced pressure. The crude product was purified by Biotage Isolera™ (5.46 g, 77%). $^1$H NMR (400 MHz, CDCl$_3$) δ 7.05 (br s, 1H), 7.01 (dd, J=2.0, 9.4 Hz, 1H), 6.60 (dd, J=10.9, 17.5 Hz, 1H), 5.75 (d, J=17.5 Hz, 1H), 5.31 (d, J=10.9 Hz, 1H), 2.42 (s, 3H) ppm.

Step 4. 4-Bromo-3-fluoro-5-methylbenzaldehyde

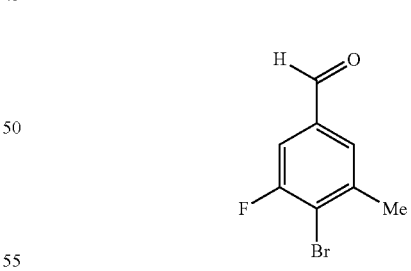

To a solution of 2-bromo-1-fluoro-3-methyl-5-vinylbenzene (5.46 g, 25.4 mmol) in acetone (46 mL) and water (4.6 mL) was sequentially added sodium periodate (21.7 g, 102 mmol) and a 4% aqueous solution of osmium tetroxide (8.07 mL, 1.27 mmol). The reaction mixture was stirred at r.t. for 2 h. The reaction mixture was then filtered over a pad of Celite. The filtrate was diluted with water and extracted with ethyl acetate. The combined organic phases were washed with brine, dried over magnesium sulfate, and concentrated under reduced pressure. The crude product was purified by Biotage Isolera™ (3.22 g, 58%). $^1$H NMR (400 MHz, CDCl$_3$) δ 9.93 (d, J=1.8 Hz, 1H), 7.55 (d, J=1.8 Hz, 1H), 7.44 (dd, J=1.8, 7.8 Hz, 1H), 2.52 (s, 3H) ppm.

Step 5. 1-(4-Bromo-3-fluoro-5-methylphenyl)-N-methylmethanamine

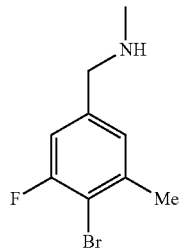

In a 20 mL scintillation vial equipped with a magnetic stir bar, 4-bromo-3-fluoro-5-methylbenzaldehyde (1.46 g, 6.70 mmol) was dissolved in MeOH (6.70 mL), and the reaction mixture was placed under a nitrogen environment. Following this, a 33% solution of methanamine (3.15 g, 33.5 mmol) in ethanol and titanium(IV) isopropoxide (0.982 mL, 3.35 mmol) were added, and the reaction mixture was stirred at r.t. for 3 hours. Sodium borohydride (1.01 g, 26.8 mmol) was then added to the reaction mixture portion wise, and stirring was continued at r.t. for an additional 1.5 hours. NH$_4$OH (30% aqueous solution) was added to the reaction mixture and stirring continued for another 15 minutes. The reaction mixture was then acidified with 1 N HCl and extracted with ethyl acetate. The water layer was then made basic and extracted with ethyl acetate. The combined organic phases were washed with brine, dried over magnesium sulfate, and concentrated under reduced pressure to afford 1-(4-bromo-3-fluoro-5-methylphenyl)-N-methylmethanamine (1.32 g, 85%) as a light yellow oil. The crude product was used in the next step without further purification. LCMS calculated for C$_9$H$_{12}$BrFN (M+H)$^+$ m/z=232.0; found 231.9.

Step 6. tert-Butyl 4-bromo-3-fluoro-5-methylbenzyl(methyl)carbamate

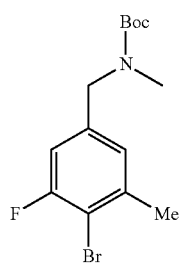 [SMILES: Cc1cc(CN(C)C(=O)OC(C)(C)C)cc(F)c1Br]

To a solution of 1-(4-bromo-3-fluoro-5-methylphenyl)-N-methylmethanamine (1.32 g, 5.67 mmol) and triethylamine (1.58 mL, 11.34 mmol) in THF (18.9 mL) was added di-tert-butyl dicarbonate (1.58 mL, 6.80 mmol). The reaction mixture was then stirred at ambient temperature for 1 hour. The reaction mixture was then diluted with water and extracted with ethyl acetate. The combined organic layers were dried with magnesium sulfate and concentrated under reduced pressure. The crude product was purified by Biotage Isolera™ (1.42 g, 78%). LCMS calculated for C$_{10}$H$_{12}$BrFNO$_2$ (M+H—C$_4$H$_8$)$^+$ m/z=276.0; found 276.0.

Step 7. tert-Butyl 3-fluoro-5-methyl-4-(4,4,5,5-tetramethyl-1,3,2-dioxaborolan-2-yl)benzyl(methyl)carbamate

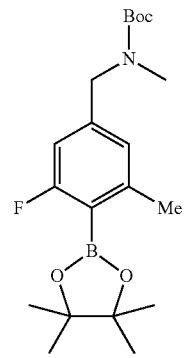 [SMILES: Cc1cc(CN(C)C(=O)OC(C)(C)C)cc(F)c1B1OC(C)(C)C(C)(C)O1]

In an oven-dried 20 mL scintillation vial with a stir bar, tert-butyl (4-bromo-3-fluoro-5-methylbenzyl)(methyl)carbamate (573 mg, 1.73 mmol) was dissolved in THF (11.5 mL). The reaction mixture was cooled to −78° C. in a dry ice/acetone bath and BuLi (1.6 M solution in hexanes, 1.19 mL, 1.90 mmol) was added dropwise. The reaction mixture was then allowed to stir for 3 minutes before 2-isopropyl-4,4,5,5-tetramethyl-1,3,2-dioxaborolane (427 μL, 2.25 mmol) was added dropwise. The mixture was warmed to r.t and stirred for an additional 5 hours. The reaction mixture was then quenched by the addition of water, acidified to pH 5-6 using 1 N HCl, and extracted with ethyl acetate. The combined organic layers were then washed with brine, dried over magnesium sulfate, and concentrated to afford tert-butyl 3-fluoro-5-methyl-4-(4,4,5,5-tetramethyl-1,3,2-dioxaborolan-2-yl)benzyl(methyl)carbamate (679 mg, quantitative yield). The crude product was used in the next step without further purification. LCMS calculated for C$_{16}$H$_{24}$BrFNO$_4$ (M+H—C$_4$H$_8$)$^+$ m/z=324.2; found 324.1.

Step 8. tert-Butyl 5-(4-((tert-butoxycarbonyl(methyl)amino)methyl)-2-fluoro-6-methylphenyl)-1H-pyrazolo[3,4-c]pyridine-1-carboxylate

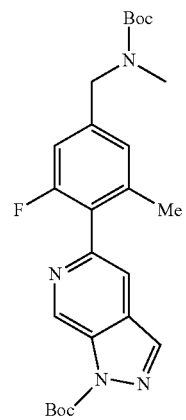 [SMILES: Cc1cc(CN(C)C(=O)OC(C)(C)C)cc(F)c1-c1cc2cnn(C(=O)OC(C)(C)C)c2cn1]

In a 20 mL scintillation vial equipped with a magnetic stir bar, tert-butyl 5-chloro-1H-pyrazolo[3,4-c]pyridine-1-carboxylate (0.649 g, 2.56 mmol) and tert-butyl (3-fluoro-5-methyl-4-(4,4,5,5-tetramethyl-1,3,2-dioxaborolan-2-yl)benzyl)(methyl)carbamate (970 mg, 2.56 mmol) were dissolved in 1,4-dioxane (8.0 mL) and water (2.0 mL). To this mixture was added chloro(2-dicyclohexylphosphino-2',4',6'-triisopropyl-1,1'-biphenyl)[2-(2'-amino-1,1'-biphenyl)]palladium (II) (Pd XPhos G2) (400 mg, 0.51 mmol) and potassium phosphate tribasic (1.6 g, 7.67 mmol). The reaction mixture was degassed (by bubbling nitrogen through it), sealed and heated to 75° C. for 1 h. After cooling to r.t., the reaction mixture was diluted with water and extracted with ethyl acetate. The combined organic layers were washed with brine, dried over magnesium sulfate, and concentrated under reduced pressure. The crude product was purified by Biotage Isolera™ (300 mg, 25%). LCMS calculated for $C_{25}H_{32}FN_4O_4$ $(M+H)^+$ m/z=471.2; found 471.2.

Step 9. tert-Butyl 5-(4-(((tert-butoxycarbonyl (methyl)amino)methyl)-2-fluoro-6-methylphenyl)-3-iodo-1H-pyrazolo[3,4-c]pyridine-1-carboxylate

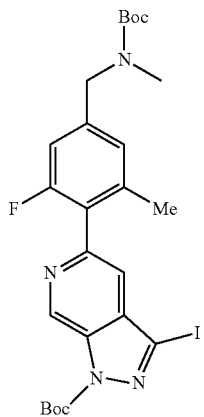 [SMILES: Cc1cc(CN(C)C(=O)OC(C)(C)C)cc(F)c1-c1cc2c(I)nn(C(=O)OC(C)(C)C)c2cn1]

In a 20 mL scintillation vial with a stir bar, tert-butyl 5-(4-(((tert-butoxycarbonyl)(methyl)amino)methyl)-2-fluoro-6-methylphenyl)-1H-pyrazolo[3,4-c]pyridine-1-carboxylate (0.30 g, 0.638 mmol) and potassium carbonate (0.441 g, 3.19 mmol) were dissolved in 1,4-dioxane (5 mL) and water (5 mL). The reaction mixture was heated to 80° C. for 2 hours. The reaction mixture was diluted with water and extracted with ethyl acetate. The combined organic phases were washed with brine, dried over magnesium sulfate, and concentrated under reduced pressure. The crude intermediate was dissolved in DMF (10 mL) and N-iodosuccinimide (0.15 g, 0.7 mmol) was added, and the reaction mixture heated to 60° C. for 1 hour. Triethylamine (0.15 ml, 1 mmol) and di-tert-butyl dicarbonate (0.168 ml, 0.72 mmol) were added to the reaction mixture, which was stirred at r.t for an additional 1 h. The reaction mixture was then concentrated under reduced pressure and the crude product was purified by Biotage Isolera™. LCMS calculated for $C_{25}H_{31}FIN_4O_4$ $(M+H)^+$ m/z=597.1; found 597.1.

Step 10. tert-Butyl 5-(4-(((tert-butoxycarbonyl(methyl) amino)methyl)-2-fluoro-6-methylphenyl)-3-(6-chloropyridin-3-yl)-1H-pyrazolo[3,4-c]pyridine-1-carboxylate

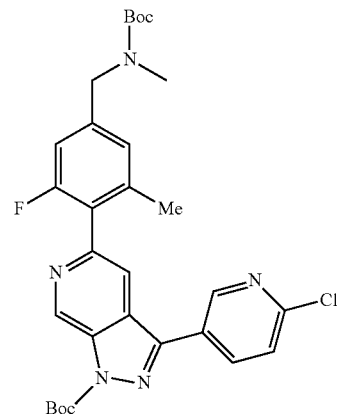 [SMILES: Cc1cc(CN(C)C(=O)OC(C)(C)C)cc(F)c1-c1cc2c(-c3ccc(Cl)nc3)nn(C(=O)OC(C)(C)C)c2cn1]

tert-Butyl 5-(4-(((tert-butoxycarbonyl)(methyl)amino) methyl)-2-fluoro-6-methylphenyl)-3-iodo-1H-pyrazolo[3,4-c]pyridine-1-carboxylate (0.3 g, 0.503 mmol), PdCl$_2$(dppf)-CH$_2$Cl$_2$ adduct (0.082 g, 0.101 mmol), (6-chloropyridin-3-yl)boronic acid (0.103 g, 0.654 mmol) and potassium phosphate (320 mg, 1.51 mmol) were placed in a flask and the flask was evacuated and backfilled with nitrogen three times. Dioxane (5 ml) and degassed water (0.5 ml) were added, and the reaction mixture was stirred at 80° C. for 1 h. After cooling to r.t. water was added, and the mixture was extracted with EtOAc. The separated organic layer was washed with brine and dried over sodium sulfate. The solvent was evaporated under reduced pressure. The crude product was purified by Biotage Isolera™. LCMS calculated for $C_{30}H_{34}ClFN_5O_4$ $(M+H)^+$ m/z=582.2; found 582.2.

Step 11. 1-(5-(5-(2-Fluoro-6-methyl-4-((methylamino)methyl)phenyl)-1H-pyrazolo[3,4-c]pyridin-3-yl)pyridin-2-yl)pyrrolidin-3-ol Pyrrolidin-3-ol (8.98 mg, 0.103 mmol) was added to a solution of tert-butyl 5-(4-(((tert-butoxycarbonyl)(methyl) amino)methyl)-2-fluoro-6-methylphenyl)-3-(6-chloropyridin-3-yl)-1H-pyrazolo[3,4-c]pyridine-1-carboxylate (0.020 g, 0.034 mmol) in 2-methoxyethan-1-ol (0.5 mL). After stirring at 120° C. overnight, the reaction mixture was diluted with acetonitrile and was purified with prep-LCMS (XBridge C18 column, eluting with a gradient of acetonitrile/water containing 0.1% TFA, at flow rate of 60 mL/min). LCMS calculated for $C_{24}H_{26}FN_6O$ $(M+H)^+$: m/z=433.2; Found: 433.2.

Example 114. 1-(3-Fluoro-4-(3-(6-(3-methoxypiperidin-1-yl)pyridin-3-yl)-1H-pyrazolo[3,4-c]pyridin-5-yl)-5-methylphenyl)-N-methylmethanamine

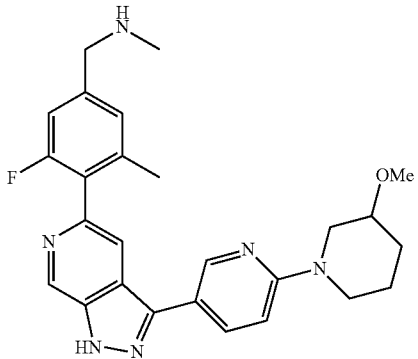 [SMILES: CNCc1cc(C)c(-c2cc3c(-c4ccc(N5CCCC(OC)C5)nc4)noc3cn2)c(F)c1]

This compound was prepared according to the procedures described in Example 113, using 3-methoxypiperidine instead of pyrrolidin-3-ol as starting material. LCMS calculated for $C_{26}H_{30}FN_6O$ (M+H)$^+$: m/z=461.2; Found: 461.2.

Example 115. 5-(2-Fluoro-6-methoxyphenyl)-3-(6-(1-methylpiperidin-4-yl)pyridin-2-yl)-1H-pyrazolo[3,4-c]pyridine

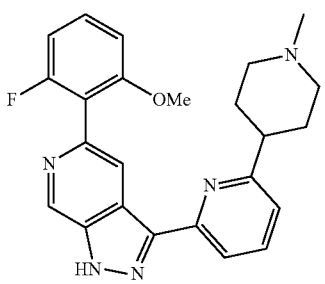 [SMILES: COc1cccc(F)c1-c1cc2c(-c3cccc(C4CCN(C)CC4)n3)n[nH]c2cn1]

Step 1. 3-(6-Bromopyridin-2-yl)-5-(2-fluoro-6-methoxyphenyl)-1-((2-(trimethylsilyl)ethoxy)methyl)-1H-pyrazolo[3,4-c]pyridine

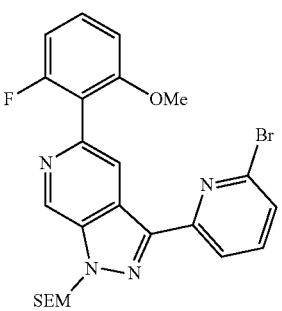 [SMILES: COc1cccc(F)c1-c1cc2c(-c3cccc(Br)n3)nn(COCC[Si](C)(C)C)c2cn1]

5-(2-Fluoro-6-methoxyphenyl)-3-iodo-1-((2-(trimethylsilyl)ethoxy)methyl)-1H-pyrazolo[3,4-c]pyridine (0.3 g, 0.6 mmol, Example 34, Step 5), triphenylphosphine palladium chloride (50 mg, 0.07 mmol) and 2-bromo-6-(tributylstannyl)pyridine (0.6 g, 1.34 mmol) were placed in a flask and the flask was evacuated and backfilled with nitrogen three times. Then DMF (4 ml) was added, and reaction mixture was stirred at 110° C. for 5 h. After cooling to r.t. water was added, the mixture was extracted with EtOAc. The separated organic layer was washed with brine and dried over sodium sulfate. The solvent was evaporated. The crude product was purified by Biotage Isolera™. LCMS calculated for $C_{24}H_{27}BrFN_4O_2Si$ (M+H)$^+$ m/z=529.1; found 529.1.

Step 2. 5-(2-Fluoro-6-methoxyphenyl)-3-(6-(1-methyl-1,2,3,6-tetrahydropyridin-4-yl)pyridin-2-yl)-1-((2-(trimethylsilyl)ethoxy)methyl)-1H-pyrazolo[3,4-c]pyridine

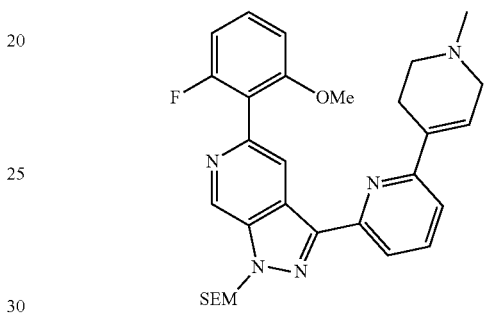

3-(6-Bromopyridin-2-yl)-5-(2-fluoro-6-methoxyphenyl)-1-((2-(trimethylsilyl)ethoxy)methyl)-1H-pyrazolo[3,4-c]pyridine (50 mg, 0.09 mmol), (1-methyl-1,2,3,6-tetrahydropyridin-4-yl)boronic acid (20 mg, 0.14 mmol), chloro(2-dicyclohexylphosphino-2',4',6'-triisopropyl-1,1'-biphenyl)[2-(2'-amino-1,1'-biphenyl)]palladium(II) (Pd XPhos G2) (5 mg, 0.006 mmol) and potassium phosphate (40 mg, 0.18 mmol) were placed in a flask and the flask was evacuated and backfilled with nitrogen three times. Dioxane (1 mL) and degassed water (0.1 mL) were added, and reaction mixture was stirred at 90° C. for 2 h. After cooling to r.t., the reaction mixture was diluted with ethyl acetate, and the resulting mixture was washed with brine. The separated organic phase was dried over sodium sulfate. The solvents were evaporated under reduced pressure and the obtained crude product was purified by Biotage LCMS calculated for $C_{30}H_{37}FN_5O_2Si$ (M+H)$^+$ m/z=546.3; found 546.2.

Step 3. 5-(2-Fluoro-6-methoxyphenyl)-3-(6-(1-methylpiperidin-4-yl)pyridin-2-yl)-1H-pyrazolo[3,4-c]pyridine Pd/C (20 mg, 5 wt %) was added to a solution of 5-(2-fluoro-6-methoxyphenyl)-3-(6-(1-methyl-1,2,3,6-tetrahydropyridin-4-yl)pyridin-2-yl)-1-((2-(trimethylsilyl)ethoxy)methyl)-1H-pyrazolo[3,4-c]pyridine (16 mg, 0.03 mmol) in MeOH (2 mL). After stirring under hydrogen for 2 h at r.t., the catalyst was filtered-off. The solvent of the filtrate was evaporated in vacuo. Then 1M solution of HCl in water (1 mL) and 4M solution of HCl in dioxane (1 mL) were added to obtained crude product, and the reaction mixture was stirred at 80° C. for 1 h. Methanol (1 mL) was added, and the reaction mixture was further stirred at 80° C. for 30 min. The reaction mixture was then diluted with acetonitrile and was purified with prep-LCMS (XBridge C18 column, eluting with a gradient of acetonitrile/water containing 0.1% TFA, at flow rate of 60 mL/min). LCMS calculated for $C_{24}H_{25}FN_5O$ (M+H)$^+$: m/z=418.2; Found: 418.2.

Example 116. 3-(4-Bromostyryl)-5-(2-fluoro-6-methoxyphenyl)-1H-pyrazolo[3,4-c]pyridine

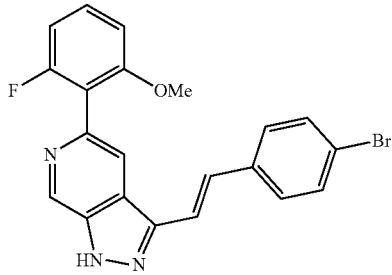 [SMILES: COc1cccc(F)c1-c1cc2c(/C=C/c3ccc(Br)cc3)n[nH]c2cn1]

5-(2-Fluoro-6-methoxyphenyl)-3-iodo-1-((2-(trimethylsilyl)ethoxy)methyl)-1H-pyrazolo[3,4-c]pyridine (50 mg, 0.1 mmol), 1-bromo-4-vinylbenzene (55 mg, 0.3 mmol), chloro(2-dicyclohexylphosphino-2',4',6'-triisopropyl-1,1'-biphenyl)[2-(2'-amino-1,1'-biphenyl)]palladium(II) (Pd XPhos G2) (5 mg, 0.006 mmol) and potassium phosphate (20 mg, 0.1 mmol) were placed in a vial, and the vial was evacuated and backfilled with nitrogen three times. Then dioxane (1 mL) and degassed water (0.1 mL) were added, and reaction mixture was stirred at 80° C. overnight. After cooling to r.t., the reaction mixture was diluted with ethyl acetate, and the resulting mixture was washed with brine. The separated organic phase was dried over sodium sulfate. The solvents were evaporated in vacuo. Then 1M solution of HCl in water (1 mL) and 4M solution of HCl in dioxane (1 mL) were added to the crude residue, and the reaction mixture was stirred at 80° C. for 1 h. Methanol (1 mL) was added, and the reaction mixture was further stirred at 80° C. for 30 min. The reaction mixture was then diluted with acetonitrile and was purified with prep-LCMS (XBridge C18 column, eluting with a gradient of acetonitrile/water containing 0.1% TFA, at flow rate of 60 mL/min). LCMS calculated for $C_{21}H_{16}BrFN_3O$ (M+H)$^+$: m/z=424.1; Found: 424.1.

Example 117. 1-(3-Fluoro-5-methyl-4-(3-(6-morpholinopyridin-2-yl)-1H-pyrazolo[3,4-c]pyridin-5-yl)phenyl)-N-methylmethanamine

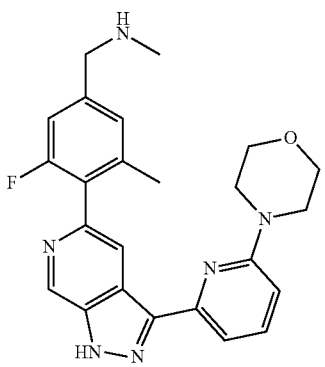 [SMILES: CNCc1cc(C)c(-c2cc3c(-c4cccc(N5CCOCC5)n4)n[nH]c3cn2)c(F)c1]

Step 1. tert-Butyl 4-(3-(6-chloropyridin-2-yl)-1-((2-(trimethylsilyl)ethoxy)methyl)-1H-pyrazolo[3,4-c]pyridin-5-yl)-3-fluoro-5-methylbenzyl(methyl)carbamate

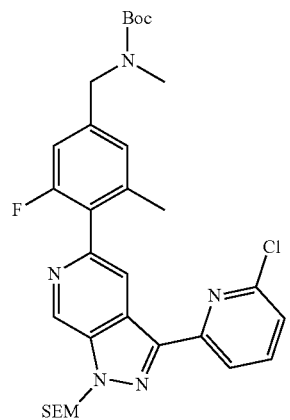 [SMILES: Cc1cc(CN(C)C(=O)OC(C)(C)C)cc(F)c1-c1cc2c(-c3cccc(Cl)n3)nn(COCC[Si](C)(C)C)c2cn1]

This compound was prepared according to the procedures described in Example 115 (Step 1), using tert-butyl 3-fluoro-5-methyl-4-(4,4,5,5-tetramethyl-1,3,2-dioxaborolan-2-yl)benzyl(methyl)carbamate instead of (2-fluoro-6-methoxyphenyl)boronic acid and 2-chloro-6-(tributylstannyl)pyridine instead of 2-bromo-6-(tributylstannyl)pyridine as starting material. LCMS calculated for $C_{31}H_{40}ClFN_5O_3Si$ (M+H)$^+$: m/z=612.2; Found: 612.2.

Step 2. 1-(3-Fluoro-5-methyl-4-(3-(6-morpholinopyridin-2-yl)-1H-pyrazolo[3,4-c]pyridin-5-yl)phenyl)-N-methylmethanamine tert-Butyl (4-(3-(6-chloropyridin-2-yl)-1-((2-(trimethylsilyl)ethoxy)methyl)-1H-pyrazolo[3,4-c]pyridin-5-yl)-3-fluoro-5-methylbenzyl)(methyl)carbamate (10 mg, 0.016 mmol), morpholine (14 mg, 0.163 mmol), cesium carbonate (5.3 mg, 0.016 mmol) and chloro(2-dicyclohexylphosphino-2',6'-di-i-propoxy-1,1'-biphenyl)(2'-amino-1,1'-biphenyl-2-yl)palladium(II) (RuPhos Pd G2, 5 mg, 6.3 µmol) were placed in a vial, and the vial was evacuated and backfilled with nitrogen three times. Dioxane (2 mL) was added and the reaction mixture was stirred at 100° C. overnight. After cooling down to r.t., the solids were filtered off, and the solvent of the filtrate was evaporated in vacuo. Then 1M solution of HCl in water (1 mL) and 4M solution of HCl in dioxane (1 mL) were added to the crude residue, and the reaction mixture was stirred at 80° C. for 1 h. Methanol (1 mL) was added, and the reaction mixture was further stirred at 80° C. for 30 min. The reaction mixture was then diluted with acetonitrile and was purified with prep-LCMS (XBridge C18 column, eluting with a gradient of acetonitrile/water containing 0.1% TFA, at flow rate of 60 mL/min). LCMS calculated for $C_{24}H_{26}FN_6O$ (M+H)$^+$: m/z=433.2; Found: 433.3.

Example 118. N-Ethyl-6-(5-(2-fluoro-6-methyl-4-((methylamino)methyl)phenyl)-1H-pyrazolo[3,4-c]pyridin-3-yl)-N-methylpyridin-2-amine

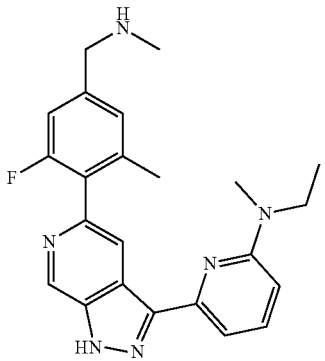 [SMILES: CCN(C)c1cccc(-c2n[nH]c3cnc(-c4c(C)cc(CNC)cc4F)cc23)n1]

This compound was prepared according to the procedures described in Example 117, using N-methylethanamine instead of morpholine as starting material. LCMS calculated for $C_{23}H_{26}FN_6$ $(M+H)^+$: m/z=405.2; Found: 405.3.

Example 119. 1-(3-Fluoro-4-(3-(6-(4-methylpiperazin-1-yl)pyridin-3-yl)-1H-pyrazolo[3,4-c]pyridin-5-yl)-5-(trifluoromethyl)phenyl)-N-methylmethanamine

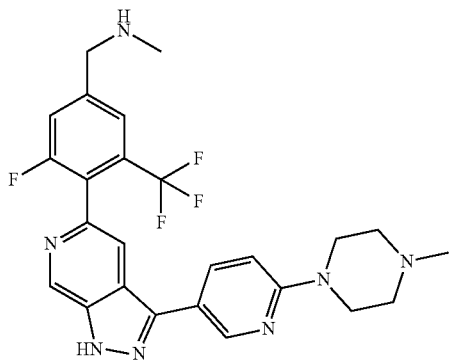 [SMILES: CNCc1cc(F)c(-c2cc3c(-c4ccc(N5CCN(C)CC5)nc4)n[nH]c3cn2)c(C(F)(F)F)c1]

Step 1. tert-Butyl 3-fluoro-5-(trifluoromethyl)benzyl(methyl)carbamate

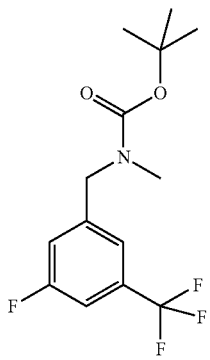 [SMILES: CN(Cc1cc(F)cc(C(F)(F)F)c1)C(=O)OC(C)(C)C]

To a solution of 3-fluoro-5-(trifluoromethyl)benzaldehyde (20.0 g, 104 mmol) in MeOH (500 ml) was added methylamine solution (104 ml, 208 mmol, 2M in THF) and the reaction was stirred at r.t. for 1 hour. After this time, sodium borohydride (7.88 g, 208 mmol) was added, and the reaction mixture was stirred for additional 30 mins. The reaction mixture was concentrated to dryness, and 300 mL of DCM was added. An aqueous solution of sodium bicarbonate was added, and the reaction mixture was stirred at r.t. for another 1 hour. The organic layer was separated, dried over MgSO$_4$, filtered, and concentrated to dryness. To a solution of the resulting residue in DCM (521 ml) was added triethylamine (14.5 ml, 104 mmol) and di-tert-butyl dicarbonate (22.7 g, 104 mmol). The resulting solution was stirred at r.t. for 1 hour. The solution was concentrated to dryness, and the residue was purified by silica gel chromatography using 0-70% ethyl acetate in hexanes to afford desired product as colorless oil (15.1 g, 47.0%). LC-MS calculated for $C_{10}H_{10}F_4NO_2$ $(M+H-C_4H_8)^+$: 252.1; found 252.2.

Step 2. tert-Butyl 5-(4-((tert-butoxycarbonyl(methyl)amino)methyl)-2-fluoro-6-(trifluoromethyl)phenyl)-1H-pyrazolo[3,4-c]pyridine-1-carboxylate

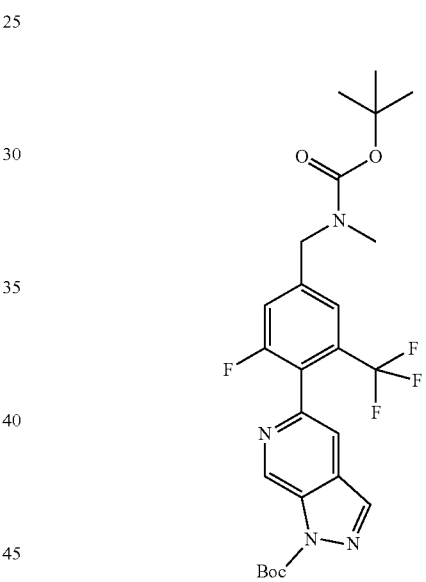

To a solution of tert-butyl (3-fluoro-5-(trifluoromethyl)benzyl)(methyl)carbamate (2.3 g, 7.5 mmol) in THF (33.3 ml) was added n-butyllithium (8.98 ml, 22.5 mmol) dropwise at −78° C., and the reaction mixture was stirred at −78° C. for 1 hour. 2-Isopropoxy-4,4,5,5-tetramethyl-1,3,2-dioxaborolane (5.57 g, 29.9 mmol) was added, and the mixture was allowed to warm up to r.t. over 1 hour. The resulting solution was quenched with water, neutralized to pH=6, and the mixture was extracted with ethyl acetate. The organic layer was washed with brine, dried over MgSO$_4$, filtered, and then concentrated to dryness. To a solution of the resulting residue in dioxane (33.3 ml) and water (8.32 ml) was added potassium phosphate (1.30 g, 7.48 mmol) and tert-butyl 5-chloro-1H-pyrazolo[3,4-c]pyridine-1-carboxylate (1.0 g, 3.94 mmol). The mixture was degassed with N$_2$, chloro(2-dicyclohexylphosphino-2',4',6'-tri-i-propyl-1,1'-biphenyl)(2'-amino-1,1'-biphenyl-2-yl) palladium(II) (0.118 g, 0.150 mmol) was added, and the reaction mixture was stirred at 60° C. for 1 hour. The mixture was concentrated to dryness. The residue was purified by silica gel chromatography using 0-100% ethyl acetate in hexanes to afford desired product as yellowish oil. LC-MS calculated for $C_{25}H_{29}F_4N_4O_4$ (M+H)$^+$: m/z=525.2; Found 525.2.

Step 3. tert-Butyl 5-(4-(((tert-butoxycarbonyl) (methyl)amino)methyl)-2-fluoro-6-(trifluoromethyl) phenyl)-3-iodo-1H-pyrazolo[3,4-c]pyridine-1-carboxylate

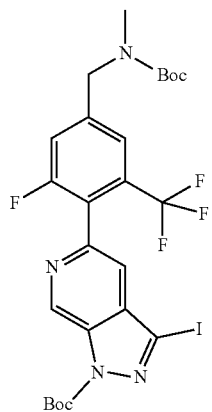 [SMILES: CN(Cc1cc(F)c(-c2cc3c(I)nn(C(=O)OC(C)(C)C)c3cn2)c(C(F)(F)F)c1)C(=O)OC(C)(C)C]

To a solution of tert-butyl 5-(4-(((tert-butoxycarbonyl) (methyl)amino)methyl)-2-fluoro-6-(trifluoromethyl)phenyl)-1H-pyrazolo[3,4-c]pyridine-1-carboxylate (0.30 g, 0.572 mmol) in dioxane (5 ml) and water (5 ml) was added potassium carbonate (0.395 g, 2.86 mmol), and the reaction mixture was stirred at 80° C. for 2 hours. The mixture was cooled to r.t., diluted with DCM, and washed with water, sodium bicarbonate and brine. The organic layer was dried over MgSO$_4$, filtered, and then concentrated to dryness.

NIS (0.143 g, 0.636 mmol) was added to a solution of the obtained residue in DMF (6 ml). After stirring at 70° C. for 2 h, the reaction mixture was cooled to r.t. and triethylamine (0.089 ml, 0.636 mmol) was added followed by di-tert-butyl dicarbonate (0.148 ml, 0.636 mmol). After stirring for an addition 2 h at r.t., water was added. The mixture was extracted with EtOAc. The separated organic layer was washed with brine, dried over sodium sulfate, and the solvent was evaporated. The crude product was purified by Biotage Isolera™. LCMS calculated for $C_{25}H_{28}F_4IN_4O_4$ (M+H)$^+$ m/z=651.1; found 651.1.

Step 4. 1-(3-Fluoro-4-(3-(6-(4-methylpiperazin-1-yl) pyridin-3-yl)-1H-pyrazolo[3,4-c]pyridin-5-yl)-5-(trifluoromethyl)phenyl)-N-methylmethanamine To a screw-cap vial equipped with a magnetic stir bar was added tert-butyl 5-(4-(((tert-butoxycarbonyl)(methyl) amino)methyl)-2-fluoro-6-(trifluoromethyl)phenyl)-3-iodo-1H-pyrazolo[3,4-c]pyridine-1-carboxylate (38.4 mg, 0.059 mmol), 1-methyl-4-(5-(4,4,5,5-tetramethyl-1,3,2-dioxaborolan-2-yl)pyridin-2-yl)piperazine (18 mg, 0.059 mmol), chloro(2-dicyclohexylphosphino-2',4',6'-triisopropyl-1,1'-biphenyl)[2-(2'-amino-1,1'-biphenyl)]palladium(II) (XPhos Pd G2, 7.0 mg, 8.90 µmol) and cesium carbonate (59.7 mg, 0.183 mmol). The vial was sealed with a Teflon-lined septum, evacuated and backfilled with nitrogen (this process was repeated a total of three times). Then 1,4-dioxane (2.00 ml) was added via syringe, followed by water (200.0 µl). The reaction mixture was heated to 60° C. for 16 h. The reaction mixture was concentrated. To the residue was added $CH_2Cl_2$ (2.0 mL) followed by TFA (2.0 mL). The mixture was stirred at room temperature for 15 min, and then concentrated. The residue was purified using prep-LCMS (XBridge C18 column, eluting with a gradient of acetonitrile/water containing 0.1% TFA, at flow rate of 60 mL/min) to afford the desired product. LCMS calculated $C_{25}H_{26}F_4N_7$ (M+H)$^+$: m/z=500.2; found: 500.2 $^1$H NMR (500 MHz, DMSO-d$_6$) δ 9.17 (d, J=1.2 Hz, 1H), 9.05 (br, 1H), 8.82 (d, J=2.3 Hz, 1H), 8.24 (dd, J=8.9, 2.4 Hz, 1H), 8.20 (s, 1H), 7.92 (s, 1H), 7.82 (d, J=9.0 Hz, 1H), 7.11 (d, J=8.9 Hz, 1H), 4.50 (d, J=13.0 Hz, 2H), 4.35 (t, J=5.6 Hz, 2H), 3.54 (d, J=11.8 Hz, 2H), 3.27-3.15 (m, 2H), 3.12 (s, 2H), 2.87 (s, 3H), 2.66 (t, J=5.2 Hz, 3H) ppm.

Example 120. 1-(4-(3-(6-Cyclopropylpyridin-3-yl)-1H-pyrazolo[3,4-c]pyridin-5-yl)-3-fluoro-5-(trifluoromethyl)phenyl)-N-methylmethanamine

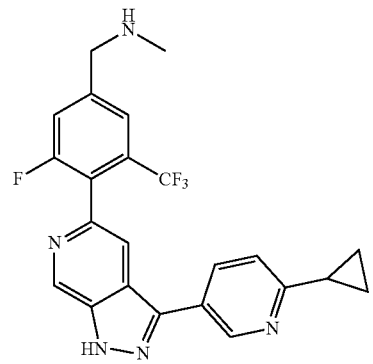

This compound was prepared according to the procedures described in Example 119, using 2-cyclopropyl-5-(4,4,5,5-tetramethyl-1,3,2-dioxaborolan-2-yl)pyridine instead of 1-methyl-4-(5-(4,4,5,5-tetramethyl-1,3,2-dioxaborolan-2-yl)pyridin-2-yl)piperazine as starting material. LCMS calculated for $C_{23}H_{20}F_4N_5$ (M+H)$^+$: m/z=442.2; Found: 442.2.

Example 121. 1-(3-Fluoro-4-(3-(6-morpholinopyridin-3-yl)-1H-pyrazolo[3,4-c]pyridin-5-yl)-5-(trifluoromethyl)phenyl)-N-methylmethanamine

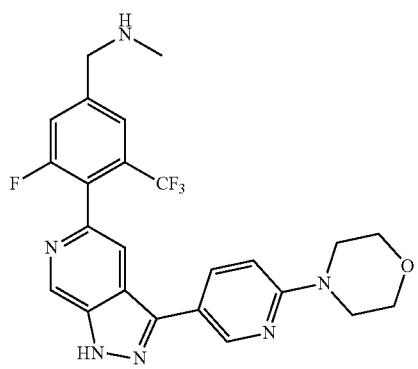 [SMILES: CNCc1cc(F)c(-c2cc3c(-c4ccc(N5CCOCC5)nc4)n[nH]c3cn2)c(C(F)(F)F)c1]

This compound was prepared according to the procedures described in Example 119, using 4-(5-(4,4,5,5-tetramethyl-1,3,2-dioxaborolan-2-yl)pyridin-2-yl)morpholine instead of 1-methyl-4-(5-(4,4,5,5-tetramethyl-1,3,2-dioxaborolan-2-yl)pyridin-2-yl)piperazine as starting material. LCMS calculated for $C_{24}H_{23}F_4N_6O$ (M+H)$^+$: m/z=487.2; Found: 487.2. $^1$H NMR (500 MHz, DMSO-d$_6$) δ 9.16 (d, J=1.2 Hz, 1H), 8.98 (br, 1H), 8.77 (d, J=2.1 Hz, 1H), 8.24-8.15 (m, 2H), 7.92 (s, 1H), 7.82 (d, J=9.5 Hz, 1H), 7.01 (d, J=8.9 Hz, 1H), 4.35 (t, J=5.8 Hz, 2H), 3.77-3.69 (m, 4H), 3.58-3.50 (m, 4H), 2.66 (t, J=5.3 Hz, 3H) ppm.

Example 122. 1-(3,5-Difluoro-4-(3-(1-methyl-1H-pyrazol-4-yl)-1H-pyrazolo[3,4-c]pyridin-5-yl)phenyl)-N-methylmethanamine

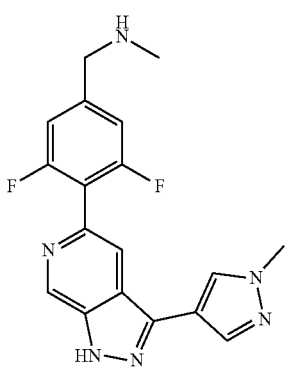 [SMILES: CNCc1cc(F)c(-c2cc3c(-c4cnn(C)c4)n[nH]c3cn2)c(F)c1]

Step 1. (3,5-Difluoro-4-(4,4,5,5-tetramethyl-1,3,2-dioxaborolan-2-yl)phenyl)methanol

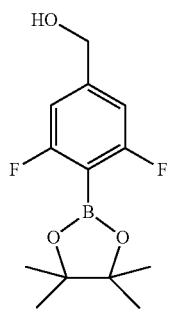 [SMILES: CC1(C)OB(c2c(F)cc(CO)cc2F)OC1(C)C]

To a solution of 3,5-difluoro-4-(4,4,5,5-tetramethyl-1,3,2-dioxaborolan-2-yl)benzaldehyde (4.0 g, 14.92 mmol) in tetrahydrofuran (149 ml) was added sodium borohydride (0.677 g, 17.91 mmol). After 2 h, the reaction was quenched with sat. sodium bicarbonate and extracted with ethyl acetate. The separated organic layer was washed with brine, dried over sodium sulfate and concentrated. The crude product was used in the next step without further purification.

Step 2. 1-(3,5-Difluoro-4-(3-(1-methyl-1H-pyrazol-4-yl)-1H-pyrazolo[3,4-c]pyridin-5-yl)phenyl)-N-methylmethanamine This compound was prepared according to the procedures described in Example 86 (Step 2-4), using (3,5-difluoro-4-(4,4,5,5-tetramethyl-1,3,2-dioxaborolan-2-yl)phenyl)methanol instead of (2-methyl-3-(4,4,5,5-tetramethyl-1,3,2-dioxaborolan-2-yl)phenyl)methanol as starting material. LCMS calculated for $C_{18}H_{17}F_2N_6$ (M+H)$^+$: m/z=355.2; Found: 355.2. $^1$H NMR (600 MHz, DMSO-d$_6$) δ 9.16 (d, J=1.2 Hz, 1H), 9.09 (br, 1H), 8.49 (s, 1H), 8.24 (s, 1H), 8.07 (d, J=0.6 Hz, 1H), 7.43-7.35 (m, 2H), 4.27 (t, J=5.5 Hz, 2H), 3.93 (s, 3H), 2.64 (t, J=5.1 Hz, 3H) ppm.

Example 123. N-(3,5-Difluoro-4-(3-(1-methyl-1H-pyrazol-4-yl)-1H-pyrazolo[3,4-c]pyridin-5-yl)benzyl)propan-2-amine

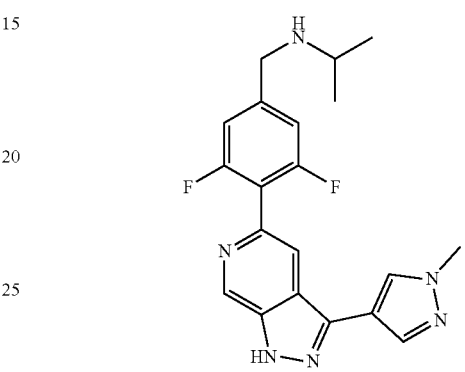

This compound was prepared according to the procedures described in Example 86 (Step 2-4) and Example 122, using propan-2-amine instead of methanamine as starting material. LCMS calculated for $C_{20}H_{21}F_2N_6$ (M+H)$^+$: m/z=383.2; Found: 383.3. $^1$H NMR (600 MHz, DMSO-d$_6$) δ 9.17 (d, J=1.2 Hz, 1H), 9.02 (br, 1H), 8.48 (s, 1H), 8.23 (s, 1H), 8.07 (d, J=0.6 Hz, 1H), 7.46 (d, J=8.0 Hz, 2H), 4.38-4.19 (m, 2H), 3.93 (s, 3H), 3.37 (dt, J=12.3, 6.0 Hz, 1H), 1.33 (d, J=6.5 Hz, 6H) ppm.

Example 124. N-(3,5-Difluoro-4-(3-(1-methyl-1H-pyrazol-4-yl)-1H-pyrazolo[3,4-c]pyridin-5-yl)benzyl)pyridin-2-amine

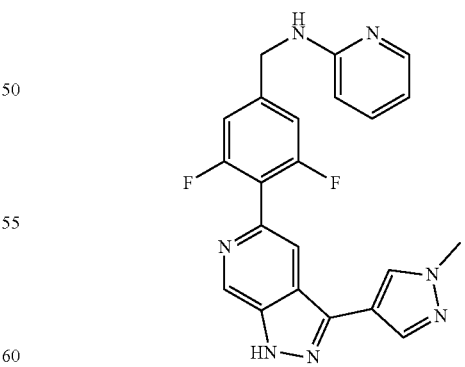

This compound was prepared according to the procedures described in Example 86 (Step 2-4) and Example 122, using pyridin-2-amine instead of methanamine as starting material. LCMS calculated for $C_{22}H_{18}F_2N_7$ (M+H)$^+$: m/z=418.2; Found: 418.2.

Example 125. N-(3,5-Difluoro-4-(3-(1-methyl-1H-pyrazol-4-yl)-1H-pyrazolo[3,4-c]pyridin-5-yl)benzyl)-1-methyl-1H-pyrazol-3-amine

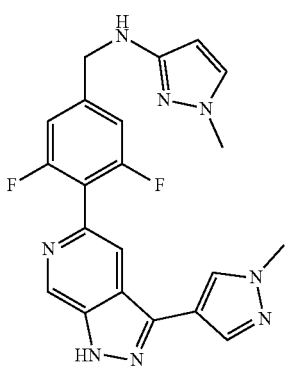 [SMILES: Cn1cc(-c2n[nH]c3cnc(-c4c(F)cc(CNc5ccn(C)n5)cc4F)cc23)cn1]

This compound was prepared according to the procedures described in Example 86 (Step 2-4) and Example 122, using 1-methyl-1H-pyrazol-3-amine instead of methanamine as starting material. LCMS calculated for $C_{21}H_{19}F_2N_8$ (M+H)$^+$: m/z=421.2; Found: 421.2.

Example 126. 2-(3,5-Difluoro-4-(3-(1-methyl-1H-pyrazol-4-yl)-1H-pyrazolo[3,4-c]pyridin-5-yl)benzylamino)ethanol

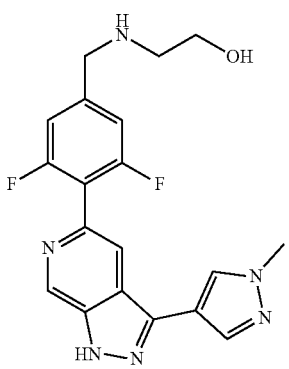

This compound was prepared according to the procedures described in Example 86 (Step 2-4) and Example 122, using 2-aminoethanol instead of methanamine as starting material. LCMS calculated for $C_{19}H_{19}F_2N_6O$ (M+H)$^+$: m/z=385.2; Found: 385.2.

Example 127. 1-(2,4-Difluoro-3-(3-(1-methyl-1H-pyrazol-4-yl)-1H-pyrazolo[3,4-c]pyridin-5-yl)phenyl)-N-methylmethanamine

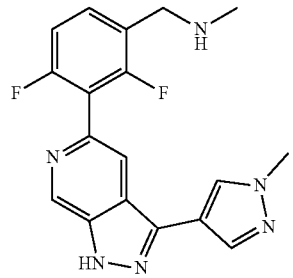

Step 1. (2,4-Difluoro-3-(4,4,5,5-tetramethyl-1,3,2-dioxaborolan-2-yl)phenyl)methanol

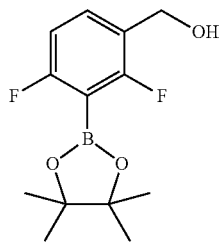

This compound was prepared according to the procedures described in Example 122 (Step 1), using 2,4-difluoro-3-(4,4,5,5-tetramethyl-1,3,2-dioxaborolan-2-yl)benzaldehyde instead of 3,5-difluoro-4-(4,4,5,5-tetramethyl-1,3,2-dioxaborolan-2-yl)benzaldehyde.

Step 2. 1-(2,4-Difluoro-3-(3-(1-methyl-1H-pyrazol-4-yl)-1H-pyrazolo[3,4-c]pyridin-5-yl)phenyl)-N-methylmethanamine This compound was prepared according to the procedures described in Example 86 (Step 2-4), using (2,4-difluoro-3-(4,4,5,5-tetramethyl-1,3,2-dioxaborolan-2-yl)phenyl)methanol instead of (2-methyl-3-(4,4,5,5-tetramethyl-1,3,2-dioxaborolan-2-yl)phenyl)methanol as starting material. LCMS calculated for $C_{18}H_{17}F_2N_6$ (M+H)$^+$: m/z=355.2; Found: 355.1.

Example 128. N-(2,4-Difluoro-3-(3-(1-methyl-1H-pyrazol-4-yl)-1H-pyrazolo[3,4-c]pyridin-5-yl)benzyl)propan-2-amine

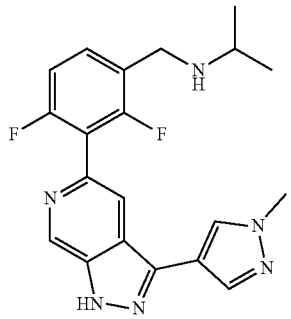 [SMILES: CC(C)NCc1ccc(F)c(-c2cc3c(-c4cnn(C)c4)n[nH]c3cn2)c1F]

This compound was prepared according to the procedures described in Example 86 (Step 2-4) and Example 127, using propan-2-amine instead of methanamine as starting material. LCMS calculated for $C_{20}H_{21}F_2N_6$ (M+H)$^+$: m/z=383.2; Found: 383.2.

Example 129. N-(2,4-Difluoro-3-(3-(1-methyl-1H-pyrazol-4-yl)-1H-pyrazolo[3,4-c]pyridin-5-yl)benzyl)cyclopropanamine

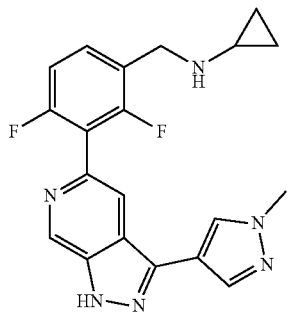 [SMILES: Cn1cc(-c2n[nH]c3cnc(-c4c(F)ccc(CNC5CC5)c4F)cc23)cn1]

This compound was prepared according to the procedures described in Example 86 (Step 2-4) and Example 127, using cyclopropanamine instead of methanamine as starting material. LCMS calculated for $C_{20}H_{19}F_2N_6$ (M+H)$^+$: m/z=381.2; Found: 381.2.

Example 130. 5-(2,6-Difluoro-3-((3-methoxypiperidin-1-yl)methyl)phenyl)-3-(1-methyl-1H-pyrazol-4-yl)-1H-pyrazolo[3,4-c]pyridine

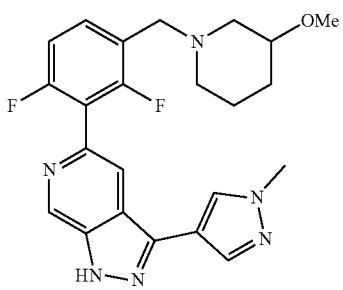 [SMILES: COC1CCCN(Cc2ccc(F)c(-c3cc4c(-c5cnn(C)c5)n[nH]c4cn3)c2F)C1]

This compound was prepared according to the procedures described in Example 86 (Step 2-4) and Example 127, using 3-methoxypiperidine instead of methanamine as starting material. LCMS calculated for $C_{23}H_{25}F_2N_6O$ (M+H)$^+$: m/z=439.2; Found: 439.2.

Example 131. 1-(3-Fluoro-4-(3-(1-methyl-1H-pyrazol-4-yl)-1H-pyrazolo[3,4-c]pyridin-5-yl)-5-(trifluoromethyl)phenyl)-N-methylmethanamine

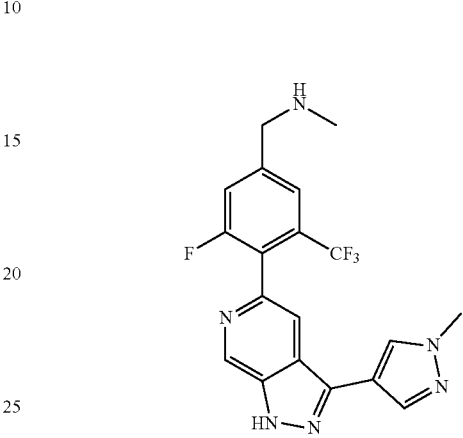

This compound was prepared according to the procedures described in Example 119, using 1-methyl-4-(4,4,5,5-tetramethyl-1,3,2-dioxaborolan-2-yl)-1H-pyrazole instead of 1-methyl-4-(5-(4,4,5,5-tetramethyl-1,3,2-dioxaborolan-2-yl)pyridin-2-yl)piperazine as starting material. LCMS calculated for $C_{19}H_{17}F_4N_6$ (M+H)$^+$: m/z=405.2; Found: 405.2. $^1$H NMR (600 MHz, DMSO-d$_6$) δ 9.22-9.03 (m, 2H), 8.46 (s, 1H), 8.21-8.14 (m, 1H), 8.04 (d, J=0.7 Hz, 1H), 7.93 (s, 1H), 7.83 (d, J=9.5 Hz, 1H), 4.36 (t, J=5.5 Hz, 2H), 3.92 (s, 3H), 2.66 (t, J=5.0 Hz, 3H) ppm.

Example 132. 1-(3-Fluoro-4-(3-(4-(4-methylpiperazin-1-yl)phenyl)-1H-pyrazolo[3,4-c]pyridin-5-yl)-5-(trifluoromethyl)phenyl)-N-methylmethanamine

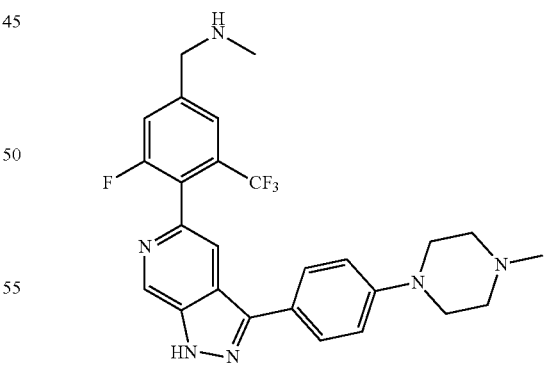

This compound was prepared according to the procedures described in Example 119, using 4-(4-methylpiperazin-1-yl)phenylboronic acid instead of 1-methyl-4-(5-(4,4,5,5-tetramethyl-1,3,2-dioxaborolan-2-yl)pyridin-2-yl)piperazine as starting material. LCMS calculated for $C_{26}H_{27}F_4N_6$ (M+H)$^+$: m/z=499.2; Found: 499.2. $^1$H NMR (500 MHz, DMSO-d$_6$) δ 9.20 (br, 1H), 9.16 (s, 1H), 8.14 (s, 1H), 8.02-7.91 (m, 3H), 7.83 (d, J=9.1 Hz, 1H), 7.15 (d, J=9.0 Hz, 2H), 4.36 (s, 2H), 4.01-3.87 (m, 2H), 3.66-3.45 (m, 2H), 3.28-3.14 (m, 2H), 3.12-2.98 (m, 2H), 2.88 (s, 3H), 2.66 (s, 3H) ppm.

Example 133. 1-(4-(3-(1-Ethyl-1H-pyrazol-4-yl)-1H-pyrazolo[3,4-c]pyridin-5-yl)-3-fluoro-5-methylphenyl)-N-methylmethanamine

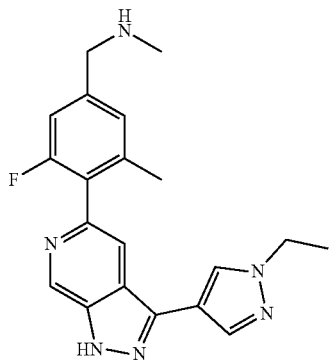 [SMILES: CCn1cc(-c2n[nH]c3cnc(-c4c(C)cc(CNC)cc4F)cc23)cn1]

To a screw-cap vial equipped with a magnetic stir bar was added tert-butyl 5-(4-(((tert-butoxycarbonyl)(methyl)amino)methyl)-2-fluoro-6-methylphenyl)-3-iodo-1H-pyrazolo[3,4-c]pyridine-1-carboxylate (300.0 mg, 0.503 mmol, Example 113, Step 9), (1-ethyl-1H-pyrazol-4-yl)boronic acid (106 mg, 0.754 mmol), chloro(2-dicyclohexylphosphino-2',4',6'-triisopropyl-1,1'-biphenyl)[2-(2'-amino-1,1'-biphenyl)]palladium(II) (XPhos Pd G2, 40 mg, 50 μmol) and potassium phosphate (213 mg, 1.006 mmol). The vial was sealed with a Teflon-lined septum, evacuated and back-filled with nitrogen (this process was repeated a total of three times). Then 1,4-dioxane (5.00 ml) was added via syringe, followed by water (500.0 μl). The reaction mixture was heated to 80° C. for 2 h. The reaction mixture was concentrated. To the residue was added CH$_2$Cl$_2$ (2.0 mL) followed by TFA (2.0 mL). The mixture was stirred at room temperature for 15 min, and then concentrated. The residue was purified using prep-LCMS (XBridge C18 column, eluting with a gradient of acetonitrile/water containing 0.1% TFA, at flow rate of 60 mL/min) to afford the desired product. LCMS calculated C$_{20}$H$_{22}$FN$_6$ (M+H)$^+$: m/z=365.2; found: 365.3. $^1$H NMR (500 MHz, DMSO-d$_6$) δ 9.17 (s, 1H), 8.99 (br, 1H), 8.53 (s, 1H), 8.13 (s, 1H), 8.07 (d, J=0.6 Hz, 1H), 7.38-7.17 (m, 2H), 4.28-4.08 (m, 4H), 2.63 (t, J=5.3 Hz, 3H), 2.18 (s, 3H), 1.44 (t, J=7.3 Hz, 3H) ppm.

Example 134. 1-(4-(3-(1-Cyclopropyl-1H-pyrazol-4-yl)-1H-pyrazolo[3,4-c]pyridin-5-yl)-3-fluoro-5-methylphenyl)-N-methylmethanamine

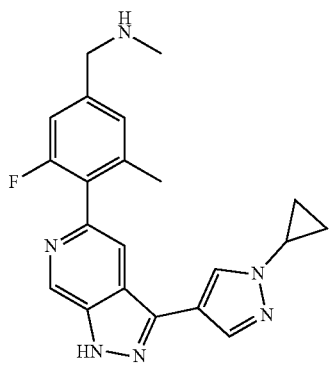 [SMILES: CNCc1cc(C)c(-c2cc3c(-c4cnn(C5CC5)c4)n[nH]c3cn2)c(F)c1]

This compound was prepared according to the procedures described in Example 133, using 1-cyclopropyl-4-(4,4,5,5-tetramethyl-1,3,2-dioxaborolan-2-yl)-1H-pyrazole instead of (1-ethyl-1H-pyrazol-4-yl)boronic acid as starting material. LCMS calculated for C$_{21}$H$_{22}$FN$_6$ (M+H)$^+$: m/z=377.2; Found: 377.2. $^1$H NMR (500 MHz, DMSO-d$_6$) δ 9.17 (s, 1H), 9.02 (br, 1H), 8.54 (s, 1H), 8.18 (s, 1H), 8.05 (s, 1H), 7.36-7.14 (m, 2H), 4.21 (t, J=5.6 Hz, 2H), 3.80 (tt, J=7.5, 3.8 Hz, 1H), 2.63 (t, J=5.2 Hz, 3H), 2.18 (s, 3H), 1.19-1.12 (m, 2H), 1.06-0.94 (m, 2H) ppm.

Example 135. 2-(4-(5-(2-Fluoro-6-methyl-4-((methylamino)methyl)phenyl)-1H-pyrazolo[3,4-c]pyridin-3-yl)-1H-pyrazol-1-yl)benzonitrile

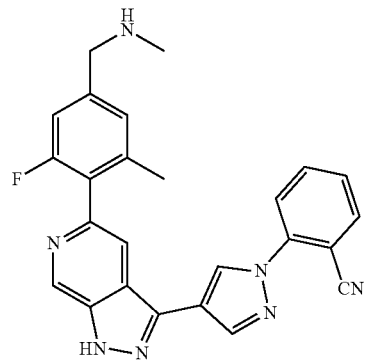 [SMILES: CNCc1cc(C)c(-c2cc3c(-c4cnn(-c5ccccc5C#N)c4)n[nH]c3cn2)c(F)c1]

This compound was prepared according to the procedures described in Example 133, using 2-(4-(4,4,5,5-tetramethyl-1,3,2-dioxaborolan-2-yl)-1H-pyrazol-1-yl)benzonitrile instead of (1-ethyl-1H-pyrazol-4-yl)boronic acid as starting material. LCMS calculated for C$_{25}$H$_{21}$FN$_7$ (M+H)$^+$: m/z=438.2; Found: 438.1.

Example 136. 1-(3-Fluoro-5-methyl-4-(3-(1-(tetrahydro-2H-pyran-4-yl)-1H-pyrazol-4-yl)-1H-pyrazolo[3,4-c]pyridin-5-yl)phenyl)-N-methylmethanamine

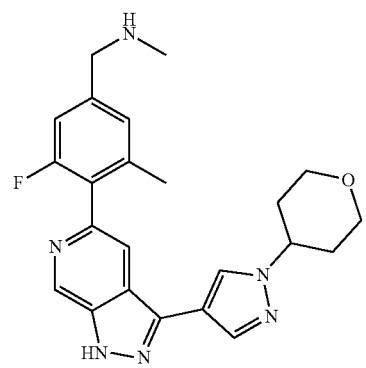 [SMILES: CNCc1cc(C)c(-c2cc3c(-c4cnn(C5CCOCC5)c4)n[nH]c3cn2)c(F)c1]

This compound was prepared according to the procedures described in Example 133, using 1-(tetrahydro-2H-pyran-4-yl)-4-(4,4,5,5-tetramethyl-1,3,2-dioxaborolan-2-yl)-1H-pyrazole instead of (1-ethyl-1H-pyrazol-4-yl)boronic acid as starting material. LCMS calculated for C$_{23}$H$_{26}$FN$_6$O (M+H)$^+$: m/z=421.2; Found: 421.2.

Example 137. 1-(3,5-Difluoro-4-(3-(1-methyl-1H-pyrazol-4-yl)-1H-pyrazolo[3,4-c]pyridin-5-yl)phenyl)-N-methylcyclopropanamine

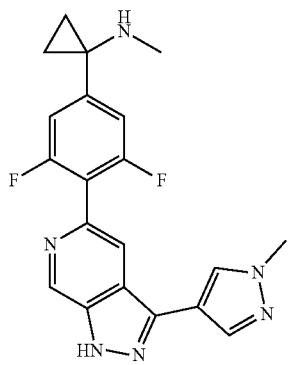 [SMILES: CNC1(c2cc(F)c(-c3cc4c(-c5cnn(C)c5)n[nH]c4cn3)c(F)c2)CC1]

This compound was prepared according to the procedures described in Example 95, using 1-(3,5-difluorophenyl)cyclopropanamine instead of 3-(3,5-difluorophenyl)cyclobutan-1-amine and formaldehyde instead of propan-2-one as starting material. LCMS calculated for $C_{20}H_{19}F_2N_6$ $(M+H)^+$: m/z=381.2; Found: 381.2.

Example 138. 1-(4-Fluoro-2-methoxy-3-(3-(1-methyl-1H-pyrazol-4-yl)-1H-pyrazolo[3,4-c]pyridin-5-yl)phenyl)-N-methylmethanamine

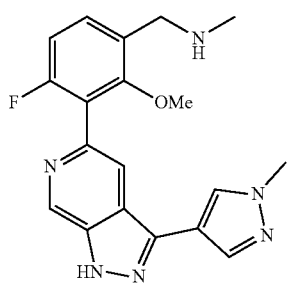 [SMILES: CNCc1ccc(F)c(-c2cc3c(-c4cnn(C)c4)n[nH]c3cn2)c1OC]

Step 1. tert-Butyl(4-fluoro-2-methoxybenzyloxy)dimethylsilane

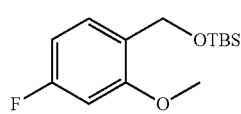

To a solution of (4-fluoro-2-methoxyphenyl)methanol (1.21 g, 7.75 mmol) in DCM (38.7 ml) were added imidazole (0.791 g, 11.62 mmol) and TBS-Cl (9.30 ml, 9.30 mmol). After 1 h at r.t., the reaction was quenched with water and the layers separated. The aqueous layer was extracted within DCM, and the combined organic layers were washed with brine, dried over sodium sulfate and concentrated. The residue was purified by Biotage Isolera™ (flash purification system with ethyl acetate/hexanes at a ratio from 0 to 20%) to provide the desired product as a brown solid. LC-MS calculated for $C_{14}H_{24}FO_2Si$ $[M+H]^+$ m/z: 271.2, found 271.2.

Step 2. 1-(4-Fluoro-2-methoxy-3-(3-(1-methyl-1H-pyrazol-4-yl)-1H-pyrazolo[3,4-c]pyridin-5-yl)phenyl)-N-methylmethanamine This compound was prepared according to the procedures described in Example 96, using tert-butyl(4-fluoro-2-methoxybenzyloxy)dimethylsilane instead of 2-(3,5-difluorophenyl)ethanol as starting material. LC-MS calculated for $C_{19}H_{20}FN_6O$ $[M+H]^+$ m/z: 367.2, found 367.2.

Example 139. N-(4-Fluoro-2-methoxy-3-(3-(1-methyl-1H-pyrazol-4-yl)-1H-pyrazolo[3,4-c]pyridin-5-yl)benzyl)ethanamine

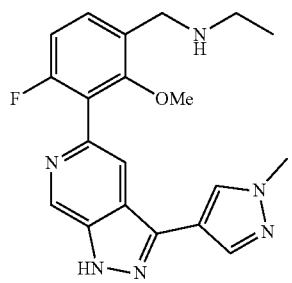 [SMILES: CCNCc1ccc(F)c(-c2cc3c(-c4cnn(C)c4)n[nH]c3cn2)c1OC]

This compound was prepared using procedures analogous to those for example 138, with ethylamine replacing methylamine. LCMS calculated for $C_{20}H_{22}FN_6O$ $[M+H]^+$ m/z: 381.1; Found: 381.2.

Example 140. N-(5-(2,6-Difluoro-4-((isopropylamino)methyl)phenyl)-1H-pyrazolo[3,4-c]pyridin-3-yl)-4-(4-methylpiperazin-1-yl)benzamide

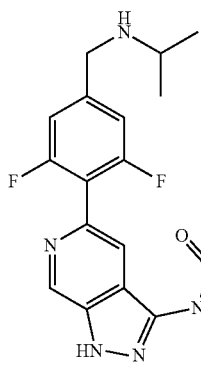

Step 1. N-(5-Bromo-1H-pyrazolo[3,4-c]pyridin-3-yl)-4-(4-methylpiperazin-1-yl)benzamide

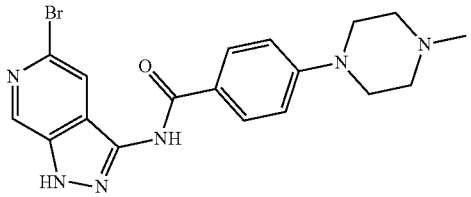 [SMILES: CN1CCN(c2ccc(C(=O)Nc3n[nH]c4cnc(Br)cc34)cc2)CC1]

To a suspension of 4-(4-methylpiperazin-1-yl)benzoic acid (528 mg, 2.395 mmol) in DCM (8 ml) was added DMF (12.36 μl, 0.160 mmol) and oxalyl chloride (419 μl, 4.79 mmol), and the reaction mixture was stirred until a fine white suspension replaced the original orange one (~2 h). The mixture was then concentrated and dried under vacuum to remove excess oxalyl chloride. THF (8 ml) was added followed by hunig's base (837 μl, 4.79 mmol). After stirring for 5 mins, tert-butyl 3-amino-5-bromo-1H-pyrazolo[3,4-c]pyridine-1-carboxylate (500 mg, 1.597 mmol) was added in one portion as a solid, and the reaction mixture was heated to 85° C. for 3 h. After cooling to r.t., the mixture was quenched with sat. sodium bicarbonate solution and extracted with ethyl acetate. The separated organic layer was dried over sodium sulfate and concentrated. The residue was purified by Biotage Isolera™ (flash purification system with methanol/dichloromethane at a ratio from 0 to 10%) to provide the desired product as a brown solid (342 mg, 46%). LC-MS calculated for $C_{18}H_{20}BrN_6O$ [M+H]$^+$ m/z: 415.2/417.2, found 415.2/417.2.

Step 2. tert-Butyl 3,5-difluoro-4-(4,4,5,5-tetramethyl-1,3,2-dioxaborolan-2-yl)benzyl(isopropyl)carbamate

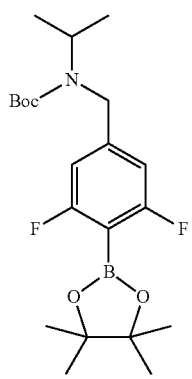

To a solution of 3,5-difluoro-4-(4,4,5,5-tetramethyl-1,3,2-dioxaborolan-2-yl)benzaldehyde (2.5 g, 9.33 mmol) in DCE (46.6 ml) was added propan-2-amine (1.621 ml, 18.65 mmol) and acetic acid (1.602 ml, 28.0 mmol). After stirring at r.t. for 30 mins, sodium triacetoxyborohydride (3.95 g, 18.65 mmol) was added, and the reaction was stirred an additional 1 h at r.t. The reaction mixture was then concentrated and redissolved in DCM (37 mL), washed with saturated sodium bicarbonate, dried over sodium sulfate and filtered. Triethylamine (2.60 ml, 18.65 mmol) and boc-anhydride (3.25 ml, 13.99 mmol) were added to the filtrate, and the resulting mixture was stirred at r.t. for 2 h. The mixture was quenched with water and extracted with DCM. The organic layer was dried over sodium sulfate and concentrated. The crude product was used in the next step without further purification.

Step 3. tert-Butyl 5-(4-(((tert-butoxycarbonyl(isopropyl)amino)methyl)-2,6-difluorophenyl)-3-(4-(4-methylpiperazin-1-yl)benzamido)-1H-pyrazolo[3,4-c]pyridine-1-carboxylate

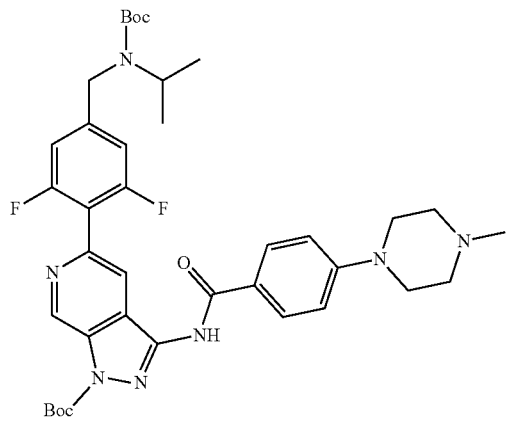 [SMILES: CC(C)N(Cc1cc(F)c(-c2cc3c(NC(=O)c4ccc(N5CCN(C)CC5)cc4)nn(C(=O)OC(C)(C)C)c3cn2)c(F)c1)C(=O)OC(C)(C)C]

To a mixture of tert-butyl 5-bromo-3-(4-(4-methylpiperazin-1-yl)benzamido)-1H-pyrazolo[3,4-c]pyridine-1-carboxylate (239 mg, 0.464 mmol), tert-butyl (3,5-difluoro-4-(4,4,5,5-tetramethyl-1,3,2-dioxaborolan-2-yl)benzyl)(isopropyl)carbamate (763 mg, 1.855 mmol), XPhos Pd G2 (36.5 mg, 0.046 mmol) and potassium phosphate (246 mg, 1.159 mmol) were added 1,4-dioxane (2 ml) and water (500 μl), and the reaction flask was evacuated, back filled with nitrogen, then stirred at 80° C. for 1 h. The reaction was then quenched with water and extracted with ethyl acetate. The organic layer was dried over sodium sulfate, concentrated and purified by Biotage Isolera™ (flash purification system with methanol/dichloromethane at a ratio from 2 to 10%) to provide the desired product as a brown solid. LC-MS calculated for $C_{38}H_{48}F_2N_7O_5$ [M+H]$^+$ m/z: 720.3, found 720.3.

Step 4. N-(5-(2,6-Difluoro-4-((isopropylamino)methyl)phenyl)-1H-pyrazolo[3,4-c]pyridin-3-yl)-4-(4-methylpiperazin-1-yl)benzamide A solution of tert-butyl 5-(4-(((tert-butoxycarbonyl)(isopropyl)amino)methyl)-2,6-difluorophenyl)-3-(4-(4-methylpiperazin-1-yl)benzamido)-1H-pyrazolo[3,4-c]pyridine-1-carboxylate (253 mg, 0.351 mmol) in DCM (900 μl) and TFA (900 μl) was stirred at r.t. for 30 mins, then concentrated and purified directly on prep-LCMS (XBridge C18 column, eluting with a gradient of acetonitrile/water containing 0.1% TFA, at flow rate of 60 mL/min) to provide the desired product. LC-MS calculated for $C_{28}H_{32}F_2N_7O$ [M+H]$^+$ m/z: 520.2, found 520.2. $^1$H NMR (500 MHz, DMSO-d$_6$) δ 13.57 (s, 1H), 10.94 (s, 1H), 10.10 (s, 1H), 9.12 (d, J=1.2 Hz, 1H), 8.94 (s, 2H), 8.03 (d, J=9.0 Hz, 2H), 7.97 (s, 1H), 7.44 (d, J=8.2 Hz, 2H), 7.12 (d, J=9.1 Hz, 2H), 4.32-4.23 (m, 2H), 4.08 (d, J=11.4 Hz, 2H), 3.54 (s, 2H), 3.37 (dt, J=12.2, 5.9 Hz, 1H), 3.12 (m, 2H), 2.88 (s, 3H), 1.32 (s, 3H), 1.30 (s, 3H).

Example 141. N-(5-(2,6-Difluoro-4-(pyrrolidin-1-ylmethyl)phenyl)-1H-pyrazolo[3,4-c]pyridin-3-yl)-4-(4-methylpiperazin-1-yl)benzamide

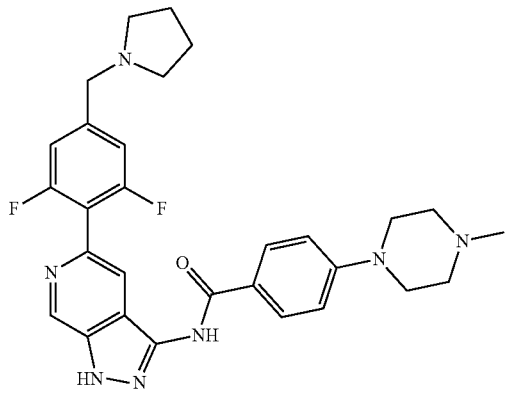 [SMILES: CN1CCN(c2ccc(C(=O)Nc3n[nH]c4cnc(-c5c(F)cc(CN6CCCC6)cc5F)cc34)cc2)CC1]

Step 1. tert-Butyl 5-(2,6-difluoro-4-formylphenyl)-3-(4-(4-methylpiperazin-1-yl)benzamido)-1H-pyrazolo[3,4-c]pyridine-1-carboxylate

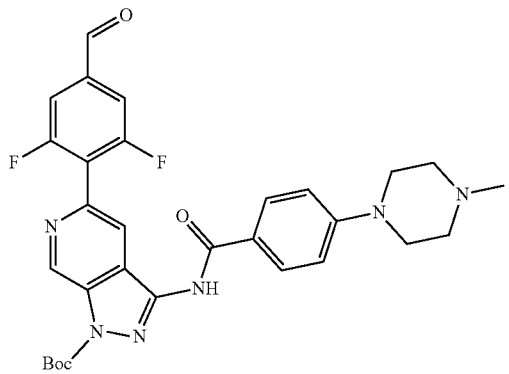 [SMILES: CN1CCN(c2ccc(C(=O)Nc3nn(C(=O)OC(C)(C)C)c4cnc(-c5c(F)cc(C=O)cc5F)cc34)cc2)CC1]

To a mixture of tert-butyl 5-bromo-3-(4-(4-methylpiperazin-1-yl)benzamido)-1H-pyrazolo[3,4-c]pyridine-1-carboxylate (319 mg, 0.619 mmol, Example 140, Step 1), (3,5-difluoro-4-(4,4,5,5-tetramethyl-1,3,2-dioxaborolan-2-yl)phenyl)methanol (585 mg, 2.166 mmol, Example 122, Step 1), XPhos Pd G2 (48.7 mg, 0.062 mmol) and potassium phosphate, tribasic (263 mg, 1.238 mmol) were added 1,4-dioxane (5 ml) and water (1 ml), and the reaction flask was evacuated and back filled with nitrogen. The reaction mixture was stirred at 80° C. for 1 h. The mixture was then cooled to r.t., diluted with DCM and filtered through a plug of Celite. The filtrate was concentrated and redissolved in DCM (4 mL). Manganese dioxide (538 mg, 6.19 mmol) was added, and the reaction mixture was heated to 60° C. overnight. The mixture was then filtered through a plug of Celite, and the solid washed with a large amount of DCM. The filtrate was concentrated, and the residue was purified by Biotage Isolera™ (flash purification system with ethyl acetate/hexanes at a ratio from 20 to 100%, then methanol/dichloromethane at a ratio from 0 to 10%) to provide the desired product as a brown solid. LC-MS calculated for $C_{30}H_{31}F_2N_6O_4$ [M+H]$^+$ m/z: 577.2, found 577.2.

Step 2. N-(5-(2,6-Difluoro-4-(pyrrolidin-1-ylmethyl)phenyl)-1H-pyrazolo[3,4-c]pyridin-3-yl)-4-(4-methylpiperazin-1-yl)benzamide To a solution of tert-butyl 5-(2,6-difluoro-4-formylphenyl)-3-(4-(4-methylpiperazin-1-yl)benzamido)-1H-pyrazolo[3,4-c]pyridine-1-carboxylate (53 mg, 0.092 mmol) and pyrrolidine (13.07 mg, 0.184 mmol) in DCE (919 µl) were added acetic acid (15.79 µl, 0.276 mmol) and sodium triacetoxyborohydride (48.7 mg, 0.230 mmol). After stirring at r.t. for 2 h, the mixture was quenched with sat. sodium bicarbonate and extracted with DCM. The organic layer was dried over sodium sulfate and concentrated. The residue was dissolved in a 1:1 mixture of TFA/DCM (1 mL) and stirred at r.t. for 30 mins, then diluted with methanol and purified directly on prep-LCMS (XBridge C18 column, eluting with a gradient of acetonitrile/water containing 0.1% TFA, at flow rate of 60 mL/min) to provide the desired product. LC-MS calculated for $C_{29}H_{32}F_2N_7O$ [M+H]$^+$ m/z: 532.2, found 532.2. $^1$H NMR (500 MHz, DMSO-d$_6$) δ 13.59 (s, 1H), 10.95 (s, 1H), 10.32 (s, 1H), 10.17 (s, 1H), 9.12 (d, J=1.2 Hz, 1H), 8.04 (d, J=9.0 Hz, 2H), 7.98 (s, 1H), 7.44 (d, J=8.0 Hz, 2H), 7.12 (d, J=9.1 Hz, 2H), 4.45 (d, J=4.3 Hz, 2H), 4.08 (d, J=10.6 Hz, 2H), 3.54 (s, 2H), 3.48 (s, 2H), 3.14 (s, 4H), 2.88 (s, 3H), 2.07 (s, 2H), 1.90 (d, J=5.8 Hz, 2H).

Example 142. N-(5-(4-(Azetidin-1-ylmethyl)-2,6-difluorophenyl)-1H-pyrazolo[3,4-c]pyridin-3-yl)-4-(4-methylpiperazin-1-yl)benzamide

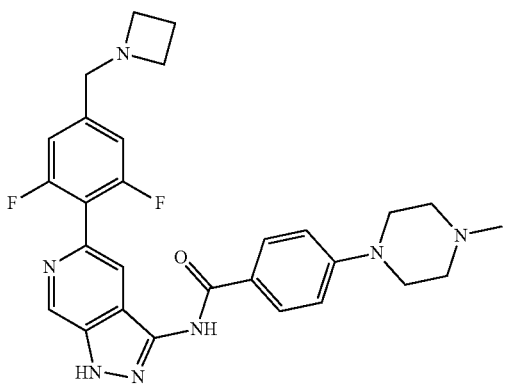 [SMILES: CN1CCN(c2ccc(C(=O)Nc3n[nH]c4cnc(-c5c(F)cc(CN6CCC6)cc5F)cc34)cc2)CC1]

This compound was prepared using procedures analogous to those for example 141, with azetadine hydrochloride replacing pyrrolidine. LCMS calculated for $C_{28}H_{30}F_2N_7O$ [M+H]$^+$ m/z: 518.2; Found: 518.2.

Example 143. N-(5-(2,6-Difluoro-4-((3-methoxyazetidin-1-yl)methyl)phenyl)-1H-pyrazolo[3,4-c]pyridin-3-yl)-4-(4-methylpiperazin-1-yl)benzamide

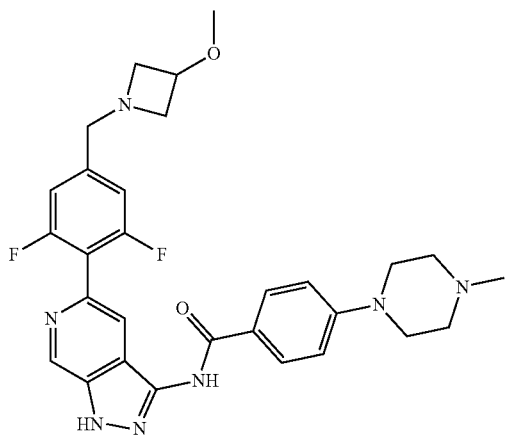 [SMILES: COC1CN(Cc2cc(F)c(-c3cc4c(NC(=O)c5ccc(N6CCN(C)CC6)cc5)n[nH]c4cn3)c(F)c2)C1]

This compound was prepared using procedures analogous to those for example 141, with 4-methoxy azetadine replacing pyrrolidine. LCMS calculated for $C_{29}H_{32}F_2N_7O_2$ [M+H]$^+$ m/z: 548.2; Found: 548.2.

Example 144. N-(5-(2,6-Difluoro-4-((methylamino)methyl)phenyl)-1H-pyrazolo[3,4-c]pyridin-3-yl)-1-methyl-1H-pyrazole-4-carboxamide

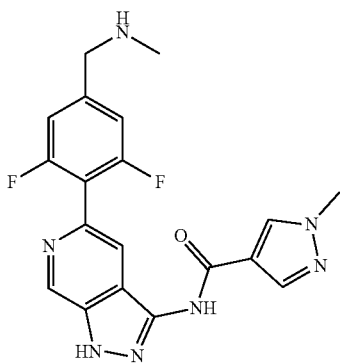 [SMILES: CNCc1cc(F)c(-c2cc3c(NC(=O)c4cnn(C)c4)n[nH]c3cn2)c(F)c1]

Step 1. tert-Butyl 3,5-difluorobenzyl(methyl)carbamate

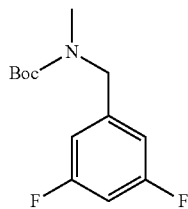

To a solution of 3,5-difluorobenzaldehyde (5.0 g, 35.2 mmol) in MeOH (176 ml) was added methanamine (21.11 ml, 42.2 mmol, 2M solution in THF) and the reaction mixture was stirred for 30 mins, then sodium borohydride (1.730 g, 45.7 mmol) was added. Stirring was continued until the bubbling subsided (~15 mins). The mixture was then concentrated, redissolved in DCM and washed with sat. sodium bicarbonate. The organic layer was dried over sodium sulfate and filtered. Triethylamine (7.36 ml, 52.8 mmol) and boc-anhydride (9.80 ml, 42.2 mmol) were added, and the reaction mixture stirred at r.t. for 2 h. The reaction mixture was then quenched with water and extracted with DCM. The organic layer was dried over sodium sulfate and concentrated. The residue purified by Biotage Isolera™ (flash purification system with ethyl acetate/hexanes at a ratio from 0 to 40%) to provide the desired product as a solid (9.0 g, 99%). LC-MS calculated for $C_{13}H_{18}F_2NO_2$ [M+H]$^+$ m/z: 258.2, found 258.2.

Step 2. tert-Butyl 3-amino-5-(4-((tert-butoxycarbonyl(methyl)amino)methyl)-2,6-difluorophenyl)-1H-pyrazolo[3,4-c]pyridine-1-carboxylate

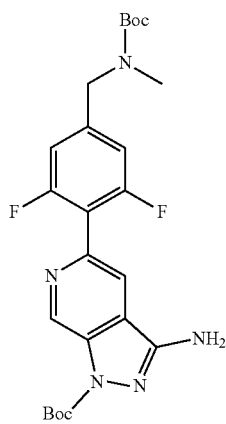 [SMILES: CN(Cc1cc(F)c(-c2cc3c(N)nn(C(=O)OC(C)(C)C)c3cn2)c(F)c1)C(=O)OC(C)(C)C]

To a solution of tert-butyl (3,5-difluorobenzyl)(methyl)carbamate (1849 mg, 7.18 mmol) in THF (16 ml) at −78° C. was added n-BuLi (5.75 ml, 14.37 mmol, 2.5M in hexane) dropwise. The reaction mixture stirred at −78° C. for 45 mins, and 2-isopropoxy-4,4,5,5-tetramethyl-1,3,2-dioxaborolane (2.204 ml, 10.78 mmol) was added dropwise. The reaction mixture was stirred at −78° C. for 30 mins, and then warmed up to r.t. The mixture was then quenched with water and extracted with ethyl acetate. The organic layer was dried over sodium sulfate and concentrated. To the residue was added 1,4-dioxane (10 ml), followed by a solid mixture of tert-butyl 3-amino-5-bromo-1H-pyrazolo[3,4-c]pyridine-1-carboxylate (750 mg, 2.395 mmol, Example 1, Step 3), potassium phosphate (1271 mg, 5.99 mmol) and XPhos Pd G2 (188 mg, 0.239 mmol). Water (2.0 ml) was added, and the reaction flask was evacuated, back filled with nitrogen. The mixture was stirred at 80° C. for 1 h. After cooling, the mixture was diluted with water and ethyl acetate, and the layers were separated. The aqueous layer was extracted with ethyl acetate, and the combined organic layers dried over sodium sulfate and concentrated. The residue was purified by Biotage Isolera™ (flash purification system with ethyl acetate/hexanes at a ratio from 0 to 100%) to provide the desired product as a solid (280 mg, 24%). LC-MS calculated for $C_{24}H_{30}F_2N_5O_4$ [M+H]$^+$ m/z: 490.2, found 490.2.

Step 3. N-(5-(2,6-Difluoro-4-((methylamino)methyl)phenyl)-1H-pyrazolo[3,4-c]pyridin-3-yl)-1-methyl-1H-pyrazole-4-carboxamide To a suspension of 1-methyl-1H-pyrazole-4-carboxylic acid (19.36 mg, 0.154 mmol) in DCM (0.5 ml) were added DMF (0.396 µl, 5.12 µmol) and oxalyl chloride (0.013 ml, 0.154 mmol). The reaction mixture stirred at r.t. for 1 h. A solution of tert-butyl 3-amino-5-(4-(((tert-butoxycarbonyl) (methyl)amino)methyl)-2,6-difluorophenyl)-1H-indazole-1-carboxylate (25 mg, 0.051 mmol) and Hunig's base (0.045 ml, 0.256 mmol) in THF (0.500 ml) were added. The reaction mixture was heated to 80° C. for 3 h. The mixture was then cooled down and concentrated. The residue was dissolved in a 1:1 mixture of TFA/DCM. The resulting mixture was stirred at r.t. for 30 mins, diluted with methanol, and purified directly on prep-LCMS (XBridge C18 column, eluting with a gradient of acetonitrile/water containing 0.1% TFA, at flow rate of 60 mL/min) to provide the desired product. LC-MS calculated for $C_{19}H_{18}F_2N_7O$ [M+H]$^+$ m/z: 398.2, found 398.2.

Example 145. N-(5-(2,6-Difluoro-4-((methylamino) methyl)phenyl)-1H-pyrazolo[3,4-c]pyridin-3-yl)-3-(4-methylpiperazin-1-yl)benzamide

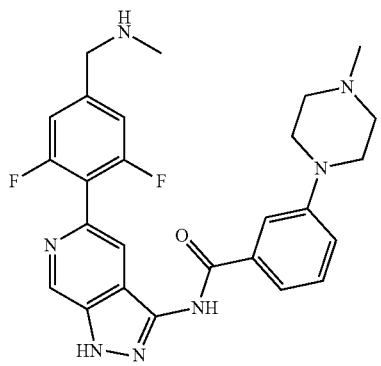 [SMILES: CNCc1cc(F)c(-c2cc3c(NC(=O)c4cccc(N5CCN(C)CC5)c4)n[nH]c3cn2)c(F)c1]

This compound was prepared using procedures analogous to those for example 144, with 3-(4-methylpiperazin-1-yl) benzoic acid replacing 1-methyl-1H-pyrazole-4-carboxylic acid. The reaction was performed at 90° C. LCMS calculated for $C_{26}H_{28}F_2N_7O$ [M+H]$^+$ m/z: 492.2; Found: 492.2.

Example 146. N-(5-(2,6-Difluoro-4-((isopropylamino)methyl)phenyl)-1H-pyrazolo[3,4-c]pyridin-3-yl)-3-methoxybenzamide

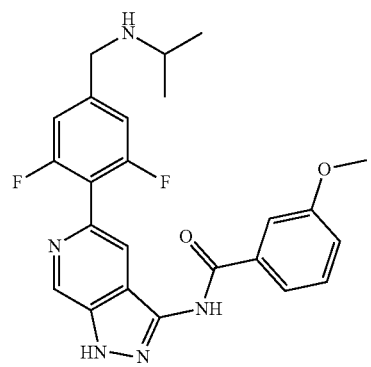 [SMILES: COc1cccc(C(=O)Nc2n[nH]c3cnc(-c4c(F)cc(CNC(C)C)cc4F)cc23)c1]

Step 1. tert-Butyl 3-amino-5-(4-((tert-butoxycarbonyl (isopropyl)amino)methyl)-2,6-difluorophenyl)-1H-pyrazolo [3,4-c]pyridine-1-carboxylate

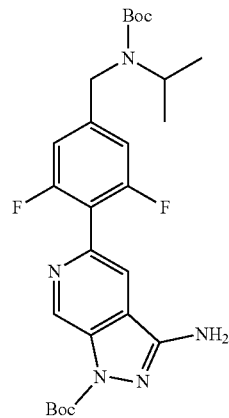 [SMILES: CC(C)N(Cc1cc(F)c(-c2cc3c(N)nn(C(=O)OC(C)(C)C)c3cn2)c(F)c1)C(=O)OC(C)(C)C]

This compound was prepared using procedures analogous to those for example 144, steps 1-2, with isopropyl amine replacing methyl amine. LC-MS calculated for $C_{26}H_{34}F_2N_5O_4$ [M+H]$^+$ m/z: 518.2, found 518.2.

Step 2. N-(5-(2,6-Difluoro-4-((isopropylamino) methyl)phenyl)-1H-pyrazolo[3,4-c]pyridin-3-yl)-3-methoxybenzamide To a solution of tert-butyl 3-amino-5-(4-(((tert-butoxycarbonyl)(isopropyl)amino)methyl)-2,6-difluorophenyl)-1H-pyrazolo[3,4-c]pyridine-1-carboxylate (25 mg, 0.048 mmol) and Hunig's base (42.2 µl, 0.242 mmol) in THF (966 µl) was added 3-methoxybenzoyl chloride (24.72 mg, 0.145 mmol). The resulting mixture stirred at 60° C. for 2 h, and then concentrated. The residue was dissolved in a 1:1 mixture of TFA/DCM. The resulting solution was stirred at for 1 h at r.t., diluted with methanol, and purified on prep-LCMS (XBridge C18 column, eluting with a gradient of acetonitrile/water containing 0.1% TFA, at flow rate of 60 mL/min) to provide the desired product. LC-MS calculated for $C_{24}H_{24}F_2N_5O_2$ [M+H]$^+$ m/z: 452.2, found 452.2.

Example 147. Methyl 4-(4-(5-(2,6-difluoro-4-((isopropylamino)methyl)phenyl)-1H-pyrazolo[3,4-c] pyridin-3-ylcarbamoyl)phenyl)piperazine-1-carboxylate

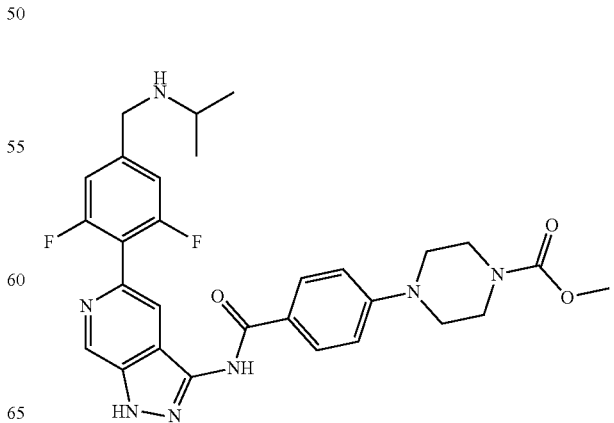

Step 1. 4-(4-(Benzyloxycarbonyl)piperazin-1-yl)benzoic acid

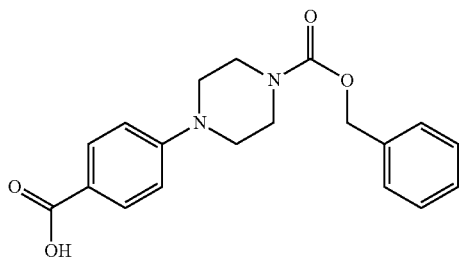 [SMILES: O=C(O)c1ccc(N2CCN(C(=O)OCc3ccccc3)CC2)cc1]

To a mixture of methyl 4-bromobenzoate (1.0 g, 4.65 mmol), benzyl piperazine-1-carboxylate (1.348 ml, 6.98 mmol), Ruphos Pd G2 (0.181 g, 0.233 mmol) and cesium carbonate (4.55 g, 13.95 mmol) was added 1,4-dioxane (15 ml), and the reaction flask was evacuated, back filled with nitrogen. The reaction mixture was stirred at 80° C. overnight. The mixture was then diluted with water and ethyl acetate and the layers separated. The aqueous layer was extracted with ethyl acetate, and the combined organic layers were dried over sodium sulfate and concentrated. The residue was purified by Biotage Isolera™ (flash purification system with ethyl acetate/hexanes at a ratio from 0 to 100%) to provide the desired product.

The obtained product was dissolved in a 1:1 mixture of THF/water (20 mL), and lithium hydroxide (0.334 g, 13.95 mmol) was added. The resulting mixture stirred at 60° C. overnight. The mixture was diluted with ethyl acetate and washed with 1N HCl and brine, and then the organic phase was dried over sodium sulfate and concentrated. The crude solid was used in the next step without further purification. LC-MS calculated for $C_{19}H_{21}N_2O_4$ [M+H]$^+$ m/z: 341.2, found 341.2.

Step 2. tert-Butyl 5-(4-((tert-butoxycarbonyl(isopropyl)amino)methyl)-2,6-difluorophenyl)-3-(4-(piperazin-1-yl)benzamido)-1H-pyrazolo[3,4-c]pyridine-1-carboxylate

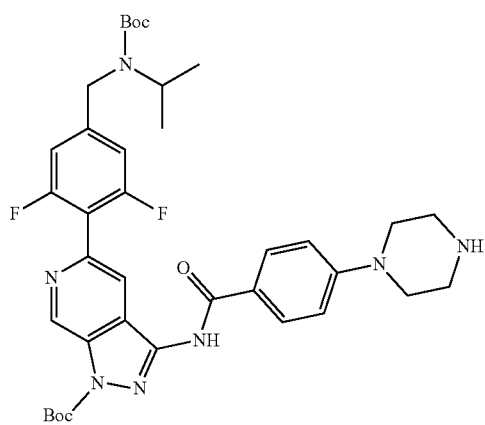 [SMILES: CC(C)N(Cc1cc(F)c(-c2cc3c(NC(=O)c4ccc(N5CCNCC5)cc4)nn(C(=O)OC(C)(C)C)c3cn2)c(F)c1)C(=O)OC(C)(C)C]

To a solution of 4-(4-((benzyloxy)carbonyl)piperazin-1-yl)benzoic acid (165 mg, 0.484 mmol) in DCM (968 μl) were added DMF (1.5 μl, 0.019 mmol) and oxalyl chloride (85 μl, 0.968 mmol). The reaction mixture was stirred for 15 minutes, and then concentrated. Toluene was added, and the resulting mixture concentrated. The resulting foam was dried under high vacuum for 2 h. The resulting solid was then dissolved in THF (968 μl), and Hunig's base (169 μl, 0.968 mmol) was added. A solution of tert-butyl 3-amino-5-(4-(((tert-butoxycarbonyl)(isopropyl)amino)methyl)-2,6-difluorophenyl)-1H-indazole-1-carboxylate (100 mg, 0.194 mmol, Example 122, Step 1) in THF was added, and the resulting mixture was stirred at 85° C. overnight. The reaction mixture was quenched with water and extracted with ethyl acetate. The organic layer was dried over sodium sulfate, concentrated and purified by Biotage Isolera™ (flash purification system with ethyl acetate/hexanes at a ratio from 0 to 100%) to provide the desired product as a solid.

The obtained solid was dissolved in methanol (2 mL), and palladium on carbon (41.2 mg, 0.039 mmol) was added. The reaction flask was evacuated and back filled with hydrogen gas from a balloon. After stirring at r.t. for 1 h, the mixture was filtered through a plug of Celite, and the filtrate was concentrated. The crude product (71 mg, 52%) was used in the next step without further purification. LC-MS calculated for $C_{37}H_{46}F_2N_7O_5$ [M+H]$^+$ m/z: 706.3, found 706.3.

Step 3. Methyl 4-(4-(5-(2,6-difluoro-4-((isopropylamino)methyl)phenyl)-1H-pyrazolo[3,4-c]pyridin-3-ylcarbamoyl)phenyl)piperazine-1-carboxylate To a solution of tert-butyl 5-(4-(((tert-butoxycarbonyl)(isopropyl)amino)methyl)-2,6-difluorophenyl)-3-(4-(piperazin-1-yl)benzamido)-1H-pyrazolo[3,4-c]pyridine-1-carboxylate (14 mg, 0.020 mmol) and Hunig's base (17.32 μl, 0.099 mmol) in DCM (400 μl) was added methyl chloroformate (4.61 μl, 0.060 mmol). The reaction mixture was stirred at r.t. for 30 mins, TFA was added, and the stirring was continued for an additional 30 mins. The mixture was then diluted with methanol and purified on prep-LCMS (XBridge C18 column, eluting with a gradient of acetonitrile/water containing 0.1% TFA, at flow rate of 60 mL/min) to provide the desired product. LC-MS calculated for $C_{29}H_{32}F_2N_7O_3$ [M+H]$^+$ m/z: 564.2, found 564.2.

Example 148. Methyl 4-(4-(5-(2,6-difluoro-4-((isopropylamino)methyl)phenyl)-1H-pyrazolo[3,4-c]pyridin-3-ylcarbamoyl)-3-fluorophenyl)piperazine-1-carboxylate

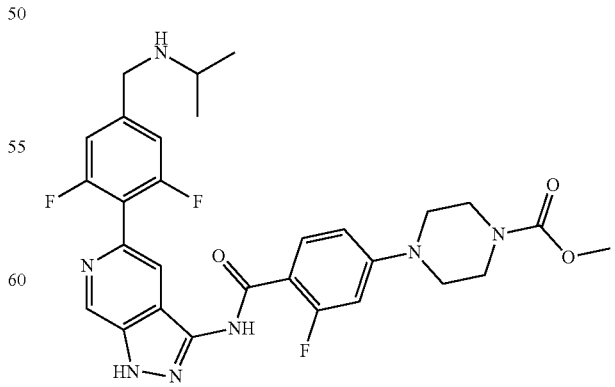

This compound was prepared in an analogous fashion to Example 147, with methyl 4-bromo-2-fluorobenzoate replacing methyl 4-bromobenzoate in Step 1. LC-MS calculated for $C_{29}H_{31}F_3N_7O_3$ [M+H]$^+$ m/z: 582.2, found 582.2.

Example 149. N-(5-(2,6-Difluoro-4-((isopropylamino)methyl)phenyl)-1H-pyrazolo[3,4-c]pyridin-3-yl)-2-methoxy-4-(4-methylpiperazin-1-yl)benzamide

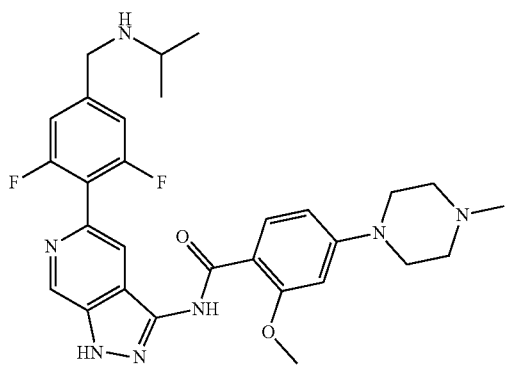 [SMILES: COc1cc(N2CCN(C)CC2)ccc1C(=O)Nc1n[nH]c2cnc(-c3c(F)cc(CNC(C)C)cc3F)cc12]

Step 1. tert-Butyl 5-(4-((tert-butoxycarbonyl(isopropyl)amino)methyl)-2,6-difluorophenyl)-3-(2-methoxy-4-(piperazin-1-yl)benzamido)-1H-pyrazolo[3,4-c]pyridine-1-carboxylate

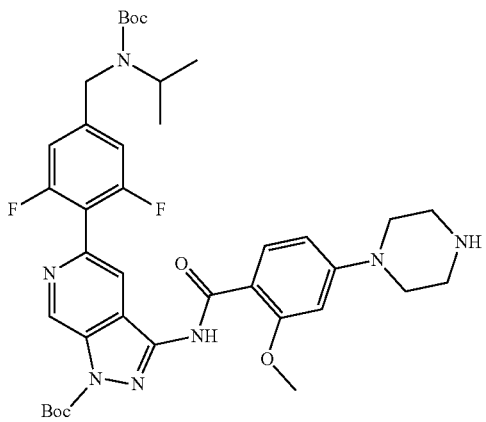 [SMILES: COc1cc(N2CCNCC2)ccc1C(=O)Nc1nn(C(=O)OC(C)(C)C)c2cnc(-c3c(F)cc(CN(C(=O)OC(C)(C)C)C(C)C)cc3F)cc12]

This compound was prepared using the procedure outlined in Example 147, steps 1-2, with methyl 4-bromo-2-methoxybenzoate replacing methyl 4-bromobenzoate. LC-MS calculated for $C_{38}H_{48}F_2N_7O_6$ [M+H]$^+$ m/z: 736.3, found 736.3.

Step 2. N-(5-(2,6-Difluoro-4-((isopropylamino)methyl)phenyl)-1H-pyrazolo[3,4-c]pyridin-3-yl)-2-methoxy-4-(4-methylpiperazin-1-yl)benzamide To a solution of tert-butyl 5-(4-(((tert-butoxycarbonyl)(isopropyl)amino)methyl)-2,6-difluorophenyl)-3-(2-methoxy-4-(piperazin-1-yl)benzamido)-1H-pyrazolo[3,4-c]pyridine-1-carboxylate (17 mg, 0.023 mmol), paraformaldehyde (10.51 µl, 0.116 mmol) and acetic acid (3.97 µl, 0.069 mmol) was added sodium triacetoxyborohydride (14.69 mg, 0.069 mmol). The reaction mixture was stirred at r.t. for 1 h. TFA (0.5 mL) was added, and the stirring was continued for 30 mins at r.t. The mixture was diluted with methanol and purified on prep-LCMS (XBridge C18 column, eluting with a gradient of acetonitrile/water containing 0.1% TFA, at flow rate of 60 mL/min) to provide the desired product. LC-MS calculated for $C_{29}H_{34}F_2N_7O_2$ [M+H]$^+$ m/z: 550.2, found 550.2.

Example 150. N-(5-(2,6-Difluoro-4-((isopropylamino)methyl)phenyl)-1H-pyrazolo[3,4-c]pyridin-3-yl)-2-fluoro-3-(4-methylpiperazin-1-yl)benzamide

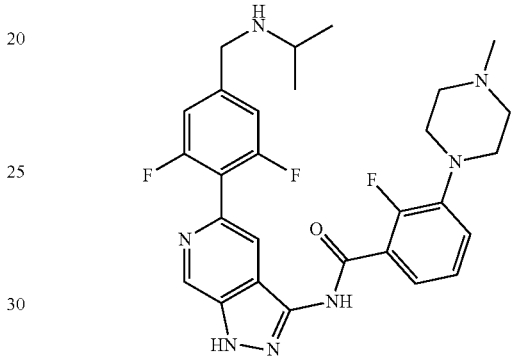

This compound was prepared in an analogous fashion to Example 149, with methyl 3-bromo-2-fluorobenzoate replacing methyl 4-bromo benzoate in Step 1. LC-MS calculated for $C_{28}H_{31}F_3N_7O$ [M+H]$^+$ m/z: 538.2, found 538.2.

Example 151. N-(5-(2,6-Difluoro-4-((isopropylamino)methyl)phenyl)-1H-pyrazolo[3,4-c]pyridin-3-yl)-4-fluoro-3-(4-methylpiperazin-1-yl)benzamide

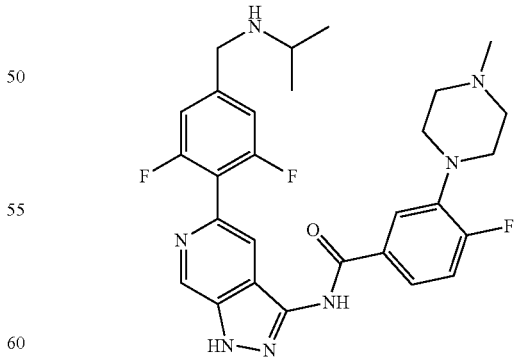

This compound was prepared in an analogous fashion to Example 149, with methyl 3-bromo-4-fluorobenzoate replacing methyl 4-bromo benzoate in Step 1. LC-MS calculated for $C_{28}H_{31}F_3N_7O$ [M+H]$^+$ m/z: 538.2, found 538.2.

Example 152. N-(5-(2-Fluoro-6-methylphenyl)-1H-pyrazolo[3,4-c]pyridin-3-yl)-4-(4-methylpiperazin-1-yl)benzamide

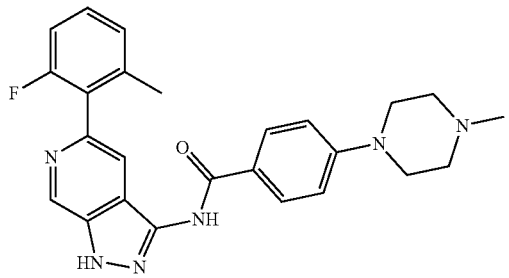 [SMILES: Cc1cccc(F)c1-c1cc2c(NC(=O)c3ccc(N4CCN(C)CC4)cc3)n[nH]c2cn1]

To a mixture of tert-butyl 5-bromo-3-(4-(4-methylpiperazin-1-yl)benzamido)-1H-pyrazolo[3,4-c]pyridine-1-carboxylate (20 mg, 0.039 mmol, Example 140, Step 1), (2-fluoro-6-methylphenyl)boronic acid (9 mg, 0.058 mmol), XPhos Pd G2 (3.05 mg, 3.88 µmol) and potassium phosphate (16.47 mg, 0.078 mmol) were added 1,4-dioxane (323 µl) and water (64 µl). The reaction flask was evacuated and backfilled with nitrogen. The reaction mixture was stirred at 80° C. for 1 h. The mixture was cooled to r.t. and quenched with water. The mixture was extracted with ethyl acetate, and the organic layer was dried over sodium sulfate and concentrated. The residue was dissolved in a 1:1 mixture of DCM/TFA. The resulting mixture was stirred at r.t. for 30 mins, diluted with methanol, and purified on prep-LCMS (XBridge C18 column, eluting with a gradient of acetonitrile/water containing 0.1% TFA, at flow rate of 60 mL/min) to provide the desired product. LC-MS calculated for $C_{25}H_{26}FN_6O$ $[M+H]^+$ m/z: 445.2, found 445.2. $^1$H NMR (600 MHz, DMSO-$d_6$) δ 13.50 (s, 1H), 10.89 (s, 1H), 9.87 (s, 1H), 9.12 (d, J=1.1 Hz, 1H), 8.03 (d, J=9.0 Hz, 2H), 7.81 (s, 1H), 7.36 (td, J=8.0, 6.0 Hz, 1H), 7.15 (dd, J=24.4, 8.3 Hz, 2H), 7.11 (d, J=9.0 Hz, 2H), 4.08 (d, J=12.6 Hz, 2H), 3.54 (d, J=11.1 Hz, 2H), 3.12 (dt, J=24.9, 10.5 Hz, 4H), 2.87 (s, 3H), 2.15 (s, 3H).

Example 153. N-(5-(2-Fluoro-6-(trifluoromethyl)phenyl)-1H-pyrazolo[3,4-c]pyridin-3-yl)-4-(4-methylpiperazin-1-yl)benzamide

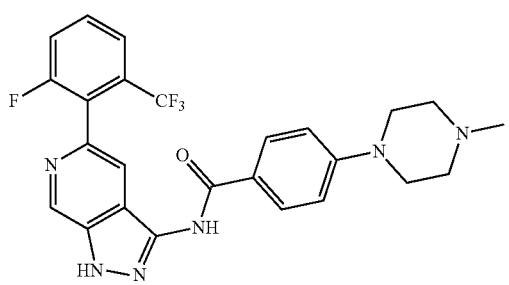 [SMILES: CN1CCN(c2ccc(C(=O)Nc3n[nH]c4cnc(-c5c(F)cccc5C(F)(F)F)cc34)cc2)CC1]

This compound was prepared in an analogous fashion to Example 152, with (2-fluoro-6-(trifluoromethyl)phenyl)boronic acid replacing (2-fluoro-6-methylphenyl)boronic acid. LC-MS calculated for $C_{25}H_{23}F_4N_6O$ $[M+H]^+$ m/z: 499.2, found 499.2.

Example 154. N-(5-(4-((Ethylamino)methyl)-2-fluoro-6-(trifluoromethyl)phenyl)-1H-pyrazolo[3,4-c]pyridin-3-yl)-4-(4-methylpiperazin-1-yl)benzamide

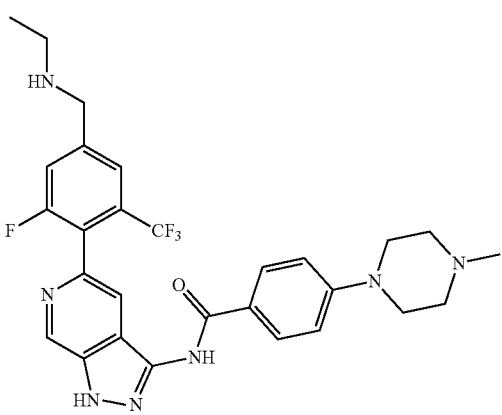 [SMILES: CCNCc1cc(F)c(-c2cc3c(NC(=O)c4ccc(N5CCN(C)CC5)cc4)n[nH]c3cn2)c(C(F)(F)F)c1]

Step 1. tert-Butyl ethyl(3-fluoro-4-(4,4,5,5-tetramethyl-1,3,2-dioxaborolan-2-yl)-5-(trifluoromethyl)benzyl)carbamate

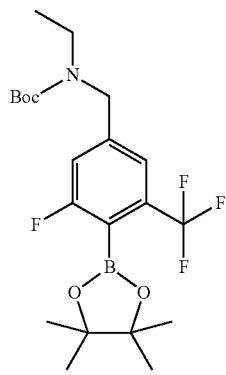 [SMILES: CCN(Cc1cc(F)c(B2OC(C)(C)C(C)(C)O2)c(C(F)(F)F)c1)C(=O)OC(C)(C)C]

This compound was prepared in an analogous fashion to Example 144 (Steps 1-2), with 3-fluoro-5-(trifluoromethyl)benzaldehyde replacing 3,5-difluorobenzaldehyde and ethanamine replacing methanamine. LC-MS calculated for $C_{21}H_{31}BF_4NO_4$ $[M+H]^+$ m/z: 448.2, found 448.2.

Step 2. N-(5-(4-((Ethylamino)methyl)-2-fluoro-6-(trifluoromethyl)phenyl)-1H-pyrazolo[3,4-c]pyridin-3-yl)-4-(4-methylpiperazin-1-yl)benzamide This compound was prepared in an analogous fashion to Example 152, with tert-butyl ethyl (3-fluoro-4-(4,4,5,5-tetramethyl-1,3,2-dioxaborolan-2-yl)-5-(trifluoromethyl)benzyl)carbamate replacing (2-fluoro-6-methylphenyl)boronic acid. LC-MS calculated for $C_{28}H_{30}F_4N_7O$ $[M+H]^+$ m/z: 556.2, found 556.2.

Example 155. 5-(2,6-Difluoro-4-((isopropylamino)methyl)phenyl)-N-(4-(4-methylpiperazin-1-yl)phenyl)-1H-pyrazolo[3,4-c]pyridine-3-carboxamide

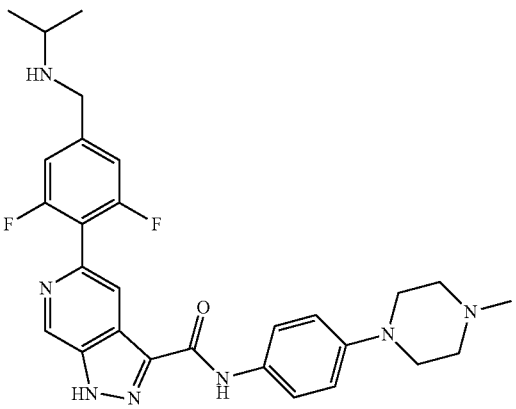 [SMILES: CC(C)NCc1cc(F)c(-c2cc3c(C(=O)Nc4ccc(N5CCN(C)CC5)cc4)n[nH]c3cn2)c(F)c1]

Step 1. Ethyl 5-chloro-1-((2-(trimethylsilyl)ethoxy)methyl)-1H-pyrazolo[3,4-c]pyridine-3-carboxylate

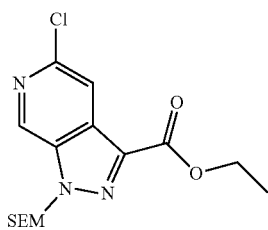 [SMILES: CCOC(=O)c1nn(COCC[Si](C)(C)C)c2cnc(Cl)cc12]

5-Chloro-3-iodo-1-((2-(trimethylsilyl)ethoxy)methyl)-1H-pyrazolo[3,4-c]pyridine (3.157 g, 7.71 mmol, Example 42, Step 2) was dissolved in DMF (11.56 ml) and ethanol (7.71 ml). Triethylamine (3.22 ml, 23.12 mmol) was added, followed by dppf-PdCl$_2$ (0.629 g, 0.771 mmol). The reaction flask was evacuated and back filled with CO gas from a balloon. The resulting solution was stirred at 80° C. overnight. The reaction mixture was quenched with water and extracted with ethyl acetate. The organic layer was washed with water and brine, dried over sodium sulfate, and concentrated. The residue was purified by Biotage Isolera™ (flash purification system with ethyl acetate/hexanes at a ratio from 0 to 75%) to provide the desired product. LC-MS calculated for C$_{15}$H$_{23}$ClN$_3$O$_3$Si [M+H]$^+$ m/z: 356.2, found 356.2.

Step 2. 5-Chloro-N-(4-(4-methylpiperazin-1-yl)phenyl)-1-((2-(trimethylsilyl)ethoxy)methyl)-1H-pyrazolo[3,4-c]pyridine-3-carboxamide

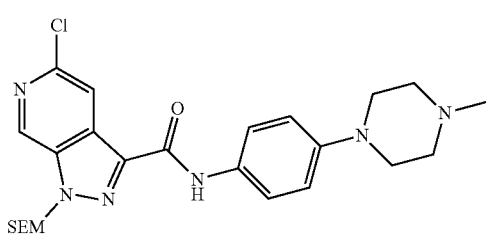 [SMILES: CN1CCN(c2ccc(NC(=O)c3nn(COCC[Si](C)(C)C)c4cnc(Cl)cc34)cc2)CC1]

To a mixture of ethyl 5-chloro-1-((2-(trimethylsilyl)ethoxy)methyl)-1H-pyrazolo[3,4-c]pyridine-3-carboxylate (82 mg, 0.230 mmol) and 4-(4-methylpiperazin-1-yl)aniline (88 mg, 0.461 mmol) in THF (1152 µl) was added potassium tert-butoxide (922 µl, 0.922 mmol), and the reaction mixture stirred at r.t. for 30 mins. The reaction was then quenched with water and extracted with ethyl acetate. The organic layer was dried over sodium sulfate and concentrated. The residue was purified by Biotage Isolera™ (flash purification system with methanol/dichlromethane at a ratio from 2 to 10%) to provide the desired product. LC-MS calculated for C$_{24}$H$_{34}$ClN$_6$O$_2$Si [M+H]$^+$ m/z: 501.2, found 501.2.

Step 3. 5-(2,6-Difluoro-4-formylphenyl)-N-(4-(4-methylpiperazin-1-yl)phenyl)-1-((2-(trimethylsilyl)ethoxy)methyl)-1H-pyrazolo[3,4-c]pyridine-3-carboxamide

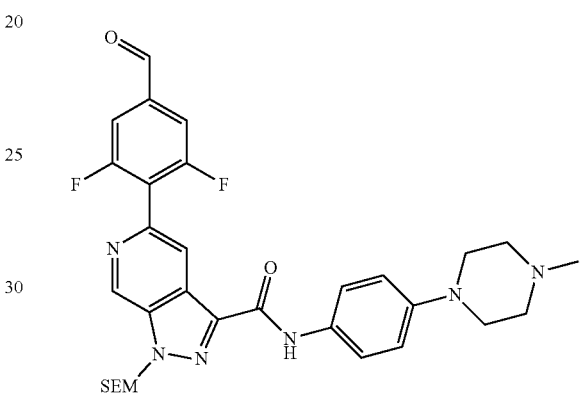

To a mixture of 5-chloro-N-(4-(4-methylpiperazin-1-yl)phenyl)-1-((2-(trimethylsilyl)ethoxy)methyl)-1H-pyrazolo[3,4-c]pyridine-3-carboxamide (250 mg, 0.499 mmol), (3,5-difluoro-4-(4,4,5,5-tetramethyl-1,3,2-dioxaborolan-2-yl)phenyl)methanol (202 mg, 0.748 mmol), Xphos Pd G2 (39.3 mg, 0.050 mmol) and potassium phosphate (212 mg, 0.998 mmol) were added 1,4-dioxane (2079 µl) and water (416 µl), and the reaction flask was evacuated and back filled with nitrogen. The reaction mixture was stirred at 80° C. for 1 h. The mixture was cooled to r.t., quenched with water and extracted with ethyl acetate. The separated organic layer was dried over sodium sulfate and concentrated. The residue was dissolved in DCM (4 mL), and manganese dioxide (434 mg, 4.99 mmol) was added. The reaction mixture was heated to 60° C. for 1 h then filtered through a plug of Celite. The filtrate was concentrated, and the residue was purified by Biotage Isolera™ (flash purification system with methanol/dichlromethane at a ratio from 2 to 10%) to provide the desired product. LC-MS calculated for C$_{31}$H$_{37}$F$_2$N$_6$O$_3$Si [M+H]$^+$ m/z: 607.2, found 607.2.

Step 4. 5-(2,6-Difluoro-4-((isopropylamino)methyl)phenyl)-N-(4-(4-methylpiperazin-1-yl)phenyl)-1H-pyrazolo[3,4-c]pyridine-3-carboxamide To a solution of 5-(2,6-difluoro-4-formylphenyl)-N-(4-(4-methylpiperazin-1-yl)phenyl)-1-((2-(trimethylsilyl)ethoxy)methyl)-1H-pyrazolo[3,4-c]pyridine-3-carboxamide (50 mg, 0.082 mmol) and propan-2-amine (13.49 µl, 0.165 mmol) in toluene (824 µl) was added acetic acid (14 µl, 0.247 mmol), and the mixture was heated to 80° C. After 1 h, it was cooled to r.t. and methanol (1 mL) was added.

Sodium borohydride (6.24 mg, 0.165 mmol) was then added at r.t. After 5 mins, 4N HCl in dioxane (1 mL) was added, and the reaction mixture heated to 80° C. for 1 h. The mixture was then cooled to r.t., diluted with methanol and purified on prep-LCMS (XBridge C18 column, eluting with a gradient of acetonitrile/water containing 0.1% TFA, at flow rate of 60 mL/min) to provide the desired product. LC-MS calculated for $C_{28}H_{32}F_2N_7O$ [M+H]$^+$ m/z: 520.2, found 520.2.

Example 156. N-(5-(2,6-Difluoro-4-(2-(pyrrolidin-1-yl)acetamido)phenyl)-1H-pyrazolo[3,4-c]pyridin-3-yl)-4-(4-methylpiperazin-1-yl)benzamide

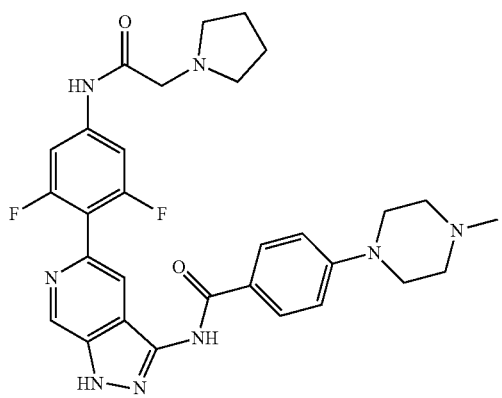 [SMILES: CN1CCN(c2ccc(C(=O)Nc3n[nH]c4cnc(-c5c(F)cc(NC(=O)CN6CCCC6)cc5F)cc34)cc2)CC1]

Step 1. tert-Butyl 5-(4-amino-2,6-difluorophenyl)-3-(4-(4-methylpiperazin-1-yl)benzamido)-1H-pyrazolo[3,4-c]pyridine-1-carboxylate

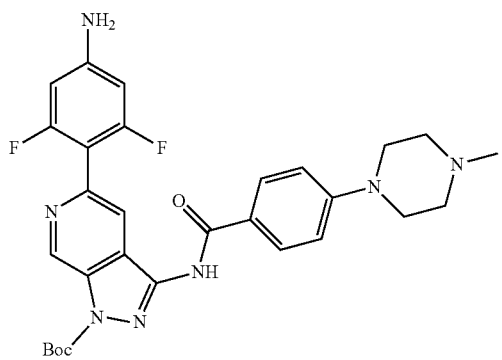 [SMILES: CN1CCN(c2ccc(C(=O)Nc3nn(C(=O)OC(C)(C)C)c4cnc(-c5c(F)cc(N)cc5F)cc34)cc2)CC1]

To a mixture of tert-butyl 5-bromo-3-(4-(4-methylpiperazin-1-yl)benzamido)-1H-pyrazolo[3,4-c]pyridine-1-carboxylate (200 mg, 0.388 mmol, Example 140, Step 1), 3,5-difluoro-4-(4,4,5,5-tetramethyl-1,3,2-dioxaborolan-2-yl)aniline (198 mg, 0.776 mmol, Example 63, Step 1), XPhos Pd G2 (28.0 mg, 0.039 mmol) and potassium phosphate (206 mg, 0.970 mmol) were added 1,4-dioxane (3234 μl) and water (647 μl), and the reaction flask was evacuated, back filled with nitrogen. The reaction mixture was stirred at 80° C. for 2 h. The mixture was cooled to r.t., diluted with DCM and filtered through a plug of Celite. The filtrate was concentrated and used in the next step without further purification. LC-MS calculated for $C_{29}H_{32}F_2N_7O_3$ [M+H]$^+$ m/z: 564.2, found 564.2.

Step 2. N-(5-(2,6-Difluoro-4-(2-(pyrrolidin-1-yl)acetamido)phenyl)-1H-pyrazolo[3,4-c]pyridin-3-yl)-4-(4-methylpiperazin-1-yl)benzamide To a solution of tert-butyl 5-(4-amino-2,6-difluorophenyl)-3-(4-(4-methylpiperazin-1-yl)benzamido)-1H-pyrazolo[3,4-c]pyridine-1-carboxylate (21 mg, 0.037 mmol) and Hunig's base (19.52 μl, 0.112 mmol) in DCM (745 μl) at 0° C. was added 2-chloroacetyl chloride (4.45 μl, 0.056 mmol), and the reaction mixture was warmed up to r.t. and stirred for 1 h. The reaction mixture was then quenched with water and extracted with DCM. The organic layer was dried over sodium sulfate and concentrated.

The residue was dissolved in DMF (745 μl), and pyrrolidine (15.41 μl, 0.186 mmol) was added. The mixture was stirred at 50° C. for 1 h, then cooled to r.t., quenched with water and extracted with ethyl acetate. The organic layer was washed with water and brine, dried over sodium sulfate and concentrated. The residue was dissolved in a 1:1 mixture of DCM:TFA and stirred at r.t. for 1 h. The mixture was diluted with methanol and purified on prep-LCMS (XBridge C18 column, eluting with a gradient of acetonitrile/water containing 0.1% TFA, at flow rate of 60 mL/min) to provide the desired product. LC-MS calculated for $C_{30}H_{33}F_2N_8O_2$ [M+H]$^+$ m/z: 575.2, found 575.2.

Example 157. 2-Amino-N-(5-(2-fluoro-6-methylphenyl)-1H-pyrazolo[3,4-c]pyridin-3-yl)-4-(4-methylpiperazin-1-yl)benzamide

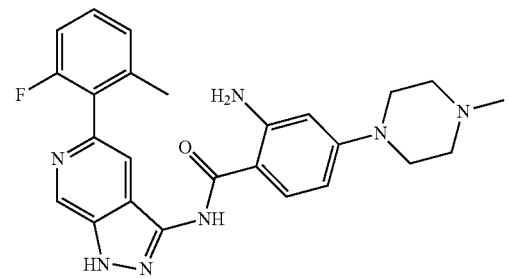 [SMILES: Cc1cccc(F)c1-c1cc2c(NC(=O)c3ccc(N4CCN(C)CC4)cc3N)n[nH]c2cn1]

Step 1. tert-Butyl 3-amino-5-(2-fluoro-6-methylphenyl)-1H-pyrazolo[3,4-c]pyridine-1-carboxylate

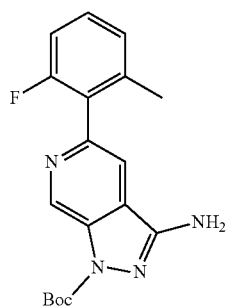 [SMILES: Cc1cccc(F)c1-c1cc2c(N)nn(C(=O)OC(C)(C)C)c2cn1]

To a mixture of tert-butyl 3-amino-5-bromo-1H-pyrazolo[3,4-c]pyridine-1-carboxylate (1.79 g, 5.72 mmol), (2-fluoro-6-methylphenyl)boronic acid (1.320 g, 8.57 mmol), XPhos Pd G2 (0.225 g, 0.286 mmol) and potassium phosphate (2.427 g, 11.43 mmol) were added 1,4-dioxane (15.24 ml) and water (3.81 ml), and the reaction flask was evacuated and back filled with nitrogen. The reaction mixture was stirred at 80° C. for 1 h. The mixture was then diluted with ethyl acetate and water, and the layers were separated. The organic layer was dried over sodium sulfate and concentrated. The residue was purified by Biotage Isolera™ (flash purification system with ethyl acetate/hexanes at a ratio from 0 to 100%) to provide the desired product as a brown powder (1.7 g, 87%). LC-MS calculated for $C_{18}H_{20}FN_4O_2$ $[M+H]^+$ m/z: 343.2, found 343.2.

Step 2. tert-Butyl 3-(4-fluoro-2-nitrobenzamido)-5-(2-fluoro-6-methylphenyl)-1H-pyrazolo[3,4-c]pyridine-1-carboxylate

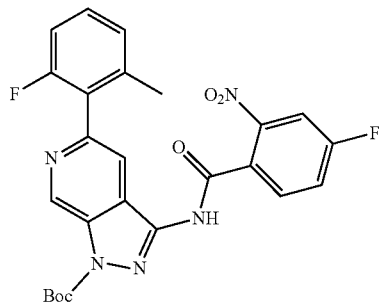 [SMILES: Cc1cccc(F)c1-c1cc2c(NC(=O)c3ccc(F)cc3[N+](=O)[O-])nn(C(=O)OC(C)(C)C)c2cn1]

To a suspension of 4-fluoro-2-nitrobenzoic acid (595 mg, 3.21 mmol) in DCM (7 mL) was added DMF (11.31 μl, 0.146 mmol) and oxalyl chloride (281 μl, 3.21 mmol), and the reaction mixture was stirred at r.t. until homogeneous (~1 h). To the mixture was added a solution of tert-butyl 3-amino-5-(2-fluoro-6-methylphenyl)-1H-pyrazolo[3,4-c]pyridine-1-carboxylate (500 mg, 1.460 mmol) and Hunig's base (765 μl, 4.38 mmol) in THF (7 mL). The mixture was stirred at r.t. overnight. 1-Methylpiperazine (488 μl, 4.38 mmol) was added, and the reaction mixture was stirred for an additional 1 h at r.t. The mixture was filtered through a plug of Celite, and the filtrate was concentrated. The residue was purified by Biotage Isolera™ (flash purification system with ethyl acetate/hexanes at a ratio from 0 to 100%) to provide the desired product as a pale yellow solid (524 mg, 70%). LC-MS calculated for $C_{25}H_{22}F_2N_5O_5$ $[M+H]^+$ m/z: 510.2, found 510.2.

Step 3. 2-Amino-N-(5-(2-fluoro-6-methylphenyl)-1H-pyrazolo[3,4-c]pyridin-3-yl)-4-(4-methylpiperazin-1-yl)benzamide To solution of tert-butyl 3-(4-fluoro-2-nitrobenzamido)-5-(2-fluoro-6-methylphenyl)-1H-pyrazolo[3,4-c]pyridine-1-carboxylate (524 mg, 1.029 mmol) and Hunig's base (539 μl, 3.09 mmol) in DMSO (10 mL) was added 1-methylpiperazine (229 μl, 2.057 mmol), and the reaction mixture was heated to 90° C. for 3 h. The mixture was quenched with water and extracted with ethyl acetate. The organic layer was washed with water and brine, dried over sodium sulfate and concentrated to provide the desired product. The crude product was dissolved in methanol (10 mL), and palladium on carbon (386 mg, 0.363 mmol) was added. The reaction flask was evacuated and back filled with hydrogen gas from a balloon. The reaction mixture was stirred at 55° C. for 1 h. The mixture was filtered through a plug of Celite, and the filtrate was purified on prep-LCMS (XBridge C18 column, eluting with a gradient of acetonitrile/water containing 0.1% TFA, at flow rate of 60 mL/min) to provide the desired product. LC-MS calculated for $C_{25}H_{27}FN_7O$ $[M+H]^+$ m/z: 460.2, found 460.2.

Example 158. N-(5-(2-Fluoro-6-methylphenyl)-1H-pyrazolo[3,4-c]pyridin-3-yl)-2-(2-hydroxypropylamino)-4-(4-methylpiperazin-1-yl)benzamide

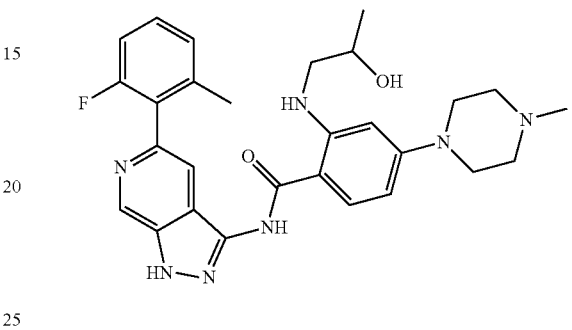

To a solution of 2-amino-N-(5-(2-fluoro-6-methylphenyl)-1H-pyrazolo[3,4-c]pyridin-3-yl)-4-(4-methylpiperazin-1-yl)benzamide (15 mg, 0.033 mmol, Example 157), tetramethylammonium triacetoxyborohydride (42.9 mg, 0.163 mmol) and TFA (12.57 μl, 0.163 mmol) in DCE (653 μl) was added 2-((tert-butyldimethylsilyl)oxy)propanal (18.4 mg, 0.098 mmol). The reaction mixture was stirred at r.t. for 5 mins, quenched with TFA (0.5 mL), and allowed to stir overnight. The reaction mixture was diluted with methanol and purified on prep-LCMS (XBridge C18 column, eluting with a gradient of acetonitrile/water containing 0.1% TFA, at flow rate of 60 mL/min) to provide the desired product. LC-MS calculated for $C_{28}H_{33}FN_7O_2$ $[M+H]^+$ m/z: 518.2, found 518.2.

Example 159. N-(5-(2-Fluoro-6-methylphenyl)-1H-pyrazolo[3,4-c]pyridin-3-yl)-2-((1-methyl-1H-pyrazol-5-yl)methylamino)-4-(4-methylpiperazin-1-yl)benzamide

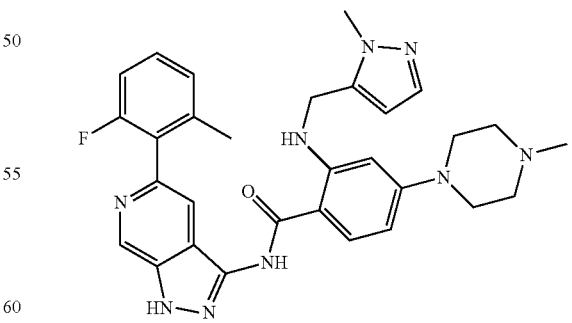

This compound was prepared in an analogous fashion to Example 158, with 1-methyl-1H-pyrazole-4-carbaldehyde replacing 2-((tert-butyldimethylsilyl)oxy)propanal. LC-MS calculated for $C_{30}H_{33}FN_9O$ $[M+H]^+$ m/z: 554.2, found 554.2.

Example 160. 2-(3-Cyanocyclopentylamino)-N-(5-(2-fluoro-6-methylphenyl)-1H-pyrazolo[3,4-c]pyridin-3-yl)-4-(4-methylpiperazin-1-yl)benzamide

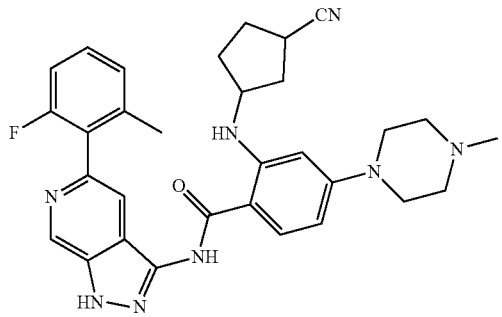 [SMILES: Cc1cccc(F)c1-c1cc2c(NC(=O)c3ccc(N4CCN(C)CC4)cc3NC3CCC(C#N)C3)n[nH]c2cn1]

This compound was prepared in an analogous fashion to Example 158, with 3-oxocyclopentane-1-carbonitrile replacing 2-((tert-butyldimethylsilyl)oxy)propanal. LC-MS calculated for $C_{31}H_{34}FN_8O$ [M+H]$^+$ m/z: 553.2, found 553.2.

Example 161. 2-(4-(5-(2,6-Difluoro-4-((methylamino)methyl)phenyl)-1H-pyrazolo[3,4-c]pyridin-3-yl)-1H-pyrazol-1-yl)benzonitrile

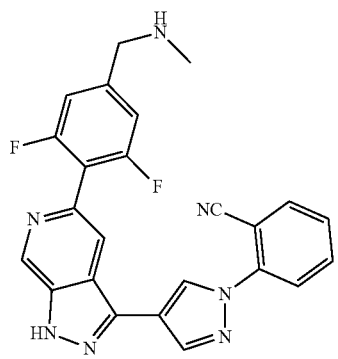 [SMILES: CNCc1cc(F)c(-c2cc3c(-c4cnn(-c5ccccc5C#N)c4)n[nH]c3cn2)c(F)c1]

Step 1. tert-Butyl 5-(4-((tert-butoxycarbonyl(methyl)amino)methyl)-2,6-difluorophenyl)-3-iodo-1H-pyrazolo[3,4-c]pyridine-1-carboxylate

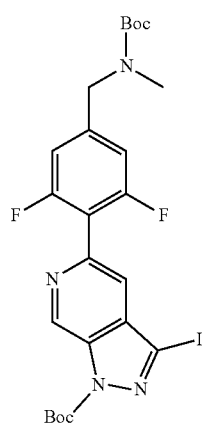

This compound was prepared according to the procedures described in Example 119, step 1-3 using 3,5-difluorobenzaldehyde instead of 3-fluoro-5-(trifluoromethyl)benzaldehyde as starting material. LCMS calculated for $C_{24}H_{28}F_2IN_4O_4$ (M+H)$^+$: m/z=601.1; Found: 601.0.

Step 2. 2-(4-(5-(2,6-Difluoro-4-((methylamino)methyl)phenyl)-1H-pyrazolo[3,4-c]pyridin-3-yl)-1H-pyrazol-1-yl)benzonitrile A mixture of tert-butyl 5-(4-(((tert-butoxycarbonyl)(methyl)amino)methyl)-2,6-difluorophenyl)-3-iodo-1H-pyrazolo[3,4-c]pyridine-1-carboxylate (20 mg, 0.033 mmol), 2-(4-(4,4,5,5-tetramethyl-1,3,2-dioxaborolan-2-yl)-1H-pyrazol-1-yl)benzonitrile (29.5 mg, 0.100 mmol), (1,1'-bis(diphenylphosphino)ferrocene)-dichloropalladium(II) complexed with dichloromethane (1:1) (2.72 mg, 3.33 μmol) and potassium carbonate (13.81 mg, 0.100 mmol) in dioxane (2 mL) and water (0.4 mL) was stirred at 70° C. for 2 h. After cooling to room temperature, the mixture was concentrated in vacuo. The crude mixture was then dissolved in DCM (2.0 mL), and TFA (2.0 mL) was added dropwise at room temperature. After stirring for 2 h, the mixture was concentrated in vacuo. The crude mixture was dissolved in MeOH (3.5 mL) and 10% aqueous NH$_4$OH (1.5 mL). The mixture was purified with prep-LCMS (XBridge C18 column, eluting with a gradient of acetonitrile/water containing 0.1% TFA, at flow rate of 60 mL/min) to give the desired product. LCMS calculated for $C_{24}H_{18}F_2N_7$ (M+H)$^+$: m/z=442.2; Found: 442.2.

Example 162. 1-(4-(3-(1-(Azetidin-3-yl)-1H-pyrazol-4-yl)-1H-pyrazolo[3,4-c]pyridin-5-yl)-3,5-difluorophenyl)-N-methylmethanamine

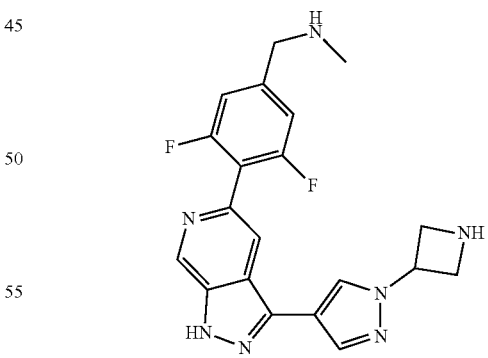

This compound was prepared according to the procedures described in Example 161, step 7 using tert-butyl 3-(4-(4,4,5,5-tetramethyl-1,3,2-dioxaborolan-2-yl)-1H-pyrazol-1-yl)azetidine-1-carboxylate instead of 2-(4-(4,4,5,5-tetramethyl-1,3,2-dioxaborolan-2-yl)-1H-pyrazol-1-yl)benzonitrile as starting material. LC-MS calculated for $C_{20}H_{20}F_2N_7$ (M+H)$^+$: m/z=396.2; found 396.2.

Example 163. 1-(3,5-Difluoro-4-(3-(2-(4-methylpiperazin-1-yl)pyridin-4-yl)-1H-pyrazolo[3,4-c]pyridin-5-yl)phenyl)-N-methylmethanamine

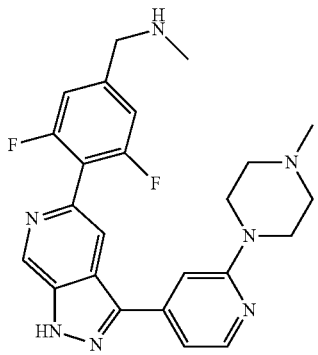 [SMILES: CNCc1cc(F)c(-c2cc3c(-c4ccnc(N5CCN(C)CC5)c4)n[nH]c3cn2)c(F)c1]

This compound was prepared according to the procedures described in Example 161, step 7 using 1-methyl-4-(4-(4,4,5,5-tetramethyl-1,3,2-dioxaborolan-2-yl)pyridin-2-yl)piperazine instead of 2-(4-(4,4,5,5-tetramethyl-1,3,2-dioxaborolan-2-yl)-1H-pyrazol-1-yl)benzonitrile as starting material. LC-MS calculated for $C_{24}H_{26}F_2N_7$ $(M+H)^+$: m/z=450.2; found 450.2.

Example 164. 2-(4-(5-(2,6-Difluoro-4-((methylamino)methyl)phenyl)-1H-pyrazolo[3,4-c]pyridin-3-yl)-1H-pyrazol-1-yl)ethanol

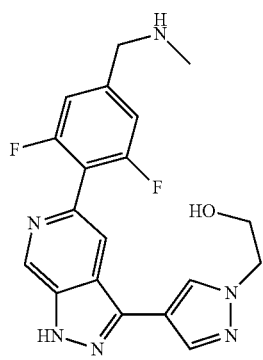 [SMILES: CNCc1cc(F)c(-c2cc3c(-c4cnn(CCO)c4)n[nH]c3cn2)c(F)c1]

This compound was prepared according to the procedures described in Example 161, step 7 using 2-(4-(4,4,5,5-tetramethyl-1,3,2-dioxaborolan-2-yl)-1H-pyrazol-1-yl)ethan-1-ol instead of 2-(4-(4,4,5,5-tetramethyl-1,3,2-dioxaborolan-2-yl)-1H-pyrazol-1-yl)benzonitrile as starting material. LC-MS calculated for $C_{19}H_{19}F_2N_6O$ $(M+H)^+$: m/z=385.2; found 385.2.

Example 165. 1-(3,5-Difluoro-4-(3-(4-methoxyphenyl)-1H-pyrazolo[3,4-c]pyridin-5-yl)phenyl)-N-methylmethanamine

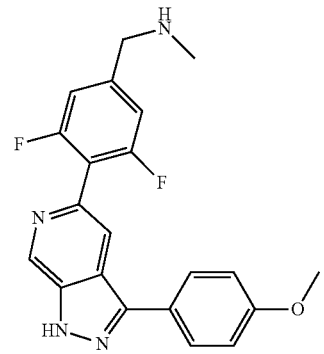 [SMILES: CNCc1cc(F)c(-c2cc3c(-c4ccc(OC)cc4)n[nH]c3cn2)c(F)c1]

This compound was prepared according to the procedures described in Example 161, step 7 using (4-methoxyphenyl)boronic acid instead of 2-(4-(4,4,5,5-tetramethyl-1,3,2-dioxaborolan-2-yl)-1H-pyrazol-1-yl)benzonitrile as starting material. LC-MS calculated for $C_{21}H_{19}F_2N_4O$ $(M+H)^+$: m/z=381.2; found 381.1.

Example 166. 1-(5-(5-(2,6-Difluoro-4-((methylamino)methyl)phenyl)-1H-pyrazolo[3,4-c]pyridin-3-yl)pyridin-2-yl)piperidin-4-ol

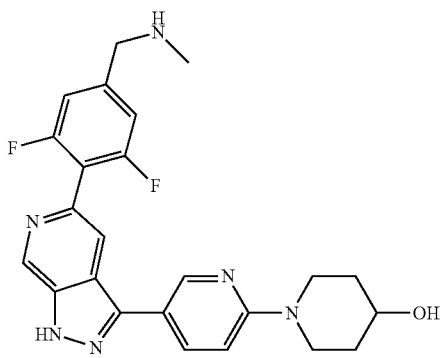 [SMILES: CNCc1cc(F)c(-c2cc3c(-c4ccc(N5CCC(O)CC5)nc4)n[nH]c3cn2)c(F)c1]

Step 1. tert-Butyl 3,5-difluoro-4-(3-iodo-1-((2-(trimethylsilyl)ethoxy)methyl)-1H-pyrazolo[3,4-c]pyridin-5-yl)benzyl(methyl)carbamate

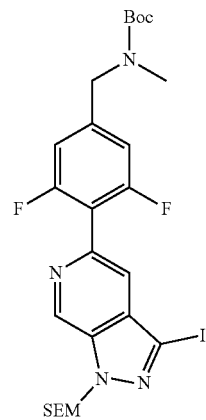 [SMILES: CN(Cc1cc(F)c(-c2cc3c(I)nn(COCC[Si](C)(C)C)c3cn2)c(F)c1)C(=O)OC(C)(C)C]

To a solution of tert-butyl (3,5-difluoro-4-(3-iodo-1H-pyrazolo[3,4-c]pyridin-5-yl)benzyl)(methyl)carbamate (3.80 g, 7.60 mmol, Example 161, Step 5) in THF (38 mL) was added N,N-diisopropylethylamine (1.99 mL, 11.4 mmol) and 2-(trimethylsilyl)ethoxymethyl chloride (1.42 mL, 7.98 mmol) at r.t. After stirring for 18 h, the mixture was quenched with water (60 mL) and extracted with ethyl acetate. The solvents of the separated organic layers were evaporated under reduced pressure to give the crude product. The obtained crude product was purified by Biotage Isolera™ to give the desired product. LCMS calculated for $C_{25}H_{34}F_2IN_4O_3Si$ (M+H)$^+$: m/z=631.1; Found: 631.2.

Step 2. tert-Butyl 4-(3-(6-chloropyridin-3-yl)-14(2-(trimethylsilyl)ethoxy)methyl)-1H-pyrazolo[3,4-c]pyridin-5-yl)-3,5-difluorobenzyl(methyl)carbamate

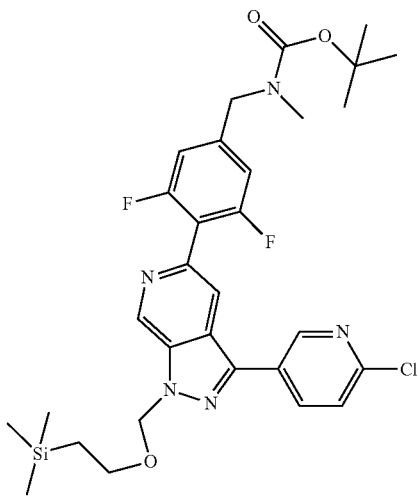 [SMILES: CN(Cc1cc(F)c(-c2cc3c(-c4ccc(Cl)nc4)nn(COCC[Si](C)(C)C)c3cn2)c(F)c1)C(=O)OC(C)(C)C]

A mixture of tert-butyl (3,5-difluoro-4-(3-iodo-1-((2-(trimethylsilyl)ethoxy)methyl)-1H-pyrazolo[3,4-c]pyridin-5-yl)benzyl)(methyl)carbamate (176 mg, 0.279 mmol), (6-chloropyridin-3-yl)boronic acid (48.3 mg, 0.307 mmol), (1,1'-bis(diphenylphosphino)ferrocene)-dichloropalladium (II) complexed with dichloromethane (1:1) (22.80 mg, 0.028 mmol) and potassium carbonate (77 mg, 0.558 mmol) in dioxane (20 mL) and water (4 mL) was stirred at 70° C. for 2 h. After cooling to r.t., the mixture was concentrated in vacuo. The obtained crude product was purified by Biotage Isolera™ to give the desired product. LCMS calculated for $C_{30}H_{37}ClF_2N_5O_3Si$ (M+H)$^+$: m/z=616.2; Found: 616.3.

Step 3. 1-(5-(5-(2,6-Difluoro-4-((methylamino)methyl)phenyl)-1H-pyrazolo[3,4-c]pyridin-3-yl)pyridin-2-yl)piperidin-4-ol A mixture of tert-butyl (4-(3-(6-chloropyridin-3-yl)-1-((2-(trimethylsilyl)ethoxy)methyl)-1H-pyrazolo[3,4-c]pyridin-5-yl)-3,5-difluorobenzyl)(methyl)carbamate (15 mg, 0.024 mmol), piperidin-4-ol (4.92 mg, 0.049 mmol), RuPhos Pd G3 (2.0 mg, 2.43 μmol) and cesium carbonate (23.8 mg, 0.073 mmol) in dioxane (1 ml) was stirred at 90° C. for 3 h. After cooling to room temperature, the mixture was concentrated in vacuo. The obtained crude product was dissolved in DCM (2.0 mL), and TFA (2.0 mL) was added dropwise at room temperature. After stirring for 2 h, the mixture was concentrated in vacuo. The crude mixture was dissolved in MeOH (3.5 mL) and 10% aqueous NH$_4$OH (1.5 mL). The resulting mixture was purified with prep-LCMS (XBridge C18 column, eluting with a gradient of acetonitrile/water containing 0.1% TFA, at flow rate of 60 mL/min) to give the desired product. LCMS calculated for $C_{24}H_{25}F_2N_6O$ (M+H)$^+$: m/z=451.2; Found: 451.2.

Example 167. 1-(3,5-Difluoro-4-(3-(5-(3-fluoropyrrolidin-1-yl)pyridin-2-yl)-1H-pyrazolo[3,4-c]pyridin-5-yl)phenyl)-N-methylmethanamine

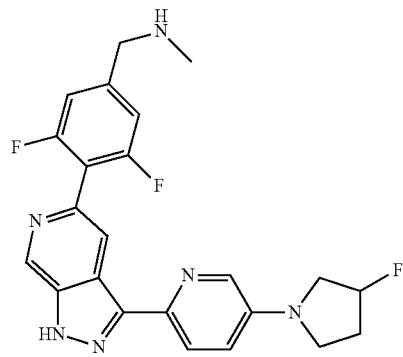 [SMILES: CNCc1cc(F)c(-c2cc3c(-c4ccc(N5CCC(F)C5)cn4)n[nH]c3cn2)c(F)c1]

Step 1. tert-Butyl 4-(3-(5-chloropyridin-2-yl)-1-((2-(trimethylsilyl)ethoxy)methyl)-1H-pyrazolo[3,4-c]pyridin-5-yl)-3,5-difluorobenzyl(methyl)carbamate

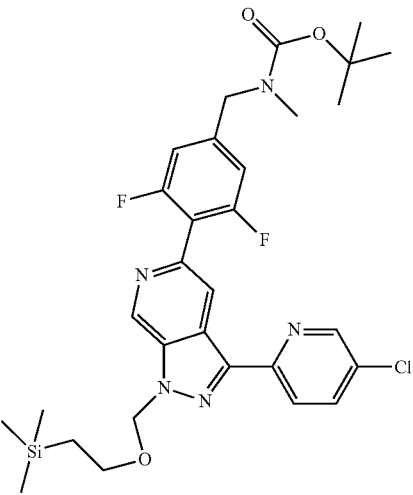 [SMILES: CN(Cc1cc(F)c(-c2cc3c(-c4ccc(Cl)cn4)nn(COCC[Si](C)(C)C)c3cn2)c(F)c1)C(=O)OC(C)(C)C]

A mixture of tert-butyl (3,5-difluoro-4-(3-iodo-1-((2-(trimethylsilyl)ethoxy)methyl)-1H-pyrazolo[3,4-c]pyridin-5-yl)benzyl)(methyl)carbamate (874 mg, 1.39 mmol, Example 166, Step 1), 5-chloro-2-(tributylstannyl)pyridine (614 mg, 1.53 mmol), tetrakis(triphenylphosphine)palladium(0) (160 mg, 0.139 mmol) and CuI (52.8 mg, 0.277 mmol) in dioxane (30 mL) was stirred at 100° C. for 2 h. After cooling to room temperature, the mixture was concentrated in vacuo. The obtained crude product was purified by Biotage Isolera™ to give the desired product. LCMS calculated for $C_{30}H_{37}ClF_2N_5O_3Si$ (M+H)$^+$: m/z=616.2; Found: 616.1.

Step 2. 1-(3,5-Difluoro-4-(3-(5-(3-fluoropyrrolidin-1-yl)pyridin-2-yl)-1H-pyrazolo[3,4-c]pyridin-5-yl)phenyl)-N-methylmethanamine A mixture of tert-butyl (4-(3-(5-chloropyridin-2-yl)-1-((2-(trimethylsilyl)ethoxy)methyl)-1H-pyrazolo[3,4-c]pyridin-5-yl)-3,5-difluorobenzyl)(methyl)carbamate (22 mg, 0.036 mmol), 3-fluoropyrrolidine (6.36 mg, 0.071 mmol), RuPhos Pd G3 (2.98 mg, 3.57 μmol) and cesium carbonate (34.9 mg, 0.107 mmol) in dioxane (1 ml) was stirred at 90° C. for 3 h. After cooling to room temperature, the mixture was concentrated in vacuo. The crude mixture was then dissolved in DCM (2.0 mL), and TFA (2.0 mL) was added dropwise at room temperature. After stirring for 2 h, the mixture was concentrated in vacuo. The crude mixture was dissolved in MeOH (3.5 mL) and 10% aqueous NH$_4$OH (1.5 mL). The mixture was purified with prep-LCMS (XBridge C18 column, eluting with a gradient of acetonitrile/water containing 0.1% TFA, at flow rate of 60 mL/min) to give the desired product. LCMS calculated for C$_{23}$H$_{22}$F$_3$N$_6$ (M+H)$^+$: m/z=439.2; Found: 439.2.

Example 168. 1-(3-Fluoro-5-methyl-4-(3-(1-methyl-1H-pyrazol-4-yl)-1H-pyrazolo[3,4-c]pyridin-5-yl)phenyl)-N-methylmethanamine

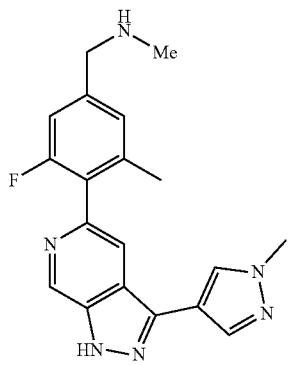

A mixture of tert-butyl (4-bromo-3-fluoro-5-methylbenzyl)(methyl)carbamate (60 mg, 0.181 mmol, Example 113, Steps 1-6), 4,4,4',4',5,5,5',5'-octamethyl-2,2'-bi(1,3,2-dioxaborolane) (68.8 mg, 0.271 mmol), potassium acetate (53.2 mg, 0.542 mmol) and (1,1'-bis(diphenylphosphino)ferrocene)-dichloropalladium(II) complexed with dichloromethane (1:1) (29.5 mg, 0.036 mmol) in dioxane (10 mL) was stirred at 110° C. for 24 h. After cooling to room temperature, the mixture was concentrated in vacuo. A mixture of this crude material, 5-chloro-3-(1-methyl-1H-pyrazol-4-yl)-1-((2-(trimethylsilyl)ethoxy)methyl)-1H-pyrazolo[3,4-c]pyridine (21.8 mg, 0.060 mmol, Intermediate 2), XPhos Pd G2 (4.42 mg, 6.00 μmol) and cesium carbonate (58.6 mg, 0.180 mmol) in dioxane (10 mL) and water (2 mL) was stirred at 70° C. for 18 h. After cooling to room temperature, the mixture was concentrated in vacuo. The crude mixture was then dissolved in DCM (2.0 mL), and TFA (2.0 mL) was added dropwise at room temperature. After stirring for 2 h, the mixture was concentrated in vacuo. The crude mixture was dissolved in MeOH (3.5 mL) and 10% aqueous NH$_4$OH (1.5 mL). The mixture was purified with prep-LCMS (XBridge C18 column, eluting with a gradient of acetonitrile/water containing 0.1% TFA, at flow rate of 60 mL/min) to give the desired product. LCMS calculated for C$_{19}$H$_{20}$FN$_6$ (M+H)$^+$: m/z=351.2; Found: 351.1. $^1$H NMR (TFA salt, 600 MHz, (CD$_3$)$_2$SO) δ 9.16 (d, J=1.3 Hz, 1H), 9.01 (br s, 2H), 8.49 (d, J=0.8 Hz, 1H), 8.10 (t, J=1.1 Hz, 1H), 8.05 (d, J=0.8 Hz, 1H), 7.34-7.27 (m, 2H), 4.19 (t, J=5.7 Hz, 2H), 3.91 (s, 3H), 2.62 (t, J=5.2 Hz, 3H), 2.17 (s, 3H).

Example 169. 4-(5-(2-Fluoro-6-methyl-4-((methylamino)methyl)phenyl)-1H-pyrazolo[3,4-c]pyridin-3-yl)-N-methylbenzamide

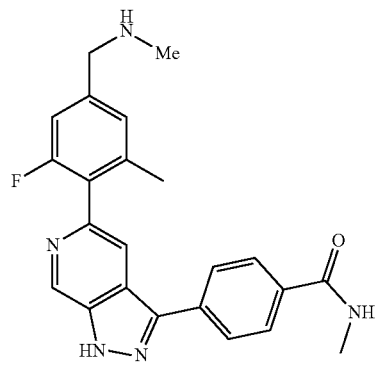 [SMILES: CNCc1cc(C)c(-c2cc3c(-c4ccc(C(=O)NC)cc4)n[nH]c3cn2)c(F)c1]

Step 1. 4-(5-Chloro-1-((2-(trimethylsilyl)ethoxy)methyl)-1H-pyrazolo[3,4-c]pyridin-3-yl)-N-methylbenzamide

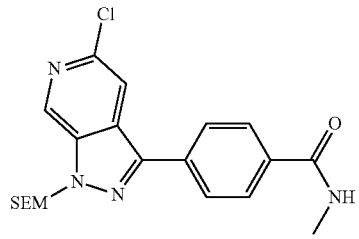 [SMILES: CNC(=O)c1ccc(-c2nn(COCC[Si](C)(C)C)c3cnc(Cl)cc23)cc1]

A solution of 5-chloro-3-iodo-1-((2-(trimethylsilyl)ethoxy)methyl)-1H-pyrazolo[3,4-c]pyridine (215 mg, 0.525 mmol, Example 42, Step 2), (4-(methylcarbamoyl)phenyl)boronic acid (94 mg, 0.525 mmol), (1,1'-bis(diphenylphosphino)ferrocene)-dichloropalladium(II) complexed with dichloromethane (1:1) (42.9 mg, 0.052 mmol) and potassium carbonate (145 mg, 1.05 mmol) in dioxane (3.0 mL) and water (0.5 mL) was stirred at 70° C. for 5 h. After cooling to room temperature, the mixture was concentrated in vacuo. The obtained crude product was purified by Biotage Isolera™ to give the desired product. LCMS calculated for C$_{20}$H$_{26}$ClN$_4$O$_2$Si (M+H)$^+$: m/z=417.2; Found: 417.2.

Step 2. 4-(5-(2-Fluoro-6-methyl-4-((methylamino)methyl)phenyl)-1H-pyrazolo[3,4-c]pyridin-3-yl)-N-methylbenzamide This compound was prepared according to the procedures described in Example 168, using 4-(5-chloro-1-((2-(trimethylsilyl)ethoxy)methyl)-1H-pyrazolo[3,4-c]pyridin-3-yl)-N-methylbenzamide instead of 5-chloro-3-(1-methyl-1H-pyrazol-4-yl)-1-((2-(trimethylsilyl)ethoxy)methyl)-1H-pyrazolo[3,4-c]pyridine as starting material. LC-MS calculated for $C_{23}H_{23}FN_5O$ (M+H)$^+$: m/z=404.2; found 404.1.

Example 170. 4-(5-(2-Fluoro-6-methyl-4-(pyrrolidin-2-yl)phenyl)-1H-pyrazolo[3,4-c]pyridin-3-yl)-N-methylbenzamide

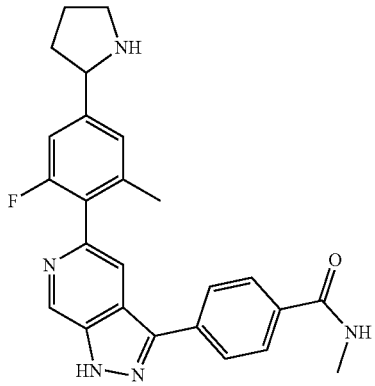 [SMILES: CNC(=O)c1ccc(-c2n[nH]c3cnc(-c4c(C)cc(C5CCCN5)cc4F)cc23)cc1]

Step 1. tert-Butyl 4-(4-bromo-3-fluoro-5-methylphenyl)-4-oxobutylcarbamate

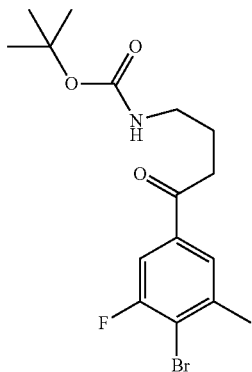 [SMILES: Cc1cc(C(=O)CCCNC(=O)OC(C)(C)C)cc(F)c1Br]

To a solution of 2-bromo-1-fluoro-5-iodo-3-methylbenzene (1.34 g, 4.25 mmol, Example 168, Step 2) in THF (30 mL) was added a solution of isopropylmagnesium chloride in THF (2.13 mL, 4.25 mmol, 2 M) dropwise at −40° C. After stirring at −40° C. for 1 h, the mixture was cooled to −78° C., and tert-butyl 2-oxopyrrolidine-1-carboxylate (0.726 mL, 4.25 mmol) was added. The resulting mixture was slowly warmed to r.t. over 1.5 h. The mixture was quenched with 1 M HCl and extracted with ethyl acetate. The separated organic layers were concentrated in vacuo. The obtained crude product was purified by Biotage Isolera™ to give the desired product. LCMS calculated for $C_{11}H_{14}BrFNO$ (M-$C_5H_8O_2$+H)$^+$: m/z=274.0; Found: 274.0.

Step 2. tert-Butyl 2-(4-bromo-3-fluoro-5-methylphenyl)pyrrolidine-1-carboxylate

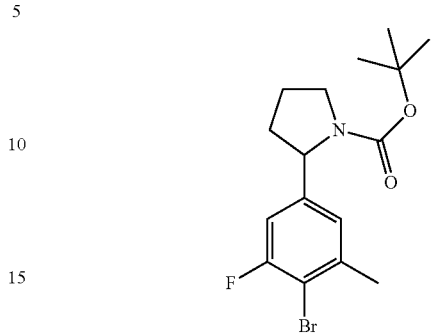

A solution of tert-butyl 4-(4-bromo-3-fluoro-5-methylphenyl)-4-oxobutylcarbamate (1.30 g, 3.47 mmol) in DCM (15 mL) was added 15 mL TFA, and the mixture was stirred at RT for 30 min. The mixture was concentrated in vacuo and dissolved in 30 mL THF. To this solution was added triethylamine (0.593 mL, 4.25 mmol) and sodium triacetoxyborohydride (1.80 g, 8.51 mmol). The mixture was stirred at r.t. for 18 h and then quenched with 1 M NaOH. The mixture was extracted with ethyl acetate. The separated organic layers were concentrated in vacuo. The obtained crude product was dissolved in THF (20 mL). To this solution was added di-tert-butyl dicarbonate (1.86 g, 8.51 mmol) and triethylamine (0.513 mL, 3.68 mmol) at r.t. After stirring for 1 h, the solvents were evaporated under reduced pressure and the obtained crude product was purified by Biotage Isolera™ to give the desired product. LCMS calculated for $C_{12}H_{14}BrFNO_2$ (M-$C_4H_8$+H)$^+$: m/z=302.0; Found: 302.0.

Step 3. 4-(5-(2-Fluoro-6-methyl-4-(pyrrolidin-2-yl)phenyl)-1H-pyrazolo[3,4-c]pyridin-3-yl)-N-methylbenzamide A mixture of tert-butyl 2-(4-bromo-3-fluoro-5-methylphenyl)pyrrolidine-1-carboxylate (65 mg, 0.181 mmol), 4,4,4',4',5,5,5',5'-octamethyl-2,2'-bi(1,3,2-dioxaborolane) (69.1 mg, 0.272 mmol), potassium acetate (53.4 mg, 0.544 mmol) and (1,1'-bis(diphenylphosphino)ferrocene)-dichloropalladium(II) complexed with dichloromethane (1:1) (29.6 mg, 0.036 mmol) in dioxane (10 mL) was stirred at 110° C. for 24 h. After cooling to room temperature, the mixture was concentrated in vacuo. A mixture of this crude material, 4-(5-chloro-1-((2-(trimethylsilyl)ethoxy)methyl)-1H-pyrazolo[3,4-c]pyridin-3-yl)-N-methylbenzamide (23.41 mg, 0.056 mmol, Example 169, Step 1), XPhos Pd G2 (4.14 mg, 5.61 µmol) and cesium carbonate (54.9 mg, 0.168 mmol) in dioxane (10 mL) and water (2 mL) was stirred at 70° C. for 18 h. After cooling to room temperature, the mixture was concentrated in vacuo. The crude mixture was then dissolved in DCM (2.0 mL), and TFA (2.0 mL) was added dropwise at room temperature. After stirring for 2 h, the mixture was concentrated in vacuo. The crude mixture was dissolved in MeOH (3.5 mL) and 10% aqueous NH$_4$OH (1.5 mL). The mixture was purified with prep-LCMS (XBridge C18 column, eluting with a gradient of acetonitrile/water containing 0.1% TFA, at flow rate of 60 mL/min) to give the desired product. LCMS calculated for $C_{25}H_{25}FN_5O$ (M+H)$^+$: m/z=430.2; Found: 430.2.

Example 171. 5-(2-Fluoro-6-methyl-4-(pyrrolidin-2-yl)phenyl)-3-(1-methyl-1H-pyrazol-4-yl)-1H-pyrazolo[3,4-c]pyridine

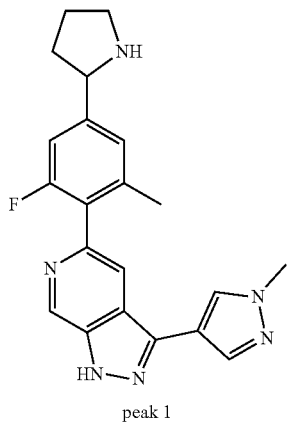 [SMILES: Cc1cc(C2CCCN2)cc(F)c1-c1cc2c(-c3cnn(C)c3)n[nH]c2cn1]

peak 1

Step 1. tert-Butyl 2-(3-fluoro-5-methyl-4-(3-(1-methyl-1H-pyrazol-4-yl)-1-((2-(trimethylsilyl)ethoxy)methyl)-1H-pyrazolo[3,4-c]pyridin-5-yl)phenyl)pyrrolidine-1-carboxylate

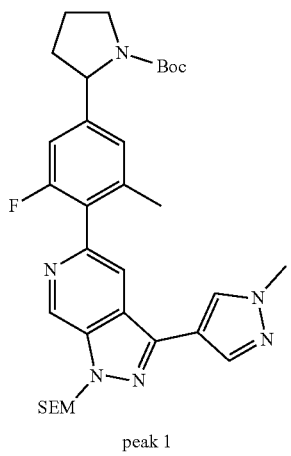

peak 1

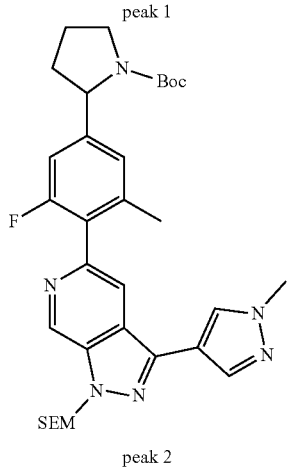

peak 2

To a solution of tert-butyl 2-(4-bromo-3-fluoro-5-methylphenyl)pyrrolidine-1-carboxylate (850 mg, 2.37 mmol, Example 170, Step 2) in THF (10 mL) was added nBuLi (1.56 mL, 2.491 mmol, 1.6 M) at −78° C. After stirring for 1 h, 2-isopropoxy-4,4,5,5-tetramethyl-1,3,2-dioxaborolane (629 µL, 3.08 mmol) was added dropwise, and the mixture was slowly warmed to RT over 6 h. The mixture was quenched with water (10 mL) and extracted with ethyl acetate. The solvents of the separated organic layers were evaporated under reduced pressure to give the crude material. A mixture of the crude material, 5-chloro-3-(1-methyl-1H-pyrazol-4-yl)-1-((2-(trimethylsilyl)ethoxy)methyl)-1H-pyrazolo[3,4-c]pyridine (691 mg, 1.90 mmol, Intermediate 2), XPhos Pd G2 (93 mg, 0.119 mmol), cesium carbonate (1.55 g, 4.75 mmol) in dioxane (20 mL) and water (4 mL) was stirred at 60° C. for 18 h. After cooling to room temperature, the mixture was concentrated in vacuo. The obtained crude product was purified by Biotage Isolera™ to give the desired product. The two enantiomers were separated with chiral prep-HPLC (Phenomenex Lux Amylose-1 21.2×250 mm, 5 micron, eluting with 15% EtOH in hexanes, at flow rate of 18 mL/min, $t_{R, peak\ 1}$=8.67 min, $t_{R, peak\ 2}$=12.75 min). Peak 1: LCMS calculated for $C_{32}H_{44}FN_6O_3Si$ (M+H)$^+$: m/z=607.3; Found: 607.3. Peak 2: LCMS calculated for $C_{32}H_{44}FN_6O_3Si$ (M+H)$^+$: m/z=607.3; Found: 607.3.

Step 2. 5-(2-Fluoro-6-methyl-4-(pyrrolidin-2-yl)phenyl)-3-(1-methyl-1H-pyrazol-4-yl)-1H-pyrazolo[3,4-c]pyridine tert-Butyl 2-(3-fluoro-5-methyl-4-(3-(1-methyl-1H-pyrazol-4-yl)-1-((2-(trimethylsilyl)ethoxy)methyl)-1H-pyrazolo[3,4-c]pyridin-5-yl)phenyl)pyrrolidine-1-carboxylate (peak 1, 200 mg) was dissolved in DCM (2.0 mL), and TFA (2.0 mL) was added dropwise at room temperature. After stirring for 2 h, the mixture was concentrated in vacuo. The crude mixture was dissolved in MeOH (3.5 mL) and 10% aqueous NH$_4$OH (1.5 mL). The mixture was purified with prep-LCMS (XBridge C18 column, eluting with a gradient of acetonitrile/water containing 0.1% TFA, at flow rate of 60 mL/min) to give the desired product. LCMS calculated for $C_{21}H_{22}FN_6$ (M+H)$^+$: m/z=377.2; Found: 377.3. $^1$H NMR (TFA salt, 500 MHz, (CD$_3$)$_2$SO) δ 9.50 (br s, 1H), 9.14 (d, J=1.3 Hz, 1H), 8.79 (br s, 1H), 8.48 (s, 1H), 8.11-8.01 (m, 2H), 7.37-7.29 (m, 2H), 4.63 (m, 1H), 3.92 (s, 3H), 3.44 (m, 1H), 3.36 (m, 1H), 2.44 (m, 1H), 2.20 (s, 3H), 2.20-1.98 (m, 3H).

Example 172. 5-(2-Fluoro-6-methyl-4-(pyrrolidin-2-yl)phenyl)-3-(1-methyl-1H-pyrazol-4-yl)-1H-pyrazolo[3,4-c]pyridine

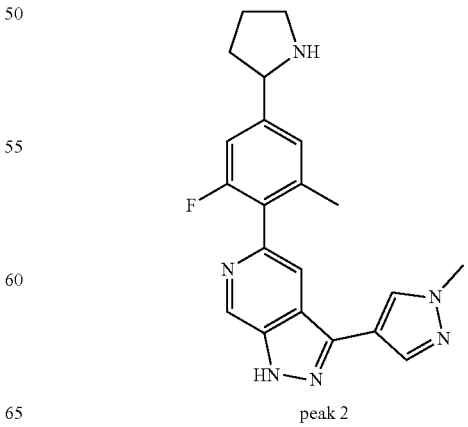

peak 2

This compound was prepared according to the procedures described in Example 171, using tert-butyl 2-(3-fluoro-5-methyl-4-(3-(1-methyl-1H-pyrazol-4-yl)-1-((2-(trimethylsilyl)ethoxy)methyl)-1H-pyrazolo[3,4-c]pyridin-5-yl)phenyl) pyrrolidine-1-carboxylate (peak 2, Example 171, Step 1) instead of tert-butyl 2-(3-fluoro-5-methyl-4-(3-(1-methyl-1H-pyrazol-4-yl)-1-((2-(trimethylsilyl)ethoxy)methyl)-1H-pyrazolo[3,4-c]pyridin-5-yl)phenyl)pyrrolidine-1-carboxylate (peak 1) as starting material. LCMS calculated for $C_{21}H_{22}FN_6$ $(M+H)^+$: m/z=377.2; Found: 377.3. $^1$H NMR (TFA salt, 500 MHz, $(CD_3)_2SO$) δ 9.50 (br s, 1H), 9.14 (d, J=1.3 Hz, 1H), 8.79 (br s, 1H), 8.48 (s, 1H), 8.11-8.01 (m, 2H), 7.37-7.29 (m, 2H), 4.63 (m, 1H), 3.92 (s, 3H), 3.44 (m, 1H), 3.36 (m, 1H), 2.44 (m, 1H), 2.20 (s, 3H), 2.20-1.98 (m, 3H).

Example 173. 5-(2-Fluoro-6-methyl-4-(1-methylpyrrolidin-2-yl)phenyl)-3-(1-methyl-1H-pyrazol-4-yl)-1H-pyrazolo[3,4-c]pyridine

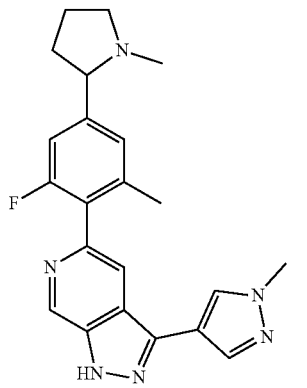 [SMILES: Cc1cc(C2CCCN2C)cc(F)c1-c1cc2c(-c3cnn(C)c3)n[nH]c2cn1]

To a solution of 5-(2-fluoro-6-methyl-4-(pyrrolidin-2-yl)phenyl)-3-(1-methyl-1H-pyrazol-4-yl)-1H-pyrazolo[3,4-c]pyridine (10 mg, 0.027 mmol, peak 1, Example 171, Step 2) in THF was added formaldehyde solution (37% in water, 20 μL) and sodium triacetoxyborohydride (22.5 mg, 0.106 mmol) at RT. After stirring for 1 h, the solvents were evaporated under reduced pressure and the obtained crude product was purified with prep-LCMS (XBridge C18 column, eluting with a gradient of acetonitrile/water containing 0.1% TFA, at flow rate of 60 mL/min) to give the desired product. LCMS calculated for $C_{22}H_{24}FN_6$ $(M+H)^+$: m/z=391.2; Found: 391.3.

Example 174. 5-(2-Fluoro-6-methyl-4-(piperidin-2-yl)phenyl)-3-(1-methyl-1H-pyrazol-4-yl)-1H-pyrazolo[3,4-c]pyridine

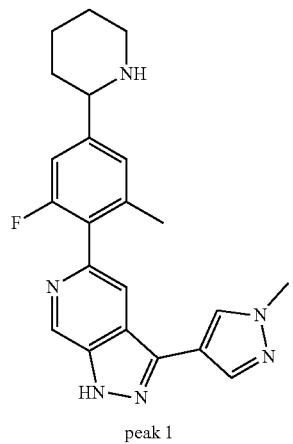

peak 1

Step 1. tert-Butyl 6-(4-bromo-3-fluoro-5-methylphenyl)-3,4-dihydropyridine-1(2H)-carboxylate

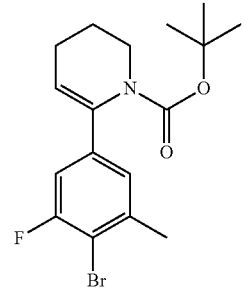 [SMILES: Cc1cc(C2=CCCCN2C(=O)OC(C)(C)C)cc(F)c1Br]

A solution of 2-bromo-1-fluoro-5-iodo-3-methylbenzene (526 mg, 1.67 mmol, Example 168, Step 2), tert-butyl 6-(4,4,5,5-tetramethyl-1,3,2-dioxaborolan-2-yl)-3,4-dihydropyridine-1(2H)-carboxylate (516 mg, 1.67 mmol), (1,1'-bis(diphenylphosphino)ferrocene)-dichloropalladium(II) complexed with dichloromethane (1:1) (136 mg, 0.167 mmol) and potassium carbonate (461 mg, 3.34 mmol) in dioxane (10 mL) and water (2 mL) was stirred at 65° C. for 18 h. After cooling to room temperature, the mixture was concentrated in vacuo. The obtained crude product was purified by Biotage Isolera™ to give the desired product. LCMS calculated for $C_{13}H_{14}BrFNO_2$ $(M-C_4H_8+H)^+$: m/z=314.0; Found: 313.9.

Step 2. tert-Butyl 2-(4-bromo-3-fluoro-5-methylphenyl)piperidine-1-carboxylate

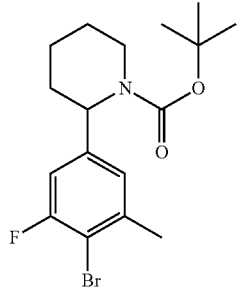

A solution of tert-butyl 6-(4-bromo-3-fluoro-5-methylphenyl)-3,4-dihydropyridine-1(2H)-carboxylate (530 mg, 1.42 mmol) in DCM (10 mL) was added 10 mL TFA, and the mixture was stirred at RT for 30 min. The mixture was concentrated in vacuo and then dissolved in 20 mL THF. To this solution was added triethylamine (0.233 mL, 1.67 mmol) and sodium triacetoxyborohydride (707 mg, 3.34 mmol). The mixture was stirred at r.t. for 18 h and then quenched with 1 M NaOH. The mixture was extracted with ethyl acetate. The separated organic layers were concentrated in vacuo. The obtained crude product was dissolved in THF (20 mL). To this solution was added di-tert-butyl dicarbonate (364 mg, 1.67 mmol) at r.t. After stirring for 3 h, the solvents were evaporated under reduced pressure and the obtained crude product was purified by Biotage Isolera™ to give the desired product. LCMS calculated for $C_{13}H_{16}BrFNO_2$ (M-$C_4H_8$+H)$^+$: m/z=316.0; Found: 315.9.

Step 3. tert-Butyl 2-(3-fluoro-5-methyl-4-(3-(1-methyl-1H-pyrazol-4-yl)-1-((2-(trimethylsilyl)ethoxy)methyl)-1H-pyrazolo[3,4-c]pyridin-5-yl)phenyl)piperidine-1-carboxylate

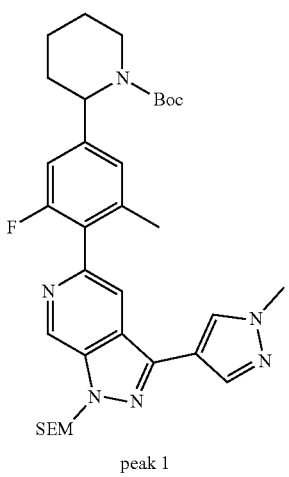

peak 1

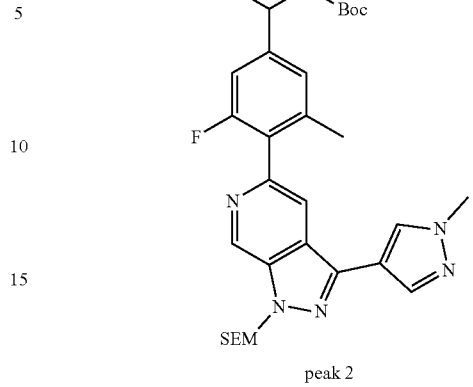

peak 2

To a solution of tert-butyl 2-(4-bromo-3-fluoro-5-methylphenyl)piperidine-1-carboxylate (258 mg, 0.693 mmol) in THF (10 mL) was added nBuLi (0.48 mL, 0.762 mmol, 1.6 M) at 78° C. After stirring for 1 h, 2-isopropoxy-4,4,5,5-tetramethyl-1,3,2-dioxaborolane (184 µL, 0.901 mmol) was added dropwise, and the resulting mixture was slowly warmed to RT over 6 h. The mixture was quenched with water (10 mL) and extracted with ethyl acetate. The separated organic layers were evaporated under reduced pressure to give the crude material. A mixture of the crude material, 5-chloro-3-(1-methyl-1H-pyrazol-4-yl)-1-((2-(trimethylsilyl)ethoxy)methyl)-1H-pyrazolo[3,4-c]pyridine (202 mg, 0.554 mmol, Intermediate 2), XPhos Pd G2 (27.3 mg, 0.035 mmol), cesium carbonate (452 mg, 1.39 mmol) in dioxane (20 mL) and water (4 mL) was stirred at 60° C. for 18 h. After cooling to room temperature, the mixture was concentrated in vacuo. The obtained crude product was purified by Biotage Isolera™ to give the desired product. The two enantiomers were separated with chiral prep-HPLC (Phenomenex Amylose-2 21.1×250 mm, 5 micron, eluting with 45% EtOH in hexanes, at flow rate of 18 mL/min, $t_{R,\ peak\ 1}$=6.33 min, $t_{R,\ peak\ 2}$=9.98 min). Peak 1: LCMS calculated for $C_{33}H_{46}FN_6O_3Si$ (M+H)$^+$: m/z=621.3; Found: 621.3. Peak 2: LCMS calculated for $C_{33}H_{46}FN_6O_3Si$ (M+H)$^+$: m/z=621.3; Found: 621.3.

Step 4. 5-(2-Fluoro-6-methyl-4-(piperidin-2-yl)phenyl)-3-(1-methyl-1H-pyrazol-4-yl)-1H-pyrazolo[3,4-c]pyridine tert-Butyl 2-(3-fluoro-5-methyl-4-(3-(1-methyl-1H-pyrazol-4-yl)-1-((2-(trimethylsilyl)ethoxy)methyl)-1H-pyrazolo[3,4-c]pyridin-5-yl)phenyl)piperidine-1-carboxylate (peak 1, 100 mg) was dissolved in DCM (2.0 mL), and TFA (2.0 mL) was added dropwise at room temperature. After stirring for 2 h, the mixture was concentrated in vacuo. The crude mixture was dissolved in MeOH (3.5 mL) and 10% aqueous NH$_4$OH (1.5 mL). The mixture was purified with prep-LCMS (XBridge C18 column, eluting with a gradient of acetonitrile/water containing 0.1% TFA, at flow rate of 60 mL/min) to give the desired product. LCMS calculated for $C_{22}H_{24}FN_6$ (M+H)$^+$: m/z=391.2; Found: 391.2. $^1$H NMR (TFA salt, 500 MHz, (CD$_3$)$_2$SO) δ 9.14 (d, J=1.3 Hz, 1H), 9.05 (m, 1H), 8.76 (m, 1H), 8.49 (s, 1H), 8.14-8.01 (m, 2H), 7.37-7.26 (m, 2H), 4.31 (t, J=11.4 Hz, 1H), 3.92 (s, 3H), 3.42 (m, 1H), 3.09 (m, 1H), 2.53 (m, 1H), 2.19 (s, 3H), 2.02 (m, 1H), 1.96-1.80 (m, 2H), 1.80-1.58 (m, 2H).

211

Example 175. 5-(2-Fluoro-6-methyl-4-(piperidin-2-yl)phenyl)-3-(1-methyl-1H-pyrazol-4-yl)-1H-pyrazolo[3,4-c]pyridine

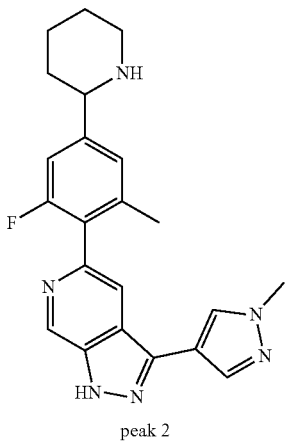 [SMILES: Cc1cc(C2CCCCN2)cc(F)c1-c1cc2c(-c3cnn(C)c3)n[nH]c2cn1]

peak 2

This compound was prepared according to the procedures described in Example 174, using tert-butyl 2-(3-fluoro-5-methyl-4-(3-(1-methyl-1H-pyrazol-4-yl)-1-((2-(trimethylsilyl)ethoxy)methyl)-1H-pyrazolo[3,4-c]pyridin-5-yl)phenyl)piperidine-1-carboxylate (peak 2, Example 174, Step 3) instead of tert-butyl 2-(3-fluoro-5-methyl-4-(3-(1-methyl-1H-pyrazol-4-yl)-1-((2-(trimethylsilyl)ethoxy)methyl)-1H-pyrazolo[3,4-c]pyridin-5-yl)phenyl)piperidine-1-carboxylate (peak 1) as starting material. LCMS calculated for $C_{22}H_{24}FN_6$ (M+H)$^+$: m/z=391.2; Found: 391.2.

Example 176. N-(3-Fluoro-5-methyl-4-(3-(1-methyl-1H-pyrazol-4-yl)-1H-pyrazolo[3,4-c]pyridin-5-yl)benzyl)ethanamine

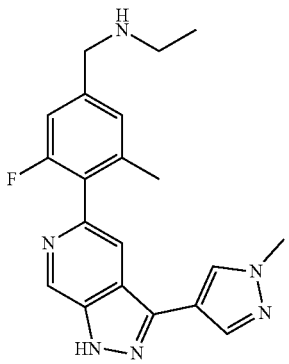

212

Step 1. 5-(2-Fluoro-6-methyl-4-vinylphenyl)-3-(1-methyl-1H-pyrazol-4-yl)-1-((2-(trimethylsilyl)ethoxy)methyl)-1H-pyrazolo[3,4-c]pyridine

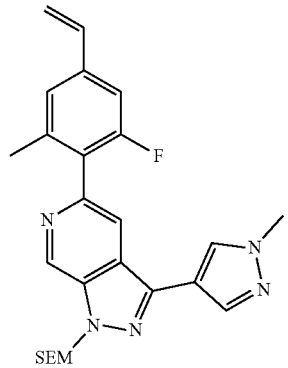

To a solution of 2-bromo-1-fluoro-3-methyl-5-vinylbenzene (1.03 g, 4.79 mmol, Example 168, Step 3) in THF (40 mL) was added nBuLi (3.14 mL, 5.03 mmol, 1.6 M) at −78° C. After stirring for 1 h, 2-isopropoxy-4,4,5,5-tetramethyl-1,3,2-dioxaborolane (1.27 mL, 6.23 mmol) was added dropwise, and the resulting mixture was slowly warmed to RT over 6 h. The mixture was quenched with water (10 mL) and extracted with ethyl acetate. The separated organic layers were concentrated under reduced pressure to give the crude material. A mixture of the crude material, 5-chloro-3-(1-methyl-1H-pyrazol-4-yl)-1-((2-(trimethylsilyl)ethoxy)methyl)-1H-pyrazolo[3,4-c]pyridine (1.39 g, 3.83 mmol, Intermediate 2), XPhos Pd G2 (188 mg, 0.239 mmol), cesium carbonate (3.12 g, 9.58 mmol) in dioxane (20 mL) and water (4 mL) was stirred at 60° C. for 18 h. After cooling to room temperature, the mixture was concentrated in vacuo. The obtained crude product was purified by Biotage Isolera™ to give the desired product. LCMS calculated for $C_{25}H_{31}FN_5OSi$ (M+H)$^+$: m/z=464.2; Found: 464.2.

Step 2. 3-Fluoro-5-methyl-4-(3-(1-methyl-1H-pyrazol-4-yl)-1-((2-(trimethylsilyl)ethoxy)methyl)-1H-pyrazolo[3,4-c]pyridin-5-yl)benzaldehyde

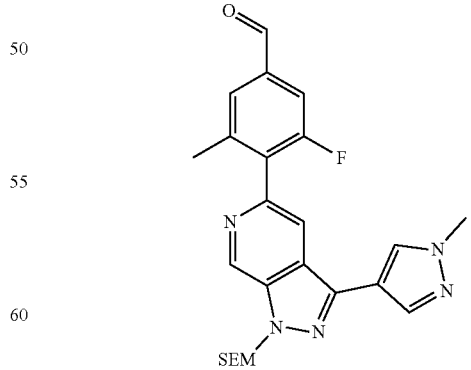

To a mixture of 5-(2-fluoro-6-methyl-4-vinylphenyl)-3-(1-methyl-1H-pyrazol-4-yl)-1-((2-(trimethylsilyl)ethoxy)methyl)-1H-pyrazolo[3,4-c]pyridine (1.82 g, 3.93 mmol), sodium periodate (3.36 g, 15.7 mmol) in acetone (20 mL)

and water (2 mL) was added osmium tetroxide solution (4% in water, 2.49 g, 0.393 mmol). After stirring at r.t. for 5 h, the mixture was quenched with water (10 mL) and extracted with ethyl acetate. The separated organic layers were concentrated under reduced pressure, and the obtained crude product was purified by Biotage Isolera™ to give the desired product. LCMS calculated for $C_{24}H_{29}FN_5O_2Si$ (M+H)$^+$: m/z=466.2; Found: 466.3.

Step 3. N-(3-Fluoro-5-methyl-4-(3-(1-methyl-1H-pyrazol-4-yl)-1H-pyrazolo[3,4-c]pyridin-5-yl)benzyl)ethanamine To a solution of 3-fluoro-5-methyl-4-(3-(1-methyl-1H-pyrazol-4-yl)-1-((2-(trimethylsilyl)ethoxy)methyl)-1H-pyrazolo[3,4-c]pyridin-5-yl)benzaldehyde (80 mg, 0.172 mmol), ethylamine solution (2 M in THF, 0.258 mL, 0.515 mmol) and acetic acid (0.030 mL, 0.515 mmol) in THF (10 mL) was added sodium triacetoxyborohydride (109 mg, 0.515 mmol). After stirring for 18 h, the mixture was concentrated in vacuo. The crude mixture was then dissolved in DCM (2.0 mL), and TFA (2.0 mL) was added dropwise at room temperature. After stirring for 2 h, the mixture was concentrated in vacuo. The crude mixture was dissolved in MeOH (3.5 mL) and 10% aqueous NH$_4$OH (1.5 mL). The mixture was purified with prep-LCMS (XBridge C18 column, eluting with a gradient of acetonitrile/water containing 0.1% TFA, at flow rate of 60 mL/min) to give the desired product. LCMS calculated for $C_{20}H_{22}FN_6$ (M+H)$^+$: m/z=365.2; Found: 365.3. $^1$H NMR (TFA salt, 600 MHz, (CD$_3$)$_2$SO) δ 13.64 (br s, 1H), 9.13 (d, J=1.4 Hz, 1H), 8.82 (br s, 2H), 8.47 (s, 1H), 8.14-7.94 (m, 2H), 7.38-7.24 (m, 2H), 4.21 (m, 2H), 3.91 (s, 3H), 3.02 (m, 2H), 2.18 (s, 3H), 1.25 (t, J=7.2 Hz, 3H).

Examples 177-188 were prepared according to the procedures described in Example 176 using indicated s.m. instead of ethylamine.

| Ex. | Structure | Name | S.m. | Analytical data |
|---|---|---|---|---|
| 177 | 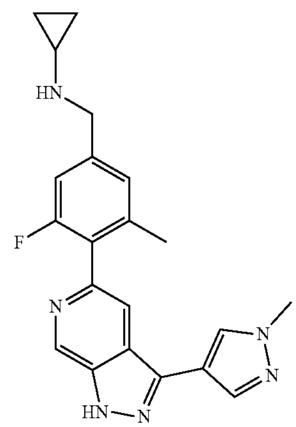 [SMILES: Cc1cc(CNC2CC2)cc(F)c1-c1cc2c(-c3cnn(C)c3)n[nH]c2cn1] | N-(3-Fluoro-5-methyl-4-(3-(1-methyl-1H-pyrazol-4-yl)-1H-pyrazolo[3,4-c]pyridin-5-yl)benzyl)cyclopropanamine | cyclopropanamine | LC-MS found 377.1 |
| 178 | 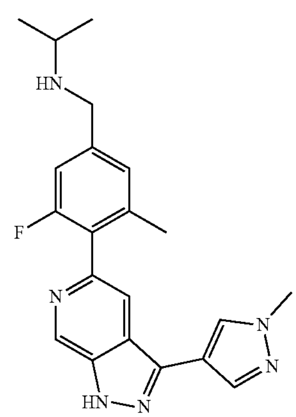 [SMILES: Cc1cc(CNC(C)C)cc(F)c1-c1cc2c(-c3cnn(C)c3)n[nH]c2cn1] | N-(3-Fluoro-5-methyl-4-(3-(1-methyl-1H-pyrazol-4-yl)-1H-pyrazolo[3,4-c]pyridin-5-yl)benzyl)propan-2-amine | propan-2-amine | LC-MS found 379.1 $^1$H NMR (TFA salt, 500 MHz, (CD$_3$)$_2$SO) δ 9.15 (d, J = 1.3 Hz, 1H), 8.82 (br s, 2H), 8.47 (s, 1H), 8.09-8.02 (m, 2H), 7.38-7.32 (m, 2H), 4.22 (t, J = 6.3 Hz, 2H), 3.94 (s, 3H), 3.36 (m, 1H), 2.19 (s, 3H), 1.32 (d, J = 6.5 Hz, 6H). |

| Ex. | Structure | Name | S.m. | Analytical data |
|---|---|---|---|---|
| 179 | 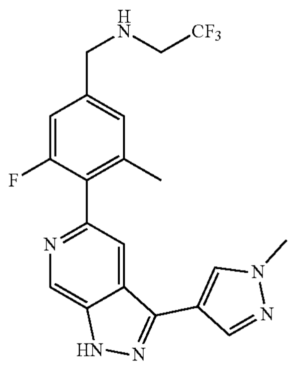 [SMILES: Cc1cc(CNCC(F)(F)F)cc(F)c1-c1cc2c(-c3cnn(C)c3)n[nH]c2cn1] | 2,2,2-Trifluoro-N-(3-fluoro-5-methyl-4-(3-(1-methyl-1H-pyrazol-4-yl)-1H-pyrazolo[3,4-c]pyridin-5-yl)benzyl)ethanamine | 2,2,2-trifluoro-ethanamine | LC-MS found 419.1 |
| 180 | 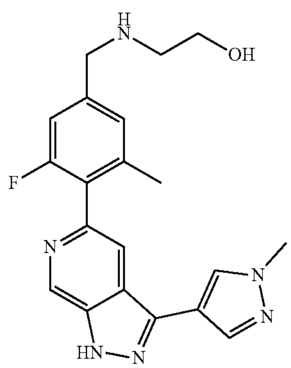 [SMILES: Cc1cc(CNCCO)cc(F)c1-c1cc2c(-c3cnn(C)c3)n[nH]c2cn1] | 2-(3-Fluoro-5-methyl-4-(3-(1-methyl-1H-pyrazol-4-yl)-1H-pyrazolo[3,4-c]pyridin-5-yl)benzylamino)ethanol | 2-aminoethanol | LC-MS found 381.2<br>$^1$H NMR (TFA salt, 500 MHz, (CD$_3$)$_2$SO) δ 9.14 (d, J = 1.3 Hz, 1H), 8.96 (br s, 2H), 8.48 (s, 1H), 8.11-8.01 (m, 2H), 7.39-7.29 (m, 2H), 4.24 (t, J = 5.5 Hz, 2H), 3.92 (s, 3H), 3.71 (m, 2H), 3.03 (m, 2H), 2.19 (s, 3H). |
| 181 | 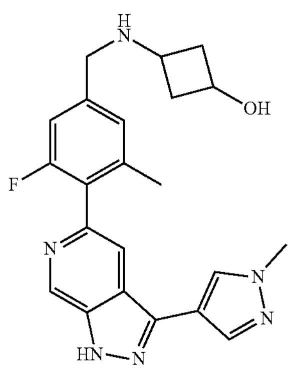 [SMILES: Cc1cc(CNC2CC(O)C2)cc(F)c1-c1cc2c(-c3cnn(C)c3)n[nH]c2cn1] | 3-(3-Fluoro-5-methyl-4-(3-(1-methyl-1H-pyrazol-4-yl)-1H-pyrazolo[3,4-c]pyridin-5-yl)benzylamino)cyclobutanol | 3-amino-cyclobutanol | LC-MS found 407.2 |
| 182 | 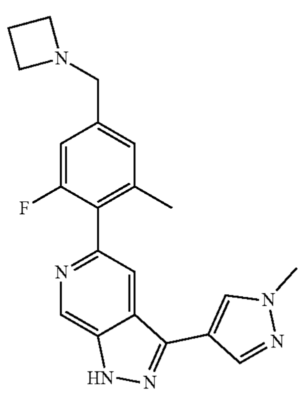 [SMILES: Cc1cc(CN2CCC2)cc(F)c1-c1cc2c(-c3cnn(C)c3)n[nH]c2cn1] | 5-(4-(Azetidin-1-ylmethyl)-2-fluoro-6-methylphenyl)-3-(1-methyl-1H-pyrazol-4-yl)-1H-pyrazolo[3,4-c]pyridine | azetidine | LC-MS found 377.2<br>$^1$H NMR (TFA salt, 400 MHz, (CD$_3$)$_2$SO) δ 10.10 (br s, 2H), 9.13 (d, J = 1.3 Hz, 1H), 8.49 (s, 1H), 8.11-8.03 (m, 2H), 7.37-7.26 (m, 2H), 4.41 (d, J = 6.1 Hz, 2H), 4.23-4.02 (m, 4H), 3.89 (s, 3H), 2.47-2.35 (m, 2H), 2.18 (s, 3H). |

-continued

| Ex. | Structure | Name | S.m. | Analytical data |
|---|---|---|---|---|
| 183 | 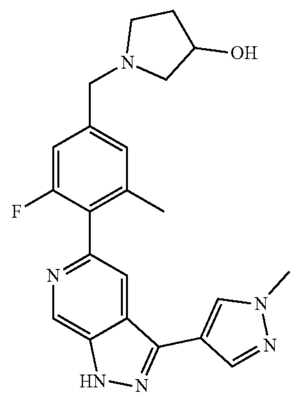 [SMILES: Cc1cc(CN2CCC(O)C2)cc(F)c1-c1cc2c(-c3cnn(C)c3)n[nH]c2cn1] | 1-(3-Fluoro-5-methyl-4-(3-(1-methyl-1H-pyrazol-4-yl)-1H-pyrazolo[3,4-c]pyridin-5-yl)benzyl)pyrrolidin-3-ol | pyrrolidin-3-ol | LC-MS found 407.2 |
| 184 | 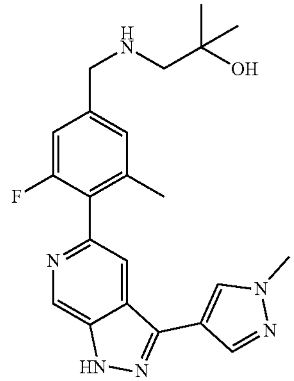 [SMILES: Cc1cc(CNCC(C)(C)O)cc(F)c1-c1cc2c(-c3cnn(C)c3)n[nH]c2cn1] | 1-(3-Fluoro-5-methyl-4-(3-(1-methyl-1H-pyrazol-4-yl)-1H-pyrazolo[3,4-c]pyridin-5-yl)benzylamino)-2-methylpropan-2-ol | 1-amino-2-methylpropan-2-ol | LC-MS found 409.2 |
| 185 | 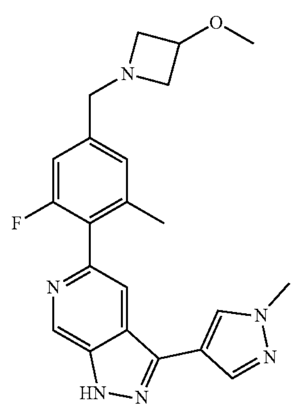 [SMILES: COC1CN(Cc2cc(C)c(-c3cc4c(-c5cnn(C)c5)n[nH]c4cn3)c(F)c2)C1] | 5-(2-Fluoro-4-((3-methoxyazetidin-1-yl)methyl)-6-methylphenyl)-3-(1-methyl-1H-pyrazol-4-yl)-1H-pyrazolo[3,4-c]pyridine | 3-methoxy-azetidine | LC-MS found 407.2 |
| 186 | 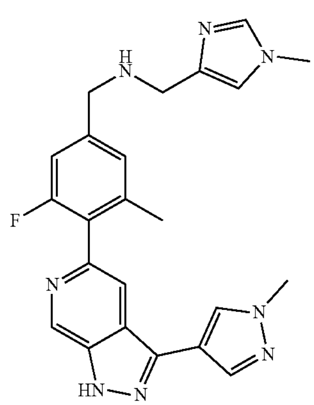 [SMILES: Cc1cc(CNCc2cn(C)cn2)cc(F)c1-c1cc2c(-c3cnn(C)c3)n[nH]c2cn1] | N-(3-Fluoro-5-methyl-4-(3-(1-methyl-1H-pyrazol-4-yl)-1H-pyrazolo[3,4-c]pyridin-5-yl)benzyl)-1-(1-methyl-1H-imidazol-4-yl)methanamine | (1-methyl-1H-imidazol-4-yl)methanamine | LC-MS found 431.2 |

| Ex. | Structure | Name | S.m. | Analytical data |
|---|---|---|---|---|
| 187 | 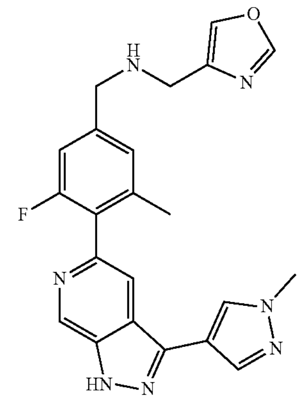 [SMILES: Cc1cc(CNCc2cocn2)cc(F)c1-c1cc2c(-c3cnn(C)c3)n[nH]c2cn1] | N-(3-Fluoro-5-methyl-4-(3-(1-methyl-1H-pyrazol-4-yl)-1H-pyrazolo[3,4-c]pyridin-5-yl)benzyl)-1-(oxazol-4-yl)methanamine | oxazol-4-ylmethanamine | LC-MS found 418.2 |
| 188 | 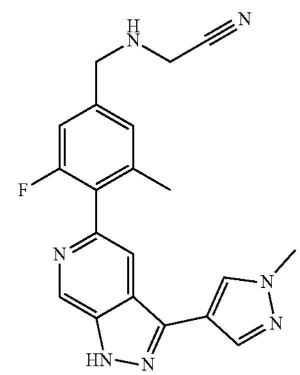 [SMILES: Cc1cc(CNCC#N)cc(F)c1-c1cc2c(-c3cnn(C)c3)n[nH]c2cn1] | 2-(3-Fluoro-5-methyl-4-(3-(1-methyl-1H-pyrazol-4-yl)-1H-pyrazolo[3,4-c]pyridin-5-yl)benzylamino)acetonitrile | 2-aminoacetonitrile | LC-MS found 376.2 |

Example 189. 1-(3-Fluoro-5-methyl-4-(3-(1-methyl-1H-pyrazol-4-yl)-1H-pyrazolo[3,4-c]pyridin-5-yl)phenyl)-N-methylethanamine

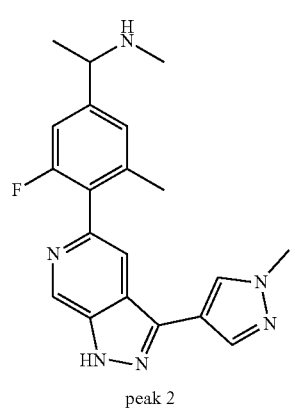 [SMILES: CNC(C)c1cc(C)c(-c2cc3c(-c4cnn(C)c4)n[nH]c3cn2)c(F)c1]

peak 2

Step 1. 1-(3-Fluoro-5-methyl-4-(3-(1-methyl-1H-pyrazol-4-yl)-1-((2-(trimethylsilyl)ethoxy)methyl)-1H-pyrazolo[3,4-c]pyridin-5-yl)phenyl)ethanone

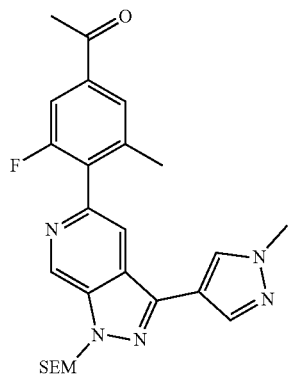

This compound was prepared according to the procedures described in Example 176, using 4,4,5,5-tetramethyl-2-(prop-1-en-2-yl)-1,3,2-dioxaborolane instead of 4,4,5,5-tetramethyl-2-vinyl-1,3,2-dioxaborolane as starting material. LC-MS calculated for $C_{25}H_{31}FN_5O_2Si$ (M+H)$^+$: m/z=480.2; found 480.3.

Step 2. tert-Butyl 1-(3-fluoro-5-methyl-4-(3-(1-methyl-1H-pyrazol-4-yl)-1-((2-(trimethylsilyl)ethoxy)methyl)-1H-pyrazolo[3,4-c]pyridin-5-yl)phenyl)ethyl(methyl)carbamate

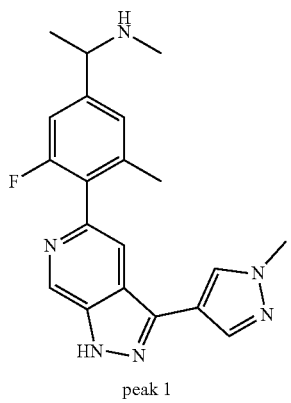 [SMILES: CNC(C)c1cc(C)c(-c2cc3c(-c4cnn(C)c4)n[nH]c3cn2)c(F)c1]

peak 1

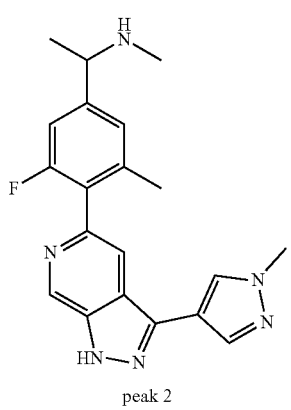

peak 2

To a solution of 1-(3-fluoro-5-methyl-4-(3-(1-methyl-1H-pyrazol-4-yl)-1-((2-(trimethylsilyl)ethoxy)methyl)-1H-pyrazolo[3,4-c]pyridin-5-yl)phenyl)ethan-1-one (1.06 g, 2.21 mmol), methylamine hydrochloride (0.448 g, 6.63 mmol) and titanium(IV) isopropoxide (1.94 mL, 6.63 mmol) in MeOH (20 mL) was added sodium borohydride (0.167 g, 4.42 mmol) at r.t. After stirring for 1 h, the mixture was quenched with 1 M NaOH, extracted with ethyl acetate and concentrated in vacuo. Then the crude product was dissolved in THF (20 mL) and di-tert-butyl dicarbonate (965 mg, 4.42 mmol) was added. After stirring for 2 h, the mixture was concentrated in vacuo. The obtained crude product was purified by Biotage Isolera™ to give the desired product. Then, the two enantiomers were separated with chiral prep-HPLC (Phenomenex Lux Cellulose-1, 21.2×250 mm, 5 micron, eluting with 3% EtOH in hexanes, at flow rate of 18 mL/min, $t_{R, peak\ 1}$=22.02 min, $t_{R, peak\ 2}$=24.22 min). Peak 1: LCMS calculated for $C_{31}H_{44}FN_6O_3Si$ (M+H)$^+$: m/z=595.3; Found: 595.4. Peak 2: LCMS calculated for $C_{31}H_{44}FN_6O_3Si$ (M+H)$^+$: m/z=595.3; Found: 595.4.

Step 3. 1-(3-Fluoro-5-methyl-4-(3-(1-methyl-1H-pyrazol-4-yl)-1H-pyrazolo[3,4-c]pyridin-5-yl)phenyl)-N-methylethanamine tert-Butyl 1-(3-fluoro-5-methyl-4-(3-(1-methyl-1H-pyrazol-4-yl)-1-((2-(trimethylsilyl)ethoxy)methyl)-1H-pyrazolo[3,4-c]pyridin-5-yl)phenyl)ethyl(methyl)carbamate (peak 2, 100 mg) was dissolved in DCM (2.0 mL) and TFA (2.0 mL) was added dropwise at room temperature. After stirring for 2 h, the mixture was concentrated in vacuo. The crude mixture was dissolved in MeOH (3.5 mL) and 10% aqueous NH$_4$OH (1.5 mL). The mixture was purified with prep-LCMS (XBridge C18 column, eluting with a gradient of acetonitrile/water containing 0.1% TFA, at flow rate of 60 mL/min) to give the desired product. LCMS calculated for $C_{20}H_{22}FN_6$ (M+H)$^+$: m/z=365.2; Found: 365.1. $^1$H NMR (TFA salt, 500 MHz, (CD$_3$)$_2$SO) δ 9.20-9.04 (m, 2H), 8.92 (br s, 1H), 8.50 (s, 1H), 8.09 (d, J=1.5 Hz, 1H), 8.05 (s, 1H), 7.38-7.25 (m, 2H), 4.38 (m, 1H), 3.92 (s, 3H), 2.52 (m, 3H), 2.19 (s, 3H), 1.59 (d, J=6.8 Hz, 3H).

Example 190. 1-(3-Fluoro-5-methyl-4-(3-(1-methyl-1H-pyrazol-4-yl)-1H-pyrazolo[3,4-c]pyridin-5-yl)phenyl)-N-methylethanamine

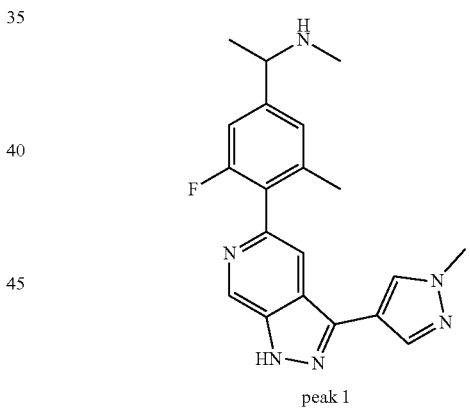

peak 1

This compound was prepared according to the procedures described in Example 189, using tert-butyl 1-(3-fluoro-5-methyl-4-(3-(1-methyl-1H-pyrazol-4-yl)-1-((2-(trimethylsilyl)ethoxy)methyl)-1H-pyrazolo[3,4-c]pyridin-5-yl)phenyl)ethyl(methyl)carbamate (peak 1, Example 189, Step 2) instead of tert-butyl 1-(3-fluoro-5-methyl-4-(3-(1-methyl-1H-pyrazol-4-yl)-1-((2-(trimethylsilyl)ethoxy)methyl)-1H-pyrazolo[3,4-c]pyridin-5-yl)phenyl)ethyl(methyl)carbamate (peak 2) as starting material. LCMS calculated for $C_{22}H_{24}FN_6$ (M+H)$^+$: m/z=391.2; Found: 391.2.

Example 191. N-(3-Fluoro-5-methyl-4-(3-(1-methyl-1H-pyrazol-4-yl)-1H-pyrazolo[3,4-c]pyridin-5-yl)benzyl)acetamide

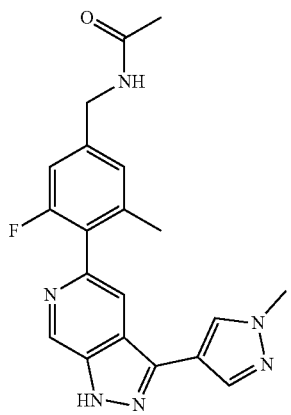 [SMILES: CC(=O)NCc1cc(C)c(-c2cc3c(-c4cnn(C)c4)n[nH]c3cn2)c(F)c1]

Step 1. (3-Fluoro-5-methyl-4-(3-(1-methyl-1H-pyrazol-4-yl)-1-((2-(trimethylsilyl)ethoxy)methyl)-1H-pyrazolo[3,4-c]pyridin-5-yl)phenyl)methanamine

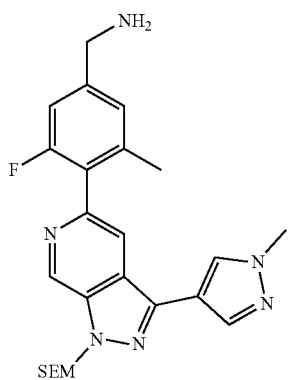 [SMILES: Cc1cc(CN)cc(F)c1-c1cc2c(-c3cnn(C)c3)nn(COCC[Si](C)(C)C)c2cn1]

To a solution of 3-fluoro-5-methyl-4-(3-(1-methyl-1H-pyrazol-4-yl)-1-((2-(trimethylsilyl)ethoxy)methyl)-1H-pyrazolo[3,4-c]pyridin-5-yl)benzaldehyde (100 mg, 0.215 mmol, Example 176, Step 2), ammonium acetate (331 mg, 4.30 mmol) in MeOH (10 mL) was added sodium cyanoborohydride (27.0 mg, 0.430 mmol). After stirring for 18 h, the mixture was concentrated in vacuo. The crude mixture was purified with prep-LCMS (XBridge C18 column, eluting with a gradient of acetonitrile/water containing 0.1% TFA, at flow rate of 60 mL/min) to give the desired product. LCMS calculated for $C_{24}H_{32}FN_6OSi$ (M+H)$^+$: m/z=467.2; Found: 467.2.

Step 2. N-(3-Fluoro-5-methyl-4-(3-(1-methyl-1H-pyrazol-4-yl)-1H-pyrazolo[3,4-c]pyridin-5-yl)benzyl)acetamide To a solution of (3-fluoro-5-methyl-4-(3-(1-methyl-1H-pyrazol-4-yl)-1-((2-(trimethylsilyl)ethoxy)methyl)-1H-pyrazolo[3,4-c]pyridin-5-yl)phenyl)methanamine (10 mg, 0.021 mmol) in THF (2 mL) was added pyridine (0.017 mL, 0.214 mmol) and acetic anhydride (10.9 mg, 0.107 mmol) at r.t. After stirring for 18 h, the mixture was concentrated in vacuo. The crude product was dissolved in DCM (2.0 mL), and TFA (2.0 mL) was added dropwise at room temperature. After stirring for 2 h, the mixture was concentrated in vacuo. The crude mixture was dissolved in MeOH (3.5 mL) and 10% aqueous NH$_4$OH (1.5 mL). The mixture was purified with prep-LCMS (XBridge C18 column, eluting with a gradient of acetonitrile/water containing 0.1% TFA, at flow rate of 60 mL/min) to give the desired product. LCMS calculated for $C_{20}H_{20}FN_6O$ (M+H)$^+$: m/z=379.2; Found: 379.2.

Example 192. Methyl 3-fluoro-5-methyl-4-(3-(1-methyl-1H-pyrazol-4-yl)-1H-pyrazolo[3,4-c]pyridin-5-yl)benzylcarbamate

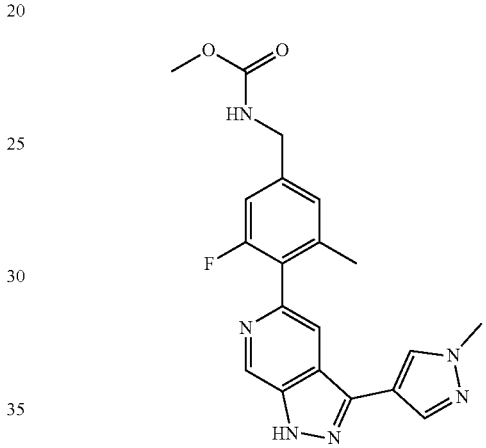

This compound was prepared according to the procedures described in Example 191, using methyl carbonochloridate instead of acetic anhydride as starting material. LC-MS calculated for $C_{20}H_{20}FN_6O_2$ (M+H)$^+$: m/z=395.2; found 395.2.

Example 193. 1-(4-(6-(5-(2-(Difluoromethoxy)-6-fluoro-4-((methylamino)methyl)phenyl)-1H-pyrazolo[3,4-c]pyridin-3-yl)pyridin-3-yl)piperazin-1-yl)ethanone

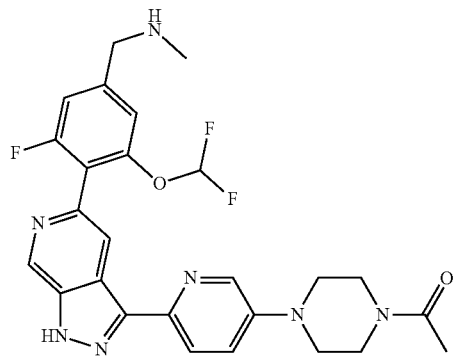 [SMILES: CNCc1cc(F)c(-c2cc3c(-c4ccc(N5CCN(C(C)=O)CC5)cn4)n[nH]c3cn2)c(OC(F)F)c1]

Step 1. tert-Butyl 4-bromo-3-(difluoromethoxy)-5-fluorobenzyl(methyl)carbamate

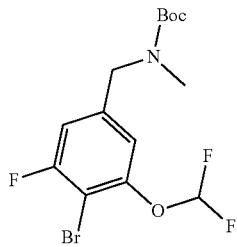 [SMILES: CN(Cc1cc(F)c(Br)c(OC(F)F)c1)C(=O)OC(C)(C)C]

This compound was prepared according to the procedures described in Example 168, using 3-(difluoromethoxy)-5-fluoroaniline (Example 72, Step 3) instead of 3-fluoro-5-methylaniline as starting material. LC-MS calculated for $C_{10}H_{10}BrF_3NO_3$ (M-$C_4H_8$+H)$^+$: m/z=328.0; found 327.9.

Step 2. tert-Butyl 4-(3-(5-chloropyridin-2-yl)-14(2-(trimethylsilyl)ethoxy)methyl)-1H-pyrazolo[3,4-c]pyridin-5-yl)-3-(difluoromethoxy)-5-fluorobenzyl (methyl)carbamate

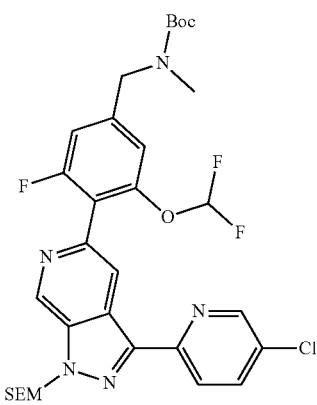 [SMILES: CN(Cc1cc(F)c(-c2cc3c(-c4ccc(Cl)cn4)nn(COCC[Si](C)(C)C)c3cn2)c(OC(F)F)c1)C(=O)OC(C)(C)C]

This compound was prepared according to the procedures described in Example 167, using tert-butyl 4-bromo-3-(difluoromethoxy)-5-fluorobenzyl(methyl)carbamate instead of tert-butyl 3,5-difluorobenzyl(methyl)carbamate as starting material. LC-MS calculated for $C_{31}H_{38}ClF_3N_5O_4Si$ (M+H)$^+$: m/z=664.2; found 664.3.

Step 3. 1-(4-(6-(5-(2-(Difluoromethoxy)-6-fluoro-4-((methylamino)methyl)phenyl)-1H-pyrazolo[3,4-c]pyridin-3-yl)pyridin-3-yl)piperazin-1-yl)ethanone This compound was prepared according to the procedures described in Example 167, using 1-(piperazin-1-yl)ethan-1-one instead of 3-fluoropyrrolidine as starting material. LC-MS calculated for $C_{26}H_{27}F_3N_7O_2$ (M+H)$^+$: m/z=526.2; found 526.0.

Example 194. 2-(3-Fluoro-2-(3-(4-(4-methylpiperazin-1-yl)phenyl)-1H-pyrazolo[3,4-c]pyridin-5-yl)phenyl)acetonitrile

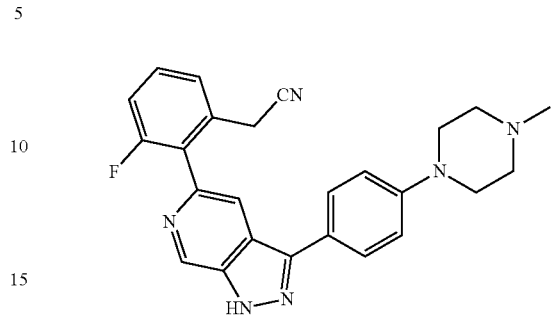

Step 1. tert-Butyl 5-chloro-3-(4-(4-methylpiperazin-1-yl)phenyl)-1H-pyrazolo[3,4-c]pyridine-1-carboxylate

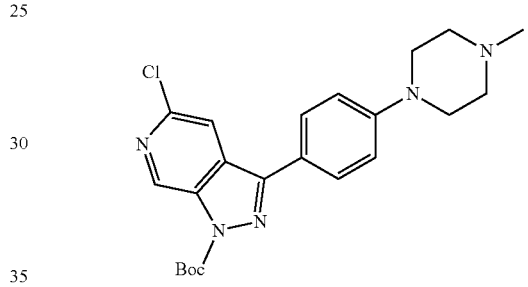

This compound was prepared according to the procedures described in Intermediate 1, using (4-(4-methylpiperazin-1-yl)phenyl)boronic acid instead of 1-methyl-4-(4,4,5,5-tetramethyl-1,3,2-dioxaborolan-2-yl)-1H-pyrazole as starting material. LCMS calculated for $C_{22}H_{27}ClN_5O_2$ (M+H)$^+$ m/z=428.2; found 428.2.

Step 2. 2-(2-Bromo-3-fluorophenyl)acetonitrile

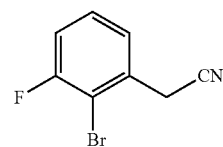

To a mixture of 2-bromo-1-(bromomethyl)-3-fluorobenzene (1.755 g, 6.55 mmol) and KCN (674.5 mg, 10.36 mmol) was added EtOH (100.0 ml) followed by water (30.00 ml). The resulting homogeneous solution was stirred at 70° C. for 16 h. After cooling to room temperature, the mixture was diluted with EtOAc, and washed with sat. NaHCO$_3$ (aq). The separated organic layer was dried over Na$_2$SO$_4$, filtered and concentrated. The residue was purified on silica gel (40 g, 0-50% EtOAc in hexanes) to give the desired product as a white solid (726.8 mg, 52%).

Step 3. 2-(3-Fluoro-2-(4,4,5,5-tetramethyl-1,3,2-dioxaborolan-2-yl)phenyl)acetonitrile

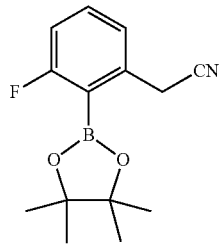 [SMILES: CC1(C)OB(c2c(F)cccc2CC#N)OC1(C)C]

To a screw-cap vial equipped with a magnetic stir bar was added 4,4,5,5,4',4',5',5'-octamethyl-[2,2']bi[[1,3,2]dioxaborolanyl] (997.2 mg, 3.93 mmol), potassium acetate (1138 mg, 11.60 mmol) and [1,1'-bis(diphenylphosphino)ferrocene]dichloropalladium(II) complexed with dichloromethane (1:1) (416.3 mg, 0.510 mmol). The vial was sealed with a Teflon-lined septum, evacuated and backfilled with nitrogen (this process was repeated a total of three times). A solution of 2-(2-bromo-3-fluorophenyl)acetonitrile (726.9 mg, 3.40 mmol) in 1,4-dioxane (15.0 mL) was added. The reaction mixture was stirred at 100° C. for 16 h. After cooling to room temperature, the mixture was diluted with $CH_2Cl_2$, and washed with brine. The organic layer was dried over anhydrous $Na_2SO_4$, filtered and concentrated. The residue was purified on silica gel (40 g, 0-100% EtOAc in hexanes) to give the desired product product (622.9 mg, 70%). LCMS calculated for $C_{14}H_{18}BFNO_2$ $(M+H)^+$ m/z=262.1; found 262.2.

Step 4. 2-(3-Fluoro-2-(3-(4-(4-methylpiperazin-1-yl)phenyl)-1H-pyrazolo[3,4-c]pyridin-5-yl)phenyl)acetonitrile To a screw-cap vial equipped with a magnetic stir bar was added tert-butyl 5-chloro-3-(4-(4-methylpiperazin-1-yl)phenyl)-1H-pyrazolo[3,4-c]pyridine-1-carboxylate (34.4 mg, 0.080 mmol), chloro(2-dicyclohexylphosphino-2',4',6'-triisopropyl-1,1'-biphenyl)[2-(2'-amino-1,1'-biphenyl)]palladium(II) (XPhos Pd G2, 9.5 mg, 0.012 mmol) and cesium carbonate (88.2 mg, 0.271 mmol). The vial was sealed with a Teflon-lined septum, evacuated and backfilled with nitrogen (this process was repeated a total of three times). A solution of 2-(3-fluoro-2-(4,4,5,5-tetramethyl-1,3,2-dioxaborolan-2-yl)phenyl)acetonitrile (35.5 mg, 0.136 mmol) in 1,4-dioxane (2.00 ml) was added, followed by water (200.0 μL). The reaction was heated to 50° C. for 16 h. The reaction mixture was concentrated. To the residue was added $CH_2Cl_2$ (2.0 mL) followed by TFA (2.0 mL). The resulting mixture was stirred at room temperature for 15 min, and then concentrated. The residue was purified using prep-LCMS (XBridge C18 column, eluting with a gradient of acetonitrile/water containing 0.1% TFA, at flow rate of 60 mL/min) to afford the desired product. LCMS calculated for $C_{25}H_{24}FN_6$ $(M+H)^+$: m/z=427.2; found: 427.2.

Example 195. (3-Fluoro-2-(3-(4-(4-methylpiperazin-1-yl)phenyl)-1H-pyrazolo[3,4-c]pyridin-5-yl)phenyl)methanamine

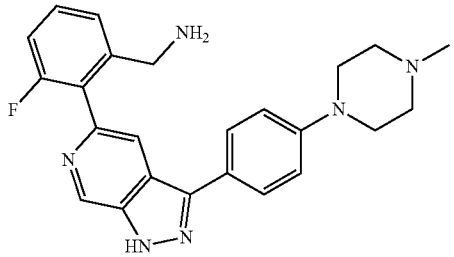 [SMILES: CN1CCN(c2ccc(-c3n[nH]c4cnc(-c5c(F)cccc5CN)cc34)cc2)CC1]

Step 1. tert-Butyl 2-bromo-3-fluorobenzylcarbamate

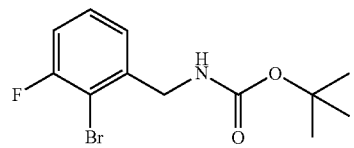 [SMILES: CC(C)(C)OC(=O)NCc1cccc(F)c1Br]

To a solution of 2-bromo-3-fluorobenzonitrile (2.460 g, 12.30 mmol) in THF (50.0 ml) at room temperature was added 1.0 M solution of borane-THF complex in THF (52.0 ml, 52.0 mmol). The mixture was stirred at 70° C. for 2 h. After cooling to room temperature, the reaction mixture was quenched with 4.0 M HCl in water (50.0 ml, 200 mmol). The mixture was stirred at 50° C. for 3 h and then cooled to 0° C. The mixture was treated with 2 M $K_2CO_3$ (aq) until pH reached 10. The mixture was extracted with $Et_2O$. The organic layer was dried over anhydrous $Na_2SO_4$, filtered and concentrated. The resulting residue was dissolved in $CH_2Cl_2$ (100 ml). Di-tert-butyldicarbonate (4.07 g, 18.65 mmol) was added. The mixture was stirred at room temperature for 10 min, and then concentrated. The residue was purified on silica gel (120 g, 0-50% EtOAc in hexanes) to give the desired product as a white solid (2.497 g, 67%). LCMS calculated for $C_8H_8BrFNO_2$ $(M+H-C_4H_8)^+$ m/z=248.0; found 248.0.

Step 2. (3-Fluoro-2-(3-(4-(4-methylpiperazin-1-yl)phenyl)-1H-pyrazolo[3,4-c]pyridin-5-yl)phenyl)methanamine This compound was prepared according to the procedures described in Example 194, using tert-butyl 2-bromo-3-fluorobenzylcarbamate instead of 2-(2-bromo-3-fluorophenyl)acetonitrile as starting material. LCMS calculated for $C_{24}H_{26}FN_6$ $(M+H)^+$: m/z=417.2; found: 417.2.

Example 196. (3-Fluoro-2-(3-(4-(4-methylpiperazin-1-yl)phenyl)-1H-pyrazolo[3,4-c]pyridin-5-yl)phenyl)methanol

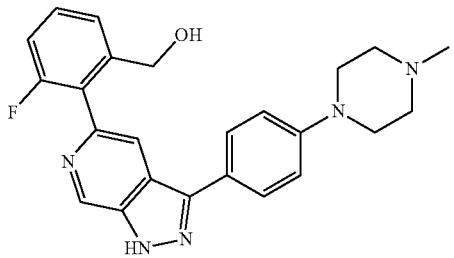 [SMILES: CN1CCN(c2ccc(-c3n[nH]c4cnc(-c5c(F)cccc5CO)cc34)cc2)CC1]

This compound was prepared according to the procedure described in Example 195, using 2-fluoro-6-(hydroxymethyl)phenylboronic acid instead of tert-butyl (3-fluoro-2-(4,4,5,5-tetramethyl-1,3,2-dioxaborolan-2-yl)benzyl)carbamate as the starting material. LCMS calculated for $C_{24}H_{25}FN_5O$ (M+H)$^+$: m/z=418.2; found: 418.2.

Example 197. 4,6-Difluoro-N-methyl-5-(3-(4-(4-methylpiperazin-1-yl)phenyl)-1H-pyrazolo[3,4-c]pyridin-5-yl)-2,3-dihydro-1H-inden-1-amine

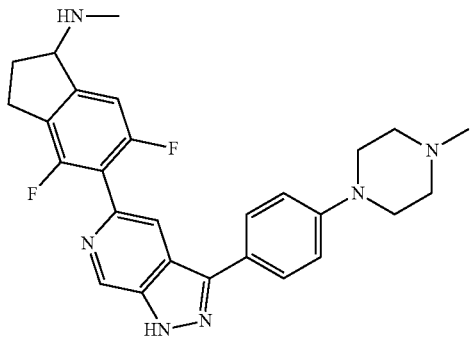 [SMILES: CNC1CCc2c1cc(F)c(-c1cc3c(-c4ccc(N5CCN(C)CC5)cc4)n[nH]c3cn1)c2F]

Step 1. tert-Butyl 4,6-difluoro-2,3-dihydro-1H-inden-1-yl(methyl)carbamate

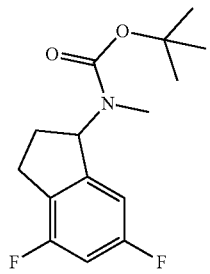 [SMILES: CN(C(=O)OC(C)(C)C)C1CCc2c(F)cc(F)cc21]

To a solution of 4,6-difluoro-2,3-dihydro-1H-inden-1-one (Ark Pharm, 4.015 g, 23.88 mmol) in 2-propanol (90.0 ml) was added methylamine (2.0 M in methanol) (60.0 ml, 120 mmol) followed by titanium(IV) isopropoxide (15.31 ml, 51.7 mmol). The mixture was stirred at 35° C. for 16 h before it was cooled to room temperature. Sodium borohydride (1.312 g, 34.7 mmol) was added. The reaction was stirred at room temperature for 1 h, and was quenched with HCl (6.0 N in water) (60.0 ml, 360 mmol). The mixture was stirred at room temperature for 2 h, and was treated with NaOH (4.0 N in water) until pH reached 10. The mixture was extracted with Et$_2$O. The organic layer was dried over anhydrous Na$_2$SO$_4$, filtered and concentrated. The residue was dissolved in CH$_2$Cl$_2$ (100 mL), and treated with Boc-anhydride (5.21 g, 23.88 mmol). After stirring at room temperature for 30 min, the reaction was concentrated. The residue was purified on silica gel (120 g, 0-100% EtOAc in hexanes) to give the desired product as an oil (5.27 g, 78%). LCMS calculated for $C_{11}H_{12}F_2NO_2$ (M+H—$C_4H_8$)$^+$: m/z=228.1; found: 228.1.

Step 2. tert-Butyl 4,6-difluoro-5-(4,4,5,5-tetramethyl-1,3,2-dioxaborolan-2-yl)-2,3-dihydro-1H-inden-1-yl(methyl)carbamate

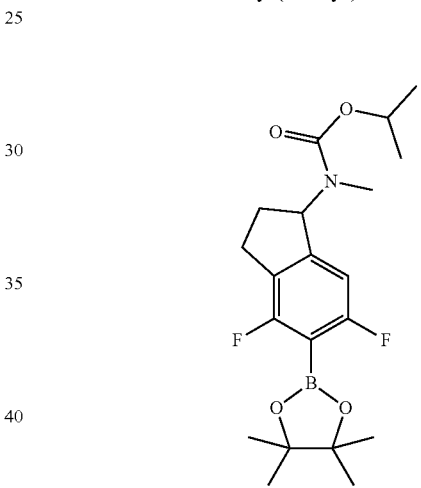

To a solution of tert-butyl (4,6-difluoro-2,3-dihydro-1H-inden-1-yl)(methyl)carbamate (5.27 g, 18.60 mmol) in THF (100.0 ml) at −78° C. under N$_2$ was added a solution of n-BuLi (2.5 M in hexanes) (15.00 ml, 37.5 mmol) slowly over a period of 20 min. The reaction was allowed to warm to −60° C. and stirred for 90 min. The reaction was then cooled back to −78° C. 2-Isopropoxy-4,4,5,5-tetramethyl-1,3,2-dioxaborolane (10.79 g, 58.0 mmol) was added slowly over a period of 20 min. After stirring at −78° C. for another 10 min, the reaction mixture was allowed to warm to room temperature and stirred for 1 h. The reaction was quenched with sat. NaHCO$_3$, and extracted with Et$_2$O. The organic layer was dried over Na$_2$SO$_4$, filtered and concentrated. The residue was purified on silica gel (120 g, 0-100% EtOAc in hexanes) to give the desired product as an oil (1.74 g, 23%). LCMS calculated for $C_{17}H_{23}BF_2NO_4$ (M+H—$C_4H_8$)$^+$: m/z=354.2; found: 354.1.

Step 3. 4,6-Difluoro-N-methyl-5-(3-(4-(4-methylpiperazin-1-yl)phenyl)-1H-pyrazolo[3,4-c]pyridin-5-yl)-2,3-dihydro-1H-inden-1-amine To a screw-cap vial equipped with a magnetic stir bar was added tert-butyl 5-chloro-3-(4-(4-methylpiperazin-1-yl)phenyl)-1H-pyrazolo[3,4-c]pyridine-1-carboxylate (31.4 mg, 0.073 mmol, Example 194, Step 1), chloro(2-dicyclohexylphosphino-2',4',6'-triisopropyl-1,1'-biphenyl)[2-(2'-amino-1,1'-biphenyl)]palladium(II) (XPhos Pd G2, 8.3 mg, 10.55 μmol) and cesium carbonate (76.3 mg, 0.234 mmol). The vial was sealed with a Teflon-lined septum, evacuated and backfilled with nitrogen (this process was repeated a total of three times). A solution of tert-butyl (4,6-difluoro-5-(4,4,5,5-tetramethyl-1,3,2-dioxaborolan-2-yl)-2,3-dihydro-1H-inden-1-yl)(methyl)carbamate (28.8 mg, 0.070 mmol) in 1,4-dioxane (2.00 ml) was added, followed by water (200.0 μl). The reaction mixture was heated to 50° C. for 16 h. and then concentrated. To the residue was added CH$_2$Cl$_2$ (2.0 mL) followed by TFA (2.0 mL). The mixture was stirred at room temperature for 15 min, and then concentrated. The residue was purified using prep-LCMS (XBridge C18 column, eluting with a gradient of acetonitrile/water containing 0.1% TFA, at flow rate of 60 mL/min) to afford the desired product. LCMS calculated for C$_{27}$H$_{29}$F$_2$N$_6$ (M+H)$^+$: m/z=475.2; found: 475.3.

Example 198. 4,6-Difluoro-N-methyl-5-(3-(1-methyl-1H-pyrazol-4-yl)-1H-pyrazolo[3,4-c]pyridin-5-yl)-2,3-dihydro-1H-inden-1-amine

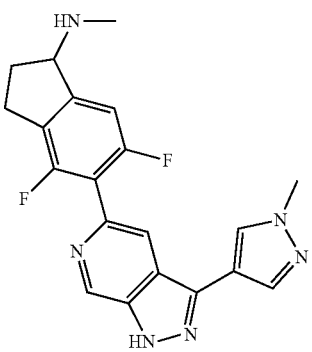 [SMILES: CNC1CCc2c1cc(F)c(-c1cc3c(-c4cnn(C)c4)n[nH]c3cn1)c2F]

This compound was prepared according to the procedure described in Example 197, using tert-butyl 5-chloro-3-(1-methyl-1H-pyrazol-4-yl)-1H-pyrazolo[3,4-c]pyridine-1-carboxylate (Intermediate 1) instead of tert-butyl 5-chloro-3-(4-(4-methylpiperazin-1-yl)phenyl)-1H-pyrazolo[3,4-c]pyridine-1-carboxylate as the starting material. LCMS calculated for C$_{20}$H$_{19}$F$_2$N$_6$ (M+H)$^+$: m/z=381.2; found: 381.2. $^1$H NMR (TFA salt, 500 MHz, DMSO-d$_6$) δ 9.14 (d, J=1.2 Hz, 1H), 9.09 (br, 2H), 8.46 (s, 1H), 8.19 (s, 1H), 8.04 (s, 1H), 7.46 (d, J=8.8 Hz, 1H), 4.88 (m, 1H), 3.91 (s, 3H), 3.13 (m, 1H), 3.05-2.90 (m, 1H), 2.66 (t, J=5.3 Hz, 3H), 2.62-2.52 (m, 1H), 2.27 (m, 1H).

Example 199. 6,8-Difluoro-N-methyl-7-(3-(4-(4-methylpiperazin-1-yl)phenyl)-1H-pyrazolo[3,4-c]pyridin-5-yl)-1,2,3,4-tetrahydronaphthalen-2-amine

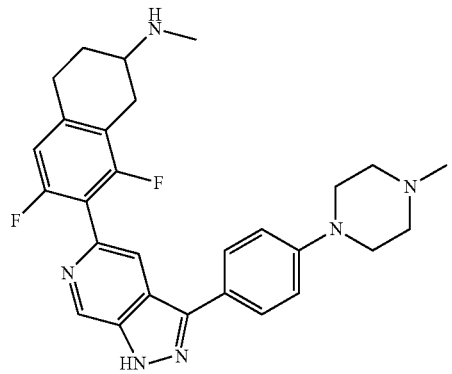 [SMILES: CNC1CCc2cc(F)c(-c3cc4c(-c5ccc(N6CCN(C)CC6)cc5)n[nH]c4cn3)c(F)c2C1]

This compound was prepared according to the procedure described in Example 197, using 6,8-difluoro-3,4-dihydronaphthalen-2(1H)-one (Ark Pharm) instead of 4,6-difluoro-2,3-dihydro-1H-inden-1-one as the starting material. LCMS calculated for C$_{28}$H$_{31}$F$_2$N$_6$ (M+H)$^+$: m/z=489.3; found: 489.3.

Example 200. 6,8-Difluoro-N-methyl-7-(3-(1-methyl-1H-pyrazol-4-yl)-1H-pyrazolo[3,4-c]pyridin-5-yl)-1,2,3,4-tetrahydronaphthalen-2-amine

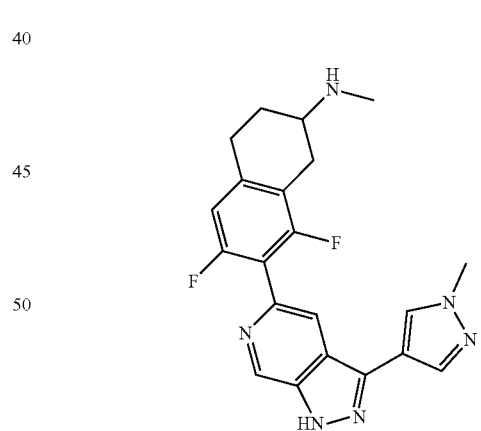

This compound was prepared according to the procedure described in Example 199, using tert-butyl 5-chloro-3-(1-methyl-1H-pyrazol-4-yl)-1H-pyrazolo[3,4-c]pyridine-1-carboxylate instead of tert-butyl 5-chloro-3-(4-(4-methylpiperazin-1-yl)phenyl)-1H-pyrazolo[3,4-c]pyridine-1-carboxylate as the starting material. LCMS calculated for C$_{21}$H$_{21}$F$_2$N$_6$ (M+H)$^+$: m/z=395.2; found: 395.2.

233

Example 201. 4-(5-(1,3-Difluoro-5-(methylamino)-5,6,7,8-tetrahydronaphthalen-2-yl)-1H-pyrazolo[3,4-c]pyridin-3-yl)-N-methylbenzamide

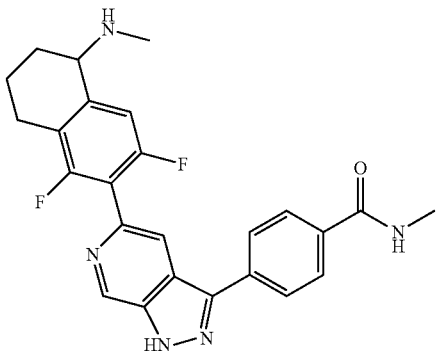 [SMILES: CNC(=O)c1ccc(-c2n[nH]c3cnc(-c4c(F)cc5c(c4F)CCCC5NC)cc23)cc1]

Step 1. tert-Butyl 5,7-difluoro-6-(4,4,5,5-tetramethyl-1,3,2-dioxaborolan-2-yl)-1,2,3,4-tetrahydronaphthalen-1-yl(methyl)carbamate

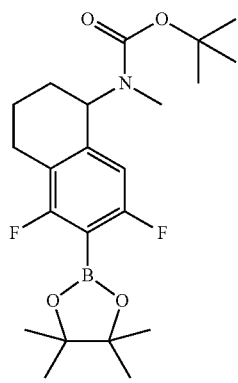

This compound was prepared according to the procedure described in Example 197, using 5,7-difluoro-3,4-dihydronaphthalen-1(2H)-one (Ark Pharm) instead of 4,6-difluoro-2,3-dihydro-1H-inden-1-one as the starting material. LCMS calculated for $C_{22}H_{32}BF_2NNaO_4$ (M+Na)$^+$: m/z=446.2; found: 446.2.

Step 2. tert-Butyl 5-chloro-3-(4-(methylcarbamoyl)phenyl)-1H-pyrazolo[3,4-c]pyridine-1-carboxylate

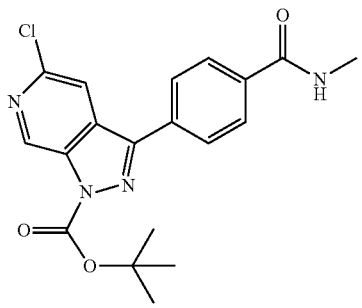 [SMILES: CNC(=O)c1ccc(-c2nn(C(=O)OC(C)(C)C)c3cnc(Cl)cc23)cc1]

234

This compound was prepared according to the procedures described in Intermediate 1, using N-methyl-4-(4,4,5,5-tetramethyl-1,3,2-dioxaborolan-2-yl)benzamide instead of 1-methyl-4-(4,4,5,5-tetramethyl-1,3,2-dioxaborolan-2-yl)-1H-pyrazole as starting material. LCMS calculated for $C_{19}H_{20}ClN_4O_3$ (M+H)$^+$ m/z=387.1; found 387.1.

Step 3. 4-(5-(1,3-Difluoro-5-(methylamino)-5,6,7,8-tetrahydronaphthalen-2-yl)-1H-pyrazolo[3,4-c]pyridin-3-yl)-N-methylbenzamide To a screw-cap vial equipped with a magnetic stir bar was added tert-butyl 5-chloro-3-(4-(methylcarbamoyl)phenyl)-1H-pyrazolo[3,4-c]pyridine-1-carboxylate (30.3 mg, 0.078 mmol), chloro(2-dicyclohexylphosphino-2',4',6'-triisopropyl-1,1'-biphenyl)[2-(2'-amino-1,1'-biphenyl)]palladium(II) (XPhos Pd G2, 8.5 mg, 10.80 μmol) and cesium carbonate (77.7 mg, 0.238 mmol). The vial was sealed with a Teflon-lined septum, evacuated and backfilled with nitrogen (this process was repeated a total of three times). A solution of tert-butyl (5,7-difluoro-6-(4,4,5,5-tetramethyl-1,3,2-dioxaborolan-2-yl)-1,2,3,4-tetrahydronaphthalen-1-yl)(methyl)carbamate (29.7 mg, 0.070 mmol) in 1,4-dioxane (2.00 ml) was added, followed by water (200.0 μl). The reaction mixture was heated to 50° C. for 16 h, and then concentrated. To the residue was added $CH_2Cl_2$ (2.0 mL) followed by TFA (2.0 mL). The mixture was stirred at room temperature for 15 min, and then concentrated. The residue was purified using prep-LCMS (XBridge C18 column, eluting with a gradient of acetonitrile/water containing 0.1% TFA, at flow rate of 60 mL/min) to afford the desired product. LCMS calculated $C_{25}H_{24}F_2N_5O$ (M+H)$^+$: m/z=448.2; found: 448.3.

Example 202. 5,7-Difluoro-N-methyl-6-(3-(1-methyl-1H-pyrazol-4-yl)-1H-pyrazolo[3,4-c]pyridin-5-yl)-1,2,3,4-tetrahydronaphthalen-1-amine

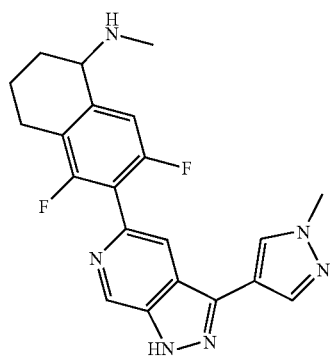 [SMILES: CNC1CCCc2c1cc(F)c(-c1cc3c(-c4cnn(C)c4)n[nH]c3cn1)c2F]

This compound was prepared according to the procedure described in Example 201, using tert-butyl 5-chloro-3-(1-methyl-1H-pyrazol-4-yl)-1H-pyrazolo[3,4-c]pyridine-1-carboxylate instead of tert-butyl 5-chloro-3-(4-(methylcarbamoyl)phenyl)-1H-pyrazolo[3,4-c]pyridine-1-carboxylate as the starting material. LCMS calculated for $C_{21}H_{21}F_2N_6$ (M+H)$^+$: m/z=395.2; found: 395.2.

235

Example 203. 5,7-Difluoro-6-(3-(6-(4-methylpiperazin-1-yl)pyridin-3-yl)-1H-pyrazolo[3,4-c]pyridin-5-yl)-1,2,3,4-tetrahydronaphthalen-1-amine

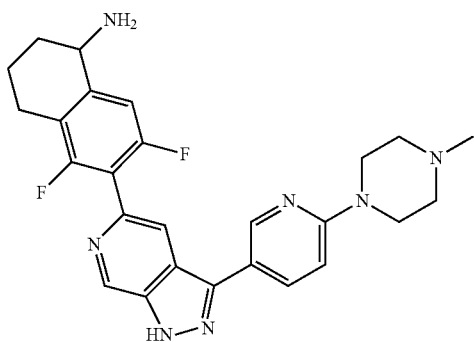 [SMILES: CN1CCN(c2ccc(-c3n[nH]c4cnc(-c5c(F)cc6c(c5F)CCCC6N)cc34)cn2)CC1]

Step 1. tert-Butyl 5,7-difluoro-6-(4,4,5,5-tetramethyl-1,3,2-dioxaborolan-2-yl)-1,2,3,4-tetrahydronaphthalen-1-ylcarbamate

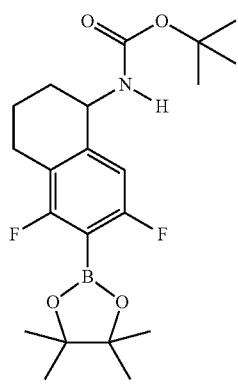 [SMILES: CC(C)(C)OC(=O)NC1CCCc2c1cc(F)c(B1OC(C)(C)C(C)(C)O1)c2F]

This compound was prepared according to the procedure described in Example 201, using ammonium acetate instead of methylamine as the starting material. LCMS calculated for $C_{21}H_{30}BF_2NNaO_4$ $(M+Na)^+$: m/z=432.2; found: 432.2.

Step 2. tert-Butyl 5-chloro-3-(6-(4-methylpiperazin-1-yl)pyridin-3-yl)-1H-pyrazolo[3,4-c]pyridine-1-carboxylate

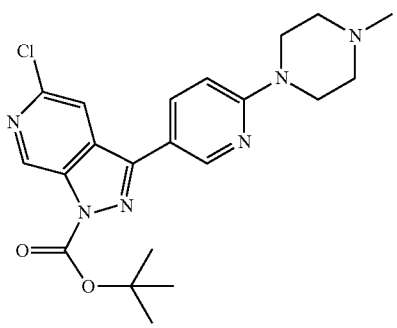 [SMILES: CN1CCN(c2ccc(-c3nn(C(=O)OC(C)(C)C)c4cnc(Cl)cc34)cn2)CC1]

236

This compound was prepared according to the procedures described in Intermediate 1, using 1-methyl-4-(5-(4,4,5,5-tetramethyl-1,3,2-dioxaborolan-2-yl)pyridin-2-yl)piperazine instead of 1-methyl-4-(4,4,5,5-tetramethyl-1,3,2-dioxaborolan-2-yl)-1H-pyrazole as starting material. LCMS calculated for $C_{21}H_{26}ClN_6O_2(M+H)^+$ m/z=429.2; found 429.1.

Step 3. 5,7-Difluoro-6-(3-(6-(4-methylpiperazin-1-yl)pyridin-3-yl)-1H-pyrazolo[3,4-c]pyridin-5-yl)-1,2,3,4-tetrahydronaphthalen-1-amine To a screw-cap vial equipped with a magnetic stir bar was added tert-butyl 5-chloro-3-(6-(4-methylpiperazin-1-yl)pyridin-3-yl)-1H-pyrazolo[3,4-c]pyridine-1-carboxylate (28.9 mg, 0.067 mmol), chloro(2-dicyclohexylphosphino-2',4',6'-triisopropyl-1,1'-biphenyl)[2-(2'-amino-1,1'-biphenyl)]palladium(II) (XPhos Pd G2, 7.5 mg, 9.53 µmol) and cesium carbonate (72.7 mg, 0.223 mmol). The vial was sealed with a Teflon-lined septum, evacuated and backfilled with nitrogen (this process was repeated a total of three times). A solution of tert-butyl (5,7-difluoro-6-(4,4,5,5-tetramethyl-1,3,2-dioxaborolan-2-yl)-1,2,3,4-tetrahydronaphthalen-1-yl)carbamate (26.0 mg, 0.064 mmol) in 1,4-dioxane (2.00 ml) was added, followed by water (200.0 µl). The reaction mixture was heated to 50° C. for 16 h, and then concentrated. To the residue was added $CH_2Cl_2$ (2.0 mL) followed by TFA (2.0 mL). The mixture was stirred at room temperature for 15 min, and then concentrated. The residue was purified using prep-LCMS (XBridge C18 column, eluting with a gradient of acetonitrile/water containing 0.1% TFA, at flow rate of 60 mL/min) to afford the desired product. LCMS calculated for $C_{26}H_{28}F_2N_7$ $(M+H)^+$: m/z=476.2; found: 476.3.

Example 204. 4-(5-(4,6-Difluoro-3-(methylamino)-2,3-dihydro-1H-inden-5-yl)-1H-pyrazolo[3,4-c]pyridin-3-yl)-N-methylbenzamide

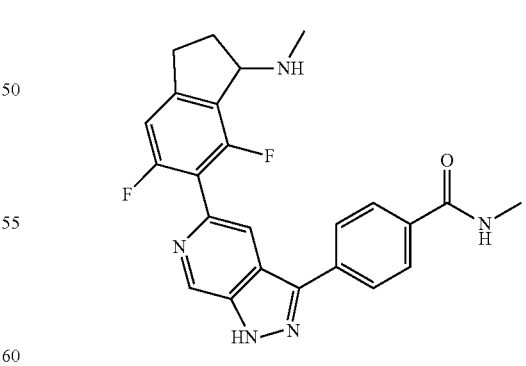

This compound was prepared according to the procedure described in Example 201, using 5,7-difluoro-2,3-dihydro-1H-inden-1-amine, HCl salt (AstaTech) instead of 5,7-difluoro-3,4-dihydronaphthalen-1(2H)-one as the starting material. LCMS calculated for $C_{24}H_{22}F_2N_5O$ $(M+H)^+$: m/z=434.2; found: 434.3.

Example 205. 5,7-Difluoro-N-methyl-6-(3-(4-(4-methylpiperazin-1-yl)phenyl)-1H-pyrazolo[3,4-c]pyridin-5-yl)-2,3-dihydro-1H-inden-1-amine

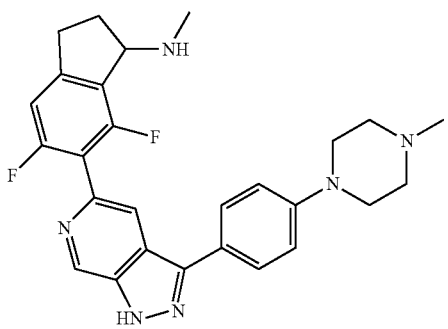 [SMILES: CNC1CCc2cc(F)c(-c3cc4c(-c5ccc(N6CCN(C)CC6)cc5)n[nH]c4cn3)c(F)c21]

This compound was prepared according to the procedure described in Example 204, using tert-butyl 5-chloro-3-(4-(4-methylpiperazin-1-yl)phenyl)-1H-pyrazolo[3,4-c]pyridine-1-carboxylate instead of tert-butyl 5-chloro-3-(4-(methylcarbamoyl)phenyl)-1H-pyrazolo[3,4-c]pyridine-1-carboxylate as the starting material. LCMS calculated for $C_{27}H_{29}F_2N_6$ (M+H)$^+$: m/z=475.2; found: 475.3.

Example 206. 5-Fluoro-7-methoxy-6-(3-(4-(4-methylpiperazin-1-yl)phenyl)-1H-pyrazolo[3,4-c]pyridin-5-yl)-2,3-dihydro-1H-inden-1-amine

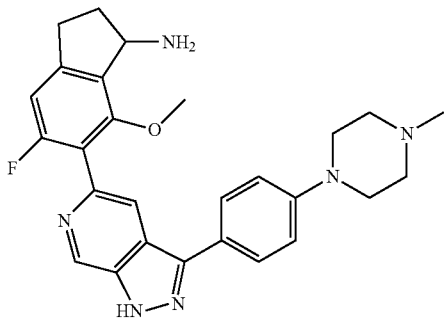 [SMILES: COc1c(-c2cc3c(-c4ccc(N5CCN(C)CC5)cc4)n[nH]c3cn2)c(F)cc2c1C(N)CC2]

This compound was prepared according to the procedure described in Example 197, using 5-fluoro-7-methoxy-2,3-dihydro-1H-inden-1-one (NetChem) instead of 4,6-difluoro-2,3-dihydro-1H-inden-1-one as the starting material. LCMS calculated for $C_{27}H_{30}FN_6O$ (M+H)$^+$: m/z=473.2; found: 473.3.

Example 207. 5-Fluoro-7-methoxy-6-(3-(1-methyl-1H-pyrazol-4-yl)-1H-pyrazolo[3,4-c]pyridin-5-yl)-2,3-dihydro-1H-inden-1-amine

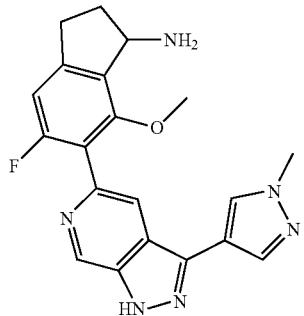 [SMILES: COc1c(-c2cc3c(-c4cnn(C)c4)n[nH]c3cn2)c(F)cc2c1C(N)CC2]

This compound was prepared according to the procedure described in Example 206, using tert-butyl 5-chloro-3-(1-methyl-1H-pyrazol-4-yl)-1H-pyrazolo[3,4-c]pyridine-1-carboxylate instead of tert-butyl 5-chloro-3-(4-(4-methylpiperazin-1-yl)phenyl)-1H-pyrazolo[3,4-c]pyridine-1-carboxylate as the starting material. LCMS calculated for $C_{20}H_{20}FN_6O$ (M+H)$^+$: m/z=379.2; found: 379.2.

Example 208. 5-(5-(2-Fluoro-5-(methylamino)-5,6,7,8-tetrahydronaphthalen-1-yl)-1H-pyrazolo[3,4-c]pyridin-3-yl)-N-methylpicolinamide

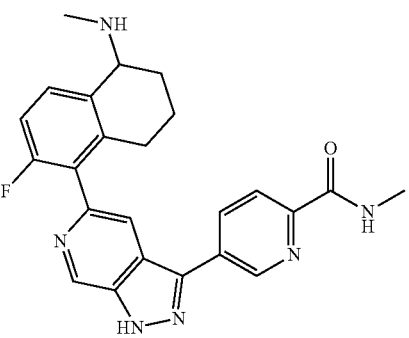 [SMILES: CNC(=O)c1ccc(-c2n[nH]c3cnc(-c4c(F)ccc5c4CCCC5NC)cc23)cn1]

Step 1. tert-Butyl 5-bromo-6-fluoro-1,2,3,4-tetrahydronaphthalen-1-yl(methyl)carbamate

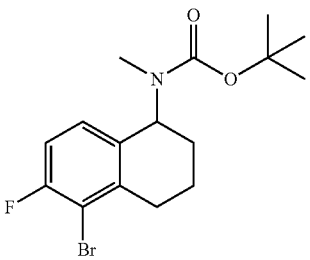 [SMILES: CN(C(=O)OC(C)(C)C)C1CCCc2c1ccc(F)c2Br]

To a solution of 5-bromo-6-fluoro-3,4-dihydronaphthalen-1(2H)-one (Ark Pharm, 352.6 mg, 1.451 mmol) in 2-propanol (10.0 ml) was added methylamine (2.0 M in methanol) (2.50 ml, 5.00 mmol) followed by titanium(IV) isopropoxide (596.0 mg, 2.097 mmol). The mixture was stirred at 35° C. for 16 h before it was cooled to room temperature. Sodium borohydride (53.4 mg, 1.412 mmol) was added. The reaction mixture was stirred at room temperature for 1 h, and was quenched with HCl (1.0 N in water) (30.0 ml, 30 mmol). The mixture was stirred at room temperature for 2 h, and was treated with NaOH (4.0 N in water) until pH reached 10. The mixture was extracted with Et$_2$O. The organic layer was dried over anhydrous Na$_2$SO$_4$, filtered and concentrated. The residue was dissolved in CH$_2$Cl$_2$ (10 ml), and treated with Boc-anhydride (426.4 mg, 1.954 mmol). After stirring at room temperature for 30 min, the reaction mixture was concentrated. The residue was purified on silica gel (40 g, 0-100% EtOAc in hexanes) to give the desired product (461.0 mg, 89%). LCMS calculated for C$_{12}$H$_{14}$BrFNO$_2$ (M+H—C$_4$H$_8$)$^+$: m/z=302.0; found: 302.1.

Step 2. tert-Butyl 6-fluoro-5-(4,4,5,5-tetramethyl-1,3,2-dioxaborolan-2-yl)-1,2,3,4-tetrahydronaphthalen-1-yl(methyl)carbamate

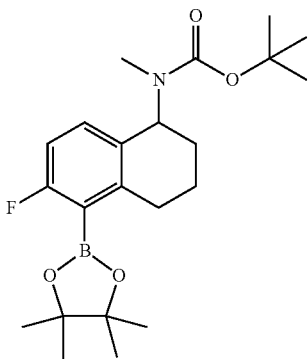 [SMILES: CN(C(=O)OC(C)(C)C)C1CCCc2c1ccc(F)c2B1OC(C)(C)C(C)(C)O1]

To a screw-cap vial equipped with a magnetic stir bar was added 4,4,5,5,4',4',5',5'-octamethyl-[2,2']bi[[1,3,2]dioxaborolanyl] (517.4 mg, 2.037 mmol), potassium acetate (416.8 mg, 4.25 mmol) and [1,1'-bis(diphenylphosphino)ferrocene]dichloropalladium(II), complexed with dichloromethane (1:1) (210.2 mg, 0.257 mmol). The vial was sealed with a Teflon-lined septum, evacuated and backfilled with nitrogen (this process was repeated a total of three times). A solution of tert-butyl (5-bromo-6-fluoro-1,2,3,4-tetrahydronaphthalen-1-yl)(methyl)carbamate (461.0 mg, 1.287 mmol) in 1,4-dioxane (6.0 ml) was added via syringe. The mixture was heated at 100° C. for 16 h. After cooling to room temperature, the reaction mixture was diluted with CH$_2$Cl$_2$ and filtered. The filtrate was concentrated. The residue was purified on silica gel (40 g, 0-100% EtOAc in hexanes) to give the desired product (337.4 mg, 65%). LCMS calculated for C$_{22}$H$_{33}$BFNNaO$_4$(M+Na)$^+$ m/z=428.2; found 428.2.

Step 3. tert-Butyl 5-chloro-3-(6-(methylcarbamoyl)pyridin-3-yl)-1H-pyrazolo[3,4-c]pyridine-1-carboxylate

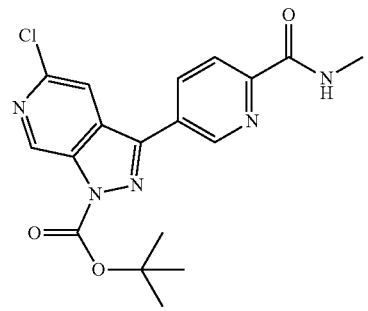 [SMILES: CNC(=O)c1ccc(-c2nn(C(=O)OC(C)(C)C)c3cnc(Cl)cc23)cn1]

This compound was prepared according to the procedures described in Intermediate 1, using N-methyl-5-(4,4,5,5-tetramethyl-1,3,2-dioxaborolan-2-yl)picolinamide instead of 1-methyl-4-(4,4,5,5-tetramethyl-1,3,2-dioxaborolan-2-yl)-1H-pyrazole as starting material. LCMS calculated for C$_{18}$H$_{19}$ClN$_5$O$_3$(M+H)$^+$ m/z=388.1; found 388.1.

Step 4. 5-(5-(2-Fluoro-5-(methylamino)-5,6,7,8-tetrahydronaphthalen-1-yl)-1H-pyrazolo[3,4-c]pyridin-3-yl)-N-methylpicolinamide To a screw-cap vial equipped with a magnetic stir bar was added tert-butyl 5-chloro-3-(6-(methylcarbamoyl)pyridin-3-yl)-1H-pyrazolo[3,4-c]pyridine-1-carboxylate (30.3 mg, 0.078 mmol), chloro(2-dicyclohexylphosphino-2',4',6'-triisopropyl-1,1'-biphenyl)[2-(2'-amino-1,1'-biphenyl)]palladium(II) (XPhos Pd G2, 8.5 mg, 10.80 µmol) and cesium carbonate (77.2 mg, 0.237 mmol). The vial was sealed with a Teflon-lined septum, evacuated and backfilled with nitrogen (this process was repeated a total of three times). A solution of tert-butyl (6-fluoro-5-(4,4,5,5-tetramethyl-1,3,2-dioxaborolan-2-yl)-1,2,3,4-tetrahydronaphthalen-1-yl)(methyl)carbamate (28.1 mg, 0.069 mmol) in 1,4-dioxane (2.00 ml) was added, followed by water (200.0 µl). The reaction mixture was heated to 50° C. for 16 h, and then concentrated. To the residue was added CH$_2$Cl$_2$ (2.0 mL) followed by TFA (2.0 mL). The mixture was stirred at room temperature for 15 min, and then concentrated. The residue was purified using prep-LCMS (XBridge C18 column, eluting with a gradient of acetonitrile/water containing 0.1% TFA, at flow rate of 60 mL/min) to afford the desired product. LCMS calculated C$_{24}$H$_{24}$FN$_6$O (M+H)$^+$: m/z=431.2; found: 431.3.

Example 209. 6-Fluoro-N-methyl-5-(3-(4-(4-methylpiperazin-1-yl)phenyl)-1H-pyrazolo[3,4-c]pyridin-5-yl)-1,2,3,4-tetrahydronaphthalen-1-amine

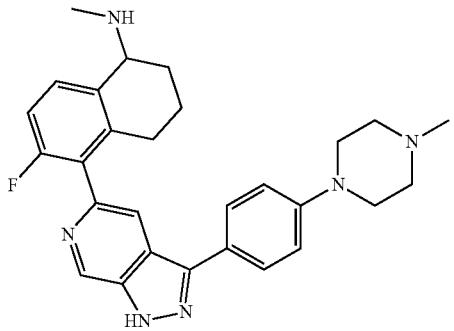 [SMILES: CNC1CCCc2c1ccc(F)c2-c1cc2c(-c3ccc(N4CCN(C)CC4)cc3)n[nH]c2cn1]

This compound was prepared according to the procedure described in Example 208, using tert-butyl 5-chloro-3-(4-(4-methylpiperazin-1-yl)phenyl)-1H-pyrazolo[3,4-c]pyridine-1-carboxylate instead of tert-butyl 5-chloro-3-(6-(methylcarbamoyl)pyridin-3-yl)-1H-pyrazolo[3,4-c]pyridine-1-carboxylate as the starting material. LCMS calculated for $C_{28}H_{32}FN_6$ $(M+H)^+$: m/z=471.3; found: 471.3.

Example 210. 6-Fluoro-5-(3-(1-methyl-1H-pyrazol-4-yl)-1H-pyrazolo[3,4-c]pyridin-5-yl)-1,2,3,4-tetrahydronaphthalen-1-amine

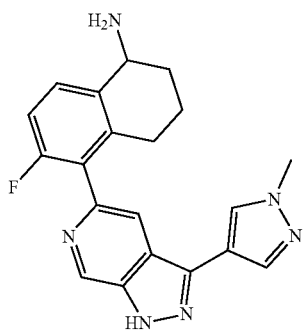 [SMILES: Cn1cc(-c2n[nH]c3cnc(-c4c(F)ccc5c4CCCC5N)cc23)cn1]

Step 1. tert-Butyl 6-fluoro-5-(4,4,5,5-tetramethyl-1,3,2-dioxaborolan-2-yl)-1,2,3,4-tetrahydronaphthalen-1-ylcarbamate

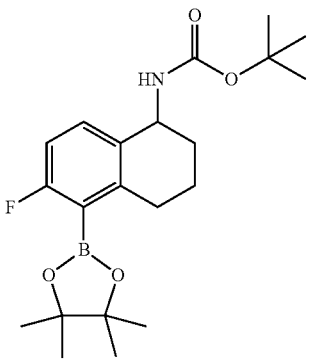

This compound was prepared according to the procedure described in Example 208, using ammonium acetate instead of methylamine as the starting material. LCMS calculated for $C_{17}H_{24}BFNO_4$ $(M+H-C_4H_8)^+$: m/z=336.2; found: 336.3.

Step 2. 6-Fluoro-5-(3-(1-methyl-1H-pyrazol-4-yl)-1H-pyrazolo[3,4-c]pyridin-5-yl)-1,2,3,4-tetrahydronaphthalen-1-amine To a screw-cap vial equipped with a magnetic stir bar was added tert-butyl 5-chloro-3-(1-methyl-1H-pyrazol-4-yl)-1H-pyrazolo[3,4-c]pyridine-1-carboxylate (24.9 mg, 0.075 mmol, Intermediate 1), chloro(2-dicyclohexylphosphino-2',4',6'-triisopropyl-1,1'-biphenyl)[2-(2'-amino-1,1'-biphenyl)]palladium(II) (XPhos Pd G2, 7.5 mg, 9.53 µmol) and cesium carbonate (72.4 mg, 0.222 mmol). The vial was sealed with a Teflon-lined septum, evacuated and backfilled with nitrogen (this process was repeated a total of three times). A solution of tert-butyl (6-fluoro-5-(4,4,5,5-tetramethyl-1,3,2-dioxaborolan-2-yl)-1,2,3,4-tetrahydronaphthalen-1-yl)carbamate (25.0 mg, 0.064 mmol) in 1,4-dioxane (2.00 ml) was added via syringe, followed by water (200.0 µl). The reaction mixture was heated to 60° C. for 16 h. The reaction mixture was concentrated. To the residue was added $CH_2Cl_2$ (2.0 mL) followed by TFA (2.0 mL). The mixture was stirred at room temperature for 15 min, and then concentrated. The residue was purified using prep-LCMS (XBridge C18 column, eluting with a gradient of acetonitrile/water containing 0.1% TFA, at flow rate of 60 mL/min) to afford the desired product. LCMS calculated for $C_{27}H_{30}FN_6$ $(M+H)^+$: m/z=457.2; found: 457.2.

Example 211. 2-(3,5-Difluoro-4-(3-(2-(4-methylpiperazin-1-yl)pyrimidin-5-yl)-1H-pyrazolo[3,4-c]pyridin-5-yl)phenyl)acetonitrile

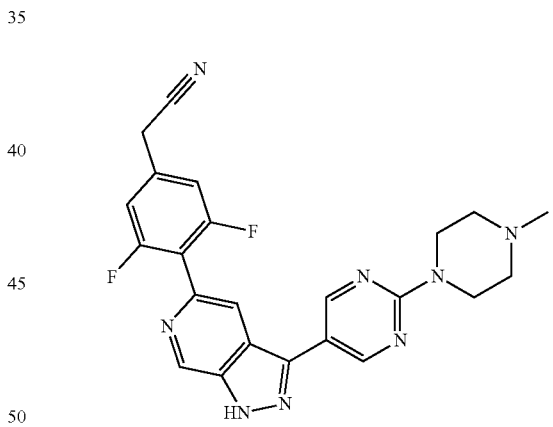

Step 1. 4-(4-Bromo-3,5-difluorophenyl)isoxazole

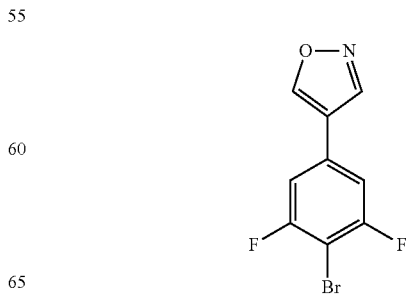

To a screw-cap vial equipped with a magnetic stir bar was added 2-bromo-1,3-difluoro-5-iodobenzene (1360.8 mg, 4.27 mmol), 4-(4,4,5,5-tetramethyl-1,3,2-dioxaborolan-2-yl)isoxazole (828.0 mg, 4.25 mmol), dichloro[1,1'-bis(diphenylphosphino)ferrocene]palladium (II) dichloromethane adduct (727.0 mg, 0.890 mmol) and cesium carbonate (2843 mg, 8.73 mmol). The vial was sealed with a Teflon-lined septum, evacuated and backfilled with nitrogen (this process was repeated a total of three times). 1,4-Dioxane (12.0 ml) was added via syringe followed by water (2.0 ml). The reaction was heated to 50° C. for 16 h. After cooling to room temperature, the organic layer was separated and concentrated. The residue was purified on silica gel (40 g, 0-100% EtOAc in hexanes) to give the desired product as a pale yellow solid (502.9 mg, 46%).

Step 2. 2-(4-Bromo-3,5-difluorophenyl)acetonitrile

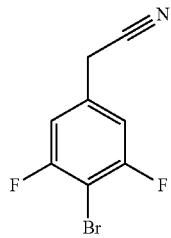 [SMILES: N#CCc1cc(F)c(Br)c(F)c1]

To a mixture of 4-(4-bromo-3,5-difluorophenyl)isoxazole (489.4 mg, 1.882 mmol) and potassium fluoride (584.8 mg, 10.07 mmol) was added DMF (5.0 ml) followed by water (5.0 ml). The reaction was heated to 90° C. for 3 h. After cooling to room temperature, the mixture was diluted with $CH_2Cl_2$, and washed with brine. The organic layer was dried over anhydrous $Na_2SO_4$, filtered and concentrated. The residue was purified on silica gel (40 g, 0-100% EtOAc in hexanes) to give the desired product as an off-white solid (363.4 mg, 83%).

Step 3. 2-(3,5-Difluoro-4-(4,4,5,5-tetramethyl-1,3,2-dioxaborolan-2-yl)phenyl)acetonitrile

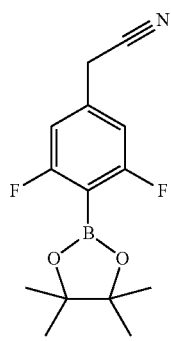 [SMILES: CC1(C)OB(c2c(F)cc(CC#N)cc2F)OC1(C)C]

This compound was prepared according to the procedure described in Example 194, using 2-(4-bromo-3,5-difluorophenyl)acetonitrile instead of 2-(2-bromo-3-fluorophenyl)acetonitrile as starting material. LCMS calculated for $C_{14}H_{17}BF_2NO_2$ (M+H)$^+$: m/z=280.1; found: 280.0.

Step 4. tert-Butyl 5-chloro-3-(2-(4-methylpiperazin-1-yl)pyrimidin-5-yl)-1H-pyrazolo[3,4-c]pyridine-1-carboxylate

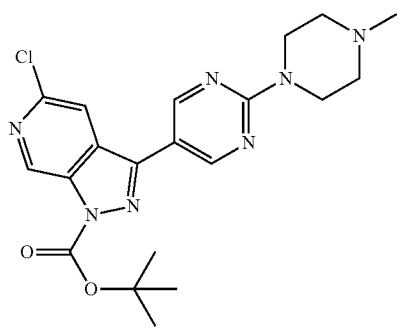 [SMILES: CN1CCN(c2ncc(-c3nn(C(=O)OC(C)(C)C)c4cnc(Cl)cc34)cn2)CC1]

This compound was prepared according to the procedures described in Intermediate 1, using 2-(4-methylpiperazin-1-yl)-5-(4,4,5,5-tetramethyl-1,3,2-dioxaborolan-2-yl)pyrimidine instead of 1-methyl-4-(4,4,5,5-tetramethyl-1,3,2-dioxaborolan-2-yl)-1H-pyrazole as starting material. LCMS calculated for $C_{20}H_{25}ClN_7O_2$ (M+H)$^+$ m/z=430.2; found 430.2.

Step 5. 2-(3,5-Difluoro-4-(3-(2-(4-methylpiperazin-1-yl)pyrimidin-5-yl)-1H-pyrazolo[3,4-c]pyridin-5-yl)phenyl)acetonitrile To a screw-cap vial equipped with a magnetic stir bar was added tert-butyl 5-chloro-3-(2-(4-methylpiperazin-1-yl)pyrimidin-5-yl)-1H-pyrazolo[3,4-c]pyridine-1-carboxylate (40.9 mg, 0.095 mmol), chloro(2-dicyclohexylphosphino-2',4',6'-triisopropyl-1,1'-biphenyl)[2-(2'-amino-1,1'-biphenyl)]palladium(II) (XPhos Pd G2, 11.2 mg, 0.014 mmol) and cesium carbonate (95.2 mg, 0.292 mmol). The vial was sealed with a Teflon-lined septum, evacuated and backfilled with nitrogen (this process was repeated a total of three times). A solution of 2-(3,5-difluoro-4-(4,4,5,5-tetramethyl-1,3,2-dioxaborolan-2-yl)phenyl)acetonitrile (66.8 mg, 0.239 mmol) in 1,4-dioxane (2.0 ml) was added via syringe, followed by water (200.0 µl). The reaction mixture was heated to 50° C. for 16 h. The reaction mixture was concentrated. To the residue was added $CH_2Cl_2$ (2.0 mL) followed by TFA (2.0 mL). The mixture was stirred at room temperature for 15 min, and then concentrated. The residue was purified using prep-LCMS (XBridge C18 column, eluting with a gradient of acetonitrile/water containing 0.1% TFA, at flow rate of 60 mL/min) to afford the desired product. LCMS calculated for $C_{23}H_{21}F_2N_8$ (M+H)$^+$: m/z=447.2; found: 447.2.

Example 212. 5,7-Difluoro-6-(3-(1-methyl-1H-pyrazol-4-yl)-1H-pyrazolo[3,4-c]pyridin-5-yl)-2,3-dihydro-1H-inden-1-ol

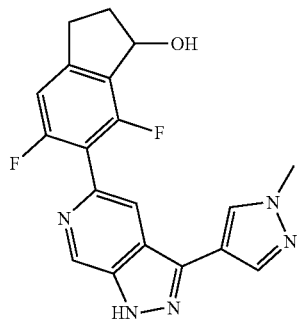 [SMILES: Cn1cc(-c2n[nH]c3cnc(-c4c(F)cc5c(c4F)C(O)CC5)cc23)cn1]

Step 1. 5,7-Difluoro-2,3-dihydro-1H-inden-1-ol

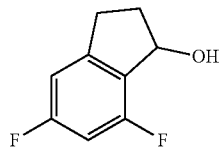

To a solution of 5,7-difluoro-2,3-dihydro-1H-inden-1-one (1.134 g, 6.74 mmol) in MeOH (24.0 ml) was added NaBH$_4$ (773.2 mg, 20.44 mmol). After stirring room temperature for 10 min., the mixture was diluted with CH$_2$Cl$_2$ and washed with sat. NaHCO$_3$(aq). The organic layer was dried over anhydrous Na$_2$SO$_4$, filtered and concentrated. The residue was purified on silica gel (40 g, 0-100% EtOAc in hexanes) to give the desired product as a colorless oil (981.4 mg, 86%).

Step 2 5,7-Difluoro-6-(4,4,5,5-tetramethyl-1,3,2-dioxaborolan-2-yl)-2,3-dihydro-1H-inden-1-ol

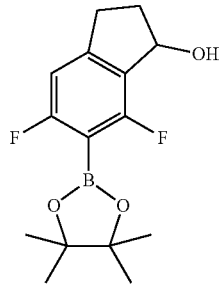 [SMILES: CC1(C)OB(c2c(F)cc3c(c2F)C(O)CC3)OC1(C)C]

To a solution of 5,7-difluoro-2,3-dihydro-1H-inden-1-ol (981.4 mg, 5.77 mmol) in THF (40.0 ml) at −78° C. under N$_2$ was added a solution of n-BuLi (2.5 M in hexanes) (7.00 ml, 17.50 mmol) slowly via syringe over a period of 20 min. The reaction mixture was allowed to warm to −60° C. and stirred for 60 min. The reaction was then cooled back to −78° C. 2-Isopropoxy-4,4,5,5-tetramethyl-1,3,2-dioxaborolane (4.64 ml, 22.73 mmol) was added slowly via syringe over a period of 20 min. After stirring at −78° C. for 20 min, the reaction mixture was allowed to warm to room temperature and stirred for 1 h. The reaction was quenched with sat. NaHCO$_3$, and extracted with Et$_2$O. The organic layer was dried over anhydrous Na$_2$SO$_4$, filtered and concentrated. The residue was purified on silica gel (40 g, 0-100% EtOAc in hexanes) to give the desired product as a colorless oil (1.085 g, 64%).

Step 3. 5,7-Difluoro-6-(3-(1-methyl-1H-pyrazol-4-yl)-1H-pyrazolo[3,4-c]pyridin-5-yl)-2,3-dihydro-1H-inden-1-ol To a screw-cap vial equipped with a magnetic stir bar was added tert-butyl 5-chloro-3-(1-methyl-1H-pyrazol-4-yl)-1H-pyrazolo[3,4-c]pyridine-1-carboxylate (26.4 mg, 0.079 mmol, Intermediate 1), chloro(2-dicyclohexylphosphino-2',4',6'-triisopropyl-1,1'-biphenyl)[2-(2'-amino-1,1'-biphenyl)]palladium(II) (XPhos Pd G2, 10.0 mg, 0.013 mmol) and cesium carbonate (86.3 mg, 0.265 mmol). The vial was sealed with a Teflon-lined septum, evacuated and backfilled with nitrogen (this process was repeated a total of three times). A solution of 5,7-difluoro-6-(4,4,5,5-tetramethyl-1,3,2-dioxaborolan-2-yl)-2,3-dihydro-1H-inden-1-ol (25.0 mg, 0.084 mmol) in 1,4-dioxane (2.00 ml) was added, followed by water (200.0 µl). The reaction mixture was heated to 50° C. for 16 h. The reaction mixture was concentrated. To the residue was added CH$_2$Cl$_2$ (2.0 mL) followed by TFA (2.0 mL). The mixture was stirred at room temperature for 15 min, and then concentrated. The residue was purified using prep-LCMS (XBridge C18 column, eluting with a gradient of acetonitrile/water containing 0.1% TFA, at flow rate of 60 mL/min) to afford the desired product. LCMS calculated for C$_{19}$H$_{16}$F$_2$N$_5$O (M+H)$^+$: m/z=368.1; found: 368.2.

Example 213. 5,7-Difluoro-6-(3-(6-(4-methylpiperazin-1-yl)pyridin-3-yl)-1H-pyrazolo[3,4-c]pyridin-5-yl)-2,3-dihydro-1H-inden-1-ol

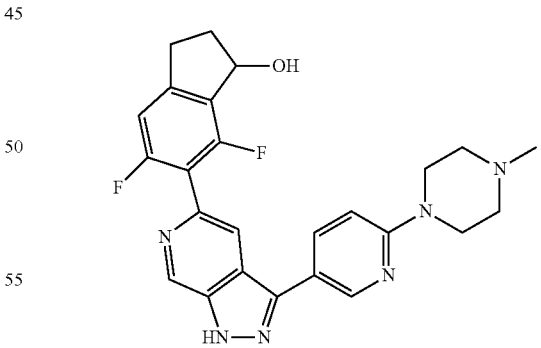

This compound was prepared according to the procedure described in Example 212, using tert-butyl 5-chloro-3-(6-(4-methylpiperazin-1-yl)pyridin-3-yl)-1H-pyrazolo[3,4-c]pyridine-1-carboxylate instead of tert-butyl 5-chloro-3-(1-methyl-1H-pyrazol-4-yl)-1H-pyrazolo[3,4-c]pyridine-1-carboxylate as the starting material. LCMS calculated for C$_{25}$H$_{25}$F$_2$N$_6$O (M+H)$^+$: m/z=463.2; found: 463.2.

Example 214. 6,8-Difluoro-7-(4-methoxy-3-(1-methyl-1H-pyrazol-4-yl)-1H-pyrazolo[3,4-c]pyridin-5-yl)-N-methyl-1,2,3,4-tetrahydronaphthalen-2-amine

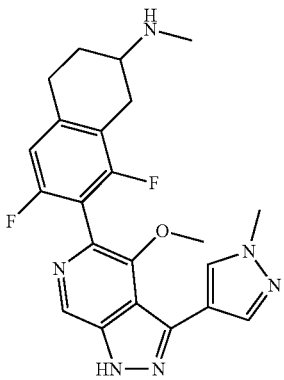 [SMILES: CNC1CCc2cc(F)c(-c3ncc4[nH]nc(-c5cnn(C)c5)c4c3OC)c(F)c2C1]

Step 1. tert-Butyl 6-chloro-5-methoxypyridin-3-ylcarbamate

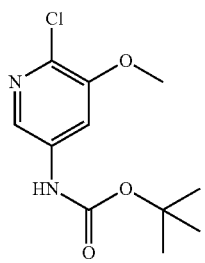 [SMILES: COc1cc(NC(=O)OC(C)(C)C)cnc1Cl]

To a solution of 6-chloro-5-methoxypyridin-3-amine (1.992 g, 12.56 mmol) in THF (100.0 mL) at 0° C. was added a solution of KHMDS (1.0 M in THF) (28.0 mL, 28.0 mmol) slowly via syringe over a period of 10 min. The mixture was stirred at 0° C. for 30 min. A solution of Boc-anhydride (3.28 g, 15.03 mmol) in THF (10.0 mL) was added slowly via syringe over a period of 20 min. The mixture was allowed to warm to room temperature. After stirring for 2 h, the reaction mixture was quenched with sat. NaHCO$_3$(aq) and extracted with Et$_2$O. The organic layer was dried over anhydrous Na$_2$SO$_4$, filtered and concentrated. The residue was purified on silica gel (120 g, 0-100% EtOAc in hexanes) to give the desired product as a yellow foamy solid (2.162 g, 67%). LCMS calculated for C$_{11}$H$_{16}$ClN$_2$O$_3$ (M+H)$^+$: m/z=259.1; found: 259.1.

Step 2. tert-Butyl 6-chloro-5-methoxy-4-methylpyridin-3-ylcarbamate

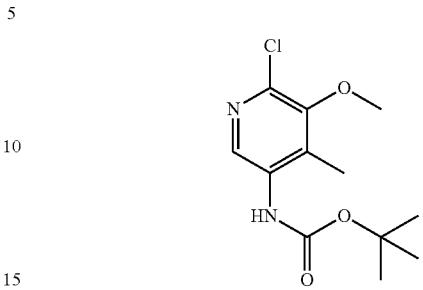

To a solution of tert-butyl (6-chloro-5-methoxypyridin-3-yl)carbamate (2.102 g, 8.13 mmol) in THF (80.0 ml) at −78° C. under N$_2$ was added TMEDA (3.81 ml, 25.3 mmol). A solution of n-BuLi (2.5 M in hexanes) (9.00 ml, 22.50 mmol) was added slowly via syringe over a period of 30 min. The reaction was allowed to warm to −30° C. and stirred for 2 h. The reaction mixture was then cooled back to −78° C. MeI (2.0 M in MTBE) (7.00 ml, 14.00 mmol) was added dropwise via syringe over a period of 30 min. After stirring at −78° C. for 1 h, the white suspension was allowed to warm to −20° C. and stirred for 2 h. The reaction was quenched with water. The mixture was extracted with Et$_2$O. The organic layer was dried over anhydrous Na$_2$SO$_4$, filtered and concentrated. The residue was purified on silica gel (120 g, 0-100% EtOAc in hexanes) to give the desired product as a white solid (2.055 g, 93%). LCMS calculated for C$_{12}$H$_{18}$ClN$_2$O$_3$ (M+H)$^+$: m/z=273.1; found: 273.1.

Step 3. 6-Chloro-5-methoxy-4-methylpyridin-3-amine

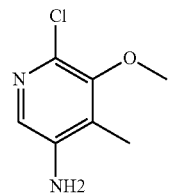

To a solution of tert-butyl (6-chloro-5-methoxy-4-methylpyridin-3-yl)carbamate (2.055 g, 7.53 mmol) in CH$_2$Cl$_2$ (20.0 ml) was added TFA (20.0 ml). The mixture was stirred at room temperature for 50 min, and then concentrated. The residue was dissolved in CH$_2$Cl$_2$, washed with sat. NaHCO$_3$ (aq). The organic layer was dried over anhydrous Na$_2$SO$_4$, filtered and concentrated. The residue was purified on silica gel (40 g, 0-100% EtOAc in hexanes) to give the desired product as a white solid (1.110 g, 85%). LCMS calculated for C$_7$H$_{10}$ClN$_2$O (M+H)$^+$: m/z=173.0; found: 173.1.

Step 4. 5-Chloro-4-methoxy-1H-pyrazolo[3,4-c]pyridine

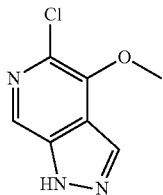

To a solution of 6-chloro-5-methoxy-4-methylpyridin-3-amine (1.104 g, 6.40 mmol) in acetic acid (22.0 mL) was added amyl nitrite (1.096 mL, 8.16 mmol). After stirring at room temperature for 5 min, the mixture was heated to 80° C. for 1 h. The reaction mixture was cooled to room temperature and concentrated in vacuo. The crude product was used directly in the next step without further purification. LCMS calculated for $C_7H_7ClN_3O$ $(M+H)^+$: m/z=184.0; found: 184.1.

Step 5. tert-Butyl 5-chloro-4-methoxy-3-(1-methyl-1H-pyrazol-4-yl)-1H-pyrazolo[3,4-c]pyridine-1-carboxylate

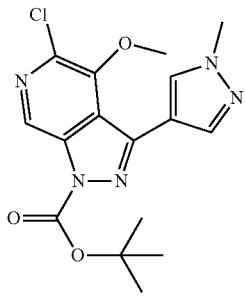 [SMILES: COc1c(Cl)ncc2c1c(-c1cnn(C)c1)nn2C(=O)OC(C)(C)C]

This compound was prepared according to the procedure described in Intermediate 1, using 5-chloro-4-methoxy-1H-pyrazolo[3,4-c]pyridine instead of 5-chloro-1H-pyrazolo[3,4-c]pyridine as the starting material. LCMS calculated for $C_{16}H_{19}Cl N_5O_3$ $(M+H)^+$ m/z=364.1; found 364.1.

Step 6. 6,8-Difluoro-7-(4-methoxy-3-(1-methyl-1H-pyrazol-4-yl)-1H-pyrazolo[3,4-c]pyridin-5-yl)-N-methyl-1,2,3,4-tetrahydronaphthalen-2-amine To a screw-cap vial equipped with a magnetic stir bar was added tert-butyl 5-chloro-4-methoxy-3-(1-methyl-1H-pyrazol-4-yl)-1H-pyrazolo[3,4-c]pyridine-1-carboxylate (31.5 mg, 0.087 mmol), chloro(2-dicyclohexylphosphino-2',4',6'-triisopropyl-1,1'-biphenyl)[2-(2'-amino-1,1'-biphenyl)]palladium(II) (XPhos Pd G2, 9.6 mg, 0.012 mmol) and cesium carbonate (99.2 mg, 0.304 mmol). The vial was sealed with a Teflon-lined septum, evacuated and backfilled with nitrogen (this process was repeated a total of three times). A solution of tert-butyl (6,8-difluoro-7-(4,4,5,5-tetramethyl-1, 3,2-dioxaborolan-2-yl)-1,2,3,4-tetrahydronaphthalen-2-yl)(methyl)carbamate (34.4 mg, 0.081 mmol, Example 199, Step 2) in 1,4-dioxane (2.00 ml) was added, followed by water (200.0 µl). The reaction mixture was heated to 50° C. for 16 h. The reaction mixture was concentrated. To the residue was added $CH_2Cl_2$ (2.0 mL) followed by TFA (2.0 mL). The mixture was stirred at room temperature for 15 min, and then concentrated. The residue was purified using prep-LCMS (XBridge C18 column, eluting with a gradient of acetonitrile/water containing 0.1% TFA, at flow rate of 60 mL/min) to afford the desired product. LCMS calculated for $C_{22}H_{23}F_2N_6O$ $(M+H)^+$: m/z=425.2; found: 425.2.

Example 215. 1-(3,5-Difluoro-4-(4-methoxy-3-(1-methyl-1H-pyrazol-4-yl)-1H-pyrazolo[3,4-c]pyridin-5-yl)phenyl)-N-methylmethanamine

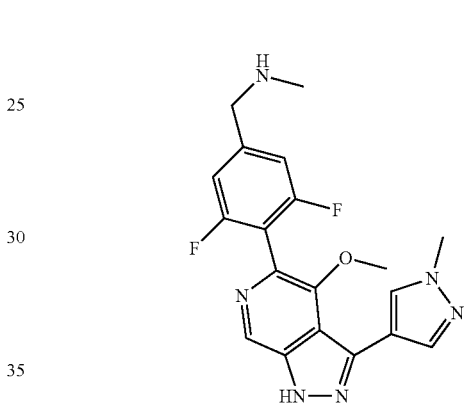

This compound was prepared according to the procedure described in Example 214, using tert-butyl 3,5-difluoro-4-(4,4,5,5-tetramethyl-1,3,2-dioxaborolan-2-yl)benzylmethyl)carbamate instead of tert-butyl (6,8-difluoro-7-(4,4,5,5-tetramethyl-1,3,2-dioxaborolan-2-yl)-1,2,3,4-tetrahydronaphthalen-2-yl)(methyl)carbamate as the starting material. LCMS calculated for $C_{19}H_{19}F_2N_6O$ $(M+H)^+$: m/z=385.2; found: 385.2.

Example 216. 5,7-Difluoro-6-(4-fluoro-3-(1-methyl-1H-pyrazol-4-yl)-1H-pyrazolo[3,4-c]pyridin-5-yl)-2,3-dihydro-1H-inden-1-amine

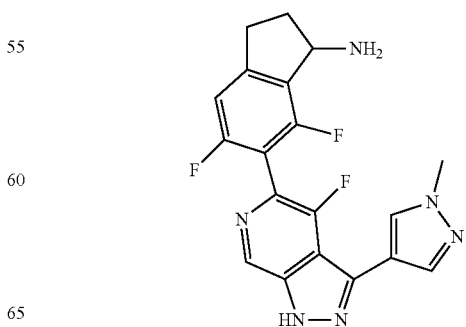

Step 1. tert-Butyl 6-chloro-5-fluoropyridin-3-ylcarbamate

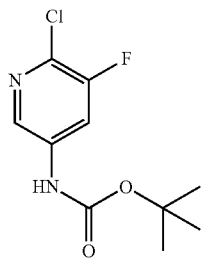 [SMILES: CC(C)(C)OC(=O)Nc1cnc(Cl)c(F)c1]

To a flask equipped with a magnetic stir bar was added 5-bromo-2-chloro-3-fluoropyridine (5.237 g, 24.89 mmol), chloro[(4,5-bis(diphenylphosphino)-9,9-dimethylxanthene)-2-(2'-amino-1,1'-biphenyl)]palladium(II) (XantPhos Pd G2, 2.254 g, 2.54 mmol), tert-butyl carbamate (3.191 g, 27.2 mmol) and cesium carbonate (20.06 g, 61.6 mmol). The flask was sealed with a septum, evacuated and backfilled with nitrogen (this process was repeated a total of three times). 1,4-Dioxane (90.0 ml) was added. The reaction mixture was stirred at 100° C. for 16 h. After cooling to room temperature, the reaction mixture was diluted with CH$_2$Cl$_2$ and filtered. The filtrate was concentrated. The residue was purified on silica gel (120 g, 0-50% EtOAc in hexanes) to give the desired product as a pale yellow oil (2.745 g, 45%). LCMS calculated for C$_{10}$H$_{13}$ClFN$_2$O$_2$ (M+H)$^+$: m/z=247.1; found: 247.1.

Step 2. tert-Butyl 6-chloro-5-fluoro-4-methylpyridin-3-ylcarbamate

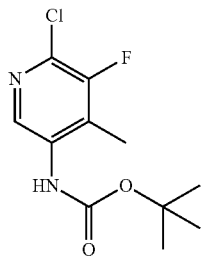 [SMILES: Cc1c(NC(=O)OC(C)(C)C)cnc(Cl)c1F]

To a solution of tert-butyl (6-chloro-5-fluoropyridin-3-yl) carbamate (2.745 g, 11.13 mmol) in THF (30.0 ml) at −78° C. under N$_2$ was added a solution of n-BuLi (2.5 M in hexanes) (12.0 ml, 30.0 mmol) slowly via syringe over a period of 30 min. The reaction mixture was allowed to warm to −30° C. and stirred for 2 h. The reaction mixture was then cooled back to −78° C. MeI (2.0 M in MTBE) (9.00 ml, 18.00 mmol) was added dropwise via syringe over a period of 30 min. After stirring at −78° C. for 1 h, the white suspension was allowed to warm to −20° C. and stirred for 2 h. The reaction mixture was quenched with water. The mixture was extracted with Et$_2$O. The organic layer was dried over anhydrous Na$_2$SO$_4$, filtered and concentrated. The residue was purified on silica gel (120 g, 0-50% EtOAc in hexanes) to give the desired product as a pale yellow solid (2.512 g, 87%). LCMS calculated for C$_{11}$H$_{15}$ClFN$_2$O$_2$ (M+H)$^+$: m/z=261.1; found: 261.1.

Step 3. 6-Chloro-5-fluoro-4-methylpyridin-3-amine

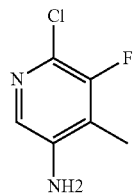

To a solution of tert-butyl (6-chloro-5-fluoro-4-methylpyridin-3-yl)carbamate (2.512 g, 9.64 mmol) CH$_2$Cl$_2$ (30.0 ml) was added TFA (30.0 ml). The mixture was stirred at room temperature for 50 min, and then concentrated. The residue was dissolved in CH$_2$Cl$_2$ and washed with sat. NaHCO$_3$ (aq). The organic layer was dried over anhydrous Na$_2$SO$_4$, filtered and concentrated. The residue was purified on silica gel (40 g, 0-100% EtOAc in hexanes) to give the desired product as a white solid (1.420 g, 92%). LCMS calculated for C$_6$H$_7$ClFN$_2$ (M+H)$^+$: m/z=161.0; found: 161.1.

Step 4. tert-Butyl 5-chloro-4-fluoro-3-(1-methyl-1H-pyrazol-4-yl)-1H-pyrazolo[3,4-c]pyridine-1-carboxylate

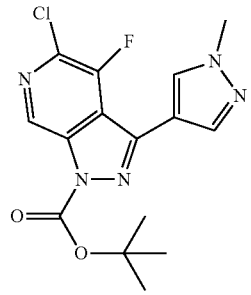 [SMILES: Cn1cc(-c2nn(C(=O)OC(C)(C)C)c3cnc(Cl)c(F)c23)cn1]

This compound was prepared according to the procedure described in Example 214, using 6-chloro-5-fluoro-4-methylpyridin-3-amine instead of 6-chloro-5-methoxy-4-methylpyridin-3-amine as the starting material. LCMS calculated for C$_{15}$H$_{16}$ClFN$_5$O$_2$ (M+H)$^+$ m/z=352.1; found 352.2.

Step 5. 5,7-Difluoro-6-(4-fluoro-3-(1-methyl-1H-pyrazol-4-yl)-1H-pyrazolo[3,4-c]pyridin-5-yl)-2,3-dihydro-1H-inden-1-amine To a screw-cap vial equipped with a magnetic stir bar was added tert-butyl 5-chloro-4-fluoro-3-(1-methyl-1H-pyrazol-4-yl)-1H-pyrazolo[3,4-c]pyridine-1-carboxylate (28.2 mg, 0.080 mmol), chloro(2-dicyclohexylphosphino-2',4',6'-triisopropyl-1,1'-biphenyl)[2-(2'-amino-1,1'-biphenyl)]palladium(II) (XPhos Pd G2, 8.5 mg, 10.80 µmol) and cesium carbonate (72.4 mg, 0.222 mmol). The vial was sealed with a Teflon-lined septum, evacuated and backfilled with nitrogen (this process was repeated a total of three times). A solution of tert-butyl (5,7-difluoro-6-(4,4,5,5-tetramethyl-1,3,2-dioxaborolan-2-yl)-2,3-dihydro-1H-inden-1-yl)carbamate (27.6 mg, 0.070 mmol, Example 204, Step 2) in 1,4-dioxane (2.00 ml) was added, followed by water (200.0 µl). The reaction mixture was heated to 50° C. for 16 h. The reaction mixture was concentrated. To the residue was added CH$_2$Cl$_2$ (2.0 mL) followed by TFA (2.0 mL). The mixture was stirred at room temperature for 15 min, and then concentrated. The residue was purified using prep-LCMS (XBridge C18 column, eluting with a gradient of acetonitrile/water containing 0.1% TFA, at flow rate of 60 mL/min) to afford the desired product. LCMS calculated for C$_{19}$H$_{16}$F$_3$N$_6$ (M+H)$^+$: m/z=385.1; found: 385.2.

Example 217. 1-(3,5-Difluoro-4-(3-(2-(4-methylpiperazin-1-yl)pyrimidin-5-yl)-1H-pyrazolo[3,4-c] pyridin-5-yl)phenyl)-N-methylmethanamine

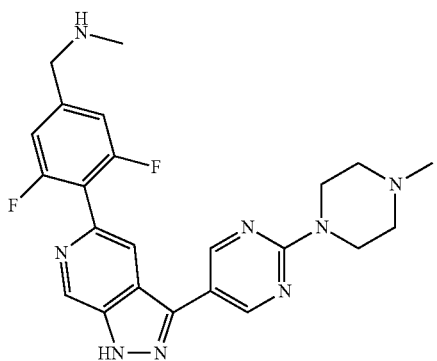 [SMILES: CNCc1cc(F)c(-c2cc3c(-c4cnc(N5CCN(C)CC5)nc4)n[nH]c3cn2)c(F)c1]

This compound was prepared according to the procedure described in Example 161, using 2-(4-methylpiperazin-1-yl)-5-(4,4,5,5-tetramethyl-1,3,2-dioxaborolan-2-yl)pyrimidine instead of 2-(4-(4,4,5,5-tetramethyl-1,3,2-dioxaborolan-2-yl)-1H-pyrazol-1-yl)benzonitrile as the starting material. LCMS calculated for C$_{23}$H$_{25}$F$_2$N$_8$ (M+H)$^+$: m/z=451.2; found: 451.3.

$^1$H NMR (TFA salt, 600 MHz, DMSO-d$_6$) δ 10.18 (br, 1H), 9.21 (d, J=1.1 Hz, 1H), 9.10 (br, 2H), 9.07 (s, 2H), 8.32 (s, 1H), 7.38 (d, J=8.0 Hz, 2H), 4.79 (m, 2H), 4.24 (t, J=4.5 Hz, 2H), 3.54 (m, 2H), 3.34 (m, 2H), 3.10 (m, 2H), 2.85 (s, 3H), 2.62 (t, J=4.5 Hz, 3H).

Example 218. 1-(5-(5-(2,6-Difluoro-4-((methylamino)methyl)phenyl)-1H-pyrazolo[3,4-c]pyridin-3-yl)pyrimidin-2-yl)piperidin-4-ol

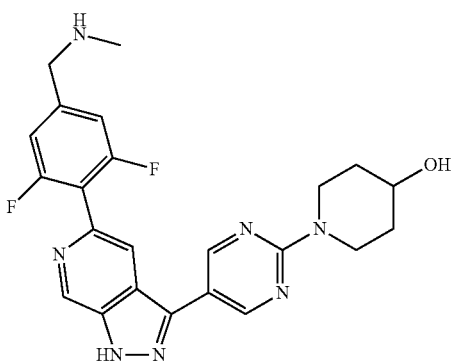 [SMILES: CNCc1cc(F)c(-c2cc3c(-c4cnc(N5CCC(O)CC5)nc4)n[nH]c3cn2)c(F)c1]

This compound was prepared according to the procedure described in Example 161, using 1-(5-(4,4,5,5-tetramethyl-1,3,2-dioxaborolan-2-yl)pyrimidin-2-yl)piperidin-4-ol instead of 2-(4-(4,4,5,5-tetramethyl-1,3,2-dioxaborolan-2-yl)-1H-pyrazol-1-yl)benzonitrile as the starting material. LCMS calculated for C$_{23}$H$_{24}$F$_2$N$_7$O (M+H)$^+$: m/z=452.2; found: 452.2.

Example 219. 1-(3,5-Difluoro-4-(3-(5-(4-methylpiperazin-1-yl)pyridin-3-yl)-1H-pyrazolo[3,4-c]pyridin-5-yl)phenyl)-N-methylmethanamine

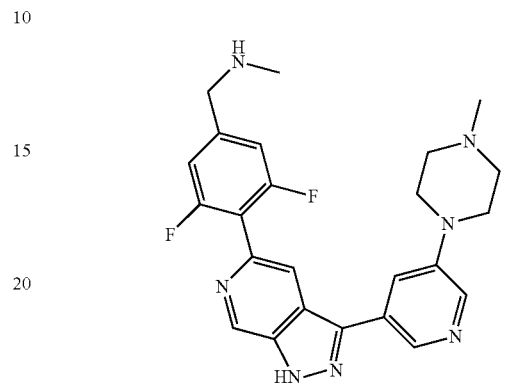

This compound was prepared according to the procedure described in Example 161, using 5-(4-methylpiperazin-1-yl)pyridin-3-ylboronic acid instead of 2-(4-(4,4,5,5-tetramethyl-1,3,2-dioxaborolan-2-yl)-1H-pyrazol-1-yl)benzonitrile as the starting material. LCMS calculated for C$_{24}$H$_{26}$F$_2$N$_7$ (M+H)$^+$: m/z=450.2; found: 450.3.

Example 220. 4-Fluoro-N,6-dimethyl-5-(3-(1-methyl-1H-pyrazol-4-yl)-1H-pyrazolo[3,4-c]pyridin-5-yl)-2,3-dihydro-1H-inden-1-amine

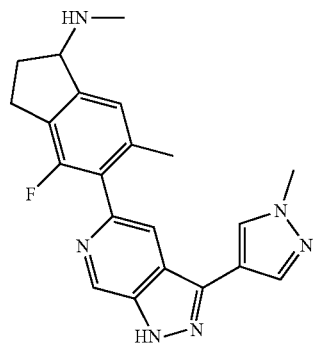 [SMILES: CNC1CCc2c1cc(C)c(-c1cc3c(-c4cnn(C)c4)n[nH]c3cn1)c2F]

Step 1. 5-(Benzyloxy)-4-fluoro-6-iodo-2,3-dihydro-1H-inden-1-one

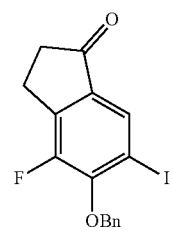 [SMILES: O=C1CCc2c1cc(I)c(OCc1ccccc1)c2F]

To a mixture of 4-fluoro-5-hydroxy-2,3-dihydro-1H-inden-1-one (2.017 g, 12.14 mmol) and NIS (2.742 g, 12.19 mmol) was added DMF (30.0 ml). The mixture was stirred at room temperature for 24 h. Benzyl bromide (2.820 g, 16.49 mmol) was added followed by K$_2$CO$_3$ (5.088 g, 36.8 mmol). The reaction was stirred at 80° C. for 16 h. After cooling to room temperature, the mixture was diluted with Et$_2$O and washed with brine. The organic layer was dried over anhydrous Na$_2$SO$_4$, filtered and concentrated. The residue was purified on silica gel (120 g, 0-100% EtOAc in hexanes) to give the desired product as a yellow solid (2.36 g, 51%). LCMS calculated for C$_{16}$H$_{13}$FIO$_2$ (M+H)$^+$: m/z=383.0; found: 383.0.

Step 2. tert-Butyl 5-(benzyloxy)-4-fluoro-6-iodo-2,3-dihydro-1H-inden-1-yl(methyl)carbamate

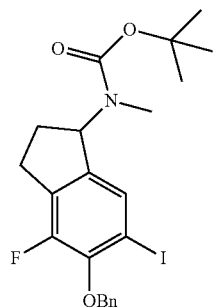 [SMILES: CN(C(=O)OC(C)(C)C)C1CCc2c1cc(I)c(OCc1ccccc1)c2F]

To a solution of 5-(benzyloxy)-4-fluoro-6-iodo-2,3-dihydro-1H-inden-1-one (2.36 g, 6.18 mmol) in 2-propanol (40.0 ml) was added methylamine (2.0 M in methanol) (16.0 ml, 32.0 mmol) followed by titanium(IV) isopropoxide (3.962 g, 13.94 mmol). The mixture was stirred at 35° C. for 16 h, and then cooled to r.t. Sodium borohydride (351.3 mg, 9.29 mmol) was added. After stirring at room temperature for 30 min, the reaction was quenched with HCl (6.0 N in water) (20.0 ml, 120 mmol). The resulting mixture was stirred at 40° C. for 2 h, and cooled to room temperature. The mixture was treated with 4N NaOH until pH reached 10 and extracted with Et$_2$O. The organic layer was dried over anhydrous Na$_2$SO$_4$, filtered and concentrated. The residue was dissolved in CH$_2$Cl$_2$. Boc-anhydride (1.505 g, 6.90 mmol) was added. After stirring at room temperature for 30 min, the reaction mixture was quenched with MeOH and concentrated. The residue was purified on silica gel (120 g, 0-100% EtOAc in hexanes) to give the desired product as a solid (2.60 g, 85%).

Step 3. tert-Butyl 5-(benzyloxy)-4-fluoro-6-methyl-2,3-dihydro-1H-inden-1-yl(methyl)carbamate

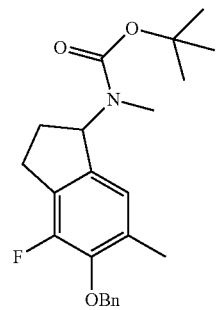 [SMILES: Cc1cc2c(c(F)c1OCc1ccccc1)CCC2N(C)C(=O)OC(C)(C)C]

To a screw-cap vial equipped with a magnetic stir bar was added tert-butyl (5-(benzyloxy)-4-fluoro-6-iodo-2,3-dihydro-1H-inden-1-yl)(methyl)carbamate (1001.4 mg, 2.013 mmol), dicyclohexyl(2',4',6'-triisopropylbiphenyl-2-yl)phosphine-(2'-aminobiphenyl-2-yl)(chloro)palladium (1:1) (XPhos Pd G2, 317.1 mg, 0.403 mmol), and potassium phosphate (1783 mg, 8.40 mmol). The vial was sealed with a Teflon-lined septum, evacuated and backfilled with nitrogen (this process was repeated a total of three times). A solution of 2,4,6-trimethyl-1,3,5,2,4,6-trioxatriborinane (830.6 mg, 6.62 mmol) in 1,4-dioxane (10.0 ml) was added followed by water (2.00 ml). The reaction was stirred at 60° C. for 16 h. After cooling to room temperature, the mixture was diluted with CH$_2$Cl$_2$, and washed with brine. The organic layer was dried over anhydrous Na$_2$SO$_4$, filtered and concentrated. The residue was purified on silica gel (40 g, 0-100% EtOAc in hexanes) to give the desired product. LCMS calculated for C$_{23}$H$_{28}$FNNaO$_3$ (M+Na)$^+$: m/z=408.2; found: 408.2.

Step 4. tert-Butyl 4-fluoro-5-hydroxy-6-methyl-2,3-dihydro-1H-inden-1-yl(methyl)carbamate

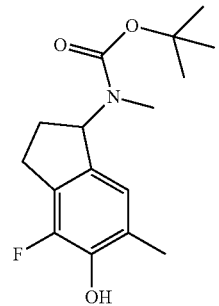

To tert-butyl (5-(benzyloxy)-4-fluoro-6-methyl-2,3-dihydro-1H-inden-1-yl)(methyl)carbamate (776.0 mg, 2.013 mmol) was added MeOH (25.0 mL) followed by THF (5.00 mL). Palladium hydroxide on carbon (20 wt %) (566.2 mg, 0.806 mmol) was added. The mixture was purged with H$_2$ and stirred under H$_2$ atmosphere (1 atm) for 16 h. The mixture was filtered through a pad of Celite. The filtrate was concentrated in vacuo, and the residue was purified on silica gel (40%, 0-100% EtOAc in hexanes) to give the desired product as a yellow foamy solid (234.1 mg, 39%).

Step 5. 1-(tert-Butoxycarbonyl(methyl)amino)-4-fluoro-6-methyl-2,3-dihydro-1H-inden-5-yl trifluoromethanesulfonate

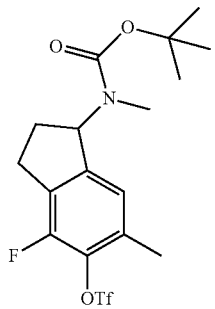 [SMILES: Cc1cc2c(c(F)c1OS(=O)(=O)C(F)(F)F)CCC2N(C)C(=O)OC(C)(C)C]

To a solution of tert-butyl (4-fluoro-5-hydroxy-6-methyl-2,3-dihydro-1H-inden-1-yl)(methyl)carbamate (234.1 mg, 0.793 mmol) in $CH_2Cl_2$ (5.0 ml) at 0° C. was added pyridine (1001.7 mg, 12.66 mmol). A solution of trifluoromethanesulfonic anhydride (671.2 mg, 2.379 mmol) in $CH_2Cl_2$ (5.0 mL) was added slowly. The reaction mixture was allowed to warm to room temperature and stirred for 6 h. The reaction mixture was quenched with 2 M $K_2CO_3$ (aq) and extracted with $CH_2Cl_2$. The organic layer was dried over anhydrous $Na_2SO_4$, filtered and concentrated. The residue was purified on silica gel (40 g, 0-100% EtOAc in hexanes) to give the desired product (284.9 mg, 84%). LCMS calculated for $C_{13}H_{14}F_4NO_5S$ $(M+H-C_4H_8)^+$: m/z=372.1; found: 372.1.

Step 6. tert-Butyl 4-fluoro-6-methyl-5-(4,4,5,5-tetramethyl-1,3,2-dioxaborolan-2-yl)-2,3-dihydro-1H-inden-1-yl(methyl)carbamate

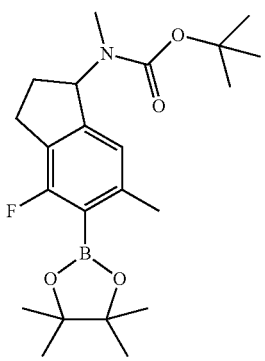 [SMILES: Cc1cc2c(c(F)c1B1OC(C)(C)C(C)(C)O1)CCC2N(C)C(=O)OC(C)(C)C]

To a screw-cap vial equipped with a magnetic stir bar was added 4,4,4',4',5,5,5',5'-octamethyl-2,2'-bi(1,3,2-dioxaborolane) (231.6 mg, 0.912 mmol), potassium acetate (227.4 mg, 2.317 mmol) and [1,1'-bis(diphenylphosphino)ferrocene]dichloropalladium(II), complexed with dichloromethane (1:1) (109.8 mg, 0.134 mmol). The vial was sealed with a Teflon-lined septum, evacuated and backfilled with nitrogen (this process was repeated a total of three times). A solution of 1-((tert-butoxycarbonyl)(methyl)amino)-4-fluoro-6-methyl-2,3-dihydro-1H-inden-5-yl trifluoromethanesulfonate (284.9 mg, 0.667 mmol) in 1,4-dioxane (5.0 mL) was added via syringe. The mixture was stirred at 100° C. for 16 h. After cooling to room temperature, the mixture was filtered. The filtrate was used directly in the next step.

Step 7. 4-Fluoro-N,6-dimethyl-5-(3-(1-methyl-1H-pyrazol-4-yl)-1H-pyrazolo[3,4-c]pyridin-5-yl)-2,3-dihydro-1H-inden-1-amine This compound was prepared according to the procedure described in Example 198, using tert-butyl 4-fluoro-6-methyl-5-(4,4,5,5-tetramethyl-1,3,2-dioxaborolan-2-yl)-2,3-dihydro-1H-inden-1-yl(methyl)carbamate instead of tert-butyl 4,6-difluoro-5-(4,4,5,5-tetramethyl-1,3,2-dioxaborolan-2-yl)-2,3-dihydro-1H-inden-1-yl(methyl)carbamate as the starting material. LCMS calculated for $C_{21}H_{22}FN_6$ $(M+H)^+$: m/z=377.2; found: 377.2. $^1$H NMR (TFA salt, 600 MHz, DMSO-$d_6$) δ 9.13 (d, J=1.0 Hz, 1H), 9.05-8.87 (m, 2H), 8.47 (s, 1H), 8.03 (s, 1H), 8.03 (d, J=0.6 Hz, 1H), 7.38 (s, 1H), 4.80 (m, 1H), 3.90 (s, 3H), 3.10 (m, 1H), 2.99-2.89 (m, 1H), 2.65 (t, J=5.4 Hz, 3H), 2.57-2.50 (m, 1H), 2.24 (m, 1H), 2.14 (s, 3H).

Example 221. 5-(3-((3,3-Dimethylazetidin-1-yl)methyl)-6-fluoro-2-methylphenyl)-3-(1-methyl-1H-pyrazol-4-yl)-1H-pyrazolo[3,4-c]pyridine

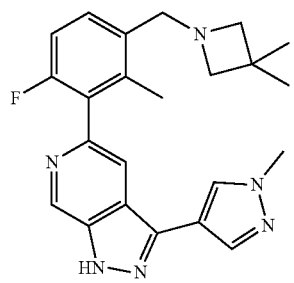 [SMILES: Cc1c(CN2CC(C)(C)C2)ccc(F)c1-c1cc2c(-c3cnn(C)c3)n[nH]c2cn1]

This compound was prepared according to the procedures described in Example 86 and 92, using 3,3-dimethylazetidine instead of methanamine as starting material. LCMS calculated for $C_{23}H_{26}FN_6$ $(M+H)^+$: m/z=405.2; Found: 405.3.
1H NMR (500 MHz, DMSO-$d_6$) δ 9.21 (s, 1H), 8.49 (s, 1H), 8.11 (s, 1H), 8.08-8.03 (m, 1H), 7.60 (dd, J=8.6, 5.7 Hz, 1H), 7.29 (t, J=8.7 Hz, 1H), 4.52 (d, J=5.7 Hz, 2H), 4.09-3.94 (m, 4H), 3.92 (s, 3H), 2.14 (s, 3H), 1.35 (s, 3H), 1.30 (s, 3H) ppm.

Example 222. trans-N-(4-Fluoro-2-methyl-3-(3-(1-methyl-1H-pyrazol-4-yl)-1H-pyrazolo[3,4-c]pyridin-5-yl)benzyl)-3-methoxycyclobutanamine

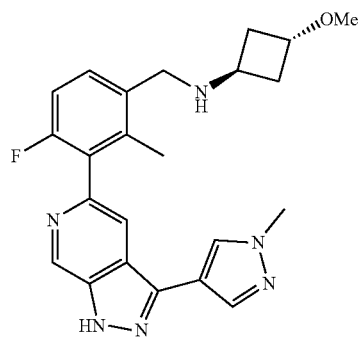 [SMILES: CO[C@H]1C[C@H](NCc2ccc(F)c(-c3cc4c(-c5cnn(C)c5)n[nH]c4cn3)c2C)C1]

This compound was prepared according to the procedures described in Example 86 and 92, using trans-3-methoxycyclobutanamine instead of methanamine as starting material. LCMS calculated for $C_{23}H_{26}FN_6O$ (M+H)$^+$: m/z=421.2; Found: 421.2.

Example 223. N-(4-Fluoro-2-methyl-3-(3-(1-methyl-1H-pyrazol-4-yl)-1H-pyrazolo[3,4-c]pyridin-5-yl)benzyl)-3,3-dimethylcyclobutanamine

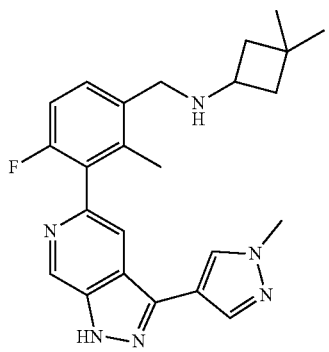 [SMILES: Cc1c(CNC2CC(C)(C)C2)ccc(F)c1-c1cc2c(-c3cnn(C)c3)n[nH]c2cn1]

This compound was prepared according to the procedures described in Example 86 and 92, using 3,3-dimethylcyclobutanamine instead of methanamine as starting material. LCMS calculated for $C_{24}H_{28}FN_6$ (M+H)$^+$: m/z=419.2; Found: 419.2.

Example 224. N-(4-Fluoro-2-methyl-3-(3-(1-methyl-1H-pyrazol-4-yl)-1H-pyrazolo[3,4-c]pyridin-5-yl)benzyl)-1-(1-methylcyclopropyl)methanamine

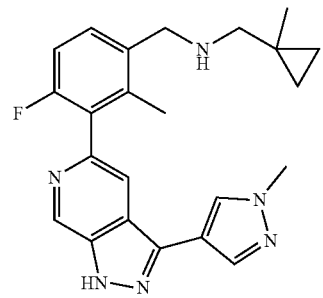 [SMILES: Cc1c(CNCC2(C)CC2)ccc(F)c1-c1cc2c(-c3cnn(C)c3)n[nH]c2cn1]

This compound was prepared according to the procedures described in Example 86 and 92, using (1-methylcyclopropyl)methanamine instead of methanamine as starting material. LCMS calculated for $C_{23}H_{26}FN_6$ (M+H)$^+$: m/z=405.2; Found: 405.2.

Example 225. 1-(4-Fluoro-3-(3-(1-methyl-1H-pyrazol-4-yl)-1H-pyrazolo[3,4-c]pyridin-5-yl)-2-(trifluoromethyl)phenyl)-N-methylmethanamine

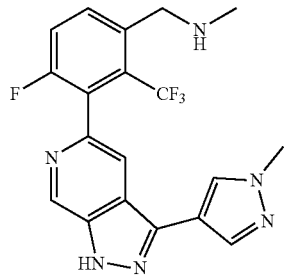 [SMILES: CNCc1ccc(F)c(-c2cc3c(-c4cnn(C)c4)n[nH]c3cn2)c1C(F)(F)F]

This compound was prepared according to the procedures described in Example 131, using 4-fluoro-2-(trifluoromethyl)benzaldehyde instead of 3-fluoro-5-(trifluoromethyl)benzaldehyde as starting material. LCMS calculated for $C_{19}H_{17}F_4N_6$ (M+H)$^+$: m/z=405.2; Found: 405.2.

1H NMR (500 MHz, DMSO-d$_6$) δ 9.14 (br, 1H), 9.10 (s, 1H), 8.46 (s, 1H), 8.14 (s, 1H), 8.04 (s, 1H), 7.97-7.82 (m, 2H), 4.39 (br, 2H), 3.91 (s, 3H), 2.73 (s, 3H) ppm.

Example 226 and 227. 5-(2-Fluoro-4-(pyrrolidin-2-yl)-6-(trifluoromethyl)phenyl)-3-(1-methyl-1H-pyrazol-4-yl)-1H-pyrazolo[3,4-c]pyridine

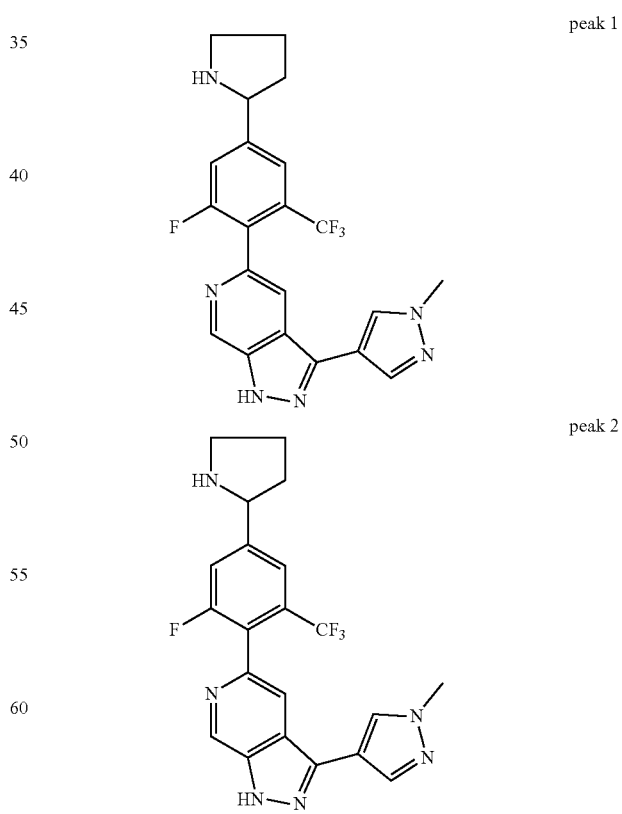

This compound was prepared according to the procedures described in Example 171, using 1-bromo-3-fluoro-5-(trifluoromethyl)benzene instead of 2-bromo-1-fluoro-5-iodo-3-methylbenzene as starting material. Peak 1: LCMS calculated for $C_{21}H_{19}F_4N_6$ (M+H)$^+$: m/z=431.2; Found: 431.2. $^1$H NMR (TFA salt, 500 MHz, (CD$_3$)$_2$SO) δ 13.70 (br s, 1H), 9.52 (br s, 1H), 9.11 (d, J=1.3 Hz, 1H), 8.95 (br s, 1H), 8.45 (s, 1H), 8.16 (d, J=1.3 Hz, 1H), 8.04 (d, J=0.8 Hz, 1H), 7.92-7.86 (m, 2H), 4.79 (m, 1H), 3.91 (s, 3H), 3.48 (m, 1H), 3.38 (m, 1H), 2.23-2.03 (m, 4H). Peak 2: LCMS calculated for $C_{21}H_{19}F_4N_6$ (M+H)$^+$: m/z=431.2; Found: 431.2.

Example 228 and 229. 1-(4-(3-(1-Cyclopropyl-1H-pyrazol-4-yl)-1H-pyrazolo[3,4-c]pyridin-5-yl)-3-fluoro-5-methylphenyl)-N-methylethanamine peak 1

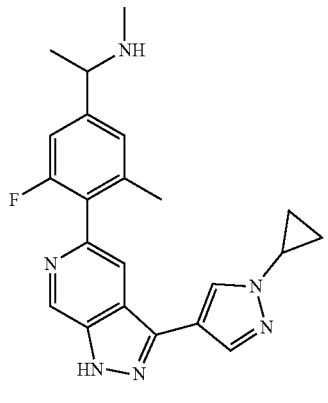

peak 2

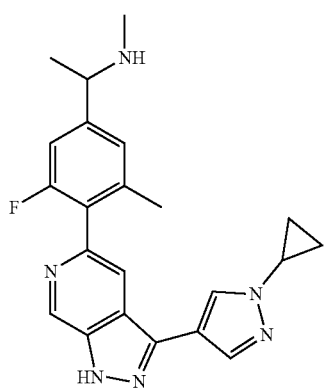

This compound was prepared according to the procedures described in Example 189, using 1-cyclopropyl-4-(4,4,5,5-tetramethyl-1,3,2-dioxaborolan-2-yl)-1H-pyrazole instead of 1-methyl-4-(4,4,5,5-tetramethyl-1,3,2-dioxaborolan-2-yl)-1H-pyrazole as starting material. Peak 1: LCMS calculated for $C_{22}H_{24}FN_6$ (M+H)$^+$: m/z=391.2; Found: 391.2. Peak 2: LCMS calculated for $C_{22}H_{24}FN_6$ (M+H)$^+$: m/z=391.2; Found: 391.2.

Example 230 and 231. 3-(1-Ethyl-1H-pyrazol-4-yl)-5-(2-fluoro-6-methyl-4-(piperidin-2-yl)phenyl)-1H-pyrazolo[3,4-c]pyridine peak 1

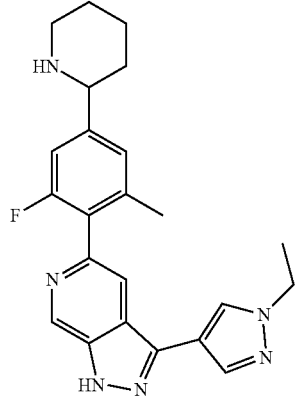

peak 2

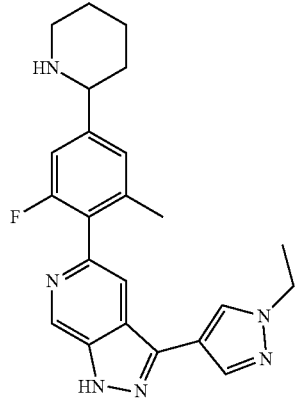

This compound was prepared according to the procedures described in Example 174, using 1-ethyl-4-(4,4,5,5-tetramethyl-1,3,2-dioxaborolan-2-yl)-1H-pyrazole instead of 1-methyl-4-(4,4,5,5-tetramethyl-1,3,2-dioxaborolan-2-yl)-1H-pyrazole as starting material. Peak 1: LCMS calculated for $C_{23}H_{26}FN_6$ (M+H)$^+$: m/z=405.2; Found: 405.2. Peak 2: LCMS calculated for $C_{23}H_{26}FN_6$ (M+H)$^+$: m/z=405.2; Found: 405.2.

Example 232 and 233. 3-(1-Cyclopropyl-1H-pyrazol-4-yl)-5-(2-fluoro-6-methyl-4-(piperidin-2-yl)phenyl)-1H-pyrazolo[3,4-c]pyridine peak 1

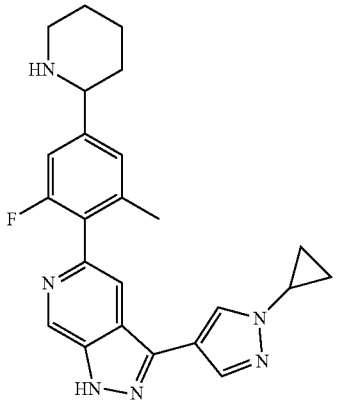

-continued

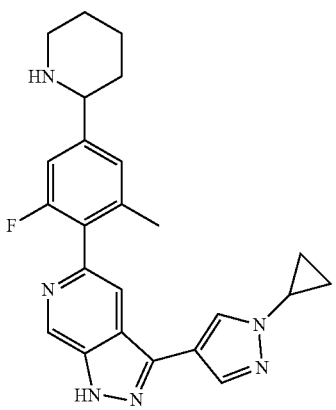

peak 2

This compound was prepared according to the procedures described in Example 174, using 1-cyclopropyl-4-(4,4,5,5-tetramethyl-1,3,2-dioxaborolan-2-yl)-1H-pyrazole instead of 1-methyl-4-(4,4,5,5-tetramethyl-1,3,2-dioxaborolan-2-yl)-1H-pyrazole as starting material. Peak 1: LCMS calculated for $C_{24}H_{26}FN_6$ (M+H)$^+$: m/z=417.2; Found: 417.2. Peak 2: LCMS calculated for $C_{24}H_{26}FN_6$ (M+H)$^+$: m/z=417.2; Found: 417.2.

Example 234. 3-(3-Fluoro-5-methyl-4-(3-(1-methyl-1H-pyrazol-4-yl)-1H-pyrazolo[3,4-c]pyridin-5-yl)phenyl)morpholine

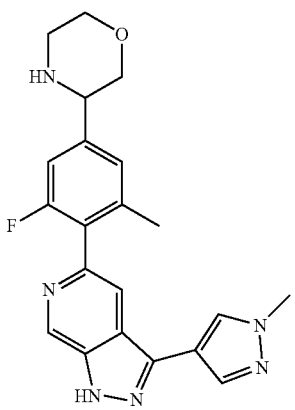 [SMILES: Cc1cc(C2COCCN2)cc(F)c1-c1cc2c(-c3cnn(C)c3)n[nH]c2cn1]

A solution of 3-fluoro-5-methyl-4-(3-(1-methyl-1H-pyrazol-4-yl)-1-((2-(trimethylsilyl)ethoxy)methyl)-1H-pyrazolo[3,4-c]pyridin-5-yl)benzaldehyde (40 mg, 0.086 mmol, Example 176, Step 2) and SnAP M reagent (31.3 mg, 0.086 mmol) in toluene (1 mL) was refluxed at 120° C. for 1 h. The mixture was concentrated under reduced pressure to afford the imine intermediate. Separately, a solution of Cu(OTf)$_2$ (31.1 mg, 0.086 mmol) in HFIP (0.7 mL) was treated with 2,6-lutidine (10.01 0.086 mmol) at RT. After stirring for 1 h, a solution of the imine intermediate in DCM (1 mL) was added and the resulting mixture was stirred at RT for 16 h. The, mixture was treated with NH$_4$OH (aq) and extracted with ethyl acetate. The combined organic phases were concentrated under reduced pressure to give the crude product. The crude product was dissolved in DCM (2.0 mL), and TFA (2.0 mL) was added dropwise at room temperature. After stirring for 2 h, the mixture was concentrated in vacuo. The crude mixture was dissolved in MeOH (3.5 mL) and 10% aqueous NH$_4$OH (1.5 mL) and purified with prep-LCMS (XBridge C18 column, eluting with a gradient of acetonitrile/water containing 0.1% TFA, at flow rate of 60 mL/min) to give the desired product. LCMS calculated for $C_{21}H_{22}FN_6O$ (M+H)$^+$: m/z=393.2; Found: 393.2.

Example 235. 1-(3-(Difluoromethyl)-5-fluoro-4-(3-(1-methyl-1H-pyrazol-4-yl)-1H-pyrazolo[3,4-c]pyridin-5-yl)phenyl)-N-methylmethanamine

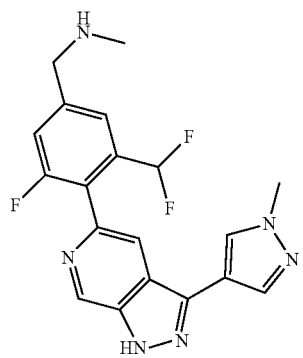 [SMILES: CNCc1cc(F)c(-c2cc3c(-c4cnn(C)c4)n[nH]c3cn2)c(C(F)F)c1]

Step 1. tert-Butyl 3-(difluoromethyl)-5-fluorobenzyl(methyl)carbamate

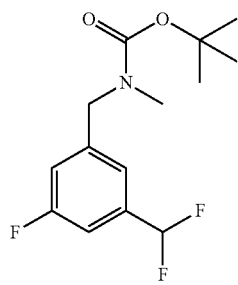 [SMILES: CN(Cc1cc(F)cc(C(F)F)c1)C(=O)OC(C)(C)C]

This compound was prepared according to the procedures described in Example 113 (Steps 3-6), using 1-bromo-3-(difluoromethyl)-5-fluorobenzene instead of 2-bromo-1-fluoro-5-iodo-3-methylbenzene as starting material. LCMS calculated for $C_{10}H_{11}F_3NO_2$ (M+H—$C_4H_8$)$^+$ m/z=234.2; found 234.1.

Step 2. tert-Butyl 3-(difluoromethyl)-5-fluoro-4-(4,4,5,5-tetramethyl-1,3,2-dioxaborolan-2-yl)benzyl (methyl)carbamate

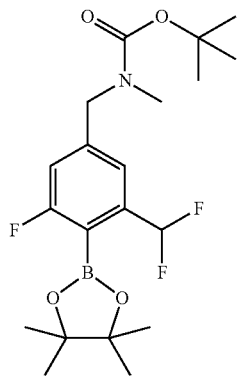

To a solution of tert-butyl (3-(difluoromethyl)-5-fluorobenzyl)(methyl)carbamate (256.5 mg, 0.887 mmol) in THF (8.0 ml) at −78° C. was added LDA (2.0 M in THF) (600.0 μl, 1.200 mmol) dropwise. The mixture was stirred at −78° C. for 30 min. A solution of 2-isopropoxy-4,4,5,5-tetramethyl-1,3,2-dioxaborolane (336.0 mg, 1.806 mmol) in THF (5.0 ml) was added dropwise. The reaction was stirred at −78° C. for 15 min and then allowed to warm to room temperature. After stirring at room temperature for 20 min, the reaction was treated with sat. NaHCO$_3$ (aq) and extracted with CH$_2$Cl$_2$. The combined organic phases were dried over anhydrous Na$_2$SO$_4$, filtered and concentrated. The residue was purified on silica gel (20 g, 0-100% EtOAc in hexanes) to give the desired product (62.6 mg, 17%). LCMS calculated for C$_{16}$H$_{22}$BF$_3$NO$_4$ (M+H—C4H$_8$)$^+$ m/z=360.2; found 360.2.

Step 3. 1-(3-(Difluoromethyl)-5-fluoro-4-(3-(1-methyl-1H-pyrazol-4-yl)-1H-pyrazolo[3,4-c]pyridin-5-yl)phenyl)-N-methylmethanamine A vial was charged with tert-butyl 5-chloro-3-(1-methyl-1H-pyrazol-4-yl)-1H-pyrazolo[3,4-c]pyridine-1-carboxylate (50.5 mg, 0.151 mmol, Intermediate 1) chloro(2-dicyclohexylphosphino-2',4',6'-triisopropyl-1,1'-biphenyl)[2-(2'-amino-1,1'-biphenyl)]palladium(II) (XPhos Pd G2, 11.9 mg, 0.015 mmol) and cesium carbonate (156.2 mg, 0.479 mmol). The vial was sealed, evacuated and backfilled with nitrogen (this process was repeated a total of three times). A solution of tert-butyl (3-(difluoromethyl)-5-fluoro-4-(4,4,5,5-tetramethyl-1,3,2-dioxaborolan-2-yl)benzyl)(methyl)carbamate (62.6 mg, 0.151 mmol) in 1,4-dioxane (3.0 ml) was added via syringe, followed by water (300.0 μl). The reaction mixture was heated to 50° C. for 16 h. The reaction mixture cooled and concentrated. The residue was dissolved in CH$_2$Cl$_2$ (5.0 mL) and treated with TFA (5.0 mL). The reaction mixture was stirred at room temperature for 15 min, and then concentrated. The crude reaction residue was purified using prep-LCMS (XBridge C18 column, eluting with a gradient of acetonitrile/water containing 0.1% TFA, at flow rate of 60 mL/min) to afford the desired product. LCMS calculated for C$_{19}$H$_{18}$F$_3$N$_6$ (M+H)$^+$: m/z=387.2; found: 387.1. $^1$H NMR (TFA salt, 500 MHz, DMSO) δ 13.72 (br, 1H), 9.14 (d, J=1.2 Hz, 1H), 8.96 (br, 2H), 8.46 (s, 1H), 8.22 (s, 1H), 8.04 (d, J=0.6 Hz, 1H), 7.79 (s, 1H), 7.68 (d, J=10.2 Hz, 1H), 7.01 (t, J=54.7 Hz, 1H), 4.31 (t, J=5.8 Hz, 2H), 3.91 (s, 3H), 2.63 (t, J=5.2 Hz, 3H).

Example 236. N-(4-Fluoro-2-methyl-3-(3-(1-methyl-1H-pyrazol-4-yl)-1H-pyrazolo[3,4-c]pyridin-5-yl)benzyl)ethanamine

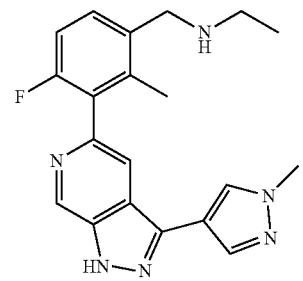 [SMILES: CCNCc1ccc(F)c(-c2cc3c(-c4cnn(C)c4)n[nH]c3cn2)c1C]

This compound was prepared according to the procedures described in Example 86 and 92, using ethanamine instead of methanamine as starting material. LCMS calculated for C$_{20}$H$_{22}$FN$_6$ (M+H)$^+$: m/z=365.2; Found: 365.2.

Example 237. N-(3-(3-(1-Methyl-1H-pyrazol-4-yl)-1H-pyrazolo[3,4-c]pyridin-5-yl)-2-(trifluoromethyl)benzyl)ethanamine

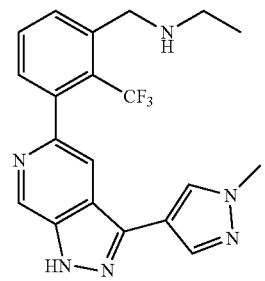 [SMILES: CCNCc1cccc(-c2cc3c(-c4cnn(C)c4)n[nH]c3cn2)c1C(F)(F)F]

This compound was prepared according to the procedures described in Example 86 and 88, using ethanamine instead of methanamine as starting material. LCMS calculated for C$_{20}$H$_{20}$F$_3$N$_6$ (M+H)$^+$: m/z=401.2; Found: 401.2.

Example 238. 4-Fluoro-N,6-dimethyl-5-(3-(1-methyl-1H-pyrazol-4-yl)-1H-pyrazolo[3,4-c]pyridin-5-yl)-2,3-dihydro-1H-inden-1-amine (Peak1)

Peak 1

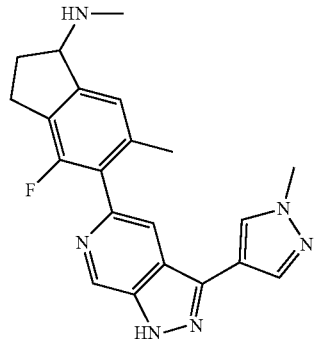

Two enantiomers of the Example 220 were separated with chiral prep-HPLC (Phenomenex Lux Cellulose-4, 21, 1×250 mm, 5 micron, eluting with 45% EtOH in hexanes, at flow rate of 18 mL/min, $t_{R, peak\ 1}$=9.5 min, $t_{R, peak\ 2}$=12.8 min). Peak 1: LCMS calculated for $C_{21}H_{22}FN_6$ (M+H)$^+$: m/z=377.2; found: 377.2.

Example 239. 4-Fluoro-N,6-dimethyl-5-(3-(1-methyl-1H-pyrazol-4-yl)-1H-pyrazolo[3,4-c]pyridin-5-yl)-2,3-dihydro-1H-inden-1-amine (Peak2)

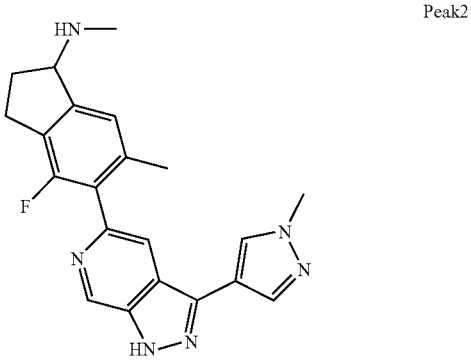 [SMILES: CNC1CCc2c1cc(C)c(-c1cc3c(-c4cnn(C)c4)n[nH]c3cn1)c2F]

The two enantiomers of example 220 were separated with chiral prep-HPLC (Phenomenex Lux Cellulose-4, 21, 1×250 mm, 5 micron, eluting with 45% EtOH in hexanes, at flow rate of 18 mL/min, $t_{R, peak\ 1}$=9.5 min, $t_{R, peak\ 2}$=12.8 min). Peak 2: LCMS calculated for $C_{21}H_{22}FN_6$ (M+H)$^+$: m/z=377.2; found: 377.2.

Example 240. 6-Fluoro-N-methyl-5-(3-(6-(4-methylpiperazin-1-yl)pyridin-3-yl)-1H-pyrazolo[3,4-c]pyridin-5-yl)-1,2,3,4-tetrahydronaphthalen-1-amine

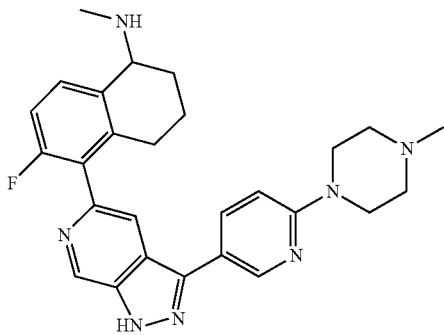 [SMILES: CNC1CCCc2c1ccc(F)c2-c1cc2c(-c3ccc(N4CCN(C)CC4)nc3)n[nH]c2cn1]

Step 1. tert-Butyl 5-bromo-6-fluoro-1,2,3,4-tetrahydronaphthalen-1-yl(methyl)carbamate

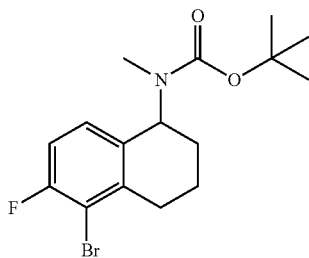 [SMILES: CN(C(=O)OC(C)(C)C)C1CCCc2c1ccc(F)c2Br]

To a solution of 5-bromo-6-fluoro-3,4-dihydronaphthalen-1(2H)-one (Ark Pharm, 312.6 mg, 1.286 mmol) in 2-propanol (10.0 ml) was added methylamine (2.0 M in methanol) (2.50 ml, 5.00 mmol) followed by titanium(IV) isopropoxide (596.0 mg, 2.097 mmol). The mixture was stirred at 35° C. for 16 h before it was cooled to room temperature. Sodium borohydride (53.4 mg, 1.412 mmol) was added. The reaction was stirred at room temperature for 1 h, and was quenched with HCl (1.0 N in water) (30.0 ml, 30 mmol). The mixture was stirred at room temperature for 2 h, and was treated with NaOH (4.0 N in water) until pH reached 10. The mixture was extracted with $Et_2O$. The organic layer was dried over anhydrous $Na_2SO_4$, filtered and concentrated. The residue was dissolved in $CH_2Cl_2$ (10 ml), and treated with boc-anhydride (426.4 mg, 1.954 mmol). After stirring at room temperature for 30 min, the reaction was concentrated. The residue was purified on silica gel (40 g, 0-100% EtOAc in hexanes) to give the desired product (461.0 mg, 89%). LCMS calculated for $C_{12}H_{14}BrFNO_2$ (M+H—$C_4H_8$)$^+$: m/z=302.0; found: 302.1.

Step 2. tert-Butyl 6-fluoro-5-(4,4,5,5-tetramethyl-1,3,2-dioxaborolan-2-yl)-1,2,3,4-tetrahydronaphthalen-1-yl(methyl)carbamate

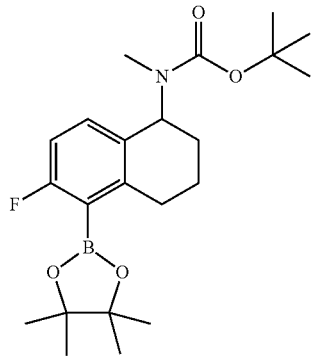 [SMILES: CN(C(=O)OC(C)(C)C)C1CCCc2c1ccc(F)c2B1OC(C)(C)C(C)(C)O1]

To a screw-cap vial equipped with a magnetic stir bar was added 4,4,5,5,4',4',5',5'-octamethyl-[2,2']bi[[1,3,2]dioxaborolanyl] (517.4 mg, 2.037 mmol), potassium acetate (416.8 mg, 4.25 mmol) and [1,1'-bis(diphenylphosphino)ferrocene]dichloropalladium(II), complexed with dichloromethane (1:1) (210.2 mg, 0.257 mmol). The vial was sealed with a Teflon-lined septum, evacuated and backfilled with nitrogen (this process was repeated a total of three times). A solution of tert-butyl (5-bromo-6-fluoro-1,2,3,4-tetrahydronaphthalen-1-yl)(methyl)carbamate (461.0 mg, 1.287 mmol) in 1,4-dioxane (6.0 ml) was added via syringe. The mixture was heated at 100° C. for 16 h. After cooling to room temperature, the reaction mixture was diluted with $CH_2Cl_2$ and filtered. The filtrate was concentrated. The residue was purified on silica gel (40 g, 0-100% EtOAc in hexanes) to give the desired product (337.4 mg, 65%). LCMS calculated for $C_{22}H_{33}BFNNaO_4$(M+Na)$^+$ m/z=428.2; found 428.2.

Step 3. 6-Fluoro-N-methyl-5-(3-(6-(4-methylpiperazin-1-yl)pyridin-3-yl)-1H-pyrazolo[3,4-c]pyridin-5-yl)-1,2,3,4-tetrahydronaphthalen-1-amine To a screw-cap vial equipped with a magnetic stir bar was added tert-butyl 5-chloro-3-(6-(4-methylpiperazin-1-yl)

pyridin-3-yl)-1H-pyrazolo[3,4-c]pyridine-1-carboxylate (34.0 mg, 0.079 mmol), chloro(2-dicyclohexylphosphino-2',4',6'-triisopropyl-1,1'-biphenyl)[2-(2'-amino-1,1'-biphenyl)]palladium(II) (XPhos Pd G2, 8.0 mg, 10.17 μmol) and cesium carbonate (81.4 mg, 0.250 mmol). The vial was sealed with a Teflon-lined septum, evacuated and backfilled with nitrogen (this process was repeated a total of three times). A solution of tert-butyl (6-fluoro-5-(4,4,5,5-tetramethyl-1,3,2-dioxaborolan-2-yl)-1,2,3,4-tetrahydronaphthalen-1-yl)(methyl)carbamate (28.1 mg, 0.069 mmol) in 1,4-dioxane (2.0 ml) was added via syringe, followed by water (200.0 μl). The reaction was heated to 50° C. for 16 h. The reaction was concentrated. To the residue was added CH$_2$Cl$_2$ (2.0 mL) followed by TFA (2.0 mL). The mixture was stirred at room temperature for 15 mins, and then concentrated. The residue was purified using prep-LCMS (XBridge C18 column, eluting with a gradient of acetonitrile/water containing 0.1% TFA, at flow rate of 60 mL/min) to afford the desired product. LCMS calculated C$_{27}$H$_{31}$FN$_7$ (M+H)$^+$: m/z=472.3; found: 472.3.

Example 241. 6-Fluoro-5-(3-(4-(4-methylpiperazin-1-yl)phenyl)-1H-pyrazolo[3,4-c]pyridin-5-yl)-1,2,3,4-tetrahydronaphthalen-1-amine

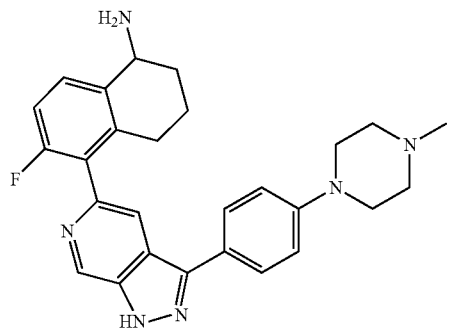 [SMILES: CN1CCN(c2ccc(-c3n[nH]c4cnc(-c5c(F)ccc6c5CCCC6N)cc34)cc2)CC1]

Step 1. tert-Butyl 5-bromo-6-fluoro-1,2,3,4-tetrahydronaphthalen-1-ylcarbamate

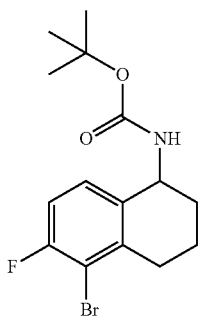 [SMILES: CC(C)(C)OC(=O)NC1CCCc2c1ccc(F)c2Br]

To a mixture of 5-bromo-6-fluoro-3,4-dihydronaphthalen-1(2H)-one (Ark Pharm, 309.5 mg, 1.273 mmol), sodium cyanoborohydride (824.0 mg, 13.11 mmol) and ammonium acetate (2.184 g, 28.3 mmol) was added 2-propanol (10.0 ml). The reaction was stirred at 70° C. for 16 h. After cooling to room temperature, the mixture was diluted with 2 M K$_2$CO$_3$ (aq) and extracted with Et$_2$O. The organic layer was dried over anhydrous Na$_2$SO$_4$, filtered and concentrated. The residue was dissolved in CH$_2$Cl$_2$ (20 ml), and was treated with Boc-anhydride (425.9 mg, 1.951 mmol). After stirring at room temperature for 30 min, the reaction was concentrated. The residue was purified on silica gel (40 g, 0-100% EtOAc in hexanes) to give the desired product as a white solid (316.3 mg, 72%). LCMS calculated for C$_{11}$H$_{12}$BrFNO$_2$ (M+H—C$_4$H$_8$)$^+$: m/z=288.0; found: 288.0.

Step 2. tert-Butyl 6-fluoro-5-(4,4,5,5-tetramethyl-1,3,2-dioxaborolan-2-yl)-1,2,3,4-tetrahydronaphthalen-1-ylcarbamate

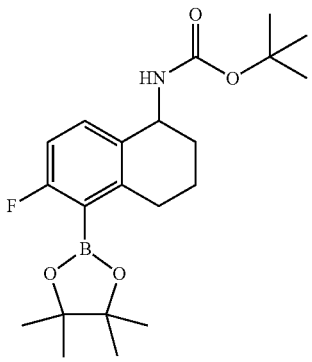 [SMILES: CC(C)(C)OC(=O)NC1CCCc2c1ccc(F)c2B1OC(C)(C)C(C)(C)O1]

To a screw-cap vial equipped with a magnetic stir bar was added 4,4,5,5,4',4',5',5'-octamethyl-[2,2']bi[[1,3,2]dioxaborolanyl] (319.0 mg, 1.256 mmol), potassium acetate (272.1 mg, 2.77 mmol) and [1,1'-bis(diphenylphosphino)ferrocene]dichloropalladium(II) complexed with dichloromethane (1:1) (150.1 mg, 0.184 mmol). The vial was sealed with a Teflon-lined septum, evacuated and backfilled with nitrogen (this process was repeated a total of three times). A solution of tert-butyl (5-bromo-6-fluoro-1,2,3,4-tetrahydronaphthalen-1-yl)carbamate (316.3 mg, 0.919 mmol) in 1,4-dioxane (6.0 ml) was added via syringe. The mixture was heated at 100° C. for 16 h. After cooling to room temperature, the reaction mixture was diluted with CH$_2$Cl$_2$ and filtered. The filtrate was concentrated. The residue was purified on silica gel (40 g, 0-100% EtOAc in hexanes) to give the desired product (200.0 mg, 56%). LCMS calculated for C$_{17}$H$_{24}$BFNO$_4$ (M+H—C$_4$H$_8$)$^+$: m/z=336.2; found: 336.3.

Step 3. 6-Fluoro-5-(3-(4-(4-methylpiperazin-1-yl)phenyl)-1H-pyrazolo[3,4-c]pyridin-5-yl)-1,2,3,4-tetrahydronaphthalen-1-amine To a screw-cap vial equipped with a magnetic stir bar was added tert-butyl 5-chloro-3-(4-(4-methylpiperazin-1-yl)phenyl)-1H-pyrazolo[3,4-c]pyridine-1-carboxylate (30.0 mg, 0.070 mmol), chloro(2-dicyclohexylphosphino-2',4',6'-triisopropyl-1,1'-biphenyl)[2-(2'-amino-1,1'-biphenyl)]palladium(H) (XPhos Pd G2, 8.0 mg, 10.17 μmol) and cesium carbonate (72.8 mg, 0.223 mmol). The vial was sealed with a Teflon-lined septum, evacuated and backfilled with nitrogen (this process was repeated a total of three times). A solution of tert-butyl (6-fluoro-5-(4,4,5,5-tetramethyl-1,3,2-dioxaborolan-2-yl)-1,2,3,4-tetrahydronaphthalen-1-yl)carbamate (25.0 mg, 0.064 mmol) in 1,4-dioxane (2.00 ml) was added via syringe, followed by water (200.0 μl). The reaction was heated to 50° C. for 16 h. The reaction was concentrated. To the residue was added CH$_2$Cl$_2$ (2.0 mL) followed by TFA (2.0 mL). The mixture was stirred at room temperature for 15 min, and then concentrated. The residue was purified using prep-LCMS (XBridge C18 column, eluting with a gradient of acetonitrile/water containing 0.1% TFA, at flow rate of 60 mL/min) to afford the desired product. LCMS calculated for $C_{27}H_{30}FN_6$ (M+H)$^+$: m/z=457.3; found: 457.3.

Example A

HPK1 Kinase Binding Assay

A stock solution of 1 mM test compound was prepared in DMSO. The compound plate was prepared by 3-fold and 11-point serial dilutions. 0.1 μL of the compound in DMSO was transferred from the compound plate to the white 384 well polystyrene plates. The assay buffer contained 50 mM HEPES, pH 7.5, 0.01% Tween-20, 5 mM $MgCl_2$, 0.01% BSA, and 5 mM DTT. 5 μl of 4 nM active HPK1 (SignalChem M23-11G) prepared in the buffer was added to the plate. The enzyme concentration given was based on the given stock concentration reported by the vender. 5 μl of 18 nM tracer 222 (ThermoFisher PV6121) and 4 nM LanthaScreen Eu-Anti GST antibody (ThermoFisher PV5595) were added. After one hour incubation at 25° C., the plates were read on a PHERAstar FS plate reader (BMG Labtech). Ki values were determined.

Compounds of the present disclosure, as exemplified in Examples, showed the Ki values in the following ranges: +=Ki≤100 nM; ++=100 nM<Ki≤500 nM; +++=500 nM<Ki≤2000 nM.

TABLE 1

| Example | HPK1 Ki, nM |
|---|---|
| 1 | + |
| 2 | + |
| 3 | + |
| 4 | + |
| 5 | + |
| 6 | + |
| 7 | + |
| 8 | + |
| 9 | + |
| 10 | + |
| 11 | + |
| 12 | + |
| 13 | + |
| 14 | + |
| 15 | + |
| 16 | + |
| 17 | + |
| 18 | + |
| 19 | + |
| 20 | + |
| 21 | + |
| 22 | + |
| 23 | + |
| 24 | + |
| 25 | + |
| 26 | + |
| 27 | + |
| 28 | + |
| 29 | + |
| 30 | + |
| 31 | + |
| 32 | + |
| 33 | + |
| 34 | + |
| 35 | + |
| 36 | + |
| 37 | + |
| 38 | + |
| 39 | + |

TABLE 1-continued

| Example | HPK1 Ki, nM |
|---|---|
| 40 | + |
| 41 | +++ |
| 42 | + |
| 43 | + |
| 44 | + |
| 45 | + |
| 46 | + |
| 47 | + |
| 48 | + |
| 49 | + |
| 50 | + |
| 51 | + |
| 52 | + |
| 53 | + |
| 54 | + |
| 55 | + |
| 56 | + |
| 57 | + |
| 58 | + |
| 59 | + |
| 60 | + |
| 61 | + |
| 62 | + |
| 63 | + |
| 64 | + |
| 65 | + |
| 66 | + |
| 67 | + |
| 68 | + |
| 69 | + |
| 70 | + |
| 71 | + |
| 72 | + |
| 73 | + |
| 74 | + |
| 75 | + |
| 76 | + |
| 77 | + |
| 78 | + |
| 79 | + |
| 80 | + |
| 81 | + |
| 82 | + |
| 83 | + |
| 84 | + |
| 85 | + |
| 86 | + |
| 87 | + |
| 88 | + |
| 89 | + |
| 90 | + |
| 91 | + |
| 92 | + |
| 93 | + |
| 94 | + |
| 95 | + |
| 96 | + |
| 97 | + |
| 98 | + |
| 99 | + |
| 100 | + |
| 101 | + |
| 102 | + |
| 103 | + |
| 104 | + |
| 105 | + |
| 106 | + |
| 107 | + |
| 108 | + |
| 109 | + |
| 110 | + |
| 111 | + |
| 112 | + |
| 113 | + |
| 114 | + |
| 115 | + |
| 116 | + |
| 117 | + |

TABLE 1-continued

| Example | HPK1 Ki, nM |
|---|---|
| 118 | + |
| 119 | + |
| 120 | + |
| 121 | + |
| 122 | + |
| 123 | + |
| 124 | + |
| 125 | + |
| 126 | + |
| 127 | + |
| 128 | + |
| 129 | + |
| 130 | + |
| 131 | + |
| 132 | + |
| 133 | + |
| 134 | + |
| 135 | + |
| 136 | + |
| 137 | + |
| 138 | + |
| 139 | + |
| 140 | + |
| 141 | + |
| 142 | + |
| 143 | + |
| 144 | + |
| 145 | + |
| 146 | + |
| 147 | + |
| 148 | + |
| 149 | + |
| 150 | + |
| 151 | + |
| 152 | + |
| 153 | + |
| 154 | + |
| 155 | + |
| 156 | + |
| 157 | + |
| 158 | + |
| 159 | + |
| 160 | + |
| 161 | + |
| 162 | + |
| 163 | + |
| 164 | + |
| 165 | + |
| 166 | + |
| 167 | + |
| 168 | + |
| 169 | + |
| 170 | + |
| 171 | + |
| 172 | + |
| 173 | + |
| 174 | + |
| 175 | + |
| 176 | + |
| 177 | + |
| 178 | + |
| 179 | + |
| 180 | + |
| 181 | + |
| 182 | + |
| 183 | + |
| 184 | + |
| 185 | + |
| 186 | + |
| 187 | + |
| 188 | + |
| 189 | + |
| 190 | + |
| 191 | + |
| 192 | + |
| 193 | + |
| 194 | + |
| 195 | + |

TABLE 1-continued

| Example | HPK1 Ki, nM |
|---|---|
| 196 | + |
| 197 | + |
| 198 | + |
| 199 | + |
| 200 | + |
| 201 | + |
| 202 | + |
| 203 | + |
| 204 | + |
| 205 | + |
| 206 | + |
| 207 | + |
| 208 | + |
| 209 | + |
| 210 | + |
| 211 | + |
| 212 | + |
| 213 | + |
| 214 | + |
| 215 | + |
| 216 | + |
| 217 | + |
| 218 | + |
| 219 | + |
| 220 | + |
| 221 | + |
| 222 | + |
| 223 | + |
| 224 | + |
| 225 | + |
| 226 | + |
| 227 | + |
| 228 | + |
| 229 | + |
| 230 | + |
| 231 | + |
| 232 | + |
| 233 | + |
| 234 | + |
| 235 | + |
| 236 | + |
| 237 | + |
| 238 | + |
| 239 | + |
| 240 | + |
| 241 | + |

Example B. p-SLP76S376 HTRF Assay

One or more compounds of the invention can be tested using the p-SLP76S376 HTRF assay described as follows. Jurkat cells (cultured in RPMI1640 media with 10% FBS) are collected and centrifuged, followed by resuspension in appropriate media at $3 \times 10^6$ cells/ml. The Jurkat cells (35 ul) are dispensed into each well in a 384 well plate. Test compounds are diluted with cell culture media for 40-fold dilution (adding 39 ul cell culture media into 1 ul compound). The Jurkat cells in the well plate are treated with the test compounds at various concentrations (adding 5 ul diluted compound into 35 ul Jurkat cells and starting from 3 uM with 1:3 dilution) for 1 hour at 37° C., 5% $CO_2$), followed by treatment with anti-CD3 (5 ug/ml, OKT3 clone) for 30 min. A 1:25 dilution of 100× blocking reagent (from p-SLP76 ser376HTRF kit) with 4×Lysis Buffer(LB) is prepared and 15 ul of the 4×LB buffer with blocking reagent is added into each well and incubated at room temperature for 45 mins with gentle shaking. The cell lysate (16 ul) is added into a Greiner white plate, treated with p-SLP76 ser376HTRF reagents (2 ul donor, 2 ul acceptor) and incubated at 4° C. for overnight. The homogeneous time resolved fluorescence (HTRF) is measured on a PHERAstar plate reader the next day. IC$_{50}$ determination is performed by fitting the curve of percent inhibition versus the log of the inhibitor concentration using the GraphPad Prism 5.0 software.

Example C. Isolation of CD4+ or CD8+ T Cells and Cytokine Measurement

Blood samples are collected from healthy donors. CD4+ or CD8+ T cells are isolated by negative selection using CD4+ or CD8+ enrichment kits (lifetech, USA). The purity of the isolated CD4+ or CD8+ T cells is determined by flow cytometry and is routinely >80%. Cells are cultured in RPMI 1640 supplemented with 10% FCS, glutamine and antibiotics (Invitrogen Life Technologies, USA). For cytokine measurement, Jurkat cells or primary CD4+ or CD8+ T cells are plated at 200 k cells/well and are stimulated for 24 h with anti-CD3/anti-CD28 beads in the presence or absence of testing compounds at various concentrations. 16 μL of supernatants are then transferred to a white detection plate and analyzed using the human IL2 or IFNγ assay kits (Cisbio).

Example D. Treg Assay

One or more compounds can be tested using the Regulatory T-cell proliferation assay described as following. Primary CD4+/CD25− T-cells and CD4+/CD25+ regulatory T-cells are isolated from human donated Peripheral Blood Mononuclear Cells, using an isolated kit from Thermo Fisher Scientific (11363D). CD4+/CD25− T-cells are labeled with CFSE (Thermo Fisher Scientific, C34554) following the protocol provided by the vendor. CFSE labeled T-cells and CD4+/CD25+ regulatory T-cells are re-suspended at the concentration of 1×106 cells/ml in RPMI-1640 medium. 100 μl of CFSE-labeled T-cells are mixed with or without 50 μl of CD4+/CD25+ regulatory T-cells, treated with 5 μl of anti-CD3/CD28 beads (Thermo Fisher Scientific, 11132D) and various concentrations of compounds diluted in 50 μl of RPMI-1640 medium. Mixed populations of cells are cultured for 5 days (37° C., 5% CO$_2$) and proliferation of CFSE-labeled T-cells is analyzed by BD LSRFortessa X-20 using FITC channel on the 5th day.

Various modifications of the invention, in addition to those described herein, will be apparent to those skilled in the art from the foregoing description. Such modifications are also intended to fall within the scope of the appended claims. Each reference, including without limitation all patent, patent applications, and publications, cited in the present application is incorporated herein by reference in its entirety.

What is claimed is:

1. A method for treating a cancer in a patient, said method comprising administering to the patient a therapeutically effective amount of a compound selected from:
   5-(3-(Azetidin-1-ylmethyl)-6-fluoro-2-methylphenyl)-3-(1-methyl-1H-pyrazol-4-yl)-1H-pyrazolo[3,4-c]pyridine;
   N-(4-Fluoro-2-methyl-3-(3-(1-methyl-1H-pyrazol-4-yl)-1H-pyrazolo[3,4-c]pyridin-5-yl)benzyl)propan-2-amine;
   5-(4-(Azetidin-1-ylmethyl)-2-fluoro-6-methylphenyl)-3-(1-methyl-1H-pyrazol-4-yl)-1H-pyrazolo[3,4-c]pyridine; and
   N-(3-Fluoro-5-methyl-4-(3-(1-methyl-1H-pyrazol-4-yl)-1H-pyrazolo[3,4-c]pyridin-5-yl)benzyl)propan-2-amine,
   or a pharmaceutically acceptable salt thereof,
   wherein said cancer is selected from breast cancer, colorectal cancer, lung cancer, ovarian cancer, pancreatic cancer, prostate cancer, colon cancer, esophageal cancer, endometrial cancer, uterine cancer, renal cancer, hepatic cancer, gastric cancer, cancers of the head and neck, thyroid cancer, glioblastoma, sarcoma, bladder cancer, acute lymphoblastic leukemia (ALL), acute myelogenous leukemia (AML), acute promyelocytic leukemia (APL), chronic lymphocytic leukemia (CLL), chronic myelogenous leukemia (CML), diffuse large B-cell lymphoma (DLBCL), mantle cell lymphoma, Non-Hodgkin lymphoma, Hodgkin lymphoma, primary myelofibrosis (PMF), polycythemia vera (PV), essential thrombocytosis (ET), myelodysplasia syndrome (MDS), T-cell acute lymphoblastic lymphoma (T-ALL), multiple myeloma, cutaneous T-cell lymphoma, Waldenstrom's Macroglubulinemia, hairy cell lymphoma, chronic myelogenic lymphoma and Burkitt's lymphoma.

2. The method of claim 1, wherein the cancer is selected from breast cancer, colorectal cancer, lung cancer, ovarian cancer, and pancreatic cancer.

3. The method of claim 1, wherein the compound is 5-(3-(Azetidin-1-ylmethyl)-6-fluoro-2-methylphenyl)-3-(1-methyl-1H-pyrazol-4-yl)-1H-pyrazolo[3,4-c]pyridine, or a pharmaceutically acceptable salt thereof.

4. The method of claim 1, wherein the compound is N-(4-Fluoro-2-methyl-3-(3-(1-methyl-1H-pyrazol-4-yl)-1H-pyrazolo[3,4-c]pyridin-5-yl)benzyl)propan-2-amine, or a pharmaceutically acceptable salt thereof.

5. The method of claim 1, wherein the compound is 5-(4-(Azetidin-1-ylmethyl)-2-fluoro-6-methylphenyl)-3-(1-methyl-1H-pyrazol-4-yl)-1H-pyrazolo[3,4-c]pyridine, or a pharmaceutically acceptable salt thereof.

6. The method of claim 1, wherein the compound is N-(3-Fluoro-5-methyl-4-(3-(1-methyl-1H-pyrazol-4-yl)-1H-pyrazolo[3,4-c]pyridin-5-yl)benzyl)propan-2-amine, or a pharmaceutically acceptable salt thereof.

7. The method of claim 1, wherein the cancer is selected from prostate cancer, colon cancer, esophageal cancer, endometrial cancer, ovarian cancer, uterine cancer, renal cancer, hepatic cancer, pancreatic cancer, gastric cancer, breast cancer, lung cancer, cancers of the head and neck, thyroid cancer, glioblastoma, sarcoma, and bladder cancer.

8. The method of claim 1, wherein the cancer is selected from acute lymphoblastic leukemia (ALL), acute myelogenous leukemia (AML), acute promyelocytic leukemia (APL), chronic lymphocytic leukemia (CLL), chronic myelogenous leukemia (CML), diffuse large B-cell lymphoma (DLBCL), mantle cell lymphoma, Non-Hodgkin lymphoma, Hodgkin lymphoma, primary myelofibrosis (PMF), polycythemia vera (PV), essential thrombocytosis (ET), myelodysplasia syndrome (MDS), T-cell acute lymphoblastic lymphoma (T-ALL), multiple myeloma, cutaneous T-cell lymphoma, Waldenstrom's Macroglubulinemia, hairy cell lymphoma, chronic myelogenic lymphoma and Burkitt's lymphoma.

* * * * *